(12) United States Patent
Ren et al.

(10) Patent No.: US 9,295,673 B2
(45) Date of Patent: Mar. 29, 2016

(54) COMBINATION OF MTOR INHIBITORS AND PI3-KINASE INHIBITORS, AND USES THEREOF

(75) Inventors: Pingda Ren, San Diego, CA (US); Yi Liu, San Diego, CA (US); Katayoun Jessen, San Diego, CA (US); Xin Guo, San Diego, CA (US); Christian Rommel, La Jolla, CA (US); Troy Edward Wilson, San Marino, CA (US)

(73) Assignee: Intellikine LLC, La Jolla, CA (US)

( * ) Notice: Subject to any disclaimer, the term of this patent is extended or adjusted under 35 U.S.C. 154(b) by 0 days.

(21) Appl. No.: 13/403,856

(22) Filed: Feb. 23, 2012

(65) Prior Publication Data
US 2012/0294930 A1    Nov. 22, 2012

Related U.S. Application Data

(60) Provisional application No. 61/446,016, filed on Feb. 23, 2011.

(51) Int. Cl.

| | | |
|---|---|---|
| *A61K 31/551* | (2006.01) | |
| *A61K 31/4439* | (2006.01) | |
| *A61K 31/4745* | (2006.01) | |
| *A61K 31/498* | (2006.01) | |
| *A61K 45/06* | (2006.01) | |
| *A61K 31/501* | (2006.01) | |
| *A61K 31/517* | (2006.01) | |
| *A61K 31/519* | (2006.01) | |
| *A61K 31/527* | (2006.01) | |
| *A61K 31/53* | (2006.01) | |

(Continued)

(52) U.S. Cl.
CPC ........... *A61K 31/551* (2013.01); *A61K 31/4439* (2013.01); *A61K 31/4745* (2013.01); *A61K 31/498* (2013.01); *A61K 31/501* (2013.01); *A61K 31/517* (2013.01); *A61K 31/519* (2013.01); *A61K 31/527* (2013.01); *A61K 31/53* (2013.01); *A61K 31/5377* (2013.01); *A61K 31/541* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 4,704,381 | A | 11/1987 | Schaumann et al. |
| 5,240,941 | A | 8/1993 | Bruneau |

(Continued)

FOREIGN PATENT DOCUMENTS

| | | |
|---|---|---|
| CA | 1338379 | 6/1996 |
| CN | 101602768 | 12/2009 |

(Continued)

OTHER PUBLICATIONS

International search report and written opinion dated May 31, 2012 for PCT/US2012/026399.

(Continued)

*Primary Examiner* — Anna Pagonakis
(74) *Attorney, Agent, or Firm* — Honigman Miller Schwartz and Cohn LLP; Lucy X. Yang; Jonathan P. O'Brien

(57) ABSTRACT

The present invention provides for a method for treating a disease condition associated with PI3-kinase α and/or mTOR in a subject. In another aspect, the invention provides for a method for treating a disease condition associated with PI3-kinase α and/or mTOR in a subject. In yet another aspect, a method of inhibiting phosphorylation of both Akt (S473) and Akt (T308) in a cell is set forth.

1 Claim, 13 Drawing Sheets

(51) Int. Cl.
  *A61K 31/5377* (2006.01)
  *A61K 31/541* (2006.01)

(56) References Cited

U.S. PATENT DOCUMENTS

| | | | |
|---|---|---|---|
| 5,310,731 A | 5/1994 | Olsson et al. | |
| 5,364,862 A | 11/1994 | Spada et al. | |
| 5,420,419 A | 5/1995 | Wood | |
| 5,428,125 A | 6/1995 | Hefner, Jr. et al. | |
| 5,442,039 A | 8/1995 | Hefner, Jr. et al. | |
| 5,506,347 A | 4/1996 | Erion et al. | |
| 5,561,134 A | 10/1996 | Spada et al. | |
| 5,563,257 A | 10/1996 | Zilch et al. | |
| 5,593,997 A | 1/1997 | Dow et al. | |
| 5,646,128 A | 7/1997 | Firestein et al. | |
| 5,652,366 A | 7/1997 | Spada et al. | |
| 5,654,307 A | 8/1997 | Bridges et al. | |
| 5,665,721 A | 9/1997 | Bhagwat et al. | |
| 5,674,998 A | 10/1997 | Boyer et al. | |
| 5,686,455 A | 11/1997 | Adams et al. | |
| 5,736,554 A | 4/1998 | Spada et al. | |
| 5,747,235 A | 5/1998 | Farid et al. | |
| 5,756,711 A | 5/1998 | Zilch et al. | |
| 5,763,596 A | 6/1998 | Boyer et al. | |
| 5,763,597 A | 6/1998 | Ugarkar et al. | |
| 5,763,885 A | 6/1998 | Murphy et al. | |
| 5,795,977 A | 8/1998 | Ugarkar et al. | |
| 5,824,492 A | 10/1998 | Hiles et al. | |
| 5,858,753 A | 1/1999 | Chantry et al. | |
| 5,914,488 A | 6/1999 | Sone | |
| 5,919,808 A | 7/1999 | Petrie et al. | |
| 5,922,753 A | 7/1999 | Petrie et al. | |
| 5,948,776 A | 9/1999 | Petrie et al. | |
| 5,965,573 A | 10/1999 | Petrie et al. | |
| 5,977,061 A | 11/1999 | Holy et al. | |
| 5,981,533 A | 11/1999 | Traxler et al. | |
| 5,985,589 A | 11/1999 | Chantry et al. | |
| 5,990,169 A | 11/1999 | Petrie et al. | |
| 5,994,358 A | 11/1999 | Petrie et al. | |
| 6,001,839 A | 12/1999 | Calderwood et al. | |
| 6,057,305 A | 5/2000 | Holy et al. | |
| 6,057,320 A | 5/2000 | Spada et al. | |
| 6,084,095 A | 7/2000 | Bridges et al. | |
| 6,093,737 A | 7/2000 | Anthony et al. | |
| 6,127,121 A | 10/2000 | Meyer, Jr. et al. | |
| 6,153,631 A | 11/2000 | Petrie et al. | |
| 6,191,170 B1 | 2/2001 | Medina | |
| 6,214,834 B1 | 4/2001 | Jadhav et al. | |
| 6,251,901 B1 | 6/2001 | Petrie et al. | |
| 6,265,410 B1 | 7/2001 | Bridges et al. | |
| 6,268,370 B1 | 7/2001 | Adams et al. | |
| 6,312,894 B1 | 11/2001 | Hedgpeth et al. | |
| 6,319,660 B1 | 11/2001 | Allway et al. | |
| 6,323,201 B1 | 11/2001 | Carson et al. | |
| 6,342,514 B1 | 1/2002 | Petrie et al. | |
| 6,350,741 B1 | 2/2002 | Golec et al. | |
| 6,383,790 B1 | 5/2002 | Shokat | |
| 6,384,039 B1 | 5/2002 | Fossa | |
| 6,387,894 B1 | 5/2002 | Fossa | |
| 6,390,821 B1 | 5/2002 | Shokat | |
| 6,417,194 B1 | 7/2002 | Fox et al. | |
| 6,455,534 B2 | 9/2002 | Bridges et al. | |
| 6,472,153 B1 | 10/2002 | Dempcy et al. | |
| 6,482,623 B1 | 11/2002 | Vanhaesebroeck et al. | |
| 6,485,906 B2 | 11/2002 | Meyer, Jr. et al. | |
| 6,492,346 B1 | 12/2002 | Hedgpeth et al. | |
| 6,506,769 B2 | 1/2003 | Snow et al. | |
| 6,518,277 B1 | 2/2003 | Sadhu et al. | |
| 6,521,417 B1 | 2/2003 | Shokat | |
| 6,521,620 B1 | 2/2003 | Bridges et al. | |
| 6,531,491 B1 | 3/2003 | Kania et al. | |
| 6,534,524 B1 | 3/2003 | Kania et al. | |
| 6,545,005 B1 | 4/2003 | Baxter et al. | |
| 6,552,065 B2 | 4/2003 | Remiszewski et al. | |
| 6,552,192 B1 | 4/2003 | Hanus et al. | |
| 6,562,819 B2 | 5/2003 | Carson et al. | |
| 6,583,161 B1 | 6/2003 | Medina | |
| 6,613,798 B1 | 9/2003 | Porter et al. | |
| 6,624,119 B1 | 9/2003 | Reinhard et al. | |
| 6,630,495 B1 | 10/2003 | Cooke et al. | |
| 6,632,789 B1 | 10/2003 | June | |
| 6,632,809 B2 | 10/2003 | Grillot et al. | |
| 6,645,989 B2 | 11/2003 | Adams et al. | |
| 6,649,631 B1 | 11/2003 | Orme et al. | |
| 6,653,296 B1 | 11/2003 | Holy et al. | |
| 6,653,306 B1 | 11/2003 | Alexander et al. | |
| 6,660,744 B1 | 12/2003 | Hirst et al. | |
| 6,660,845 B1 | 12/2003 | Gall et al. | |
| 6,664,269 B2 | 12/2003 | Martin et al. | |
| 6,667,300 B2 | 12/2003 | Sadhu et al. | |
| 6,690,583 B1 | 2/2004 | Bergstedt et al. | |
| 6,713,474 B2 | 3/2004 | Hirst et al. | |
| 6,713,484 B2 | 3/2004 | Bridges et al. | |
| 6,720,344 B2 | 4/2004 | Kerwin et al. | |
| 6,734,187 B1 | 5/2004 | Tanaka et al. | |
| 6,770,639 B2 | 8/2004 | Snow et al. | |
| 6,777,425 B2 | 8/2004 | Burli et al. | |
| 6,777,439 B2 | 8/2004 | Durden | |
| 6,790,844 B2 | 9/2004 | Ueno et al. | |
| 6,800,620 B2 | 10/2004 | Sadhu et al. | |
| 6,800,633 B2 | 10/2004 | Castelhano et al. | |
| 6,849,420 B2 | 2/2005 | Vanhasebroeck et al. | |
| 6,849,713 B2 | 2/2005 | Zhang et al. | |
| 6,852,727 B2 | 2/2005 | Goulet et al. | |
| 6,906,103 B2 | 6/2005 | Zhang et al. | |
| 6,919,332 B2 | 7/2005 | Noe et al. | |
| 6,921,763 B2 | 7/2005 | Hirst et al. | |
| 6,949,535 B2 | 9/2005 | Sadhu et al. | |
| 7,026,461 B1 | 4/2006 | Shokat | |
| 7,041,676 B2 | 5/2006 | McDonald et al. | |
| 7,049,116 B2 | 5/2006 | Shokat | |
| 7,049,312 B1 | 5/2006 | Rafferty et al. | |
| 7,064,218 B2 | 6/2006 | Dyatkina et al. | |
| 7,071,355 B2 | 7/2006 | Leban et al. | |
| 7,115,627 B2 | 10/2006 | Pinto et al. | |
| 7,115,653 B2 | 10/2006 | Baxter et al. | |
| 7,144,903 B2 | 12/2006 | Collins et al. | |
| 7,148,228 B2 | 12/2006 | Kasibhatla et al. | |
| 7,157,487 B2 | 1/2007 | Nakayama et al. | |
| 7,166,293 B2 | 1/2007 | Teng et al. | |
| 7,208,601 B2 | 4/2007 | Mjalli et al. | |
| 7,217,794 B2 | 5/2007 | Abdel-Meguid et al. | |
| 7,241,890 B2 | 7/2007 | Kasibhatla et al. | |
| 7,244,741 B2 | 7/2007 | Simon et al. | |
| 7,247,736 B2 | 7/2007 | Leban et al. | |
| 7,262,204 B2 | 8/2007 | Collins et al. | |
| 7,265,111 B2 | 9/2007 | Bigot et al. | |
| 7,265,131 B2 | 9/2007 | Johnson et al. | |
| 7,271,262 B2 | 9/2007 | La Greca et al. | |
| 7,329,765 B2 | 2/2008 | Burli et al. | |
| 7,332,497 B2 | 2/2008 | Hirst et al. | |
| 7,348,427 B2 | 3/2008 | Burli et al. | |
| RE40,245 E | 4/2008 | Grillot et al. | |
| 7,365,094 B2 | 4/2008 | Leban et al. | |
| 7,384,967 B2 | 6/2008 | Polisetti et al. | |
| 7,396,836 B2 | 7/2008 | Harada et al. | |
| 7,414,036 B2 | 8/2008 | Sevillano et al. | |
| 7,429,596 B2 | 9/2008 | Tanaka et al. | |
| 7,439,254 B2 | 10/2008 | Bergnes | |
| 7,459,462 B2 | 12/2008 | Simon et al. | |
| 7,459,472 B2 | 12/2008 | Mjalli et al. | |
| 7,470,721 B2 | 12/2008 | Durden | |
| 7,501,538 B2 | 3/2009 | Mjalli et al. | |
| 7,534,797 B2 | 5/2009 | Arnold et al. | |
| 7,541,373 B2 | 6/2009 | Polisetti et al. | |
| 7,569,571 B2 | 8/2009 | Dong et al. | |
| 7,572,913 B2 | 8/2009 | McKerracher et al. | |
| 7,579,348 B2 | 8/2009 | Wang et al. | |
| 7,585,868 B2 | 9/2009 | Knight et al. | |
| 7,608,594 B2 | 10/2009 | Blagg et al. | |
| 7,615,552 B2 | 11/2009 | Ono et al. | |
| 7,622,451 B2 | 11/2009 | Blagg et al. | |
| 7,651,687 B2 | 1/2010 | Buck et al. | |
| 7,678,803 B2 | 3/2010 | Huang et al. | |

(56) References Cited

U.S. PATENT DOCUMENTS

| | | |
|---|---|---|
| 7,700,607 B2 | 4/2010 | Hu et al. |
| 7,745,485 B2 | 6/2010 | Durden |
| 7,772,231 B2 | 8/2010 | Sheppard et al. |
| 7,932,260 B2 | 4/2011 | Fowler et al. |
| 8,476,282 B2 | 7/2013 | Ren et al. |
| 8,476,431 B2 | 7/2013 | Ren et al. |
| 2001/0024833 A1 | 9/2001 | Laborde et al. |
| 2001/0027197 A1 | 10/2001 | Bridges et al. |
| 2002/0016460 A1 | 2/2002 | Snow et al. |
| 2002/0016976 A1 | 2/2002 | Shokat |
| 2002/0037856 A1 | 3/2002 | Zhang et al. |
| 2002/0102590 A1 | 8/2002 | Taing et al. |
| 2002/0146690 A1 | 10/2002 | Meyer et al. |
| 2002/0147160 A1 | 10/2002 | Bhat et al. |
| 2002/0156081 A1 | 10/2002 | Hirst et al. |
| 2002/0161014 A1 | 10/2002 | Sadhu et al. |
| 2002/0173524 A1 | 11/2002 | Collins et al. |
| 2003/0001141 A1 | 1/2003 | Sun et al. |
| 2003/0008896 A1 | 1/2003 | Martin et al. |
| 2003/0018022 A1 | 1/2003 | Collins et al. |
| 2003/0022344 A1 | 1/2003 | Williams et al. |
| 2003/0064997 A1 | 4/2003 | Adams et al. |
| 2003/0073218 A1 | 4/2003 | Shokat et al. |
| 2003/0083268 A1 | 5/2003 | Burli et al. |
| 2003/0109248 A1 | 6/2003 | Lewis |
| 2003/0113765 A1 | 6/2003 | Dempcy et al. |
| 2003/0119479 A1 | 6/2003 | Arima et al. |
| 2003/0119791 A1 | 6/2003 | Kerwin et al. |
| 2003/0139427 A1 | 7/2003 | Castelhano et al. |
| 2003/0143602 A1 | 7/2003 | Meyer, Jr. et al. |
| 2003/0166929 A1 | 9/2003 | Snow et al. |
| 2003/0180924 A1 | 9/2003 | DeSimone |
| 2003/0186987 A1 | 10/2003 | Bridges et al. |
| 2003/0187001 A1 | 10/2003 | Calderwood et al. |
| 2003/0195211 A1 | 10/2003 | Sadhu et al. |
| 2003/0199516 A1 | 10/2003 | Moser et al. |
| 2003/0212113 A1 | 11/2003 | Dyatkina et al. |
| 2003/0225098 A1 | 12/2003 | Hirst et al. |
| 2003/0232849 A1 | 12/2003 | Noe et al. |
| 2003/0235822 A1 | 12/2003 | Lokhov et al. |
| 2004/0039035 A1 | 2/2004 | Collins et al. |
| 2004/0043983 A1 | 3/2004 | Li |
| 2004/0067901 A1 | 4/2004 | Bhat et al. |
| 2004/0067915 A1 | 4/2004 | McMahon et al. |
| 2004/0072766 A1 | 4/2004 | June |
| 2004/0072788 A1 | 4/2004 | Bhat et al. |
| 2004/0102423 A1 | 5/2004 | MacLaughlan et al. |
| 2004/0102437 A1 | 5/2004 | Takami et al. |
| 2004/0110717 A1 | 6/2004 | Bhat et al. |
| 2004/0110945 A1 | 6/2004 | Nakayama et al. |
| 2004/0116689 A1 | 6/2004 | Gall et al. |
| 2004/0122235 A1 | 6/2004 | Polisetti et al. |
| 2004/0127434 A1 | 7/2004 | Bigot et al. |
| 2004/0176458 A1 | 9/2004 | Leban et al. |
| 2004/0176601 A1 | 9/2004 | Goulet et al. |
| 2004/0192758 A1 | 9/2004 | Leban et al. |
| 2004/0266780 A1 | 12/2004 | Sadhu et al. |
| 2005/0004149 A1 | 1/2005 | Harada et al. |
| 2005/0043239 A1 | 2/2005 | Douangpanya et al. |
| 2005/0049310 A1 | 3/2005 | Mjalli et al. |
| 2005/0054614 A1 | 3/2005 | Diacovo et al. |
| 2005/0059713 A1 | 3/2005 | Mjalli et al. |
| 2005/0085472 A1 | 4/2005 | Tanaka et al. |
| 2005/0101551 A1 | 5/2005 | Sevillano et al. |
| 2005/0124637 A1 | 6/2005 | Cheng et al. |
| 2005/0143317 A1 | 6/2005 | Abdel-Meguid et al. |
| 2005/0153997 A1 | 7/2005 | Simon et al. |
| 2005/0171148 A1 | 8/2005 | Mjalli et al. |
| 2005/0182045 A1 | 8/2005 | Nagase et al. |
| 2005/0187230 A1 | 8/2005 | Ding et al. |
| 2005/0187418 A1 | 8/2005 | Small et al. |
| 2005/0197340 A1 | 9/2005 | Arora et al. |
| 2005/0215579 A1 | 9/2005 | Simon et al. |
| 2005/0222177 A1 | 10/2005 | Sim et al. |
| 2005/0239809 A1 | 10/2005 | Watts et al. |
| 2005/0250770 A1 | 11/2005 | Ono et al. |
| 2005/0256066 A1 | 11/2005 | Abel et al. |
| 2005/0261317 A1 | 11/2005 | Sadhu et al. |
| 2005/0272751 A1 | 12/2005 | McKerracher et al. |
| 2006/0019988 A1 | 1/2006 | McDonald et al. |
| 2006/0069034 A1 | 3/2006 | Burli et al. |
| 2006/0079538 A1 | 4/2006 | Hallahan et al. |
| 2006/0106013 A1 | 5/2006 | Breitfelder et al. |
| 2006/0106038 A1 | 5/2006 | Bouscary et al. |
| 2006/0116326 A1 | 6/2006 | Burli et al. |
| 2006/0135790 A1 | 6/2006 | Hyett et al. |
| 2006/0156485 A1 | 7/2006 | Lim |
| 2006/0166997 A1 | 7/2006 | Zhang et al. |
| 2006/0183783 A1 | 8/2006 | Polisetti et al. |
| 2006/0199776 A1 | 9/2006 | Blagg et al. |
| 2006/0235031 A1 | 10/2006 | Arnold et al. |
| 2006/0246551 A1 | 11/2006 | Stack et al. |
| 2006/0276470 A1 | 12/2006 | Jackson et al. |
| 2006/0287295 A1 | 12/2006 | Barlaam et al. |
| 2007/0015773 A1 | 1/2007 | Bergeron et al. |
| 2007/0027193 A1 | 2/2007 | Leban et al. |
| 2007/0032640 A1 | 2/2007 | Varghese et al. |
| 2007/0054915 A1 | 3/2007 | Arora et al. |
| 2007/0072897 A1 | 3/2007 | Mahaney et al. |
| 2007/0099871 A1 | 5/2007 | Davis et al. |
| 2007/0112005 A1 | 5/2007 | Chen et al. |
| 2007/0142405 A1 | 6/2007 | Dong et al. |
| 2007/0149521 A1 | 6/2007 | Crew et al. |
| 2007/0203143 A1 | 8/2007 | Sheppard et al. |
| 2007/0213355 A1 | 9/2007 | Capraro et al. |
| 2007/0224672 A1 | 9/2007 | Leban et al. |
| 2007/0249598 A1 | 10/2007 | Wang et al. |
| 2007/0254883 A1 | 11/2007 | Cres et al. |
| 2007/0270452 A1 | 11/2007 | Blagg et al. |
| 2007/0293489 A1 | 12/2007 | Adams et al. |
| 2007/0293516 A1 | 12/2007 | Knight et al. |
| 2008/0003254 A1 | 1/2008 | Mack et al. |
| 2008/0032960 A1 | 2/2008 | Knight et al. |
| 2008/0039491 A1 | 2/2008 | Ronan et al. |
| 2008/0058521 A1 | 3/2008 | Krishnan et al. |
| 2008/0070935 A1 | 3/2008 | Huang et al. |
| 2008/0119454 A1 | 5/2008 | Polisetti et al. |
| 2008/0119455 A1 | 5/2008 | Polisetti et al. |
| 2008/0119461 A1 | 5/2008 | Sin et al. |
| 2008/0200465 A1 | 8/2008 | Burli et al. |
| 2008/0234262 A1 | 9/2008 | Zask et al. |
| 2008/0249090 A1 | 10/2008 | Hu et al. |
| 2008/0261956 A1 | 10/2008 | Choi et al. |
| 2008/0274189 A1 | 11/2008 | Collingwood et al. |
| 2008/0287469 A1 | 11/2008 | Diacovo et al. |
| 2008/0292626 A1 | 11/2008 | Wang et al. |
| 2008/0293674 A1 | 11/2008 | Schwarz et al. |
| 2008/0306053 A1 | 12/2008 | Tachdjian et al. |
| 2008/0306093 A1 | 12/2008 | Servant et al. |
| 2008/0312180 A1 | 12/2008 | Liang et al. |
| 2008/0318942 A1 | 12/2008 | Simon et al. |
| 2009/0030023 A1 | 1/2009 | Harada et al. |
| 2009/0053192 A1 | 2/2009 | Millan et al. |
| 2009/0054405 A1 | 2/2009 | Booker et al. |
| 2009/0088452 A1 | 4/2009 | Coleman et al. |
| 2009/0099214 A1 | 4/2009 | Fairhurst et al. |
| 2009/0105233 A1 | 4/2009 | Chua et al. |
| 2009/0118283 A1 | 5/2009 | Defert et al. |
| 2009/0124638 A1 | 5/2009 | Shokat et al. |
| 2009/0124654 A1 | 5/2009 | Mjalli et al. |
| 2009/0163481 A1 | 6/2009 | Murphy et al. |
| 2009/0163709 A1 | 6/2009 | Blagg |
| 2009/0170879 A1 | 7/2009 | Szucova et al. |
| 2009/0181920 A1 | 7/2009 | Watkins et al. |
| 2009/0181988 A1 | 7/2009 | Tanaka et al. |
| 2009/0187014 A1 | 7/2009 | Blagg |
| 2009/0203689 A1 | 8/2009 | Dhalla et al. |
| 2009/0208505 A1 | 8/2009 | Samuels et al. |
| 2009/0232768 A1 | 9/2009 | Birkus et al. |
| 2009/0247513 A1 | 10/2009 | Burli et al. |
| 2009/0253694 A1 | 10/2009 | Ono et al. |
| 2009/0264409 A1 | 10/2009 | Dong et al. |
| 2009/0264423 A2 | 10/2009 | Chua et al. |
| 2009/0270567 A1 | 10/2009 | Small et al. |

(56) References Cited

U.S. PATENT DOCUMENTS

| | | |
|---|---|---|
| 2009/0274698 A1 | 11/2009 | Bhagwat et al. |
| 2009/0286779 A1 | 11/2009 | Imbach et al. |
| 2009/0312319 A1 | 12/2009 | Ren et al. |
| 2009/0312406 A1 | 12/2009 | Hsieh et al. |
| 2009/0325967 A1 | 12/2009 | Fairhurst et al. |
| 2010/0009963 A1 | 1/2010 | Knight et al. |
| 2010/0009978 A1 | 1/2010 | Gerspacher et al. |
| 2010/0022585 A1 | 1/2010 | deLong et al. |
| 2010/0029658 A1 | 2/2010 | Gavish et al. |
| 2010/0029693 A1 | 2/2010 | Douangpanya et al. |
| 2010/0048540 A1 | 2/2010 | Boyle et al. |
| 2010/0048882 A1 | 2/2010 | Blagg et al. |
| 2010/0056494 A1 | 3/2010 | Winzeler et al. |
| 2010/0087456 A1 | 4/2010 | Baik et al. |
| 2010/0105630 A1 | 4/2010 | Blagg |
| 2010/0184760 A1 | 7/2010 | Ren et al. |
| 2010/0190749 A1 | 7/2010 | Ren et al. |
| 2010/0239496 A1 | 9/2010 | Gangadharmath et al. |
| 2010/0331297 A1 | 12/2010 | Bulawa et al. |
| 2011/0046165 A1 | 2/2011 | Ren et al. |
| 2011/0077268 A1 | 3/2011 | Liu et al. |
| 2011/0124641 A1 | 5/2011 | Ren et al. |
| 2011/0144134 A1 | 6/2011 | Shokat et al. |
| 2011/0160232 A1 | 6/2011 | Ren et al. |
| 2011/0172228 A1 | 7/2011 | Ren et al. |
| 2011/0195966 A1 | 8/2011 | Garcia-Echeverria et al. |
| 2011/0212053 A1 | 9/2011 | Qian et al. |
| 2011/0224223 A1 | 9/2011 | Shokat et al. |
| 2011/0230476 A1 | 9/2011 | Niu et al. |
| 2011/0269779 A1 | 11/2011 | Wilson et al. |
| 2011/0281866 A1 | 11/2011 | Ren et al. |
| 2011/0301144 A1 | 12/2011 | Knight et al. |
| 2012/0065154 A1 | 3/2012 | Tanaka et al. |
| 2012/0322814 A1 | 12/2012 | Korennykh et al. |
| 2013/0035324 A1 | 2/2013 | Ren et al. |
| 2013/0261102 A1 | 10/2013 | Ren et al. |
| 2014/0030256 A1 | 1/2014 | Ren et al. |
| 2014/0128599 A1 | 5/2014 | Ren et al. |

FOREIGN PATENT DOCUMENTS

| | | |
|---|---|---|
| DE | 2004713 A1 | 8/1971 |
| EP | 0773023 A1 | 5/1997 |
| EP | 0837063 | 4/1998 |
| EP | 0564409 B1 | 1/2000 |
| EP | 1488792 A2 | 12/2004 |
| EP | 1488792 A3 | 1/2005 |
| EP | 871448 B1 | 3/2005 |
| EP | 1557410 A2 | 7/2005 |
| EP | 1557410 A3 | 4/2006 |
| EP | 1341769 B1 | 10/2007 |
| EP | 1020445 B1 | 8/2008 |
| EP | 1557410 B1 | 9/2009 |
| GB | 812366 | 4/1959 |
| GB | 937725 | 9/1963 |
| JP | 61109797 | 5/1986 |
| JP | 5256693 A | 10/1993 |
| JP | 8295667 A | 11/1996 |
| JP | 9143163 A | 6/1997 |
| JP | 10206995 A | 8/1998 |
| JP | 2000072773 A | 3/2000 |
| JP | 2002131859 A | 5/2002 |
| JP | 2003073357 A | 3/2003 |
| JP | 2004161716 A | 6/2004 |
| WO | WO 83/01446 A1 | 4/1983 |
| WO | WO 91/17161 A1 | 11/1991 |
| WO | WO 92/14733 A1 | 9/1992 |
| WO | WO 93/16091 A1 | 8/1993 |
| WO | WO 93/16092 A1 | 8/1993 |
| WO | WO 93/18035 A1 | 9/1993 |
| WO | WO 93/22443 A1 | 11/1993 |
| WO | WO 94/13677 A1 | 6/1994 |
| WO | WO 94/17803 A1 | 8/1994 |
| WO | WO 95/12588 A1 | 5/1995 |
| WO | WO 95/29673 A1 | 11/1995 |
| WO | WO 95/32984 A1 | 12/1995 |
| WO | WO 96/31510 A1 | 10/1996 |
| WO | WO 96/40706 A1 | 12/1996 |
| WO | WO 97/28133 A1 | 8/1997 |
| WO | WO 97/28161 A1 | 8/1997 |
| WO | WO 98/14450 A1 | 4/1998 |
| WO | WO 98/41525 A1 | 9/1998 |
| WO | WO 98/52611 A1 | 11/1998 |
| WO | WO 98/57952 A1 | 12/1998 |
| WO | WO 00/17202 A1 | 3/2000 |
| WO | WO 00/42042 A2 | 7/2000 |
| WO | WO 00/42042 A3 | 11/2000 |
| WO | WO 01/02369 A2 | 1/2001 |
| WO | WO 01/16114 A2 | 3/2001 |
| WO | WO 01/19829 A2 | 3/2001 |
| WO | WO 01/25238 A2 | 4/2001 |
| WO | WO 01/31063 A1 | 5/2001 |
| WO | WO 01/38584 A2 | 5/2001 |
| WO | WO 01/16114 A3 | 8/2001 |
| WO | WO 01/55140 A1 | 8/2001 |
| WO | WO 01/56988 A1 | 8/2001 |
| WO | WO 01/19829 A3 | 9/2001 |
| WO | WO 01/25238 A3 | 10/2001 |
| WO | WO 01/38584 A3 | 10/2001 |
| WO | WO 01/81346 A2 | 11/2001 |
| WO | WO 02/06192 A1 | 1/2002 |
| WO | WO 01/81346 A3 | 3/2002 |
| WO | WO 01/02369 A3 | 4/2002 |
| WO | WO 02/30944 A2 | 4/2002 |
| WO | WO 02/057425 A2 | 7/2002 |
| WO | WO 02/060879 A2 | 8/2002 |
| WO | WO 02/076986 A1 | 10/2002 |
| WO | WO 02/080926 A1 | 10/2002 |
| WO | WO 02/083143 A1 | 10/2002 |
| WO | WO 02/088025 A1 | 11/2002 |
| WO | WO 02/090334 A1 | 11/2002 |
| WO | WO 02/30944 A3 | 1/2003 |
| WO | WO 03/000187 A2 | 1/2003 |
| WO | WO 03/000688 A1 | 1/2003 |
| WO | WO 03/016275 A1 | 2/2003 |
| WO | WO 02/060879 A3 | 3/2003 |
| WO | WO 03/020880 A2 | 3/2003 |
| WO | WO 03/024969 A1 | 3/2003 |
| WO | WO 03/035075 A1 | 5/2003 |
| WO | WO 03/059884 A1 | 7/2003 |
| WO | WO 03/020880 A3 | 10/2003 |
| WO | WO 03/082341 A1 | 10/2003 |
| WO | WO 03/106426 A1 | 12/2003 |
| WO | WO 2004/004644 A2 | 1/2004 |
| WO | WO 2004/006906 A2 | 1/2004 |
| WO | WO 2004/006906 A3 | 3/2004 |
| WO | WO 2004/018058 A2 | 3/2004 |
| WO | WO 2004/031177 A1 | 4/2004 |
| WO | WO 2004/004644 A3 | 5/2004 |
| WO | WO 2004/039774 A2 | 5/2004 |
| WO | WO 2004/018058 A3 | 7/2004 |
| WO | WO 2004/039774 A3 | 7/2004 |
| WO | WO 03/000187 A3 | 8/2004 |
| WO | WO 2004/087053 A2 | 10/2004 |
| WO | WO 2004/111014 A1 | 12/2004 |
| WO | WO 2005/002585 A2 | 1/2005 |
| WO | WO 2005/007085 A2 | 1/2005 |
| WO | WO 2005/009389 A2 | 2/2005 |
| WO | WO 2005/012323 A2 | 2/2005 |
| WO | WO 2005/016348 A1 | 2/2005 |
| WO | WO 2005/016349 A1 | 2/2005 |
| WO | WO 2005/016528 A2 | 2/2005 |
| WO | WO 2005/021533 A1 | 3/2005 |
| WO | WO 02/057425 A3 | 4/2005 |
| WO | WO 2005/012323 A3 | 5/2005 |
| WO | WO 2005/016528 A3 | 5/2005 |
| WO | WO 2005/044181 A2 | 5/2005 |
| WO | WO 2005/047289 A1 | 5/2005 |
| WO | WO 2005/061460 A1 | 7/2005 |
| WO | WO 2005/063258 A1 | 7/2005 |
| WO | WO 2005/067901 A2 | 7/2005 |
| WO | WO 2005/074603 A2 | 8/2005 |
| WO | WO 2005/007085 A3 | 9/2005 |

(56) References Cited

FOREIGN PATENT DOCUMENTS

| | | |
|---|---|---|
| WO | WO 2005/009389 A3 | 9/2005 |
| WO | WO 2005/085248 A1 | 9/2005 |
| WO | WO 2005/097800 A1 | 10/2005 |
| WO | WO 2005/105760 A1 | 11/2005 |
| WO | WO 2005/067901 A3 | 12/2005 |
| WO | WO 2005/112935 A1 | 12/2005 |
| WO | WO 2005/113556 A1 | 12/2005 |
| WO | WO 2005/117889 A1 | 12/2005 |
| WO | WO 2005/120511 A1 | 12/2005 |
| WO | WO 2005/044181 A3 | 3/2006 |
| WO | WO 2006/030032 A1 | 3/2006 |
| WO | WO 2006/038865 A1 | 4/2006 |
| WO | WO 2006/050501 A2 | 5/2006 |
| WO | WO 2006/050946 A1 | 5/2006 |
| WO | WO 2006/068760 A2 | 6/2006 |
| WO | WO 2004/087053 A3 | 8/2006 |
| WO | WO 2006/089106 A2 | 8/2006 |
| WO | WO 2006/108107 A1 | 10/2006 |
| WO | WO 2006/112666 A1 | 10/2006 |
| WO | WO 2005/074603 A3 | 11/2006 |
| WO | WO 2006/114064 A2 | 11/2006 |
| WO | WO 2006/114065 A2 | 11/2006 |
| WO | WO 2006/068760 A3 | 12/2006 |
| WO | WO 2006/089106 A3 | 12/2006 |
| WO | WO 2007/002293 A2 | 1/2007 |
| WO | WO 2007/006547 A1 | 1/2007 |
| WO | WO 2007/020046 A1 | 2/2007 |
| WO | WO 2007/002293 A3 | 3/2007 |
| WO | WO 2007/023115 A2 | 3/2007 |
| WO | WO 2007/025090 A2 | 3/2007 |
| WO | WO 2007/023115 A3 | 4/2007 |
| WO | WO 2006/050501 A3 | 5/2007 |
| WO | WO 2007/061737 A2 | 5/2007 |
| WO | WO 2006/114064 A3 | 6/2007 |
| WO | WO 2006/114065 A3 | 6/2007 |
| WO | WO 2007/025090 A3 | 6/2007 |
| WO | WO 2007/075554 A2 | 7/2007 |
| WO | WO 2007/079164 A2 | 7/2007 |
| WO | WO 2007/095588 A1 | 8/2007 |
| WO | WO 2007/075554 A3 | 9/2007 |
| WO | WO 2007/103308 A2 | 9/2007 |
| WO | WO 2007/106503 A2 | 9/2007 |
| WO | WO 2007/112005 A2 | 10/2007 |
| WO | WO 2007/114926 A2 | 10/2007 |
| WO | WO 2007/121453 A2 | 10/2007 |
| WO | WO 2007/121920 A2 | 11/2007 |
| WO | WO 2007/121924 A2 | 11/2007 |
| WO | WO 2007/124405 A2 | 11/2007 |
| WO | WO 2007/124854 A1 | 11/2007 |
| WO | WO 2007/125310 A2 | 11/2007 |
| WO | WO 2007/125315 A2 | 11/2007 |
| WO | WO 2007/126841 A2 | 11/2007 |
| WO | WO 2007/134828 A1 | 11/2007 |
| WO | WO 2007/135380 A2 | 11/2007 |
| WO | WO 2007/135398 A1 | 11/2007 |
| WO | WO 2007/061737 A3 | 12/2007 |
| WO | WO 2007/125315 A3 | 12/2007 |
| WO | WO 2007/121920 A3 | 1/2008 |
| WO | WO 2008/012326 A1 | 1/2008 |
| WO | WO 2007/103308 A3 | 2/2008 |
| WO | WO 2007/112005 A3 | 2/2008 |
| WO | WO 2007/125310 A3 | 3/2008 |
| WO | WO 2008/025755 A1 | 3/2008 |
| WO | WO 2008/047821 A1 | 4/2008 |
| WO | WO 2007/106503 A3 | 5/2008 |
| WO | WO 2008/063625 A2 | 5/2008 |
| WO | WO 2008/064018 A1 | 5/2008 |
| WO | WO 2007/121453 A3 | 7/2008 |
| WO | WO 2007/135380 A3 | 7/2008 |
| WO | WO 2008/063625 A3 | 7/2008 |
| WO | WO 2008/079028 A1 | 7/2008 |
| WO | WO 2008/082487 A2 | 7/2008 |
| WO | WO 2008/083070 A1 | 7/2008 |
| WO | WO 2008/094737 A2 | 8/2008 |
| WO | WO 2007/121924 A3 | 9/2008 |
| WO | WO 2008/112715 A2 | 9/2008 |
| WO | WO 2007/114926 A3 | 10/2008 |
| WO | WO 2008/118454 A2 | 10/2008 |
| WO | WO 2008/118455 A1 | 10/2008 |
| WO | WO 2008/118468 A1 | 10/2008 |
| WO | WO 2008/125014 A1 | 10/2008 |
| WO | WO 2008/125207 A1 | 10/2008 |
| WO | WO 2008/127226 A2 | 10/2008 |
| WO | WO 2007/126841 A3 | 11/2008 |
| WO | WO 2008/112715 A3 | 11/2008 |
| WO | WO 2008/118454 A3 | 11/2008 |
| WO | WO 2008/136457 A1 | 11/2008 |
| WO | WO 2007/124405 A3 | 12/2008 |
| WO | WO 2008/082487 A3 | 12/2008 |
| WO | WO 2008/127226 A3 | 12/2008 |
| WO | WO 2008 152394 | 12/2008 |
| WO | WO 2009/000412 A1 | 12/2008 |
| WO | WO 2009/004621 A1 | 1/2009 |
| WO | WO 2009/010925 A2 | 1/2009 |
| WO | WO 2009/017822 A2 | 2/2009 |
| WO | WO 2009/021990 A1 | 2/2009 |
| WO | WO 2009/023718 A2 | 2/2009 |
| WO | WO 2008/094737 A3 | 3/2009 |
| WO | WO 2009/017822 A3 | 4/2009 |
| WO | WO 2009/023718 A3 | 4/2009 |
| WO | WO 2009/044707 A1 | 4/2009 |
| WO | WO 2009/050506 A2 | 4/2009 |
| WO | WO 2009/059304 A2 | 5/2009 |
| WO | WO 2009/064802 A2 | 5/2009 |
| WO | WO 2009/010925 A3 | 7/2009 |
| WO | WO 2009/064802 A3 | 7/2009 |
| WO | WO 2009/085945 A1 | 7/2009 |
| WO | WO 2009/088986 A1 | 7/2009 |
| WO | WO 2009/088990 A1 | 7/2009 |
| WO | WO 2009/059304 A3 | 8/2009 |
| WO | WO 2009 097446 | 8/2009 |
| WO | WO 2009 097490 A1 | 8/2009 |
| WO | WO 2009/100406 A2 | 8/2009 |
| WO | WO 2007/079164 A3 | 9/2009 |
| WO | WO 2009/114874 A2 | 9/2009 |
| WO | WO 2009/117157 A1 | 9/2009 |
| WO | WO 2009/050506 A3 | 11/2009 |
| WO | WO 2009/100406 A3 | 11/2009 |
| WO | WO 2009/114874 A3 | 12/2009 |
| WO | WO 2010/009207 A1 | 1/2010 |
| WO | WO 2010/019210 A2 | 2/2010 |
| WO | WO 2010/036380 A1 | 4/2010 |
| WO | WO 2010/039534 A2 | 4/2010 |
| WO | WO 2010 045542 A2 | 4/2010 |
| WO | WO 2010/019210 A3 | 5/2010 |
| WO | WO 2010/051043 A1 | 5/2010 |
| WO | WO 2010/039534 A3 | 8/2010 |
| WO | WO 2010/088050 A2 | 8/2010 |
| WO | WO 2010/099139 A2 | 9/2010 |
| WO | WO 2010/099139 A3 | 10/2010 |
| WO | WO 2010/118367 A2 | 10/2010 |
| WO | WO 2010/088050 A3 | 11/2010 |
| WO | WO 2010/129816 A2 | 11/2010 |
| WO | WO 2010/118367 A3 | 3/2011 |
| WO | WO 2011 025889 A1 | 3/2011 |

OTHER PUBLICATIONS

U.S. Appl. No. 13/112,611, filed May 20, 2011, Ren et al.
U.S. Appl. No. 13/289,540, filed Nov. 4, 2011, Ren et al.
"Report of the Expert Committee on the Diagnosis and Classification of Diabetes Mellitus", Diabetes Care (1992) 2(Suppl 1):S5-S19.
Abdel-Mohsen. Synthesis, Reactions and Antimicrobial Activity of 2-Amino-4-(8-quinolinol-5-yl)-1-(p-tolyl)-pyrrole-3-carbonitrile. Bull. Korean Chem. Soc. 2005;26(5):719-728.
Ames et al., "Heterocyclic Synthesis from o-Halogen-acids. Part II. Thienopyridinones and Thienopyranones from 3- bromothiophene -2- and 4-Bromothiophene-3-Carboxylic Acids", Journal of the Chemical Society, Perkin Transactions 1, Jan., 14:1390-1395 (1975).
Andrews, R.C., et al. "Effects of the 11β-Hydroxysteroid Dehydrogenase Inhibitor Carbenoxolone on Insulin Sensitivity in Men with Type 2 Diabetes", J. Clin. Endocrinol. Metab. (2003) 88(1):285-291.

(56) References Cited

OTHER PUBLICATIONS

Apsel, et al. Targeted polypharmacology: discovery of dual inhibitors of tyrosine and phosphoinositide kinases. Nat Chem Biol. Nov. 2008;4(11):691-9.

Arnold, et al. "Pyrrolo[2,3-d]pyrimidines containing an extended 5-substituent as potent and selective inhibitors of lck I", Bioorg. & Med. Chem. Lett (2000) 10:2167-70.

Banker, G.S., et al. Modern Pharmaceutics, 3ed, Marcel Dekker, New York, 1996, pp. 451-596.

Barf, T. et al. "Arylsulfonamidothiazoles as a New Class of Potential Antidiabetic Drugs. Discovery of Potent and Selective Inhibitors of the 11β-Hydroxysteroid Dehydrogenase Type 1", J. Med. Chem. (2002) 45(18):3813-3815.

Barnes, P.J., et al. "Efficacy and Safety of Inhaled Corticosteroids in Asthma", Am. Rev. Respir. Dis. (1993) 148:S1-26.

Basotest®, "Test Kit for the Quantitative Determination of the Degranulation of Basophilic Granulocytes in Heparinized Human Whole Blood", [www.biocarta.com/TDS/10-0500.pdf], Retreived from the Internet Nov. 29, 2011.

Beeram, et al. Akt-induced endocrine therapy resistance is reversed by inhibition of mTOR signaling. Ann Oncol. Aug. 2007;18(8):1323-8.

Bell, G., et al. "Glucokinase Mutations Insulin Secretion, and Diabetes Mellitus", Annu. Rev. Physiol., (1996) 58:171-186.

Bhat, et al. Pyrazolopyrimidine nucleosides. 12. Synthesis and biological activity of certain pyrazolo[3,4-d]pyrimidine nucleosides related to adenosine. J Med Chem. Oct. 1981;24(10):1165-72.

Bishop, A.C. et al. "Generation of monospecific nanomolar tyrosine kinase inhibitors via a chemical genetic approach", Journal of the American Chemical Society, American Chemical Society, Washington, DC, US, vol. 121, No. 4, 1999, pp. 627-631.

Bohren, K.M., et al. "Expression, Crystallization and Preliminary Crystallographic Analysis of Human Carbonyl Reductase", J. Mol. Biol. (1994) 224:659-664.

Cámpora, et al. Binuclear complexes of nickel bridged by hydrocarbon ligands. Isocyanide insertion chemistry and amide formation by intramolecular coupling of acyl and imidoyl functionalities. Organometallics. Jan. 1992;11(1):11-13.

Cámpora, et al. Isocyanide insertion chemistry. Synthesis and structural characterization of bridging imidoyl complexes of nickel and amide formation by intramolecular coupling of acyl and imidoyl functionalities. Organometallics. Oct. 1993;12(10):4025-31.

Chaisuparat, et al. Dual Inhibition of PI3K(alpha) and mTOR as an Alternative Treatment for Kaposi's Sarcoma. Cancer Research. 2008;68:8361.

Chappelow, et al. Neovascular Age-Related Macular Degeneration: Potential Therapies. Drugs. 2008;68(8):1029-1036.

Cox, B., et al. "Human Colorectal Cancer Cells Efficiently Conjugate the Cyclopentenone Prostaglandin, Prostaglandin J2 to Glutathione", Biochim. Biophys. Acta (2002) 1584:37-45.

Davis, et al. The Preparation of Substituted 1(2H)-Isoquinolinones from Dilithiated 2-Methyl-N-arylbenzamides, 2-Methyl-N-(arylmethyl)-benzamides, or 2-Methylbenzoic Acid, 2,2-Dimethylhydrazide. Synthetic Communications. Sep. 1997;27(17):2961-9.

Diederich, S., et al. "In the Search for Specific Inhibitors of Human 11β-Hydroxysteroid-Dehydrogenases (11β-HSDs): Chenodeoxycholic Acid Selectively Inhibits 11β-HSD-I", Eur. J. Endocrinol. (2000) 142:200-207.

Dijksman, et al. 271. 1 : 2-Dihydro-2-thianaphthalene derivatives. Part I. Preparation and reactions of 1 : 2-dihydro-1-keto-2-thianaphthalenes. J. Chem. Soc. 1951:1213-18.

Ding, S., et al. "A Combinatorial Scaffold Approach Toward Kinase-Directed Heterocycle Libraries", J. Am. Chem. Soc. (2002) 124(8):1594-1596.

Ding, S., et al. "A Concise and Traceless. Linker Strategy Toward Combinatorial Libraries of 2,6,9-Substituted Purines", J. Org. Chem. (2001) 66:8273-8276.

Ding, S., et al. "Resin-Capture and Release Strategy Toward Combinatorial Libraries of 2,6,9-Substituted Purines", J. Comb. Chem.(2002) 4:183-186.

Donati. Emerging Therapies for Neovascular Age-Related Macular Degeneration: State of the Art. Ophthalmologica. 2007;221:366-377.

European Examination Report dated Sep. 14, 2011 for EP Application No. 07873406.8, 4 pages.

European extended search report and search opinion dated Jan. 31, 2012 for EP Application No. 09795147.9.

European search report and search opinion dated Oct. 26, 2011 for Application No. 9700424.6.

European search report dated Feb. 4, 2011 for EP Application No. 05857011.0.

European search report dated Feb. 24, 2010 for EP Application No. 07754845.1.

European Search Report dated Mar. 1, 2010 for EP Application No. 07873406.8.

Examination report dated Oct. 27, 2010 for GB Application No. GB0819947.3.

Extended European Search Report from corresponding European Application No. 09700784.3 dated Oct. 28, 2011.

Fajans, S., et al."Maturity Onset Diabetes of the Young (MODY)", Diabet. Med. (1996) 13:S90-S95.

Fan, et al. A dual phosphoinositide-3-kinase alpha/mTOR inhibitor cooperates with blockade of epidermal growth factor receptor in PTEN-mutant glioma. Cancer Res. Sep. 1, 2007;67(17):7960-5.

Farag, et al. Synthesis and reactivity of 2-(benzothiazol-2-yl)-1-bromo-1,2-ethanedione-l-arylhydrazones. Heteroatom Chemistry. 1997; 8(1):45-50.

Feinstein, M.B., et al. "Regulation of the Action of Hydrocotisone in Airway Epithelial Cells by 11β-Hydroxysteroid Dehydrogenase", Am. J. Respir. Cell. Mol. Biol. (1999) 21:403-408.

Feldman, et al. Active-site inhibitors of mTOR target rapamycin-resistant outputs of mTORC1 and mTORC2. PLoS Biol. Feb. 10, 2009;7(2):371-383.

Fingl, E., et al. "General Principles", The Pharmacological Basis of Therapeutics, Fifth Edition (1975), Ch. 1, 1-46.

Forrest, G.L., et al. "Carbonyl Reductase", Chem. Biol. Interact. (2000) 129:21-40.

Forrest, G.L., et al. "Induction of a Human Carbonyl Reductase Gene Located on Chromosome 21", Biochim. Biophys. Acta. (1990) 1048:149-155.

Franzen, R. "The Suzuki, the Heck, and the Stille reaction—three versative methods for the introduction of new C—C bonds on solid support", Can J . Chem. (2000) 78:957-962.

Funder, J.W., et al. "Mineralocorticoid Action: Target Tissue Specificity Is Enzyme, Not Receptor, Mediated", Science (1998) 242:583-585.

Garber, M.E., et al. "Diversity of Gene Expression in Adenocarcinoma of the Lung", Proc. Nat. Acad. Sci. USA (2001) 98(24):13784-13789.

Gonzalez, B., et al. "Protection against Daunorubicin Cytotoxicity by Expression of a Cloned Human Carbonyl Reductase cDNA in K562 Leukemia Cells", Cancer Res. (1995) 55:4646-4650.

Graupera, et al. Angiogenesis selectively requires the p110 isoform of PI3K to control endothelial cell migration. Nature. 2008;453:662-666.

Haase, A.,et al. "Detection of Viral Nucleic Acids by in Situ Hybridization", Methods in Virology (1984) VII:189-226.

Hanefeld, U., et al. "One-pot Synthesis of Tetrasubstituted Pyrazoles Proof of Regiochemistry", J. Chem. Soc. Perkin Trans. (1996) 1:1545-1552.

Hellwinkel, et al. Heterocyclensynthesen mit MF/Al2O3-Baserisystemen: 2-Arylbenzofurane and 2,3-Diarylisochinolin-1(2H)-one. Synthesis. 1995;1995(9):1135-41.

International Preliminary Report on Patentability and Written Opinion dated Apr. 19, 2011 for International Application No. PCT/US2009/060985, 6 pages.

International Preliminary Report on Patentability and Written Opinion dated Jan. 1, 2011 for International Application No. PCT/US2009/049969, 7 pages.

(56) References Cited

OTHER PUBLICATIONS

International Preliminary Report on Patentability and Written Opinion dated May 22, 2007 for International Application No. PCT/US2005/042524, 12 pages.
International Preliminary Report on Patentability and Written Opinion dated Nov. 4, 2008 for International Application No. PCT/US2007/008355, 7 pages.
International Preliminary Report on Patentability and Written Opinion dated Oct. 8, 2008 for International Application No. PCT/US2007/008395, 6 pages.
International Preliminary Report on Patentability from International Application No. PCT/US2009/000042 issued Jul. 6, 2010.
International search report and written opinion dated Jan. 15, 2010 for PCT/US2009/064717.
International search report and written opinion dated Jul. 22, 2005 for PCT/US2004/019782.
International search report and written opinion dated Aug. 22, 2011 for PCT Application No. US11/37742.
International search report and written opinion dated Aug. 22, 2011 for PCT/US2011/037412.
International search report and written opinion dated Nov. 16, 2010 for PCT Application No. US10/45816.
International search report and written opinion dated Nov. 20, 2009 for PCT/US2009/005380.
International search report and written opinion dated Dec. 11, 2008 for PCT Application No. US08/78990.
International search report and written opinion dated Mar. 15, 2010 for PCT Application No. US2009/049969.
International search report dated Feb. 17, 2010 for PCT Application No. US2009/049983.
International search report dated Apr. 5, 2006 for PCT/FR2005/051073.
International search report dated Aug. 27, 2008 for PCT/US2007/008395.
International search report dated Sep. 25, 2008 for PCT/US2007/008355.
International search report dated Jan. 11, 2010 for PCT Application No. US2009/05959.
International search report dated Jan. 12, 2010 for PCT Application No. US2009/05958.
International search report dated Oct. 2, 2006 for PCT/US2005/042524.
International search report dated Nov. 2, 2010 for PCT Application No. US10/02020.
International search report dated Dec. 24, 2009 for PCT Application No. US09/37313.
International search report dated Mar. 11, 2009 for PCT Application No. US2009/00038.
International search report dated Mar. 23, 2009 for PCT Application No. US2009/00042.
International search report dated Aug. 13, 2010 for PCT Applilcation No. US09/37324.
International Search Report. dated Jun. 28, 2010 for International Application No. PCT/US2009/060985, 5 pages.
Ishiyama, T., et al. "A Stoichiometric Aromatic C—H Borylation Catalyzed by Iridium(I)/2,2'-Bipyridine Complexes at Room Temperature", Angew. Chem. Int. Ed. (2002) 41(16):3056-3058.
Ishiyama, T., et al. "Mild Iridium-Catalyzed Borylation of Arenes. High Turnover Numbers, Room Temperature Reactions, and Isolation of a Potential Intermediate", J. Am. Chem. Soc. (2002) 124(3):390-391.
Kajita, et al. Nickel-catalyzed decarbonylative addition of phthalimides to alkynes. J Am Chem Soc. May 14, 2008;130(19):6058-9.
Kallberg, et al. Short-Chain Dehydrogenase/Reductase (SDR) Relationships: a Large Family with Eight Clusters Common to Human, Animal, and Plant Genomes. Protein Sci. (2002) 11:636-641.
Kallberg, et al. Short-Chain Dehydrogenases/Reductases (SDRs). Eur. J. Biochem. (2002) 269:4409-4417.

Kim, et al. Activation and function of the mTORC1 pathway in mast cells. J Immunol. Apr. 1, 2008;180(7):4586-95.
Knight, et al. "A Pharmacological Map of the PI3-K Family Defines a Role for p110α in Insulin Signaling", Cell (2006) 125:733-747.
Koch, et al. N-{4-[3-(4-Fluorophenyl)pyrido[2,3-b]-pyrazin-2-yl]-2-pyridyl}isopropylamine. Acta Crystallogr Sect E Struct Rep Online. Oct. 1, 2009; 65(Pt 10): o2557. Published online Sep. 26, 2009. doi: 10.1107/S1600536809038173.
Kost et al., "Recyclization of 3-Alkyl- and 1,3-Dialkylisoquinolinium Salts to Naphthylamines", Chemistry of Heterocyclic Compounds, Jan., 16(9):965-970 (1981).
Kraybill, B.C. et al. "Inhibitor scaffolds as new allele specific kinase substrates", Journal of the American Chemical Society, American Chemical Society, Washington, DC, US, vol. 124, No. 41, Oct. 16, 2002, pp. 12118-12128.
Kreutzberger, et al. 5-Substituierte 4-Aminopyrimidine durch Aminomethinylierung von Acetonitrilen. Liebigs Ann. Chem. 1977:537-544.
Kumar et al., "Keten Dithioacetals. Part II. Reaction of 3-Cyano-4-Methylthio-2(1H)-pyridones with Hydazine and Guanidine: Synthesis of Novel Substituted and Fused Pyrazolo[4,3-c]pyridone and Pyrido[4,3-d]pyrimidine Derivatives", Journal of the Chemical Society, Perkin Transactions 1, Chemical Society, Letchworth, Jan., 8:857-862 (1978).
Kundu, et al. Palladium-Catalysed Heteroannulation with Terminal Alkynes: a Highly Regio- and Stereoselective Synthesis of (Z)-3-Aryl(alkyl)idene Isoindolin-1-ones1. Tetrahedron. Jun. 30, 2000;56(27):4777-92.
Kwok, B.H., et al. "The Anti-Inflammatory Natural Product Parthenolide from the Medicinal Herb Feverfew Directly Binds to and Inhibits IkB Kinase", Chem. Biol. (2001) 8:759-766.
Lee, et al. All roads lead to mTOR: integrating inflammation and tumor angiogenesis.. Cell Cycle. 2007;6(24):3011-3014.
Majumder, et al. mTOR inhibition reverses Akt-dependent prostate intraepithelial neoplasia through regulation of apoptotic and HIF-1-dependent pathways. Nature Medicine. 2004;10:594-601.
Mayer, T.U., et al. "Small Molecule Inhibitor of Mitotic Spindle Bipolarity Identified in a Pheontype-Based Screen", Science (1999) 286:971-974.
Mellinghoff, et al. TORward AKTually useful mouse models. Nature Medicine. 2004;10:579-580.
Miyaura, N., et al., "Palladium-Catalyzed Cross-Coupling Reactions of Organoboron Compounds," Chem. Rev. (1995) 95(7):2457-2483.
Modi, et at. Isoquinolones: Part IV—Synthesis of 3-Methyl, 3-Formyl & Other 3-Substituted N-Arylisoquinolones, Indian J. Chem. 1979; 18B:304-306.
Moon, H.S., et al. "A Novel Microtubule Destabilizing Entity from Orthogonal Synthesis of Triazine Library and Zebrafish Embryo Screening", J. Am. Chem. Soc. (2002) 124:11608-11609.
Nakanishi, M., et al. "Cloning and Sequence Analysis of a cDNA Encoding Tetrameric Carbonyl Reductase of Pig Lung", Biochem. Biophys. Acta (1993) 194(3):1311-1316.
Nemazanyi, et al. 3-Amino-4-aryl-1(2H)-isoquinolones. Chemistry of Heterocyclic Compounds. Mar. 1991;27(3):307-8.
Niswender, C.M., et al. "Protein Engineering of Protein Kinase A Catalytic Subunits Results in the Acquisition of Novel Inhibitor Sensitivity", The Journal of Biological Chemistry (2002) 277(32):28916-28922.
Nobel, C.S.I., et al. "Purification of Full-Length Recombinant Human and Rat Type 1 11β-hydroxysteroid Dehydrogenases with Retained Oxidoreductase Activities", Protein Expr. Purif. (2002) 26:349-356.
Oda, et al. PIK3CA Cooperates with Other Phosphatidylinositol 3'-Kinase Pathway Mutations to Effect Oncogenic Transformation. Cancer Research. 2008;68:8127.
Oppermann, U.C., et al. "Forms and Functions of Human SDR Enzymes", Chem. Biol. Interact. (2001) 130-132(1-3):699-705.
Ozaki, et al. Studies on 4 (1H)-Quinazolinones. IV. Convenient Syntheses of 12-Methyl-6H-isoquino [2,1-a] quinazolin-6-one and 6-Methyl-13H-quinazolino [3,4-a] quinazolin-13-one. Chem. Pharm. Bull. Jun. 25, 1984;32(6):2160-4.

(56) References Cited

OTHER PUBLICATIONS

Ozol, et al. Autoxidative transformations of 2-substituted 3-alkyl-4-hydroxy-1-oxo-1, 2-dihydroisoquinolines. Chemistry of Heterocyclic Compounds. Jun. 1978;14(6):644-8.
Patel, et al. Immunopathological aspects of age-related macular degeneration. Seminars in Immunopathology. 2008;30(2):97-110.
Persson, C.G. "Glucocorticoids for Asthma—Early Contributions", Pulm. Pharmacol. (1989) 2:163-166.
Petrie, et al. A novel biotinylated adenylate analogue derived from pyrazolo[3,4-d]pyrimidine for labeling DNA probes. Bioconjug Chem. Nov.-Dec. 1991;2(6):441-6.
Pudlo, J.S., et al. "Synthesis, Antiproliferative, and Antiviral Activity of Certain 4-Substituted and 4,5 Disubstituted 7-[1,3-Dihydroxy-2-propoxy)methyl]pyrrolo[2,3-d]pyrimidines", J. Med. Chem. (1990) 33:1984-1992.
Robertson, R.P. "Eicosandoids and Human Disease", Harrison's Principles of Internal Medicine, Isselbacher K.J., et al. (eds.), McGraw-Hill, New York City (1994) 1:431-435.
Romero, D.G., et al. "Cloning and Expression of the Bovine 11β—hydroxysteroid Dehydrogenase Type-2", J. Steroid Biochm. Mol. Biol. (2000) 72:231-237.
Singer, R.H., et al. "Optimization of in situ Hybridization Using Isotopic and Non-Isotopic Detection Methods", Biotechniques (1986) 4(3):230-250.
Soldan, M., et al. "Induction of Daunorubicin Carbonyl Reducing Enzymes by Daunorubicin in Sensitive and Resistant Pancreas Carcinoma Cells", Biochem. Pharmacol. (1996) 51:117-123.
Stanoeva et al. Homophthalic anhydrides and their application to the synthesis of heterocyclic compounds (review). Chemistry of Heterocyclic Compounds. Dec. 1984;20(12);1305-15.
Supplementary European Examination Report dated Sep. 20, 2011 for EP Application No. 07754845.1, 4 pages.
Supplementary European Search Report dated Feb. 24, 2010 for EP Application No. 07754845.1, 4 pages.
Takeuchi, et al. Synergistic augmentation of rapamycin-induced autophagy in malignant glioma cells by phosphatidylinositol 3-kinase/protein kinase B inhibitors. Cancer Res. Apr. 15, 2005;65(8):3336-46.
Tanaka, M., et al. "An Unbiased Cell Morphology-Based Screen for New, Biologically Active Small Molecules", PLoS Biology (2005) 3(5):0764-0776.
Ugarkar, B.G., et al. "Adenosine Kinase Inhibitors. 2. Synthesis, Enzyme Inhibition, and Antiseizure Activity of Diaryltubeicidin Analogues", J. Med. Chem. (2000) 43:2894-2905.
Vasilevsky et al., "Study of the Heterocyclization of vic-Substituted Hydrazides of Acetylenylpyrazolecarboxylic Acids into N-Amino Pyrazolopyridinones", Journal of Heterocyclic Chemistry, Nov., 39(6):1229-1233 (2002).
Vasilevsky et al., "Unexpected results in the heterocyclization of 5-acetylenylpyrazole-4-carboxylic acid hydrazides under the influence of CuCI: formatin of a diazepinone and dehydrodimerization into the corresponding bis(pyrazolo [4,3-d] [1,2] diazepinone)", Tetrahedron Letters, Jan., 46(26): 4457- 4459 (2005).
White, P.C., et al. "11β—Hydroxysteroid Dehydrogenase and the Syndrome of Apparent Mineralocorticoid Excess", Endocr. Rev. (1997) 18(1):135-156.
Widler, L., et al. "7-Alkyl- and 7-Cycloalkyl-5-aryl-pyrrolo[2,3-d]pyrimidines—Potent Inhibitors of the Tyrosine Kinase c-Src," Bioorganic & Medicinal Chemistry Letters (2001) 11(6):849-852.
Wolff, M. E. Burger's Medicinal Chemistry, 5ed, Part 1, John Wiley & Sons, 1995, pp. 975-977.
Wu, et al. One-pot two-step microwave-assisted reaction in constructing 4,5-disubstituted pyrazolopyrimidines. Org Lett. Oct. 2, 2003;5(20):3587-90.
Yaguchi, et al. Antitumor activity of ZSTK474, a new phosphatidylinositol 3-kinase inhibitor. J Natl Cancer Inst. Apr. 19, 2006;98(8):545-56.
Yaguchi, et al. Antitumor activity of ZSTK474, a new phosphatidylinositol 3-kinase inhibitor. J. Natl. Cancer. Inst. 2006; 98(8): 545-556. Abstract only.
U.S. Appl. No. 14/253,782, Intellikine LLC.
U.S. Appl. No. 14/640,773, Intellikine LLC.
Berenbau M. The expected effect of a combination of agents: the general solution. J Theor Biol. Jun. 7, 1985;114(3):413-31.
Berndt et al. The p11delta crystal structure uncovers mechanism for selectivity and potency of novel PI3K inhibitors. Nat. Chem. Biol 6(2), pp. 1-17 [pp. 117-124], Feb. 2010., p. 2-p. 8. http:/www.ncbi.nlm.nih.gov/pmc/articles/PMC2880452/pd/ukmss-28219.pdf.
Bishop, Anthony C. et al., "Design of allele-specific inhibitors to probe protein kinase signalling", Current Biology 8:257-266, 1998.
Blethrow, Justin et al., "Design and Use of Analog-Sensitive Protein Kinases", Current Protocols in Molecular Biology 18.11.1-18.11.19, 2004.
Buzko, et al. Modified AutoDock for accurate docking of protein kinase inhibitors. J Comput Aided Mol Des. Feb. 2002;16(2)113-27.
Chou, et al. Quantitative analysis of dose-effect relationships: the combined effects of multiple drugs or enzyme inhibitors. Adv Enzyme Regul. 1984;22:27-55.
Donahue, et al. Measuring phosphorylated Akt and other phosphoinositide 3-kinase-regulated phosphoproteins in primary lymphocytes. Methods Enzymol. 2007;434:131-54.
Edgar, et al. Isoform-specific phosphoinositide 3-kinase inhibitors exert distinct effects in solid tumors. Cancer Res. Feb. 1, 2010;70(3):1164-72. doi: 10.1158/0008-5472.CAN-09-2525. Epub Jan. 26, 2010.
Gaestel, et al. Protein kinases as small molecule inhibitor targets in inflammation. Curr Med Chem. 2007;14(21):2214-34.
Peterson, et al. Nonlinear blending: a useful general concept for the assessment of combination drug synergy. J Recept Signal Transduct Res. 2007;27(2-3):125-46.
Pinedo, et al. Translational research: the role of VEGF in tumor angiogenesis. The Oncologist. 2000; 5(suppl 1):1-2.
West, et al. Activation of the PI3K/Akt pathway and chemotherapeutic resistance. Drug Resist Updat. Dec. 2002;5(6):234-48.

Figure 6
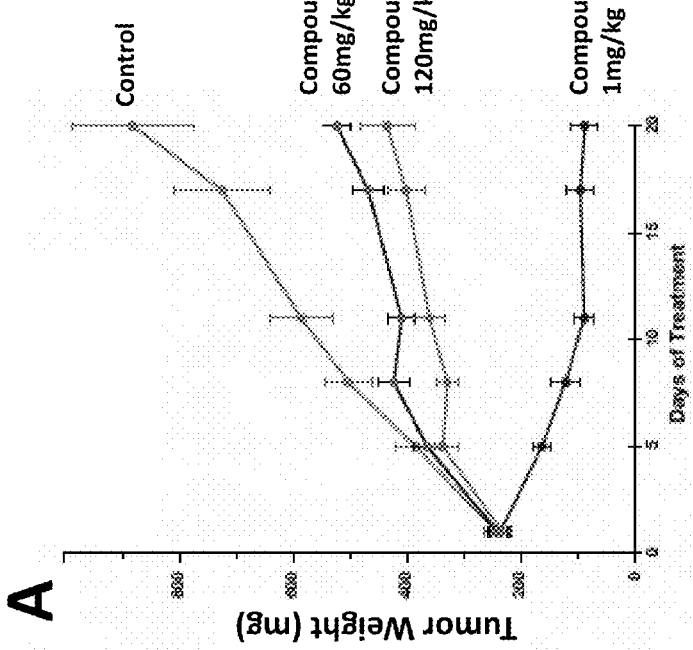
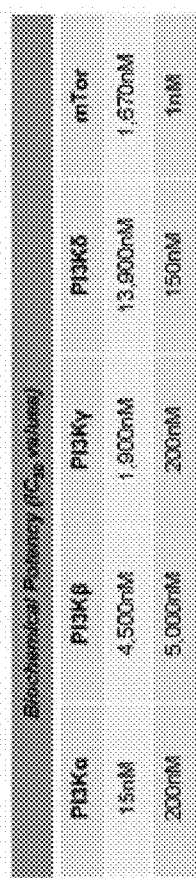

Figure 13

| Cell Line | Genetic Background | Compound A |
|---|---|---|
| BT20 | PI3KCA (H1047R) PTEN wt, ER, PR, Her2 | 2250.5 |
| SK-Br-3 | Her2 amp PI3KCA/PTEN wt | 1950 |
| MCF-7 | PI3KCA (E545K) ER+, PR+ | 2397.5 |
| MDA-MB-361 | PI3KCA (E545K) Her2 amp, ER+, PR- | 1918 |
| MDA-MB-453 | PI3KCA (H1047R) Her2 amp, ER+, PR+ | 3860 |
| T47D | PI3KCA (H1047R) ER+, PR+, Her2+ | 1190 |
| AN3-CA | PTEN null FGFR3 | 8867 |
| PC-3 | PTEN null | >10000 |
| SW620 | KRAS (G12V) | >10000 |
| MDA-MB-468 | PTEN null EGFR amp ER-, PR-, Her2- | >10000 |
| Hec-1A | PI3KCA (G1049R) KRAS (G12D) | 5867 |
| HCT-116 | PI3KCA (H1047R) KRAS (G12D) | 4750 |

COMBINATION OF MTOR INHIBITORS AND PI3-KINASE INHIBITORS, AND USES THEREOF

CROSS-REFERENCE

This application claims the benefit of U.S. Provisional Application No. 61/446,016, filed on Feb. 23, 2011, which is hereby incorporated herein by reference in its entirety.

BACKGROUND OF THE INVENTION

Kinase signaling pathways play a central role in numerous biological processes. Defects in various components of signal transduction pathways have been found to account for a vast number of diseases, including numerous forms of cancer, inflammatory disorders, metabolic disorders, vascular and neuronal diseases (Gaestel et al. Current Medicinal Chemistry (2007) 14:2214-2234). In recent years, kinases that are associated with oncogenic signaling pathways have emerged as important drug targets in the treatment of various diseases including many types of cancers.

The mammalian target of rapamycin (mTOR), also known as mechanistic target of rapamycin, is a serine/threonine protein kinase that regulates cell growth, translational control, angiogenesis and/or cell survival. mTOR is encoded by the FK506 binding protein 12-rapamycin associated protein 1 (FRAP1) gene. mTOR is the catalytic subunit of two complexes, mTORC1 and mTORC2. mTORC1 is composed of mTOR, regulatory associated protein of mTOR (Raptor), mammalian LST8/G-protein β-subunit like protein (mLST8/GβL), PRAS40, and DEPTOR. mTOR Complex 2 (mTORC2) is composed of mTOR, rapamycin-insensitive companion of mTOR (Rictor), GβL, and mammalian stress-activated protein kinase interacting protein 1 (mSIN1).

Apart from their subunits, mTORC1 and mTORC2 are distinguished by their differential sensitivities to rapamycin and its analogs (also known as rapalogs). Rapamycin binds to and allosterically inhibits mTORC1, but mTORC2 is generally rapamycin-insensitive. As a result of this rapamycin-insensitive mTOR signaling mediated by mTORC2, cancer cells treated with rapamycin analogs usually display only partial inhibition of mTOR signaling, which can lead to enhanced survival and resistance to rapamycin treatment.

Another group of kinases involved in cellular functions that are commonly deregulated in diseases is the Phosphatidylinositol 3-kinases (PI 3-kinases or PI3Ks) family of enzymes. These lipid kinases phosphorylate the 3-position hydroxyl group of the inositol ring of phosphatidylinositol (PtdIns), activating signaling cascades associated with such processes as cell growth, proliferation, differentiation, motility, survival and intracellular trafficking. Disruption of these processes involving PI3K leads to many diseases including cancer, allergic contact dermatitis, rheumatoid arthritis, osteoarthritis, inflammatory bowel diseases, chronic obstructive pulmonary disorder, psoriasis, multiple sclerosis, asthma, disorders related to diabetic complications, and inflammatory complications of the cardiovascular system such as acute coronary syndrome.

The PI3K family comprises 15 kinases with distinct substrate specificities, expression patterns, and modes of regulation. The class I PI3Ks (p110α, p110β, p110δ, and p110γ) are typically activated by tyrosine kinases or G-protein coupled receptors to generate phosphatidylinositol-3,4,5-trisphosphate ($PIP_3$), which engages downstream effectors such as those in the Akt/PDK1 pathway, mTOR, the Tec family kinases, and the Rho family GTPases.

The alpha (α) isoform of type I PI3K has been implicated in a variety of human cancers. Angiogenesis has been shown to selectively require the α isoform of PI3K in the control of endothelial cell migration. (Graupera et al, Nature 2008; 453; 662-6). Mutations in the gene coding for PI3K α or mutations which lead to upregulation of PI3K α are believed to occur in many human cancers such as lung, stomach, endometrial, ovarian, bladder, breast, colon, brain and skin cancers. Often, mutations in the gene coding for PI3K α are point mutations clustered within several hotspots in helical and kinase domains, such as E542K, E545K, and H1047R. Many of these mutations have been shown to be oncogenic gain-of-function mutations. While other PI3K isoforms such as PI3K δ or PI3K γ are expressed primarily in hematopoietic cells, PI3K α, along with PI3K β, is expressed constitutively.

The delta (δ) isoform of class I PI3K has been implicated, in particular, in a number of diseases and biological processes. PI3K δ is expressed primarily in hematopoietic cells including leukocytes such as T-cells, dendritic cells, neutrophils, mast cells, B-cells, and macrophages. PI3K δ is integrally involved in mammalian immune system functions such as T-cell function, B-cell activation, mast cell activation, dendritic cell function, and neutrophil activity. Due to its integral role in immune system function, PI3K δ is also involved in a number of diseases related to undesirable immune response such as allergic reactions, inflammatory diseases, inflammation mediated angiogenesis, rheumatoid arthritis, auto-immune diseases such as lupus, asthma, emphysema and other respiratory diseases. Other class I PI3K involved in immune system function includes PI3K γ, which plays a role in leukocyte signaling and has been implicated in inflammation, rheumatoid arthritis, and autoimmune diseases such as lupus.

PI3K β has been implicated primarily in various types of cancer including PTEN-negative cancer (Edgar et al. Cancer Research (2010) 70(3): 1164-1172), and HER2-overexpressing cancer such as breast cancer and ovarian cancer.

SUMMARY OF THE INVENTION

Due to the diverse essential functions of mTOR and PI3Ks, drugs that bind to and inhibit a broad range of kinase isoforms and complexes with low specificity can lead to deleterious side effects. For example, excessive inhibition of PI3K β may lead to undesirable effects on metabolic pathways and disruption of insulin signaling. Alternatively, excessive inhibition of PI3K δ and/or PI3K γ may disrupt or reduce immune function. The present disclosure provides an alternative approache that effectively targets disease-related pathways, while limiting undesirable side effects.

Accordingly, the invention provides a method for treating a disease condition associated with PI3-kinase α and/or mTOR in a subject, comprising administering to said subject simultaneously or sequentially a therapeutically effective amount of a combination of a PI3-kinase α inhibitor and an mTOR inhibitor, wherein the PI3-kinase α inhibitor exhibits selective inhibition of PI3-kinase α relative to one or more type I phosphatidylinositol 3-kinases (PI3-kinase) ascertained by an in vitro kinase assay, wherein the one or more type I PI3-kinase is selected from the group consisting of PI3-kinase β, PI3-kinase γ, and PI3-kinase δ. In one aspect, the combination comprises a therapeutic effective amount of a PI3-kinase α inhibitor and a therapeutic effective amount of an mTOR inhibitor. In another aspect, the combination comprises a synergistically effective therapeutic amount of PI3-kinase α inhibitor and an mTOR inhibitor, wherein the PI3-kinase α inhibitor and/or the mTOR inhibitor is present in a sub-therapeutic amount.

In some embodiments, the disease condition associated with PI3-kinase α and/or mTOR can include but are not limited to a neoplastic condition, autoimmune disease, inflammatory disease, fibrotic disease and kidney disease. For example, the neoplastic condition can be NSCLC, head and neck squamous cell carcinoma, pancreatic, breast and ovarian cancers, renal cell carcinoma, prostate cancer, neuroendocrine cancer, endometrial cancers, and other forms of cancer.

The invention further provides a method of inhibiting phosphorylation of both Akt (S473) and Akt (T308) in a cell, comprising contacting a cell with an effective amount of a PI3-kinase α inhibitor and an mTOR inhibitor that selectively inhibits both mTORC1 and mTORC2 activity relative to one or more type I phosphatidylinositol 3-kinases (PI3-kinase) as ascertained by a cell-based assay or an in vitro kinase assay, wherein the PI3-kinase α inhibitor exhibits selective inhibition of PI3-kinase α relative to one or more type I phosphatidylinositol 3-kinases (PI3-kinase) ascertained by an in vitro kinase assay, wherein the one or more type I PI3-kinase is selected from the group consisting of PI3-kinase β, PI3-kinase γ, and PI3-kinase δ. In some embodiments, the PI3-kinase α inhibitor selectively inhibits PI3-kinase α relative to all other type I phosphatidylinositol 3-kinases (PI3-kinase) consisting of PI3-kinase β, PI3-kinase γ, and PI3-kinase δ.

For instance, the PI3-kinase α inhibitor utilized in the subject methods inhibits PI3-kinase α with an IC50 value of about 500 nM or less, 400 nM or less, 300 nM or less, 200 nM or less, 100 nM or less, 10 nM or less, 1 nM or less as ascertained in an in vitro kinase assay. In another instance, the PI3-kinase α inhibitor selectively inhibits PI3-kinase α with an IC50 value that is at least 2, 5, 10, 50, 100, 1000 times less than its IC50 value against one, two, three or all other type I PI3-kinases selected from the group consisting of PI3-kinase β, PI3-kinase γ, and PI3-kinase δ. In some embodiments, the PI3-kinase α inhibitor selectively inhibits PI3-kinase α with an IC50 value that is less than about 200 nM, and said IC50 value is at least 2, 5 or 10 times less than its IC50 value against all other type I PI3-kinases selected from the group consisting of PI3-kinase β, PI3-kinase γ, and PI3-kinase δ.

In some embodiments, the PI3-kinase α inhibitor selectively inhibits PI3-kinase α and/or PI3-kinase β with an IC50 value that is at least 5 times less than its IC50 value against PI3-kinase γ or PI3-kinase δ. In yet other embodiments, the PI3-kinase α inhibitor selectively inhibits PI3-kinase α and/or PI3-kinase β with an IC50 value that is at least 50 times less than its IC50 value against PI3-kinase γ or PI3-kinase δ. In still other embodiments, the PI3-kinase α inhibitor selectively inhibits PI3-kinase α with an IC50 value that is at least 50 times less than its IC50 value against PI3-kinase γ or PI3-kinase δ.

In some embodiments of the methods of the invention, the mTOR inhibitor binds to and directly inhibits both mTORC1 and mTORC2. For example, the mTOR inhibitor inhibits both mTORC1 and mTORC2 with an IC50 value of about 500 nM or less, 400 nM or less, 300 nM or less, 200 nM or less, 100 nM or less, 50 nM or less, 10 nM or less, or 1 nM or less, as ascertained in an in vitro kinase assay. In another embodiment, the mTOR inhibitor inhibits both mTORC1 and mTORC2 with an IC50 value of about 10 nM or less as ascertained in an in vitro kinase assay, and the mTOR inhibitor is substantially inactive against one or more types I PI3-kinases selected from the group consisting of PI3-kinase α, PI3-kinase β, PI3-kinase γ, and PI3-kinase δ. Alternatively, the mTOR inhibitor inhibits both mTORC1 and mTORC2 with an IC50 value of about 100 nM or less as ascertained in an in vitro kinase assay, and the IC50 value is at least 2, 5 or 10 times less than its IC50 value against all other type I PI3-kinases selected from the group consisting of PI3-kinase α, PI3-kinase β, PI3-kinase γ, and PI3-kinase δ.

In some embodiments, the mTor inhibitor inhibits mTORC1 selectively. For example, the mTor inhibitor inhibits mTORC1 with an IC50 value of about 1000 nM or less, 500 nM or less, 100 nM or less, 50 nM or less, 10 nM or less, as ascertained in an in vitro kinase. In some embodiments, the mTor inhibitor is rapamycin or an analogue of rapamycin. In other embodiments, the mTor inhibitor is sirolimus (rapamycin), deforolimus (AP23573, MK-8669), everolimus (RAD-001), temsirolimus (CCI-779), zotarolimus (ABT-578), or biolimus A9 (umirolimus).

In some embodiments, the mTOR inhibitor is a compound of Formula I:

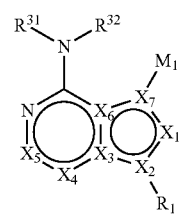

Formula I or a pharmaceutically acceptable salt thereof, wherein:

$X_1$ is N or C-$E^1$, $X_2$ is N or C, $X_3$ is N or C, $X_4$ is C—$R^9$ or N, $X_5$ is N or C-$E^1$, $X_6$ is C or N, and $X_7$ is C or N; and wherein no more than two nitrogen ring atoms are adjacent;

$R_1$ is H, -L-$C_{1-10}$alkyl, -L-$C_{3-8}$cycloalkyl, —$C_{3-8}$cycloalkyl, -L-aryl, -L-heteroaryl, -L-$C_{1-10}$alkylaryl, -L-$C_{1-10}$alkylhetaryl, -L-$C_{1-10}$alkylheterocyclyl, -L-$C_{2-10}$alkenyl, -L-$C_{2-10}$alkynyl, -L-$C_{2-10}$alkenyl-$C_{3-8}$cycloalkyl, -L-$C_{2-10}$alkynyl-$C_{3-8}$cycloalkyl, -L-heteroalkyl, -L-heteroalkylaryl, -L-heteroalkylheteroaryl, -L-heteroalkyl-heterocyclyl, -L-heteroalkyl-$C_{3-8}$cycloalkyl, -L-aralkyl, -L-heteroaralkyl, or -L-heterocyclyl, each of which is unsubstituted or is substituted by one or more independent $R^3$;

L is absent, —C(=O)—, —C(=O)O—, —C(=O)N($R^{31}$)—, —S—, —S(O)—, —S(O)$_2$—, —S(O)$_2$N($R^{31}$)—, or —N($R^{31}$)—;

$E^1$ and $E^2$ are independently —($W^1$)$_j$—$R^4$;

$M_1$ is a 5, 6, 7, 8, 9, or -10 membered ring system, wherein the ring system is monocyclic or bicyclic, substituted with $R_5$ and additionally optionally substituted with one or more —($W^2$)$_k$—$R^2$;

each k is 0 or 1;

j in $E^1$ or j in $E^2$, is independently 0 or 1;

$W^1$ is —O—, —$NR^7$—, —S(O)$_{0-2}$—, —C(O)—, —C(O)N($R^7$)—, —N($R^7$)C(O)—, —N($R^7$)S(O)—, —N($R^7$)S(O)$_2$—, —C(O)O—, —CH($R^7$)N(C(O)O$R^8$)—, —CH($R^7$)N(C(O)$R^8$)—, —CH($R^7$)N(SO$_2$$R^8$)—, —CH($R^7$)N($R^8$)—, —CH($R^7$)C(O)N($R^8$)—, —CH($R^7$)N($R^8$)C(O)—, —CH($R^7$)N($R^8$)S(O)—, or —CH($R^7$)N($R^8$)S(O)$_2$—;

$W^2$ is —O—, —$NR^7$—, —S(O)$_{0-2}$—, —C(O)—, —C(O)N($R^7$)—, —N($R^7$)C(O)—, —N($R^7$)C(O)N($R^8$)—, —N($R^7$)S(O)—, —N($R^7$)S(O)$_2$—, —C(O)O—, —CH($R^7$)N(C(O)O$R^8$)—, —CH($R^7$)N(C(O)$R^8$)—, —CH($R^7$)N(SO$_2$$R^8$)—, —CH($R^7$)N($R^8$)—, —CH($R^7$)C(O)N($R^8$)—, —CH($R^7$)N($R^8$)C(O)—, —CH($R^7$)N($R^8$)S(O)—, or —CH($R^7$)N($R^8$)S(O)$_2$—;

$R^2$ is hydrogen, halogen, —OH, —$R^{31}$, —CF$_3$, —OCF$_3$, —O$R^{31}$, —N$R^{31}R^{32}$, —N$R^{34}R^{35}$, —C(O)$R^{31}$, —CO$_2$$R^{31}$, —C(=O)N$R^{31}R^{32}$, —C(=O)N$R^{34}R^{35}$, —NO$_2$, —CN, —S(O)$_{0-2}$$R^{31}$, —SO$_2$N$R^{31}R^{32}$, —SO$_2$N$R^{34}R^{35}$, —N$R^{31}$C (=O)R$^{32}$, —NR$^{31}$C(=O)OR$^{32}$, —NR$^{31}$C(=O)NR$^{32}$R$^{33}$, —NR$^{31}$S(O)$_{0-2}$R$^{32}$, —C(=S)OR$^{31}$, —C(=O)SR$^{31}$, —NR$^{31}$C(=NR$^{32}$)NR$^{33}$R$^{32}$, —NR$^{31}$C(=NR$^{32}$)OR$^{33}$, —NR$^{31}$C(=NR$^{32}$)SR$^{33}$, —OC(=O)OR$^{33}$, —OC(=O)NR$^{31}$R$^{32}$, —OC(=O)SR$^{31}$, —SC(=O)OR$^{31}$, —P(O)OR$^{31}$OR$^{32}$, —SC(=O)NR$^{31}$R$^{32}$, aryl (e.g. bicyclic aryl, unsubstituted aryl, or substituted monocyclic aryl), hetaryl, C$_{1-10}$alkyl, C$_{3-8}$cycloalkyl, C$_{1-10}$alkyl-C$_{3-8}$cycloalkyl, C$_{3-8}$cycloalkyl-C$_{1-10}$alkyl, C$_{3-8}$cycloalkyl-C$_{2-10}$alkenyl, C$_{3-8}$cycloalkyl-C$_{2-10}$alkynyl, C$_{1-10}$alkyl-C$_{2-10}$alkynyl, C$_{1-10}$alkyl-C$_{2-10}$alkenyl, C$_{1-10}$alkyl-C$_{2-10}$alkynyl, C$_{1-10}$alkylaryl (e.g. C$_{2-10}$alkyl-monocyclic aryl, C$_{1-10}$alkyl-substituted monocyclic aryl, or C$_{1-10}$alkylbicycloaryl), C$_{1-10}$alkyl-hetaryl, C$_{1-10}$alkylheterocyclyl, C$_{2-10}$alkenyl, C$_{2-10}$alkynyl, C$_{2-10}$alkenyl-C$_{1-10}$alkyl, C$_{2-10}$alkynyl-C$_{1-10}$alkyl, C$_{2-10}$alkenylaryl, C$_{2-10}$alkenylhetaryl, C$_{2-10}$alkenylheteroalkyl, C$_{2-10}$alkenylheterocycicyl, C$_{2-10}$alkenyl-C$_{3-8}$cycloalkyl, C$_{2-10}$alkynylaryl, C$_{2-10}$alkynylhetaryl, C$_{2-10}$alkynylheteroalkyl, C$_{2-10}$alkynylheterocylyl, C$_{2-10}$alkynyl-C$_{3-8}$cycloalkenyl, C$_{1-10}$alkoxy C$_{1-10}$alkyl, C$_{1-10}$alkoxy-C$_{2-10}$alkenyl, C$_{1-10}$alkoxy-C$_{2-10}$alkynyl, heterocyclyl, heteroalkyl, heterocyclyl-C$_{1-10}$alkyl, heterocyclyl-C$_{2-10}$alkenyl, heterocyclyl-C$_{2-10}$alkynyl, aryl-C$_{1-10}$alkyl (e.g. monocyclic aryl-C$_{2-10}$alkyl, substituted monocyclic aryl-C$_{1-10}$alkyl, or bicycloaryl-C$_{1-10}$alkyl), aryl-C$_{2-10}$alkenyl, aryl-C$_{2-10}$alkynyl, aryl-heterocyclyl, hetaryl-C$_{1-10}$alkyl, hetaryl-C$_{2-10}$alkenyl, hetaryl-C$_{2-10}$alkynyl, hetaryl-C$_{3-8}$cycloalkyl, hetaryl-heteroalkyl, or hetaryl-heterocyclyl, wherein each of said bicyclic aryl or heteroaryl moiety is unsubstituted, or wherein each of bicyclic aryl, heteroaryl moiety or monocyclic aryl moiety is substituted with one or more independent alkyl, heteroalkyl, alkenyl, alkynyl, cycloalkyl, heterocycloalkyl, aryl, arylalkyl, heteroaryl, heteroarylalkyl, halo, —OH, —R$^{31}$, —CF$_3$, —OCF$_3$, —OR$^{31}$, —NR$^{31}$R$^{32}$, —NR$^{34}$R$^{35}$, —C(O)R$^{31}$, —CO$_2$R$^{31}$, —C(=O)NR$^{31}$R$^{32}$, —C(=O)NR$^{34}$R$^{35}$, —NO$_2$, —CN, —S(O)$_{0-2}$R$^{31}$, —SO$_2$NR$^{31}$R$^{32}$, —SO$_2$NR$^{34}$R$^{35}$, —NR$^{31}$C(=O)R$^{32}$, —NR$^{31}$C(=O)OR$^{32}$, —NR$^{31}$C(=O)NR$^{32}$R$^{33}$, —NR$^{31}$S(O)$_{0-2}$R$^{32}$, —C(=S)OR$^{31}$, —C(=O)SR$^{31}$, —NR$^{31}$C(=NR$^{32}$)NR$^{33}$R$^{32}$, —NR$^{31}$C(=NR$^{32}$)OR$^{33}$, —NR$^{31}$C(=NR$^{32}$)SR$^{33}$, —C(=O)OR$^{33}$, —OC(=O)NR$^{31}$R$^{32}$, —OC(=O)SR$^{31}$, —SC(=O)OR$^{31}$, —P(O)OR$^{31}$OR$^{32}$, or —SC(=O)NR$^{31}$R$^{32}$, and wherein each of said alkyl, cycloalkyl, heterocyclyl, or heteroalkyl moiety is unsubstituted or is substituted with one or more alkyl, heteroalkyl, alkenyl, alkynyl, cycloalkyl, heterocycloalkyl, aryl, arylalkyl, heteroaryl, heteroarylalkyl, halo, —OH, —R$^{31}$, —CF$_3$, —OCF$_3$, —OR$^{31}$, —O-aryl, —NR$^{31}$R$^{32}$, —NR$^{34}$R$^{35}$, —C(O)R$^{31}$, —CO$_2$R$^{31}$, —C(=O)NR$^{34}$R$^{35}$, or —C(=O)NR$^{31}$R$^{32}$;

R$^3$ and R$^4$ are independently hydrogen, halogen, —OH, —R$^{31}$, —CF$_3$, —OCF$_3$, —OR$^{31}$, —NR$^{31}$R$^{32}$, —NR$^{34}$R$^{35}$, —C(O)R$^{31}$, —CO$_2$R$^{31}$, —C(=O)NR$^{31}$R$^{32}$, —C(=O)NR$^{34}$R$^{35}$, —NO$_2$, —CN, —S(O)$_{0-2}$R$^{31}$, —SO$_2$NR$^{31}$R$^{32}$, —SO$_2$NR$^{34}$R$^{35}$, —NR$^{31}$C(=O)R$^{32}$, —NR$^{31}$C(=O)OR$^{32}$, —NR$^{31}$C(=O)NR$^{32}$R$^{33}$, —NR$^{31}$S(O)$_{0-2}$R$^{32}$, —C(=S)OR$^{31}$, —C(=O)SR$^{31}$, —NR$^{31}$C(=NR$^{32}$)NR$^{33}$R$^{32}$, —NR$^{31}$C(=NR$^{32}$)OR$^{33}$, —NR$^{31}$C(=NR$^{32}$)SR$^{33}$, —C(=O)OR$^{33}$, —OC(=O)NR$^{31}$R$^{32}$, —OC(=O)SR$^{31}$, —SC(=O)OR$^{31}$, —P(O)OR$^{31}$OR$^{32}$, —SC(=O)NR$^{31}$R$^{32}$ aryl, hetaryl, C$_{1-4}$alkyl, C$_{1-10}$alkyl, C$_{3-8}$cycloalkyl, C$_{1-10}$alkyl-C$_{3-8}$cycloalkyl, C$_{3-8}$cycloalkyl-C$_{1-10}$alkyl, C$_{3-8}$cycloalkyl-C$_{2-10}$alkenyl, C$_{3-8}$cycloalkyl-C$_{2-10}$alkynyl, C$_{1-10}$alkyl-C$_{2-10}$alkenyl, C$_{1-10}$alkyl-C$_{2-10}$alkynyl, C$_{1-10}$alkylaryl, C$_{1-10}$alkylhetaryl, C$_{1-10}$alkylheterocyclyl, C$_{2-10}$alkenyl, C$_{2-10}$alkynyl, C$_{2-10}$alkenyl-C$_{1-10}$alkyl, C$_{2-10}$alkynyl-C$_{1-10}$alkyl, C$_{2-10}$-alkenylaryl, C$_{2-10}$alkenylhetaryl, C$_{2-10}$alkenylheteroalkyl, C$_{2-10}$alkenylheterocycicyl, C$_{2-10}$alkenyl-C$_{3-8}$cycloalkyl, C$_{2-10}$alkynyl-C$_{3-8}$cycloalkyl, C$_{2-10}$alkynylaryl, C$_{2-10}$alkynylhetaryl, C$_{2-10}$alkynylheteroalkyl, C$_{2-10}$-alkynylheterocyclyl, C$_{2-10}$alkynyl-C$_{3-8}$cycloalkenyl, C$_{1-10}$alkoxy C$_{1-10}$alkyl, C$_{1-10}$alkoxy-C$_{2-10}$alkenyl, C$_{1-10}$alkoxy-C$_{2-10}$alkynyl, heterocyclyl, heterocyclyl-C$_{1-10}$alkyl, heterocyclyl-C$_{2-10}$alkenyl, heterocyclyl-C$_{2-10}$-alkynyl, aryl-C$_{1-10}$alkyl, aryl-C$_{2-10}$alkenyl, aryl-C$_{2-10}$alkynyl, aryl-heterocyclyl, hetaryl-C$_{1-10}$alkyl, hetaryl-C$_{2-10}$alkenyl, hetaryl-C$_{2-10}$alkynyl, hetaryl-C$_{3-8}$cycloalkyl, heteroalkyl, hetaryl-heteroalkyl, or hetaryl-heterocyclyl, wherein each of said aryl or heteroaryl moiety is unsubstituted or is substituted with one or more independent halo, —OH, —R$^{31}$, —CF$_3$, —OCF$_3$, —OR$^{31}$, —NR$^{31}$R$^{32}$, —NR$^{34}$R$^{35}$, —C(O)R$^{31}$, —CO$_2$R$^{31}$, —C(=O)NR$^{31}$R$^{32}$, —C(=O)NR$^{34}$R$^{35}$, —NO$_2$, —CN, —S(O)$_{0-2}$R$^{31}$, —SO$_2$NR$^{31}$R$^{32}$, —SO$_2$NR$^{34}$R$^{35}$, —NR$^{31}$C(=O)R$^{32}$, —NR$^{31}$C(=O)OR$^{32}$, —NR$^{31}$C(=O)NR$^{32}$R$^{33}$, —NR$^{31}$S(O)$_{0-2}$R$^{32}$, —C(=S)OR$^{31}$, —C(=O)SR$^{31}$, —NR$^{31}$C(=NR$^{32}$)NR$^{33}$R$^{32}$, —NR$^{31}$C(=NR$^{32}$)OR$^{33}$, —NR$^{31}$C(=NR$^{32}$)SR$^{33}$, —C(=O)OR$^{33}$, —OC(=O)NR$^{31}$R$^{32}$, —OC(=O)SR$^{31}$, —SC(=O)OR$^{31}$, —P(O)OR$^{31}$OR$^{32}$, or —SC(=O)NR$^{31}$R$^{32}$, and wherein each of said alkyl, cycloalkyl, heterocyclyl, or heteroalkyl moiety is unsubstituted or is substituted with one or more halo, —OH, —R$^{31}$, —CF$_3$, —OCF$_3$, —OR$^{31}$, —O-aryl, —NR$^{31}$R$^{32}$, —NR$^{34}$R$^{35}$, —C(O)R$^{31}$, —CO$_2$R$^{31}$, —C(=O)NR$^{34}$R$^{35}$, or —C(=O)NR$^{31}$R$^{32}$;

R$^5$ is hydrogen, halogen, —OH, —R$^{31}$, —CF$_3$, —OCF$_3$, —OR$^{31}$, —NR$^{31}$R$^{32}$, —NR$^{34}$R$^{35}$, —C(O)R$^{31}$, —CO$_2$R$^{31}$, —C(=O)NR$^{31}$R$^{32}$, —C(=O)NR$^{34}$R$^{35}$, —NO$_2$, —CN, —S(O)$_{0-2}$R$^{31}$, —SO$_2$NR$^{31}$R$^{32}$, —SO$_2$NR$^{34}$R$^{35}$, —NR$^{31}$C(=O)R$^{32}$, —NR$^{31}$C(=O)OR$^{32}$, —NR$^{31}$C(=O)NR$^{32}$R$^{33}$, —NR$^{31}$S(O)$_{0-2}$R$^{32}$, —C(=S)OR$^{31}$, —C(=O)SR$^{31}$, —NR$^{31}$C(=NR$^{32}$)NR$^{33}$R$^{32}$, —NR$^{31}$C(=NR$^{32}$)OR$^{33}$, —NR$^{31}$C(=NR$^{32}$)SR$^{33}$, —OC(=O)OR$^{33}$, —OC(=O)NR$^{31}$R$^{32}$, —OC(=O)SR$^{31}$, —SC(=O)OR$^{31}$, —P(O)OR$^{31}$OR$^{32}$, or —SC(=O)NR$^{31}$R$^{32}$;

each of R$^{31}$, R$^{32}$, and R$^{33}$ is independently H or C$_{1-10}$alkyl, wherein the C$_{1-10}$alkyl is unsubstituted or is substituted with one or more aryl, heteroalkyl, heterocyclyl, or hetaryl group, wherein each of said aryl, heteroalkyl, heterocyclyl, or hetaryl group is unsubstituted or is substituted with one or more halo, —OH, —C$_{1-10}$alkyl, —CF$_3$, —O-aryl, —OCF$_3$, —OC$_{1-10}$alkyl, —NH$_2$, —N(C$_{1-10}$alkyl)(C$_{1-10}$alkyl), —NH(C$_{1-10}$alkyl), —NH(aryl), —NR$^{34}$R$^{35}$, —C(O)(C$_{1-10}$alkyl), —C(O)(C$_{1-10}$alkyl-aryl), —C(O)(aryl), —CO$_2$—C$_{1-10}$alkyl, —CO$_2$—C$_{1-10}$alkylaryl, —CO$_2$-aryl, —C(=O)N(C$_{1-10}$alkyl)(C$_{1-10}$alkyl), —C(=O)NH(C$_{1-10}$alkyl), —C(=O)NR$^{34}$R$^{35}$, —C(=O)NH$_2$, —OCF$_3$, —O(C$_{1-10}$alkyl), —O-aryl, —N(aryl)(C$_{1-10}$alkyl), —NO$_2$, —CN, —S(O)$_{0-2}$C$_{1-10}$alkyl, —S(O)$_{0-2}$C$_{1-10}$alkylaryl, —S(O)$_{0-2}$ aryl, —SO$_2$N(aryl), —SO$_2$N(C$_{1-10}$alkyl)(C$_{1-10}$alkyl), —SO$_2$NH(C$_{1-10}$alkyl) or —SO$_2$NR$^{34}$R$^{35}$;

R$^{34}$ and R$^{35}$ in —NR$^{34}$R$^{35}$, —C(=O)NR$^{34}$R$^{35}$, or —SO$_2$NR$^{34}$R$^{35}$, are taken together with the nitrogen atom to which they are attached to form a 3-10 membered saturated or unsaturated ring; wherein said ring is independently unsubstituted or is substituted by one or more —NR$^{31}$R$^{32}$, hydroxyl, halogen, oxo, aryl, hetaryl, C$_{1-6}$alkyl, or O-aryl, and wherein said 3-10 membered saturated or unsaturated ring independently contains 0, 1, or 2 more heteroatoms in addition to the nitrogen atom;

each of R$^7$ and R$^8$ is independently hydrogen, C$_{1-10}$alkyl, C$_{2-10}$alkenyl, aryl, heteroaryl, heterocyclyl or C$_{3-10}$cycloalkyl, each of which except for hydrogen is unsubstituted or is substituted by one or more independent R$^6$;

$R^6$ is halo, —$OR^{31}$, —SH, —$NH_2$, —$NR^{34}R^{35}$, —$NR^{31}R^{32}$, —$CO_2R^{31}$, —$CO_2$aryl, —$C(=O)NR^{31}R^{32}$, $C(=O)NR^{34}R^{35}$, —$NO_2$, —CN, —$S(O)_{0-2}C_{1-10}$alkyl, —$S(O)_{0-2}$aryl, —$SO_2NR^{34}R^{35}$, —$SO_2NR^{31}R^{32}$, $C_{1-10}$alkyl, $C_{2-10}$alkenyl, $C_{2-10}$alkynyl; aryl-$C_{1-10}$alkyl, aryl-$C_{2-10}$alkenyl, aryl-$C_{2-10}$alkynyl, hetaryl-$C_{1-10}$alkyl, hetaryl-$C_{2-10}$alkenyl, hetaryl-$C_{2-10}$alkynyl, wherein each of said alkyl, alkenyl, alkynyl, aryl, heteroalkyl, heterocyclyl, or hetaryl group is unsubstituted or is substituted with one or more independent halo, cyano, nitro, —$OC_{1-10}$alkyl, $C_{1-10}$alkyl, $C_{2-10}$alkenyl, $C_{2-10}$alkynyl, halo$C_{1-10}$alkyl, halo$C_{2-10}$alkenyl, halo$C_{2-10}$alkynyl, —COOH, —$C(=O)NR^{31}R^{32}$, —$C(=O)NR^{34}R^{35}$, —$SO_2NR^{34}R^{35}$, —$SO_2NR^{31}R^{32}$, —$NR^{31}R^{32}$, or —$NR^{34}R^{35}$; and $R^9$ is H, halo, —$OR^{31}$, —SH, —$NH_2$, —$NR^{34}R^{35}$, —$NR^{31}R^{32}$, —$CO_2R^{31}$, —$CO_2$aryl, $C(=O)NR^{31}R^{32}$, $C(=O)NR^{34}R^{35}$, —$NO_2$, —CN, —$S(O)_{0-2}C_{1-10}$alkyl, —$S(O)_{0-2}$aryl, —$SO_2NR^{34}R^{35}$, —$SO_2NR^{31}R^{32}$, $C_{1-10}$alkyl, $C_{2-10}$-alkenyl, $C_{2-10}$alkynyl; aryl-$C_{1-10}$alkyl, aryl-$C_{2-10}$alkenyl, aryl-$C_{2-10}$alkynyl, hetaryl-$C_{1-10}$alkyl, hetaryl-$C_{2-10}$-alkenyl, hetaryl-$C_{2-10}$alkynyl, wherein each of said alkyl, alkenyl, alkynyl, aryl, heteroalkyl, heterocyclyl, or hetaryl group is unsubstituted or is substituted with one or more independent halo, cyano, nitro, —$OC_{1-10}$alkyl, $C_{1-10}$alkyl, $C_{2-10}$alkenyl, $C_{2-10}$alkynyl, halo$C_{1-10}$alkyl, halo$C_{2-10}$alkenyl, halo$C_{2-10}$alkynyl, —COOH, —$C(=O)NR^{31}R^{32}$, —$C(=O)NR^{34}R^{35}$, —$SO_2NR^{34}R^{35}$, —$SO_2NR^{31}R^{32}$, —$NR^{31}R^{32}$, or —$NR^{34}R^{35}$.

In other embodiments, the PI3-kinase α inhibitor is a compound of formula:

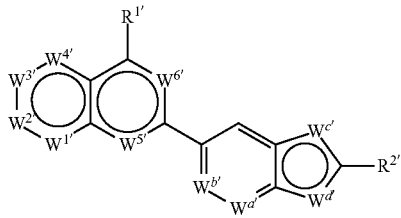

Formula II or its pharmaceutically acceptable salts thereof, wherein:
$W^{1'}$ is N, $NR^{3'}$, or $CR^{3'}$; $W^{2'}$ is N, $NR^{4'}$, $CR^{4'}$, or C=O; $W^{3'}$ is N, $NR^{5'}$ or $CR^{5'}$; $W^{4'}$ is N, wherein no more than two N atoms and no more than two C=O groups are adjacent;
$W^{5'}$ is N;
$W^{6'}$ is N or $CR^{8'}$;
$W^{a'}$ and $W^{b'}$ are independently N or $CR^{9'}$;
one of $W^{c'}$ and $W^{d'}$ is N, and the other is O, $NR^{10'}$, or S;
$R^{1'}$ and $R^{2'}$ are independently hydrogen, alkyl, heteroalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, halo, cyano, hydroxy, nitro, phosphate, urea, carbonate, or NR'R" wherein R' and R" are taken together with nitrogen to form a cyclic moiety;
$R^{3'}$ and $R^{4'}$ are independently hydrogen, alkyl, heteroalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, halo, cyano, hydroxy, nitro, phosphate, urea, carbonate, or NR'R" wherein R' and R" are taken together with nitrogen to form a cyclic moiety;
or $R^{3'}$ and $R^{4'}$ taken together form a cyclic moiety;

$R^{5'}$, $R^{6'}$, $R^{7'}$ and $R^{8'}$ are independently hydrogen, alkyl, heteroalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, halo, cyano, hydroxy, nitro, phosphate, urea, carbonate, or NR'R" wherein R' and R" are taken together with nitrogen to form a cyclic moiety;
$R^{9'}$ is alkyl or halo; and
$R^{10'}$ is hydrogen, alkyl, heteroalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, halo, cyano, hydroxy, nitro, phosphate, urea, carbonate, or NR'R" wherein R' and R" are taken together with nitrogen to form a cyclic moiety.

In still other embodiments, the PI3-kinase α inhibitor is a compound of formula:

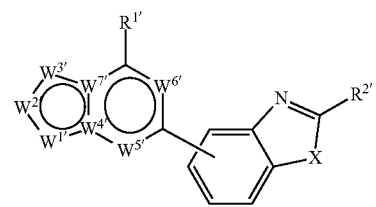

or its pharmaceutically acceptable salts thereof, where:
X is O or S or N;
$W^{1'}$ is S, N, $NR^{3'}$ or $CR^{3'}$, $W^{2'}$ is N or $CR^{4'}$, $W^{3'}$ is S, N or $CR^{5'}$, $W^{4'}$ is N or C, and $W^{7'}$ is N or C, wherein no more than two N atoms and no more than two C=O groups are adjacent;
$W^{5'}$ is N or $CR^{7'}$;
$W^{6'}$ is N or $CR^{8'}$;
$R^{1'}$ and $R^{2'}$ are independently hydrogen, alkyl, heteroalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, halo, cyano, hydroxy, nitro, phosphate, urea, carbonate, or NR'R" wherein R' and R" are taken together with nitrogen to form a cyclic moiety;
$R^{3'}$ and $R^{4'}$ are independently hydrogen, alkyl, heteroalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, halo, cyano, hydroxy, nitro, phosphate, urea, carbonate, or NR'R" wherein R' and R" are taken together with nitrogen to form a cyclic moiety;
or $R^{3'}$ and $R^{4'}$ taken together form a cyclic moiety; and
$R^{5'}$, $R^{7'}$ and $R^{8'}$ are independently hydrogen, alkyl, heteroalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, halo, cyano, hydroxy, nitro, phosphate, urea, carbonate, or NR'R" wherein R' and R" are taken together with nitrogen to form a cyclic moiety.

For any of the methods of the invention, the PI3-kinase α inhibitor and/or the mTOR inhibitor can be administered parenterally, orally, intraperitoneally, intravenously, intraarterially, transdermally, intramuscularly, liposomally, via local delivery by catheter or stent, subcutaneously, intraadiposally, or intrathecally. In some embodiments, the PI3-kinase α inhibitor and/or the mTOR inhibitor are co-administered to the subject in the same formulation. In other embodiments, the PI3-kinase α inhibitor and/or the mTOR inhibitor are co-administered to the subject in different formulations.

The invention also provides a pharmaceutical composition comprising a combination of an amount of PI3-kinase α inhibitor and an amount of mTOR inhibitor, wherein said combination provides a synergistic therapeutic effect in a subject in need thereof. For example, the pharmaceutical composition is formulated in an oral dosage. In some embodiments, at least one of the amounts is administered as a subtherapeutic amount. In other embodiments, the pharmaceutical composition is formulated a tablet or a capsule. For example, the PI3-kinase α inhibitor and the mTOR inhibitor are packaged as separate tablets. In other embodiments, the PI3-kinase α inhibitor and the mTOR inhibitor are formulated as a single oral dosage form.

The invention also provides a method comprising: (a) determining the presence in a subject of a mutation in PI3-kinase α that is associated with a disease condition mediated by PI3-kinase α; and (b) administering to said subject a pharmaceutical composition of the invention. For example, the mutation is in the nucleotide sequence coding for PI3-kinase α. Exemplary mutations can include without limitation, deletion, insertion, translation, which can result in point mutations, frame shifts, and/or translation of the nucleic acid sequence coding for PI3-kinase α. In another example, the mutation is in the amino acid sequence of PI3-kinase α.

In some embodiments of any of the methods of the invention, the subject or cell comprises a mutation in PI3-kinase α which is associated with a disease condition mediated by PI3-kinase α.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 6 shows A) a graph depicting the selectivity of Compound B over Compound A in a PTEN-mutant negative control tumor model, B) a western blot depicting selective inhibition of Akt, S6, and 4EBP phosphorylation by Compound B and not Compound A in PTEN mutant cells, and C) a chart depicting the specificity of Compound A in inhibiting PI3K α over mTOR and other PI3K isoforms, and the specificity of Compound B in inhibiting mTOR over PI3K isoforms.

FIG. 13 is a chart showing that Compound A preferentially inhibits proliferation of tumor cells harboring PI3K α mutations.

DETAILED DESCRIPTION OF THE INVENTION

Figure 1:
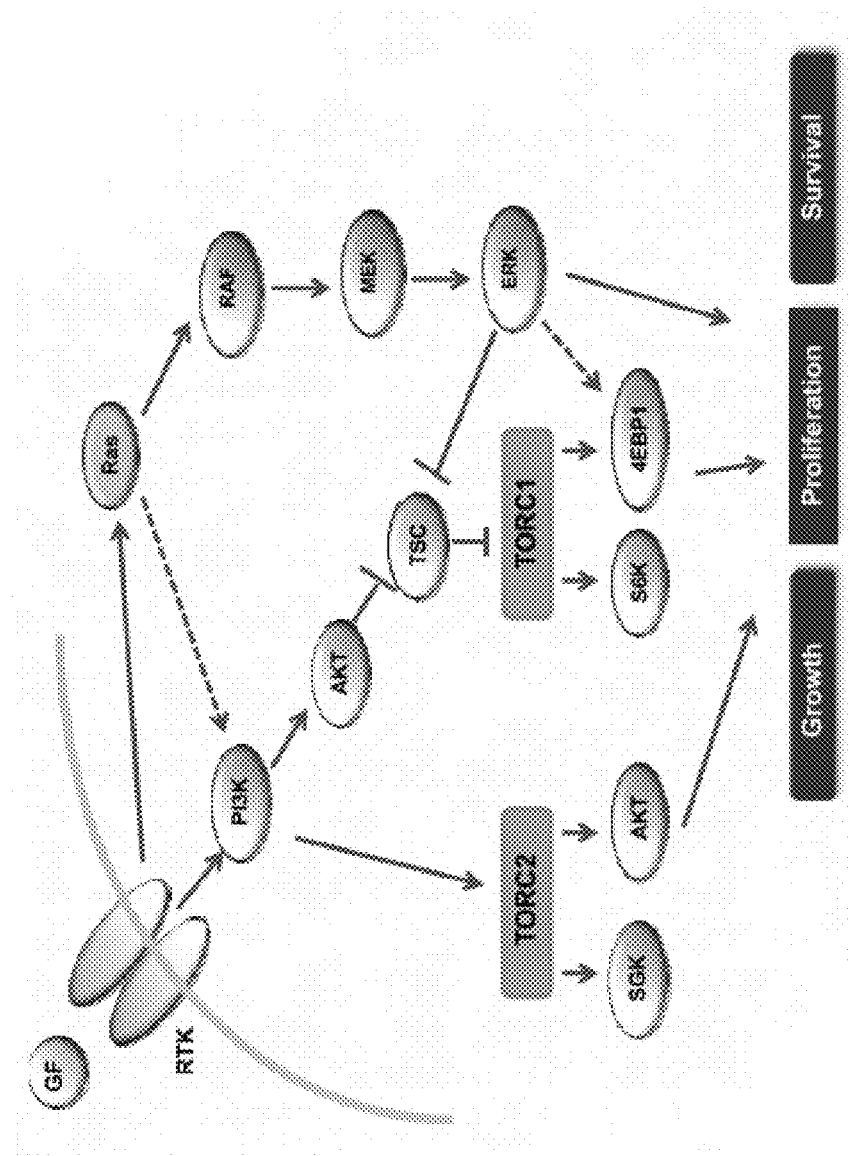
FIG. 1 is a schematic illustration of multiple and distinct signaling pathways that are activated in human cancer.

Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. The present invention is not limited by the illustrated ordering of acts or events, as some acts may occur in different orders and/or concurrently with other acts or events. Furthermore, not all illustrated acts or events are required to implement a methodology in accordance with the present invention.

The terminology used herein is for the purpose of describing particular embodiments only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising".

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

"Treatment", "treating", "palliating" and "ameliorating", as used herein, are used interchangeably. These terms refer to an approach for obtaining beneficial or desired results including but not limited to therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made.

As used herein, the term "neoplastic condition" refers to the presence of cells possessing abnormal growth characteristics, such as uncontrolled proliferation, immortality, metastatic potential, rapid growth and proliferation rate, perturbed oncogenic signaling, and certain characteristic morphological features. This includes the abnormal growth of: (1) tumor cells (tumors) that proliferate by expressing a mutated tyrosine kinase or overexpression of a receptor tyrosine kinase; (2) benign and malignant cells of other proliferative diseases in which aberrant tyrosine kinase activation occurs; (3) any tumors that proliferate by receptor tyrosine kinases; (4) any tumors that proliferate by aberrant serine/threonine kinase activation; and (5) benign and malignant cells of other proliferative diseases in which aberrant serine/threonine kinase activation occurs.

The term "effective amount" or "therapeutically effective amount" refers to that amount of an inhibitor described herein that is sufficient to effect the intended application including but not limited to disease treatment, as defined below. The therapeutically effective amount may vary depending upon the intended application (in vitro or in vivo), or the subject and disease condition being treated, e.g., the weight and age of the subject, the severity of the disease condition, the manner of administration and the like, which can readily be determined by one of ordinary skill in the art. The term also applies to a dose that will induce a particular response in target cells, e.g., reduction of proliferation or downregulation of activity of a target protein. The specific dose will vary depending on the particular compounds chosen, the dosing regimen to be followed, whether it is administered in combination with other compounds, timing of administration, the tissue to which it is administered, and the physical delivery system in which it is carried.

A "sub-therapeutic amount" of an agent or therapy is an amount less than the effective amount for that agent or therapy, but when combined with an effective or sub-therapeutic amount of another agent or therapy can produce a result desired by the physician, due to, for example, synergy in the resulting efficacious effects, or reduced side effects.

A "synergistically effective therapeutic amount" of an agent or therapy is an amount which, when combined with an effective or sub-therapeutic amount of another agent or therapy, produces a greater effect than when either of the two agents are therapies are used alone. In some embodiments, a syngergistically effective therapeutic amount of an agent or therapy produces a greater effect when used in combination than the additive effects of each of the two agents or therapies when used alone.

As used herein, "agent" or "biologically active agent" refers to a biological, pharmaceutical, or chemical compound or other moiety. Non-limiting examples include simple or complex organic or inorganic molecule, a peptide, a protein, an oligonucleotide, an antibody, an antibody derivative, antibody fragment, a vitamin derivative, a carbohydrate, a toxin, or a chemotherapeutic compound. Various compounds can be synthesized, for example, small molecules and oligomers (e.g., oligopeptides and oligonucleotides), and synthetic organic compounds based on various core structures. In addition, various natural sources can provide compounds for screening, such as plant or animal extracts, and the like. A skilled artisan can readily recognize that there is no limit as to the structural nature of the agents of the present invention.

The term "agonist" as used herein refers to a compound having the ability to initiate or enhance a biological function of a target protein, whether by inhibiting the activity or expression of the target protein. Accordingly, the term "agonist" is defined in the context of the biological role of the target polypeptide. While preferred agonists herein specifically interact with (e.g., bind to) the target, compounds that initiate or enhance a biological activity of the target polypeptide by interacting with other members of the signal transduction pathway of which the target polypeptide is a member are also specifically included within this definition.

The terms "antagonist" and "inhibitor" are used interchangeably, and they refer to a compound having the ability to inhibit a biological function of a target protein, whether by inhibiting the activity or expression of the target protein. Accordingly, the terms "antagonist" and "inhibitors" are defined in the context of the biological role of the target protein. While preferred antagonists herein specifically interact with (e.g., bind to) the target, compounds that inhibit a biological activity of the target protein by interacting with other members of the signal transduction pathway of which the target protein is a member are also specifically included within this definition. A preferred biological activity inhibited by an antagonist is associated with the development, growth, or spread of a tumor, or an undesired immune response as manifested in autoimmune disease.

The phrase "mTOR inhibitor that binds to and directly inhibits both mTORC1 and mTORC2 kinases" when used: herein refers to an mTOR inhibitor that interacts with and reduces the kinase activity of both mTORC1 and mTORC2 complexes.

An "anti-cancer agent", "anti-tumor agent" or "chemotherapeutic agent" refers to any agent useful in the treatment of a neoplastic condition. One class of anti-cancer agents comprises chemotherapeutic agents. "Chemotherapy" means the administration of one or more chemotherapeutic drugs and/or other agents to a cancer patient by various methods, including intravenous, oral, intramuscular, intraperitoneal, intravesical, subcutaneous, transdermal, buccal, or inhalation or in the form of a suppository.

The term "cell proliferation" refers to a phenomenon by which the cell number has changed as a result of division.

This term also encompasses cell growth by which the cell morphology has changed (e.g., increased in size) consistent with a proliferative signal.

The terms "co-administration," "administered in combination with," and their grammatical equivalents, encompass administration of two or more agents to an animal so that both agents and/or their metabolites are present in the animal at the same time. Co-administration includes simultaneous administration in separate compositions, administration at different times in separate compositions, or administration in a composition in which both agents are present. Co-administered agents may be in the same formulation. Co-administered agents may also be in different formulations.

A "therapeutic effect," as used herein, encompasses a therapeutic benefit and/or a prophylactic benefit as described above. A prophylactic effect includes delaying or eliminating the appearance of a disease or condition, delaying or eliminating the onset of symptoms of a disease or condition, slowing, halting, or reversing the progression of a disease or condition, or any combination thereof.

The term "pharmaceutically acceptable salt" refers to salts derived from a variety of organic and inorganic counter ions well known in the art. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. In some embodiments, the pharmaceutically acceptable base addition salt is chosen from ammonium, potassium, sodium, calcium, and magnesium salts.

"Pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions of the invention is contemplated. Supplementary active ingredients can also be incorporated into the compositions.

"Signal transduction" is a process during which stimulatory or inhibitory signals are transmitted into and within a cell to elicit an intracellular response. A modulator of a signal transduction pathway refers to a compound which modulates the activity of one or more cellular proteins mapped to the same specific signal transduction pathway. A modulator may augment (agonist) or suppress (antagonist) the activity of a signaling molecule.

The term "selective inhibition" or "selectively inhibit" as applied to a biologically active agent refers to the agent's ability to selectively reduce the target signaling activity as compared to off-target signaling activity, via direct or interact interaction with the target.

"Subject" refers to an animal, such as a mammal, for example a human. The methods described herein can be useful in both human therapeutics, pre-clinical, and veterinary applications. In some embodiments, the subject is a mammal, and in some embodiments, the subject is human.

The term "in vivo" refers to an event that takes place in a subject's body.

The term "in vitro" refers to an event that takes places outside of a subject's body. For example, an in vitro assay encompasses any assay run outside of a subject assay. In vitro assays encompass cell-based assays in which cells alive or dead are employed. In vitro assays also encompass a cell-free assay in which no intact cells are employed.

When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range may vary from, for example, between 1% and 15% of the stated number or numerical range. The term "comprising" (and related terms such as "comprise" or "comprises" or "having" or "including") includes those embodiments, for example, an embodiment of any composition of matter, composition, method, or process, or the like, that "consist of" or "consist essentially of" the described features.

The following abbreviations and terms have the indicated meanings throughout: PI3K=Phosphoinositide 3-kinase; PI=phosphatidylinositol.

Unless otherwise stated, the connections of compound name moieties are at the rightmost recited moiety. That is, the substituent name starts with a terminal moiety, continues with any linking moieties, and ends with the linking moiety. For example, heteroarylthio $C_{1-4}$alkyl has a heteroaryl group connected through a thio sulfur to a $C_{1-4}$alkyl radical that connects to the chemical species bearing the substituent. This condition does not apply where a formula such as, for example "-L-$C_{1-10}$ alkyl-$C_{3-8}$cycloalkyl" is represented. In such case, the terminal group is a $C_{3-8}$cycloalkyl group attached to a linking $C_{1-10}$ alkyl moiety which is attached to an element L, which is itself connected to the chemical species bearing the substituent.

"Alkyl" refers to a straight or branched hydrocarbon chain radical consisting solely of carbon and hydrogen atoms, containing no unsaturation, having from one to ten carbon atoms (e.g., $C_1$-$C_{10}$ alkyl). Whenever it appears herein, a numerical range such as "1 to 10" refers to each integer in the given range; e.g., "1 to 10 carbon atoms" means that the alkyl group may consist of 1 carbon atom, 2 carbon atoms, 3 carbon atoms, etc., up to and including 10 carbon atoms, although the present definition also covers the occurrence of the term "alkyl" where no numerical range is designated. In some embodiments, it is a $C_1$-$C_4$ alkyl group. Typical alkyl groups include, but are in no way limited to, methyl, ethyl, propyl, isopropyl, n-butyl, iso-butyl, sec-butyl isobutyl, tertiary butyl, pentyl, isopentyl, neopentyl, hexyl, septyl, octyl, nonyl, decyl, and the like. The alkyl is attached to the rest of the molecule by a single bond, for example, methyl (Me), ethyl (Et), n-propyl, 1-methylethyl (iso-propyl), n-butyl, n-pentyl, 1,1-dimethylethyl (t-butyl), 3-methylhexyl, 2-methylhexyl, and the like. Unless stated otherwise specifically in the specification, an alkyl group is optionally substituted by one or more of substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)—R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, —N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$ where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

The term "halo" or "halogen" refers to fluoro, chloro, bromo, or iodo.

The term "haloalkyl" refers to an alkyl group substituted with one or more halo groups, for example chloromethyl, 2-bromoethyl, 3-iodopropyl, trifluoromethyl, perfluoropropyl, 8-chlorononyl, and the like.

"Acyl" refers to the groups (alkyl)-C(O)—, (aryl)-C(O)—, (heteroaryl)-C(O)—, (heteroalkyl)-C(O)—, and (heterocycloalkyl)-C(O)—, wherein the group is attached to the parent structure through the carbonyl functionality. In some embodiments, it is a C$_1$-C$_{10}$ acyl radical which refers to the total number of chain or ring atoms of the alkyl, aryl, heteroaryl or heterocycloalkyl portion of the acyloxy group plus the carbonyl carbon of acyl, i.e three other ring or chain atoms plus carbonyl. If the R radical is heteroaryl or heterocycloalkyl, the hetero ring or chain atoms contribute to the total number of chain or ring atoms. Unless stated otherwise specifically in the specification, the "R" of an acyloxy group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, SR$^a$, —OC(O)—R$^a$, —N(R$^a$)$_2$, —C(O)—R$^a$, —C(O)OR$^a$, —OC(O)N(R$^a$)$_2$, —C(O)N(R$^a$)$_2$, —N(R$^a$)C(O)OR$^a$, —N(R$^a$)C(O)—R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Cycloalkyl" refers to a monocyclic or polycyclic radical that contains only carbon and hydrogen, and may be saturated, or partially unsaturated. Cycloalkyl groups include groups having from 3 to 10 ring atoms (i.e., C$_2$-C$_{10}$ cycloalkyl). Whenever it appears herein, a numerical range such as "3 to 10" refers to each integer in the given range; e.g., "3 to 10 carbon atoms" means that the cycloalkyl group may consist of 3 carbon atoms, etc., up to and including 10 carbon atoms. In some embodiments, it is a C$_3$-C$_8$ cycloalkyl radical. In some embodiments, it is a C$_3$-C$_5$ cycloalkyl radical. Illustrative examples of cycloalkyl groups include, but are not limited to the following moieties: cyclopropyl, cyclobutyl, cyclopentyl, cyclopentenyl, cyclohexyl, cyclohexenyl, cycloseptyl, cyclooctyl, cyclononyl, cyclodecyl, norbornyl, and the like. Unless stated otherwise specifically in the specification, a cycloalkyl group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)—R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

The term "C$_{1-10}$alkyl-C$_{3-8}$cycloalkyl" is used to describe an alkyl group, branched or straight chain and containing 1 to 10 carbon atoms, attached to a linking cycloalkyl group which contains 3 to 8 carbons, such as for example, 2-methyl cyclopropyl, and the like. Either portion of the moiety is unsubstituted or substituted.

The term "bicycloalkyl" refers to a structure consisting of two cycloalkyl moieties, unsubstituted or substituted, that have two or more atoms in common. If the cycloalkyl moieties have exactly two atoms in common they are said to be "fused". Examples include, but are not limited to, bicyclo[3.1.0]hexyl, perhydronaphthyl, and the like. If the cycloalkyl moieties have more than two atoms in common they are said to be "bridged". Examples include, but are not limited to, bicyclo[3.2.1]heptyl ("norbornyl"), bicyclo[2.2.2]octyl, and the like.

As used herein, the term "heteroatom" or "ring heteroatom" is meant to include oxygen (O), nitrogen (N), sulfur (S), phosphorus (P), and silicon (Si).

"Heteroalkyl", "heteroalkenyl" and "heteroalkynyl" include optionally substituted alkyl, alkenyl and alkynyl radicals and which have one or more skeletal chain atoms selected from an atom other than carbon, e.g., oxygen, nitrogen, sulfur, phosphorus or combinations thereof. A numerical range may be given, e.g., C$_1$-C$_4$ heteroalkyl which refers to the chain length in total, which in this example is 4 atoms long. For example, a —CH$_2$OCH$_2$CH$_3$ radical is referred to as a "C$_4$" heteroalkyl, which includes the heteroatom center in the atom chain length description. Connection to the rest of the molecule may be through either a heteroatom or a carbon in the heteroalkyl chain. A heteroalkyl group may be substituted with one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, nitro, oxo, thioxo, trimethylsilanyl, —OR$^a$, —SR$^a$, —OC(O)—R$^a$, —N(R$^a$)$_2$, —C(O)—R$^a$, —C(O)OR$^a$, —C(O)N(R$^a$)$_2$, —N(R$^a$)C(O)OR$^a$, —N(R$^a$)C(O)—R$^a$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

The term "heteroalkylaryl" refers to a heteroalkyl group as defined above which is attached to an aryl group, and may be attached at a terminal point or through a branched portion of the heteroalkyl, for example, an benzyloxymethyl moiety. Either portion of the moiety is unsubstituted or substituted.

The term "heteroalkylheteroaryl" refers likewise to a heteroalkyl group which is attached to a heteroaryl moiety, for example, an ethoxymethylpyridyl group. Either portion of the moiety is unsubstituted or substituted.

The term "heteroalkyl-heterocyclyl" refers to a heteroalkyl group as defined above, which is attached to a heterocyclic group, for example, 4(3-aminopropyl)-N-piperazinyl. Either portion of the moiety is unsubstituted or substituted.

The term "heteroalkyl-C$_{3-8}$cycloalkyl" refers to a heteroalkyl group as defined above, which is attached to a cyclic alkyl containing 3 to 8 carbons, for example, 1-aminobutyl-4-cyclohexyl. Either portion of the moiety is unsubstituted or substituted.

The term "heterobicycloalkyl" refers to a bicycloalkyl structure, which is unsubstituted or substituted, in which at least one carbon atom is replaced with a heteroatom independently selected from oxygen, nitrogen, and sulfur.

The term "heterospiroalkyl" refers to a spiroalkyl structure, which is unsubstituted or substituted, in which at least one carbon atom is replaced with a heteroatom independently selected from oxygen, nitrogen, and sulfur.

An "alkene" moiety refers to a group consisting of at least two carbon atoms and at least one carbon-carbon double bond, and an "alkyne" moiety refers to a group consisting of at least two carbon atoms and at least one carbon-carbon triple bond. The alkyl moiety, whether saturated or unsaturated, may be branched, straight chain, or cyclic.

"Alkenyl" refers to a straight or branched hydrocarbon chain radical group consisting solely of carbon and hydrogen atoms, containing at least one double bond, and having from two to ten carbon atoms (i.e., $C_2$-$C_{10}$ alkenyl). Whenever it appears herein, a numerical range such as "2 to 10" refers to each integer in the given range; e.g., "2 to 10 carbon atoms" means that the alkenyl group may consist of 2 carbon atoms, 3 carbon atoms, etc., up to and including 10 carbon atoms. In certain embodiments, an alkenyl comprises two to eight carbon atoms. In other embodiments, an alkenyl comprises two to five carbon atoms (e.g., $C_2$-$C_5$ alkenyl). The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —$OR^a$, —$SR^a$, —OC(O)—$R^a$, —$N(R^a)_2$, —$C(O)R^a$, —$C(O)OR^a$, —$OC(O)N(R^a)_2$, —$C(O)N(R^a)_2$, —$N(R^a)C(O)OR^a$, —$N(R^a)C(O)R^a$, —$N(R^a)C(O)N(R^a)_2$, $N(R^a)C(NR^a)N(R^a)_2$, —$N(R^a)S(O)_tR^a$ (where t is 1 or 2), —$S(O)_tOR^a$ (where t is 1 or 2), —$S(O)_tN(R^a)_2$ (where t is 1 or 2), or $PO_3(R^a)_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

The term "$C_{2-10}$ alkenyl-heteroalkyl" refers to a group having an alkenyl moiety, containing 2 to 10 carbon atoms and is branched or straight chain, which is attached to a linking heteroalkyl group, such as, for example, allyloxy, and the like. Either portion of the moiety is unsubstituted or substituted.

The term "$C_{2-10}$ alkynyl-heteroalkyl" refers to a group having an alkynyl moiety, which is unsubstituted or substituted, containing 2 to 10 carbon atoms and is branched or straight chain, which is attached to a linking heteroalkyl group, such as, for example, 4-but-1-ynoxy, and the like. Either portion of the moiety is unsubstituted or substituted.

The term "haloalkenyl" refers to an alkenyl group substituted with one or more halo groups.

Unless otherwise specified, the term "cycloalkenyl" refers to a cyclic aliphatic 3 to 8 membered ring structure, optionally substituted with alkyl, hydroxy and halo, having 1 or 2 ethylenic bonds such as methylcyclopropenyl, trifluoromethylcyclopropenyl, cyclopentenyl, cyclohexenyl, 1,4-cyclohexadienyl, and the like.

"Alkynyl" refers to a straight or branched hydrocarbon chain radical group consisting solely of carbon and hydrogen atoms, containing at least one triple bond, having from two to ten carbon atoms (i.e., $C_2$-$C_{10}$ alkynyl). Whenever it appears herein, a numerical range such as "2 to 10" refers to each integer in the given range; e.g., "2 to 10 carbon atoms" means that the alkynyl group may consist of 2 carbon atoms, 3 carbon atoms, etc., up to and including 10 carbon atoms. In certain embodiments, an alkynyl comprises two to eight carbon atoms. In other embodiments, an alkynyl has two to five carbon atoms (e.g., $C_2$-$C_5$ alkynyl). The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —$OR^a$, $SR^a$, —OC(O)—$R^a$, —$N(R^a)_2$, —$C(O)R^a$, —$C(O)OR^a$, —$OC(O)N(R^a)_2$, —$C(O)N(R^a)_2$, —$N(R^a)C(O)OR^a$, —$N(R^a)C(O)R^a$, —$N(R^a)C(O)N(R^a)_2$, $N(R^a)C(NR^a)N(R^a)_2$, —$N(R^a)S(O)_tR^a$ (where t is 1 or 2), —$S(O)_tOR^a$ (where t is 1 or 2), —$S(O)_tN(R^a)_2$ (where t is 1 or 2), or $PO_3(R^a)_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

The term $C_{2-10}$ alkynyl-$C_{3-8}$cycloalkyl refers to a group containing an alkynyl group, containing 2 to 10 carbons and branched or straight chain, which is attached to a linking cycloalkyl group containing 3 to 8 carbons, such as, for example 3-prop-3-ynyl-cyclopent-1yl, and the like. Either portion of the moiety is unsubstituted or substituted.

The term "haloalkynyl" refers to an alkynyl group substituted with one or more independent halo groups.

"Amino" or "amine" refers to a —$N(R^a)_2$ radical group, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl, unless stated otherwise specifically in the specification. When a —$N(R^a)_2$ group has two $R^a$ other than hydrogen they can be combined with the nitrogen atom to form a 4-, 5-, 6-, or 7-membered ring. For example, —$N(R^a)_2$ is meant to include, but not be limited to, 1-pyrrolidinyl and 4-morpholinyl. Unless stated otherwise specifically in the specification, an amino group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —$OR^a$, —$SR^a$, —OC(O)—$R^a$, —$N(R^a)_2$, —$C(O)R^a$, —$C(O)OR^a$, —$OC(O)N(R^a)_2$, —$C(O)N(R^a)_2$, —$N(R^a)C(O)OR^a$, —$N(R^a)C(O)R^a$, —$N(R^a)C(O)N(R^a)_2$, —$N(R^a)C(NR^a)N(R^a)_2$, —$N(R^a)S(O)_tR^a$ (where t is 1 or 2), —$S(O)_tOR^a$ (where t is 1 or 2), —$S(O)_tN(R^a)_2$ (where t is 1 or 2), or $PO_3(R^a)_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl and each of these moieties may be optionally substituted as defined herein.

"Amide" or "amido" refers to a chemical moiety with formula —$C(O)N(R)_2$ or —$NHC(O)R$, where R is selected from the group consisting of hydrogen, alkyl, cycloalkyl, aryl, heteroaryl (bonded through a ring carbon) and heteroalicyclic (bonded through a ring carbon), each of which moiety may itself be optionally substituted. In some embodiments it is a $C_1$-$C_4$ amido or amide radical, which includes the amide carbonyl in the total number of carbons in the radical. The $R^{2'}$ of —$N(R)_2$ of the amide may optionally be taken together with the nitrogen to which it is attached to form a 4-, 5-, 6-, or 7-membered ring. Unless stated otherwise specifically in the specification, an amido group is optionally substituted independently by one or more of the substituents as described herein for alkyl, cycloalkyl, aryl, heteroaryl, or heterocycloalkyl. An amide may be an amino acid or a peptide molecule attached to a compound of Formula (I), thereby forming a prodrug. Any amine, hydroxy, or carboxyl side chain on the compounds described herein can be amidified. The procedures and specific groups to make such amides are known to those of skill in the art and can readily be found in reference sources such as Greene and Wuts, Protective Groups in Organic Synthesis, 3$^{rd}$ Ed., John Wiley & Sons, New York, N.Y., 1999, which is incorporated herein by reference in its entirety.

"Aromatic" or "aryl" refers to an aromatic radical with six to ten ring atoms (e.g., $C_6$-$C_{10}$ aromatic or $C_6$-$C_{10}$ aryl) which has at least one ring having a conjugated pi electron system which is carbocyclic (e.g., phenyl, fluorenyl, and naphthyl). Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. Whenever it appears herein, a numerical range such as "6 to 10" refers to each integer in the given range; e.g., "6 to 10 ring atoms" means that the aryl group may consist of 6 ring atoms, 7 ring atoms, etc., up to and including 10 ring atoms. The term includes monocyclic or fused-ring polycyclic (i.e., rings which share adjacent pairs of ring atoms) groups. Unless stated otherwise specifically in the specification, an aryl moiety is optionally substituted by one or more substituents which are independently: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$_a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Heteroaryl" or, alternatively, "heteroaromatic" refers to a 5- to 18-membered aromatic radical (e.g., $C_5$-$C_{13}$ heteroaryl) that includes one or more ring heteroatoms selected from nitrogen, oxygen and sulfur, and which may be a monocyclic, bicyclic, tricyclic or tetracyclic ring system. Whenever it appears herein, a numerical range such as "5 to 18" refers to each integer in the given range; e.g., "5 to 18 ring atoms" means that the heteroaryl group may consist of 5 ring atoms, 6 ring atoms, etc., up to and including 18 ring atoms. Bivalent radicals derived from univalent heteroaryl radicals whose names end in "-yl" by removal of one hydrogen atom from the atom with the free valence are named by adding "-idene" to the name of the corresponding univalent radical, e.g., a pyridyl group with two points of attachment is a pyridylidene. An N-containing "heteroaromatic" or "heteroaryl" moiety refers to an aromatic group in which at least one of the skeletal atoms of the ring is a nitrogen atom. The polycyclic heteroaryl group may be fused or non-fused. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzoxazolyl, benzopyranyl, benzopyranonyl, benzofuranyl, benzofuranonyl, benzofurazanyl, benzothiazolyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furazanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyranyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, thiapyranyl, triazolyl, tetrazolyl, triazinyl, thieno[2,3-d]pyrimidinyl, thieno[3,2-d]pyrimidinyl, thieno[2,3-c]pridinyl, and thiophenyl (i.e. thienyl). Unless stated otherwise specifically in the specification, a heteraryl moiety is optionally substituted by one or more substituents which are independently: alkyl, heteroalkyl, alkenyl, alkynyl, cycloalkyl, heterocycloalkyl, aryl, arylalkyl, heteroaryl, heteroarylalkyl, hydroxy, halo, cyano, nitro, oxo, thioxo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

The terms "aryl-alkyl", "arylalkyl" and "aralkyl" are used to describe a group wherein the alkyl chain can be branched or straight chain forming a linking portion with the terminal aryl, as defined above, of the aryl-alkyl moiety. Examples of aryl-alkyl groups include, but are not limited to, optionally substituted benzyl, phenethyl, phenpropyl and phenbutyl such as 4-chlorobenzyl, 2,4-dibromobenzyl, 2-methylbenzyl, 2-(3-fluorophenyl)ethyl, 2-(4-methylphenyl)ethyl, 2-(4-(trifluoromethyl)phenyl)ethyl, 2-(2-methoxyphenyl)ethyl, 2-(3-nitrophenyl)ethyl, 2-(2,4-dichlorophenyl)ethyl, 2-(3,5-dimethoxyphenyl)ethyl, 3-phenylpropyl, 3-(3-chlorophenyl)propyl, 3-(2-methylphenyl)propyl, 3-(4-methoxyphenyl)propyl, 3-(4-(trifluoromethyl)phenyl)propyl, 3-(2,4-dichlorophenyl)propyl, 4-phenylbutyl, 4-(4-chlorophenyl)butyl, 4-(2-methylphenyl)butyl, 4-(2,4-dichlorophenyl)butyl, 4-(2-methoxphenyl)butyl, and 10-phenyldecyl. Either portion of the moiety is unsubstituted or substituted.

The term "$C_{1-10}$alkylaryl" as used herein refers to an alkyl group, as defined above, containing 1 to 10 carbon atoms, branched or unbranched, wherein the aryl group replaces one hydrogen on the alkyl group, for example, 3-phenylpropyl. Either portion of the moiety is unsubstituted or substituted.

The term $C_{2-10}$ alkyl monocycloaryl" refers to a group containing a terminal alkyl group, branched or straight chain and containing 2 to 10 atoms attached to a linking aryl group which has only one ring, such as for example, 2-phenyl ethyl. Either portion of the moiety is unsubstituted or substituted.

The term "$C_{1-10}$ alkyl bicycloaryl" refers to a group containing a terminal alkyl group, branched or straight chain and containing 2 to 10 atoms attached to a linking aryl group which is bicyclic, such as for example, 2-(1-naphthyl)-ethyl. Either portion of the moiety is unsubstituted or substituted.

The terms "aryl-cycloalkyl" and "arylcycloalkyl" are used to describe a group wherein the terminal aryl group is attached to a cycloalkyl group, for example phenylcyclopentyl and the like. Either portion of the moiety is unsubstituted or substituted.

The terms "heteroaryl-$C_{3-8}$cycloalkyl" and "heteroaryl-$C_{3-8}$cycloalkyl" are used to describe a group wherein the terminal heteroaryl group is attached to a cycloalkyl group, which contains 3 to 8 carbons, for example pyrid-2-yl-cyclopentyl and the like. Either portion of the moiety is unsubstituted or substituted.

The term "heteroaryl-heteroalkyl" refers to a group wherein the terminal heteroaryl group is attached to a linking heteroalkyl group, such as for example, pyrid-2-yl methylenoxy, and the like. Either portion of the moiety is unsubstituted or substituted.

The terms "aryl-alkenyl", "arylalkenyl" and "aralkenyl" are used to describe a group wherein the alkenyl chain can be branched or straight chain forming a linking portion of the aralkenyl moiety with the terminal aryl portion, as defined above, for example styryl (2-phenylvinyl), phenpropenyl, and the like. Either portion of the moiety is unsubstituted or substituted.

The term "aryl-$C_{2-10}$alkenyl" means an arylalkenyl as described above wherein the alkenyl moiety contains 2 to 10 carbon atoms such as for example, styryl (2-phenylvinyl), and the like. Either portion of the moiety is unsubstituted or substituted.

The term "$C_{2-10}$alkenyl-aryl" is used to describe a group wherein the terminal alkenyl group, which contains 2 to 10 carbon atoms and can be branched or straight chain, is attached to the aryl moiety which forms the linking portion of the alkenyl-aryl moiety, such as, for example, 3-propenyl-naphth-1-yl, and the like. Either portion of the moiety is unsubstituted or substituted.

The terms "aryl-alkynyl", "arylalkynyl" and "aralkynyl" are used to describe a group wherein the alkynyl chain can be branched or straight chain forming a linking portion of the aryl-alkynyl moiety with the terminal aryl portion, as defined above, for example 3-phenyl-1-propynyl, and the like. Either portion of the moiety is unsubstituted or substituted.

The term "aryl-$C_{2-10}$alkynyl" means an arylalkynyl as described above wherein the alkynyl moiety contains two to ten carbons, such as, for example 3-phenyl-1-propynyl, and the like. Either portion of the moiety is unsubstituted or substituted.

The term "$C_{2-10}$alkynyl-aryl" means a group containing an alkynyl moiety attached to an aryl linking group, both as defined above, wherein the alkynyl moiety contains two to ten carbons, such as, for example 3-propynyl-naphth-1-yl. Either portion of the moiety is unsubstituted or substituted.

The terms "aryl-oxy", "aryloxy" and "aroxy" are used to describe a terminal aryl group attached to a linking oxygen atom. Typical aryl-oxy groups include phenoxy, 3,4-dichlorophenoxy, and the like. Either portion of the moiety is unsubstituted or substituted.

The terms "aryl-oxyalkyl", "aryloxyalkyl" and "aroxyalkyl" are used to describe a group wherein an alkyl group is substituted with a terminal aryl-oxy group, for example pentafluorophenoxymethyl and the like. Either portion of the moiety is unsubstituted or substituted.

The term "$C_{1-10}$alkoxy-$C_{1-10}$alkyl" refers to a group wherein an alkoxy group, containing 1 to 10 carbon atoms and an oxygen atom within the branching or straight chain, is attached to a linking alkyl group, branched or straight chain which contains 1 to 10 carbon atoms, such as, for example methoxypropyl, and the like. Either portion of the moiety is unsubstituted or substituted.

The term "$C_{1-10}$alkoxy-$C_{2-10}$alkenyl" refers to a group wherein an alkoxy group, containing 1 to 10 carbon atoms and an oxygen atom within the branching or straight chain, is attached to a linking alkenyl group, branched or straight chain which contains 1 to 10 carbon atoms, such as, for example 3-methoxybut-2-en-1-yl, and the like. Either portion of the moiety is unsubstituted or substituted.

The term "$C_{1-10}$alkoxy-$C_{2-10}$alkynyl" refers to a group wherein an alkoxy group, containing 1 to 10 carbon atoms and an oxygen atom within the branching or straight chain, is attached to a linking alkynyl group, branched or straight chain which contains 1 to 10 carbon atoms, such as, for example 3-methoxybut-2-in-1-yl, and the like. Either portion of the moiety is unsubstituted or substituted.

The term "heterocycloalkenyl" refers to a cycloalkenyl structure, which is unsubstituted or substituted in which at least one carbon atom is replaced with a heteroatom selected from oxygen, nitrogen, and sulfur.

The terms "heteroaryl-oxy", "heteroaryl-oxy", "heteroaryloxy", "heteroaryloxy", "hetaroxy" and "heteroaroxy" are used to describe a terminal heteroaryl group, which is unsubstituted or substituted, attached to a linking oxygen atom. Typical heteroaryl-oxy groups include 4,6-dimethoxypyrimidin-2-yloxy and the like.

The terms "heteroarylalkyl", "heteroarylalkyl", "heteroaryl-alkyl", "heteroaryl-alkyl", "hetaralkyl" and "heteroaralkyl" are used to describe a group wherein the alkyl chain can be branched or straight chain forming a linking portion of the heteroaralkyl moiety with the terminal heteroaryl portion, as defined above, for example 3-furylmethyl, thenyl, furfuryl, and the like. Either portion of the moiety is unsubstituted or substituted.

The term "heteroaryl-$C_{1-10}$alkyl" is used to describe a heteroaryl alkyl group as described above where the alkyl group contains 1 to 10 carbon atoms. Either portion of the moiety is unsubstituted or substituted.

The term "$C_{1-10}$alkyl-heteroaryl" is used to describe a alkyl attached to a hetary group as described above where the alkyl group contains 1 to 10 carbon atoms. Either portion of the moiety is unsubstituted or substituted.

The terms "heteroarylalkenyl", "heteroarylalkenyl", "heteroaryl-alkenyl", "heteroaryl-alkenyl", "hetaralkenyl" and "heteroaralkenyl" are used to describe a heteroarylalkenyl group wherein the alkenyl chain can be branched or straight chain forming a linking portion of the heteroaralkenyl moiety with the terminal heteroaryl portion, as defined above, for example 3-(4-pyridyl)-1-propenyl. Either portion of the moiety is unsubstituted or substituted.

The term "heteroaryl-$C_{2-10}$alkenyl" group is used to describe a group as described above wherein the alkenyl group contains 2 to 10 carbon atoms. Either portion of the moiety is unsubstituted or substituted.

The term "$C_{2-10}$alkenyl-heteroaryl" is used to describe a group containing an alkenyl group, which is branched or straight chain and contains 2 to 10 carbon atoms, and is attached to a linking heteroaryl group, such as, for example 2-styryl-4-pyridyl, and the like. Either portion of the moiety is unsubstituted or substituted.

The terms "heteroarylalkynyl", "heteroarylalkynyl", "heteroaryl-alkynyl", "heteroaryl-alkynyl", "hetaralkynyl" and "heteroaralkynyl" are used to describe a group wherein the alkynyl chain can be branched or straight chain forming a linking portion of the heteroaralkynyl moiety with the heteroaryl portion, as defined above, for example 4-(2-thienyl)-1-butynyl, and the like. Either portion of the moiety is unsubstituted or substituted.

The term "heteroaryl-$C_{2-10}$alkynyl" is used to describe a heteroarylalkynyl group as described above wherein the alkynyl group contains 2 to 10 carbon atoms. Either portion of the moiety is unsubstituted or substituted.

The term "$C_{2-10}$alkynyl-heteroaryl" is used to describe a group containing an alkynyl group which contains 2 to 10 carbon atoms and is branched or straight chain, which is attached to a linking heteroaryl group such as, for example, 4(but-1-ynyl) thien-2-yl, and the like. Either portion of the moiety is unsubstituted or substituted.

The term "heterocyclyl" refers to a four-, five-, six-, or seven-membered ring containing one, two, three or four heteroaroms independently selected from nitrogen, oxygen and sulfur. The four-membered ring has zero double bonds, the five-membered ring has zero to two double bonds, and the six- and seven-membered rings have zero to three double bonds. The term "heterocyclyl" also includes bicyclic groups in which the heterocyclyl ring is fused to another monocyclic heterocyclyl group, or a four- to se-membered aromatic or nonaromatic carbocyclic ring. The heterocyclyl group can be attached to the parent molecular moiety through any carbon atom or nitrogen atom in the group.

"Heterocycloalkyl" refers to a stable 3- to 18-membered non-aromatic ring radical that comprises two to twelve carbon atoms and from one to six heteroatoms selected from nitrogen, oxygen and sulfur. Whenever it appears herein, a numerical range such as "3 to 18" refers to each integer in the given range; e.g., "3 to 18 ring atoms" means that the heterocycloalkyl group may consist of 3 ring atoms, 4 ring atoms, etc., up to and including 18 ring atoms. In some embodiments, it is a $C_5$-$C_{10}$ heterocycloalkyl. In some embodiments, it is a $C_4$-$C_{10}$ heterocycloalkyl. In some embodiments, it is a $C_3$-$C_{10}$ heterocycloalkyl. Unless stated otherwise specifically in the specification, the heterocycloalkyl radical is a monocyclic, bicyclic, tricyclic or tetracyclic ring system, which may include fused or bridged ring systems. The heteroatoms in the heterocycloalkyl radical may be optionally oxidized. One or more nitrogen atoms, if present, are optionally quaternized. The heterocycloalkyl radical is partially or fully saturated. The heterocycloalkyl may be attached to the rest of the molecule through any atom of the ring(s). Examples of such heterocycloalkyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxothiomorpholinyl. Unless stated otherwise specifically in the specification, a heterocycloalkyl moiety is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, nitro, oxo, thioxo, trimethylsilanyl, —OR$^a$, SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heteroaryl or heteroarylalkyl.

"Heterocycloalkyl" also includes bicyclic ring systems wherein one non-aromatic ring, usually with 3 to 7 ring atoms, contains at least 2 carbon atoms in addition to 1-3 heteroatoms independently selected from oxygen, sulfur, and nitrogen, as well as combinations comprising at least one of the foregoing heteroatoms; and the other ring, usually with 3 to 7 ring atoms, optionally contains 1-3 heteroatoms independently selected from oxygen, sulfur, and nitrogen and is not aromatic.

The terms "heterocyclylalkyl", "heterocyclyl-alkyl", "hetcyclylalkyl", and "hetcyclyl-alkyl" are used to describe a group wherein the alkyl chain can be branched or straight chain forming a linking portion of the heterocyclylalkyl moiety with the terminal heterocyclyl portion, as defined above, for example 3-piperidinylmethyl and the like. The term "heterocycloalkylene" refers to the divalent derivative of heterocycloalkyl.

The term "$C_{1-10}$alkyl-heterocycyl" refers to a group as defined above where the alkyl moiety contains 1 to 10 carbon atoms. Either portion of the moiety is unsubstituted or substituted.

The term "heterocycyl-$C_{1-10}$alkyl" refers to a group containing a terminal heterocyclic group attached to a linking alkyl group which contains 1 to 10 carbons and is branched or straight chain, such as, for example, 4-morpholinyl ethyl, and the like. Either portion of the moiety is unsubstituted or substituted.

The terms "heterocyclylalkenyl", "heterocyclyl-alkenyl", "hetcyclylalkenyl" and "hetcyclyl-alkenyl" are used to describe a group wherein the alkenyl chain can be branched or straight chain forming a linking portion of the heterocyclylalkenyl moiety with the terminal heterocyclyl portion, as defined above, for example 2-morpholinyl-1-propenyl and the like. The term "heterocycloalkenylene" refers to the divalent derivative of heterocyclylalkenyl. Either portion of the moiety is unsubstituted or substituted.

The term "heterocycyl-$C_{2-10}$ alkenyl" refers to a group as defined above where the alkenyl group contains 2 to 10 carbon atoms and is branched or straight chain, such as, for example, 4-(N-piperazinyl)-but-2-en-1-yl, and the like. Either portion of the moiety is unsubstituted or substituted.

The terms "heterocyclylalkynyl", "heterocyclyl-alkynyl", "hetcyclylalkynyl" and "hetcyclyl-alkynyl" are used to describe a group wherein the alkynyl chain can be branched or straight chain forming a linking portion of the heterocyclylalkynyl moiety with the terminal heterocyclyl portion, as defined above, for example 2-pyrrolidinyl-1-butynyl and the like. Either portion of the moiety is unsubstituted or substituted.

The term "heterocycyl-$C_{2-10}$ alkynyl" refers to a group as defined above where the alkynyl group contains 2 to 10 carbon atoms and is branched or straight chain, such as, for example, 4-(N-piperazinyl)-but-2-yn-1-yl, and the like.

The term "aryl-heterocycyl" refers to a group containing a terminal aryl group attached to a linking heterocyclic group, such as for example, N4-(4-phenyl)-piperazinyl, and the like. Either portion of the moiety is unsubstituted or substituted.

The term "heteroaryl-heterocycyl" refers to a group containing a terminal heteroaryl group attached to a linking heterocyclic group, such as for example, N4-(4-pyridyl)-piperazinyl, and the like. Either portion of the moiety is unsubstituted or substituted.

The term "carboxylalkyl" refers to a terminal carboxyl (—COOH) group attached to branched or straight chain alkyl groups as defined above.

The term "carboxylalkenyl" refers to a terminal carboxyl (—COOH) group attached to branched or straight chain alkenyl groups as defined above.

The term "carboxylalkynyl" refers to a terminal carboxyl (—COOH) group attached to branched or straight chain alkynyl groups as defined above.

The term "carboxylcycloalkyl" refers to a terminal carboxyl (—COOH) group attached to a cyclic aliphatic ring structure as defined above.

The term "carboxylcycloalkenyl" refers to a terminal carboxyl (—COOH) group attached to a cyclic aliphatic ring structure having ethylenic bonds as defined above.

The terms "cycloalkylalkyl" and "cycloalkyl-alkyl" refer to a terminal cycloalkyl group as defined above attached to an alkyl group, for example cyclopropylmethyl, cyclohexylethyl, and the like. Either portion of the moiety is unsubstituted or substituted.

The terms "cycloalkylalkenyl" and "cycloalkyl-alkenyl" refer to a terminal cycloalkyl group as defined above attached to an alkenyl group, for example cyclohexylvinyl, cycloheptylallyl, and the like. Either portion of the moiety is unsubstituted or substituted.

The terms "cycloalkylalkynyl" and "cycloalkyl-alkynyl" refer to a terminal cycloalkyl group as defined above attached to an alkynyl group, for example cyclopropylpropargyl, 4-cyclopentyl-2-butynyl, and the like. Either portion of the moiety is unsubstituted or substituted.

The terms "cycloalkenylalkyl" and "cycloalkenyl-alkyl" refer to a terminal cycloalkenyl group as defined above attached to an alkyl group, for example 2-(cyclopenten-1-yl) ethyl and the like. Either portion of the moiety is unsubstituted or substituted.

The terms "cycloalkenylalkenyl" and "cycloalkenyl-alkenyl" refer to terminal a cycloalkenyl group as defined above attached to an alkenyl group, for example 1-(cyclohexen-3-yl)allyl and the like.

The terms "cycloalkenylalkynyl" and "cycloalkenyl-alkynyl" refer to terminal a cycloalkenyl group as defined above attached to an alkynyl group, for example 1-(cyclohexen-3-yl)propargyl and the like. Either portion of the moiety is unsubstituted or substituted.

The term "alkoxy" refers to the group —O-alkyl, including from 1 to 8 carbon atoms of a straight, branched, cyclic configuration and combinations thereof attached to the parent structure through an oxygen. Examples include methoxy, ethoxy, propoxy, isopropoxy, cyclopropyloxy, cyclohexyloxy and the like. "Lower alkoxy" refers to alkoxy groups containing one to six carbons. In some embodiments, $C_1$-$C_4$ alkyl, is an alkyl group which encompasses both straight and branched chain alkyls of from 1 to 4 carbon atoms.

The term "haloalkoxy" refers to an alkoxy group substituted with one or more halo groups, for example chloromethoxy, trifluoromethoxy, difluoromethoxy, perfluoroisobutoxy, and the like.

The term "alkoxyalkoxyalkyl" refers to an alkyl group substituted with an alkoxy moiety which is in turn is substituted with a second alkoxy moiety, for example methoxymethoxymethyl, isopropoxymethoxyethyl, and the like.

This moiety is substituted with further substituents or not substituted with other substituents.

The term "alkylthio" includes both branched and straight chain alkyl groups attached to a linking sulfur atom, for example methylthio and the like.

The term "alkoxyalkyl" refers to an alkyl group substituted with an alkoxy group, for example isopropoxymethyl and the like. Either portion of the moiety is unsubstituted or substituted.

The term "alkoxyalkenyl" refers to an alkenyl group substituted with an alkoxy group, for example 3-methoxyallyl and the like. Either portion of the moiety is unsubstituted or substituted.

The term "alkoxyalkynyl" refers to an alkynyl group substituted with an alkoxy group, for example 3-methoxypropargyl and the like. Either portion of the moiety is unsubstituted or substituted.

The term "$C_{2-10}$alkenyl$C_{3-8}$cycloalkyl" refers to an alkenyl group as defined above substituted with a three to eight membered cycloalkyl group, for example, 4-(cyclopropyl)-2-butenyl and the like. Either portion of the moiety is unsubstituted or substituted.

The term "$C_{2-10}$alkynyl$C_{3-8}$cycloalkyl" refers to an alkynyl group as defined above substituted with a three to eight membered cycloalkyl group, for example, 4-(cyclopropyl)-2-butynyl and the like. Either portion of the moiety is unsubstituted or substituted.

The term "heterocyclyl-$C_{1-10}$alkyl" refers to a heterocyclic group as defined above substituted with an alkyl group as defined above having 1 to 10 carbons, for example, 4-(N-methyl)-piperazinyl, and the like. Either portion of the moiety is unsubstituted or substituted.

The term "heterocyclyl-$C_{2-10}$alkenyl" refers to a heterocyclic group as defined above, substituted with an alkenyl group as defined above, having 2 to 10 carbons, for example, 4-(N-allyl)piperazinyl, and the like. Moieties wherein the heterocyclic group is substituted on a carbon atom with an alkenyl group are also included. Either portion of the moiety is unsubstituted or substituted.

The term "heterocyclyl-$C_{2-10}$alkynyl" refers to a heterocyclic group as defined above, substituted with an alkynyl group as defined above, having 2 to 10 carbons, for example, 4-(N-propargyl)piperazinyl, and the like. Moieties wherein the heterocyclic group is substituted on a carbon atom with an alkenyl group are also included. Either portion of the moiety is unsubstituted or substituted.

The term "oxo" refers to an oxygen that is double bonded to a carbon atom. One in the art understands that an "oxo" requires a second bond from the atom to which the oxo is attached. Accordingly, it is understood that oxo cannot be subststituted onto an aryl or heteroaryl ring, unless it forms part of the aromatic system as a tautomer.

The term "oligomer" refers to a low-molecular weight polymer, whose number average molecular weight is typically less than about 5000 g/mol, and whose degree of polymerization (average number of monomer units per chain) is greater than one and typically equal to or less than about 50.

"Sulfonamidyl" or "sulfonamido" refers to a —S(=O)$_2$—NR'R' radical, where each R' is selected independently from the group consisting of hydrogen, alkyl, cycloalkyl, aryl, heteroaryl (bonded through a ring carbon) and heteroalicyclic (bonded through a ring carbon). The R' groups in —NR'R' of the —S(=O)$_2$—NR'R' radical may be taken together with the nitrogen to which it is attached to form a 4-, 5-, 6-, or 7-membered ring. A sulfonamido group is optionally substituted by one or more of the substituents described for alkyl, cycloalkyl, aryl, heteroaryl respectively.

Compounds described can contain one or more asymmetric centers and may thus give rise to diastereomers and optical isomers. The present invention includes all such possible diastereomers as well as their racemic mixtures, their substantially pure resolved enantiomers, all possible geometric isomers, and pharmaceutically acceptable salts thereof. Compounds may be shown without a definitive stereochemistry at certain positions. The present invention includes all stereoisomers of the disclosed compounds and pharmaceutically acceptable salts thereof. Further, mixtures of stereoisomers as well as isolated specific stereoisomers are also included. During the course of the synthetic procedures used to prepare such compounds, or in using racemization or epimerization procedures known to those skilled in the art, the products of such procedures can be a mixture of stereoisomers.

The present invention includes all manner of rotamers and conformationally restricted states of an inhibitor of the invention.

Substituents for alkyl, heteroalkyl, cycloalkyl, heterocycloalkyl monovalent and divalent derivative radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: alkyl, heteroalkyl, alkenyl, alkynyl, cycloalkyl, heterocycloalkyl, aryl, arylalkyl, heteroaryl, heteroarylalkyl, —OR', =O, =NR', =N—OR', —NR'R", —SR', -halogen, —SiR'R"R''', —OC(O)R', —C(O)R', —CO$_2$R', —C(O)NR'R", —OC(O)NR'R", —NR"C(O)R', —NR'—C(O)NR"R''', —NR"C(O)OR', —NR—C(NR'R")=NR''', —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R', R", R''' and R'''' each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy or thioalkoxy groups, or arylalkyl groups. When an inhibitor of the invention includes more than one R group, for example, each of the R groups is independently selected as are each R', R", R''' and R'''' groups when more than one of these groups is present.

When R' and R" or R" and R''' are attached to the same nitrogen atom, they can be combined with the nitrogen atom to form a 4-, 5-, 6-, or 7-membered ring. For example, —NR'R" is meant to include, but not be limited to, 1-pyrrolidinyl, 4 piperazinyl, and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for alkyl radicals above, exemplary substituents for aryl and heteroaryl groups (as well as their divalent derivatives) are varied and are selected from, for example: halogen, alkyl, heteroalkyl, alkenyl, alkynyl, cycloalkyl, heterocycloalkyl, aryl, arylalkyl, heteroaryl, heteroarylalkyl, —OR', —NR'R", —SR', -halogen, —SiR'R"R''', —OC(O)R', —C(O)R', —CO$_2$R', —C(O)NR'R", —OC(O)NR'R", —NR"C(O)R', —NR'—C(O)NR"R''', —NR"C(O)OR', —NR—C(NR'R"R''')=NR'''', —NR—C(NR'R")=NR''', —S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$)alkoxo, and fluoro(C$_1$-C$_4$)alkyl, in a number ranging from zero to the total number of open valences on aromatic ring system; and where R', R", R''' and R'''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. When an inhibitor of the invention includes more than one R group, for example, each of the R groups is independently selected as are each R', R", R''' and R'''' groups when more than one of these groups is present.

As used herein, 0-2 in the context of —S(O)$_{(0-2)}$— are integers of 0, 1, and 2.

Two of the substituents on adjacent atoms of aryl or heteroaryl ring may optionally form a ring of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of aryl or heteroaryl ring may optionally be replaced with a substituent of the formula —(CRR')$_s$—X'—(C"R''')$_d$—, where s and d are independently integers of from 0 to 3, and X' is —O—, —NR'—, —S—, —S(O)—, —S(O)$_2$—, or —S(O)$_2$NR'—. The substituents R, R', R" and R''' are preferably independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this invention.

The compounds of the present invention may also contain unnatural proportions of atomic isotopes at one or more of atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are encompassed within the scope of the present invention.

Methods

In one aspect, the present invention provides a method for treating a disease condition associated with PI3-kinase α and/or mTOR in a subject. The method typically comprises administering to a subject simultaneously or sequentially a therapeutically effective amount of a combination of a PI3-kinase α inhibitor and an mTOR inhibitor.

As used herein, a therapeutically effective amount of a combination of a PI3-kinase α inhibitor and an mTOR inhibitor refers to a combination of a PI3-kinase α inhibitor and an mTOR inhibitor, wherein the combination is sufficient to effect the intended application including but not limited to disease treatment, as defined herein. Encompassed in this subject method is the use of therapeutically effective amount of a PI3-kinase α inhibitor and/or an mTOR inhibitor in combination to effect such treatment. Also contemplated in the subject methods is the use of a sub-therapeutic amount of a PI3-kinase α inhibitor and/or an mTOR inhibitor in the combination for treating an intended disease condition. The individual inhibitors, though present in sub-therapeutic amounts, synergistically yield an efficacious effect and/or reduced a side effect in an intended application.

Accordingly, in a separate but related aspect, the present invention provides for a method for treating a disease condition associated with PI3-kinase α and/or mTOR in a subject, comprising administering to the subject simultaneously or sequentially a synergistically effective therapeutic amount of a combination of a PI3-kinase α inhibitor and an mTOR inhibitor.

The therapeutically effective amount of the subject combination of compounds may vary depending upon the intended application (in vitro or in vivo), or the subject and disease condition being treated, e.g., the weight and age of the subject, the severity of the disease condition, the manner of administration and the like, which can readily be determined by one of ordinary skill in the art. The term also applies to a dose that will induce a particular response in target cells, e.g., reduction of proliferation or downregulation of activity of a target protein. The specific dose will vary depending on the particular compounds chosen, the dosing regimen to be followed, whether it is administered in combination with other compounds, timing of administration, the tissue to which it is administered, and the physical delivery system in which it is carried.

The PI3-kinase α inhibitor utilized in the subject methods typically exhibits selective inhibition of PI3-kinase α relative to one or more type I phosphatidylinositol 3-kinases (PI3-kinase) including, e.g., PI3-kinase β, PI3-kinase γ, and PI3-kinase δ.

Selective inhibition of PI3-kinase α can be ascertained by an in vitro or an in vivo method. Any assay known in the art may be used, including without limitation, immunoassays, immunoprecipitation, fluorescence or cell-based assays. In some embodiments, an in vitro assay is used to determine selective inhibition of PI3-kinase α by an assay which measures the activity of the PI3Kα protein relative to the activity of another PI3-kinase such as PI3-kinase β, PI3-kinase γ, and PI3-kinase δ. For example, a time resolved FRET assay that indirectly measures PIP3 product formed by the activity of a PI3-K may be used to determine an IC50 value for a test compound for PI3-kinase α and/or any of the other PI3-kinases.

As used herein, the term "IC50" refers to the half maximal inhibitory concentration of an inhibitor in inhibiting biological or biochemical function. This quantitative measure indicates how much of a particular inhibitor is needed to inhibit a given biological process (or component of a process, i.e. an enzyme, cell, cell receptor or microorganism) by half. In other words, it is the half maximal (50%) inhibitory concentration (IC) of a substance (50% IC, or IC50). EC50 refers to the plasma concentration required for obtaining 50% of a maximum effect in vivo.

Determination of IC50 can be made by determining and constructing a dose-response curve and examining the effect of different concentrations of an inhibitor on reversing agonist activity. In vitro assays that are useful in making these determinations are referred to as "in vitro kinase assays."

In some embodiments, an in vitro kinase assay includes the use of labeled ATP as phosphodonor, and following the kinase reaction the substrate peptide is captured on an appropriate filter. Unreacted labeled ATP and metabolites are resolved from the radioactive peptide substrate by various techniques, involving trichloroacetic acid precipitation and extensive washing. Addition of several positively charged residues allows capture on phosphocellulose paper followed by washing. Radioactivity incorporated into the substrate peptide is detected by scintillation counting. This assay is relatively simple, reasonably sensitive, and the peptide substrate can be adjusted both in terms of sequence and concentration to meet the assay requirements.

Other exemplary kinase assays are detailed in U.S. Pat. No. 5,759,787 and U.S. application Ser. No. 12/728,926, both of which are incorporated herein by reference.

In other embodiments, a cell-based assay is used to ascertain selective inhibition of PI3-kinase α. For example, an inhibitor can be shown to be selective for PI3-kinase α if it selectively down-regulates PI3-kinase signal transduction in cells that express PI3-kinase α, preferably in cells that exhibit abnormally high level or activity of PI3-kinase α. A variety of cells having PI3-kinase α mutations and hence exhibiting such PI3-kinase α abnormalities are known in the art. Non-limiting examples of cell lines harboring such mutations include those that carry point mutations, deletions, substitutions, or translation of nucleic acid sequence of the PI3-kinase α gene. Examples of such cell lines include but are not limited to BT20 (H1047R mutation), MCF-7 (E545K mutation), MDA-MB-361 (E545K mutation), MDA-MB-453 (H1047R mutation), T47D (H1047R mutation), Hec-1A (G1049R mutation) and HCT-116 (H1047R mutation). Other cell lines having mutations in the PI3Kα protein may be used, such as cells harboring mutations in the p85, C2, helical or kinase domains.

In addition, inhibition of PI3-kinase α activity can be determined by a reduction in signal transduction of the PI3-kinase α pathway. A wide variety of readouts can be utilized to establish a reduction of the output of such signaling pathway. Some non-limiting exemplary readouts include (1) a decrease in phosphorylation of Akt at residues, including but not limited to S473 and T308; (2) a decrease in activation of Akt as evidenced by a reduction of phosphorylation of Akt substrates including but not limited to FoxO1/O3a T24/32, GSK3α/β S21/9, and TSC2 T1462; (3) a decrease in phosphorylation of signaling molecules downstream of PI3-kinase α, including but not limited to ribosomal S6 S240/244, 70S6K T389, and 4EBP1 T37/46; (4) inhibition of proliferation of cells including but not limited to normal or neoplastic cells, mouse embryonic fibroblasts, leukemic blast cells, cancer stem cells, and cells that mediate autoimmune reactions; (5) induction of apoptosis of cells or cell cycle arrest; (6) reduction of cell chemotaxis; and (7) an increase in binding of 4EBP1 to eIF4E. The term "eIF4E" refers to a 24-kD eukaryotic translation initiation factor involved in directing ribosomes to the cap structure of mRNAs, having human gene locus 4q21-q25.

In some embodiments, the PI3-kinase α inhibitor selectively inhibits PI3-kinase α relative to one, two or three other type I phosphatidylinositol 3-kinases (PI3-kinases) consisting of PI3-kinase β, PI3-kinase γ, and PI3-kinase δ. In other embodiments, some of the subject inhibitors selectively inhibit PI3-kinase α and PI3-kinase γ as compared to the rest of the type I PI3-kinases. In yet other embodiments, some of the subject inhibitors selectively inhibit PI3-kinase α and PI3-kinase β as compared to the rest of the type I PI3-kinases. In still yet other embodiments, some of the subject inhibitors selectively inhibit PI3-kinase α and PI3-kinase δ as compared to the rest of the type I PI3-kinases.

In some embodiments, the subject methods utilizes a PI3-kinase α inhibitor with an IC50 value of about or less than a predetermined value, as ascertained in an in vitro kinase assay. In some embodiments, the PI3-kinase α inhibitor inhibits PI3-kinase α with an IC50 value of about 1 nM or less, 2 nM or less, 5 nM or less, 7 nM or less, 10 nM or less, 20 nM or less, 30 nM or less, 40 nM or less, 50 nM or less, 60 nM or less, 70 nM or less, 80 nM or less, 90 nM or less, 100 nM or less, 120 nM or less, 140 nM or less, 150 nM or less, 160 nM or less, 170 nM or less, 180 nM or less, 190 nM or less, 200 nM or less, 225 nM or less, 250 nM or less, 275 nM or less, 300 nM or less, 325 nM or less, 350 nM or less, 375 nM or less, 400 nM or less, 425 nM or less, 450 nM or less, 475 nM or less, 500 nM or less, 550 nM or less, 600 nM or less, 650 nM or less, 700 nM or less, 750 nM or less, 800 nM or less, 850 nM or less, 900 nM or less, 950 nM or less, 1 µM or less, 1.2 µM or less, 1.3 µM or less, 1.4 µM or less, 1.5 µM or less, 1.6 µM or less, 1.7 µM or less, 1.8 µM or less, 1.9 µM or less, 2 µM or less, 5 µM or less, 10 µM or less, 15 µM or less, 20 µM or less, 25 µM or less, 30 µM or less, 40 µM or less, 50 µM, 60 µM, 70 µM, 80 µM, 90 µM, 100 µM, 200 µM, 300 µM, 400 µM, or 500 µM, or less.

In some embodiments, the PI3-kinase α inhibitor selectively inhibits PI3-kinase α with an IC50 value that is at least 2, 3, 4, 5, 6, 7, 8, 9, 10, 15, 20, 25, 30, 35, 40, 45, 50, 100, or 1000 times less than its IC50 value against one, two, or three other type I PI3-kinase(s) selected from the group consisting of PI3-kinase β, PI3-kinase γ, and PI3-kinase δ.

In some embodiments, the PI3-kinase α inhibitor selectively inhibits PI3-kinase α with an IC50 value that is less than about 1 nM, 2 nM, 5 nM, 7 nM, 10 nM, 20 nM, 30 nM, 40 nM, 50 nM, 60 nM, 70 nM, 80 nM, 90 nM, 100 nM, 120 nM, 140 nM, 150 nM, 160 nM, 170 nM, 180 nM, 190 nM, 200 nM, 225 nM, 250 nM, 275 nM, 300 nM, 325 nM, 350 nM, 375 nM, 400 nM, 425 nM, 450 nM, 475 nM, 500 nM, 550 nM, 600 nM, 650 nM, 700 nM, 750 nM, 800 nM, 850 nM, 900 nM, 950 nM, 1 µM, 1.2 µM, 1.3 µM, 1.4 µM, 1.5 µM, 1.6 µM, 1.7 µM, 1.8 µM, 1.9 µM, 2 µM, 5 µM, 10 µM, 15 µM, 20 µM, 25 µM, 30 µM, 40 µM, 50 µM, 60 µM, 70 µM, 80 µM, 90 µM, 100 µM, 200 µM, 300 µM, 400 µM, or 500 µM, and said IC50 value is at least 2, 3, 4, 5, 6, 7, 8, 9, 10, 15, 20, 25, 30, 35, 40, 45, 50, 100, or 1000 times less than its IC50 value against one, two or three other type I PI3-kinases selected from the group consisting of PI3-kinase β, PI3-kinase γ, and PI3-kinase δ. In some embodiments, the PI3-kinase α inhibitor inhibits PI3-kinase α with an IC50 value of about 100 nM or less as ascertained in an in vitro kinase assay.

In some instances, the PI3-kinase α inhibitor inhibits PI3-kinase α with an IC50 value of about 200 nM or less as ascertained in an in vitro kinase assay and the IC50 value is at least 5, 10, 15, 20, 25, 50, 100, or 1000 times less than its IC50 value against all other type I PI3-kinases selected from the group consisting of PI3-kinase β, PI3-kinase γ, and PI3-kinase δ. In some embodiments, the PI3-kinase α inhibitor selectively inhibits PI3-kinase α with an IC50 value that is less than about 100 nM, and said IC50 value is at 5, 10, 15, 20, 25, 50, or 100, 1000 times less than its IC50 value against all other type I PI3-kinases selected from the group consisting of PI3-kinase β, PI3-kinase γ, and PI3-kinase δ.

In some instances, the PI3-kinase α inhibitor inhibits PI3-kinase α with an IC50 value of about 50 nM or less as ascertained in an in vitro kinase assay and the IC50 value is at least 5, 10, 15, 20, 25, 50, 100, or 1000 times less than its IC50 value against all other type I PI3-kinases selected from the group consisting of PI3-kinase β, PI3-kinase γ, and PI3-kinase δ.

In some embodiments, the PI3-kinase α inhibitor selectively inhibits PI3-kinase α with an IC50 value that is less than about 20 nM, and said IC50 value is at 5, 10, 15, 20, 25, 50, or 100, 1000 times less than its IC50 value against all other type I PI3-kinases selected from the group consisting of PI3-kinase β, PI3-kinase γ, and PI3-kinase δ.

In some embodiments, the PI3-kinase α inhibitor selectively inhibits PI3-kinase α with an IC50 value that is less than about 20 nM, and said IC50 value is at 5, 10, 15, 20, 25, 50, or 100, 1000 times less than its IC50 value against all other type I PI3-kinases selected from the group consisting of PI3-kinase β, PI3-kinase γ, and PI3-kinase δ.

In some instances, the PI3-kinase α inhibitor inhibits PI3-kinase α with an IC50 value of about 20 nM or less as ascertained in an in vitro kinase assay and the IC50 value is at least 100 times less than its IC50 value against all other type I PI3-kinases selected from the group consisting of PI3-kinase β, PI3-kinase γ, and PI3-kinase δ.

Alternatively, the PI3-kinase α inhibitor inhibits PI3-kinase α with an EC50 value of about 10 µM or less, 5 µM or less, 2.5 µM or less, 1 µM or less, 500 nM or less, 100 nM or less, 75 nM or less, 50 nM or less, 25 nM or less, 10 nM or less, 5 nM or less, 1 nM or less, 500 pM or less, or 100 pM or less as ascertained in an in vitro kinase assay.

In some embodiments, the PI3-kinase α inhibitor selectively inhibits PI3-kinase α with an EC50 value that is at least 5, 10, 15, 20, 25, 50, 100, or 1000 times less than its EC50 value against one, two or three other type I PI3-kinases selected from the group consisting of PI3-kinase β, PI3-kinase γ, and PI3-kinase δ.

In some embodiments, the PI3-kinase α inhibitor inhibits PI3-kinase α with an EC50 value of about 10 µM or less, 5 µM or less, 2.5 µM or less, 1 µM or less, 500 nM or less, 100 nM or less, 75 nM or less, 50 nM or less, 25 nM or less, 10 nM or less, 5 nM or less, 1 nM or less, 500 pM or less, or 100 pM or less as ascertained in an in vitro kinase assay, and such EC50 value is at least 5, 10, 15, 20, 25, 50, or 100, 1000 times less than its EC50 value against one, two or three other type I PI3-kinases selected from the group consisting of PI3-kinase β, PI3-kinase γ, and PI3-kinase δ.

The mTOR inhibitor utilized in the subject methods is typically highly selective for the target molecule. In one aspect, the mTOR inhibitor binds to and directly inhibits both mTORC1 and mTORC2. Such ability can be ascertained using any method known in the art or described herein. For example, inhibition of mTorC1 and/or mTorC2 activity can be determined by a reduction in signal transduction of the PI3K/Akt/mTor pathway. A wide variety of readouts can be utilized to establish a reduction of the output of such signaling pathway. Some non-limiting exemplary readouts include (1) a decrease in phosphorylation of Akt at residues, including but not limited to S473 and T308; (2) a decrease in activation of Akt as evidenced by a reduction of phosphorylation of Akt substrates including but not limited to FoxO1/O3a T24/32, GSK3α/β S21/9, and TSC2 T1462; (3) a decrease in phosphorylation of signaling molecules downstream of mTor, including but not limited to ribosomal S6 S240/244, 70S6K T389, and 4EBP1 T37/46; (4) inhibition of proliferation of cells including but not limited to normal or neoplastic cells, mouse embryonic fibroblasts, leukemic blast cells, cancer stem cells, and cells that mediate autoimmune reactions; (5) induction of apoptosis of cells or cell cycle arrest; (6) reduction of cell chemotaxis; and (7) an increase in binding of 4EBP1 to eIF4E.

mTor exists in two types of complexes, mTorC1 containing the raptor subunit and mTorC2 containing rictor. As known in the art, "rictor" refers to a cell growth regulatory protein having human gene locus 5p13.1. These complexes are regulated differently and have a different spectrum of substrates. For instance, mTorC1 phosphorylates S6 kinase (S6K) and 4EBP1, promoting increased translation and ribosome biogenesis to facilitate cell growth and cell cycle progression. S6K also acts in a feedback pathway to attenuate PI3K/Akt activation. Thus, inhibition of mTorC1 (e.g. by a biologically active agent as discussed herein) results in activation of 4EBP1, resulting in inhibition of (e.g. a decrease in) RNA translation.

mTorC2 is generally insensitive to rapamycin and selective inhibitors and is thought to modulate growth factor signaling by phosphorylating the C-terminal hydrophobic motif of some AGC kinases such as Akt. In many cellular contexts, mTorC2 is required for phosphorylation of the S473 site of Akt. Thus, mTorC1 activity is partly controlled by Akt whereas Akt itself is partly controlled by mTorC2.

Growth factor stimulation of PI3K causes activation of Akt by phosphorylation at the two key sites, S473 and T308. It has been reported that full activation of Akt requires phosphorylation of both S473 and T308Active. Akt promotes cell survival and proliferation in many ways including suppressing apoptosis, promoting glucose uptake, and modifying cellular metabolism. Of the two phosphorylation sites on Akt, activation loop phosphorylation at T308, mediated by PDK1, is believed to be indispensable for kinase activity, while hydrophobic motif phosphorylation at S473 enhances Akt kinase activity.

Selective mTor inhibition may also be determined by expression levels of the mTor genes, its downstream signaling genes (for example by RT-PCR), or expression levels of the proteins (for example by immunocytochemistry, immunohistochemistry, Western blots) as compared to other PI3-kinases or protein kinases.

Cell-based assays for establishing selective inhibition of mTorC1 and/or mTorC2 can take a variety of formats. This generally will depend on the biological activity and/or the signal transduction readout that is under investigation. For example, the ability of the agent to inhibit mTorC1 and/or mTorC2 to phosphorylate the downstream substrate(s) can be determined by various types of kinase assays known in the art. Representative assays include but are not limited to immunoblotting and immunoprecipitation with antibodies such as anti-phosphotyrosine, anti-phosphoserine or anti-phosphothreonine antibodies that recognize phosphorylated proteins. Alternatively, antibodies that specifically recognize a particular phosphorylated form of a kinase substrate (e.g. anti-phospho AKT S473 or anti-phospho AKT T308) can be used. In addition, kinase activity can be detected by high throughput chemiluminescent assays such as AlphaScreen™ (available from Perkin Elmer) and eTag™ assay (Chan-Hui, et al. (2003) *Clinical Immunology* 111: 162-174). In another aspect, single cell assays such as flow cytometry as described in the phosflow experiment can be used to measure phosphorylation of multiple downstream mTOR substrates in mixed cell populations.

One advantage of the immunoblotting and phosflow methods is that the phosphorylation of multiple kinase substrates can be measured simultaneously. This provides the advantage that efficacy and selectivity can be measured at the same time. For example, cells may be contacted with an mTOR inhibitor at various concentrations and the phosphorylation levels of substrates of both mTOR and other kinases can be measured. In one aspect, a large number of kinase substrates are assayed in what is termed a "comprehensive kinase survey." Selective mTOR inhibitors are expected to inhibit phosphorylation of mTOR substrates without inhibiting phosphorylation of the substrates of other kinases. Alternatively, selective mTOR inhibitors may inhibit phosphorylation of substrates of other kinases through anticipated or unanticipated mechanisms such as feedback loops or redundancy.

Effect of inhibition of mTorC1 and/or mTorC2, or PI3-kinase α can be established by cell colony formation assay or other forms of cell proliferation assay. A wide range of cell proliferation assays are available in the art, and many of which are available as kits. Non-limiting examples of cell proliferation assays include testing for tritiated thymidine uptake assays, BrdU (5'-bromo-2'-deoxyuridine) uptake (kit marketed by Calibochem), MTS uptake (kit marketed by Promega), MTT uptake (kit marketed by Cayman Chemical), CyQUANT® dye uptake (marketed by Invitrogen).

Apoptosis and cell cycle arrest analysis can be performed with any methods exemplified herein as well other methods known in the art. Many different methods have been devised to detect apoptosis. Exemplary assays include but are not limited to the TUNEL (TdT-mediated dUTP Nick-End Labeling) analysis, ISEL (in situ end labeling), and DNA laddering analysis for the detection of fragmentation of DNA in populations of cells or in individual cells, Annexin-V analysis that measures alterations in plasma membranes, detection of apoptosis related proteins such p53 and Fas.

A cell-based assay typically proceeds with exposing the target cells (e.g., in a culture medium) to a test compound which is a potential mTorC1 and/or mTorC2 selective inhibitor, or a PI3-kinase α inhibitor and then assaying for readout under investigation. Depending on the nature of the candidate mTor inhibitors or PI3-kinase α inhibitors, they can directly be added to the cells or in conjunction with carriers. For instance, when the agent is nucleic acid, it can be added to the cell culture by methods well known in the art, which include without limitation calcium phosphate precipitation, microinjection or electroporation. Alternatively, the nucleic acid can be incorporated into an expression or insertion vector for incorporation into the cells. Vectors that contain both a promoter and a cloning site into which a polynucleotide can be operatively linked are well known in the art. Such vectors are capable of transcribing RNA in vitro or in vitro, and are commercially available from sources such as Stratagene (La Jolla, Calif.) and Promega Biotech (Madison, Wis.). In order to optimize expression and/or in vitro transcription, it may be necessary to remove, add or alter 5' and/or 3' untranslated portions of the clones to eliminate extra, potential inappropriate alternative translation initiation codons or other sequences that may interfere with or reduce expression, either at the level of transcription or translation. Alternatively, consensus ribosome binding sites can be inserted immediately 5' of the start codon to enhance expression. Examples of vectors are viruses, such as baculovirus and retrovirus, bacteriophage, adenovirus, adeno-associated virus, cosmid, plasmid, fungal vectors and other recombination vehicles typically used in the art which have been described for expression in a variety of eukaryotic and prokaryotic hosts, and may be used for gene therapy as well as for simple protein expression. Among these are several non-viral vectors, including DNA/liposome complexes, and targeted viral protein DNA complexes. To enhance delivery to a cell, the nucleic acid or proteins of this invention can be conjugated to antibodies or binding fragments thereof which bind cell surface antigens. Liposomes that also comprise a targeting antibody or fragment thereof can be used in the methods of this invention. Other biologically acceptable carriers can be utilized, including those described in, for example, REMINGTON'S PHARMACEUTICAL SCIENCES, 19th Ed. (2000), in conjunction with the subject compounds.

The subject agents can also be utilized to inhibit phosphorylation of both Akt (S473) and Akt (T308) in a cell. Accordingly, the present invention provides a method comprises the step of contacting a cell with an effective amount of such biologically active agent such that Akt phosphorylation at residues S473 and T308 is simultaneously inhibited. In one aspect, the biologically active agent inhibits phosphorylation of S473 of Akt more effectively than phosphorylation of T308 of Akt when tested at a comparable molar concentration, preferably at an identical molar concentration.

Inhibition of Akt phosphorylation can be determined using any methods known in the art or described herein. Representative assays include but are not limited to immunoblotting and immunoprecipitation with antibodies such as anti-phosphotyrosine antibodies that recognize the specific phosphorylated proteins. Cell-based ELISA kit quantifies the amount of activated (phosphorylated at S473) Akt relative to total Akt protein is also available (SuperArray Biosciences).

In practicing the subject methods, any cells that express PI3-kinase α, mTorC1, mTorC2 and/or Akt can be utilized. Non-limiting examples of specific cell types whose proliferation can be inhibited include fibroblast, cells of skeletal tissue (bone and cartilage), cells of epithelial tissues (e.g. liver, lung, breast, skin, bladder and kidney), cardiac and smooth muscle cells, neural cells (glia and neurones), endocrine cells (adrenal, pituitary, pancreatic islet cells), melanocytes, and many different types of haemopoietic cells (e.g., cells of B-cell or T-cell lineage, and their corresponding stem cells, lymphoblasts). Also of interest are cells exhibiting a neoplastic propensity or phenotype. Of particular interest is the type of cells that differentially expresses (over-expresses or under-expresses) a disease-causing gene. The types of diseases involving abnormal functioning of genes include but are not limited to autoimmune diseases, cancer, obesity, hypertension, diabetes, neuronal and/or muscular degenerative diseases, cardiac diseases, endocrine disorders, and any combinations thereof.

In some embodiments, the mTOR inhibitor inhibits both mTORC1 and mTORC2 with an IC50 value of about 1 nM, 2 nM, 5 nM, 7 nM, 10 nM, 20 nM, 30 nM, 40 nM, 50 nM, 60 nM, 70 nM, 80 nM, 90 nM, 100 nM, 120 nM, 140 nM, 150 nM, 160 nM, 170 nM, 180 nM, 190 nM, 200 nM, 225 nM, 250 nM, 275 nM, 300 nM, 325 nM, 350 nM, 375 nM, 400 nM, 425 nM, 450 nM, 475 nM, 500 nM, 550 nM, 600 nM, 650 nM, 700 nM, 750 nM, 800 nM, 850 nM, 900 nM, 950 nM, 1 µM, 1.2 µM, 1.3 µM, 1.4 µM, 1.5 µM, 1.6 µM, 1.7 µM, 1.8 µM, 1.9 µM, 2 µM, 5 µM, 10 µM, 15 µM, 20 µM, 25 µM, 30 µM, 40 µM, 50 µM, 60 µM, 70 µM, 80 µM, 90 µM, 100 µM, 200 µM, 300 µM, 400 µM, or 500 µM or less as ascertained in an in vitro kinase assay, and said IC50 value is at least 2, 3, 4, 5, 6, 7, 8, 9, 10, 15, 20, 25, 30, 35, 40, 45, 50, 100, or 1000 times less than its IC50 value against all other type I PI3-kinases selected from the group consisting of PI3-kinase α, PI3-kinase β, PI3-kinase γ, and PI3-kinase δ. For example, the mTOR inhibitor inhibits both mTORC1 and mTORC2 with an IC50 value of about 200, 100, 75, 50, 25, 10, 5, 1 or 0.5 nM or less as ascertained in an in vitro kinase assay. In one instance, the mTOR inhibitor inhibits both mTORC1 and mTORC2 with an IC50 value of about 100 nM or less as ascertained in an in vitro kinase assay. Alternatively, the mTOR inhibitor inhibits both mTORC1 and mTORC2 with an IC50 value of about 10 nM or less as ascertained in an in vitro kinase assay.

In some embodiments, the present invention provides the use of an mTOR inhibitor, wherein the mTOR inhibitor directly binds to and inhibits both mTORC1 and mTORC2 with an IC50 value of about or less than a predetermined value, as ascertained in an in vitro kinase assay. In some embodiments, the mTOR inhibitor inhibits both mTORC1 and mTORC2 with an IC50 value of about 1 nM or less, 2 nM or less, 5 nM or less, 7 nM or less, 10 nM or less, 20 nM or less, 30 nM or less, 40 nM or less, 50 nM or less, 60 nM or less, 70 nM or less, 80 nM or less, 90 nM or less, 100 nM or less, 120 nM or less, 140 nM or less, 150 nM or less, 160 nM or less, 170 nM or less, 180 nM or less, 190 nM or less, 200 nM or less, 225 nM or less, 250 nM or less, 275 nM or less, 300 nM or less, 325 nM or less, 350 nM or less, 375 nM or less, 400 nM or less, 425 nM or less, 450 nM or less, 475 nM or less, 500 nM or less, 550 nM or less, 600 nM or less, 650 nM or less, 700 nM or less, 750 nM or less, 800 nM or less, 850 nM or less, 900 nM or less, 950 nM or less, 1 µM or less, 1.2 µM or less, 1.3 µM or less, 1.4 µM or less, 1.5 µM or less, 1.6 µM or less, 1.7 µM or less, 1.8 µM or less, 1.9 µM or less, 2 µM or less, 5 µM or less, 10 µM or less, 15 µM or less, 20 µM or less, 25 µM or less, 30 µM or less, 40 µM or less, 50 µM or less, 60 µM or less, 70 µM or less, 80 µM or less, 90 µM or less, 100 µM or less, 200 µM or less, 300 µM or less, 400 µM or less, or 500 µM or less.

In some embodiments, the mTOR inhibitor inhibits both mTORC1 and mTORC2 with an IC50 value of about 1 nM or less, 2 nM or less, 5 nM or less, 7 nM or less, 10 nM or less, 20 nM or less, 30 nM or less, 40 nM or less, 50 nM or less, 60 nM or less, 70 nM or less, 80 nM or less, 90 nM or less, 100 nM or less, 120 nM or less, 140 nM or less, 150 nM or less, 160 nM or less, 170 nM or less, 180 nM or less, 190 nM or less, 200 nM or less, 225 nM or less, 250 nM or less, 275 nM or less, 300 nM or less, 325 nM or less, 350 nM or less, 375 nM or less, 400 nM or less, 425 nM or less, 450 nM or less, 475 nM or less, 500 nM or less, 550 nM or less, 600 nM or less, 650 nM or less, 700 nM or less, 750 nM or less, 800 nM or less, 850 nM or less, 900 nM or less, 950 nM or less, 1 µM or less, 1.2 µM or less, 1.3 µM or less, 1.4 µM or less, 1.5 µM or less, 1.6 µM or less, 1.7 µM or less, 1.8 µM or less, 1.9 µM or less, 2 µM or less, 5 µM or less, 10 µM or less, 15 µM or less, 20 µM or less, 25 µM or less, 30 µM or less, 40 µM or less, 50 µM or less, 60 µM or less, 70 µM or less, 80 µM or less, 90 µM or less, 100 µM or less, 200 µM or less, 300 µM or less, 400 µM or less, or 500 µM or less, and the mTOR inhibitor is substantially inactive against one or more types I PI3-kinases selected from the group consisting of PI3-kinase α, PI3-kinase β, PI3-kinase γ, and PI3-kinase δ. In some embodiments, the mTOR inhibitor inhibits both mTORC1 and mTORC2 with an IC50 value of about 10 nM or less as ascertained in an in vitro kinase assay, and the mTOR inhibitor is substantially inactive against one or more types I PI3-kinases selected from the group consisting of PI3-kinase α, PI3-kinase β, PI3-kinase γ, and PI3-kinase δ.

As used herein, the terms "substantially inactive" refers to an inhibitor that inhibits the activity of its target by less than approximately 1%, 5%, 10%, 15% or 20% of its maximal activity in the absence of the inhibitor, as determined by an in vitro enzymatic assay (e.g. in vitro kinase assay).

In other embodiments, the mTOR inhibitor inhibits both mTORC1 and mTORC2 with an IC50 value of about 1000, 500, 100, 75, 50, 25, 10, 5, 1, or 0.5 nM or less as ascertained in an in vitro kinase assay, and said IC50 value is at least 2, 5, 10, 15, 20, 50, 100 or 100 times less than its IC50 value against all other type I PI3-kinases selected from the group consisting of PI3-kinase α, PI3-kinase β, PI3-kinase γ, and PI3-kinase δ. For example, the mTOR inhibitor inhibits both mTORC1 and mTORC2 with an IC50 value of about 100 nM or less as ascertained in an in vitro kinase assay, and said IC50 value is at least 5 times less than its IC50 value against all other type I PI3-kinases selected from the group consisting of PI3-kinase α, PI3-kinase β, PI3-kinase γ, and PI3-kinase δ.

In some embodiments, the mTOR inhibitor inhibits both mTORC1 and mTORC2 with an IC50 value of about 100 nM or less as ascertained in an in vitro kinase assay, and said IC50 value is at least 5 times less than its IC50 value against all other type I PI3-kinases selected from the group consisting of PI3-kinase α, PI3-kinase β, PI3-kinase γ, and PI3-kinase δ.

In some embodiments, the mTOR inhibitor utilized in the subject methods inhibits one of mTORC1 and mTORC2 selectively with an IC50 value of about 1000, 500, 100, 75, 50, 25, 10, 5, 1, or 0.5 nM or less as ascertained in an in vitro kinase. For example, the mTOR inhibitor utilized in the subject methods inhibits mTORC1 selectively with an IC50 value of about 1000, 500, 100, 75, 50, 25, 10, 5, 1, or 0.5 nM or less as ascertained in an in vitro kinase. For example, rapamycin and rapamycin derivatives or analogues have been shown to primarily inhibit mTORC1 and not mTORC2. Suitable mTORC1 inhibitors compounds include, for example, sirolimus (rapamycin), deforolimus (AP23573, MK-8669), everolimus (RAD-001), temsirolimus (CCI-779), zotarolimus (ABT-578), and biolimus A9 (umirolimus).

PI3-kinase α inhibitors or mTOR inhibitors suitable for use in the subject methods can be selected from a variety types of molecules. For example, an inhibitor can be biological or chemical compound such as a simple or complex organic or inorganic molecule, peptide, peptide mimetic, protein (e.g. antibody), liposome, or a polynucleotide (e.g. small interfering RNA, microRNA, anti-sense, aptamer, ribozyme, or triple helix). Some exemplary classes of chemical compounds suitable for use in the subject methods are detailed in the sections below.

The advantages of selective inhibition of a cellular target as a way of treating a disease condition mediated by such target are manifold. Because healthy cells depend on the signaling pathways that are activated in cancers for survival, inhibition of these pathways during cancer treatment can cause harmful side effects. In order for a method of treating cancer to be successful without causing excessive damage to healthy cells, a very high degree of specificity in targeting the aberrant signaling component or components is desirable. Moreover, cancer cells may depend on overactive signaling for their survival (known as the oncogene addiction hypothesis). In this way, cancer cells are frequently observed to adapt to drug inhibition of an aberrant signaling component by selecting for mutations in the same pathway that overcome the effect of the drug. Therefore, cancer therapies may be more successful in overcoming the problem of drug resistance if they target a signaling pathway as a whole, or target more than one component within a signaling pathway.

Without being bound by theory, selective inhibition of PI3-kinase α provides a more targeted treatment to a disease condition mediated by PI3-kinase without disrupting one or more pathways that are implicated by one or more other type I phosphatidylinositol 3-kinases, namely PI3-kinase β, PI3-kinase γ, and PI3-kinase δ.

Some signaling pathways that contain PI3K and mTOR are illustrated in FIG. 1. One major downstream effector of PI3K and mTOR signaling is the Akt serine/threonine kinase. Akt possesses a protein domain known as a PH domain, or Pleckstrin Homology domain, which binds to phosphoinositides with high affinity. In the case of the PH domain of Akt, it binds either PIP3 (phosphatidylinositol (3,4,5)-trisphosphate, PtdIns(3,4,5)P3) or PIP2 (phosphatidylinositol (3,4)-bisphosphate, PtdIns(3,4)P2). PI3K phosphorylates PIP2 in response to signals from chemical messengers, such as ligand binding to G protein-coupled receptors or receptor tyrosine kinases. Phosphorylation by PI3K converts PIP2 to PIP3, recruiting Akt to the cell membrane where it is phosphorylated at serine 473 (S473) by mTORC2. Phosphorylation of Akt at another site, threonine 308 (T308), is not directly dependent on mTORC2, but requires PI3K activity. Therefore, PI3K activity towards Akt can be isolated from mTOR activity by examining Akt threonine 308 phosphorylation status in cells lacking mTORC2 activity.

The subject methods are useful for treating a disease condition associated with PI3-kinase α and/or mTOR. Any disease condition that results directly or indirectly from an abnormal activity or expression level of PI3-kinase α and/or mTOR can be an intended disease condition.

A vast diversity of disease conditions associated with PI3-kinase α and/or mTOR have been reported. PI3-kinase α has been implicated, for example, in a variety of human cancers. Angiogenesis has been shown to selectively require the α isoform of PI3K in the control of endothelial cell migration. (Graupera et al, Nature 2008; 453; 662-6). Mutations in the gene coding for PI3K α or mutations which lead to upregulation of PI3K α are believed to occur in many human cancers such as lung, stomach, endometrial, ovarian, bladder, breast, colon, brain and skin cancers. Often, mutations in the gene coding for PI3K α are point mutations clustered within several hotspots in helical and kinase domains, such as E542K, E545K, and H1047R. Many of these mutations have been shown to be oncogenic gain-of-function mutations. Because of the high rate of PI3K α mutations, targeting of this pathway provides valuable therapeutic opportunities. While other PI3K isoforms such as PI3K δ or PI3K γ are expressed primarily in hematopoietic cells, PI3K α, along with PI3K β, is expressed constitutively.

Disease conditions associated with PI3-kinase α and/or mTOR can also be characterized by abnormally high level of activity and/or expression of downstream messengers of PI3-kinase α. For example, proteins or messengers such as PIP2, PIP3, PDK, Akt, PTEN, PRAS40, GSK-313, p21, p27 may be present in abnormal amounts which can be identified by any assays known in the art.

Deregulation of the mTOR pathway is emerging as a common theme in diverse human diseases and as a consequence drugs that target mTOR have therapeutic value. The diseases associated with deregulation of mTORC1 include, but are not limited to, tuberous sclerosis complex (TSC) and lymphangioleiomyomatosis (LAM), both of which are caused by mutations in TSC1 or TSC2 tumor suppressors. Patients with TSC develop benign tumors that when present in brain, however, can cause seizures, mental retardation and death. LAM is a serious lung disease Inhibition of mTORC1 may help patients with Peutz-Jeghers cancer-prone syndrome caused by the LKB 1 mutation. mTORC1 may also have role in the genesis of sporadic cancers. Inactivation of several tumor suppressors, in particular PTEN, p53, VHL and NF1, has been linked to mTORC1 activation. Rapamycin and its analogues (eg CCI-779, RAD001 and AP23573) inhibit TORC1 and have shown moderate anti-cancer activity in phase II clinical trials. However, due to the negative signal from S6K1 to the insulin/PI3K/Akt pathway, it is important to note that inhibitors of mTORC1, like rapalogs, can activate PKB/Akt. If this effect persists with chronic rapamycin treatment, it may provide cancer cells with an increased survival signal that may be clinically undesirable. The PI3K/Akt pathway is activated in many cancers. Activated Akt regulates cell survival, cell proliferation and metabolism by phosphorylating proteins such as BAD, FOXO, NF-KB, p21Cip1, p27Kip1, GSK313 and others. Akt might also promote cell growth by phosphorylating TSC2. Akt activation probably promotes cellular transformation and resistance to apoptosis by collectively promoting growth, proliferation and survival, while inhibiting apoptotic pathways. The combination of an inhibitor of mTORC1 and mTORC2 and a PI3-kinase α inhibitor is beneficial for treatment of tumors with elevated Akt phosphorylation, and should down-regulate cell growth, cell survival and cell proliferation.

Where desired, the subject to be treated is tested prior to treatment using a diagnostic assay to determine the sensitivity of tumor cells to a PI3Kα kinase inhibitor. Any method known in the art that can determine the sensitivity of the tumor cells of a subject to a PI3Kα kinase inhibitor can be employed. Where the subject is tested prior to treatment using a diagnostic assay to determine the sensitivity of tumor cells to an PI3Kα kinase inhibitor, in one embodiment, when the subject is identified as one whose tumor cells are predicted to have low sensitivity to an PI3Kα kinase inhibitor as a single agent, are likely to display enhanced sensitivity in the presence of an mTOR inhibitor, or vice versa, when the subject is administered, simultaneously or sequentially, a therapeutically effective amount of a combination of an PI3Kα kinase inhibitor and an mTOR inhibitor. In another embodiment, when the subject is identified as one whose tumor cells are predicted to have high sensitivity to an PI3Kα kinase inhibitor as a single agent, but may also display enhanced sensitivity in the presence of an mTOR inhibitor based on the results described herein, the subject is administered, simultaneously or sequentially, a therapeutically effective amount of a combination of an PI3Kα kinase inhibitor and an mTOR inhibitor. In these methods one or more additional anti-cancer agents or treatments can be co-administered simultaneously or sequentially with the PI3Kα kinase inhibitor and mTOR inhibitor, as judged to be appropriate by the administering physician given the prediction of the likely responsiveness of the subject to the combination of PI3Kα kinase inhibitor and mTOR inhibitor, in combination with any additional circumstances pertaining to the individual subject.

Accordingly, in some embodiments, the present invention provides for a method comprising: (a) determining the presence in a subject of a mutation in PI3-kinase α that is associated with a disease condition mediated by PI3-kinase α; and (b) administering to said subject a pharmaceutical composition of the invention.

In yet another embodiment, the present invention provides for a method of inhibiting phosphorylation of both Akt (S473) and Akt (T308) in a cell, comprising contacting a cell with an effective amount of a PI3-kinase α inhibitor and an mTOR inhibitor, biologically active agent that selectively inhibits both mTORC1 and mTORC2 activity relative to one or more type I phosphatidylinositol 3-kinases (PI3-kinase) as ascertained by a cell-based assay or an in vitro kinase assay, wherein the PI3-kinase α inhibitor exhibits selective inhibition of PI3-kinase α relative to one or more type I phosphatidylinositol 3-kinases (PI3-kinase) ascertained by an in vitro kinase assay, wherein the one or more type I PI3-kinase is selected from the group consisting of PI3-kinase β, PI3-kinase γ, and PI3-kinase δ.

The data presented in the Examples herein below demonstrate that the anti-tumor effects of a combination of an mTOR inhibitor and PI3K α inhibitor are superior to the anti-tumor effects of either inhibitor by itself, and co-administration of an mTOR inhibitor with a PI3K α inhibitor can be effective for treatment of a neoplastic condition associated with PI3-kinase α and/or mTOR. Non-limiting examples of such conditions include but are not limited to Acanthoma, Acinic cell carcinoma, Acoustic neuroma, Acral lentiginous melanoma, Acrospiroma, Acute eosinophilic leukemia, Acute lymphoblastic leukemia, Acute megakaryoblastic leukemia, Acute monocytic leukemia, Acute myeloblastic leukemia with maturation, Acute myeloid dendritic cell leukemia, Acute myeloid leukemia, Acute promyelocytic leukemia, Adamantinoma, Adenocarcinoma, Adenoid cystic carcinoma, Adenoma, Adenomatoid odontogenic tumor, Adrenocortical carcinoma, Adult T-cell leukemia, Aggressive NK-cell leukemia, AIDS-Related Cancers, AIDS-related lymphoma, Alveolar soft part sarcoma, Ameloblastic fibroma, Anal cancer, Anaplastic large cell lymphoma, Anaplastic thyroid cancer, Angioimmunoblastic T-cell lymphoma, Angiomyolipoma, Angiosarcoma, Appendix cancer, Astrocytoma, Atypical teratoid rhabdoid tumor, Basal cell carcinoma, Basal-like carcinoma, B-cell leukemia, B-cell lymphoma, Bellini duct carcinoma, Biliary tract cancer, Bladder cancer, Blastoma, Bone Cancer, Bone tumor, Brain Stem Glioma, Brain Tumor, Breast Cancer, Brenner tumor, Bronchial Tumor, Bronchioloalveolar carcinoma, Brown tumor, Burkitt's lymphoma, Cancer of Unknown Primary Site, Carcinoid Tumor, Carcinoma, Carcinoma in situ, Carcinoma of the penis, Carcinoma of Unknown Primary Site, Carcinosarcoma, Castleman's Disease, Central Nervous System Embryonal Tumor, Cerebellar Astrocytoma, Cerebral Astrocytoma, Cervical Cancer, Cholangiocarcinoma, Chondroma, Chondrosarcoma, Chordoma, Choriocarcinoma, Choroid plexus papilloma, Chronic Lymphocytic Leukemia, Chronic monocytic leukemia, Chronic myelogenous leukemia, Chronic Myeloproliferative Disorder, Chronic neutrophilic leukemia, Clear-cell tumor, Colon Cancer, Colorectal cancer, Craniopharyngioma, Cutaneous T-cell lymphoma, Degos disease, Dermatofibrosarcoma protuberans, Dermoid cyst, Desmoplastic small round cell tumor, Diffuse large B cell lymphoma, Dysembryoplastic neuroepithelial tumor, Embryonal carcinoma, Endodermal sinus tumor, Endometrial cancer, Endometrial Uterine Cancer, Endometrioid tumor, Enteropathy-associated T-cell lymphoma, Ependymoblastoma, Ependymoma, Epithelioid sarcoma, Erythroleukemia, Esophageal cancer, Esthesioneuroblastoma, Ewing Family of Tumor, Ewing Family Sarcoma, Ewing's sarcoma, Extracranial Germ Cell Tumor, Extragonadal Germ Cell Tumor, Extrahepatic Bile Duct Cancer, Extramammary Paget's disease, Fallopian tube cancer, Fetus in fetu, Fibroma, Fibrosarcoma, Follicular lymphoma, Follicular thyroid cancer, Gallbladder Cancer, Gallbladder cancer, Ganglioglioma, Ganglioneuroma, Gastric Cancer, Gastric lymphoma, Gastrointestinal cancer, Gastrointestinal Carcinoid Tumor, Gastrointestinal Stromal Tumor, Gastrointestinal stromal tumor, Germ cell tumor, Germinoma, Gestational choriocarcinoma, Gestational Trophoblastic Tumor, Giant cell tumor of bone, Glioblastoma multiforme, Glioma, Gliomatosis cerebri, Glomus tumor, Glucagonoma, Gonadoblastoma, Granulosa cell tumor, Hairy Cell Leukemia, Hairy cell leukemia, Head and Neck Cancer, Head and neck cancer, Heart cancer, Hemangioblastoma, Hemangiopericytoma, Hemangiosarcoma, Hematological malignancy, Hepatocellular carcinoma, Hepatosplenic T-cell lymphoma, Hereditary breast-ovarian cancer syndrome, Hodgkin Lymphoma, Hodgkin's lymphoma, Hypopharyngeal Cancer, Hypothalamic Glioma, Inflammatory breast cancer, Intraocular Melanoma, Islet cell carcinoma, Islet Cell Tumor, Juvenile myelomonocytic leukemia, Kaposi Sarcoma, Kaposi's sarcoma, Kidney Cancer, Klatskin tumor, Krukenberg tumor, Laryngeal Cancer, Laryngeal cancer, Lentigo maligna melanoma, Leukemia, Leukemia, Lip and Oral Cavity Cancer, Liposarcoma, Lung cancer, Luteoma, Lymphangioma, Lymphangiosarcoma, Lymphoepithelioma, Lymphoid leukemia, Lymphoma, Macroglobulinemia, Malignant Fibrous Histiocytoma, Malignant fibrous histiocytoma, Malignant Fibrous Histiocytoma of Bone, Malignant Glioma, Malignant Mesothelioma, Malignant peripheral nerve sheath tumor, Malignant rhabdoid tumor, Malignant triton tumor, MALT lymphoma, Mantle cell lymphoma, Mast cell leukemia, Mediastinal germ cell tumor, Mediastinal tumor, Medullary thyroid cancer, Medulloblastoma, Medulloblastoma, Medulloepithelioma, Melanoma, Melanoma, Meningioma, Merkel Cell Carcinoma, Mesothelioma, Mesothelioma, Metastatic Squamous Neck Cancer with Occult Primary, Metastatic urothelial carcinoma, Mixed Mullerian tumor, Monocytic leukemia, Mouth Cancer, Mucinous tumor, Multiple Endocrine Neoplasia Syndrome, Multiple Myeloma, Multiple myeloma, Mycosis Fungoides, Mycosis fungoides, Myelodysplastic Disease, Myelodysplastic Syndromes, Myeloid leukemia, Myeloid sarcoma, Myeloproliferative Disease, Myxoma, Nasal Cavity Cancer, Nasopharyngeal Cancer, Nasopharyngeal carcinoma, Neoplasm, Neurinoma, Neuroblastoma, Neuroblastoma, Neurofibroma, Neuroma, Nodular melanoma, Non-Hodgkin Lymphoma, Non-Hodgkin lymphoma, Nonmelanoma Skin Cancer, Non-Small Cell Lung Cancer, Ocular oncology, Oligoastrocytoma, Oligodendroglioma, Oncocytoma, Optic nerve sheath meningioma, Oral Cancer, Oral cancer, Oropharyngeal Cancer, Osteosarcoma, Osteosarcoma, Ovarian Cancer, Ovarian cancer, Ovarian Epithelial Cancer, Ovarian Germ Cell Tumor, Ovarian Low Malignant Potential Tumor, Paget's disease of the breast, Pancoast tumor, Pancreatic Cancer, Pancreatic cancer, Papillary thyroid cancer, Papillomatosis, Paraganglioma, Paranasal Sinus Cancer, Parathyroid Cancer, Penile Cancer, Perivascular epithelioid cell tumor, Pharyngeal Cancer, Pheochromocytoma, Pineal Parenchymal Tumor of Intermediate Differentiation, Pineoblastoma, Pituicytoma, Pituitary adenoma, Pituitary tumor, Plasma Cell Neoplasm, Pleuropulmonary blastoma, Polyembryoma, Precursor T-lymphoblastic lymphoma, Primary central nervous system lymphoma, Primary effusion lymphoma, Primary Hepatocellular Cancer, Primary Liver Cancer, Primary peritoneal cancer, Primitive neuroectodermal tumor, Prostate cancer, Pseudomyxoma peritonei, Rectal Cancer, Renal cell carcinoma, Respiratory Tract Carcinoma Involving the NUT Gene on Chromosome 15, Retinoblastoma, Rhabdomyoma, Rhabdomyosarcoma, Richter's transformation, Sacrococcygeal teratoma, Salivary Gland Cancer, Sarcoma, Schwannomatosis, Sebaceous gland carcinoma, Secondary neoplasm, Seminoma, Serous tumor, Sertoli-Leydig cell tumor, Sex cord-stromal tumor, Sezary Syndrome, Signet ring cell carcinoma, Skin Cancer, Small blue round cell tumor, Small cell carcinoma, Small Cell Lung Cancer, Small cell lymphoma, Small intestine cancer, Soft tissue sarcoma, Somatostatinoma, Soot wart, Spinal Cord Tumor, Spinal tumor, Splenic marginal zone lymphoma, Squamous cell carcinoma, Stomach cancer, Superficial spreading melanoma, Supratentorial Primitive Neuroectodermal Tumor, Surface epithelial-stromal tumor, Synovial sarcoma, T-cell acute lymphoblastic leukemia, T-cell large granular lymphocyte leukemia, T-cell leukemia, T-cell lymphoma, T-cell prolymphocytic leukemia, Teratoma, Terminal lymphatic cancer, Testicular cancer, Thecoma, Throat Cancer, Thymic Carcinoma, Thymoma, Thyroid cancer, Transitional Cell Cancer of Renal Pelvis and Ureter, Transitional cell carcinoma, Urachal cancer, Urethral cancer, Urogenital neoplasm, Uterine sarcoma, Uveal melanoma, Vaginal Cancer, Verner Morrison syndrome, Verrucous carcinoma, Visual Pathway Glioma, Vulvar Cancer, Waldenstrom's macroglobulinemia, Warthin's tumor, Wilms' tumor, or any combination thereof.

In other embodiments, the methods of using a PI3Kα inhibitor and an mTOR inhibitor described herein are applied to the treatment of heart conditions including atherosclerosis, heart hypertrophy, cardiac myocyte dysfunction, elevated blood pressure and vasoconstriction. The invention also relates to a method of treating diseases related to vasculogenesis or angiogenesis in a mammal that comprises administering to said mammal a therapeutically effective amount of a PI3Kα inhibitor and an mTOR inhibitor of the present invention, or any pharmaceutically acceptable salt, ester, prodrug, solvate, hydrate or derivative thereof.

In some embodiments, said method is for treating a disease selected from the group consisting of tumor angiogenesis, chronic inflammatory disease such as rheumatoid arthritis, atherosclerosis, inflammatory bowel disease, skin diseases such as psoriasis, eczema, and scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer.

In some embodiments, the invention provides for the use of a PI3Kα inhibitor and an mTOR inhibitor for treating a disease condition associated with PI3-kinase α and/or mTOR, including, but not limited to, conditions related to an undesirable, over-active, harmful or deleterious immune response in a mammal, collectively termed "autoimmune disease." Autoimmune disorders include, but are not limited to, Crohn's disease, ulcerative colitis, psoriasis, psoriatic arthritis, juvenile arthritis and ankylosing spondilitis, Other non-limiting examples of autoimmune disorders include autoimmune diabetes, multiple sclerosis, systemic lupus erythematosus (SLE), rheumatoid spondylitis, gouty arthritis, allergy, autoimmune uveitis, nephrotic syndrome, multi-system autoimmune diseases, autoimmune hearing loss, adult respiratory distress syndrome, shock lung, chronic pulmonary inflammatory disease, pulmonary sarcoidosis, pulmonary fibrosis, silicosis, idiopathic interstitial lung disease, chronic obstructive pulmonary disease, asthma, restenosis, spondyloarthropathies, Reiter's syndrome, autoimmune hepatitis, inflammatory skin disorders, vasculitis of large vessels, medium vessels or small vessels, endometriosis, prostatitis and Sjogren's syndrome. Undesirable immune response can also be associated with or result in, e.g., asthma, emphysema, bronchitis, psoriasis, allergy, anaphylaxis, autoimmune diseases, rheumatoid arthritis, graft versus host disease, transplantation rejection, lung injuries, and lupus erythematosus. The pharmaceutical compositions of the present invention can be used to treat other respiratory diseases including but not limited to diseases affecting the lobes of lung, pleural cavity, bronchial tubes, trachea, upper respiratory tract, or the nerves and muscle for breathing. The compositions of the invention can be further used to treat multiorgan failure.

The invention also provides methods of using a PI3Kα inhibitor and an mTOR inhibitor for the treatment of liver diseases (including diabetes), pancreatitis or kidney disease (including proliferative glomerulonephritis and diabetes-induced renal disease) or pain in a mammal.

The invention also provides a method of using a PI3Kα inhibitor and an mTOR inhibitor for the treatment of sperm motility. The invention further provides a method of using a PI3Kα inhibitor and an mTOR inhibitor for the treatment of neurological or neurodegenerative diseases including, but not limited to, Alzheimer's disease, Huntington's disease, CNS trauma, and stroke.

The invention further provides a method of using a PI3Kα inhibitor and an mTOR inhibitor for the prevention of blastocyte implantation in a mammal.

The invention also relates to a method of using a PI3Kα inhibitor and an mTOR inhibitor for treating a disease related to vasculogenesis or angiogenesis in a mammal which can manifest as tumor angiogenesis, chronic inflammatory disease such as rheumatoid arthritis, inflammatory bowel disease, atherosclerosis, skin diseases such as psoriasis, eczema, and scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer.

The invention further provides a method of using a PI3Kα inhibitor and an mTOR inhibitor for the treatment of disorders involving platelet aggregation or platelet adhesion, including but not limited to Bernard-Soulier syndrome, Glanzmann's thrombasthenia, Scott's syndrome, von Willebrand disease, Hermansky-Pudlak Syndrome, and Gray platelet syndrome.

In some embodiments, methods of using a PI3Kα inhibitor and an mTOR inhibitor are provided for treating a disease which is skeletal muscle atrophy, skeletal muscle hypertrophy, leukocyte recruitment in cancer tissue, invasion metastasis, melanoma, Kaposi's sarcoma, acute and chronic bacterial and viral infections, sepsis, glomerulo sclerosis, glomerulo, nephritis, or progressive renal fibrosis.

Certain embodiments contemplate a human subject such as a subject that has been diagnosed as having or being at risk for developing or acquiring a disease condition associated with PI3-kinase α and/or mTOR. Certain other embodiments contemplate a non-human subject, for example a non-human primate such as a macaque, chimpanzee, gorilla, vervet, orangutan, baboon or other non-human primate, including such non-human subjects that can be known to the art as preclinical models, including preclinical models for inflammatory disorders. Certain other embodiments contemplate a non-human subject that is a mammal, for example, a mouse, rat, rabbit, pig, sheep, horse, bovine, goat, gerbil, hamster, guinea pig or other mammal. There are also contemplated other embodiments in which the subject or biological source can be a non-mammalian vertebrate, for example, another higher vertebrate, or an avian, amphibian or reptilian species, or another subject or biological source. In certain embodiments of the present invention, a transgenic animal is utilized. A transgenic animal is a non-human animal in which one or more of the cells of the animal includes a nucleic acid that is non-endogenous (i.e., heterologous) and is present as an extrachromosomal element in a portion of its cell or stably integrated into its germ line DNA (i.e., in the genomic sequence of most or all of its cells).

Exemplary mTor Inhibitor Compounds

In one aspect, the invention provides a compound which is an inhibitor of mTor of the Formula I:

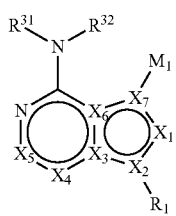

Formula I or a pharmaceutically acceptable salt thereof, wherein:

$X_1$ is N or C-$E^1$, $X_2$ is N or C, $X_3$ is N or C, $X_4$ is C—$R^9$ or N, $X_5$ is N or C-$E^1$, $X_6$ is C or N, and $X_7$ is C or N; and wherein no more than two nitrogen ring atoms are adjacent;

$R_1$ is H, -L-$C_{3-8}$cycloalkyl, —$C_{3-8}$cycloalkyl, -L-aryl, -L-heteroaryl, -L-$C_{1-10}$alkylaryl, -L-$C_{1-10}$alkylhetaryl, -L-$C_{1-10}$alkylheterocylyl, -L-$C_{2-10}$alkenyl, -L-$C_{2-10}$alkynyl, -L-$C_{2-10}$alkenyl-$C_{3-8}$cycloalkyl, -L-$C_{2-10}$alkynyl-$C_{3-8}$cycloalkyl, -L-heteroalkyl, -L-heteroalkylaryl, -L-heteroalkylheteroaryl, -L-heteroalkyl-heterocylyl, -L-heteroalkyl-$C_{3-8}$cycloalkyl, -L-aralkyl, -L-heteroaralkyl, or -L-heterocyclyl, each of which is unsubstituted or is substituted by one or more independent $R^3$;

L is absent, —(C═O)—, —C(═O)O—, —C(═O)—S(O)—, —S(O)$_2$—, —S(O)$_2$N($R^{31}$)—, or —N($R^{31}$)—;

$E^1$ and $E^2$ are independently —($W^1$)$_j$—$R^4$;

$M_1$ is a 5, 6, 7, 8, 9, or -10 membered ring system, wherein the ring system is monocyclic or bicyclic, substituted with $R_5$ and additionally optionally substituted with one or more —($W^2$)$_k$—$R^2$;

each k is 0 or 1;

j in $E^1$ or j in $E^2$, is independently 0 or 1;

$W^1$ is —O—, —N$R^7$—, —S(O)$_{0-2}$—, —C(O)—, —C(O)N($R^7$)—, —N($R^7$)C(O)—, —N($R^7$)S(O)—, —N($R^7$)S(O)$_2$—, —C(O)O—, —CH($R^7$)N(C(O)O$R^8$)—, —CH($R^7$)N(C(O)$R^8$)—, —CH($R^7$)N(SO$_2$$R^8$)—, —CH($R^7$)N($R^8$)—, —CH($R^7$)C(O)N($R^8$)—, —CH($R^7$)N($R^8$)C(O)—, —CH($R^7$)N($R^8$)S(O)—, or —CH($R^7$)N($R^8$)S(O)$_2$—;

$W^2$ is —O—, —N$R^7$—, —S(O)$_{0-2}$—, —C(O)—, —C(O)N($R^7$)—, —N($R^7$)C(O)—, —N($R^7$)C(O)N($R^8$)—, —N($R^7$)S(O)—, —N($R^7$)S(O)$_2$—, —C(O)O—, —CH($R^7$)N(C(O)O$R^8$)—, —CH($R^7$)N(C(O)$R^8$)—, —CH($R^7$)N(SO$_2$$R^8$)—, —CH($R^7$)N($R^8$)—, —CH($R^7$)C(O)N($R^8$)—, —CH($R^7$)N($R^8$)C(O)—, —CH($R^7$)N($R^8$)S(O)—, or —CH($R^7$)N($R^8$)S(O)$_2$—;

$R^2$ is hydrogen, halogen, —OH, —$R^{31}$, —CF$_3$, —OCF$_3$, —O$R^{31}$, —N$R^{31}R^{32}$, —N$R^{34}R^{35}$, —C(O)$R^{31}$, —CO$_2R^{31}$, —C(═O)N$R^{31}R^{32}$, —C(═O)N$R^{34}R^{35}$, —NO$_2$, —CN, —S(O)$_{0-2}R^{31}$, —SO$_2$N$R^{31}R^{32}$, —SO$_2$N$R^{34}R^{35}$, —N$R^{31}$C(═O)$R^{32}$, —N$R^{31}$C(═O)O$R^{32}$, —N$R^{31}$C(═O)N$R^{32}R^{33}$, —N$R^{31}$S(O)$_{0-2}R^{32}$, —C(═S)O$R^{31}$, —C(═O)S$R^{31}$, —N$R^{31}$C(═N$R^{32}$)N$R^{33}R^{32}$, —N$R^{31}$C(═N$R^{32}$)O$R^{33}$, —N$R^{31}$C(═N$R^{32}$)S$R^{33}$, —OC(═O)O$R^{33}$, —OC(═O)N$R^{31}R^{32}$, —OC(═O)S$R^{31}$, —SC(═O)O$R^{31}$, —P(O)O$R^{31}$O$R^{32}$, —SC(═O)N$R^{31}R^{32}$, aryl (e.g. bicyclic aryl, unsubstituted aryl, or substituted monocyclic aryl), hetaryl, $C_{1-10}$alkyl, $C_{3-8}$cycloalkyl, $C_{1-10}$alkyl-$C_{3-8}$cycloalkyl, $C_{3-8}$cycloalkyl-$C_{1-10}$alkyl, $C_{3-8}$cycloalkyl-$C_{2-10}$alkenyl, $C_{3-8}$cycloalkyl-$C_{2-10}$alkynyl, $C_{1-10}$alkyl-$C_{2-10}$alkenyl, $C_{1-10}$alkyl-$C_{2-10}$-alkynyl, $C_{1-10}$alkylaryl (e.g. $C_{2-10}$alkyl-monocyclic aryl, $C_{1-10}$alkyl-substituted monocyclic aryl, or $C_{1-10}$alkylbicycloaryl), $C_{1-10}$alkylhetaryl, $C_{1-10}$alkylheterocyclyl, $C_{2-10}$alkenyl, $C_{2-10}$alkynyl, $C_{2-10}$alkenyl-$C_{1-10}$alkyl, $C_{2-10}$alkynyl-$C_{1-10}$alkyl, $C_{2-10}$alkenylaryl, $C_{2-10}$alkenylhetaryl, $C_{2-10}$alkenylheteroalkyl, $C_{2-10}$-alkenylheterocyclyl, $C_{2-10}$alkenyl-$C_{3-8}$cycloalkyl, $C_{2-10}$alkynylaryl, $C_{2-10}$alkynylhetaryl, $C_{2-10}$alkynylheteroalkyl, $C_{2-10}$alkynylheterocylyl, $C_{2-10}$alkynyl-$C_{3-8}$cycloalkenyl, $C_{1-10}$alkoxy$C_{1-10}$alkyl, $C_{1-10}$alkoxy-$C_{2-10}$alkenyl, $C_{1-10}$alkoxy-$C_{2-10}$alkynyl, heterocyclyl, heteroalkyl, heterocyclyl-$C_{1-10}$alkyl, heterocyclyl-$C_{2-10}$alkenyl, heterocyclyl-$C_{2-10}$alkynyl, aryl-$C_{1-10}$alkyl (e.g. monocyclic aryl-$C_{2-10}$alkyl, substituted monocyclic aryl-$C_{1-10}$alkyl, or bicycloaryl-$C_{1-10}$alkyl), aryl-$C_{2-10}$alkenyl, aryl-$C_{2-10}$alkynyl, aryl-heterocyclyl, hetaryl-$C_{1-10}$alkyl, hetaryl-$C_{2-10}$alkenyl, hetaryl-$C_{2-10}$alkynyl, hetaryl-$C_{3-8}$cycloalkyl, hetaryl-heteroalkyl, or hetaryl-heterocyclyl, wherein each of said bicyclic aryl or heteroaryl moiety is unsubstituted, or wherein each of bicyclic aryl, heteroaryl moiety or monocyclic aryl moiety is substituted with one or more independent alkyl, heteroalkyl, alkenyl, alkynyl, cycloalkyl, heterocycloalkyl, aryl, arylalkyl, heteroaryl, heteroarylalkyl, halo, —OH, —$R^{31}$, —CF$_3$, —OCF$_3$, —O$R^{31}$, —N$R^{31}R^{32}$, —N$R^{34}R^{35}$, —C(O)$R^{31}$, —CO$_2R^{31}$, —C(═O)N$R^{31}R^{32}$, —C(═O)N$R^{34}R^{35}$, —NO$_2$, —CN, —S(O)$_{0-2}R^{31}$, —SO$_2$N$R^{31}R^{32}$, —SO$_2$N$R^{34}R^{35}$, —N$R^{31}$C(═O)$R^{32}$, —N$R^{31}$C(═O)O$R^{32}$, —N$R^{31}$C(═O)N$R^{32}R^{33}$, —N$R^{31}$S(O)$_{0-2}R^{32}$, —C(═S)

$OR^{31}$, —C(=O)$SR^{31}$, —$NR^{31}$C(=$NR^{32}$)$NR^{33}R^{32}$, —$NR^{31}$C(=$NR^{32}$)$OR^{33}$, —$NR^{31}$C(=$NR^{32}$)$SR^{33}$, —OC(=O)$OR^{33}$, —OC(=O)$NR^{31}R^{32}$, —OC(=O)$SR^{31}$, —SC(=O)$OR^{31}$, —P(O)$OR^{31}OR^{32}$, or —SC(=O)$NR^{31}R^{32}$, and wherein each of said alkyl, cycloalkyl, heterocyclyl, or heteroalkyl moiety is unsubstituted or is substituted with one or more alkyl, heteroalkyl, alkenyl, alkynyl, cycloalkyl, heterocycloalkyl, aryl, arylalkyl, heteroaryl, heteroarylalkyl, halo, —OH, —$R^{31}$, —$CF_3$, —$OCF_3$, —$OR^{31}$, —O-aryl, —$NR^{31}R^{32}$, —$NR^{34}R^{35}$, —C(O)$R^{31}$, —$CO_2R^{31}$, —C(=O)$NR^{34}R^{35}$, or —C(=O)$NR^{31}R^{32}$;

$R^3$ and $R^4$ are independently hydrogen, halogen, —OH, —$R^{31}$, —$CF_3$, —$OCF_3$, —$OR^{31}$, —$NR^{31}R^{32}$, —$NR^{34}R^{35}$, —C(O)$R^{31}$—C(=O)$NR^{31}R^{32}$, —C(=O)$NR^{34}R^{35}$, —$NO_2$, —CN, —S(O)$_{0-2}R^{31}$, —$SO_2NR^{31}R^{32}$, —$SO_2NR^{34}R^{35}$, —$NR^{31}$C(=O)$R^{32}$, —$NR^{31}$C(=O)$OR^{32}$, —$NR^{31}$C(=O)$NR^{32}R^{33}$, —$NR^{31}$S(O)$_{0-2}R^{32}$, —C(=S)$OR^{31}$, —C(=O)$SR^{31}$, —$NR^{31}$C(=$NR^{32}$)$NR^{33}R^{32}$, —$NR^{31}$C(=$NR^{32}$)$OR^{33}$, —$NR^{31}$C(=$NR^{32}$)$SR^{33}$, —OC(=O)$OR^{33}$, —OC(=O)$NR^{31}R^{32}$, —OC(=O)$SR^{31}$, —SC(=O)$OR^{31}$, —P(O)$OR^{31}OR^{32}$, —SC(=O)$NR^{31}R^{32}$ aryl, hetaryl, $C_{1-4}$alkyl, $C_{1-10}$alkyl, $C_{3-8}$cycloalkyl, $C_{1-10}$alkyl-$C_{3-8}$cycloalkyl, $C_{3-8}$cycloalkyl-$C_{1-10}$alkyl, $C_{3-8}$cycloalkyl-$C_{2-10}$alkenyl, $C_{3-8}$cycloalkyl-$C_{2-10}$alkynyl, $C_{1-10}$alkyl-$C_{2-10}$alkenyl, $C_{1-10}$alkyl-$C_{2-10}$alkynyl, $C_{1-10}$alkylaryl, $C_{1-10}$alkylhetaryl, $C_{1-10}$alkylheterocyclyl, $C_{2-10}$alkenyl, $C_{2-10}$alkynyl, $C_{2-10}$alkenyl-$C_{1-10}$alkyl, $C_{2-10}$alkynyl-$C_{1-10}$alkyl, $C_{2-10}$-alkenylaryl, $C_{2-10}$alkenylhetaryl, $C_{2-10}$alkenylheteroalkyl, $C_{2-10}$alkenylheterocycicyl, $C_{2-10}$alkenyl-$C_{3-8}$-cycloalkyl, $C_{2-10}$alkynyl-$C_{3-8}$cycloalkyl, $C_{2-10}$alkynylaryl, $C_{2-10}$alkynylhetaryl, $C_{2-10}$alkynylheteroalkyl, $C_{2-10}$-alkynylheterocyclyl, $C_{2-10}$alkynyl-$C_{3-8}$cycloalkenyl, $C_{1-10}$alkoxy $C_{1-10}$alkyl, $C_{1-10}$alkoxy-$C_{2-10}$alkenyl, $C_{1-10}$alkoxy-$C_{2-10}$alkynyl, heterocyclyl, heterocyclyl-$C_{1-10}$alkyl, heterocyclyl-$C_{2-10}$alkenyl, heterocyclyl-$C_{2-10}$-alkynyl, aryl-$C_{1-10}$alkyl, aryl-$C_{2-10}$alkenyl, aryl-$C_{2-10}$alkynyl, aryl-heterocyclyl, hetaryl-$C_{1-10}$alkyl, hetaryl-$C_{2-10}$alkenyl, hetaryl-$C_{2-10}$alkynyl, hetaryl-$C_{3-8}$cycloalkyl, heteroalkyl, hetaryl-heteroalkyl, or hetaryl-heterocyclyl, wherein each of said aryl or heteroaryl moiety is unsubstituted or is substituted with one or more independent halo, —OH, —$R^{31}$, —$CF_3$, —$OCF_3$, —$OR^{31}$, —$NR^{31}R^{32}$, —$NR^{34}R^{35}$, —C(O)$R^{31}$, —$CO_2R^{31}$, —C(=O)$NR^{31}R^{32}$, —C(=O)$NR^{34}R^{35}$, —$NO_2$, —CN, —S(O)$_{0-2}R^{31}$, —$SO_2NR^{31}R^{32}$, —$SO_2NR^{34}R^{35}$, —$NR^{31}$C(=O)$R^{32}$, —$NR^{31}$C(=O)$OR^{32}$, —$NR^{31}$C(=O)$NR^{32}R^{33}$, —$NR^{31}$S(O)$_{0-2}R^{32}$, —C(=S)$OR^{31}$, —C(=O)$SR^{31}$, —$NR^{31}$C(=$NR^{32}$)$NR^{33}R^{32}$, —$NR^{31}$C(=$NR^{32}$)$OR^{33}$, —$NR^{31}$C(=$NR^{32}$)$SR^{33}$, —OC(=O)$OR^{33}$, —OC(=O)$NR^{31}R^{32}$, —OC(=O)$SR^{31}$, —SC(=O)$OR^{31}$, —P(O)$OR^{31}OR^{32}$, or —SC(=O)$NR^{31}R^{32}$, and wherein each of said alkyl, cycloalkyl, heterocyclyl, or heteroalkyl moiety is unsubstituted or is substituted with one or more halo, —OH, —$R^{31}$, —$CF_3$, —$OCF_3$, —$OR^{31}$, —O-aryl, —$NR^{31}R^{32}$, —$NR^{34}R^{35}$, —C(O)$R^{31}$, —$CO_2R^{31}$, —C(=O)$NR^{34}R^{35}$, or —C(=O)$NR^{31}R^{32}$;

$R^5$ is hydrogen, halogen, —OH, —$R^{31}$, —$CF_3$, —$OCF_3$, —$OR^{31}$, —$NR^{31}R^{32}$, —$NR^{34}R^{35}$, —C(O)$R^{31}$, —$CO_2R^{31}$, —C(=O)$NR^{31}R^{32}$, —C(=O)$NR^{34}R^{35}$, —$NO_2$, —CN, —S(O)$_{0-2}R^{31}$, —$SO_2NR^{31}R^{32}$, —$SO_2NR^{34}R^{35}$, —$NR^{31}$C(=O)$R^{32}$, —$NR^{31}$C(=O)$OR^{32}$, —$NR^{31}$C(=O)$NR^{32}R^{33}$, —$NR^{31}$S(O)$_{0-2}R^{32}$, —C(=S)$OR^{31}$, —C(=O)$SR^{31}$, —$NR^{31}$C(=$NR^{32}$)$NR^{33}R^{32}$, —$NR^{31}$C(=$NR^{32}$)$OR^{33}$, —$NR^{31}$C(=$NR^{32}$)$SR^{33}$, —OC(=O)$OR^{33}$, —OC(=O)$NR^{31}R^{32}$, —OC(=O)$SR^{31}$, —SC(=O)$OR^{31}$, —P(O)$OR^{31}OR^{32}$, or —SC(=O)$NR^{31}R^{32}$;

each of $R^{31}$, $R^{32}$, and $R^{33}$ is independently H or $C_{1-10}$alkyl, wherein the $C_{1-10}$alkyl is unsubstituted or is substituted with one or more aryl, heteroalkyl, heterocyclyl, or hetaryl group, wherein each of said aryl, heteroalkyl, heterocyclyl, or hetaryl group is unsubstituted or is substituted with one or more halo, —OH, —$C_{1-10}$alkyl, —$CF_3$, —O-aryl, —$OCF_3$, —$OC_{1-10}$alkyl, —$NH_2$, —N($C_{1-10}$alkyl)($C_{1-10}$alkyl), —NH($C_{1-10}$alkyl), —NH(aryl), —$NR^{34}R^{35}$, —C(O)($C_{1-10}$alkyl), —C(O)($C_{1-10}$alkyl-aryl), —C(O)(aryl), —$CO_2$—$C_{1-10}$alkyl, —$CO_2$-aryl, —C(=O)N($C_{1-10}$alkyl)($C_{1-10}$alkyl), —C(=O)NH($C_{1-10}$alkyl), —C(=O)$NR^{34}R^{35}$, —C(=O)$NH_2$, —$OCF_3$, —O($C_{1-10}$alkyl), —O-aryl, —N(aryl)($C_{1-10}$alkyl), —$NO_2$, —CN, —S(O)$_{0-2}C_{1-10}$alkyl, —S(O)$_{0-2}C_{1-10}$alkylaryl, —S(O)$_{0-2}$aryl, —$SO_2$N(aryl), —$SO_2$N($C_{1-10}$alkyl)($C_{1-10}$alkyl), —$SO_2$NH($C_{1-10}$alkyl) or —$SO_2NR^{34}R^{35}$;

$R^{34}$ and $R^{35}$ in —$NR^{34}R^{35}$, —C(=O)$NR^{34}R^{35}$, or —$SO_2NR^{34}R^{35}$, are taken together with the nitrogen atom to which they are attached to form a 3-10 membered saturated or unsaturated ring; wherein said ring is independently unsubstituted or is substituted by one or more —$NR^{31}R^{32}$, hydroxyl, halogen, oxo, aryl, hetaryl, $C_{1-6}$alkyl, or O-aryl, and wherein said 3-10 membered saturated or unsaturated ring independently contains 0, 1, or 2 more heteroatoms in addition to the nitrogen atom;

each of $R^7$ and $R^8$ is independently hydrogen, $C_{1-10}$alkyl, $C_{2-10}$alkenyl, aryl, heteroaryl, heterocyclyl or $C_{3-10}$cycloalkyl, each of which except for hydrogen is unsubstituted or is substituted by one or more independent $R^6$;

$R^6$ is halo, —$OR^{31}$, —SH, —$NH_2$, —$NR^{34}R^{35}$, —$NR^{31}R^{32}$, —$CO_2R^{31}$, —$CO_2$aryl, —C(=O)$NR^{31}R^{32}$, C(=O)$NR^{34}R^{35}$, —$NO_2$, —CN, —S(O)$_{0-2}C_{1-10}$alkyl, —S(O)$_{0-2}$aryl, —$SO_2NR^{34}R^{35}$, —$SO_2NR^{31}R^{32}$, $C_{1-10}$alkyl, $C_{2-10}$alkenyl, $C_{2-10}$alkynyl; aryl-$C_{1-10}$alkyl, aryl-$C_{2-10}$alkenyl, aryl-$C_{2-10}$alkynyl, hetaryl-$C_{1-10}$alkyl, hetaryl-$C_{2-10}$-alkenyl, hetaryl-$C_{2-10}$alkynyl, wherein each of said alkyl, alkenyl, alkynyl, aryl, heteroalkyl, heterocyclyl, or hetaryl group is unsubstituted or is substituted with one or more independent halo, cyano, nitro, —$OC_{1-10}$alkyl, $C_{1-10}$alkyl, $C_{2-10}$alkenyl, $C_{2-10}$alkynyl, halo$C_{1-10}$alkyl, halo$C_{2-10}$alkenyl, halo$C_{2-10}$alkynyl, —COOH, —C(=O)$NR^{31}R^{32}$, —C(=O)$NR^{34}R^{35}$, —$SO_2NR^{34}R^{35}$, —$SO_2NR^{31}R^{32}$, —$NR^{31}R^{32}$, or —$NR^{34}R^{35}$; and $R^9$ is H, halo, —$OR^{31}$, —SH, —$NH_2$, —$NR^{34}R^{35}$, —$NR^{31}R^{32}$, —$CO_2R^{31}$, —$CO_2$aryl, —C(=O)$NR^{31}R^{32}$, C(=O)$NR^{34}R^{35}$, —$NO_2$, —CN, —S(O)$_{0-2}C_{1-10}$alkyl, —S(O)$_{0-2}$aryl, —$SO_2NR^{34}R^{35}$, —$SO_2NR^{31}R^{32}$, $C_{1-10}$alkyl, $C_{2-10}$alkenyl, $C_{2-10}$alkynyl; aryl-$C_{1-10}$alkyl, aryl-$C_{2-10}$alkenyl, aryl-$C_{2-10}$alkynyl, hetaryl-$C_{1-10}$alkyl, hetaryl-$C_{2-10}$-alkenyl, hetaryl-$C_{2-10}$alkynyl, wherein each of said alkyl, alkenyl, alkynyl, aryl, heteroalkyl, heterocyclyl, or hetaryl group is unsubstituted or is substituted with one or more independent halo, cyano, nitro, —$OC_{1-10}$alkyl, $C_{1-10}$alkyl, $C_{2-10}$alkenyl, $C_{2-10}$alkynyl, halo$C_{1-10}$alkyl, halo$C_{2-10}$alkenyl, halo$C_{2-10}$alkynyl, —COOH, —C(=O)$NR^{31}R^{32}$, —C(=O)$NR^{34}R^{35}$, —$SO_2NR^{34}R^{35}$, —$SO_2NR^{31}R^{32}$, —$NR^{31}R^{32}$, or —$NR^{34}R^{35}$.

$M_1$ is a 5, 6, 7, 8, 9, or -10 membered ring system, wherein the ring system is monocyclic or bicyclic. The monocyclic $M_1$ ring is unsubstituted or substituted with one or more $R^5$ substituents (including 0, 1, 2, 3, 4, or 5 $R^5$ substituents). In some embodiments, the monocyclic $M_1$ ring is aromatic (including phenyl) or heteroaromatic (including but not limited to pyridinyl, pyrrolyl, imidazolyl, thiazolyl, or pyrimidinyl). The monocyclic $M_1$ ring may be a 5 or 6 membered ring (including but not limited to pyridinyl, pyrrolyl, imidazolyl, thiazolyl, or pyrimidinyl). In some embodiments, $M_2$ is a five membered heteroaromatic group with one heteroatom, wherein the heteroatom is N, S, or O. In another embodiment, $M_2$ is a five membered heteroaromatic group with two heteroatoms, wherein the heteroatoms are nitrogen and oxygen or nitrogen and sulfur.

The bicyclic $M_1$ ring is unsubstituted or substituted with one or more $R^5$ substituents (including 0, 1, 2, 3, 4, 5, 6 or 7 $R^5$ substituents). Bicyclic $M_1$ ring is a 7, 8, 9, or 10 membered aromatic or heteroaromatic. Examples of an aromatic bicyclic $M_1$ ring include naphthyl. In other embodiments the bicyclic $M_1$ ring is heteroaromatic and includes but is not limited to benzothiazolyl, quinolinyl, quinazolinyl, benzoxazolyl, and benzoimidazolyl.

The invention also provides compounds wherein $M_1$ is a moiety having a structure of Formula M1-A or Formula M1-B:

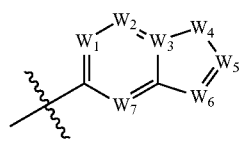

Formula M1-A

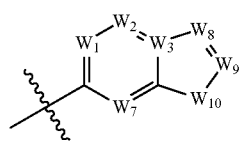

Formula M1-B wherein $W_1$, $W_2$, and $W_7$ are independently N or C—$R^5$; $W_4$ and $W_{10}$ are independently N—$R^5$, O, or S; $W_6$ and $W_8$ are independently N or C—$R^5$; $W_5$ and $W_9$ are independently N or C—$R^2$; and $W_3$ is C or N, provided no more than two N and/or N—$R^5$ are adjacent and no two O or S are adjacent.

In some embodiments of the invention, the $M_1$ moiety of Formula M1-A is a moiety of Formula M1-A1, Formula M1-A2, Formula M1-A3, or Formula M1-A4:

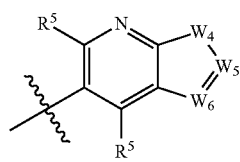

Formula M1-A1

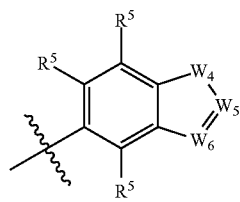

Formula M1-A2

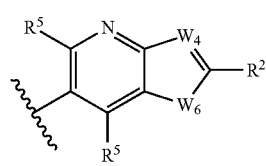

Formula M1-A3

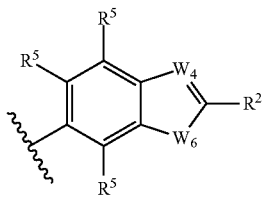

Formula M1-A4 wherein $W_4$ is N—$R^5$, O, or S; $W_6$ is N or C—$R^5$ and $W_5$ is N or C—$R^2$.

Some nonlimiting examples of the $M_1$ moiety of Formula M1-A include:

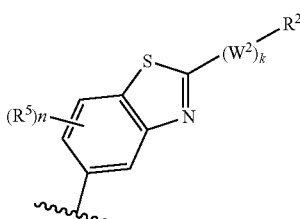

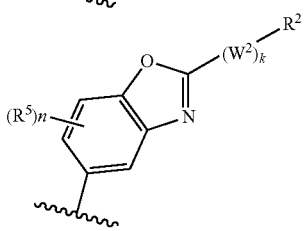

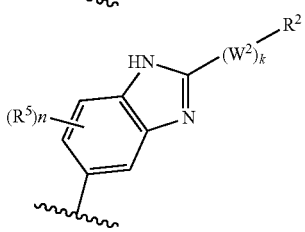

wherein $R^5$ is —$(W^1)_k$—$R^{53}$ or $R^{55}$; each k is independently 0 or 1, n is 0, 1, 2, or 3, and —$(W^1)_k$—$R^{53}$ and $R^{55}$ are as defined above.

In other embodiments of the invention, the $M_1$ moiety of Formula M1-B is a moiety of Formula M1-B1, Formula M1-B2, Formula M1-B3, or Formula M1-B4:

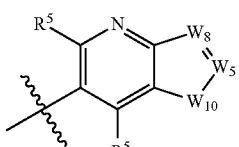

Formula M1-B1

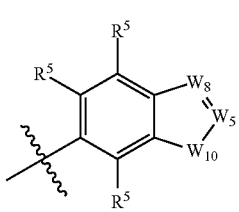

Formula M1-B2

-continued

Formula M1-B3

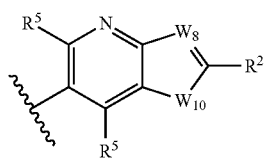

Formula M1-B4

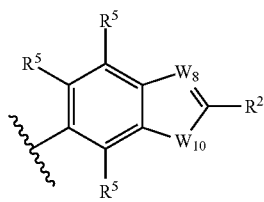

wherein $W_{10}$ is $N—R^5$, O, or S, $W_8$ is N or $C—R^5$, and $W_5$ is N or $C—R^2$.

Some nonlimiting examples of the $M_1$ moiety of Formula M1-B include:

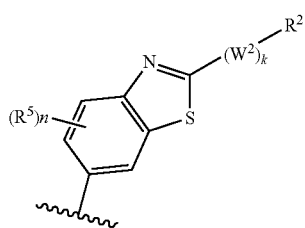

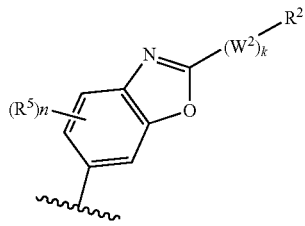

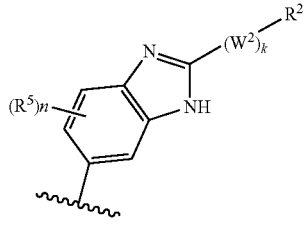

wherein $R'^5$ is $—(W^1)_k—R^{53}$ or $R^{55}$; k is 0 or 1, n is 0, 1, 2, or 3, and $—(W^1)_k—R^{53}$ and $R^{55}$ are as defined above.

The invention also provides compounds wherein $M_1$ is a moiety having a structure of Formula M1-C or Formula M1-D:

Formula M1-C

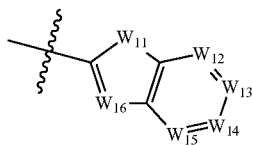

-continued

Formula M1-D

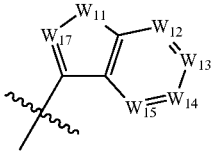

wherein $W_{12}$, $W_{13}$, $W_{14}$, and $W_{15}$ are independently N or $C—R^5$; $W_{11}$ and $W_{18}$ are independently $N—R^5$, O, or S; $W_{16}$ and $W_{17}$ are independently N or $C—R^5$; provided no more than two N are adjacent.

In other embodiments of the invention, the $M_1$ moiety of Formula M1-C or Formula M1-D is a moiety of Formula M1-C1 or Formula M1-D1:

Formula M1-D1

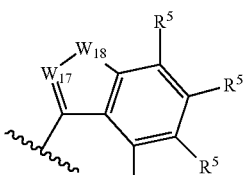

Formula M1-C1

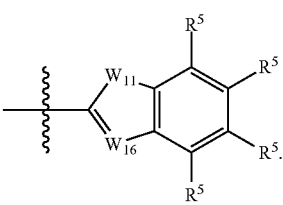

wherein $W_{11}$ and $W_{18}$ are $N—R^5$, O, or S; and $W_{16}$ and $W_{17}$ are N or $C—R^5$.

Some nonlimiting examples of the $M_1$ moiety of Formula M1-C and Formula M1-D include:

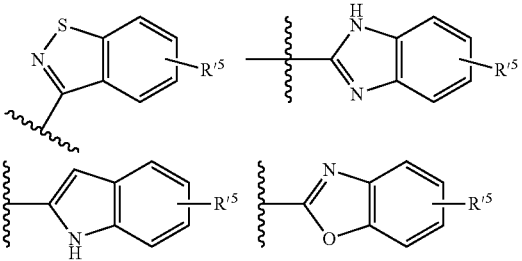

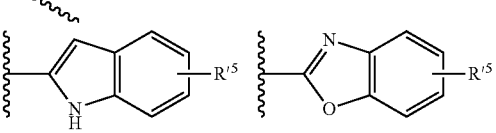

wherein $R'^5$ is $—(W^1)_k—R^{53}$ or $R^{55}$; k is 0 or 1, and $—(W^1)_k—R^{53}$ and $R^{55}$ are as defined above.

The invention also provides compounds wherein $M_1$ is a moiety having a structure of Formula M1-E:

Formula M1-E

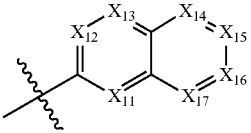

wherein $X_{11}$, $X_{12}$, $X_{13}$, $X_{14}$, $X_{15}$, $X_{16}$, and $X_{17}$ are independently N, or C—$R^5$; provided that no more than two N are adjacent.

In some embodiments of the invention, the $M_1$ moiety having a structure of Formula M1-E, is a moiety having a structure of Formula M1-E1, M1-E2, M1-E3, M1-E4, M1-E5, M1-E6, M1-E7, or M1-E8:

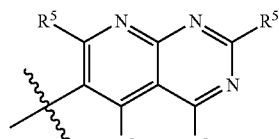

Formula M1-E1

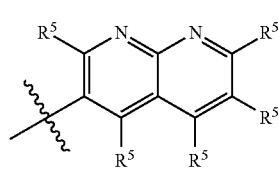

Formula M1-E2

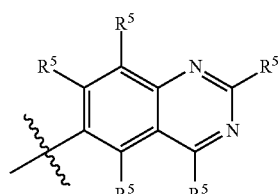

Formula M1-E3

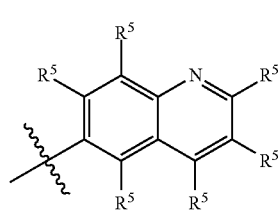

Formula M1-E4

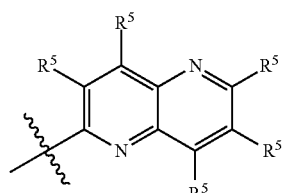

Formula M1-E5

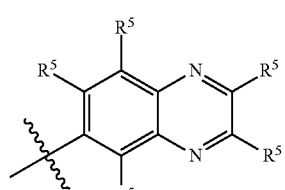

Formula M1-E6

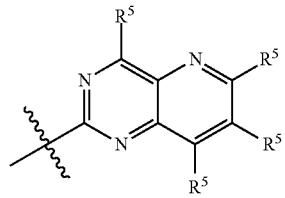

Formula M1-E7

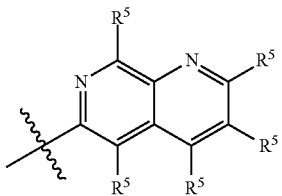

Formula M1-E8

In some embodiments of the invention, the $M_1$ moiety having a structure of Formula M1-E, is a moiety having a structure:

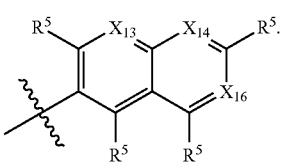

Some nonlimiting examples of the $M_1$ moiety of Formula M1-E include:

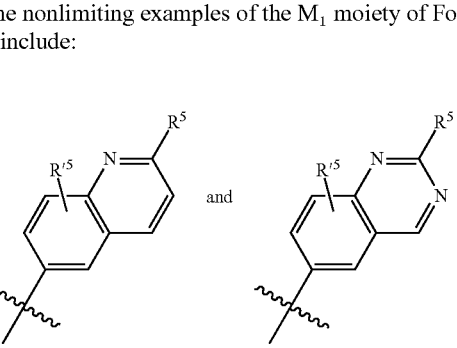

wherein $R'^5$ is —$(W^1)_k$—$R^{53}$ or $R^{55}$; k is 0 or 1, n is 0, 1, 2, or 3, and —$(W^1)_k$—$R^{53}$ or $R^{55}$ are as defined above. In some embodiments, k is 0, and $R^5$ is $R^{53}$.

In some embodiments, $R^{53}$ is hydrogen, unsubstituted or substituted $C_1$-$C_{10}$alkyl (which includes but is not limited to —$CH_3$, —$CH_2CH_3$, n-propyl, isopropyl, n-butyl, tert-butyl, sec-butyl, pentyl, hexyl, and heptyl), or unsubstituted or substituted $C_3$-$C_8$cycloalkyl (which includes but is not limited to cyclopropyl, cyclobutyl, cyclopentyl, and cyclohexyl). In other embodiments, $R^{53}$ is monocyclic or bicyclic aryl, wherein the $R^{53}$ aryl is unsubstituted or substituted. Some examples of aryl include but are not limited to phenyl, naphthyl or fluorenyl. In some other embodiments, $R^{53}$ is unsubstituted or substituted heteroaryl, including but not limited to monocyclic and bicyclic heteroaryl. Monocyclic heteroaryl includes but is not limited to pyrrolyl, thienyl, furyl, pyridinyl, pyranyl, imidazolyl, thiazolyl, pyrazolyl, and oxazolyl. Bicyclic heteroaryl $R^{53}$ includes but is not limited to benzothiophenyl, benzofuryl, indolyl, quinolinyl, isoquinolinyl, benzimidazolyl, benzoxazolyl, benzothiazolyl, quinazolinyl, azaindolyl, pyrazolopyrimidinyl, and purinyl. Additionally, $R^{53}$ may be alkylcycloalkyl (including but not limited to cyclopropylethyl, cyclopentylethyl, and cyclobutylpropyl), -alkylaryl (including but not limited to benzyl, phenylethyl, and phenylnaphthyl), -alkylhetaryl (including but not limited to pyridinylmethyl, pyrrolylethyl, and imidazolylpropyl), or -alkylheterocyclyl (non-limiting examples are morpholinylmethyl, 1-piperazinylmethyl, and azetidinylpropyl). For each of alkylcycloalkyl, alkylaryl, alkylhetaryl, or -alkylheterocyclyl, the moiety is connected to $M_1$ through the alkyl portion of the moiety In other embodiments, $R^{53}$ is unsubstituted or substituted $C_2$-$C_{10}$alkenyl (including but not limited to alkenyl such as, for example, vinyl, allyl, 1-methyl propen-1-yl, butenyl, or pentenyl) or unsubstituted or substituted alkynyl (including but not limited to unsubstituted or substituted $C_2$-$C_{10}$alkynyl such as acetylenyl, propargyl, butynyl, or pentynyl).

Further embodiments provide $R^{53}$ wherein $R^{53}$ is alkenylaryl, alkenylheteroaryl, alkenylheteroalkyl, or alkenylheterocycicyl, wherein each of alkenyl, aryl, heteroaryl, heteroalkyl, and heterocyclyl is as described herein and wherein the alkenylaryl, alkenylhetaryl, alkenylheteroalkyl, or alkenylheterocycicyl moiety is attached to $M_1$ through the alkenyl. Some nonlimiting examples in include styryl, 3-pyridinylallyl, 2-methoxyethoxyvinyl, and 3-morpholinlyallyl In other embodiments, $R^{53}$ is -alkynylaryl, -alkynylhetaryl, -alkynylheteroalkyl, -alkynylheterocylyl, -alkynylcycloalkyl, or -alkynyl$C_{3-8}$cycloalkenyl, wherein each of alkynyl, aryl, heteroaryl, heteroalkyl, and heterocyclyl is as described herein and wherein the alkynylaryl, alkynylhetaryl, alkynylheteroalkyl, or alkynylheterocycicyl moiety is attached to $M_1$ through the alkynyl. Alternatively, $R^{53}$ is -alkoxyalkyl, -alkoxyalkenyl, or -alkoxyalkynyl, wherein each of alkoxy, alkyl, alkenyl, and alkynyl is as described herein and wherein the -alkoxyalkyl, -alkoxyalkenyl, or -alkoxyalkynyl moiety is attached to $M_1$ through the alkoxy. In yet other embodiments, $R^{53}$ is -heterocyclylalkyl, -heterocyclylalkenyl, or -heterocyclylalkynyl, wherein the heterocyclyl, alkyl, alkenyl, or alkynyl is as described herein and wherein the -heterocyclylalkyl, -heterocyclylalkenyl, or -heterocyclylalkynyl is attached to $M_1$ through the heterocyclyl portion of the moiety. Further, $R^{53}$ may be aryl-alkenyl, aryl-alkynyl, or aryl-heterocyclyl, wherein the aryl, alkenyl, alkynyl, or heterocyclyl is as described herein and wherein the aryl-alkenyl, aryl-alkynyl, or aryl-heterocyclyl moiety is attached to $M_1$ through the aryl portion of the moiety. In some other embodiments, $R^{53}$ is heteroaryl-alkyl, heteroaryl-alkenyl, heteroaryl-alkynyl, heteroaryl-cycloalkyl, heteroaryl-heteroalkyl, or heteroaryl-heterocyclyl, wherein each of heteroaryl, alkyl, alkenyl, alkynyl, cycloalkyl, heteroalkyl, and heterocyclyl is as described herein and wherein the heteroaryl-alkyl, heteroaryl-alkenyl, heteroaryl-alkynyl, heteroaryl-cycloalkyl, heteroaryl-heteroalkyl, or heteroaryl-heterocyclyl moiety is attached to $M_1$ through the heteroaryl portion of the moiety.

For each of the aryl or heteroaryl moieties forming part or all of $R^{53}$, the aryl or heteroaryl is unsubstituted or is substituted with one or more independent halo, —OH, —$R^{31}$, —$CF_3$, —$OCF_3$, —$OR^{31}$, —$NR^{31}R^{32}$, —$NR^{34}R^{35}$, —C(O)$R^{31}$, —$CO_2R^{31}$, —C(=O)$NR^{31}R^{32}$, —C(=O)$NNR^{34}R^{35}$, —$NO_2$, —CN, —S(O)$_{0-2}R^{31}$, —$SO_2NR^{31}R^{32}$, —$SO_2NR^{34}R^{35}$, —$NR^{31}$C(=O)$R^{32}$, —$NR^{31}$C(=O)$OR^{32}$, —$NR^{31}$C(=O)$NR^{32}R^{33}$, —$NR^{31}$S(O)$_{0-2}R^{32}$, —C(=S)$OR^{31}$, —C(=O)$SR^{31}$, —$NR^{31}$C(=$NR^{32}$)$NR^{33}R^{32}$, —$NR^{31}$C(=$NR^{3}$)$OR^{33}$, —$NR^{31}$C(=$NR^{32}$)$SR^{33}$, —OC(=O)$OR^{33}$, —OC(=O)$NR^{31}R^{32}$, —OC(=O)$SR^{31}$, —SC(=O)$OR^{31}$, —P(O)$OR^{31}OR^{32}$, or —SC(=O)$NR^{31}R^{32}$ substituents. Additionally, each of the alkyl, cycloalkyl, heterocyclyl, or heteroalkyl moieties forming part of all of $R^{53}$ is unsubstituted or substituted with one or more halo, —OH, —$R^{31}$, —$CF_3$, —$OCF_3$, —$OR^{31}$, —O-aryl, —$NR^{31}R^{32}$, —$NR^{34}R^{35}$, —C(O)$R^{31}$, —$CO_2R^{31}$, —C(=O)$NNR^{34}R^{35}$, or —C(=O)$NR^{31}R^{32}$ substituents.

In other embodiments, $R^5$ is —$W^1$—$R^{53}$. In some embodiments, $R^5$ is —$OR^{53}$, including but not limited to Oalkyl (including but not limited to methoxy or ethoxy), -Oaryl (including but not limited to phenoxy), —O-heteroaryl (including but not limited to pyridinoxy) and —O-heterocycloxy (including but not limited to 4-N-piperidinoxy). In some embodiments $R^5$ is —$NR^6R^{53}$ including but not limited to anilinyl, diethylamino, and 4-N-piperidinylamino. In yet other embodiments $R^5$ is —S(O)$_{0-2}R^{53}$, including but not limited to phenylsulfonyl and pyridinylsulfonyl. The invention also provides compounds wherein $R^5$ is —C(O) (including but not limited to acetyl, benzoyl, and pyridinoyl) or —C(O)$OR^{53}$ (including but not limited to carboxyethyl, and carboxybenzyl). In other embodiments, $R^5$ is —C(O)N($R^6$)$R^{53}$ (including but not limited to C(O)NH(cyclopropyl) and C(O)N(Me)(phenyl)) or —CH($R^6$)N($R^7$)$R^{53}$ (including but not limited to —$CH_2$—NH-pyrrolidinyl, $CH_2$—NHcyclopropyl, and $CH_2$-anilinyl). Alternatively, $R^5$ is —N($R^6$)C(O)$R^{53}$ (including but not limited to —NHC(O)phenyl, —NHC(O)cyclopentyl, and to —NHC(O)piperidinyl) or —N($R^6$)S(O)$_2R^{53}$ (including but not limited to —NHS(O)$_2$-phenyl, —NHS(O)$_2$piperazinyl, and —NHS(O)$_2$-methyl. Additionally, $R^5$ is —N($R^6$)S(O)$R^{53}$, —CH($R^6$)N(C(O)$OR^7$) $R^{53}$, —CH($R^7$)N(C(O)$R^7$) $R^{53}$, —CH($R^6$)N(SO$_2R^7$) $R^{53}$, —CH($R^6$)N($R^7$) $R^{53}$, —CH($R^6$)C(O)N($R^7$) $R^{53}$, —CH($R^6$)N($R^7$)C(O)$R^{53}$, —CH($R^6$)N($R^7$)S(O)$R^{53}$, or —CH($R^6$)N($R^7$)S(O)$_2R^{53}$.

Alternatively, $R^5$ is $R^{55}$. $R^{55}$ is halo, —OH, —$NO_2$, —$CF_3$, —$OCF_3$, or —CN. In some other embodiments, $R^{55}$ is —$R^{31}$, —$OR^{31}$ (including but not limited to methoxy, ethoxy, and butoxy) —C(O)$R^{31}$ (non-limiting examples include acetyl, propionyl, and pentanoyl), or —$CO_2R^{31}$ (including but not limited to carboxymethyl, carboxyethyl and carboxypropyl). In further embodiments, $R^{55}$ is —$NR^{31}R^{32}$, —C(=O)$NR^{31}R^{32}$, —$SO_2NR^{31}R^{32}$, or —S(O)$_{0-2}R^{31}$. In other embodiments, $R^{55}$ is —$NR^{34}R^{35}$ or —$SO_2NR^{34}R^{35}$, wherein $R^{34}R^{35}$ are taken together with the nitrogen to which $R^{34}R^{35}$ are attached to form a cyclic moiety. The cyclic moiety so formed may be unsubstituted or substituted, wherein the substituents are selected from the group consisting of alkyl, —C(O)alkyl, —S(O)$_2$alkyl, and —S(O)$_2$aryl. Examples include but are not limited to morpholinyl, piperazinyl, or —$SO_2$-(4-N-methyl-piperazin-1-yl. Additionally, $R^{55}$ is —$NR^{31}$C(=O)$R^{32}$, —$NR^{31}$C(=O)$OR^{32}$, —$NR^{31}$C(=O)$NR^{32}R^{33}$, —$NR^{31}$S(O)$_{0-2}R^{32}$, —C(=S)$OR^{31}$, —C(=O)$SR^{31}$, —$NR^{31}$C(=$NR^{32}$)$NR^{33}R^{32}$, —$NR^{31}$C(=$NR^{32}$)$OR^{33}$, —$NR^{31}$C(=$NR^{32}$)$SR^{33}$, —OC(=O)$OR^{33}$, —OC(=O)$NR^{31}R^{32}$, —C(=O)$NNR^{34}R^{35}$, —OC(=O)$SR^{31}$, —SC(=O)$OR^{31}$, —P(O)$OR^{31}OR^{32}$, or —SC(=O)$NR^{31}R^{32}$; In yet another embodiment, $R^{55}$ is —O-aryl, including but not limited to phenoxy, and naphthyloxy.

The invention further provides a compound which is an mTor inhibitor, wherein the compound has the Formula I-A:

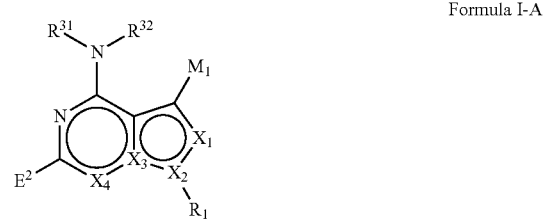

Formula I-A or a pharmaceutically acceptable salt thereof, wherein:
$X_1$ is N or C-$E^1$, $X_2$ is N, $X_3$ is C, and $X_4$ is C—$R^9$ or N; or
$X_1$ is N or C-$E^1$, $X_2$ is C, $X_3$ is N, and $X_4$ is C—$R^9$ or N;
$R_1$ is —H, -L-$C_{1-10}$alkyl, -L-$C_{3-8}$cycloalkyl, -L-$C_{1-10}$alkyl-$C_{3-8}$cycloalkyl, -L-aryl, -L-heteroaryl, -L-

C$_{1-10}$alkylaryl, -L-C$_{1-10}$alkylheteroaryl, -L-C$_{1-10}$alkylheterocyclyl, -L-C$_{2-10}$alkenyl, -L-C$_{2-10}$alkynyl, -L-C$_{2-10}$alkenyl-C$_{3-8}$cycloalkyl, -L-C$_{2-10}$alkynyl-C$_{3-8}$cycloalkyl, -L-heteroalkyl, -L-heteroalkylaryl, -L-heteroalkylheteroaryl, -L-heteroalkyl-heterocyclyl, -L-heteroalkyl-C$_{3-8}$cycloalkyl, -L-aralkyl, -L-heteroarkyl, or -L-heterocyclyl, each of which is unsubstituted or is substituted by one or more independent R$^3$;

L is absent, —(C=O)—, —C(=O)O—, —C(=O)N(R$^{31}$)—, —S—, —S(O)—, —S(O)$_2$—, —S(O)$_2$N(R$^{31}$)—, or —N(R$^{31}$)—;

M$_1$ is a moiety having the structure of Formula M1-F1 or M1-F2:

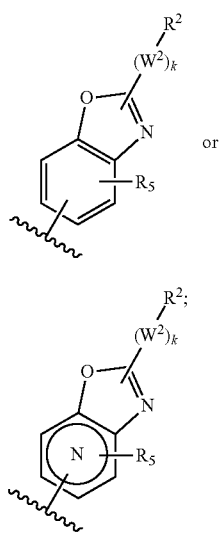

Formula M1-F1 or

Formula M1-F2 k is 0 or 1;

E$^1$ and E$^2$ are independently —(W$^1$)$_j$—R$^4$;

j, in each instance (i.e., in E$^1$ or j in E$^2$), is independently 0 or 1

W$^1$ is —O—, —NR$^7$—, —S(O)$_{0-2}$—, —C(O)—, —C(O)N(R$^7$)—, —N(R$^7$)C(O)—, —N(R$^7$)S(O)—, —N(R$^7$)S(O)$_2$—, —C(O)O—, —CH(R$^7$)N(C(O)OR$^8$)—, —CH(R$^7$)N(C(O)R$^8$)—, —CH(R$^7$)N(SO$_2$R$^8$)—, —CH(R$^7$)N(R$^8$)—, —CH(R$^7$)C(O)N(R$^8$)—, —CH(R$^7$)N(R$^8$)C(O)—, —CH(R$^7$)N(R$^8$)S(O)—, or —CH(R$^7$)N(R$^8$)S(O)$_2$—;

W$^2$ is —O—, —NR$^7$—, —S(O)$_{0-2}$—, —C(O)—, —C(O)N(R$^7$)—, —N(R$^7$)C(O)—, —N(R$^7$)C(O)N(R$^8$)—, —N(R$^7$)S(O)—, —N(R$^7$)S(O)$_2$—, —C(O)O—, —CH(R$^7$)N(C(O)OR$^8$)—, —CH(R$^7$)N(C(O)R$^8$)—, —CH(R$^7$)N(SO$_2$R$^8$)—, —CH(R$^7$)N(R$^8$)—, —CH(R$^7$)C(O)N(R$^8$)—, —CH(R$^7$)N(R$^8$)C(O)—, —CH(R$^7$)N(R$^8$)S(O)—, or —CH(R$^7$)N(R$^8$)S(O)$_2$—;

R$^2$ is hydrogen, halogen, —OH, —R$^{31}$, —CF$_3$, —OR$^{31}$, —NR$^{31}$R$^{32}$, —NR$^{34}$R$^{35}$, —C(O)R$^{31}$, —CO$_2$R$^{31}$, —C(=O)NR$^{31}$R$^{32}$, —C(=O)NR$^{34}$R$^{35}$, —NO$_2$, —CN, —S(O)$_{0-2}$R$^{31}$, —SO$_2$NR$^{31}$R$^{32}$, —SO$_2$NR$^{34}$R$^{35}$, —NR$^{31}$C(=O)R$^{32}$, —NR$^{31}$C(=O)OR$^{32}$, —NR$^{31}$C(=O)NR$^{32}$R$^{33}$, —NR$^{31}$S(O)$_{0-2}$R$^{32}$, —C(=S)OR$^{31}$, —C(=O)SR$^{31}$, —NR$^{31}$C(=NR$^{32}$)NR$^{33}$R$^{32}$, —NR$^{31}$C(=NR$^{32}$)OR$^{33}$, —NR$^{31}$C(=NR$^{32}$)SR$^{33}$, —OC(=O)OR$^{33}$, —OC(=O)NR$^{31}$R$^{32}$, —OC(=O)SR$^{31}$, —SC(=O)OR$^{31}$, —P(O)OR$^{31}$OR$^{32}$, —SC(=O)NR$^{31}$R$^{32}$ aryl (e.g. bicyclic aryl, unsubstituted aryl, or substituted monocyclic aryl), heteroaryl, C$_{1-10}$alkyl, C$_{3-8}$cycloalkyl, C$_{1-10}$alkyl-C$_{3-8}$cycloalkyl, C$_{3-8}$cycloalkyl-C$_{1-10}$alkyl, C$_{3-8}$cycloalkyl-C$_{2-10}$alkenyl, C$_{3-8}$cycloalkyl-C$_{2-10}$-alkynyl, C$_{1-10}$alkyl-C$_{2-10}$alkenyl, C$_{1-10}$alkyl-C$_{2-10}$alkynyl, C$_{1-10}$alkylaryl (e.g. C$_{2-10}$alkyl-monocyclic aryl, C$_{1-10}$alkyl-substituted monocyclic aryl, or C$_{1-10}$alkylbicycloaryl), C$_{1-10}$alkylheteroaryl, C$_{1-10}$alkylheterocyclyl, C$_{2-10}$alkenyl, C$_{2-10}$alkynyl, C$_{2-10}$alkenyl-C$_{1-10}$alkyl, C$_{2-10}$alkynyl-C$_{1-10}$alkyl, C$_{2-10}$-alkenylaryl, C$_{2-10}$alkenylheteroaryl, C$_{2-10}$alkenylheteroalkyl, C$_{2-10}$alkenylheterocycicyl, C$_{2-10}$alkenyl-C$_{3-8}$cycloalkyl, C$_{2-10}$alkynylaryl, C$_{2-10}$alkynylheteroaryl, C$_{2-10}$alkynylheteroalkyl, C$_{2-10}$alkynylheterocyclyl, C$_{2-10}$alkynyl-C$_{3-8}$cycloalkenyl, C$_{1-10}$alkoxy C$_{1-10}$alkyl, C$_{1-10}$alkoxy-C$_{2-10}$alkenyl, C$_{1-10}$alkoxy-C$_{2-10}$alkynyl, heterocyclyl, heteroalkyl, heterocyclyl-C$_{1-10}$alkyl, heterocyclyl-C$_{2-10}$alkenyl, heterocyclyl-C$_{2-10}$alkynyl, aryl-C$_{1-10}$alkyl (e.g. monocyclic aryl-C$_{2-10}$alkyl, substituted monocyclic aryl-C$_{1-10}$alkyl, or bicycloaryl-C$_{1-10}$alkyl), aryl-C$_{2-10}$alkenyl, aryl-C$_{2-10}$alkynyl, aryl-heterocyclyl, heteroaryl-C$_{1-10}$alkyl, heteroaryl-C$_{2-10}$alkenyl, heteroaryl-C$_{2-10}$alkynyl, heteroaryl-C$_{3-8}$cycloalkyl, heteroaryl-heteroalkyl, or heteroaryl-heterocyclyl, wherein each of said bicyclic aryl or heteroaryl moiety is unsubstituted, or wherein each of bicyclic aryl, heteroaryl moiety or monocyclic aryl moiety is substituted with one or more independent alkyl, heteroalkyl, alkenyl, alkynyl, cycloalkyl, heterocycloalkyl, aryl, arylalkyl, heteroaryl, heteroarylalkyl, halo, —OH, —R$^{31}$, —CF$_3$, —OCF$_3$, —OR$^{31}$, —NR$^{31}$R$^{32}$, —NR$^{34}$R$^{35}$, —C(O)R$^{31}$, —CO$_2$R$^{31}$, —C(=O)NR$^{31}$R$^{32}$, —C(=O)NR$^{34}$R$^{35}$, —NO$_2$, —CN, —S(O)$_{0-2}$R$^{31}$, —SO$_2$NR$^{31}$R$^{32}$, —SO$_2$NR$^{34}$R$^{35}$, —NR$^{31}$C(=O)R$^{32}$, —NR$^{31}$C(=O)OR$^{32}$, —NR$^{31}$C(=O) NR$^{32}$R$^{33}$, —NR$^{31}$S(O)$_{0-2}$R$^{32}$, —C(=S)OR$^{31}$, —C(=O) SR$^{31}$, —NR$^{31}$C(=NR$^{32}$)NR$^{33}$R$^{32}$, —NR$^{31}$C(=NR$^{32}$) OR$^{33}$, —NR$^{31}$C(=NR$^{32}$)SR$^{33}$, —OC(=O)OR$^{33}$, —OC (=O)NR$^{31}$R$^{32}$, —C(=O)SR$^{31}$, —SC(=O)OR$^{31}$, —P(O) OR$^{31}$OR$^{32}$, or —SC(=O)NR$^{31}$R$^{32}$, and wherein each of said alkyl, cycloalkyl, heterocyclyl, or heteroalkyl moiety is unsubstituted or is substituted with one or more alkyl, heteroalkyl, alkenyl, alkynyl, cycloalkyl, heterocycloalkyl, aryl, arylalkyl, heteroaryl, heteroarylalkyl, halo, —OH, —R$^{31}$, —CF$_3$, —OCF$_3$, —OR$^{31}$, —O-aryl, —NR$^{31}$R$^{32}$, —NR$^{34}$R$^{35}$, —C(O)R$^{31}$, —CO$_2$R$^{31}$, —C(=O)NR$^{34}$R$^{35}$, or —C(=O)NR$^{31}$R$^{32}$;

R$^3$ and R$^4$ are independently hydrogen, halogen, —OH, —R$^{31}$, —CF$_3$, —OCF$_3$, —OR$^{31}$, —NR$^{31}$R$^{32}$, —NR$^{34}$R$^{35}$, —C(O)R$^{31}$, —CO$_2$R$^{31}$, —C(=O)NR$^{31}$R$^{32}$, —C(=O) NR$^{34}$R$^{35}$, —NO$_2$, —CN, —S(O)$_{0-2}$R$^{31}$, —SO$_2$NR$^{31}$R$^{32}$, —SO$_2$NR$^{34}$R$^{35}$, —NR$^{31}$C(=O)R$^{32}$, —NR$^{31}$C(=O)OR$^{32}$, —NR$^{31}$C(=O)NR$^{32}$R$^{33}$, —NR$^{31}$S(O)$_{0-2}$R$^{32}$, —C(=S) OR$^{31}$, —C(=O)SR$^{31}$, —NR$^{31}$C(=NR$^{32}$)NR$^{33}$R$^{32}$, —NR$^{31}$C(=NR$^{32}$)OR$^{33}$, —NR$^{31}$C(=NR$^{32}$)SR$^{33}$, —OC (=O)OR$^{33}$, —OC(=O)NR$^{31}$R$^{32}$, —C(=O)SR$^{31}$, —SC (=O)OR$^{31}$, —P(O)OR$^{31}$OR$^{32}$, —SC(=O)NR$^{31}$R$^{32}$, aryl, heteroaryl, C$_{1-4}$alkyl, C$_{1-10}$alkyl, C$_{3-8}$cycloalkyl, C$_{1-10}$alkyl-C$_{3-8}$cycloalkyl, C$_{3-8}$cycloalkyl-C$_{1-10}$alkyl, C$_{3-8}$cycloalkyl-C$_{2-10}$alkenyl, C$_{3-8}$cycloalkyl-C$_{2-10}$alkynyl, C$_{1-10}$alkyl-C$_{2-10}$alkenyl, C$_{1-10}$alkyl-C$_{2-10}$alkynyl, C$_{1-10}$alkylheteroaryl, C$_{1-10}$alkylheterocyclyl, C$_{2-10}$alkenyl, C$_{2-10}$alkynyl, C$_{2-10}$alkenyl-C$_{1-10}$alkyl, C$_{2-10}$alkynyl-C$_{1-10}$alkyl, C$_{2-10}$alkenylaryl, C$_{2-10}$alkenylheteroaryl, C$_{2-10}$-alkenylheteroalkyl, C$_{2-10}$alkenylheterocyicyl, C$_{2-10}$alkenyl-C$_{3-8}$cycloalkyl, C$_{2-10}$alkynyl-C$_{3-8}$cycloalkyl, C$_{2-10}$alkynylaryl, C$_{2-10}$alkynylheteroaryl, C$_{2-10}$alkynylheteroalkyl, C$_{2-10}$alkynylheterocyclyl, C$_{2-10}$alkynyl-C$_{3-8}$cycloalkenyl, C$_{1-10}$alkoxy C$_{1-10}$alkyl, C$_{1-10}$alkoxy-C$_{2-10}$alkenyl, C$_{1-10}$alkoxy-C$_{2-10}$alkynyl, heterocyclyl, heterocyclyl-C$_{1-10}$alkyl, heterocyclyl-C$_{2-10}$alkenyl, heterocyclyl-C$_{2-10}$alkynyl, aryl-C$_{1-10}$alkyl, aryl-C$_{2-10}$alkenyl, aryl-C$_{2-10}$alkynyl, aryl-heterocyclyl, heteroaryl-C$_{1-10}$alkyl, heteroaryl-C$_{2-10}$alkenyl, heteroaryl-C$_{2-10}$alkynyl, heteroaryl-C$_{3-8}$cycloalkyl, heteroalkyl, heteroaryl-heteroalkyl, or heteroaryl-heterocyclyl, wherein each of said aryl or heteroaryl moiety is unsubstituted or is substituted with one or more independent halo, —OH, —$R^{31}$, —$CF_3$, —$OCF_3$, —$OR^{31}$, —$NR^{31}R^{32}$, —$NR^{34}R^{35}$, —$C(O)R^{31}$, —$CO_2R^{31}$, —$C(=O)NR^{31}R^{32}$, —$C(=O)NR^{34}R^{35}$, —$NO_2$, —CN, —$S(O)_{0-2}R^{31}$, —$SO_2NR^{31}R^{32}$, —$SO_2NR^{34}R^{35}$, —$NR^{31}C(=O)R^{32}$, —$NR^{31}C(=O)OR^{32}$, —$NR^{31}C(=O)NR^{32}R^{33}$, —$NR^{31}S(O)_{0-2}R^{32}$, —$C(=S)OR^{31}$, —$C(=O)SR^{31}$, —$NR^{31}C(=NR^{32})NR^{33}R^{32}$, —$NR^{31}C(=NR^{32})OR^{33}$, —$NR^{31}C(=NR^{32})SR^{33}$, —$OC(=O)OR^{33}$, —$OC(=O)NR^{31}R^{32}$, —$OC(=O)SR^{31}$, —$SC(=O)OR^{31}$, —$P(O)OR^{31}OR^{32}$, or —$SC(=O)NR^{31}R^{32}$, and wherein each of said alkyl, cycloalkyl, heterocyclyl, or heteroalkyl moiety is unsubstituted or is substituted with one or more halo, —OH, —$R^{31}$, —$CF_3$, —$OCF_3$, —$OR^{31}$, —O-aryl, —$NR^{31}R^{32}$, —$NR^{34}R^{35}$, —$C(O)R^{31}$, —$CO_2R^{31}$, —$C(=O)NR^{34}R^{35}$, or —$C(=O)NR^{31}R^{32}$;

$R^5$ is hydrogen, halogen, —OH, —$R^{31}$, —$CF_3$, —$OCF_3$, —$OR^{31}$, —$NR^{31}R^{32}$, —$NR^{34}R^{35}$, —$C(O)R^{31}$, —$CO_2R^{31}$, —$C(=O)NR^{31}R^{32}$, —$C(=O)NR^{34}R^{35}$, —$NO_2$, —CN, —$S(O)_{0-2}R^{31}$, —$SO_2NR^{31}R^{32}$, —$SO_2NR^{34}R^{35}$, —$NR^{31}C(=O)R^{32}$, —$NR^{31}C(=O)OR^{32}$, —$NR^{31}C(=O)NR^{32}R^{33}$, —$NR^{31}S(O)_{0-2}R^{32}$, —$C(=S)OR^{31}$, —$C(=O)SR^{31}$, —$NR^{31}C(=NR^{32})NR^{33}R^{32}$, —$NR^{31}C(=NR^{32})OR^{33}$, —$NR^{31}C(=NR^{32})SR^{33}$, —$OC(=O)OR^{33}$, —$OC(=O)NR^{31}R^{32}$, —$OC(=O)SR^{31}$, —$SC(=O)OR^{31}$, —$P(O)OR^{31}OR^{32}$, or —$SC(=O)NR^{31}R^{32}$;

$R^{31}$, $R^{32}$, and $R^{33}$, in each instance, are independently H or $C_{1-10}$alkyl, wherein the $C_{1-10}$alkyl is unsubstituted or is substituted with one or more aryl, heteroalkyl, heterocyclyl, or heteroaryl group, wherein each of said aryl, heteroalkyl, heterocyclyl, or heteroaryl group is unsubstituted or is substituted with one or more halo, —OH, —$C_{1-10}$alkyl, —$CF_3$, —O-aryl, —$OCF_3$, —$OC_{1-10}$alkyl, —$NH_2$, —$N(C_{1-10}$alkyl)$(C_{1-10}$alkyl), —$NH(C_{1-10}$alkyl), —NH(aryl), —$NR^{34}R^{35}$, —$C(O)(C_{1-10}$alkyl), —$C(O)(C_{1-10}$alkyl-aryl), —C(O)(aryl), —$CO_2$—$C_{1-10}$alkyl, —$CO_2$—$C_{1-10}$alkylaryl, —$CO_2$-aryl, —$C(=O)N(C_{1-10}$alkyl)$(C_{1-10}$alkyl), —$C(=O)NH(C_{1-10}$alkyl), —$C(=O)NR^{34}R^{35}$, —$C(=O)NH_2$, —$OCF_3$, —$O(C_{1-10}$alkyl), —O-aryl, —N(aryl)$(C_{1-10}$alkyl), —$NO_2$, —CN, —$S(O)_{0-2}C_{1-10}$alkyl, —$S(O)_{0-2}C_{1-10}$alkylaryl, —$S(O)_{0-2}$ aryl, —$SO_2$N(aryl), —$SO_2$N$(C_{1-10}$alkyl)$(C_{1-10}$alkyl), —$SO_2$NH$(C_{1-10}$alkyl) or —$SO_2NR^{34}R^{35}$;

$R^{34}$ and $R^{35}$ in —$NR^{34}R^{35}$, —$C(=O)NR^{34}R^{35}$, or —$SO_2NR^{34}R^{35}$, are taken together with the nitrogen atom to which they are attached to form a 3-10 membered saturated or unsaturated ring; wherein said ring is independently unsubstituted or is substituted by one or more —$NR^{31}R^{32}$, hydroxyl, halogen, oxo, aryl, heteroaryl, $C_{1-6}$alkyl, or O-aryl, and wherein said 3-10 membered saturated or unsaturated ring independently contains 0, 1, or 2 more heteroatoms in addition to the nitrogen atom;

$R^7$ and $R^8$ are each independently hydrogen, $C_{1-10}$alkyl, $C_{2-10}$alkenyl, aryl, heteroaryl, heterocyclyl or $C_{3-10}$cycloalkyl, each of which except for hydrogen is unsubstituted or is substituted by one or more independent $R^6$;

$R^6$ is halo, —$OR^{31}$, —SH, —$NH_2$, —$NR^{34}R^{35}$, —$NR^{31}R^{32}$, —$CO_2R^{31}$, —$CO_2$aryl, —$C(=O)NR^{31}R^{32}$, $C(=O)NR^{34}R^{35}$, —$NO_2$, —CN, —$S(O)_{0-2}C_{1-10}$alkyl, —$S(O)_{0-2}$aryl, —$SO_2NR^{34}R^{35}$, —$SO_2NR^{31}R^{32}$, $C_{1-10}$-alkyl, $C_{2-10}$alkenyl, $C_{2-10}$alkynyl; aryl-$C_{1-10}$alkyl, aryl-$C_{2-10}$alkenyl, aryl-$C_{2-10}$alkynyl, heteroaryl-$C_{1-10}$alkyl, heteroaryl-$C_{2-10}$alkenyl, heteroaryl-$C_{2-10}$alkynyl, wherein each of said alkyl, alkenyl, alkynyl, aryl, heteroalkyl, heterocyclyl, or heteroaryl group is unsubstituted or is substituted with one or more independent halo, cyano, nitro, —$OC_{1-10}$alkyl, $C_{1-10}$alkyl, $C_{2-10}$alkenyl, $C_{2-10}$alkynyl, halo$C_{1-10}$alkyl, halo$C_{2-10}$alkenyl, halo$C_{2-10}$alkynyl, —COOH, —$C(=O)NR^{31}R^{32}$, —$C(=O)NR^{34}R^{35}$, —$SO_2NR^{34}R^{35}$, —$SO_2NR^{31}R^{32}$, —$NR^{31}R^{32}$, or —$NR^{34}R^{35}$; and $R^9$ is H, halo, —$OR^{31}$, —SH, —$NH_2$, —$NR^{34}R^{35}$, —$NR^{31}R^{32}$, —$CO_2R^{31}$, —$CO_2$aryl, —$C(=O)NR^{31}R^{32}$, $C(=O)NR^{34}R^{35}$, —$NO_2$, —CN, —$S(O)_{0-2}C_{1-10}$alkyl, —$S(O)_{0-2}$ aryl, —$SO_2NR^{34}R^{35}$, —$SO_2NR^{31}R^{32}$, $C_{1-10}$alkyl, $C_{2-10}$alkenyl, $C_{2-10}$alkynyl; aryl-$C_{1-10}$alkyl, aryl-$C_{2-10}$alkenyl, aryl-$C_{2-10}$alkynyl, heteroaryl-$C_{1-10}$alkyl, heteroaryl-$C_{2-10}$alkenyl, heteroaryl-$C_{2-10}$alkynyl, wherein each of said alkyl, alkenyl, alkynyl, aryl, heteroalkyl, heterocyclyl, or heteroaryl group is unsubstituted or is substituted with one or more independent halo, cyano, nitro, —$OC_{1-10}$alkyl, $C_{1-10}$alkyl, $C_{2-10}$alkenyl, $C_{2-10}$alkynyl, halo$C_{1-10}$alkyl, halo$C_{2-10}$alkenyl, halo$C_{2-10}$alkynyl, —COOH, —$C(=O)NR^{31}R^{32}$, —$C(=O)NR^{34}R^{35}$, —$SO_2NR^{34}R^{35}$, —$SO_2NR^{31}R^{32}$, —$NR^{31}R^{32}$, or —$NR^{34}R^{35}$.

In some embodiments, $X_4$ is C—$R^9$.

The invention also provides an inhibitor as defined above, wherein the compound is of Formula I:

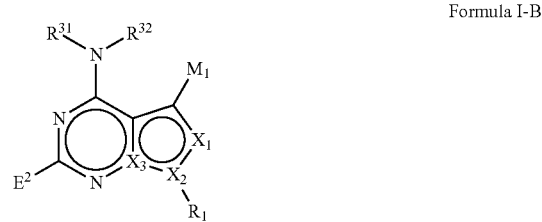

Formula I-B or a pharmaceutically acceptable salt thereof, and wherein the substituents are as defined above.

In various embodiments the compound of Formula I-B or its pharmaceutically acceptable salt thereof, is a compound having the structure of Formula I-B1 or Formula I-B2:

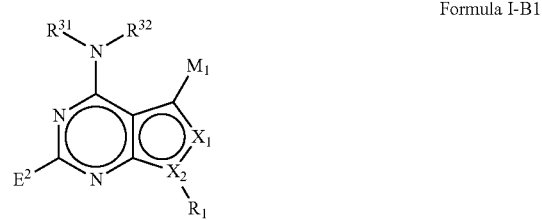

Formula I-B1

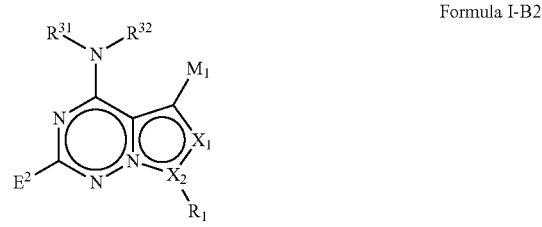

Formula I-B2 or a pharmaceutically acceptable salt thereof.

In various embodiments of Formula I-B1, $X_1$ is N and $X_2$ is N. In other embodiments, $X_1$ is C-$E^1$ and $X_2$ is N. In yet other embodiments, $X_1$ is NH and $X_2$ is C. In further embodiments, $X_1$ is CH-$E^1$ and $X_2$ is C.

In various embodiments of Formula I-B2, $X_1$ is N and $X_2$ is C. In further embodiments, $X_1$ is C-$E^1$ and $X_2$ is C.

In various embodiments, $X_1$ is C—$(W^1)_j$—$R^4$, where j is 0.

In another embodiment, $X_1$ is CH. In yet another embodiment, $X_1$ is C-halogen, where halogen is Cl, F, Br, or I.

In various embodiments of $X_1$, it is $C-(W^1)_j-R^4$. In various embodiments of $X_1$, j is 1, and $W^1$ is $-O-$. In various embodiments of $X_1$, j is 1, and $W^1$ is $-NR^7-$. In various embodiments of $X_1$, j is 1, and $W^1$ is $-NH-$. In various embodiments of $X_1$, j is 1, and $W^1$ is $-S(O)_{0-2}-$. In various embodiments of $X_1$, j is 1, and $W^1$ is $-C(O)-$. In various embodiments of $X_1$, j is 1, and $W^1$ is $-C(O)N(R^7)-$. In various embodiments of $X_1$, j is 1, and $W^1$ is $-N(R^7)C(O)-$. In various embodiments of $X_1$, j is 1, and $W^1$ is $-N(R^7)S(O)-$. In various embodiments of $X_1$, j is 1, and $W^1$ is $-N(R^7)S(O)_2-$. In various embodiments of $X_1$, j is 1, and $W^1$ is $-C(O)O-$. In various embodiments of $X_1$, j is 1, and $W^1$ is $CH(R^7)N(C(O)OR^8)-$. In various embodiments of $X_1$, j is 1, and $W^1$ is $-CH(R^7)N(C(O)R^8)-$. In various embodiments of $X_1$, j is 1, and $W^1$ is $-CH(R^7)N(SO_2R^8)-$. In various embodiments of $X_1$, j is 1, and $W^1$ is $-CH(R^7)N(R^8)-$. In various embodiments of $X_1$, j is 1, and $W^1$ is $-CH(R^7)C(O)N(R^8)-$. In various embodiments of $X_1$, j is 1, and $W^1$ is $-CH(R^7)N(R^8)C(O)-$. In various embodiments of $X_1$, j is 1, and $W^1$ is $-CH(R^7)N(R^8)S(O)-$. In various embodiments of $X_1$, j is 1, and $W^1$ is $-CH(R^7)N(R^8)S(O)_2-$.

In another embodiment, $X_1$ is $CH_2$. In yet another embodiment, $X_1$ is CH-halogen, where halogen is Cl, F, Br, or I.

In another embodiment, $X_1$ is N.

In various embodiments, $X_2$ is N. In other embodiments, $X_2$ is C.

In various embodiments, $E^2$ is $-(W^1)_j-R^4$, where j is 0.

In another embodiment, $E^2$ is CH. In yet another embodiment, $E^2$ is C-halogen, where halogen is Cl, F, Br, or I.

In various embodiments of $E^2$, it is $-(W^1)_j-R^4$. In various embodiments of $E^2$, j is 1, and $W^1$ is $-O-$. In various embodiments of $E^2$, j is 1, and $W^1$ is $-NR^7-$. In various embodiments of $E^2$, j is 1, and $W^1$ is $-NH-$. In various embodiments of $E^2$, j is 1, and $W^1$ is $-S(O)_{0-2}-$. In various embodiments of $E^2$, j is 1, and $W^1$ is $-C(O)-$. In various embodiments of $E^2$, j is 1, and $W^1$ is $-C(O)N(R^7)-$. In various embodiments of $E^2$, j is 1, and $W^1$ is $-N(R^7)C(O)-$. In various embodiments of $E^2$, j is 1, and $W^1$ is $-N(R^7)S(O)-$. In various embodiments of $E^2$, j is 1, and $W^1$ is $-N(R^7)S(O)_2-$. In various embodiments of $E^2$, j is 1, and $W^1$ is $-C(O)O-$. In various embodiments of $E^2$, j is 1, and $W^1$ is $CH(R^7)N(C(O)OR^8)-$. In various embodiments of $E^2$, j is 1, and $W^1$ is $-CH(R^7)N(C(O)R^8)-$. In various embodiments of $E^2$, j is 1, and $W^1$ is $-CH(R^7)N(SO_2R^8)-$. In various embodiments of $E^2$, j is 1, and $W^1$ is $-CH(R^7)N(R^8)-$. In various embodiments of $E^2$, j is 1, and $W^1$ is $-CH(R^7)C(O)N(R^8)-$. In various embodiments of $E^2$, j is 1, and $W^1$ is $-CH(R^7)N(R^8)C(O)-$. In various embodiments of $E^2$, j is 1, and $W^1$ is $-CH(R^7)N(R^8)S(O)-$. In various embodiments of $E^2$, j is 1, and $W^1$ is $-CH(R^7)N(R^8)S(O)_2-$.

In various embodiments when $M_1$ is a moiety of Formula M1-F1, $M_1$ is benzoxazolyl substituted with $-(W_2)_k-R^2$. In some embodiments, $M_1$ is a benzoxazolyl substituted at the 2-position with $-(W^2)_j-R^2$. In some embodiments, $M_1$ is either a 5-benzoxazolyl or a 6-benzoxazolyl moiety, optionally substituted at the 2-position with $-(W^2)_j-R^2$. Exemplary Formula M1-F1 $M_1$ moieties include but are not limited to the following:

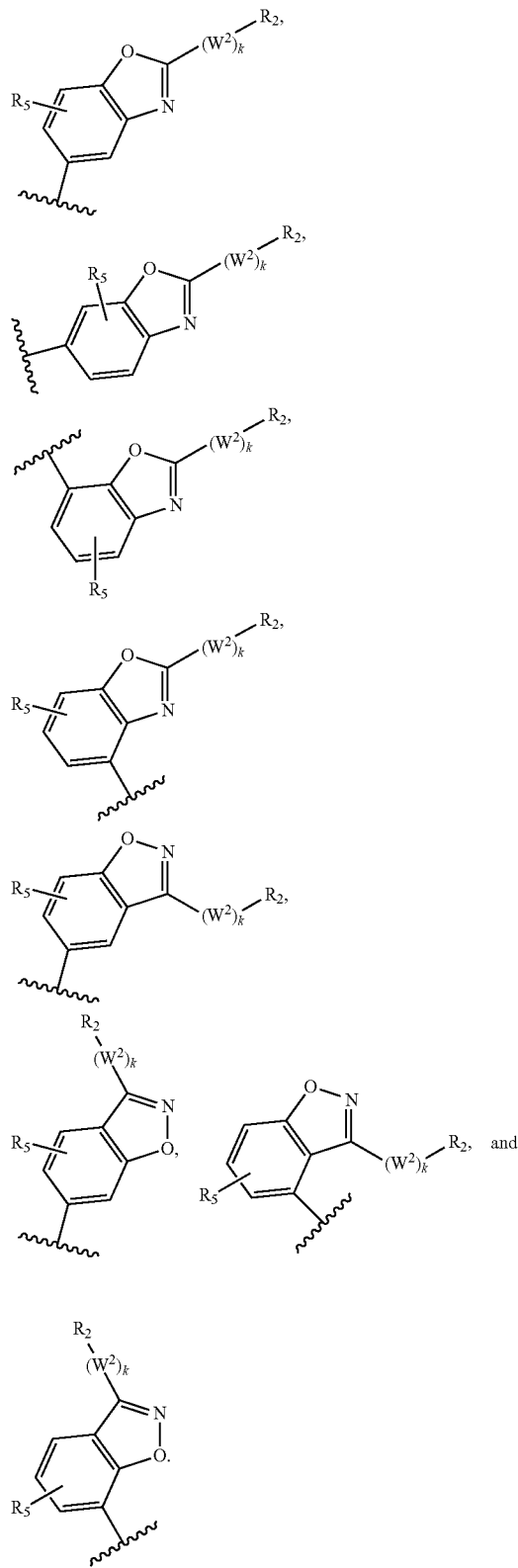

In various embodiments when $M_1$ is a moiety of Formula M1-F2, Formula M1-F2 is an aza-substituted benzoxazolyl moiety having a structure of one of the following formulae:

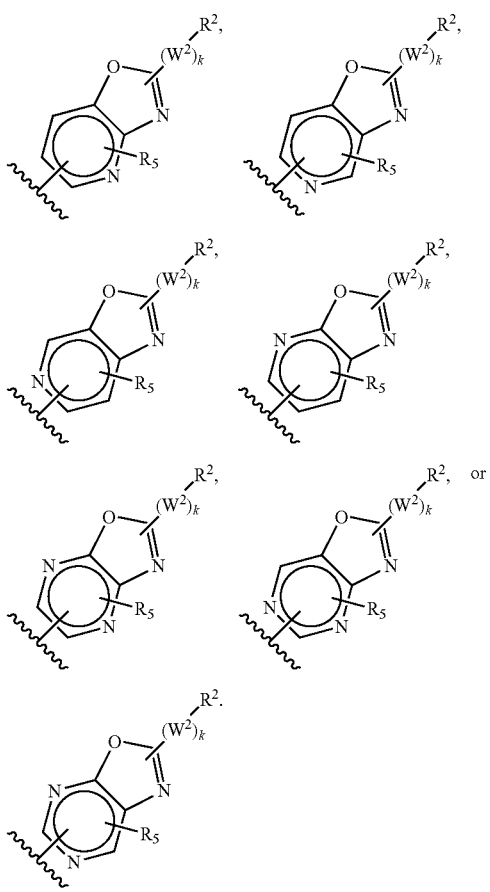
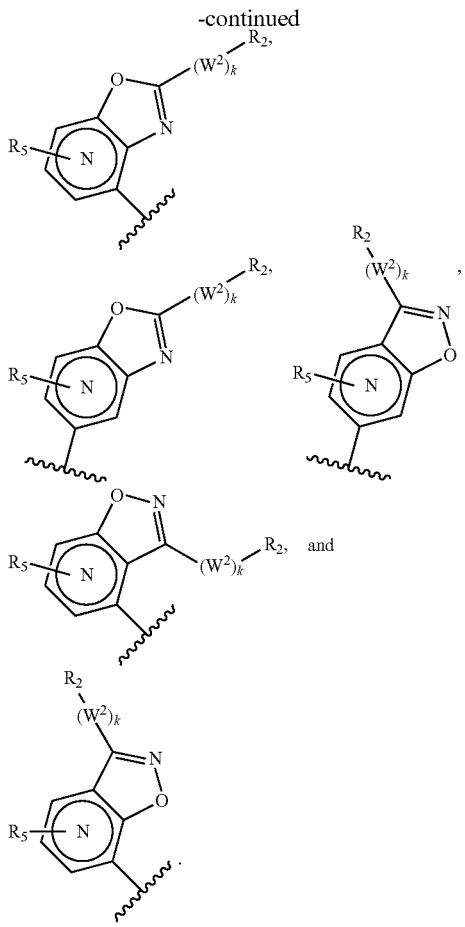

Exemplary Formula M1-F2 $M_1$ moieties include but are not limited to the following:

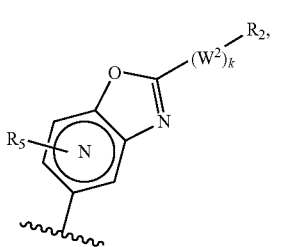
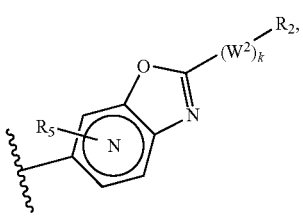
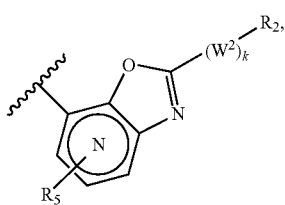

In various embodiments of $M_1$, k is 0. In other embodiments of $M_1$, k is 1, and $W^2$ is selected from one of the following: —O—, —NR$^7$—, —S(O)$_{0-2}$—, —C(O)—, —C(O)N(R$^7$)—, —N(R$^7$)C(O)—, or —N(R$^7$)C(O)N(R$^8$)—. In yet another embodiment of $M_1$, k is 1, and $W^2$ is —N(R$^7$)S(O)—, —N(R$^7$)S(O)$_2$—, —C(O)O—, —CH(R$^7$)N(C(O)OR$^8$)—, —CH(R$^7$)N(C(O)R$^8$)—, or —CH(R$^7$)N(SO$_2$R$^8$)—. In a further embodiment of $M_1$, k is 1, and $W^2$ is —CH(R$^7$)N(R$^8$)—, —CH(R$^7$)C(O)N(R$^8$)—, —CH(R$^7$)N(R$^8$)C(O)—, or —CH(R$^7$)N(R$^8$)S(O)—. In yet another embodiment of $M_1$, k is 1, and $W^2$ is —CH(R$^7$)N(R$^8$)S(O)$_2$—.

The invention provides an inhibitor of mTor which is a compound of Formula I-C or Formula I-D:

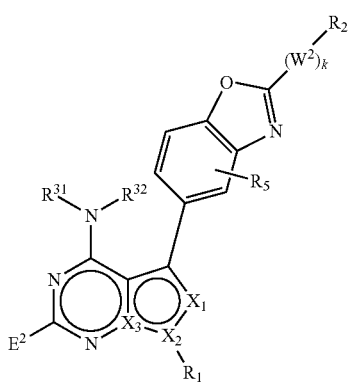

Formula I-C

Formula I-D

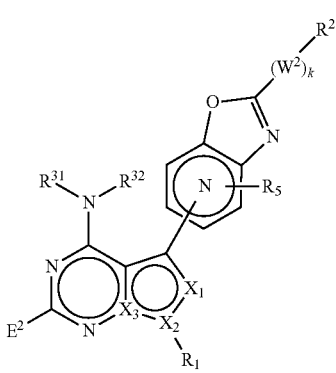

or a pharmaceutically acceptable salt thereof, wherein $X_1$ is N or C-$E^1$, $X_2$ is N, and $X_3$ is C; or $X_1$ is N or C-$E^1$, $X_2$ is C, and $X_3$ is N;

$R_1$ is —H, -L-$C_{1-10}$alkyl, -L-$C_{3-8}$cycloalkyl, -L-$C_{1-10}$alkyl-$C_{3-8}$cycloalkyl, -L-aryl, -L-heteroaryl, -L-$C_{1-10}$alkylaryl, -L-$C_{1-10}$alkylheteroaryl, -L-$C_{1-10}$alkylheterocyclyl, -L-$C_{2-10}$alkenyl, -L-$C_{2-10}$alkynyl, -L-$C_{2-10}$alkenyl-$C_{3-8}$cycloalkyl, -L-$C_{2-10}$alkynyl-$C_{3-8}$cycloalkyl, -L-heteroalkyl, -L-heteroalkylaryl, -L-heteroalkylheteroaryl, -L-heteroalkyl-heterocyclyl, -L-heteroalkyl-$C_{3-8}$cycloalkyl, -L-aralkyl, -L-heteroaralkyl, or -L-heterocyclyl, each of which is unsubstituted or is substituted by one or more independent $R^3$;

L is absent, —(C=O)—, —C(=O)O—, —C(=O)N($R^{31}$)—, —S—, —S(O)—, —S(O)$_2$—, —S(O)$_2$N($R^{31}$)—, or —N($R^{31}$)—;

$E^1$ and $E^2$ are independently —($W^1$)$_j$—$R^4$;

j in $E^1$ or j in $E^2$, is independently 0 or 1;

$W^1$ is —O—, —N$R^7$—, —S(O)$_{0-2}$—, —C(O)—, —C(O)N($R^7$)—, —N($R^7$)C(O)—, —N($R^7$)S(O)—, —N($R^7$)S(O)$_2$—, —C(O)O—, —CH($R^7$)N(C(O)O$R^8$)—, —CH($R^7$)N(C(O)$R^8$)—, —CH($R^7$)N(SO$_2R^8$)—, —CH($R^7$)N($R^8$)—, —CH($R^7$)C(O)N($R^8$)—, —CH($R^7$)N($R^8$)C(O)—, —CH($R^7$)N($R^8$)S(O)—, or —CH($R^7$)N($R^8$)S(O)$_2$—;

$W^2$ is —O—, —N$R^7$—, —S(O)$_{0-2}$—, —C(O)—, —C(O)N($R^7$)—, —N($R^7$)C(O)—, —N($R^7$)C(O)N($R^8$)—, —N($R^7$)S(O)—, —N($R^7$)S(O)$_2$—, —C(O)O—, —CH($R^7$)N(C(O)$R^8$)—, —CH($R^7$)N(C(O)O$R^8$)—, —CH($R^7$)N(SO$_2R^8$)—, —CH($R^7$)N($R^8$)—, —CH($R^7$)C(O)N($R^8$)—, —CH($R^7$)N($R^8$)C(O)—, —CH($R^7$)N($R^8$)S(O)—, or —CH($R^7$)N($R^8$)S(O)$_2$—;

k is 0 or 1;

$R^2$ is hydrogen, halogen, —OH, —$R^{31}$, —CF$_3$, —OCF$_3$, —O$R^{31}$, —N$R^{31}R^{32}$, —N$R^{34}R^{35}$, —C(O)$R^{31}$, —CO$_2R^{31}$, —C(=O)N$R^{31}R^{32}$, —C(=O)N$R^{34}R^{35}$, —NO$_2$, —CN, —S(O)$_{0-2}R^{31}$, —SO$_2$N$R^{31}R^{32}$, —SO$_2$N$R^{34}R^{35}$, —N$R^{31}$C(=O)$R^{32}$, —N$R^{31}$C(=O)O$R^{32}$, —N$R^{31}$C(=O)N$R^{32}R^{33}$, —N$R^{31}$S(O)$_{0-2}R^{32}$, —C(=S)O$R^{31}$, —C(=O)S$R^{31}$, —N$R^{31}$C(=N$R^{32}$)N$R^{33}R^{32}$, —N$R^{31}$C(=N$R^{32}$)O$R^{33}$, —N$R^{31}$C(=N$R^{32}$)S$R^{33}$, —OC(=O)O$R^{33}$, —OC(=O)N$R^{31}R^{32}$, —OC(=O)S$R^{31}$, —SC(=O)O$R^{31}$, —P(O)O$R^{31}$O$R^{32}$, —SC(=O)N$R^{31}R^{32}$ aryl (e.g. bicyclic aryl, unsubstituted aryl, or substituted monocyclic aryl), heteroaryl, $C_{1-10}$alkyl, $C_{3-8}$cycloalkyl, $C_{1-10}$alkyl-$C_{3-8}$cycloalkyl, $C_{3-8}$cycloalkyl-$C_{1-10}$alkyl, $C_{3-8}$cycloalkyl-$C_{2-10}$alkenyl, $C_{3-8}$cycloalkyl-$C_{2-10}$-alkynyl, $C_{1-10}$alkyl-$C_{2-10}$alkenyl, $C_{1-10}$alkyl-$C_{2-10}$alkynyl, $C_{1-10}$alkylaryl (e.g. $C_{2-10}$alkyl-monocyclic aryl, $C_{1-10}$alkyl-substituted monocyclic aryl, or $C_{1-10}$alkylbicycloaryl), $C_{1-10}$alkylheteroaryl, $C_{1-10}$alkylheterocyclyl, $C_{2-10}$alkenyl, $C_{2-10}$alkynyl, $C_{2-10}$alkenyl-$C_{1-10}$alkyl, $C_{2-10}$alkynyl-$C_{1-10}$alkyl, $C_{2-10}$-alkenylaryl, $C_{2-10}$alkenylheteroaryl, $C_{2-10}$alkenylheteroalkyl, $C_{2-10}$alkenylheterocyicyl, $C_{2-10}$alkenyl-$C_{3-8}$cycloalkyl, $C_{2-10}$alkynylaryl, $C_{2-10}$alkynylheteroaryl, $C_{2-10}$alkynylheteroalkyl, $C_{2-10}$alkynylheterocyclyl, $C_{2-10}$alkynyl-$C_{3-8}$cycloalkenyl, $C_{1-10}$alkoxy $C_{1-10}$alkyl, $C_{1-10}$alkoxy-$C_{2-10}$alkenyl, $C_{1-10}$alkoxy-$C_{2-10}$alkynyl, heterocyclyl-$C_{1-10}$alkyl, heterocyclyl-$C_{2-10}$alkenyl, heterocyclyl-$C_{2-10}$alkynyl, aryl-$C_{1-10}$alkyl (e.g. monocyclic aryl-$C_{2-10}$alkyl, substituted monocyclic aryl-$C_{1-10}$alkyl, or bicycloaryl-$C_{1-10}$alkyl), aryl-$C_{2-10}$alkenyl, aryl-$C_{2-10}$alkynyl, aryl-heterocyclyl, heteroaryl-$C_{1-10}$alkyl, heteroaryl-$C_{2-10}$alkenyl, heteroaryl-$C_{2-10}$alkynyl, heteroaryl-$C_{3-8}$cycloalkyl, heteroaryl-heteroalkyl, or heteroaryl-heterocyclyl, wherein each of said bicyclic aryl or heteroaryl moiety is unsubstituted, or wherein each of bicyclic aryl, heteroaryl moiety or monocyclic aryl moiety is substituted with one or more independent alkyl, heteroalkyl, alkenyl, alkynyl, cycloalkyl, heterocycloalkyl, aryl, arylalkyl, heteroaryl, heteroarylalkyl, halo, —OH, —$R^{31}$, —CF$_3$, —OCF$_3$, —O$R^{31}$, —N$R^{31}R^{32}$, —N$R^{34}R^{35}$, —C(O)$R^{31}$, —CO$_2R^{31}$, —C(=O)N$R^{31}R^{32}$, —C(=O)N$R^{34}R^{35}$, —NO$_2$, —CN, —S(O)$_{0-2}R^{31}$, —SO$_2$N$R^{31}R^{32}$, —N$R^{31}$C(=O)$R^{32}$, —N$R^{31}$C(=O)O$R^{32}$, —N$R^{31}$C(=O)N$R^{32}R^{33}$, —N$R^{31}$S(O)$_{0-2}R^{32}$, —C(=S)O$R^{31}$, —C(=O)S$R^{31}$, —N$R^{31}$C(=N$R^{32}$)N$R^{33}R^{32}$, —N$R^{31}$C(=N$R^{32}$)O$R^{33}$, —N$R^{31}$C(=N$R^{32}$)S$R^{33}$, —OC(=O)O$R^{33}$, —OC(=O)N$R^{31}R^{32}$, —OC(=O)S$R^{31}$, —SC(=O)O$R^{31}$, —P(O)O$R^{31}$O$R^{32}$, or —SC(=O)N$R^{31}R^{32}$ s, and wherein each of said alkyl, cycloalkyl, heterocyclyl, or heteroalkyl moiety is unsubstituted or is substituted with one or more alkyl, heteroalkyl, alkenyl, alkynyl, cycloalkyl, heterocycloalkyl, aryl, arylalkyl, heteroaryl, heteroarylalkyl, halo, —OH, —$R^{31}$, —CF$_3$, —OCF$_3$, —O$R^{31}$, —O-aryl, —N$R^{31}R^{32}$, —N$R^{34}R^{35}$, —C(O)$R^{31}$, —CO$_2R^{31}$, —C(=O)N$R^{34}R^{35}$, or —C(=O)N$R^{31}R^{32}$;

$R^3$ and $R^4$ are independently hydrogen, halogen, —OH, —$R^{31}$, —CF$_3$, —OCF$_3$, —O$R^{31}$, —N$R^{31}R^{32}$, —N$R^{34}R^{35}$, —C(O)$R^{31}$, —CO$R^{31}$—C(=O)N$R^{31}R^{32}$, —C(=O)N$R^{34}R^{35}$, —NO$_2$, —CN, —S(O)$_{0-2}R^{31}$, —SO$_2$N$R^{31}R^{32}$, —SO$_2$N$R^{34}R^{35}$, —N$R^{31}$C(=O)$R^{32}$, —N$R^{31}$C(=O)O$R^{32}$, —N$R^{31}$C(=O)N$R^{32}R^{33}$, —N$R^{31}$S(O)$_{0-2}R^{32}$, —C(=S)O$R^{31}$, —C(=O)S$R^{31}$, —N$R^{31}$C(=N$R^{32}$)N$R^{33}R^{32}$, —N$R^{31}$C(=N$R^{32}$)O$R^{33}$, —N$R^{31}$C(=N$R^{32}$)S$R^{33}$, —OC(=O)O$R^{33}$, —OC(=O)N$R^{31}R^{32}$, —OC(=O)S$R^{31}$, —SC(=O)O$R^{31}$, —P(O)O$R^{31}$O$R^{32}$, —SC(=O)N$R^{31}R^{32}$, aryl, heteroaryl, $C_{1-10}$alkyl, $C_{3-8}$cycloalkyl, $C_{1-10}$alkyl-$C_{3-8}$cycloalkyl, $C_{3-8}$cycloalkyl-$C_{1-10}$alkyl, $C_{3-8}$cycloalkyl-$C_{2-10}$alkenyl, $C_{3-8}$cycloalkyl-$C_{2-10}$alkynyl, $C_{1-10}$alkyl-$C_{2-10}$alkenyl, $C_{1-10}$alkyl-$C_{2-10}$alkynyl, $C_{1-10}$alkylaryl, $C_{1-10}$alkylheteroaryl, $C_{1-10}$alkylheterocyclyl, $C_{2-10}$alkenyl, $C_{2-10}$alkynyl, $C_{2-10}$alkenyl-$C_{1-10}$alkyl, $C_{2-10}$alkynyl-$C_{1-10}$alkyl, $C_{2-10}$alkenylaryl, $C_{2-10}$alkenylheteroaryl, $C_{2-10}$-alkenylheteroalkyl, $C_{2-10}$alkenylheterocycicyl, $C_{2-10}$alkenyl-$C_{3-8}$cycloalkyl, $C_{2-10}$alkynylaryl, $C_{2-10}$alkynylheteroaryl, $C_{2-10}$alkynylheteroalkyl, $C_{2-10}$alkynylheterocyclyl, $C_{2-10}$alkynyl-$C_{3-8}$cycloalkenyl, $C_{1-10}$alkoxy $C_{1-10}$alkyl, $C_{1-10}$alkoxy-$C_{2-10}$alkenyl, $C_{1-10}$alkoxy-$C_{2-10}$alkynyl, heterocyclyl-$C_{1-10}$alkyl, heterocyclyl-$C_{2-10}$alkenyl, heterocyclyl-$C_{2-10}$alkynyl, aryl-$C_{1-10}$alkyl, aryl-$C_{2-10}$alkenyl, aryl-$C_{2-10}$alkynyl aryl-heterocyclyl, heteroaryl-$C_{1-10}$alkyl, heteroaryl-$C_{2-10}$alkenyl, heteroaryl-$C_{2-10}$alkynyl, heteroaryl-$C_{3-8}$cycloalkyl, heteroaryl-heteroalkyl, or heteroaryl-heterocyclyl, wherein each of said aryl or heteroaryl moiety is unsubstituted or is substituted with one or more independent alkyl, heteroalkyl, alkenyl, alkynyl, cycloalkyl, heterocycloalkyl, aryl, arylalkyl, heteroaryl, heteroarylalkyl, halo, —OH, —$R^{31}$, —CF$_3$, —OCF$_3$, —O$R^{31}$, —N$R^{31}R^{32}$, —NR³⁴R³⁵, —C(O)R³¹ —C(=O)NR³¹R³², —C(=O)NR³⁴R³⁵, —NO₂, —CN, —S(O)₀₋₂R³¹, —SO₂NR³¹R³², —SO₂NR³⁴R³⁵, —NR³¹C(=O)R³², —NR³¹C(=O)OR³², —NR³¹C(=O)NR³²R³³, —NR³¹S(O)₀₋₂R³², —C(=S)OR³¹, —C(=O)SR³¹, —NR³¹C(=NR³²)NR³³R³², —NR³¹C(=NR³²)OR³³, —NR³¹C(=NR³²)SR³³, —OC(=O)OR³³, —OC(=O)NR³¹R³², —OC(=O)SR³¹, —SC(=O)OR³¹, —P(O)OR³¹OR³², or —SC(=O)NR³¹R³², and wherein each of said alkyl, cycloalkyl, heterocyclyl, or heteroalkyl moiety is unsubstituted or is substituted with one or more alkyl, heteroalkyl, alkenyl, alkynyl, cycloalkyl, heterocycloalkyl, aryl, arylalkyl, heteroaryl, heteroarylalkyl, halo, —OH, —R³¹, —CF₃, —OCF₃, —OR³¹, —O-aryl, —NR³¹R³², —NR³⁴R³⁵, —C(O)R³¹, —CO₂R³¹, —C(=O)NR³⁴R³⁵, or —C(=O)NR³¹R³²;

R⁵ is hydrogen, halogen, —OH, —R³¹, —CF₃, —OCF₃, —OR³¹, —NR³¹R³², —NR³⁴R³⁵, —C(O)R³¹, —CO₂R³¹, —C(=O)NR³¹R³², —C(=O)NR³⁴R³⁵, —NO₂, —CN, —S(O)₀₋₂R³¹, —SO₂NR³¹R³², —SO₂NR³⁴R³⁵, —NR³¹C(=O)R³², —NR³¹C(=O)OR³², —NR³¹C(=O)NR³²R³³, —NR³¹S(O)₀₋₂R³², —C(=S)OR³¹, —C(=O)SR³¹, —NR³¹C(=NR³²)NR³³R³², —NR³¹C(=NR³²)OR³³, —NR³¹C(=NR³²)SR³³, —OC(=O)OR³³, —OC(=O)NR³¹R³², —OC(=O)SR³¹, —SC(=O)OR³¹, —P(O)OR³¹OR³², or —SC(=O)NR³¹R³²;

R³¹, R³², and R³³, in each instance, are independently H or C₁₋₁₀alkyl, wherein the C₁₋₁₀alkyl is unsubstituted or is substituted with one or more aryl, heteroalkyl, heterocyclyl, or heteroaryl group, wherein each of said aryl, heteroalkyl, heterocyclyl, or heteroaryl group is unsubstituted or is substituted with one or more halo, —OH, —C₁₋₁₀alkyl, —CF₃, —O-aryl, —OCF₃, —OC₁₋₁₀alkyl, —NH₂, —N(C₁₋₁₀alkyl)(C₁₋₁₀alkyl), —NH(C₁₋₁₀alkyl), —NH(aryl), —NR³⁴R³⁵, —C(O)(C₁₋₁₀alkyl), —C(O)(C₁₋₁₀alkyl-aryl), —C(O)(aryl), —CO₂—C₁₋₁₀alkyl, —CO₂—C₁₋₁₀alkylaryl, —CO₂-aryl, —C(=O)N(C₁₋₁₀alkyl)(C₁₋₁₀alkyl), —C(=O)NH(C₁₋₁₀alkyl), —C(=O)NR³⁴R³⁵, —C(=O)NH₂, —OCF₃, —O(C₁₋₁₀alkyl), —O-aryl, —N(aryl)(C₁₋₁₀alkyl), —NO₂, —CN, —S(O)₀₋₂C₁₋₁₀alkyl, —S(O)₀₋₂C₁₋₁₀alkylaryl, —S(O)₀₋₂aryl, —SO₂N(aryl), —SO₂N(C₁₋₁₀alkyl)(C₁₋₁₀alkyl), —SO₂NH(C₁₋₁₀alkyl) or —SO₂NR³⁴R³⁵;

R³⁴ and R³⁵ in —NR³⁴R³⁵, —C(=O)NR³⁴R³⁵, or —SO₂NR³⁴R³⁵, are taken together with the nitrogen atom to which they are attached to form a 3-10 membered saturated or unsaturated ring; wherein said ring is independently unsubstituted or is substituted by one or more —NR³¹R³², hydroxyl, halogen, oxo, aryl, heteroaryl, C₁₋₆alkyl, or O-aryl, and wherein said 3-10 membered saturated or unsaturated ring independently contains 0, 1, or 2 more heteroatoms in addition to the nitrogen atom; and R⁷ and R⁸ are each independently hydrogen, C₁₋₁₀alkyl, C₂₋₁₀alkenyl, aryl, heteroaryl, heterocyclyl or C₃₋₁₀cycloalkyl, each of which except for hydrogen is unsubstituted or is substituted by one or more independent R⁶; and R⁶ is halo, —OR³¹, —SH, NH₂, —NR³⁴R³⁵, —NR³¹R³², —CO₂R³¹, —CO₂aryl, —C(=O)NR³¹R³², C(=O)NR³⁴R³⁵, —NO₂, —CN, —S(O)₀₋₂C₁₋₁₀alkyl, —S(O)₀₋₂aryl, —SO₂NR³⁴R³⁵, —SO₂NR³¹R³², C₁₋₁₀alkyl, C₂₋₁₀alkenyl, or C₂₋₁₀alkynyl; or R⁶ is aryl-C₁₋₁₀alkyl, aryl-C₂₋₁₀alkenyl, aryl-C₂₋₁₀alkynyl, heteroaryl-C₁₋₁₀alkyl, heteroaryl-C₂₋₁₀alkenyl, heteroaryl-C₂₋₁₀alkynyl, each of which is unsubstituted or is substituted with one or more independent halo, cyano, nitro, —OC₁₋₁₀alkyl, C₁₋₁₀alkyl, C₂₋₁₀alkenyl, C₂₋₁₀alkynyl, haloC₁₋₁₀alkyl, haloC₂₋₁₀alkenyl, haloC₂₋₁₀alkynyl, —COOH, —C(=O)NR³¹R³², —C(=O)NR³⁴R³⁵, —SO₂NR³⁴R³⁵, —SO₂NR³¹R³², —NR³¹R³², or —NR³⁴R³⁵.

In various embodiments of the compound of Formula I-C, the compound has a structure of Formula I-C1 or Formula I-C2:

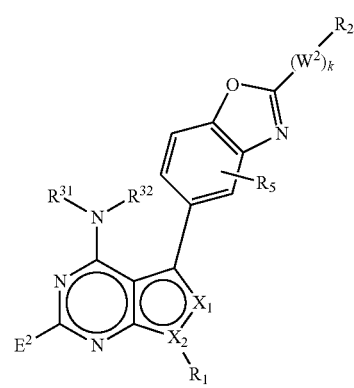

Formula I-C1

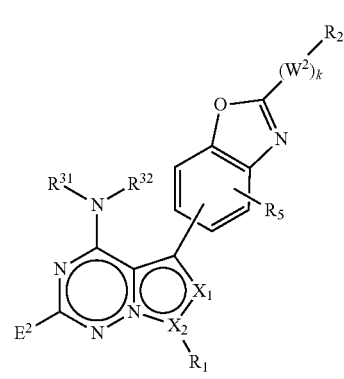

Formula I-C2 or a pharmaceutically acceptable salt thereof.

In some embodiments of Formula I-C1, X₁ is N and X₂ is N. In other embodiments, X₁ is C-E¹ and X₂ is N. In yet other embodiments, X₁ is NH and X₂ is C. In further embodiments, X₁ is CH-E¹ and X₂ is C.

In several embodiments of Formula I-C2, X₁ is N and X₂ is C. In yet other embodiments, X₁ is NH and X₂ is C. In further embodiments, X₁ is CH-E¹ and X₂ is C.

In various embodiments of the compound of Formula I-D, the compound has a structure of Formula I-D1 or Formula I-D2:

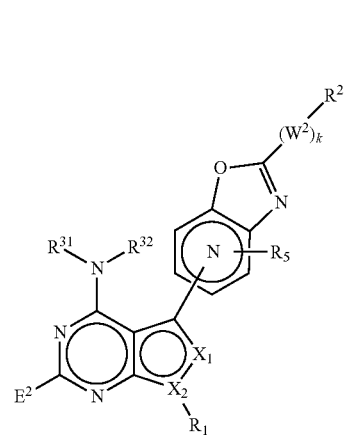

Formula I-D1

-continued

Formula I-D2

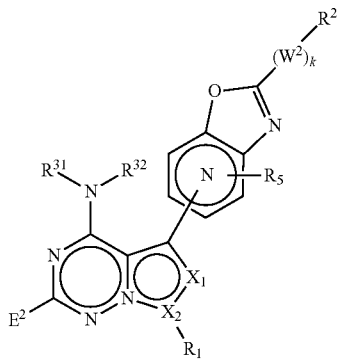

or a pharmaceutically acceptable salt thereof.

In some embodiments of Formula I-D1, $X_1$ is N and $X_2$ is N. In other embodiments, $X_1$ is C-$E^1$ and $X_2$ is N. In yet other embodiments, $X_1$ is NH and $X_2$ is C. In further embodiments, $X_1$ is CH-$E^1$ and $X_2$ is C.

In several embodiments of Formula I-D2, $X_1$ is N and $X_2$ is C. In further embodiments, $X_1$ is C-$E^1$ and $X_2$ is C.

In various embodiments, $X_1$ is C—$(W^1)_j$—$R^4$, where j is 0.

In another embodiment, $X_1$ is CH. In yet another embodiment, $X_1$ is C-halogen, where halogen is Cl, F, Br, or I.

In various embodiments of $X_1$, it is C—$(W^1)_j$—$R^4$. In various embodiments of $X_1$, j is 1, and $W^1$ is —O—. In various embodiments of $X_1$, j is 1, and $W^1$ is —$NR^7$—. In various embodiments of $X_1$, j is 1, and $W^1$ is —NH—. In various embodiments of $X_1$, j is 1, and $W^1$ is —$S(O)_{0-2}$—. In various embodiments of $X_1$, j is 1, and $W^1$ is —C(O)—. In various embodiments of $X_1$, j is 1, and $W^1$ is —C(O)N($R^7$)—. In various embodiments of $X_1$, j is 1, and $W^1$ is —N($R^7$)C(O)—. In various embodiments of $X_1$, j is 1, and $W^1$ is —N($R^7$)S(O)—. In various embodiments of $X_1$, j is 1, and $W^1$ is —N($R^7$)S(O)$_2$—. In various embodiments of $X_1$, j is 1, and $W^1$ is —C(O)O—. In various embodiments of $X_1$, j is 1, and $W^1$ is CH($R^7$)N(C(O)O$R^8$)—. In various embodiments of $X_1$, j is 1, and $W^1$ is —CH($R^7$)N(C(O)$R^8$)—. In various embodiments of $X_1$, j is 1, and $W^1$ is —CH($R^7$)N(SO$_2$$R^8$)—. In various embodiments of $X_1$, j is 1, and $W^1$ is —CH($R^7$)N($R^8$)—. In various embodiments of $X_1$, j is 1, and $W^1$ is —CH($R^7$)C(O)N($R^8$)—. In various embodiments of $X_1$, j is 1, and $W^1$ is —CH($R^7$)N($R^8$)C(O)—. In various embodiments of $X_1$, j is 1, and $W^1$ is —CH($R^7$)N($R^8$)S(O)—. In various embodiments of $X_1$, j is 1, and $W^1$ is —CH($R^7$)N($R^8$)S(O)$_2$—.

In various embodiments, $X_1$ is CH—$(W^1)_j$—$R^4$, where j is 0.

In another embodiment, $X_1$ is CH$_2$. In yet another embodiment, $X_1$ is CH-halogen, where halogen is Cl, F, Br, or I.

In various embodiments of $X_1$, it is CH—$(W^1)_j$—$R^4$. In various embodiments of $X_1$, j is 1, and $W^1$ is —O—. In various embodiments of $X_1$, j is 1, and $W^1$ is —$NR^7$—. In various embodiments of $X_1$, j is 1, and $W^1$ is —NH—. In various embodiments of $X_1$, j is 1, and $W^1$ is —$S(O)_{0-2}$—. In various embodiments of $X_1$, j is 1, and $W^1$ is —C(O)—. In various embodiments of $X_1$, j is 1, and $W^1$ is —C(O)N($R^7$)—. In various embodiments of $X_1$, j is 1, and $W^1$ is —N($R^7$)C(O)—. In various embodiments of $X_1$, j is 1, and $W^1$ is —N($R^7$)S(O)—. In various embodiments of $X_1$, j is 1, and $W^1$ is —N($R^7$)S(O)$_2$—. In various embodiments of $X_1$, j is 1, and $W^1$ is —C(O)O—. In various embodiments of $X_1$, j is 1, and $W^1$ is CH($R^7$)N(C(O)O$R^8$)—. In various embodiments of $X_1$, j is 1, and $W^1$ is —CH($R^7$)N(C(O)$R^8$)—. In various embodiments of $X_1$, j is 1, and $W^1$ is —CH($R^7$)N(SO$_2$$R^8$)—. In various embodiments of $X_1$, j is 1, and $W^1$ is —CH($R^7$)N($R^8$)—. In various embodiments of $X_1$, j is 1, and $W^1$ is —CH($R^7$)C(O)N($R^8$)—. In various embodiments of $X_1$, j is 1, and $W^1$ is —CH($R^7$)N($R^8$)C(O)—. In various embodiments of $X_1$, j is 1, and $W^1$ is —CH($R^7$)N($R^8$)S(O)—. In various embodiments of $X_1$, j is 1, and $W^1$ is —CH($R^7$)N($R^8$)S(O)$_2$—.

In another embodiment, $X_1$ is N.

In various embodiments, $X_2$ is N. In other embodiments, $X_2$ is C.

In various embodiments, $E^2$ is —$(W^1)_j$—$R^4$, where j is 0.

In another embodiment, $E^2$ is CH. In yet another embodiment, $E^2$ is C-halogen, where halogen is Cl, F, Br, or I.

In various embodiments of $E^2$, it is —$(W^1)_j$—$R^4$. In various embodiments of $E^2$, j is 1, and $W^1$ is —O—. In various embodiments of $E^2$, j is 1, and $W^1$ is —$NR^7$—. In various embodiments of $E^2$, j is 1, and $W^1$ is —NH—. In various embodiments of $E^2$, j is 1, and $W^1$ is —$S(O)_{0-2}$—. In various embodiments of $E^2$, j is 1, and $W^1$ is —C(O)—. In various embodiments of $E^2$, j is 1, and $W^1$ is —C(O)N($R^7$)—. In various embodiments of $E^2$, j is 1, and $W^1$ is —N($R^7$)C(O)—. In various embodiments of $E^2$, j is 1, and $W^1$ is —N($R^7$)S(O)—. In various embodiments of $E^2$, j is 1, and $W^1$ is —N($R^7$)S(O)$_2$—. In various embodiments of $E^2$, j is 1, and $W^1$ is —C(O)O—. In various embodiments of $E^2$, j is 1, and $W^1$ is CH($R^7$)N(C(O)O$R^8$)—. In various embodiments of $E^2$, j is 1, and $W^1$ is —CH($R^7$)N(C(O)$R^8$)—. In various embodiments of $E^2$, j is 1, and $W^1$ is —CH($R^7$)N(SO$_2$$R^8$)—. In various embodiments of $E^2$, j is 1, and $W^1$ is —CH($R^7$)N($R^8$)—. In various embodiments of $E^2$, j is 1, and $W^1$ is —CH($R^7$)C(O)N($R^8$)—. In various embodiments of $E^2$, j is 1, and $W^1$ is —CH($R^7$)N($R^8$)C(O)—. In various embodiments of $E^2$, j is 1, and $W^1$ is —CH($R^7$)N($R^8$)S(O)—. In various embodiments of $E^2$, j is 1, and $W^1$ is —CH($R^7$)N($R^8$)S(O)$_2$—.

In various embodiments, k is 0. In other embodiments, k is 1 and $W^2$ is —O—. In another embodiment, k is 1 and $W^2$ is —$NR^7$—. In yet another embodiment of, k is 1, and $W^2$ is —$S(O)_{0-2}$—. In another embodiment of, k is 1 and $W^2$ is —C(O)—. In a further embodiment, k is 1 and $W^2$ is —C(O)N($R^7$)—. In another embodiment, k is 1, and $W^2$ is —N($R^7$)C(O)—. In another embodiment, k is 1 and $W^2$ is —N($R^7$)C(O)N($R^8$)—. In yet another embodiment, k is 1 and $W^2$ is —N($R^7$)S(O)—. In still yet another embodiment, k is 1 and $W^2$ is —N($R^7$)S(O)$_2$—. In a further embodiment, k is 1 and $W^2$ is —C(O)O—. In another embodiment, k is 1 and $W^2$ is —CH($R^7$)N(C(O)O$R^8$)—. In another embodiment, k is 1 and $W^2$ is —CH($R^7$)N(C(O)$R^8$)—. In another embodiment, k is 1 and $W^2$ is —CH($R^7$)N(SO$_2$$R^8$)—. In a further embodiment, k is 1 and $W^2$ is —CH($R^7$)N($R^8$)—. In another embodiment, k is 1 and $W^2$ is —CH($R^7$)C(O)N($R^8$)—. In yet another embodiment, k is 1 and $W^2$ is —CH($R^7$)N($R^8$)C(O)—. In another embodiment, k is 1 and $W^2$ is —CH($R^7$)N($R^8$)S(O)—. In yet another embodiment, k is 1 and $W^2$ is —CH($R^7$)N($R^8$)S(O)$_2$—.

The invention also provides a compound which is an mTor inhibitor of Formula I-E:

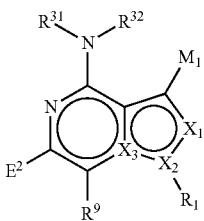

Formula I-E or a pharmaceutically acceptable salt thereof, wherein: $X_1$ is N or C-$E^1$, $X_2$ is N, and $X_3$ is C; or $X_1$ is N or C-$E^1$, $X_2$ is C, and $X_3$ is N;

$R_1$ is —H, -L-$C_{1-10}$alkyl, -L-$C_{3-8}$cycloalkyl, -L-$C_{1-10}$alkyl-$C_{3-8}$cycloalkyl, -L-aryl, -L-heteroaryl, -L-$C_{1-10}$alkylaryl, -L-$C_{1-10}$alkylheteroaryl, -L-$C_{1-10}$alkylheterocyclyl, -L-$C_{2-10}$alkenyl, -L-$C_{2-10}$alkynyl, -L-$C_{2-10}$alkenyl-$C_{3-8}$cycloalkyl, -L-$C_{2-10}$alkynyl-$C_{3-8}$cycloalkyl, -L-heteroalkyl, -L-heteroalkylaryl, -L-heteroalkylheteroaryl, -L-heteroalkyl-heterocyclyl, -L-heteroalkyl-$C_{3-8}$cycloalkyl, -L-aralkyl, -L-heteroaralkyl, or -L-heterocyclyl, each of which is unsubstituted or is substituted by one or more independent $R^3$;

L is absent, —(C═O)—, —C(═O)O—, —C(═O)N($R^{31}$)—, —S—, —S(O)—, —S(O)$_2$—, —S(O)$_2$N($R^{31}$)—, or —N($R^{31}$)—;

$M_1$ is a moiety having the structure of Formula M1-F1 or Formula M1-F2:

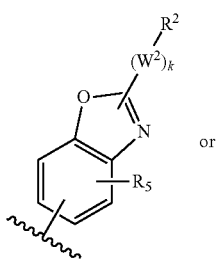

Formula M1-F1 or

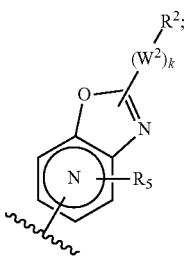

Formula M1-F2 k is 0 or 1;
$E^1$ and $E^2$ are independently —($W^1$)$_j$—$R^4$;
j in $E^1$ or j in $E^2$, is independently 0 or 1;
$W^1$ is —O—, —N$R^7$—, —S(O)$_{0-2}$—, —C(O)—, —C(O)N($R^7$)—, —N($R^7$)C(O)—, —N($R^7$)S(O)—, —N($R^7$)S(O)$_2$—, —C(O)O—, —CH($R^7$)N(C(O)O$R^8$)—, —CH($R^7$)N(C(O)$R^8$)—, —CH($R^7$)N(SO$_2R^8$)—, —CH($R^7$)N($R^8$)—, —CH($R^7$)C(O)N($R^8$)—, —CH($R^7$)N($R^8$)C(O)—, —CH($R^7$)N($R^8$)S(O)—, or —CH($R^7$)N($R^8$)S(O)$_2$—;
$W^2$ is —O—, —N$R^7$—, —S(O)$_{0-2}$—, —C(O)—, —C(O)N($R^7$)—, —N($R^7$)C(O)—, —N($R^7$)C(O)N($R^8$)—, —N($R^7$)S(O)—, —N($R^7$)S(O)$_2$—, —C(O)O—, —CH($R^7$)N(C(O)O$R^8$)—, —CH($R^7$)N(C(O)$R^8$)—, —CH($R^7$)N(SO$_2R^8$)—, —CH($R^7$)N($R^8$)—, —CH($R^7$)C(O)N($R^8$)—, —CH($R^7$)N($R^8$)C(O)—, —CH($R^7$)N($R^8$)S(O)—, or —CH($R^7$)N($R^8$)S(O)$_2$—;

$R^2$ is hydrogen, halogen, —OH, —$R^{31}$, —CF$_3$, —OCF$_3$, —O$R^{31}$, —N$R^{31}R^{32}$, —N$R^{34}R^{35}$, —C(O)$R^{31}$, —CO$_2R^{31}$, —C(═O)N$R^{31}R^{32}$, —C(═O)N$R^{34}R^{35}$, —NO$_2$, —CN, —S(O)$_{0-2}R^{31}$, —SO$_2$N$R^{31}R^{32}$, —SO$_2$N$R^{34}R^{35}$, —N$R^{31}$C(═O)$R^{32}$, —N$R^{31}$C(═O)O$R^{32}$, —N$R^{31}$C(═O)N$R^{32}R^{33}$, —N$R^{31}$S(O)$_{0-2}R^{32}$, —C(═S)O$R^{31}$, —C(═O)S$R^{31}$, —N$R^{31}$C(═N$R^{32}$)N$R^{33}R^{32}$, —N$R^{31}$C(═N$R^{32}$)O$R^{33}$, —N$R^{31}$C(═N$R^{32}$)S$R^{33}$, —OC(═O)O$R^{33}$, —OC(═O)N$R^{31}R^{32}$, —OC(═O)S$R^{31}$, —SC(═O)O$R^{31}$, —P(O)O$R^{31}$O$R^{32}$, —SC(═O)N$R^{31}R^{32}$ aryl (e.g. bicyclic aryl, unsubstituted aryl, or substituted monocyclic aryl), heteroaryl, $C_{1-10}$alkyl, $C_{3-8}$cycloalkyl, $C_{1-10}$alkyl-$C_{3-8}$cycloalkyl, $C_{3-8}$cycloalkyl-$C_{1-10}$alkyl, $C_{3-8}$cycloalkyl-$C_{2-10}$alkenyl, $C_{3-8}$cycloalkyl-$C_{2-10}$-alkynyl, $C_{1-10}$alkyl-$C_{2-10}$alkenyl, $C_{1-10}$alkyl-$C_{2-10}$alkynyl, $C_{1-10}$alkylaryl (e.g. $C_{2-10}$alkyl-monocyclic aryl, $C_{1-10}$alkyl-substituted monocyclic aryl, or $C_{1-10}$alkylbicycloaryl), $C_{1-10}$alkylheteroaryl, $C_{1-10}$alkylheterocyclyl, $C_{2-10}$alkenyl, $C_{2-10}$alkynyl, $C_{2-10}$alkenyl-$C_{1-10}$alkyl, $C_{2-10}$alkynyl-$C_{1-10}$alkyl, $C_{2-10}$-alkenylaryl, $C_{2-10}$alkenylheteroaryl, $C_{2-10}$alkenylheteroalkyl, $C_{2-10}$alkenylheterocycicyl, $C_{2-10}$alkenyl-$C_{3-8}$cycloalkyl, $C_{2-10}$alkynylaryl, $C_{2-10}$alkynylheteroaryl, $C_{2-10}$alkynylheteroalkyl, $C_{2-10}$alkynylheterocyclyl, $C_{2-10}$alkynyl-$C_{3-8}$cyclo alkenyl, $C_{1-10}$alkoxy $C_{1-10}$alkyl, $C_{1-10}$alkoxy-$C_{2-10}$alkenyl, $C_{1-10}$alkoxy-$C_{2-10}$alkynyl, heterocyclyl-$C_{1-10}$alkyl, heterocyclyl-$C_{2-10}$alkenyl, heterocyclyl-$C_{2-10}$-alkynyl, aryl-$C_{1-10}$alkyl (e.g. monocyclic aryl-$C_{2-10}$alkyl, substituted monocyclic aryl-$C_{1-10}$alkyl, or bicycloaryl-$C_{1-10}$alkyl), aryl-$C_{2-10}$alkenyl, aryl-$C_{2-10}$alkynyl, aryl-heterocyclyl, heteroaryl-$C_{1-10}$alkyl, heteroaryl-$C_{2-10}$alkenyl, heteroaryl-$C_{2-10}$alkynyl, heteroaryl-$C_{3-8}$cycloalkyl, heteroaryl-heteroalkyl, or heteroaryl-heterocyclyl, wherein each of said bicyclic aryl or heteroaryl moiety is unsubstituted, or wherein each of bicyclic aryl, heteroaryl moiety or monocyclic aryl moiety is substituted with one or more independent alkyl, heteroalkyl, alkenyl, alkynyl, cycloalkyl, heterocycloalkyl, aryl, arylalkyl, heteroaryl, heteroarylalkyl, halo, —OH, —$R^{31}$, —CF$_3$, —OCF$_3$, —O$R^{31}$, —N$R^{31}R^{32}$, —N$R^{34}R^{35}$, —C(O)$R^{31}$, —CO$_2R^{31}$, —C(═O)N$R^{31}R^{32}$, —C(═O)N$R^{34}R^{35}$, —NO$_2$, —CN, —S(O)$_{0-2}R^{31}$—SO$_2$N$R^{34}R^{35}$, —N$R^{31}$C(═O)$R^{32}$, —N$R^{31}$C(═O)O$R^{32}$, —N$R^{31}$C(═O)N$R^{32}R^{33}$, —N$R^{31}$S(O)$_{0-2}R^{32}$, —C(═S)O$R^{31}$, —C(═O)S$R^{31}$, —N$R^{31}$C(═N$R^{32}$)N$R^{33}R^{32}$, —N$R^{31}$C(═N$R^{32}$)O$R^{33}$, —N$R^{31}$C(═N$R^{32}$)S$R^{33}$, —OC(═O)O$R^{33}$, —OC(═O)N$R^{31}R^{32}$, —OC(═O)S$R^{31}$, —SC(═O)O$R^{31}$, —P(O)O$R^{31}$O$R^{32}$, or —SC(═O)N$R^{31}R^{32}$, and wherein each of said alkyl, cycloalkyl, heterocyclyl, or heteroalkyl moiety is unsubstituted or is substituted with one or more alkyl, heteroalkyl, alkenyl, alkynyl, cycloalkyl, heterocycloalkyl, aryl, arylalkyl, heteroaryl, heteroarylalkyl, halo, —OH, —$R^{31}$, —CF$_3$, —OCF$_3$, —O$R^{31}$, —O-aryl, —N$R^{31}R^{32}$, —N$R^{34}R^{35}$, —C(O)$R^{31}$, —CO$_2R^{31}$, —C(═O)N$R^{34}R^{35}$, or —C(═O)N$R^{31}R^{32}$;

$R^3$ and $R^4$ are independently hydrogen, halogen, —OH, —$R^{31}$, —CF$_3$, —OCF$_3$, —O$R^{31}$, —N$R^{31}R^{32}$, —N$R^{34}R^{35}$, —C(O)$R^{31}$, —CO$_2R^{31}$, —C(═O)N$R^{31}R^{32}$, —C(═O)N$R^{34}R^{35}$, —NO$_2$, —CN, —S(O)$_{0-2}R^{31}$, —SO$_2$N$R^{31}R^{32}$, —SO$_2$N$R^{34}R^{35}$, —N$R^{31}$C(═O)$R^{32}$, —N$R^{31}$C(═O)O$R^{32}$, —N$R^{31}$C(═O)N$R^{32}R^{33}$, —N$R^{31}$S(O)$_{0-2}R^{32}$, —C(═S)O$R^{31}$, —C(═O)S$R^{31}$, —N$R^{31}$C(═N$R^{32}$)N$R^{33}R^{32}$, —N$R^{31}$C(═N$R^{32}$)O$R^{33}$, —N$R^{31}$C(═N$R^{32}$)S$R^{33}$, —OC(═O)O$R^{33}$, —OC(═O)N$R^{31}R^{32}$, —OC(═O)S$R^{31}$, —SC(═O)O$R^{31}$, —P(O)O$R^{31}$O$R^{32}$, —SC(═O)N$R^{31}R^{32}$, aryl, heteroaryl, $C_{1-4}$alkyl, $C_{1-10}$alkyl, $C_{3-8}$cycloalkyl, $C_{1-10}$alkyl- $C_{3-8}$cycloalkyl, $C_{3-8}$cycloalkyl-$C_{1-10}$alkyl, $C_{3-8}$cycloalkyl-$C_{2-10}$alkenyl, $C_{3-8}$cycloalkyl-$C_{2-10}$alkynyl, $C_{1-10}$alkyl-$C_{2-10}$alkenyl, $C_{1-10}$alkyl-$C_{2-10}$alkynyl, $C_{1-10}$alkylaryl, $C_{1-10}$alkylheteroaryl, $C_{1-10}$alkylheterocyclyl, $C_{2-10}$alkenyl, $C_{2-10}$alkynyl, $C_{2-10}$alkenyl-$C_{1-10}$alkyl, $C_{2-10}$alkynyl-$C_{1-10}$alkyl, $C_{2-10}$alkenylaryl, $C_{2-10}$alkenylheteroaryl, $C_{2-10}$alkenylheteroalkyl, $C_{2-10}$alkenylheterocycicyl, $C_{2-10}$alkenyl-$C_{3-8}$cycloalkyl, $C_{2-10}$alkynyl-$C_{3-8}$cycloalkyl, $C_{2-10}$alkynylaryl, $C_{2-10}$alkynylheteroaryl, $C_{2-10}$alkynylheteroalkyl, $C_{2-10}$alkynylheterocyclyl, $C_{2-10}$alkynyl-$C_{3-8}$cycloalkenyl, $C_{1-10}$alkoxy $C_{1-10}$alkyl, $C_{1-10}$alkoxy-$C_{2-10}$alkenyl, $C_{1-10}$alkoxy-$C_{2-10}$alkynyl, heterocyclyl, heterocyclyl-$C_{1-10}$alkyl, heterocyclyl-$C_{2-10}$alkenyl, heterocyclyl-$C_{2-10}$alkynyl, aryl-$C_{1-10}$alkyl, aryl-$C_{2-10}$alkenyl, aryl-$C_{2-10}$alkynyl, aryl-heterocyclyl, heteroaryl-$C_{1-10}$alkyl, heteroaryl-$C_{2-10}$alkenyl, heteroaryl-$C_{2-10}$alkynyl, heteroaryl-$C_{3-8}$cycloalkyl, heteroalkyl, heteroaryl-heteroalkyl, or heteroaryl-heterocyclyl, wherein each of said aryl or heteroaryl moiety is unsubstituted or is substituted with one or more independent halo, —OH, —$R^{31}$, —$CF_3$, —$OCF_3$, —$OR^{31}$, —$NR^{31}R^{32}$, —$NR^{34}R^{35}$, —$C(O)R^{31}$, —$COR^{31}$, —$C(=O)NR^{31}R^{32}$, —$C(=O)NR^{34}R^{35}$, —$NO_2$, —CN, —$S(O)_{0-2}R^{31}$, —$SO_2NR^{31}R^{32}$, —$SO_2NR^{34}R^{35}$, —$NR^{31}C(=O)R^{32}$, —$NR^{31}C(=O)OR^{32}$, —$NR^{31}C(=O)NR^{32}R^{33}$, —$NR^{31}S(O)_{0-2}R^{32}$, —$C(=S)OR^{31}$, —$C(=O)SR^{31}$, —$NR^{31}C(=O)OR^{32}$, —$NR^{31}C(=NR^{32})OR^{33}$, —$NR^{31}C(=NR^{32})SR^{33}$, —$OC(=O)OR^{33}$, —$OC(=O)NR^{31}R^{32}$, —$OC(=O)SR^{31}$, —$SC(=O)OR^{31}$, —$P(O)OR^{31}OR^{32}$, or —$SC(=O)NR^{31}R^{32}$, and wherein each of said alkyl, cycloalkyl, heterocyclyl, or heteroalkyl moiety is unsubstituted or is substituted with one or more halo, —OH, —$R^{31}$—$CF_3$, —$OCF_3$, —$OR^{31}$, —O-aryl, —$NR^{31}R^{32}$, —$NR^{34}R^{35}$, —$C(O)R^{31}$, —$CO_2R^{31}$, —$C(=O)NR^{34}R^{35}$, or —$C(=O)NR^{31}R^{32}$;

$R^5$ is hydrogen, halogen, —OH, —$R^{31}$, —$CF_3$, —$OCF_3$, —$OR^{31}$, —$NR^{31}R^{32}$, —$NR^{34}R^{35}$, —$C(O)R^{31}$, —$CO_2R^{31}$, —$C(=O)NR^{31}R^{32}$, —$C(=O)NR^{34}R^{35}$, —$NO_2$, —CN, —$S(O)_{0-2}R^{31}$, —$SO_2NR^{31}R^{32}$, —$SO_2NR^{34}R^{35}$, —$NR^{31}C(=O)R^{32}$, —$NR^{31}C(=O)OR^{32}$, —$NR^{31}C(=O)NR^{32}R^{33}$, —$NR^{31}S(O)_{0-2}R^{32}$, —$C(=S)OR^{31}$, —$C(=O)SR^{31}$, —$NR^{31}C(=NR^{32})NR^{33}R^{32}$, —$NR^{31}C(=NR^{32})OR^{33}$, —$NR^{31}C(=NR^{32})SR^{33}$, —$OC(=O)OR^{33}$, —$OC(=O)NR^{31}R^{32}$, —$OC(=O)SR^{31}$, —$SC(=O)OR^{31}$, —$P(O)OR^{31}OR^{32}$, or —$SC(=O)NR^{31}R^{32}$;

$R^{31}$, $R^{32}$, and $R^{33}$, in each instance, are independently H or $C_{1-10}$alkyl, wherein the $C_{1-10}$alkyl is unsubstituted or is substituted with one or more aryl, heteroalkyl, heterocyclyl, or heteroaryl group wherein each of said aryl, heteroalkyl, heterocyclyl, or heteroaryl group is unsubstituted or is substituted with one or more halo, —OH, —$C_{1-10}$alkyl, —$CF_3$, —O-aryl, —$OCF_3$, —$OC_{1-10}$alkyl, —$NH_2$, —$N(C_{1-10}$alkyl)$(C_{1-10}$alkyl), —$NH(C_{1-10}$alkyl), —NH(aryl), —$NR^{34}R^{35}$, —$C(O)(C_{1-10}$alkyl), —$C(O)(C_{1-10}$alkyl-aryl), —C(O)(aryl), —$CO_2$—$C_{1-10}$alkyl, —$CO_2$—$C_{1-10}$alkylaryl, —$CO_2$-aryl, —$C(=O)N(C_{1-10}$alkyl)$(C_{1-10}$alkyl), —C(=O)NH$(C_{1-10}$alkyl), —$C(=O)NR^{34}R^{35}$, —$C(=O)NH_2$, —$OCF_3$, —$O(C_{1-10}$alkyl), —O-aryl, —N(aryl)$(C_{1-10}$alkyl), —$NO_2$, —CN, —$S(O)_{0-2}C_{1-10}$alkyl, —$S(O)_{0-2}C_{1-10}$alkylaryl, —$S(O)_{0-2}$aryl, —$SO_2$N(aryl), —$SO_2$N$(C_{1-10}$alkyl)$(C_{1-10}$alkyl), —$SO_2$NH$(C_{1-10}$alkyl) or —$SO_2NR^{34}R^{35}$;

$R^{34}$ and $R^{35}$ in —$NR^{34}R^{35}$, —$C(=O)NR^{34}R^{35}$, or —$SO_2NR^{34}R^{35}$, are taken together with the nitrogen atom to which they are attached to form a 3-10 membered saturated or unsaturated ring; wherein said ring is independently unsubstituted or is substituted by one or more —$NR^{31}R^{32}$, hydroxyl, halogen, oxo, aryl, heteroaryl, $C_{1-6}$alkyl, or O-aryl, and wherein said 3-10 membered saturated or unsaturated ring independently contains 0, 1, or 2 more heteroatoms in addition to the nitrogen atom;

$R^7$ and $R^8$ are each independently hydrogen, $C_{1-10}$alkyl, $C_{2-10}$alkenyl, aryl, heteroaryl, heterocyclyl or $C_{3-10}$cycloalkyl, each of which except for hydrogen is unsubstituted or is substituted by one or more independent $R^6$;

$R^6$ is halo, —$OR^{31}$, —SH, —$NH_2$, —$NR^{34}R^{35}$, —$NR^{31}R^{32}$, —$CO_2R^{31}$, —$CO_2$aryl, —$C(=O)NR^{31}R^{32}$, $C(=O)NR^{34}R^{35}$, —$NO_2$, —CN, —$S(O)_{0-2}C_{1-10}$alkyl, —$S(O)_{0-2}$aryl, —$SO_2NR^{34}R^{35}$, —$SO_2NR^{31}R^{32}$, $C_{1-10}$alkyl, $C_{2-10}$alkenyl, $C_{2-10}$alkynyl; aryl-$C_{1-10}$alkyl, aryl-$C_{2-10}$alkenyl, aryl-$C_{2-10}$alkynyl, heteroaryl-$C_{1-10}$alkyl, heteroaryl-$C_{2-10}$alkenyl, heteroaryl-$C_{2-10}$alkynyl, wherein each of said alkyl, alkenyl, alkynyl, aryl, heteroalkyl, heterocyclyl, or heteroaryl group is unsubstituted or is substituted with one or more independent halo, cyano, nitro, —$OC_{1-10}$alkyl, $C_{1-10}$alkyl, $C_{2-10}$alkenyl, $C_{2-10}$alkynyl, halo$C_{1-10}$alkyl, halo$C_{2-10}$alkenyl, halo$C_{2-10}$alkynyl, —COOH, —$C(=O)NR^{31}R^{32}$, —$C(=O)NR^{34}R^{35}$, —$SO_2NR^{34}R^{35}$, —$SO_2NR^{31}R^{32}$, —$NR^{31}R^{32}$, or —$NR^{34}R^{35}$; and $R^9$ is H, halo, —$OR^{31}$, —SH, —$NH_2$, —$NR^{34}R^{35}$, —$NR^{31}R^{32}$, —$CO_2R^{31}$, —$CO_2$aryl, —$C(=O)NR^{31}R^{32}$, $C(=O)NR^{34}R^{35}$, —$NO_2$, —CN, —$S(O)_{0-2}C_{1-10}$alkyl, —$S(O)_{0-2}$aryl, —$SO_2NR^{34}R^{35}$, —$SO_2NR^{31}R^{32}$, $C_{1-10}$alkyl, $C_{2-10}$alkenyl, $C_{2-10}$alkynyl; aryl-$C_{1-10}$alkyl, aryl-$C_{2-10}$alkenyl, aryl-$C_{2-10}$alkynyl, heteroaryl-$C_{1-10}$alkyl, heteroaryl-$C_{2-10}$alkenyl, heteroaryl-$C_{2-10}$alkynyl, wherein each of said alkyl, alkenyl, alkynyl, aryl, heteroalkyl, heterocyclyl, or heteroaryl group is unsubstituted or is substituted with one or more independent halo, cyano, nitro, —$OC_{1-10}$alkyl, $C_{1-10}$alkyl, $C_{2-10}$alkenyl, $C_{2-10}$alkynyl, halo$C_{1-10}$alkyl, halo$C_{2-10}$alkenyl, halo$C_{2-10}$alkynyl, —COOH, —$C(=O)NR^{31}R^{32}$, —$C(=O)NR^{34}R^{35}$, —$SO_2NR^{34}R^{35}$, —$SO_2NR^{31}R^{32}$, —$NR^{31}R^{32}$, or —$NR^{34}R^{35}$.

In various embodiments of the compound of Formula I-E, the compound has a structure of Formula I-E1 or Formula I-E2:

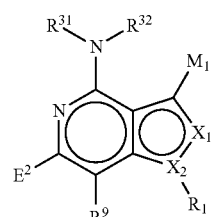

Formula I-E1

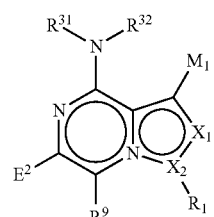

Formula I-E2 or a pharmaceutically acceptable salt thereof.

In some embodiments of Formula I-E1, $X_1$ is N and $X_2$ is N. In other embodiments, $X_1$ is C-$E^1$ and $X_2$ is N. In yet other embodiments, $X_1$ is NH and $X_2$ is C. In further embodiments, $X_1$ is CH-$E^1$ and $X_2$ is C.

In several embodiments of Formula I-E2, $X_1$ is N and $X_2$ is C. In further embodiments, $X_1$ is C-$E^1$ and $X_2$ is C.

In various embodiments, $X_1$ is C—$(W^1)_j$—$R^4$, where j is 0.

In another embodiment, $X_1$ is CH. In yet another embodiment, $X_1$ is C-halogen, where halogen is Cl, F, Br, or I.

In various embodiments of $X_1$, it is C—$(W^1)_j$—$R^4$. In various embodiments of $X_1$, j is 1, and $W^1$ is —O—. In various embodiments of $X_1$, j is 1, and $W^1$ is —$NR^7$—. In various embodiments of $X_1$, j is 1, and $W^1$ is —NH—. In various embodiments of $X_1$, j is 1, and $W^1$ is —$S(O)_{0-2}$—. In various embodiments of $X_1$, j is 1, and $W^1$ is —C(O)—. In various embodiments of $X_1$, j is 1, and $W^1$ is —$C(O)N(R^7)$—. In various embodiments of $X_1$, j is 1, and $W^1$ is —$N(R^7)C(O)$—. In various embodiments of $X_1$, j is 1, and $W^1$ is —$N(R^7)S(O)$—. In various embodiments of $X_1$, j is 1, and $W^1$ is —$N(R^7)S(O)_2$—. In various embodiments of $X_1$, j is 1, and $W^1$ is —C(O)O—. In various embodiments of $X_1$, j is 1, and $W^1$ is $CH(R^7)N(C(O)OR^8)$—. In various embodiments of $X_1$, j is 1, and $W^1$ is —$CH(R^7)N(C(O)R^8)$—. In various embodiments of $X_1$, j is 1, and $W^1$ is —$CH(R^7)N(SO_2R^8)$—. In various embodiments of $X_1$, j is 1, and $W^1$ is —$CH(R^7)N(R^8)$—. In various embodiments of $X_1$, j is 1, and $W^1$ is —$CH(R^7)C(O)N(R^8)$—. In various embodiments of $X_1$, j is 1, and $W^1$ is —$CH(R^7)N(R^8)C(O)$—. In various embodiments of $X_1$, j is 1, and $W^1$ is —$CH(R^7)N(R^8)S(O)$—. In various embodiments of $X_1$, j is 1, and $W^1$ is —$CH(R^7)N(R^8)S(O)_2$—.

In another embodiment, $X_1$ is N.

In various embodiments, $X_2$ is N. In other embodiments, $X_2$ is C.

In various embodiments, $E^2$ is —$(W^1)_j$—$R^4$, where j is 0.

In another embodiment, $E^2$ is CH. In yet another embodiment, $E^2$ is C-halogen, where halogen is Cl, F, Br, or I.

In various embodiments of $E^2$, it is —$(W^1)_j$—$R^4$. In various embodiments of $E^2$, j is 1, and $W^1$ is —O—. In various embodiments of $E^2$, j is 1, and $W^1$ is —$NR^7$—. In various embodiments of $E^2$, j is 1, and $W^1$ is —NH—. In various embodiments of $E^2$, j is 1, and $W^1$ is —$S(O)_{0-2}$—. In various embodiments of $E^2$, j is 1, and $W^1$ is —C(O)—. In various embodiments of $E^2$, j is 1, and $W^1$ is —$C(O)N(R^7)$—. In various embodiments of $E^2$, j is 1, and $W^1$ is —$N(R^7)C(O)$—. In various embodiments of $E^2$, j is 1, and $W^1$ is —$N(R^7)S(O)$—. In various embodiments of $E^2$, j is 1, and $W^1$ is —$N(R^7)S(O)_2$—. In various embodiments of $E^2$, j is 1, and $W^1$ is —C(O)O—. In various embodiments of $E^2$, j is 1, and $W^1$ is $CH(R^7)N(C(O)OR^8)$—. In various embodiments of $E^2$, j is 1, and $W^1$ is —$CH(R^7)N(C(O)R^8)$—. In various embodiments of $E^2$, j is 1, and $W^1$ is —$CH(R^7)N(SO_2R^8)$—. In various embodiments of $E^2$, j is 1, and $W^1$ is —$CH(R^7)N(R^8)$—. In various embodiments of $E^2$, j is 1, and $W^1$ is —$CH(R^7)C(O)N(R^8)$—. In various embodiments of $E^2$, j is 1, and $W^1$ is —$CH(R^7)N(R^8)C(O)$—. In various embodiments of $E^2$, j is 1, and $W^1$ is —$CH(R^7)N(R^8)S(O)$—. In various embodiments of $E^2$, j is 1, and $W^1$ is —$CH(R^7)N(R^8)S(O)_2$—.

In various embodiments when $M_1$ is a moiety of Formula I-E1, $M_1$ is benzoxazolyl substituted with —$(W_2)_k$—$R_2$. In some embodiments, $M_1$ is a benzoxazolyl moiety, substituted at the 2-position with —$(W_2)_k$—$R_2$. In some embodiments, $M_1$ is either a 5-benzoxazolyl or a 6-benzoxazolyl moiety, optionally substituted with —$(W_2)_k$—$R_2$. Exemplary Formula I-E1 $M_1$ moieties include but are not limited to the following:

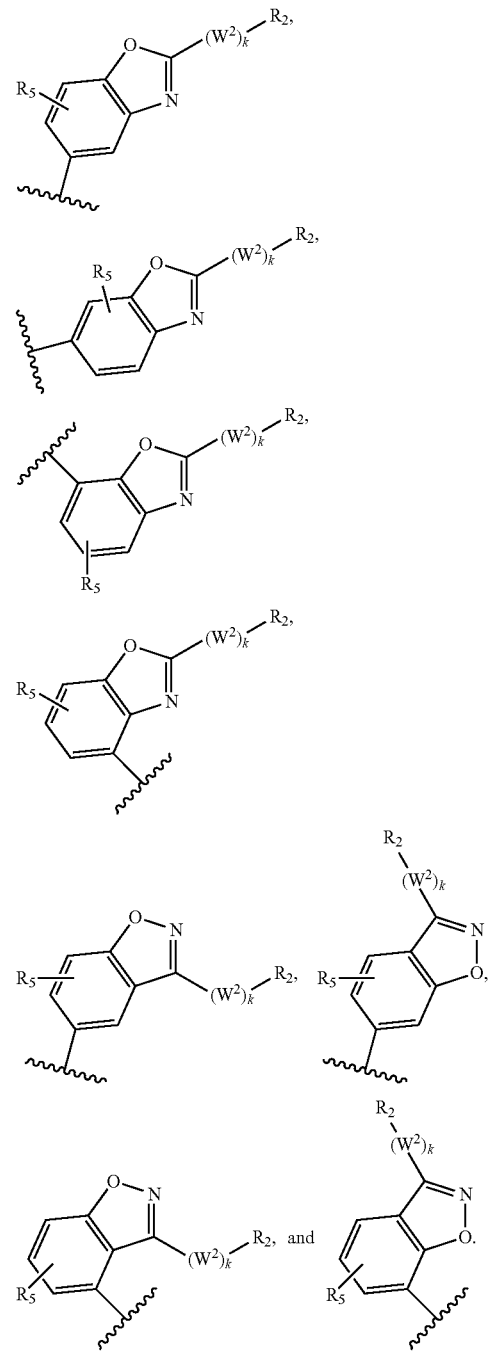

In various embodiments when $M_1$ is a moiety of Formula I-E2, Formula I-E2 is an aza-substituted benzoxazolyl moiety having a structure of one of the following formulae:

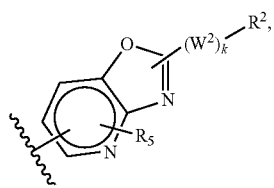

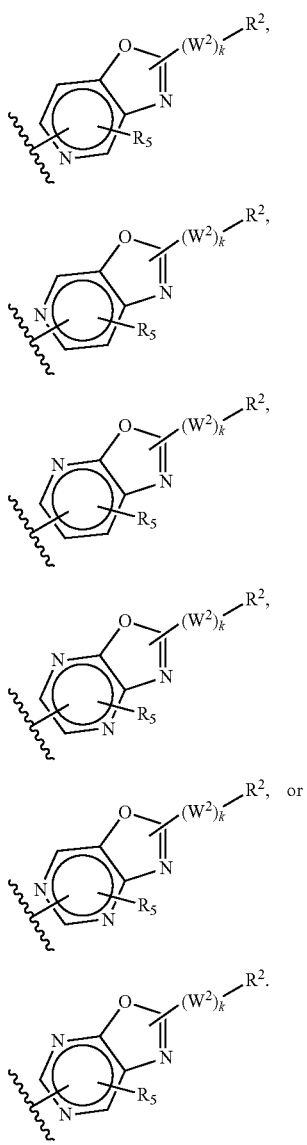

Exemplary Formula I-E2 M₁ moieties include but are not limited to the following:

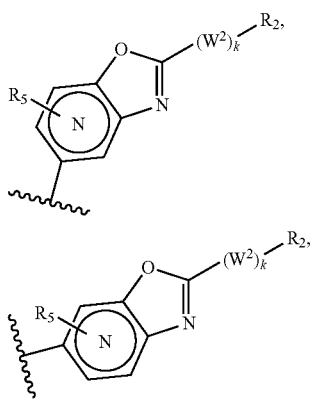

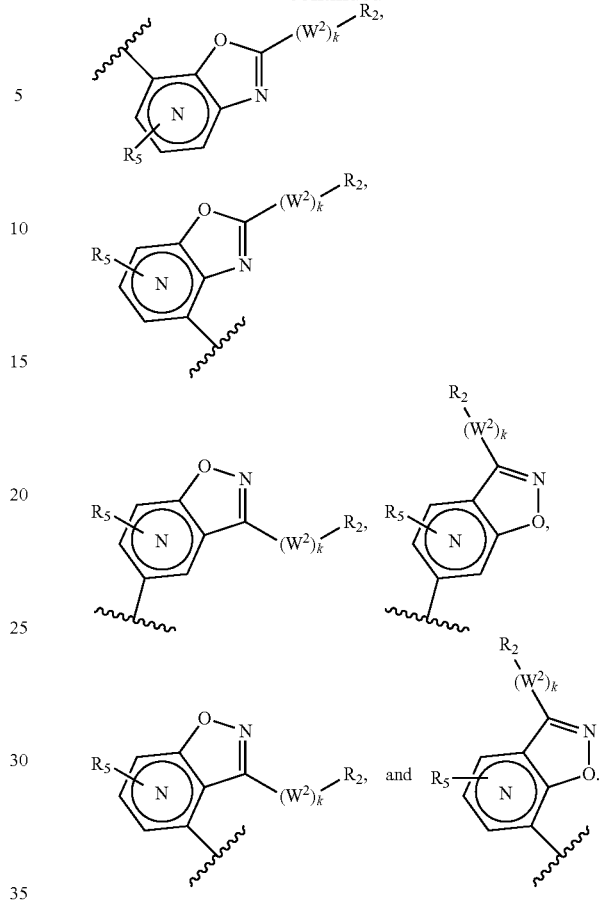

In various embodiments of $M_1$, k is 0. In other embodiments of $M_1$, k is 1 and $W^2$ is —O—. In another embodiment of $M_1$, k is 1 and $W^2$ is —$NR^7$—. In yet another embodiment of $M_1$, k is 1 and $W^2$ is —$S(O)_{0-2}$—. In another embodiment of $M_1$, k is 1 and $W^2$ is —C(O)—. In a further embodiment of $M_1$, k is 1 and $W^2$ is —$C(O)N(R^7)$—. In another embodiment of $M_1$, k is 1 and $W^2$ is —$N(R^7)C(O)$—. In another embodiment, k is 1 and $W^2$ is —$N(R^7)C(O)N(R^8)$—. In yet another embodiment of $M_1$, k is 1 and $W^2$ is —$N(R^7)S(O)$—. In still yet another embodiment of $M_1$, k is 1 and $W^2$ is —$N(R^7)S(O)_2$—. In a further embodiment of $M_1$, k is 1 and $W^2$ is —C(O)O—. In another embodiment of $M_1$, k is 1 and $W^2$ is —$CH(R^7)N(C(O)OR^8)$—. In another embodiment of $M_1$, k is 1 and $W^2$ is —$CH(R^7)N(C(O)R^8)$—. In another embodiment of $M_1$, k is 1 and $W^2$ is —$CH(R^7)N(SO_2R^8)$—. In a further embodiment of $M_1$, k is 1 and $W^2$ is —$CH(R^7)N(R^8)$—. In another embodiment of $M_1$, k is 1 and $W^2$ is —$CH(R^7)C(O)N(R^8)$—. In yet another embodiment of $M_1$, k is 1 and $W^2$ is —$CH(R^7)N(R^8)C(O)$—. In another embodiment of $M_1$, k is 1 and $W^2$ is —$CH(R^7)N(R^8)S(O)$—. In yet another embodiment of $M_1$, k is 1 and $W^2$ is —$CH(R^7)N(R^8)S(O)_2$—.

Additional embodiments of compounds of Formula I, including I-A, I-B, I-C, I-D, I-E and others are described below.

In various embodiments of compounds of Formula I, L is absent. In another embodiment, L is —(C=O)—. In another embodiment, L is C(=O)O—. In a further embodiment, L is —C(=O)$NR^{31}$—. In yet another embodiment, L is —S—. In one embodiment, L is —S(O)—. In another embodiment, L is —$S(O)_2$—. In yet another embodiment, L is —$S(O)_2NR^{31}$—. In another embodiment, L is —$NR^{31}$—.

In various embodiments of compounds of Formula I, $R_1$ is -L-$C_{1-10}$alkyl, which is unsubstituted. In another embodiment, $R_1$ is -L-$C_{1-10}$alkyl, which is substituted by one or more independent $R^3$. In yet another embodiment, $R_1$ is -L-unsubstituted $C_{1-10}$alkyl, where L is absent. In another embodiment, $R_1$ is -L-$C_{1-10}$alkyl, which is substituted by one or more independent $R^3$, and L is absent.

In various embodiments of compounds of Formula I, $R_1$ is -L-$C_{3-8}$cycloalkyl, which is unsubstituted. In another embodiment, $R_1$ is L-$C_{3-8}$cycloalkyl, which is substituted by one or more independent $R^3$. In yet another embodiment, $R_1$ is -L-$C_{3-8}$cycloalkyl, which is unsubstituted, and L is absent. In a further embodiment, $R_1$ is -L-$C_{3-8}$cycloalkyl which is substituted by one or more independent $R^3$, and L is absent.

In various embodiments of compounds of Formula I, $R_1$ is H.

In various embodiments of compounds of Formula I, $R_1$ is -L-aryl, which is unsubstituted. In another embodiment, $R_1$ is -L-aryl, which is substituted by one or more independent $R^3$. In another embodiment, $R_1$ is -L-aryl which is unsubstituted, and L is absent. In yet another embodiment, $R_1$ is -L-aryl, which is substituted by one or more independent $R^3$, and L is absent.

In various embodiments of compounds of Formula I, $R_1$ is -L-heteroaryl, which is unsubstituted. In another embodiment, $R_1$ is -L-heteroaryl, which is substituted by one or more independent $R^3$. In a further embodiment, $R_1$ is -L-heteroaryl which is unsubstituted and L is absent. In yet another embodiment, $R_1$ is -L-heteroaryl, which is substituted by one or more independent $R^3$, and L is absent.

In various embodiments of compounds of Formula I, $R_1$ is -L-$C_{1-10}$alkyl-$C_{3-8}$cycloalkyl, which is unsubstituted. In another embodiment, $R_1$ is -L-$C_{1-10}$alkyl-$C_{3-8}$cycloalkyl, which is substituted by one or more independent $R^3$. In a further embodiment, $R_1$ is -L-$C_{1-10}$alkyl-$C_{3-8}$cycloalkyl which is unsubstituted and L is absent. In yet another embodiment, $R_1$ is -L-$C_{1-10}$alkyl-$C_{3-8}$cycloalkyl, which is substituted by one or more independent $R^3$, and L is absent.

In various embodiments of compounds of Formula I, $R_1$ is -L-$C_{1-10}$alkylaryl, which is unsubstituted. In another embodiment, $R_1$ is -L-$C_{1-10}$alkylaryl, which is substituted by one or more independent $R^3$. In a further embodiment, $R_1$ is -L-$C_{1-10}$alkylaryl which is unsubstituted and L is absent. In yet another embodiment, $R_1$ is -L-$C_{1-10}$alkylaryl, which is substituted by one or more independent $R^3$, where L is absent.

In various embodiments of compounds of Formula I, $R_1$ is -L-$C_{1-10}$alkylheteroaryl, which is unsubstituted. In another embodiment, $R_1$ is -L-$C_{1-10}$alkylheteroaryl, which is substituted by one or more independent $R^3$. In a further embodiment, $R_1$ is -L-$C_{1-10}$alkylheteroaryl which is unsubstituted and L is absent. In yet another embodiment, $R_1$ is -L-$C_{1-10}$alkylheteroaryl, which is substituted by one or more independent $R^3$, where L is absent.

In various embodiments of compounds of Formula I, $R_1$ is -L-$C_{1-10}$alkylheterocyclyl, which is unsubstituted. In another embodiment, $R_1$ is -L-$C_{1-10}$alkylheterocyclyl, which is substituted by one or more independent $R^3$. In a further embodiment, $R_1$ is -L-$C_{1-10}$alkylheterocyclyl which is unsubstituted and L is absent. In yet another embodiment, $R_1$ is -L-$C_{1-10}$alkylheterocyclyl, which is substituted by one or more independent $R^3$, where L is absent.

In various embodiments of compounds of Formula I, $R_1$ is -L-$C_{2-10}$alkenyl, which is unsubstituted. In another embodiment, $R_1$ is -L-$C_{2-10}$alkenyl which is substituted by one or more independent $R^3$. In a further embodiment, $R_1$ is -L-$C_{2-10}$alkenyl which is unsubstituted and L is absent. In yet another embodiment, $R_1$ is -L-$C_{2-10}$alkenyl, which is substituted by one or more independent $R^3$, where L is absent.

In various embodiments of compounds of Formula I, $R_1$ is -L-$C_{2-10}$alkynyl, which is unsubstituted. In another embodiment, $R_1$ is -L-$C_{2-10}$alkynyl which is substituted by one or more independent $R^3$. In a further embodiment, $R_1$ is -L-$C_{2-10}$alkynyl which is unsubstituted and L is absent. In yet another embodiment, $R_1$ is -L-$C_{2-10}$alkynyl, which is substituted by one or more independent $R^3$, where L is absent.

In various embodiments of compounds of Formula I, $R_1$ is -L-$C_{2-10}$alkenyl-$C_{3-8}$cycloalkyl, which is unsubstituted. In another embodiment, $R_1$ is -L-$C_{2-10}$alkenyl-$C_{3-8}$cycloalkyl which is substituted by one or more independent $R^3$. In a further embodiment, $R_1$ is -L-$C_{2-10}$alkenyl-$C_{3-8}$cycloalkyl which is unsubstituted and L is absent. In yet another embodiment, $R_1$ is -L-$C_{2-10}$alkenyl-$C_{3-8}$cycloalkyl, which is substituted by one or more independent $R^3$, where L is absent.

In various embodiments of compounds of Formula I, $R_1$ is -L-$C_{2-10}$alkynyl-$C_{3-8}$cycloalkyl, which is unsubstituted. In another embodiment, $R_1$ is -L-$C_{2-10}$alkynyl-$C_{3-8}$cycloalkyl which is substituted by one or more independent $R^3$. In a further embodiment, $R_1$ is -L-$C_{2-10}$alkynyl-$C_{3-8}$cycloalkyl which is unsubstituted and L is absent. In yet another embodiment, $R_1$ is -L-$C_{2-10}$alkynyl-$C_{3-8}$cycloalkyl, which is substituted by one or more independent $R^3$, where L is absent.

In various embodiments of compounds of Formula I, $R_1$ is -L-$C_{2-10}$alkynyl-$C_{3-8}$cycloalkyl, which is unsubstituted. In another embodiment, $R_1$ is -L-$C_{2-10}$alkynyl-$C_{3-8}$cycloalkyl which is substituted by one or more independent $R^3$. In a further embodiment, $R_1$ is -L-$C_{2-10}$alkynyl-$C_{3-8}$cycloalkyl which is unsubstituted and L is absent. In yet another embodiment, $R_1$ is -L-$C_{2-10}$alkynyl-$C_{3-8}$cycloalkyl, which is substituted by one or more independent $R^3$, where L is absent.

In various embodiments of compounds of Formula I, $R_1$ is -L-heteroalkyl, which is unsubstituted. In another embodiment, $R_1$ is -L-heteroalkyl which is substituted by one or more independent $R^3$. In a further embodiment, $R_1$ is -L-heteroalkyl which is unsubstituted and L is absent. In yet another embodiment, $R_1$ is -L-heteroalkyl, which is substituted by one or more independent $R^3$, where L is absent.

In various embodiments of compounds of Formula I, $R_1$ is -L-heteroalkylaryl, which is unsubstituted. In another embodiment, $R_1$ is -L-heteroalkylaryl which is substituted by one or more independent $R^3$. In a further embodiment, $R_1$ is -L-heteroalkylaryl which is unsubstituted and L is absent. In yet another embodiment, $R_1$ is -L-heteroalkylaryl, which is substituted by one or more independent $R^3$, where L is absent.

In various embodiments of compounds of Formula I, $R_1$ is -L-heteroalkylheteroaryl, which is unsubstituted. In another embodiment, $R_1$ is -L-heteroalkylheteroaryl, which is substituted by one or more independent $R^3$. In a further embodiment, $R_1$ is -L-heteroalkylheteroaryl which is unsubstituted and L is absent. In yet another embodiment, $R_1$ is -L-heteroalkylheteroaryl, which is substituted by one or more independent $R^3$, where L is absent.

In various embodiments of compounds of Formula, $R_1$ is -L-heteroalkyl-heterocyclyl, which is unsubstituted. In another embodiment, $R_1$ is -L-heteroalkyl-heterocyclyl, which is substituted by one or more independent $R^3$. In a further embodiment, $R_1$ is -L-heteroalkyl-heterocyclyl which is unsubstituted, and L is absent. In yet another embodiment, $R_1$ is -L-heteroalkyl-heterocyclyl, which is substituted by one or more independent $R^3$, where L is absent.

In various embodiments of compounds of Formula I, $R_1$ is -L-heteroalkyl-$C_{3-8}$cycloalkyl, which is unsubstituted. In another embodiment, $R_1$ is -L-heteroalkyl-$C_{3-8}$cycloalkyl, which is substituted by one or more independent $R^3$. In a further embodiment, $R_1$ is -L-heteroalkyl-$C_{3-8}$cycloalkyl which is unsubstituted and L is absent. In yet another embodiment, $R_1$ is -L-heteroalkyl-$C_{3-8}$cycloalkyl, which is substituted by one or more independent $R^3$, where L is absent.

In various embodiments of compounds of Formula I, $R_1$ is -L-aralkyl, which is unsubstituted. In another embodiment, $R_1$ is -L-aralkyl, which is substituted by one or more independent $R^3$. In a further embodiment, $R_1$ is -L-aralkyl which is unsubstituted. In yet another embodiment, $R_1$ is -L-aralkyl, which is substituted by one or more independent $R^3$, where L is absent.

In various embodiments of compounds of Formula I, $R_1$ is -L-heteroaralkyl, which is unsubstituted. In another embodiment, $R_1$ is -L-heteroaralkyl, which is substituted by one or more independent $R^3$. In a further embodiment, $R_1$ is -L-heteroaralkyl which is unsubstituted and L is absent. In yet another embodiment, $R_1$ is -L-heteroaralkyl, which is substituted by one or more independent $R^3$, where L is absent.

In various embodiments of compounds of Formula I, $R_1$ is -L-heterocyclyl, which is unsubstituted. In another embodiment, $R_1$ is -L-heterocyclyl, which is substituted by one or more independent $R^3$. In a further embodiment, $R_1$ is -L-heterocyclyl which is unsubstituted and L is absent. In yet another embodiment, $R_1$ is -L-heterocyclyl, which is substituted by one or more independent $R^3$, where L is absent.

In various embodiments of compounds of Formula I, $R_1$ is a substituent as shown below:

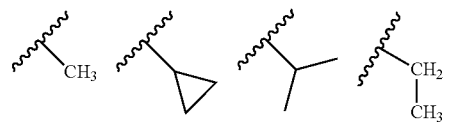
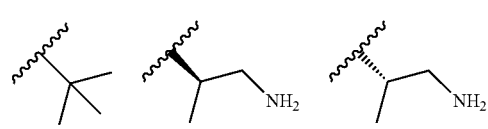
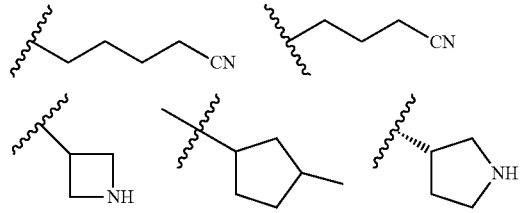
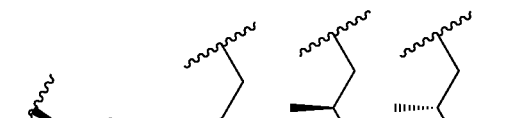
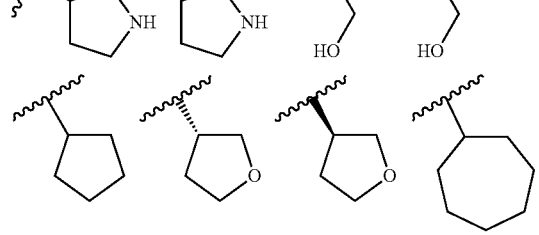

-continued

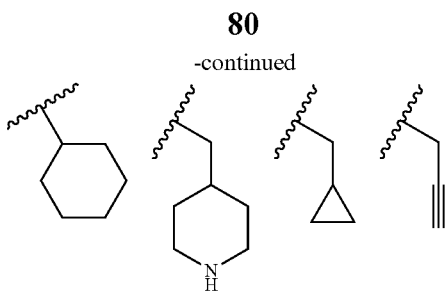
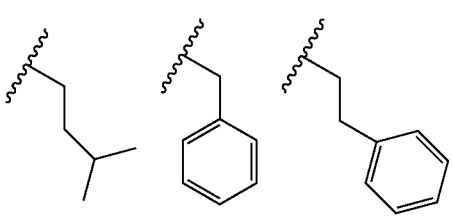
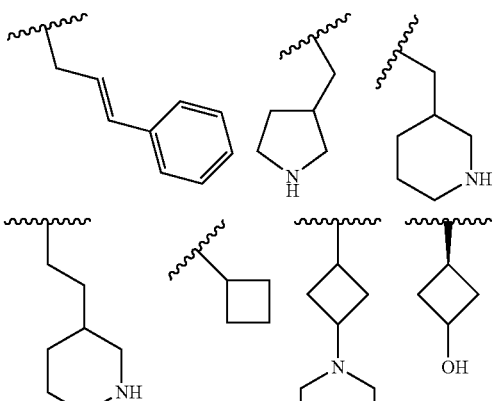
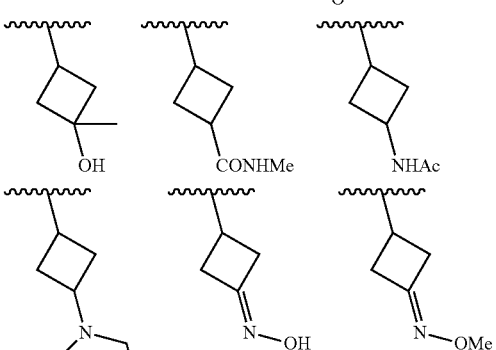
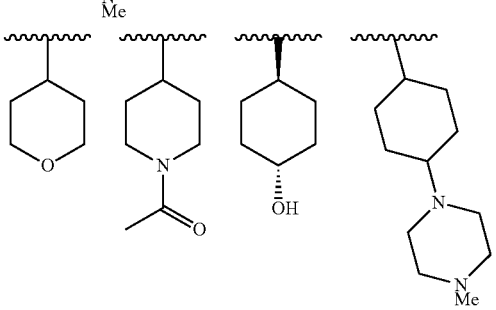

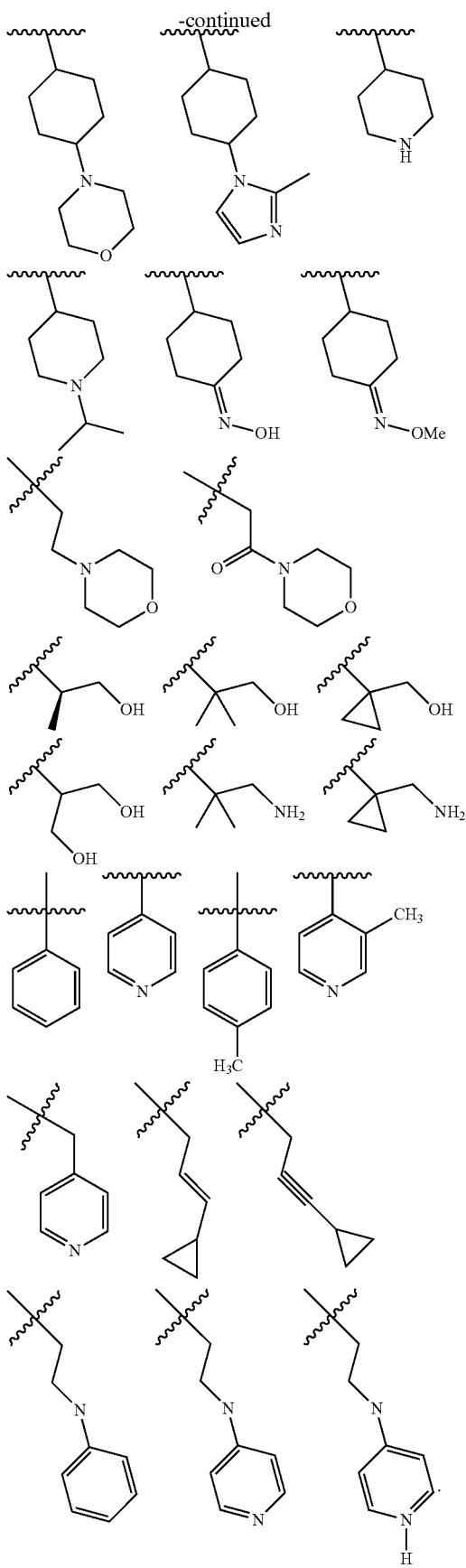

In various embodiments of compounds of Formula I, $R^2$ is hydrogen. In another embodiment, $R^2$ is halogen. In another embodiment, $R^2$ is —OH. In another embodiment, $R^2$ is —$R^{31}$. In another embodiment, $R^2$ is —$CF_3$. In another embodiment, $R^2$ is —$OCF_3$. In another embodiment, $R^2$ is —$OR^{31}$. In another embodiment, $R^2$ is —$NR^{31}R^{32}$. In another embodiment, $R^2$ is —$NR^{34}R^{35}$. In another embodiment, $R^2$ is —$C(O)R^{31}$. In another embodiment, $R^2$ is —$CO_2R^{31}$. In another embodiment, $R^2$ is —$C(=O)NR^{31}R^{32}$. In another embodiment, $R^2$ is —$C(=O)NR^{34}R^{35}$. In another embodiment, $R^2$ is —$NO_2$. In another embodiment, $R^2$ is —CN. In another embodiment, $R^2$ is —$S(O)_{0-2}R^3$. In another embodiment, $R^2$ is —$SO_2NR^{31}R^{32}$. In another embodiment, $R^2$ is —$SO_2NR^{34}R^{35}$. In another embodiment, $R^2$ is —$NR^{31}C(=O)R^{32}$. In another embodiment, $R^2$ is —$NR^{31}C(=O)OR^{32}$. In another embodiment, $R^2$ is —$NR^{31}C(=O)NR^{32}R^{33}$. In another embodiment, $R^2$ is —$NR^{31}S(O)_{0-2}R^{32}$. In another embodiment, $R^2$ is —$C(=S)OR^{31}$. In another embodiment, $R^2$ is —$C(=O)SR^{31}$. In another embodiment, $R^2$ is —$NR^{31}C(=NR^{32})NR^{33}R^{32}$. In another embodiment, $R^2$ is —$NR^{31}C(=NR^{32})OR^{33}$. In another embodiment, $R^2$ is —$NR^{31}C(=NR^{32})SR^{33}$. In another embodiment, $R^2$ is —$OC(=O)OR^{33}$. In another embodiment, $R^2$ is —$OC(=O)NR^{31}R^{32}$. In another embodiment, $R^2$ is —$OC(=O)SR^{31}$. In another embodiment, $R^2$ is —$SC(=O)OR^{31}$. In another embodiment, $R^2$ is —$P(O)OR^{31}OR^{32}$. In another embodiment, $R^2$ is —$SC(=O)NR^{31}R^{32}$. In another embodiment, $R^2$ is monocyclic aryl. In another embodiment, $R^2$ is bicyclic aryl. In another embodiment, $R^2$ is substituted monocyclic aryl. In another embodiment, $R^2$ is heteroaryl. In another embodiment, $R^2$ is $C_{1-4}$alkyl. In another embodiment, $R^2$ is $C_{1-10}$alkyl. In another embodiment, $R^2$ is $C_{3-8}$cycloalkyl. In another embodiment, $R^2$ is $C_{3-8}$cycloalkyl-$C_{1-10}$alkyl. In another embodiment, $R^2$ is $C_{1-10}$alkyl-$C_{3-8}$cycloalkyl. In another embodiment, $R^2$ is $C_{1-10}$alkyl-monocyclic aryl. In another embodiment, $R^2$ is $C_{2-10}$alkyl-monocyclic aryl. In another embodiment, $R^2$ is monocyclic aryl-$C_{2-10}$alkyl. In another embodiment, $R^2$ is $C_{1-10}$alkyl-bicyclicaryl. In another embodiment, $R^2$ is bicyclicaryl-$C_{1-10}$alkyl. In another embodiment, $R^2$ is —$C_{1-10}$alkylheteroaryl. In another embodiment, $R^2$ is —$C_{1-10}$alkylheterocyclyl. In another embodiment, $R^2$ is —$C_{2-10}$alkenyl. In another embodiment, $R^2$ is —$C_{2-10}$alkynyl. In another embodiment, $R^2$ is $C_{2-10}$alkenylaryl. In another embodiment, $R^2$ is $C_{2-10}$alkenylheteroaryl. In another embodiment, $R^2$ is $C_{2-10}$alkenylheteroalkyl. In another embodiment, $R^2$ is $C_{2-10}$alkenylheterocycicyl. In another embodiment, $R^2$ is —$C_{2-10}$alkynylaryl. In another embodiment, $R^2$ is —$C_{2-10}$alkynylheteroaryl. In another embodiment, $R^2$ is —$C_{2-10}$alkynylheteroalkyl. In another embodiment, $R^2$ is —$C_{2-10}$alkynylheterocyclyl. In another embodiment, $R^2$ is —$C_{2-10}$alkynyl$C_{3-8}$cycloalkyl. In another embodiment, $R^2$ is —$C_{2-10}$alkynyl$C_{3-8}$cycloalkenyl. In another embodiment, $R^2$ is —$C_{1-10}$alkoxy-$C_{1-10}$alkyl. In another embodiment, $R^2$ is —$C_{1-10}$alkoxy-$C_{2-10}$alkenyl. In another embodiment, $R^2$ is —$C_{1-10}$alkoxy-$C_{2-10}$alkynyl. In another embodiment, $R^2$ is -heterocyclyl $C_{1-10}$alkyl. In another embodiment, $R^2$ is heterocyclyl$C_{2-10}$alkenyl. In another embodiment, $R^2$ is heterocyclyl$C_{2-10}$alkynyl. In another embodiment, $R^2$ is aryl-$C_{2-10}$alkyl. In another embodiment, $R^2$ is aryl-$C_{1-10}$alkyl. In another embodiment, $R^2$ is aryl-$C_{2-10}$alkenyl. In another embodiment, $R^2$ is aryl-$C_{2-10}$alkynyl. In another embodiment, $R^2$ is aryl-heterocyclyl. In another embodiment, $R^2$ is heteroaryl-$C_{1-10}$alkyl. In another embodiment, $R^2$ is heteroaryl-$C_{2-10}$alkenyl. In another embodiment, $R^2$ is heteroaryl-$C_{2-10}$alkynyl. In another embodiment, $R^2$ is heteroaryl-$C_{3-8}$cycloalkyl. In another embodiment, $R^2$ is heteroaryl-heteroalkyl. In another embodiment, $R^2$ is heteroaryl-heterocyclyl.

In various embodiments of compounds of Formula I, when $R^2$ is bicyclic aryl, monocyclic aryl, heteroaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$alkyl, heterocyclyl $C_{1-10}$alkyl, or $C_{3-8}$cycloalkyl-$C_{1-10}$alkyl, it is unsubstituted. In various embodiments, when $R^2$ is bicyclic aryl, monocyclic aryl, heteroaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$alkyl, heterocyclyl $C_{1-10}$alkyl, or $C_{3-8}$cycloalkyl-$C_{1-10}$alkyl, it is substituted with one or more independent halo. In another embodiment, when $R^2$ is bicyclic aryl, monocyclic aryl, heteroaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$alkyl, heterocyclyl $C_{1-10}$alkyl, or $C_{3-8}$cycloalkyl-$C_{1-10}$alkyl, it is substituted with one or more independent —OH. In another embodiment, when $R^2$ is bicyclic aryl, monocyclic aryl, heteroaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$alkyl, heterocyclyl $C_{1-10}$alkyl, or $C_{3-8}$cycloalkyl-$C_{1-10}$alkyl, it is substituted with one or more independent —$R^{31}$. In another embodiment, when $R^2$ is bicyclic aryl, monocyclic aryl, heteroaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$alkyl, heterocyclyl $C_{1-10}$alkyl, or $C_{3-8}$cycloalkyl-$C_{1-10}$alkyl, it is substituted with one or more independent —$CF_3$. In another embodiment, when $R^2$ is bicyclic aryl, monocyclic aryl, heteroaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$alkyl, heterocyclyl $C_{1-10}$alkyl, or $C_{3-8}$cycloalkyl-$C_{1-10}$alkyl, it is substituted with one or more independent —OCF. In another embodiment, when $R^2$ is bicyclic aryl, monocyclic aryl, heteroaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$alkyl, heterocyclyl $C_{1-10}$alkyl, or $C_{3-8}$cycloalkyl-$C_{1-10}$alkyl, it is substituted with one or more independent —$OR^{31}$. In another embodiment, when $R^2$ is bicyclic aryl, monocyclic aryl, heteroaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$alkyl, heterocyclyl $C_{1-10}$alkyl, or $C_{3-8}$cycloalkyl-$C_{1-10}$alkyl, it is substituted with one or more independent —$NR^{31}R^{32}$. In another embodiment, when $R^2$ is bicyclic aryl, monocyclic aryl, heteroaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$alkyl, heterocyclyl $C_{1-10}$alkyl, or $C_{3-8}$cycloalkyl-$C_{1-10}$alkyl, it is substituted with one or more independent —$NR^{34}R^{35}$. In another embodiment, when $R^4$ is bicyclic aryl, monocyclic aryl, heteroaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$alkyl, heterocyclyl $C_{1-10}$alkyl, or $C_{3-8}$cycloalkyl-$C_{1-10}$alkyl, it is substituted with one or more independent —$C(O)R^{31}$. In another embodiment, when $R^2$ is bicyclic aryl, monocyclic aryl, heteroaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$alkyl, heterocyclyl $C_{1-10}$alkyl, or $C_{3-8}$cycloalkyl-$C_{1-10}$alkyl, it is substituted with one or more independent —$CO_2R^{31}$. In another embodiment, when $R^2$ is bicyclic aryl, monocyclic aryl, heteroaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$alkyl, heterocyclyl $C_{1-10}$alkyl, or $C_{3-8}$cycloalkyl-$C_{1-10}$alkyl, it is substituted with one or more independent —$C(=O)NR^{31}R^{32}$. In another embodiment, when $R^2$ is bicyclic aryl, monocyclic aryl, heteroaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$alkyl, heterocyclyl $C_{1-10}$alkyl, or $C_{3-8}$cycloalkyl-$C_{1-10}$alkyl, it is substituted with one or more independent —$C(=O)NR^{34}R^{35}$. In another embodiment, when $R^2$ is bicyclic aryl, monocyclic aryl, heteroaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$alkyl, heterocyclyl $C_{1-10}$alkyl, or $C_{3-8}$cycloalkyl-$C_{1-10}$alkyl, it is substituted with one or more independent —$NO_2$. In another embodiment, when $R^2$ is bicyclic aryl, monocyclic aryl, heteroaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$alkyl, heterocyclyl $C_{1-10}$alkyl, or $C_{3-8}$cycloalkyl-$C_{1-10}$alkyl, it is substituted with one or more independent —CN. In another embodiment, when $R^2$ is bicyclic aryl, monocyclic aryl, heteroaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$alkyl, heterocyclyl $C_{1-10}$alkyl, or $C_{3-8}$cycloalkyl-$C_{1-10}$alkyl, it is substituted with one or more independent —$S(O)_{0-2}R^{31}$. In another embodiment, when $R^2$ is bicyclic aryl, monocyclic aryl, heteroaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$alkyl, heterocyclyl $C_{1-10}$alkyl, or $C_{3-8}$cycloalkyl-$C_{1-10}$alkyl, it is substituted with one or more independent —$SO_2NR^{31}R^{32}$. In another embodiment, when $R^2$ is bicyclic aryl, monocyclic aryl, heteroaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$alkyl, heterocyclyl $C_{1-10}$alkyl, or $C_{3-8}$cycloalkyl-$C_{1-10}$alkyl, it is substituted with one or more independent —$SO_2NR^{34}R^{35}$. In another embodiment, when $R^2$ is bicyclic aryl, monocyclic aryl, heteroaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$alkyl, heterocyclyl $C_{1-10}$alkyl, or $C_{3-8}$cycloalkyl-$C_{1-10}$alkyl, it is substituted with one or more independent $NR^{31}C(=O)R^{32}$. In another embodiment, when $R^2$ is bicyclic aryl, monocyclic aryl, heteroaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$alkyl, heterocyclyl $C_{1-10}$alkyl, or $C_{3-8}$cycloalkyl-$C_{1-10}$alkyl, it is substituted with one or more independent —$NR^{31}C(=O)OR^{32}$. In another embodiment, when $R^2$ is bicyclic aryl, monocyclic aryl, heteroaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$alkyl, heterocyclyl $C_{1-10}$alkyl, or $C_{3-8}$cycloalkyl-$C_{1-10}$alkyl, it is substituted with one or more independent —$NR^{31}C(=O)NR^{32}R^{33}$. In another embodiment, when $R^2$ is bicyclic aryl, monocyclic aryl, heteroaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$alkyl, heterocyclyl $C_{1-10}$alkyl, or $C_{3-8}$cycloalkyl-$C_{1-10}$alkyl, it is substituted with one or more independent —$NR^{31}S(O)_{0-2}R^{32}$. In another embodiment, when $R^2$ is bicyclic aryl, monocyclic aryl, heteroaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$alkyl, heterocyclyl $C_{1-10}$alkyl, or $C_{3-8}$cycloalkyl-$C_{1-10}$alkyl, it is substituted with one or more independent —$C(=S)OR^{31}$. In another embodiment, when $R^2$ is bicyclic aryl, monocyclic aryl, heteroaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$alkyl, heterocyclyl $C_{1-10}$alkyl, or $C_{3-8}$cycloalkyl-$C_{1-10}$alkyl, it is substituted with one or more independent —$C(=O)SR^{31}$. In another embodiment, when $R^2$ is bicyclic aryl, monocyclic aryl, heteroaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$alkyl, heterocyclyl $C_{1-10}$alkyl, or $C_{3-8}$cycloalkyl-$C_{1-10}$alkyl, it is substituted with one or more independent —$NR^{31}C(=NR^{32})NR^{33}R^{32}$. In another embodiment, when $R^2$ is bicyclic aryl, monocyclic aryl, heteroaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$alkyl, heterocyclyl $C_{1-10}$alkyl, or $C_{3-8}$cycloalkyl-$C_{1-10}$alkyl, it is substituted with one or more independent, —$NR^{31}C(=NR^{32})OR^{33}$. In another embodiment, when $R^2$ is bicyclic aryl, monocyclic aryl, heteroaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$alkyl, heterocyclyl $C_{1-10}$alkyl, or $C_{3-8}$cycloalkyl-$C_{1-10}$alkyl, it is substituted with one or more independent —$NR^{31}C(=NR^{32})SR^{33}$. In another embodiment, when $R^2$ is bicyclic aryl, monocyclic aryl, heteroaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$alkyl, heterocyclyl $C_{1-10}$alkyl, or $C_{3-8}$cycloalkyl-$C_{1-10}$alkyl, it is substituted with one or more independent —$OC(=O)OR^{33}$. In another embodiment, when $R^2$ is bicyclic aryl, monocyclic aryl, heteroaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$alkyl, heterocyclyl $C_{1-10}$alkyl, or $C_{3-8}$cycloalkyl-$C_{1-10}$alkyl, it is substituted with one or more independent —$OC(=O)NR^{31}R^{32}$. In another embodiment, when $R^2$ is bicyclic aryl, monocyclic aryl, heteroaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$alkyl, heterocyclyl $C_{1-10}$alkyl, or $C_{3-8}$cycloalkyl-$C_{1-10}$alkyl, it is substituted with one or more independent —$OC(=O)SR^{31}$. In another embodiment, when $R^2$ is bicyclic aryl, monocyclic aryl, heteroaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$alkyl, heterocyclyl $C_{1-10}$alkyl, or $C_{3-8}$cycloalkyl-$C_{1-10}$alkyl, it is substituted with one or more independent —$SC(=O)OR^{31}$. In another embodiment, when $R^2$ is bicyclic aryl, monocyclic aryl, heteroaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$alkyl, heterocyclyl $C_{1-10}$alkyl, or $C_{3-8}$cycloalkyl-$C_{1-10}$alkyl, it is substituted with one or more independent —$P(O)OR^{31}OR^{32}$. In another embodiment, when $R^2$ is bicyclic aryl, monocyclic aryl, heteroaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$alkyl, heterocyclyl $C_{1-10}$alkyl, or $C_{3-8}$cycloalkyl-$C_{1-10}$alkyl, it is substituted with one or more independent —$SC(=O)NR^{31}R^{32}$. In another embodiment, when $R^2$ is bicyclic aryl, monocyclic aryl, heteroaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$alkyl, heterocyclyl $C_{1-10}$alkyl, or $C_{3-8}$cycloalkyl-$C_{1-10}$alkyl, it is substituted with one or more independent alkyl. In another embodiment, when $R^2$ is bicyclic aryl, monocyclic aryl, heteroaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$-alkyl, heterocyclyl $C_{1-10}$alkyl, or $C_{3-8}$cycloalkyl-$C_{1-10}$alkyl, it is substituted with one or more independent heteroalkyl. In another embodiment, when $R^2$ is bicyclic aryl, monocyclic aryl, heteroaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$alkyl, heterocyclyl $C_{1-10}$alkyl, or $C_{3-8}$cycloalkyl-$C_{1-10}$alkyl, it is substituted with one or more independent alkenyl. In another embodiment, when $R^2$ is bicyclic aryl, monocyclic aryl, heteroaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$-alkyl, heterocyclyl $C_{1-10}$alkyl, or $C_{3-8}$cycloalkyl-$C_{1-10}$alkyl, it is substituted with one or more independent alkynyl. In another embodiment, when $R^2$ is bicyclic aryl, monocyclic aryl, heteroaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$alkyl, heterocyclyl $C_{1-10}$alkyl, or $C_{3-8}$cycloalkyl-$C_{1-10}$alkyl, it is substituted with one or more independent cycloalkyl. In another embodiment, when $R^2$ is bicyclic aryl, monocyclic aryl, heteroaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$alkyl, heterocyclyl $C_{1-10}$alkyl, or $C_{3-8}$cycloalkyl-$C_{1-10}$alkyl, it is substituted with one or more independent heterocycloalkyl. In another embodiment, when $R^2$ is bicyclic aryl, monocyclic aryl, heteroaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$alkyl, heterocyclyl $C_{1-10}$alkyl, or $C_{3-8}$cycloalkyl-$C_{1-10}$alkyl, it is substituted with one or more independent aryl. In another embodiment, when $R^2$ is bicyclic aryl, monocyclic aryl, heteroaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$-alkyl, heterocyclyl $C_{1-10}$alkyl, or $C_{3-8}$cycloalkyl-$C_{1-10}$alkyl, it is substituted with one or more independent arylalkyl. In another embodiment, when $R^2$ is bicyclic aryl, monocyclic aryl, heteroaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$-alkyl, heterocyclyl $C_{1-10}$alkyl, or $C_{3-8}$cycloalkyl-$C_{1-10}$alkyl, it is substituted with one or more independent heteroaryl. In another embodiment, when $R^2$ is bicyclic aryl, monocyclic aryl, heteroaryl, $C_{1-10}$alkyl, $C_{3-8}$cycloalkyl, heterocyclyl, heteroalkyl, $C_{2-10}$alkenyl, $C_{2-10}$alkynyl, monocyclic aryl-$C_{2-10}$-alkyl, heterocyclyl $C_{1-10}$alkyl, or $C_{3-8}$cycloalkyl-$C_{1-10}$alkyl, it is substituted with one or more independent heteroarylalkyl.

In various embodiments of compounds of Formula I, $R^3$ is hydrogen. In another embodiment, $R^3$ is halogen. In another embodiment, $R^3$ is —OH. In another embodiment, $R^3$ is —$R^{31}$. In another embodiment, $R^3$ is —$CF_3$. In another embodiment, $R^3$ is —$OCF_3$. In another embodiment, $R^3$ is —$OR^{31}$. In another embodiment, $R^3$ is —$NR^{31}R^{32}$. In another embodiment, $R^3$ is —$NR^{34}R^{35}$. In another embodiment, $R^3$ is —$C(O)R^{31}$. In another embodiment, $R^3$ is —$CO_2R^{31}$. In another embodiment, $R^3$ is —$C(=O)NR^{31}R^{32}$. In another embodiment, $R^3$ is —$C(=O)NR^{34}R^{35}$. In another embodiment, $R^3$ is —$NO_2$. In another embodiment, $R^3$ is —CN. In another embodiment, $R^3$ is —$S(O)_{0-2}R^3$. In another embodiment, $R^3$ is —$SO_2NR^{31}R^{32}$. In another embodiment, $R^3$ is —$SO_2NR^{34}R^{35}$. In another embodiment, $R^3$ is —$NR^{31}C(=O)R^{32}$. In another embodiment, $R^3$ is —$NR^{31}C(=O)OR^{32}$. In another embodiment, $R^3$ is —$NR^{31}C(=O)NR^{32}R^{33}$. In another embodiment, $R^3$ is —$NR^{31}S(O)_{0-2}R^{32}$. In another embodiment, $R^3$ is —$C(=S)OR^{31}$. In another embodiment, $R^3$ is —$C(=O)SR^{31}$. In another embodiment, $R^3$ is —$NR^{31}C(=NR^{32})NR^{33}R^{32}$. In another embodiment, $R^3$ is —$NR^{31}C(=NR^{32})OR^{33}$. In another embodiment, $R^3$ is —$NR^{31}C(=NR^{32})SR^{33}$. In another embodiment, $R^3$ is —$OC(=O)OR^{33}$. In another embodiment, $R^3$ is —$OC(=O)NR^{31}R^{32}$. In another embodiment, $R^3$ is —$OC(=O)SR^{31}$. In another embodiment, $R^3$ is —$SC(=O)OR^{31}$. In another embodiment, $R^3$ is —$P(O)OR^{31}OR^{32}$. In another embodiment, $R^3$ is —$SC(=O)NR^{31}R^{32}$. In another embodiment, $R^3$ is aryl. In another embodiment, $R^2$ is heteroaryl. In another embodiment, $R^3$ is $C_{1-4}$alkyl. In another embodiment, $R^3$ is $C_{1-10}$alkyl. In another embodiment, $R^3$ is $C_{3-8}$cycloalkyl. In another embodiment, $R^3$ is $C_{3-8}$cycloalkyl-$C_{1-10}$alkyl. In another embodiment, $R^3$ is —$C_{1-10}$alkyl-$C_{3-8}$cycloalkyl. In another embodiment, $R^3$ is $C_{2-10}$alkyl-monocyclic aryl. In another embodiment, $R^3$ is monocyclic aryl-$C_{2-10}$alkyl. In another embodiment, $R^3$ is $C_{1-10}$alkyl-bicyclicaryl. In another embodiment, $R^3$ is bicyclicaryl-$C_{1-10}$alkyl. In another embodiment, $R^3$ is $C_{1-10}$alkylheteroaryl. In another embodiment, $R^3$ is $C_{1-10}$alkylheterocyclyl. In another embodiment, $R^3$ is $C_{2-10}$alkenyl. In another embodiment, $R^3$ is $C_{2-10}$alkynyl. In another embodiment, $R^3$ is $C_{2-10}$alkenylaryl. In another embodiment, $R^3$ is $C_{2-10}$alkenylheteroaryl. In another embodiment, $R^3$ is $C_{2-10}$alkenylheteroalkyl. In another embodiment, $R^3$ is $C_{2-10}$alkenylheterocyicyl. In another embodiment, $R^3$ is $C_{2-10}$alkynylaryl. In another embodiment, $R^3$ is —$C_{2-10}$alkynylheteroaryl. In another embodiment, $R^3$ is —$C_{2-10}$alkynylheteroalkyl. In another embodiment, $R^3$ is $C_{2-10}$alkynylheterocyclyl. In another embodiment, $R^3$ is —$C_{2-10}$alkynyl$C_{3-8}$cycloalkyl. In another embodiment, $R^3$ is $C_{2-10}$alkynyl$C_{3-8}$cycloalkenyl. In another embodiment, $R^3$ is —$C_{1-10}$alkoxy $C_{1-10}$alkyl. In another embodiment, $R^3$ is $C_{1-10}$alkoxy-$C_{2-10}$alkenyl. In another embodiment, $R^3$ is —$C_{1-10}$alkoxy-$C_{2-10}$alkynyl. In another embodiment, $R^3$ is heterocyclyl-$C_{1-10}$alkyl. In another embodiment, $R^3$ is -heterocyclyl$C_{2-10}$alkenyl. In another embodiment, $R^3$ is heterocyclyl-$C_{2-10}$alkynyl. In another embodiment, $R^3$ is aryl-$C_{1-10}$alkyl. In another embodiment, $R^3$ is aryl-$C_{2-10}$alkenyl. In another embodiment, $R^3$ is aryl-$C_{2-10}$alkynyl. In another embodiment, $R^3$ is aryl-heterocyclyl. In another embodiment, $R^3$ is heteroaryl-$C_{1-10}$alkyl. In another embodiment, $R^3$ is heteroaryl-$C_{2-10}$alkenyl. In another embodiment, $R^3$ is heteroaryl-$C_{2-10}$alkynyl. In another embodiment, $R^3$ is heteroaryl-$C_{3-8}$cycloalkyl. In another embodiment, $R^3$ is heteroaryl-heteroalkyl. In another embodiment, $R^3$ is heteroaryl-heterocyclyl.

In various embodiments of compounds of Formula I, when $R^3$ is aryl, heteroaryl, $C_{1-10}$alkyl, $C_{3-8}$cycloalkyl, $C_{3-8}$cycloalkyl-$C_{1-10}$alkyl, heterocyclyl, heterocyclyl $C_{1-10}$alkyl, or heteroalkyl, it is unsubstituted. In another embodiment, when $R^3$ is aryl, heteroaryl, $C_{1-10}$alkyl, $C_{3-8}$cycloalkyl, $C_{3-8}$cycloalkyl-$C_{1-10}$alkyl, heterocyclyl, heterocyclyl $C_{1-10}$alkyl, or heteroalkyl, it is substituted with one or more independent halo. In another embodiment, when $R^3$ is aryl, heteroaryl, $C_{1-10}$alkyl, $C_{3-8}$cycloalkyl, $C_{3-8}$cycloalkyl-$C_{1-10}$alkyl, heterocyclyl, heterocyclyl $C_{1-10}$alkyl, or heteroalkyl, it is substituted with one or more independent —OH. In another embodiment, when $R^3$ is aryl, heteroaryl, $C_{1-10}$alkyl, $C_{3-8}$cycloalkyl, $C_{3-8}$cycloalkyl-$C_{1-10}$alkyl, heterocyclyl, heterocyclyl $C_{1-10}$alkyl, or heteroalkyl, it is substituted with one or more independent —$R^{31}$. In another embodiment, when $R^3$ is aryl, heteroaryl, $C_{1-10}$alkyl, $C_{3-8}$cycloalkyl, $C_{3-8}$cycloalkyl-$C_{1-10}$alkyl, heterocyclyl, heterocyclyl $C_{1-10}$alkyl, or heteroalkyl, it is substituted with one or more independent —$CF_3$. In another embodiment, when $R^3$ is aryl, heteroaryl, $C_{1-10}$alkyl, $C_{3-8}$cycloalkyl, $C_{3-8}$cycloalkyl-$C_{1-10}$alkyl, heterocyclyl, heterocyclyl $C_{1-10}$alkyl, or heteroalkyl, it is substituted with one or more independent —OCF. In another embodiment, when $R^3$ is aryl, heteroaryl, $C_{1-10}$alkyl, $C_{3-8}$cycloalkyl, $C_{3-8}$cycloalkyl-$C_{1-10}$alkyl, heterocyclyl, heterocyclyl $C_{1-10}$alkyl, or heteroalkyl, it is substituted with one or more independent —$OR^{31}$. In another embodiment, when $R^3$ is aryl, heteroaryl, $C_{1-10}$alkyl, $C_{3-8}$cycloalkyl, $C_{3-8}$cycloalkyl-$C_{1-10}$alkyl, heterocyclyl, heterocyclyl $C_{1-10}$alkyl, or heteroalkyl, it is substituted with one or more independent —$NR^{31}R^{32}$. In another embodiment, when $R^3$ is aryl, heteroaryl, $C_{1-10}$alkyl, $C_{3-8}$cycloalkyl, $C_{3-8}$cycloalkyl-$C_{1-10}$alkyl, heterocyclyl, heterocyclyl $C_{1-10}$alkyl, or heteroalkyl, it is substituted with one or more independent —$NR^{34}R^{35}$. In another embodiment, when $R^3$ is aryl, heteroaryl, $C_{1-10}$alkyl, $C_{3-8}$cycloalkyl, $C_{3-8}$cycloalkyl-$C_{1-10}$alkyl, heterocyclyl, heterocyclyl $C_{1-10}$alkyl, or heteroalkyl, it is substituted with one or more independent —$C(O)R^{31}$. In another embodiment, when $R^3$ is aryl, heteroaryl, $C_{1-10}$alkyl, $C_{3-8}$cycloalkyl, $C_{3-8}$cycloalkyl-$C_{1-10}$alkyl, heterocyclyl, heterocyclyl $C_{1-10}$alkyl, or heteroalkyl, it is substituted with one or more independent —$CO_2R^{31}$. In another embodiment, when $R^3$ is aryl, heteroaryl, $C_{1-10}$alkyl, $C_{3-8}$cycloalkyl, $C_{3-8}$cycloalkyl-$C_{1-10}$alkyl, heterocyclyl, heterocyclyl $C_{1-10}$alkyl, or heteroalkyl, it is substituted with one or more independent —$C(=O)NR^{31}R^{32}$. In another embodiment, when $R^3$ is aryl, heteroaryl, cycloalkyl, heterocyclyl, heteroalkyl, $C_{2-10}$alkenyl, $C_{2-10}$alkynyl, aryl-$C_{2-10}$alkyl, heterocyclyl $C_{1-10}$alkyl, or $C_{3-8}$cycloalkyl-$C_{1-10}$alkyl, it is substituted with one or more independent —$C(=O)NR^{34}R^{35}$. In another embodiment, when $R^3$ is aryl, heteroaryl, $C_{1-10}$alkyl, $C_{3-8}$cycloalkyl, $C_{3-8}$cycloalkyl-$C_{1-10}$alkyl, heterocyclyl, heterocyclyl $C_{1-10}$alkyl, or heteroalkyl, it is substituted with one or more independent —$NO_2$. In another embodiment, when $R^3$ is aryl, heteroaryl, $C_{1-10}$alkyl, $C_{3-8}$cycloalkyl, $C_{3-8}$cycloalkyl-$C_{1-10}$alkyl, heterocyclyl, heterocyclyl $C_{1-10}$alkyl, or heteroalkyl, it is substituted with one or more independent —CN. In another embodiment, when $R^3$ is aryl, heteroaryl, $C_{1-10}$alkyl, $C_{3-8}$cycloalkyl, $C_{3-8}$cycloalkyl-$C_{1-10}$alkyl, heterocyclyl, heterocyclyl $C_{1-10}$alkyl, or heteroalkyl, it is substituted with one or more independent —$S(O)_{0-2}R^{31}$. In another embodiment, when $R^3$ is aryl, heteroaryl, $C_{1-10}$alkyl, $C_{3-8}$cycloalkyl, $C_{3-8}$cycloalkyl-$C_{1-10}$alkyl, heterocyclyl, heterocyclyl $C_{1-10}$alkyl, or heteroalkyl, it is substituted with one or more independent —$SO_2NR^{31}R^{32}$. In another embodiment, when $R^3$ is aryl, heteroaryl, $C_{1-10}$alkyl, $C_{3-8}$cycloalkyl, $C_{3-8}$cycloalkyl-$C_{1-10}$alkyl, heterocyclyl, heterocyclyl $C_{1-10}$alkyl, or heteroalkyl, it is substituted with one or more independent —$SO_2NR^{34}R^{35}$. In another embodiment, when $R^3$ is aryl, heteroaryl, $C_{1-10}$alkyl, cycloalkyl, heterocyclyl, heteroalkyl, $C_{2-10}$alkenyl, $C_{2-10}$alkynyl, aryl-$C_{2-10}$alkyl, heterocyclyl $C_{1-10}$alkyl, or $C_{3-8}$cycloalkyl-$C_{1-10}$alkyl, it is substituted with one or more independent $NR^{31}C(=O)R^{32}$. In another embodiment, when $R^3$ is aryl, heteroaryl, cycloalkyl, heterocyclyl, heteroalkyl, $C_{2-10}$-alkenyl, $C_{2-10}$alkynyl, aryl-$C_{2-10}$alkyl, heterocyclyl $C_{1-10}$alkyl, or $C_{3-8}$cycloalkyl-$C_{1-10}$alkyl, it is substituted with one or more independent —$NR^{31}C(=O)OR^{32}$. In another embodiment, when $R^3$ is aryl, heteroaryl, cycloalkyl, heterocyclyl, heteroalkyl, $C_{2-10}$alkenyl, $C_{2-10}$alkynyl, aryl-$C_{2-10}$-alkyl, heterocyclyl $C_{1-10}$alkyl, or $C_{3-8}$cycloalkyl-$C_{1-10}$alkyl, it is substituted with one or more independent —$NR^{31}C(=O)NR^{32}R^{33}$. In another embodiment, when $R^3$ is aryl, heteroaryl, $C_{1-10}$alkyl, cycloalkyl, heterocyclyl, heteroalkyl, $C_{2-10}$alkenyl, $C_{2-10}$alkynyl, aryl-$C_{2-10}$alkyl, heterocyclyl $C_{1-10}$alkyl, or $C_{3-8}$cycloalkyl-$C_{1-10}$alkyl, it is substituted with one or more independent —$NR^{31}S(O)_{0-2}R^{32}$. In another embodiment, when $R^3$ is aryl, heteroaryl, $C_{1-10}$alkyl, cycloalkyl, heterocyclyl, heteroalkyl, $C_{2-10}$alkenyl, $C_{2-10}$alkynyl, aryl-$C_{2-10}$alkyl, heterocyclyl $C_{1-10}$alkyl, or $C_{3-8}$cycloalkyl-$C_{1-10}$alkyl, it is substituted with one or more independent —$C(=S)OR^{31}$. In another embodiment, when $R^3$ is aryl, heteroaryl, $C_{1-10}$alkyl, cycloalkyl, heterocyclyl, heteroalkyl, $C_{2-10}$alkenyl, $C_{2-10}$alkynyl, aryl-$C_{2-10}$alkyl, heterocyclyl $C_{1-10}$alkyl, or $C_{3-8}$cycloalkyl-$C_{1-10}$alkyl, it is substituted with one or more independent —$C(=O)SR^{31}$. In another embodiment, when $R^3$ is aryl, heteroaryl, $C_{1-10}$alkyl, $C_{3-8}$cycloalkyl, $C_{3-8}$cycloalkyl-$C_{1-10}$alkyl, heterocyclyl, heterocyclyl $C_{1-10}$alkyl, or heteroalkyl, it is substituted with one or more independent —$NR^{31}C(=NR^{32})NR^{33}R^{32}$. In another embodiment, when $R^3$ is aryl, heteroaryl, $C_{1-10}$alkyl, cycloalkyl, heterocyclyl, heteroalkyl, $C_{2-10}$alkenyl, $C_{2-10}$alkynyl, aryl-$C_{2-10}$alkyl, heterocyclyl $C_{1-10}$alkyl, or $C_{3-8}$cycloalkyl-$C_{1-10}$alkyl, it is substituted with one or more independent, —$NR^{31}C(=NR^{32})OR^{33}$. In another embodiment, when $R^3$ is aryl, heteroaryl, $C_{1-10}$alkyl, cycloalkyl, heterocyclyl, heteroalkyl, $C_{2-10}$alkenyl, $C_{2-10}$alkynyl, aryl-$C_{2-10}$alkyl, heterocyclyl $C_{1-10}$alkyl, or $C_{3-8}$cycloalkyl-$C_{1-10}$alkyl, it is substituted with one or more independent —$NR^{31}C(=NR^{32})SR^{33}$. In another embodiment, when $R^3$ is aryl, heteroaryl, $C_{1-10}$alkyl, cycloalkyl, heterocyclyl, heteroalkyl, $C_{2-10}$-alkenyl, $C_{2-10}$alkynyl, aryl-$C_{2-10}$alkyl, heterocyclyl $C_{1-10}$alkyl, or $C_{3-8}$cycloalkyl-$C_{1-10}$alkyl, it is substituted with one or more independent —OC(=O)OR$^{33}$. In another embodiment, when R$^3$ is aryl, heteroaryl, $C_{1-10}$alkyl, cycloalkyl, heterocyclyl, heteroalkyl, $C_{2-10}$alkenyl, $C_{2-10}$alkynyl, aryl-$C_{2-10}$alkyl, heterocyclyl $C_{1-10}$alkyl, or $C_{3-8}$cycloalkyl-$C_{1-10}$alkyl, it is substituted with one or more independent —OC(=O)NR$^{31}$R$^{32}$. In another embodiment, when R$^3$ is aryl, heteroaryl, $C_{1-10}$alkyl, cycloalkyl, heterocyclyl, heteroalkyl, $C_{2-10}$alkenyl, $C_{2-10}$alkynyl, aryl-$C_{2-10}$alkyl, heterocyclyl $C_{1-10}$alkyl, or $C_{3-8}$cycloalkyl-$C_{1-10}$alkyl, it is substituted with one or more independent —OC(=O)SR$^{31}$. In another embodiment, when R$^3$ is aryl, heteroaryl, $C_{1-10}$alkyl, cycloalkyl, heterocyclyl, heteroalkyl, $C_{2-10}$-alkenyl, $C_{2-10}$alkynyl, aryl-$C_{2-10}$alkyl, heterocyclyl $C_{1-10}$alkyl, or $C_{3-8}$cycloalkyl-$C_{1-10}$alkyl, it is substituted with one or more independent —SC(=O)OR$^{31}$. In another embodiment, when R$^3$ is aryl, heteroaryl, $C_{1-10}$alkyl, $C_{3-8}$cycloalkyl, $C_{3-8}$cycloalkyl-$C_{1-10}$alkyl, heterocyclyl, heterocyclyl $C_{1-10}$alkyl, or heteroalkyl, it is substituted with one or more independent —P(O)OR$^{31}$OR$^{32}$. In another embodiment, when R$^3$ is aryl, heteroaryl, $C_{1-10}$alkyl, cycloalkyl, heterocyclyl, heteroalkyl, $C_{2-10}$-alkenyl, $C_{2-10}$alkynyl, aryl-$C_{2-10}$alkyl, heterocyclyl $C_{1-10}$alkyl, or $C_{3-8}$cycloalkyl-$C_{1-10}$alkyl, it is substituted with one or more independent —SC(=O)NR$^{31}$R$^{32}$.

In various embodiments of compounds of Formula I, R$^4$ is hydrogen. In another embodiment, R$^4$ is halogen. In another embodiment, R$^4$ is —OH. In another embodiment, R$^4$ is —R$^{31}$. In another embodiment, R$^4$ is —CF$_3$. In another embodiment, R$^4$ is —OCF$_3$. In another embodiment, R$^4$ is —OR$^{31}$. In another embodiment, R$^4$ is —NR$^{31}$R$^{32}$. In another embodiment, R$^4$ is —NR$^{34}$R$^{35}$. In another embodiment, R$^4$ is —C(O)R$^{31}$. In another embodiment, R$^4$ is —CO$_2$R$^{31}$. In another embodiment, R$^4$ is —C(=O)NR$^{31}$R$^{32}$. In another embodiment, R$^4$ is —C(=O)NR$^{34}$R$^{35}$. In another embodiment, R$^4$ is —NO$_2$. In another embodiment, R$^4$ is —CN. In another embodiment, R$^4$ is —S(O)$_{0-2}$R$^3$. In another embodiment, R$^4$ is —SO$_2$NR$^{31}$R$^{32}$. In another embodiment, R$^4$ is —SO$_2$NR$^{34}$R$^{35}$. In another embodiment, R$^4$ is —NR$^{31}$C(=O)R$^{32}$. In another embodiment, R$^4$ is —NR$^{31}$C(=O)OR$^{32}$. In another embodiment, R$^4$ is —NR$^{31}$C(=O)NR$^{32}$R$^{33}$. In another embodiment, R$^4$ is —NR$^{31}$S(O)$_{0-2}$R$^{32}$. In another embodiment, R$^4$ is —C(=S)OR$^{31}$. In another embodiment, R$^4$ is —C(=O)SR$^{31}$. In another embodiment, R$^4$ is —NR$^{31}$C(=NR$^{32}$)NR$^{33}$R$^{32}$. In another embodiment, R$^4$ is —NR$^{31}$C(=NR$^{32}$)OR$^{33}$. In another embodiment, R$^4$ is —NR$^{31}$C(=NR$^{32}$)SR$^{33}$. In another embodiment, R$^4$ is —OC(=O)OR$^{33}$. In another embodiment, R$^4$ is —OC(=O)NR$^{31}$R$^{32}$. In another embodiment, R$^4$ is —OC(=O)SR$^{31}$. In another embodiment, R$^4$ is —SC(=O)OR$^{31}$. In another embodiment, R$^4$ is —P(O)OR$^{31}$OR$^{32}$. In another embodiment, R$^4$ is —SC(=O)NR$^{31}$R$^{32}$. In another embodiment, R$^4$ is aryl. In another embodiment, R$^4$ is heteroaryl. In another embodiment, R$^4$ is $C_{1-4}$alkyl. In another embodiment, R$^4$ is $C_{1-10}$alkyl. In another embodiment, R$^4$ is $C_{3-8}$cycloalkyl. In another embodiment, R$^4$ is $C_{1-10}$alkyl-$C_{3-8}$cycloalkyl. In another embodiment, R$^4$ is $C_{1-10}$alkylaryl. In another embodiment, R$^4$ is $C_{1-10}$alkylheteroaryl. In another embodiment, R$^4$ is $C_{1-10}$alkylheterocyclyl. In another embodiment, R$^4$ is $C_{2-10}$alkenyl. In another embodiment, R$^4$ is $C_{2-10}$alkynyl. In another embodiment, R$^4$ is $C_{2-10}$alkynyl-$C_{3-8}$cycloalkyl. R$^4$ is $C_{2-10}$alkenyl-$C_{3-8}$cycloalkyl. In another embodiment, R$^4$ is $C_{2-10}$alkenylaryl. In another embodiment, R$^4$ is $C_{2-10}$alkenylheteroaryl. In another embodiment, R$^4$ is $C_{2-10}$alkenylheteroalkyl. In another embodiment, R$^4$ is $C_{2-10}$alkenylheterocyclyl. In another embodiment, R$^4$ is —$C_{2-10}$alkynylaryl. In another embodiment, R$^4$ is $C_{2-10}$alkynylheteroaryl. In another embodiment, R$^4$ is $C_{2-10}$alkynylheteroalkyl. In another embodiment, R$^4$ is $C_{2-10}$alkynylheterocyclyl. In another embodiment, R$^4$ is $C_{2-10}$alkynyl$C_{3-8}$cycloalkyl. In another embodiment, R$^4$ is heterocyclyl $C_{1-10}$alkyl. In another embodiment, R$^4$ is heterocyclylC$_{2-10}$alkenyl. In another embodiment, R$^4$ is heterocyclyl-$C_{2-10}$alkynyl. In another embodiment, R$^4$ is aryl-$C_{1-10}$alkyl. In another embodiment, R$^4$ is aryl-$C_{2-10}$alkenyl. In another embodiment, R$^4$ is aryl-$C_{2-10}$alkynyl. In another embodiment, R$^4$ is aryl-heterocyclyl. In another embodiment, R$^4$ is heteroaryl-$C_{1-10}$alkyl. In another embodiment, R$^4$ is heteroaryl-$C_{2-10}$alkenyl. In another embodiment, R$^4$ is heteroaryl-$C_{2-10}$alkynyl. In another embodiment, R$^4$ is $C_{3-8}$cycloalkyl-$C_{1-10}$alkyl. In another embodiment, R$^4$ is $C_{3-8}$cycloalkyl-$C_{2-10}$alkenyl. In another embodiment, R$^4$ is $C_{3-8}$cycloalkyl-$C_{2-10}$alkynyl.

In various embodiments of compounds of Formula I, when R$^4$ is aryl, heteroaryl, $C_{1-10}$alkyl, $C_{3-8}$cycloalkyl, $C_{3-8}$cycloalkyl-$C_{1-10}$alkyl, heterocyclyl, heterocyclyl $C_{1-10}$alkyl, or heteroalkyl, it is unsubstituted. In another embodiment, when R$^4$ is aryl, heteroaryl, $C_{1-10}$alkyl, $C_{3-8}$cycloalkyl, $C_{3-8}$cycloalkyl-$C_{1-10}$alkyl, heterocyclyl, heterocyclyl $C_{1-10}$alkyl, or heteroalkyl, it is substituted with one or more independent halo. In another embodiment, when R$^4$ is aryl, heteroaryl, $C_{1-10}$alkyl, $C_{3-8}$cycloalkyl, $C_{3-8}$cycloalkyl-$C_{1-10}$alkyl, heterocyclyl, heterocyclyl $C_{1-10}$alkyl, or heteroalkyl, it is substituted with one or more independent —OH. In another embodiment, when R$^4$ is aryl, heteroaryl, $C_{1-10}$alkyl, $C_{3-8}$cycloalkyl, $C_{3-8}$cycloalkyl-$C_{1-10}$alkyl, heterocyclyl, heterocyclyl $C_{1-10}$alkyl, or heteroalkyl, it is substituted with one or more independent —R$^{31}$. In another embodiment, when R$^4$ is aryl, heteroaryl, $C_{1-10}$alkyl, $C_{3-8}$cycloalkyl, $C_{3-8}$cycloalkyl-$C_{1-10}$alkyl, heterocyclyl, heterocyclyl $C_{1-10}$alkyl, or heteroalkyl, it is substituted with one or more independent —CF$_3$. In another embodiment, when R$^4$ is aryl, heteroaryl, $C_{1-10}$alkyl, $C_{3-8}$cycloalkyl, $C_{3-8}$cycloalkyl-$C_{1-10}$alkyl, heterocyclyl, heterocyclyl $C_{1-10}$alkyl, or heteroalkyl, it is substituted with one or more independent —OCF. In another embodiment, when R$^4$ is aryl, heteroaryl, $C_{1-10}$alkyl, $C_{3-8}$cycloalkyl, $C_{3-8}$cycloalkyl-$C_{1-10}$alkyl, heterocyclyl, heterocyclyl $C_{1-10}$alkyl, or heteroalkyl, it is substituted with one or more independent —OR$^{31}$. In another embodiment, when R$^4$ is aryl, heteroaryl, $C_{1-10}$alkyl, $C_{3-8}$cycloalkyl, $C_{3-8}$cycloalkyl-$C_{1-10}$alkyl, heterocyclyl, heterocyclyl $C_{1-10}$alkyl, or heteroalkyl, it is substituted with one or more independent —NR$^{31}$R$^{32}$. In another embodiment, when R$^4$ is aryl, heteroaryl, $C_{1-10}$alkyl, $C_{3-8}$cycloalkyl, $C_{3-8}$cycloalkyl-$C_{1-10}$alkyl, heterocyclyl, heterocyclyl $C_{1-10}$alkyl, or heteroalkyl, it is substituted with one or more independent —NR$^{34}$R$^{35}$. In another embodiment, when R$^4$ is aryl, heteroaryl, $C_{1-10}$alkyl, $C_{3-8}$cycloalkyl, $C_{3-8}$cycloalkyl-$C_{1-10}$alkyl, heterocyclyl, heterocyclyl $C_{1-10}$alkyl, or heteroalkyl, it is substituted with one or more independent —C(O)R$^{31}$. In another embodiment, when R$^4$ is aryl, heteroaryl, $C_{1-10}$alkyl, $C_{3-8}$cycloalkyl, $C_{3-8}$cycloalkyl-$C_{1-10}$alkyl, heterocyclyl, heterocyclyl $C_{1-10}$alkyl, or heteroalkyl, it is substituted with one or more independent —CO$_2$R$^{31}$. In another embodiment, when R$^4$ is aryl, heteroaryl, $C_{1-10}$alkyl, $C_{3-8}$cycloalkyl, $C_{3-8}$cycloalkyl-$C_{1-10}$alkyl, heterocyclyl, heterocyclyl $C_{1-10}$alkyl, or heteroalkyl, it is substituted with one or more independent —C(=O)NR$^{31}$R$^{32}$. In another embodiment, when R$^4$ is aryl, heteroaryl, $C_{1-10}$alkyl, cycloalkyl, heterocyclyl, heteroalkyl, $C_{2-10}$-alkenyl, $C_{2-10}$alkynyl, aryl-$C_{2-10}$alkyl, heterocyclyl $C_{1-10}$alkyl, or $C_{3-8}$cycloalkyl-$C_{1-10}$alkyl, it is substituted with one or more independent —C(=O)NR$^{34}$R$^{35}$. In another embodiment, when R$^4$ is aryl, heteroaryl, C$_{1-10}$alkyl, C$_{3-8}$cycloalkyl, C$_{3-8}$cycloalkyl-C$_{1-10}$alkyl, heterocyclyl, heterocyclyl C$_{1-10}$alkyl, or heteroalkyl, it is substituted with one or more independent —NO$_2$. In another embodiment, when R$^4$ is aryl, heteroaryl, C$_{1-10}$alkyl, C$_{3-8}$cycloalkyl, C$_{3-8}$cycloalkyl-C$_{1-10}$alkyl, heterocyclyl, heterocyclyl C$_{1-10}$alkyl, or heteroalkyl, it is substituted with one or more independent —CN. In another embodiment, when R$^4$ is aryl, heteroaryl, C$_{1-10}$alkyl, C$_{3-8}$cycloalkyl, C$_{3-8}$cycloalkyl-C$_{1-10}$alkyl, heterocyclyl, heterocyclyl C$_{1-10}$alkyl, or heteroalkyl, it is substituted with one or more independent —S(O)$_{0-2}$R$^{31}$. In another embodiment, when R$^4$ is aryl, heteroaryl, C$_{1-10}$alkyl, C$_{3-8}$cycloalkyl, C$_{3-8}$cycloalkyl-C$_{1-10}$alkyl, heterocyclyl, heterocyclyl C$_{1-10}$alkyl, or heteroalkyl, it is substituted with one or more independent —SO$_2$NR$^{31}$R$^{32}$. In another embodiment, when R$^4$ is aryl, heteroaryl, C$_{1-10}$alkyl, C$_{3-8}$cycloalkyl, C$_{3-8}$cycloalkyl-C$_{1-10}$alkyl, heterocyclyl, heterocyclyl C$_{1-10}$alkyl, or heteroalkyl, it is substituted with one or more independent —SO$_2$NR$^{34}$R$^{35}$. In another embodiment, when R$^4$ is aryl, heteroaryl, C$_{1-10}$alkyl, cycloalkyl, heterocyclyl, heteroalkyl, C$_{2-10}$alkenyl, C$_{2-10}$alkynyl, aryl-C$_{2-10}$alkyl, heterocyclyl C$_{1-10}$alkyl, or C$_{3-8}$cycloalkyl-C$_{1-10}$alkyl, it is substituted with one or more independent NR$^{31}$C(=O)R$^{32}$. In another embodiment, when R$^4$ is aryl, heteroaryl, C$_{1-10}$alkyl, cycloalkyl, heterocyclyl, heteroalkyl, C$_{2-10}$alkenyl, C$_{2-10}$alkynyl, aryl-C$_{2-10}$alkyl, heterocyclyl C$_{1-10}$alkyl, or C$_{3-8}$cycloalkyl-C$_{1-10}$alkyl, it is substituted with one or more independent —NR$^{31}$C(=O)OR$^{32}$. In another embodiment, when R$^4$ is aryl, heteroaryl, C$_{1-10}$alkyl, cycloalkyl, heterocyclyl, heteroalkyl, C$_{2-10}$alkenyl, C$_{2-10}$alkynyl, aryl-C$_{2-10}$alkyl, heterocyclyl C$_{1-10}$alkyl, or C$_{3-8}$cycloalkyl-C$_{1-10}$alkyl, it is substituted with one or more independent —NR$^{31}$C(=O)NR$^{32}$R$^{33}$. In another embodiment, when R$^4$ is aryl, heteroaryl, C$_{1-10}$alkyl, cycloalkyl, heterocyclyl, heteroalkyl, C$_{2-10}$alkenyl, C$_{2-10}$alkynyl, aryl-C$_{2-10}$alkyl, heterocyclyl C$_{1-10}$alkyl, or C$_{3-8}$cycloalkyl-C$_{1-10}$alkyl, it is substituted with one or more independent —NR$^{31}$S(O)$_{0-2}$R$^{32}$. In another embodiment, when R$^4$ is aryl, heteroaryl, C$_{1-10}$alkyl, cycloalkyl, heterocyclyl, heteroalkyl, C$_{2-10}$alkenyl, C$_{2-10}$alkynyl, aryl-C$_{2-10}$alkyl, heterocyclyl C$_{1-10}$alkyl, or C$_{3-8}$cycloalkyl-C$_{1-10}$alkyl, it is substituted with one or more independent —C(=S)OR$^{31}$. In another embodiment, when R$^4$ is aryl, heteroaryl, C$_{1-10}$alkyl, cycloalkyl, heterocyclyl, heteroalkyl, C$_{2-10}$alkenyl, C$_{2-10}$alkynyl, aryl-C$_{2-10}$alkyl, heterocyclyl C$_{1-10}$alkyl, or C$_{3-8}$cycloalkyl-C$_{1-10}$alkyl, it is substituted with one or more independent —C(=O)SR$^{31}$. In another embodiment, when R$^4$ is aryl, heteroaryl, C$_{1-10}$alkyl, C$_{3-8}$cycloalkyl, C$_{3-8}$cycloalkyl-C$_{1-10}$alkyl, heterocyclyl, heterocyclyl C$_{1-10}$alkyl, or heteroalkyl, it is substituted with one or more independent —NR$^{31}$C(=NR$^{32}$)NR$^{33}$R$^{32}$. In another embodiment, when R$^4$ is aryl, heteroaryl, C$_{1-10}$alkyl, cycloalkyl, heterocyclyl, heteroalkyl, C$_{2-10}$alkenyl, C$_{2-10}$alkynyl, aryl C$_{2-10}$alkyl heterocyclyl C$_{1-10}$alkyl, or C$_{3-8}$cycloalkyl-C$_{1-10}$alkyl, it is substituted with one or more independent, —NR$^{31}$C(=NR$^{32}$)OR$^{33}$. In another embodiment, when R$^4$ is aryl, heteroaryl, C$_{1-10}$alkyl, cycloalkyl, heterocyclyl, heteroalkyl, C$_{2-10}$alkenyl, C$_{2-10}$alkynyl, aryl-C$_{2-10}$alkyl, heterocyclyl C$_{1-10}$alkyl, or C$_{3-8}$cycloalkyl-C$_{1-10}$alkyl, it is substituted with one or more independent —NR$^{31}$C(=NR$^{32}$)SR$^{33}$. In another embodiment, when R$^4$ is aryl, heteroaryl, C$_{1-10}$alkyl, cycloalkyl, heterocyclyl, heteroalkyl, C$_{2-10}$alkenyl, C$_{2-10}$alkynyl, aryl-C$_{2-10}$alkyl, heterocyclyl C$_{1-10}$alkyl, or C$_{3-8}$cycloalkyl-C$_{1-10}$alkyl, it is substituted with one or more independent —OC(=O)OR$^{33}$. In another embodiment, when R$^4$ is aryl, heteroaryl, C$_{1-10}$alkyl, cycloalkyl, heterocyclyl, heteroalkyl, C$_{2-10}$alkenyl, C$_{2-10}$alkynyl, aryl-C$_{2-10}$alkyl, heterocyclyl C$_{1-10}$alkyl, or C$_{3-8}$cycloalkyl-C$_{1-10}$alkyl, it is substituted with one or more independent —OC(=O)NR$^{31}$R$^{32}$. In another embodiment, when R$^4$ is aryl, heteroaryl, C$_{1-10}$alkyl, cycloalkyl, heterocyclyl, heteroalkyl, C$_{2-10}$alkenyl, C$_{2-10}$alkynyl, aryl-C$_{2-10}$alkyl, heterocyclyl C$_{1-10}$alkyl, or C$_{3-8}$cycloalkyl-C$_{1-10}$alkyl, it is substituted with one or more independent —OC(=O)SR$^{31}$. In another embodiment, when R$^4$ is aryl, heteroaryl, C$_{1-10}$alkyl, cycloalkyl, heterocyclyl, heteroalkyl, C$_{2-10}$alkenyl, C$_{2-10}$alkynyl, aryl-C$_{2-10}$alkyl, heterocyclyl C$_{1-10}$alkyl, or C$_{3-8}$cycloalkyl-C$_{1-10}$alkyl, it is substituted with one or more independent —SC(=O)OR$^{31}$. In another embodiment, when R$^4$ is aryl, heteroaryl, C$_{1-10}$alkyl, C$_{3-8}$cycloalkyl, C$_{3-8}$cycloalkyl-C$_{1-10}$alkyl, heterocyclyl, heterocyclyl C$_{1-10}$alkyl, or heteroalkyl, it is substituted with one or more independent —P(O)OR$^{31}$OR$^{32}$. In another embodiment, when R$^4$ is aryl, heteroaryl, C$_{1-10}$alkyl, cycloalkyl, heterocyclyl, heteroalkyl, C$_{2-10}$alkenyl, C$_{2-10}$alkynyl, aryl-C$_{2-10}$alkyl, heterocyclyl C$_{1-10}$alkyl, or C$_{3-8}$cycloalkyl-C$_{1-10}$alkyl, it is substituted with one or more independent —SC(=O)NR$^{31}$R$^{32}$.

In various embodiments of compounds of Formula I, R$^5$ is hydrogen. In another embodiment, R$^5$ is halogen. In another embodiment, R$^5$ is —OH. In another embodiment, R$^5$ is —R$^{31}$. In another embodiment, R$^5$ is —CF$_3$. In another embodiment, R$^5$ is —OCF$_3$. In another embodiment, R$^5$ is —OR$^{31}$. In another embodiment, R$^5$ is —NR$^{31}$R$^{32}$. In another embodiment, R$^5$ is —NR$^{34}$R$^{35}$. In another embodiment, R$^5$ is —C(O)R$^{31}$. In another embodiment, R$^5$ is —CO$_2$R$^{31}$. In another embodiment, R$^5$ is —C(=O)NR$^{31}$R$^{32}$. In another embodiment, R$^5$ is —C(=O)NR$^{34}$R$^{35}$. In another embodiment, R$^5$ is —NO$_2$. In another embodiment, R$^5$ is —CN. In another embodiment, R$^5$ is —S(O)$_{0-2}$R$^{31}$. In another embodiment, R$^5$ is —SO$_2$NR$^{31}$R$^{32}$. In another embodiment, R$^5$ is —SO$_2$NR$^{34}$R$^{35}$. In another embodiment, R$^5$ is —NR$^{31}$C(=O)R$^{32}$. In another embodiment, R$^5$ is —NR$^{31}$C(=O)OR$^{32}$. In another embodiment, R$^5$ is —NR$^{31}$C(=O)NR$^{32}$R$^{33}$. In another embodiment, R$^5$ is —NR$^{31}$S(O)$_{0-2}$R$^{32}$. In another embodiment, R$^5$ is —C(=S)OR$^{31}$. In another embodiment, R$^5$ is —C(=O)SR$^{31}$. In another embodiment, R$^5$ is —NR$^{31}$C(=NR$^{32}$)NR$^{33}$R$^{32}$. In another embodiment, R$^5$ is —NR$^{31}$C(=NR$^{32}$)OR$^{33}$. In another embodiment, R$^5$ is —NR$^{31}$C(=NR$^{32}$)SR$^{33}$. In another embodiment, R$^5$ is —OC(=O)OR$^{33}$. In another embodiment, R$^5$ is —OC(=O)NR$^{31}$R$^{32}$. In another embodiment, R$^5$ is —OC(=O)SR$^{31}$. In another embodiment, R$^5$ is —SC(=O)OR$^{31}$. In another embodiment, R$^5$ is —P(O)OR$^{31}$OR$^{32}$. In another embodiment, R$^5$ is or —SC(=O)NR$^{31}$R$^{32}$.

In various embodiments of compounds of Formula I, R$^7$ is hydrogen. In another embodiment, R$^7$ is unsubstituted C$_{1-10}$alkyl. In another embodiment, R$^7$ is unsbustituted C$_{2-10}$alkenyl. In another embodiment, R$^7$ is unsubstituted aryl. In another embodiment, R$^7$ is unsubstituted heteroaryl. In another embodiment, R$^7$ is unsubstituted heterocyclyl. In another embodiment, R$^7$ is unsubstituted C$_{3-10}$cycloalkyl. In another embodiment, R$^7$ is C$_{1-10}$alkyl substituted by one or more independent R$^6$. In another embodiment, R$^7$ is C$_{2-10}$alkenyl substituted by one or more independent R$^6$. In another embodiment, R$^7$ is aryl substituted by one or more independent R$^6$. In another embodiment, R$^7$ is heteroaryl substituted by one or more independent R$^6$. In another embodiment, R$^7$ is heterocycly substituted by one or more independent R$^6$. In another embodiment, R$^7$ is C$_{3-10}$cycloalkyl substituted by one or more independent R$^6$.

In various embodiments of compounds of Formula I, R$^8$ is hydrogen. In another embodiment, R$^8$ is unsubstituted $C_{1-10}$alkyl. In another embodiment, $R^8$ is unsubstituted $C_{2-10}$alkenyl. In another embodiment, $R^8$ is unsubstituted aryl. In another embodiment, $R^8$ is unsubstituted heteroaryl. In another embodiment, $R^8$ is unsubstituted heterocyclyl. In another embodiment, $R^8$ is unsubstituted $C_{3-10}$cycloalkyl. In another embodiment, $R^8$ is $C_{1-10}$alkyl substituted by one or more independent $R^6$. In another embodiment, $R^8$ is $C_{2-10}$alkenyl substituted by one or more independent $R^6$. In another embodiment, $R^8$ is aryl substituted by one or more independent $R^6$. In another embodiment, $R^8$ is heteroaryl substituted by one or more independent $R^6$. In another embodiment, $R^8$ is heterocyclyl substituted by one or more independent $R^6$. In another embodiment, leis $C_{3-10}$cycloalkyl substituted by one or more independent $R^6$.

In various embodiments of compounds of Formula I, $R^6$ is halo, In another embodiment, $R^6$ is —$OR^{31}$. In another embodiment, $R^6$ is —SH. In another embodiment, $R^6$ is $NH_2$. In another embodiment, $R^6$ is —$NR^{34}R^{35}$. In another embodiment, $R^6$ is —$NR^{31}R^{32}$. In another embodiment, $R^6$ is —$CO_2R^{31}$. In another embodiment, $R^6$ is —$CO_2$aryl. In another embodiment, $R^6$ is —$C(=O)NR^{31}R^{32}$. In another embodiment, $R^6$ is $C(=O)NR^{34}R^{35}$. In another embodiment, $R^6$ is —$NO_2$. In another embodiment, $R^6$ is —CN. In another embodiment, $R^6$ is —$S(O)_{0-2}C_{1-10}$alkyl. In another embodiment, $R^6$ is —$S(O)_{0-2}$aryl. In another embodiment, $R^6$ is —$SO_2NR^{34}R^{35}$. In another embodiment, $R^6$ is —$SO_2NR^{31}R^{32}$. In another embodiment, $R^6$ is $C_{1-10}$alkyl. In another embodiment, $R^6$ is $C_{2-10}$alkenyl. In another embodiment, $R^6$ is $C_{2-10}$alkynyl. In another embodiment, $R^6$ is unsubstituted aryl-$C_{1-10}$alkyl. In another embodiment, $R^6$ is unsubstituted aryl-$C_{2-10}$alkenyl. In another embodiment, $R^6$ is unsubstituted aryl-$C_{2-10}$alkynyl. In another embodiment, $R^6$ is unsubstituted heteroaryl-$C_{1-10}$alkyl. In another embodiment, $R^6$ is unsubstituted heteroaryl-$C_{2-10}$alkenyl. In another embodiment, $R^6$ is aryl-$C_{1-10}$alkyl, aryl-$C_{2-10}$alkenyl, aryl-$C_{2-10}$alkynyl, heteroaryl-$C_{1-10}$alkyl, or heteroaryl-$C_{2-10}$alkenyl substituted by one or more independent halo. In another embodiment, $R^6$ is aryl-$C_{1-10}$alkyl, aryl-$C_{2-10}$alkenyl, aryl-$C_{2-10}$alkynyl, heteroaryl-$C_{1-10}$alkyl, or heteroaryl-$C_{2-10}$alkenyl substituted by one or more independent cyano. In another embodiment, $R^6$ is aryl-$C_{1-10}$alkyl, aryl-$C_{2-10}$alkenyl, aryl-$C_{2-10}$alkynyl, heteroaryl-$C_{1-10}$alkyl, or heteroaryl-$C_{2-10}$alkenyl substituted by one or more independent nitro. In another embodiment, $R^6$ is aryl-$C_{1-10}$alkyl, aryl-$C_{2-10}$alkenyl, aryl-$C_{2-10}$alkynyl, heteroaryl-$C_{1-10}$alkyl, or heteroaryl-$C_{2-10}$alkenyl substituted by one or more independent —O$C_{1-10}$alkyl. In another embodiment, $R^6$ is aryl-$C_{1-10}$alkyl, aryl-$C_{2-10}$alkenyl, aryl-$C_{2-10}$alkynyl, heteroaryl-$C_{1-10}$alkyl, or heteroaryl-$C_{2-10}$alkenyl substituted by one or more independent —$C_{1-10}$alkyl. In another embodiment, $R^6$ is aryl-$C_{1-10}$alkyl, aryl-$C_{2-10}$alkenyl, aryl-$C_{2-10}$alkynyl, heteroaryl-$C_{1-10}$alkyl, or heteroaryl-$C_{2-10}$alkenyl substituted by one or more independent —$C_{2-10}$alkenyl. In another embodiment, $R^6$ is aryl-$C_{1-10}$alkyl, aryl-$C_{2-10}$alkenyl, aryl-$C_{2-10}$alkynyl, heteroaryl-$C_{1-10}$alkyl, or heteroaryl-$C_{2-10}$alkenyl substituted by one or more independent —$C_{2-10}$alkynyl. In another embodiment, $R^6$ is aryl-$C_{1-10}$alkyl, aryl-$C_{2-10}$alkenyl, aryl-$C_{2-10}$alkynyl, heteroaryl-$C_{1-10}$alkyl, or heteroaryl-$C_{2-10}$alkenyl substituted by one or more independent -(halo)$C_{1-10}$alkyl. In another embodiment, $R^6$ is aryl-$C_{1-10}$alkyl, aryl-$C_{2-10}$alkenyl, aryl-$C_{2-10}$alkynyl, heteroaryl-$C_{1-10}$alkyl, or heteroaryl-$C_{2-10}$alkenyl substituted by one or more independent -(halo)$C_{2-10}$alkenyl. In another embodiment, $R^6$ is aryl-$C_{1-10}$alkyl, aryl-$C_{2-10}$alkenyl aryl-$C_{2-10}$alkynyl, heteroaryl-$C_{1-10}$alkyl, or heteroaryl-$C_{2-10}$alkenyl substituted by one or more independent -(halo)$C_{2-10}$alkynyl. In another embodiment, $R^6$ is aryl-$C_{1-10}$alkyl, aryl-$C_{2-10}$-alkenyl, aryl-$C_{2-10}$alkynyl, heteroaryl-$C_{1-10}$alkyl, or heteroaryl-$C_{2-10}$alkenyl substituted by one or more independent —COOH. In another embodiment, $R^6$ is aryl-$C_{1-10}$alkyl, aryl-$C_{2-10}$alkenyl, aryl-$C_{2-10}$alkynyl, heteroaryl-$C_{1-10}$alkyl, or heteroaryl-$C_{2-10}$alkenyl substituted by one or more independent —$C(=O)NR^{31}R^{32}$. In another embodiment, $R^6$ is aryl-$C_{1-10}$alkyl, aryl-$C_{2-10}$alkenyl, aryl-$C_{2-10}$alkynyl, heteroaryl-$C_{1-10}$alkyl, or heteroaryl-$C_{2-10}$alkenyl substituted by one or more independent —$C(=O)NR^{34}R^{35}$. In another embodiment, $R^6$ is aryl-$C_{1-10}$alkyl, aryl-$C_{2-10}$alkenyl, aryl-$C_{2-10}$alkynyl, heteroaryl-$C_{1-10}$alkyl, or heteroaryl-$C_{2-10}$alkenyl substituted by one or more independent —$SO_2NR^{34}R^{35}$. In another embodiment, $R^6$ is aryl-$C_{1-10}$alkyl, aryl-$C_{2-10}$alkenyl, aryl-$C_{2-10}$alkynyl, heteroaryl-$C_{1-10}$alkyl, or heteroaryl-$C_{2-10}$alkenyl substituted by one or more independent —$SO_2NR^{31}R^{32}$. In another embodiment, $R^6$ is aryl-$C_{1-10}$alkyl, aryl-$C_{2-10}$alkenyl, aryl-$C_{2-10}$alkynyl, heteroaryl-$C_{1-10}$alkyl, or heteroaryl-$C_{2-10}$alkenyl substituted by one or more independent —$NR^{31}R^{32}$. In another embodiment, $R^6$ is aryl-$C_{1-10}$alkyl, aryl-$C_{2-10}$alkenyl, aryl-$C_{2-10}$alkynyl, heteroaryl-$C_{1-10}$alkyl, or heteroaryl-$C_{2-10}$alkenyl substituted by one or more independent —$NR^{34}R^{35}$.

In various embodiments of compounds of Formula I, $R^9$ is H. In another embodiment, $R^9$ is halo. In another embodiment, $R^9$ is —$OR^{31}$. In another embodiment, $R^9$ is —SH. In another embodiment, $R^9$ is $NH_2$. In another embodiment, $R^9$ is —$NR^{34}R^{35}$. In another embodiment, $R^9$ is —$NR^{31}R^{32}$. In another embodiment, $R^9$ is —$CO_2R^{31}$. In another embodiment, $R^9$ is —$CO_2$aryl. In another embodiment, $R^9$ is —$C(=O)NR^{31}R^{32}$. In another embodiment, $R^9$ is $C(=O)NR^{34}R^{35}$. In another embodiment, $R^9$ is —$NO_2$. In another embodiment, $R^9$ is —CN. In another embodiment, $R^9$ is —$S(O)_{0-2}C_{1-10}$alkyl. In another embodiment, $R^9$ is —$S(O)_{0-2}$aryl. In another embodiment, $R^9$ is —$SO_2NR^{34}R^{35}$. In another embodiment, $R^9$ is —$SO_2NR^{31}R^{32}$. In another embodiment, $R^9$ is $C_{1-10}$alkyl. In another embodiment, $R^9$ is $C_{2-10}$alkenyl. In another embodiment, $R^9$ is $C_{2-10}$alkynyl. In another embodiment, $R^9$ is unsubstituted aryl-$C_{1-10}$alkyl. In another embodiment, $R^9$ is unsubstituted aryl-$C_{2-10}$alkenyl. In another embodiment, $R^9$ is unsubstituted aryl-$C_{2-10}$alkynyl. In another embodiment, $R^9$ is unsubstituted heteroaryl-$C_{1-10}$alkyl. In another embodiment, $R^9$ is unsubstituted heteroaryl-$C_{2-10}$alkenyl. In another embodiment, $R^9$ is aryl-$C_{1-10}$alkyl, aryl-$C_{2-10}$alkenyl, aryl-$C_{2-10}$alkynyl, heteroaryl-$C_{1-10}$alkyl, or heteroaryl-$C_{2-10}$alkenyl substituted by one or more independent halo. In another embodiment, $R^9$ is aryl-$C_{1-10}$alkyl, aryl-$C_{2-10}$alkenyl, aryl-$C_{2-10}$alkynyl, heteroaryl-$C_{1-10}$alkyl, or heteroaryl-$C_{2-10}$alkenyl substituted by one or more independent cyano. In another embodiment, $R^9$ is aryl-$C_{1-10}$alkyl, aryl-$C_{2-10}$alkenyl, aryl-$C_{2-10}$alkynyl, heteroaryl-$C_{1-10}$alkyl, or heteroaryl-$C_{2-10}$alkenyl substituted by one or more independent nitro. In another embodiment, $R^9$ is aryl-$C_{1-10}$alkyl, aryl-$C_{2-10}$alkenyl, aryl-$C_{2-10}$alkynyl, heteroaryl-$C_{1-10}$alkyl, or heteroaryl-$C_{2-10}$alkenyl substituted by one or more independent —O$C_{1-10}$alkyl. In another embodiment, $R^9$ is aryl-$C_{1-10}$alkyl, aryl-$C_{2-10}$alkenyl, aryl-$C_{2-10}$alkynyl, heteroaryl-$C_{1-10}$alkyl, or heteroaryl-$C_{2-10}$alkenyl substituted by one or more independent —$C_{1-10}$alkyl. In another embodiment, $R^9$ is aryl-$C_{1-10}$alkyl, aryl-$C_{2-10}$alkenyl, aryl-$C_{2-10}$alkynyl, heteroaryl-$C_{1-10}$alkyl, or heteroaryl-$C_{2-10}$alkenyl substituted by one or more independent —$C_{2-10}$alkenyl. In another embodiment, $R^9$ is aryl-$C_{1-10}$alkyl, aryl-$C_{2-10}$alkenyl, aryl-$C_{2-10}$alkynyl, heteroaryl-$C_{1-10}$alkyl, or heteroaryl-$C_{2-10}$alkenyl substituted by one or more independent —$C_{2-10}$alkynyl. In another embodiment, $R^9$ is aryl-$C_{1-10}$alkyl, aryl-$C_{2-10}$alkenyl, aryl-$C_{2-10}$alkynyl, heteroaryl-$C_{1-10}$alkyl, or heteroaryl-$C_{2-10}$alkenyl substituted by one or more independent -(halo)$C_{1-10}$alkyl. In another embodiment, $R^9$ is aryl-$C_{1-10}$alkyl, aryl-$C_{2-10}$alkenyl, aryl-$C_{2-10}$alkynyl, heteroaryl-$C_{1-10}$alkyl, or heteroaryl-$C_{2-10}$alkenyl substituted by one or more independent -(halo)$C_{2-10}$alkenyl. In another embodiment, $R^9$ is aryl-$C_{1-10}$alkyl, aryl-$C_{2-10}$alkenyl, aryl-$C_{2-10}$alkynyl, heteroaryl-$C_{1-10}$alkyl, or heteroaryl-$C_{2-10}$alkenyl substituted by one or more independent -(halo)$C_{2-10}$alkynyl. In another embodiment, $R^9$ is aryl-$C_{1-10}$alkyl, aryl-$C_{2-10}$alkenyl, aryl-$C_{2-10}$alkynyl, heteroaryl-$C_{1-10}$alkyl, or heteroaryl-$C_{2-10}$alkenyl substituted by one or more independent —COOH. In another embodiment, $R^9$ is aryl-$C_{1-10}$alkyl, aryl-$C_{2-10}$alkenyl, aryl-$C_{2-10}$alkynyl, heteroaryl-$C_{1-10}$alkyl, or heteroaryl-$C_{2-10}$alkenyl substituted by one or more independent —C(=O)$NR^{31}R^{32}$. In another embodiment, $R^9$ is aryl-$C_{1-10}$alkyl, aryl-$C_{2-10}$alkenyl, aryl-$C_{2-10}$alkynyl, heteroaryl-$C_{1-10}$alkyl, or heteroaryl-$C_{2-10}$alkenyl substituted by one or more independent —C(=O)$NR^{34}R^{35}$. In another embodiment, $R^9$ is aryl-$C_{1-10}$alkyl, aryl-$C_{2-10}$alkenyl, aryl-$C_{2-10}$alkynyl, heteroaryl-$C_{1-10}$alkyl, or heteroaryl-$C_{2-10}$alkenyl substituted by one or more independent —$SO_2NR^{34}R^{35}$. In another embodiment, $R^9$ is aryl-$C_{1-10}$alkyl, aryl-$C_{2-10}$alkenyl, aryl-$C_{2-10}$alkynyl, heteroaryl-$C_{1-10}$alkyl, or heteroaryl-$C_{2-10}$alkenyl substituted by one or more independent —$SO_2NR^{31}R^{32}$. In another embodiment, $R^9$ is aryl-$C_{1-10}$alkyl, aryl-$C_{2-10}$alkenyl, aryl-$C_{2-10}$alkynyl, heteroaryl-$C_{1-10}$alkyl, or heteroaryl-$C_{2-10}$alkenyl substituted by one or more independent —$NR^{31}R^{32}$. In another embodiment, $R^9$ is aryl-$C_{1-10}$alkyl, aryl-$C_{2-10}$alkenyl, aryl-$C_{2-10}$alkynyl, heteroaryl-$C_{1-10}$alkyl, or heteroaryl-$C_{2-10}$alkenyl substituted by one or more independent —$NR^{34}R^{35}$.

In various embodiments of compounds of Formula I, $R^{31}$ is H. In some embodiments, $R^{31}$ is unsubstituted $C_{1-10}$alkyl. In some embodiments, $R^{31}$ is substituted $C_{1-10}$alkyl. In some embodiments, $R^{31}$ is $C_{1-10}$alkyl substituted with one or more aryl. In some embodiments, $R^{31}$ is $C_{1-10}$alkyl substituted with one or more heteroalkyl. In some embodiments, $R^{31}$ is $C_{1-10}$alkyl substituted with one or more heterocyclyl. In some embodiments, $R^{31}$ is $C_{1-10}$alkyl substituted with one or more heteroaryl. In some embodiments, when $R^{31}$ is $C_{1-10}$alkyl substituted with one or more aryl, each of said aryl substituents is unsubstituted or substituted with one or more halo, —OH, —$C_{1-10}$alkyl, —$CF_3$, —O-aryl, —$OCF_3$, —$OC_{1-10}$alkyl, —$NH_2$, —N($C_{1-10}$alkyl)($C_{1-10}$alkyl), —NH($C_{1-10}$alkyl), —NH(aryl), —$NR^{34}R^{35}$, —C(O)($C_{1-10}$alkyl), —C(O)($C_{1-10}$alkyl-aryl), —C(O)(aryl), —$CO_2$—$C_{1-10}$alkyl, —$CO_2$—$C_{1-10}$alkylaryl, —$CO_2$-aryl, —C(=O)N($C_{1-10}$alkyl)($C_{1-10}$alkyl), —C(=O)NH($C_{1-10}$alkyl), —C(=O)$NR^{34}R^{35}$, —C(=O)$NH_2$, —$OCF_3$, —O($C_{1-10}$alkyl), —O-aryl, —N(aryl)($C_{1-10}$alkyl), —$NO_2$, —CN, —$S(O)_{0-2}C_{1-10}$alkyl, —$S(O)_{0-2}C_{1-10}$alkylaryl, —$S(O)_{0-2}$ aryl, —$SO_2N$(aryl), —$SO_2N(C_{1-10}$alkyl)($C_{1-10}$alkyl), —$SO_2NH(C_{1-10}$alkyl) or —$SO_2NR^{34}R^{35}$. In some embodiments, when $R^{31}$ is $C_{1-10}$alkyl substituted with one or more heteroalkyl, each of said heteroalkyl group is unsubstituted or substituted with one or more halo, —OH, —$C_{1-10}$alkyl, —$CF_3$, —O-aryl, —$OCF_3$, —$OC_{1-10}$alkyl, —$NH_2$, —N($C_{1-10}$alkyl)($C_{1-10}$alkyl), —NH($C_{1-10}$alkyl), —NH(aryl), —$NR^{34}R^{35}$, —C(O)($C_{1-10}$alkyl), —C(O)($C_{1-10}$alkyl-aryl), —C(O)(aryl), —$CO_2$—$C_{1-10}$alkyl, —$CO_2$—$C_{1-10}$alkylaryl, —$CO_2$-aryl, —C(=O)N($C_{1-10}$alkyl)($C_{1-10}$alkyl), —C(=O)NH($C_{1-10}$alkyl), —C(=O)$NR^{34}R^{35}$, —C(=O)$NH_2$, —$OCF_3$, —O($C_{1-10}$alkyl), —O-aryl, —N(aryl)($C_{1-10}$alkyl), —$NO_2$, —CN, —$S(O)_{0-2}C_{1-10}$alkyl, —$S(O)_{0-2}C_{1-10}$alkylaryl, —$S(O)_{0-2}$ aryl, —$SO_2N$(aryl), —$SO_2N(C_{1-10}$alkyl)($C_{1-10}$alkyl), —$SO_2NH(C_{1-10}$alkyl) or —$SO_2NR^{34}R^{35}$ substituents. In some embodiments, when $R^{31}$ is $C_{1-10}$alkyl substituted with one or more heterocyclyl, each of said heterocyclyl group is unsubstituted or substituted with one or more halo, —OH, —$C_{1-10}$alkyl, —$CF_3$, —O-aryl, —$OCF_3$, —$OC_{1-10}$alkyl, —$NH_2$, —N($C_{1-10}$alkyl)($C_{1-10}$alkyl), —NH($C_{1-10}$alkyl), —NH(aryl), —$NR^{34}R^{35}$, —C(O)($C_{1-10}$alkyl), —C(O)($C_{1-10}$alkyl-aryl), —C(O)(aryl), —$CO_2$—$C_{1-10}$alkyl, —$CO_2$—$C_{1-10}$alkylaryl, —$CO_2$-aryl, —C(=O)N($C_{1-10}$alkyl)($C_{1-10}$alkyl), —C(=O)NH($C_{1-10}$alkyl), —C(=O)$NR^{34}R^{35}$, —C(=O)$NH_2$, —$OCF_3$, —O($C_{1-10}$alkyl), —O-aryl, —N(aryl)($C_{1-10}$alkyl), —$NO_2$, —CN, —$S(O)_{0-2}C_{1-10}$alkyl, —$S(O)_{0-2}C_{1-10}$alkylaryl, —$S(O)_{0-2}$aryl, —$SO_2N$(aryl), —$SO_2N(C_{1-10}$alkyl)($C_{1-10}$alkyl), —$SO_2NH(C_{1-10}$alkyl) or —$SO_2NR^{34}R^{35}$. In some embodiments, when $R^{31}$ is $C_{1-10}$alkyl substituted with one or more heteroaryl, each of said heteroaryl group is unsubstituted or substituted with one or more halo, —OH, —$C_{1-10}$alkyl, —$CF_3$, —O-aryl, —$OCF_3$, —$OC_{1-10}$alkyl, —$NH_2$, —N($C_{1-10}$alkyl)($C_{1-10}$alkyl), —NH($C_{1-10}$alkyl), —NH(aryl), —$NR^{34}R^{35}$, —C(O)($C_{1-10}$alkyl), —C(O)($C_{1-10}$alkyl-aryl), —C(O)(aryl), —$CO_2$—$C_{1-10}$alkyl, —$CO_2$—$C_{1-10}$alkylaryl, —$CO_2$-aryl, —C(=O)N($C_{1-10}$alkyl)($C_{1-10}$alkyl), —C(=O)NH($C_{1-10}$alkyl), —C(=O)$NR^{34}R^{35}$, —C(=O)$NH_2$, —$OCF_3$, —O($C_{1-10}$alkyl), —O-aryl, —N(aryl)($C_{1-10}$alkyl), —$NO_2$, —CN, —$S(O)_{0-2}C_{1-10}$alkyl, —$S(O)_{0-2}C_{1-10}$alkylaryl, —$S(O)_{0-2}$aryl, —$SO_2N$(aryl), —$SO_2N(C_{1-10}$alkyl)($C_{1-10}$alkyl), —$SO_2NH(C_{1-10}$alkyl) or —$SO_2NR^{34}R^{35}$. In some embodiments, when $R^{31}$ is substituted $C_{1-10}$alkyl, it is substituted by a combination of aryl, heteroalkyl, heterocyclyl, or heteroaryl groups.

In various embodiments of compounds of Formula I, $R^{32}$ is H. In some embodiments, $R^{32}$ is unsubstituted $C_{1-10}$alkyl. In some embodiments, $R^{32}$ is substituted $C_{1-10}$alkyl. In some embodiments, $R^{32}$ is $C_{1-10}$alkyl substituted with one or more aryl. In some embodiments, $R^{32}$ is $C_{1-10}$alkyl substituted with one or more heteroalkyl. In some embodiments, $R^{32}$ is $C_{1-10}$alkyl substituted with one or more heterocyclyl. In some embodiments, $R^{32}$ is $C_{1-10}$alkyl substituted with one or more heteroaryl. In some embodiments, when $R^{32}$ is $C_{1-10}$alkyl substituted with one or more aryl, each of said aryl group is unsubstituted or substituted with one or more halo, —OH, —$C_{1-10}$alkyl, —$CF_3$, —O-aryl, —$OCF_3$, —$OC_{1-10}$alkyl, —$NH_2$, —N($C_{1-10}$alkyl)($C_{1-10}$alkyl), —NH($C_{1-10}$alkyl), —NH(aryl), —$NR^{34}R^{35}$, —C(O)($C_{1-10}$alkyl), —C(O)($C_{1-10}$alkyl-aryl), —C(O)(aryl), —$CO_2$—$C_{1-10}$alkyl, —$CO_2$—$C_{1-10}$alkylaryl, —$CO_2$-aryl, —C(=O)N($C_{1-10}$alkyl)($C_{1-10}$alkyl), —C(=O)NH($C_{1-10}$alkyl), —C(=O)$NR^{34}R^{35}$, —C(=O)$NH_2$, —$OCF_3$, —O($C_{1-10}$alkyl), —O-aryl, —N(aryl)($C_{1-10}$alkyl), —$NO_2$, —CN, —$S(O)_{0-2}C_{1-10}$alkyl, —$S(O)_{0-2}C_{1-10}$alkylaryl, —$S(O)_{0-2}$ aryl, —$SO_2N$(aryl), —$SO_2N(C_{1-10}$alkyl)($C_{1-10}$alkyl), —$SO_2NH(C_{1-10}$alkyl) or —$SO_2NR^{34}R^{35}$. In some embodiments, when $R^{32}$ is $C_{1-10}$alkyl substituted with one or more heteroalkyl, each of said heteroalkyl group is unsubstituted or substituted with one or more halo, —OH, —$C_{1-10}$alkyl, —$CF_3$, —O-aryl, —$OCF_3$, —$OC_{1-10}$alkyl, —$NH_2$, —N($C_{1-10}$alkyl)($C_{1-10}$alkyl), —NH($C_{1-10}$alkyl), —NH(aryl), —$NR^{34}R^{35}$, —C(O)($C_{1-10}$alkyl), —C(O)($C_{1-10}$alkyl-aryl), —C(O)(aryl), —$CO_2$—$C_{1-10}$alkyl, —$CO_2$—$C_{1-10}$alkylaryl, —$CO_2$-aryl, —C(=O)N($C_{1-10}$alkyl)($C_{1-10}$alkyl), —C(=O)NH($C_{1-10}$alkyl), —C(=O)$NR^{34}R^{35}$, —C(=O)$NH_2$, —$OCF_3$, —O($C_{1-10}$alkyl), —O-aryl, —N(aryl)($C_{1-10}$alkyl), —$NO_2$, —CN, —$S(O)_{0-2}C_{1-10}$alkyl, —$S(O)_{0-2}C_{1-10}$alkylaryl, —$S(O)_{0-2}$ aryl, —$SO_2N$(aryl), —$SO_2N(C_{1-10}$alkyl)($C_{1-10}$alkyl), —$SO_2NH(C_{1-10}$alkyl) or —$SO_2NR^{34}R^{35}$. In some embodiments, when $R^{32}$ is $C_{1-10}$alkyl substituted with one or more heterocyclyl, each of said heterocyclyl group is unsubstituted or substituted with one or more halo, —OH, —$C_{1-10}$alkyl, —$CF_3$, —O-aryl, —$OCF_3$, —$OC_{1-10}$alkyl, —$NH_2$, —$N(C_{1-10}$alkyl$)(C_{1-10}$alkyl$)$, —NH($C_{1-10}$alkyl), —NH(aryl), —$NR^{34}R^{35}$, —C(O)($C_{1-10}$alkyl), —C(O)($C_{1-10}$alkyl-aryl), —C(O)(aryl), —$CO_2$—$C_{1-10}$alkyl, —$CO_2$—$C_{1-10}$alkylaryl, —$CO_2$-aryl, —C(=O)N($C_{1-10}$alkyl)($C_{1-10}$alkyl), —C(=O)NH($C_{1-10}$alkyl), —C(=O)$NR^{34}R^{35}$, —C(=O)$NH_2$, —$OCF_3$, —O($C_{1-10}$alkyl), —O-aryl, —N(aryl)($C_{1-10}$alkyl), —$NO_2$, —CN, —S(O)$_{0-2}C_{1-10}$alkyl, —S(O)$_{0-2}C_{1-10}$alkylaryl, —S(O)$_{0-2}$ aryl, —$SO_2$N(aryl), —$SO_2$N($C_{1-10}$alkyl)($C_{1-10}$alkyl), —$SO_2$NH($C_{1-10}$alkyl) or —$SO_2NR^{34}R^{35}$. In some embodiments, when $R^{32}$ is $C_{1-10}$alkyl substituted with one or more heteroaryl, each of said heteroaryl group is unsubstituted or substituted with one or more halo, —OH, —$C_{1-10}$alkyl, —$CF_3$, —O-aryl, —$OCF_3$, —$OC_{1-10}$alkyl, —$NH_2$, —$N(C_{1-10}$alkyl$)(C_{1-10}$alkyl$)$, —NH($C_{1-10}$alkyl), —NH(aryl), —$NR^{34}R^{35}$, —C(O)($C_{1-10}$alkyl), —C(O)($C_{1-10}$alkyl-aryl), —C(O)(aryl), —$CO_2$—$C_{1-10}$alkyl, —$CO_2$—$C_{1-10}$alkylaryl, —$CO_2$-aryl, —C(=O)N($C_{1-10}$alkyl)($C_{1-10}$alkyl), —C(=O)NH($C_{1-10}$alkyl), —C(=O)$NR^{34}R^{35}$, —C(=O)$NH_2$, —$OCF_3$, —O($C_{1-10}$alkyl), —O-aryl, —N(aryl)($C_{1-10}$alkyl), —$NO_2$, —CN, —S(O)$_{0-2}C_{1-10}$alkyl, —S(O)$_{0-2}C_{1-10}$alkylaryl, —S(O)$_{0-2}$ aryl, —$SO_2$N(aryl), —$SO_2$N($C_{1-10}$alkyl)($C_{1-10}$alkyl), —$SO_2$NH($C_{1-10}$alkyl) or —$SO_2NR^{34}R^{35}$. In some embodiments, when $R^{32}$ is substituted $C_{1-10}$alkyl, it is substituted by a combination of aryl, heteroalkyl, heterocyclyl, or heteroaryl groups.

In various embodiments of compounds of Formula I, $R^{33}$ is unsubstituted $C_{1-10}$alkyl. In some embodiments, $R^{33}$ is substituted $C_{1-10}$alkyl. In some embodiments, $R^{33}$ is $C_{1-10}$alkyl substituted with one or more aryl. In some embodiments, $R^{33}$ is $C_{1-10}$alkyl substituted with one or more heteroalkyl. In some embodiments, $R^{33}$ is $C_{1-10}$alkyl substituted with one or more heterocyclyl. In some embodiments, $R^{33}$ is $C_{1-10}$alkyl substituted with one or more heteroaryl. In some embodiments, when $R^{33}$ is $C_{1-10}$alkyl substituted with one or more aryl, each of said aryl group is unsubstituted or substituted with one or more halo, —OH, —$C_{1-10}$alkyl, —$CF_3$, —O-aryl, —$OCF_3$, —$OC_{1-10}$alkyl, —$NH_2$, —$N(C_{1-10}$alkyl$)$ ($C_{1-10}$alkyl), —NH($C_{1-10}$alkyl), —NH(aryl), —$NR^{34}R^{35}$, —C(O)($C_{1-10}$alkyl), —C(O)($C_{1-10}$alkyl-aryl), —C(O)(aryl), —$CO_2$—$C_{1-10}$alkyl, —$CO_2$—$C_{1-10}$alkylaryl, —$CO_2$-aryl, —C(=O)N($C_{1-10}$alkyl)($C_{1-10}$alkyl), —C(=O)NH ($C_{1-10}$alkyl), —C(=O)$NR^{34}R^{35}$, —C(=O)$NH_2$, —$OCF_3$, —O($C_{1-10}$alkyl), —O-aryl, —N(aryl)($C_{1-10}$alkyl), —$NO_2$, —CN, —S(O)$_{0-2}C_{1-10}$alkyl, —S(O)$_{0-2}C_{1-10}$alkylaryl, —S(O)$_{0-2}$ aryl, —$SO_2$N(aryl), —$SO_2$N($C_{1-10}$alkyl) ($C_{1-10}$alkyl), —$SO_2$NH($C_{1-10}$alkyl) or —$SO_2NR^{34}R^{35}$. In some embodiments, when $R^{33}$ is $C_{1-10}$alkyl substituted with one or more heteroalkyl, each of said heteroalkyl group is unsubstituted or substituted with one or more halo, —OH, —$C_{1-10}$alkyl, —$CF_3$, —O-aryl, —$OCF_3$, —$OC_{1-10}$alkyl, —$NH_2$, —$N(C_{1-10}$alkyl$)(C_{1-10}$alkyl$)$, —NH($C_{1-10}$alkyl), —NH(aryl), —$NR^{34}R^{35}$, —C(O)($C_{1-10}$alkyl), —C(O)($C_{1-10}$alkyl-aryl), —C(O)(aryl), —$CO_2$—$C_{1-10}$alkyl, —$CO_2$—$C_{1-10}$alkylaryl, —$CO_2$-aryl, —C(=O)N($C_{1-10}$alkyl)($C_{1-10}$alkyl), —C(=O)NH($C_{1-10}$alkyl), —C(=O)$NR^{34}R^{35}$, —C(=O)$NH_2$, —$OCF_3$, —O($C_{1-10}$alkyl), —O-aryl, —N(aryl)($C_{1-10}$alkyl), —$NO_2$, —CN, —S(O)$_{0-2}C_{1-10}$alkyl, —S(O)$_{0-2}C_{1-10}$alkylaryl, —S(O)$_{0-2}$ aryl, —$SO_2$N(aryl), —$SO_2$N($C_{1-10}$alkyl)($C_{1-10}$alkyl), —$SO_2$NH($C_{1-10}$alkyl) or —$SO_2NR^{34}R^{35}$. In some embodiments, when $R^{33}$ is $C_{1-10}$alkyl substituted with one or more heterocyclyl, each of said heterocyclyl group is unsubstituted or substituted with one or more halo, —OH, —$C_{1-10}$alkyl, —$CF_3$, —O-aryl, —$OCF_3$, —$OC_{1-10}$alkyl, —$NH_2$, —$N(C_{1-10}$alkyl$)(C_{1-10}$alkyl$)$, —NH($C_{1-10}$alkyl), —NH(aryl), —$NR^{34}R^{35}$, —C(O)($C_{1-10}$alkyl), —C(O) ($C_{1-10}$alkyl-aryl), —C(O)(aryl), —$CO_2$—$C_{1-10}$alkyl, —$CO_2$—$C_{1-10}$alkylaryl, —$CO_2$-aryl, —C(=O)N($C_{1-10}$alkyl)($C_{1-10}$alkyl), —C(=O)NH($C_{1-10}$alkyl), —C(=O)$NR^{34}R^{35}$, —C(=O)$NH_2$, —$OCF_3$, —O($C_{1-10}$alkyl), —O-aryl, —N(aryl)($C_{1-10}$alkyl), —$NO_2$, —CN, —S(O)$_{0-2}C_{1-10}$alkyl, —S(O)$_{0-2}C_{1-10}$alkylaryl, —S(O)$_{0-2}$ aryl, —$SO_2$N(aryl), —$SO_2$N($C_{1-10}$alkyl)($C_{1-10}$alkyl), —$SO_2$NH($C_{1-10}$alkyl) or —$SO_2NR^{34}R^{35}$. In some embodiments, when $R^{33}$ is $C_{1-10}$alkyl substituted with one or more heteroaryl, each of said heteroaryl group is unsubstituted or substituted with one or more halo, —OH, —$C_{1-10}$alkyl, —$CF_3$, —O-aryl, —$OCF_3$, —$OC_{1-10}$alkyl, —$NH_2$, —$N(C_{1-10}$alkyl$)(C_{1-10}$alkyl$)$, —NH($C_{1-10}$alkyl), —NH(aryl), —$NR^{34}R^{35}$, —C(O)($C_{1-10}$alkyl), —C(O) ($C_{1-10}$alkyl-aryl), —C(O)(aryl), —$CO_2$—$C_{1-10}$alkyl, —$CO_2$—$C_{1-10}$alkylaryl, —$CO_2$-aryl, —C(=O)N($C_{1-10}$alkyl)($C_{1-10}$alkyl), —C(=O)NH($C_{1-10}$alkyl), —C(=O)$NR^{34}R^{35}$, —C(=O)$NH_2$, —$OCF_3$, —O($C_{1-10}$alkyl), —O-aryl, —N(aryl)($C_{1-10}$alkyl), —$NO_2$, —CN, —S(O)$_{0-2}C_{1-10}$alkyl, —S(O)$_{0-2}C_{1-10}$alkylaryl, —S(O)$_{0-2}$ aryl, —$SO_2$N(aryl), —$SO_2$N($C_{1-10}$alkyl)($C_{1-10}$alkyl), —$SO_2$NH($C_{1-10}$alkyl) or —$SO_2NR^{34}R^{35}$. In some embodiments, when $R^{33}$ is substituted $C_{1-10}$alkyl, it is substituted by a combination of aryl, heteroalkyl, heterocyclyl, or heteroaryl groups.

In various embodiments of compounds of Formula I, $R^{34}$ and $R^{35}$ in —$NR^{34}R^{35}$, —C(=O)$NR^{34}R^{35}$, or —$SO_2NR^{34}R^{35}$, are taken together with the nitrogen atom to which they are attached to form a 3-10 membered saturated or unsaturated ring; wherein said ring is independently unsubstituted or is substituted by one or more —$NR^{31}R^{32}$, hydroxyl, halogen, oxo, aryl, heteroaryl, $C_{1-6}$alkyl, or O-aryl, and wherein said 3-10 membered saturated or unsaturated ring independently contains 0, 1, or 2 more heteroatoms in addition to the nitrogen.

In some embodiments, the $R^{34}$ and $R^{35}$ in —$NR^{34}R^{35}$, —C(=O)$NR^{34}R^{35}$, or —$SO_2NR^{34}R^{35}$, are taken together with the nitrogen atom to which they are attached to form:

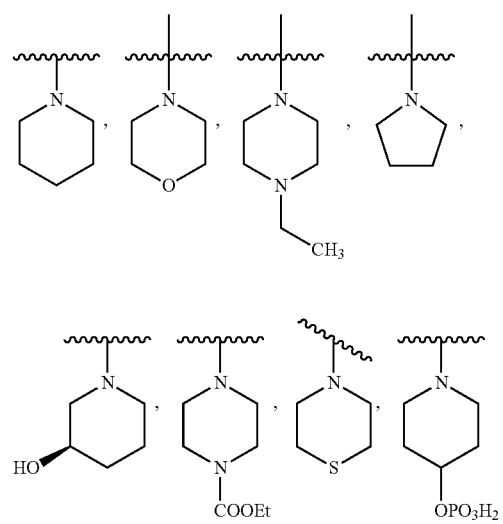

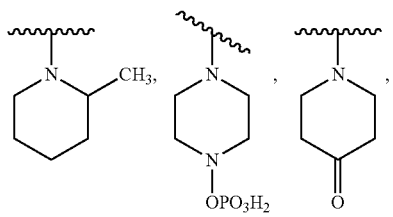

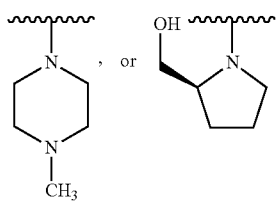

In another embodiment, $X_1$ is C—NH$_2$.

In various embodiments, $X_1$ is C—NH—R$^4$, where —NH—R$^4$ is:

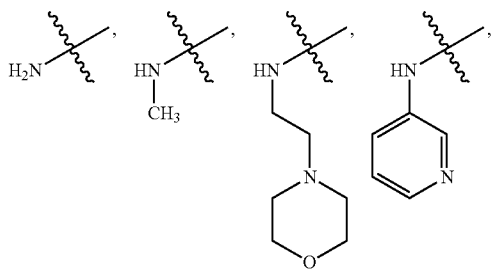

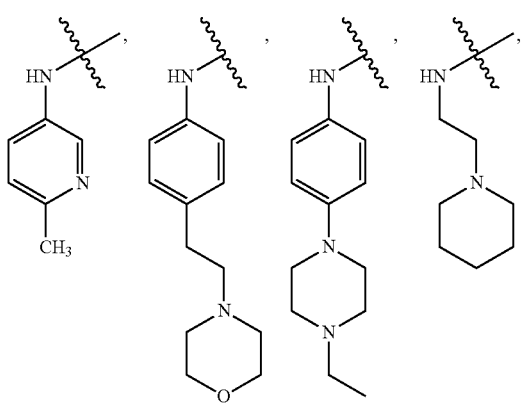

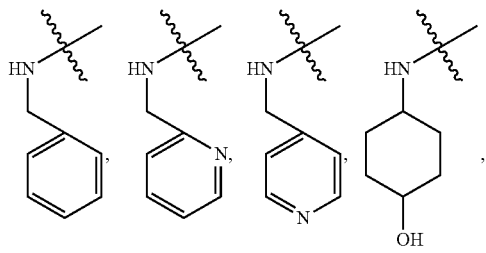

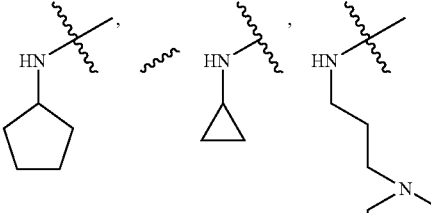

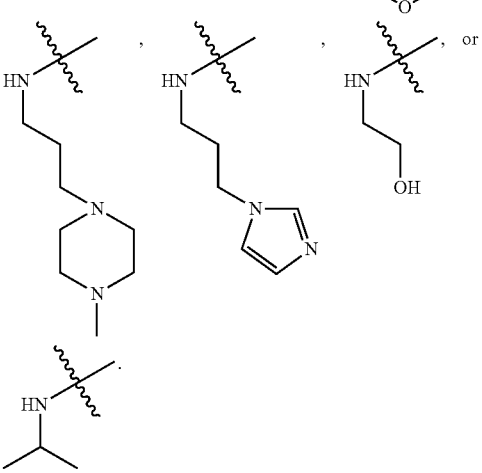

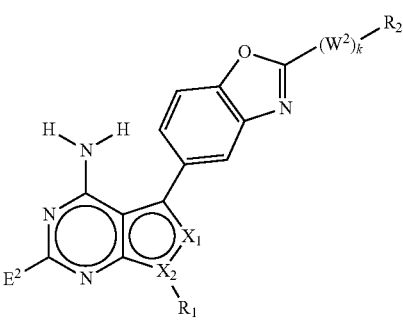

In one embodiment, the invention provides an inhibitor of Formula I-C1 where R$^5$ is H. In another embodiment, the invention provides an inhibitor of Formula I-C2 where R$^5$ is H.

In some embodiments, the invention provides an inhibitor of Formula I-C1a:

Formula I-C1a or a pharmaceutically acceptable salt thereof wherein:

$E^2$ is —H;

$X_1$ and $X_2$ are N;

$R_1$ is -L-C$_{1-10}$alkyl, -L-C$_{3-8}$cycloalkyl, -L-C$_{1-10}$alkylheterocyclyl, or -L-heterocyclyl, each of which is unsubstituted or is substituted by one or more independent R$^3$;

L is absent, —(C=O)—, —C(=O)O—, —C(=O)N(R$^{31}$)—, —S—, —S(O)—, —S(O)$_2$—, —S(O)$_2$N(R$^{31}$)—, or —N(R$^{31}$)—;

R$^3$ is hydrogen, —OH, —OR$^{31}$, —NR$^{31}$R$^{32}$, —C(O)R$^{31}$, —C(=O)NR$^{31}$R$^{32}$, —C(=O)NR$^{34}$R$^{35}$, aryl, heteroaryl, C$_{1-4}$alkyl, C$_{1-10}$alkyl, C$_{3-8}$cycloalkyl, or heterocyclyl, wherein each of said aryl or heteroaryl moiety is unsubstituted or is substituted with one or more independent alkyl, heteroalkyl, alkenyl, alkynyl, cycloalkyl, heterocycloalkyl, aryl, arylalkyl, heteroaryl, heteroarylalkyl, halo, —OH, —R$^{31}$, —CF$_3$, —OCF$_3$, —OR$^{31}$, —NR$^{31}$R$^{32}$, —NR$^{34}$R$^{35}$, —C(O)R$^{31}$, —CO$_2$R$^{31}$, —C(=O)NR$^{31}$R$^{32}$, —C(=O)NR$^{34}$R$^{35}$, —NO$_2$, —CN, —S(O)$_{0-2}$R$^{31}$R$^{32}$, —SO$_2$NR$^{34}$R$^{35}$, —NR$^{31}$C(=O)R$^{32}$, —NR$^{31}$C(=O)OR$^{32}$, —NR$^{31}$C(=O)NR$^{32}$R$^{33}$, —NR$^{31}$S(O)$_{0-2}$R$^{32}$, —C(=S)OR$^{31}$, —C(=O)SR$^{31}$, —NR$^{31}$C(=NR$^{32}$)NR$^{33}$R$^{32}$, —NR$^{31}$C(=NR$^{32}$)OR$^{33}$, —NR$^{31}$C(=NR$^{32}$)SR$^{33}$, —OC(=O)OR$^{33}$, —OC(=O)NR$^{31}$R$^{32}$, —OC(=O)SR$^{31}$, —SC(=O)OR$^{31}$, —P(O)OR$^{31}$OR$^{32}$, or —SC(=O)NR$^{31}$R$^{32}$, and wherein each of said alkyl, cycloalkyl, or heterocyclyl moiety is unsubstituted or is substituted with one or more alkyl, heteroalkyl, alkenyl, alkynyl, cycloalkyl, heterocycloalkyl, aryl, arylalkyl, heteroaryl, heteroarylalkyl, halo, —OH, —R$^{31}$, —CF$_3$, —OCF$_3$, —OR$^{31}$, —O-aryl, —NR$^{31}$R$^{32}$, —NR$^{34}$R$^{35}$, —C(O)R$^{31}$, —CO$_2$R$^{31}$, —C(=O)NR$^{34}$R$^{35}$, or —C(=O)NR$^{31}$R$^{32}$;

—(W$^2$)$_k$— is —NH—, —N(H)C(O)— or —N(H)S(O)$_2$—;

R$^2$ is hydrogen, halogen, —OR$^{31}$, —NR$^{31}$R$^{32}$, —NR$^{34}$R$^{35}$, —C(O)R$^{31}$, —CO$_2$R$^{31}$, —C(=O)NR$^{31}$R$^{32}$, —C(=O)NR$^{34}$R$^{35}$, —S(O)$_{0-2}$R$^{31}$, —SO$_2$NR$^{31}$R$^{32}$, —SO$_2$NR$^{34}$R$^{35}$, bicyclic aryl, substituted monocyclic aryl, heteroaryl, C$_{1-10}$alkyl, C$_{3-8}$cycloalkyl, C$_{1-10}$alkyl-C$_{3-8}$cycloalkyl, C$_{3-8}$cycloalkyl-C$_{1-10}$alkyl, C$_{3-8}$cycloalkyl-C$_{2-10}$alkenyl, C$_{3-8}$cycloalkyl-C$_{2-10}$alkynyl, C$_{2-10}$alkyl-monocyclic aryl, monocyclic aryl-C$_{2-10}$alkyl, C$_{1-10}$alkylbicycloaryl, bicycloaryl-C$_{1-10}$alkyl, substituted C$_{1-10}$alkylaryl, substituted aryl-C$_{1-10}$alkyl, C$_{1-10}$alkylheteroaryl, C$_{1-10}$alkylheterocyclyl, C$_{2-10}$alkenyl, C$_{2-10}$alkynyl, C$_{2-10}$alkenylaryl, C$_{2-10}$alkenylheteroaryl, C$_{2-10}$alkenylheteroalkyl, C$_{2-10}$alkenylheterocycicyl, C$_{2-10}$alkynylaryl, C$_{2-10}$alkynylheteroaryl, C$_{2-10}$alkynylheteroalkyl, C$_{2-10}$alkynylheterocyclyl, C$_{2-10}$alkenyl-C$_{3-8}$cycloalkyl, C$_{2-10}$alkynyl-C$_{3-8}$cycloalkenyl, C$_{1-10}$alkoxy C$_{1-10}$alkyl, C$_{1-10}$alkoxyC$_{2-10}$alkenyl, C$_{1-10}$alkoxyC$_{2-10}$alkynyl, heterocyclyl, heterocyclyl C$_{1-10}$alkyl, heterocyclylC$_{2-10}$alkenyl, heterocyclyl-C$_{2-10}$alkynyl, aryl-C$_{2-10}$alkenyl, aryl-C$_{2-10}$alkynyl, aryl-heterocyclyl, heteroaryl-C$_{1-10}$alkyl, heteroaryl-C$_{2-10}$alkenyl, heteroaryl-C$_{2-10}$alkynyl, heteroaryl-C$_{3-8}$cycloalkyl, heteroaryl-heteroalkyl, or heteroaryl-heterocyclyl, wherein each of said bicyclic aryl or heteroaryl moiety is unsubstituted, or wherein each of bicyclic aryl, heteroaryl moiety or monocyclic aryl moiety is substituted with one or more independent halo, —OH, —R$^{31}$, —CF$_3$, —OCF$_3$, —OR$^{31}$, —NR$^{31}$R$^{32}$, —NR$^{34}$R$^{35}$, —C(O)R$^{31}$, —CO$_2$R$^{31}$, —C(=O)NR$^{31}$R$^{32}$, —C(=O)NR$^{34}$R$^{35}$, —NO$_2$, —CN, —S(O)$_{0-2}$R$^{31}$, —SO$_2$NR$^{31}$R$^{32}$, —SO$_2$NR$^{34}$R$^{35}$, —NR$^{31}$C(=O)R$^{32}$, —NR$^{31}$C(=O)OR$^{32}$, —NR$^{31}$C(=O)NR$^{32}$R$^{33}$, —NR$^{31}$S(O)$_{0-2}$R$^{32}$, —C(=S)OR$^{31}$, —C(=O)SR$^{31}$, —NR$^{31}$C(=NR$^{32}$)NR$^{33}$R$^{32}$, —NR$^{31}$C(=NR$^{32}$)OR$^{33}$, —NR$^{31}$C(=NR$^{32}$)SR$^{33}$, —OC(=O)OR$^{33}$, —OC(=O)NR$^{31}$R$^{32}$, —OC(=O)SR$^{31}$, —SC(=O)OR$^{31}$, —P(O)OR$^{31}$OR$^{32}$, or —SC(=O)NR$^{31}$R$^{32}$, and wherein each of said alkyl, cycloalkyl, heterocyclyl, or heteroalkyl moiety is unsubstituted or is substituted with one or more halo, —OH, —R$^{31}$, —CF$_3$, —OCF$_3$, —OR$^{31}$, —O-aryl, —NR$^{31}$R$^{32}$, —NR$^{34}$R$^{35}$, —C(O)R$^{31}$, —CO$_2$R$^{31}$, —C(=O)NR$^{34}$R$^{35}$, or —C(=O)NR$^{31}$R$^{32}$;

R$^{31}$, R$^{32}$, and R$^{33}$, in each instance, are independently H or C$_{1-10}$alkyl, wherein the C$_{1-10}$alkyl is unsubstituted; and R$^{34}$ and R$^{35}$ in —NR$^{34}$R$^{35}$, —C(=O)NR$^{34}$R$^{35}$, or —SO$_2$NR$^{34}$R$^{35}$, are taken together with the nitrogen atom to which they are attached to form a 3-10 membered saturated or unsaturated ring; wherein said ring is independently unsubstituted or is substituted by one or more —NR$^{31}$R$^{32}$, hydroxyl, halogen, oxo, aryl, heteroaryl, C$_{1-6}$alkyl, or O-aryl, and wherein said 3-10 membered saturated or unsaturated ring independently contains 0, 1, or 2 more heteroatoms in addition to the nitrogen.

In another aspect, an inhibitor of Formula I-C1 is a compound of Formula I-C1a:

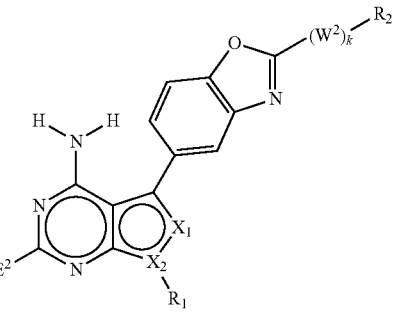

Formula I-C1b or a pharmaceutically acceptable salt thereof, wherein: E$^2$ is —H; X$_1$ is CH and X$_2$ is N;

R$_1$ is -L-C$_{1-10}$alkyl, -L-C$_{3-8}$cycloalkyl, -L-C$_{1-10}$alkylheterocyclyl, or -L-heterocyclyl, each of which is unsubstituted or is substituted by one or more independent R$^3$;

L is absent, —(C=O)—, —C(=O)O—, —C(=O)N(R$^{31}$)—, —S—, —S(O)—, —S(O)$_2$—, —S(O)$_2$N(R$^{31}$)—, or —N(R$^{31}$)—;

R$^3$ is hydrogen, —OH, —OR$^{31}$, —NR$^{31}$R$^{32}$, —C(O)R$^{31}$, —C(=O)NR$^{31}$R$^{32}$, —C(=O)NR$^{34}$R$^{35}$, aryl, heteroaryl, C$_{1-4}$alkyl, C$_{1-10}$alkyl, C$_{3-8}$cycloalkyl, or heterocyclyl, wherein each of said aryl or heteroaryl moiety is unsubstituted or is substituted with one or more independent alkyl, heteroalkyl, alkenyl, alkynyl, cycloalkyl, heterocycloalkyl, aryl, arylalkyl, heteroaryl, heteroarylalkyl, halo, —OH, —R$^{31}$, —CF$_3$, —OCF$_3$, —OR$^{31}$, —NR$^{31}$R$^{32}$, —NR$^{34}$R$^{35}$, —C(O)R$^{31}$, —CO$_2$R$^{31}$, —C(=O)NR$^{31}$R$^{32}$, —C(=O)NR$^{34}$R$^{35}$, —NO$_2$, —CN, —S(O)$_{0-2}$R$^{31}$, —SO$_2$NR$^{31}$R$^{32}$, —SO$_2$NR$^{34}$R$^{35}$, —NR$^{31}$C(=O)R$^{32}$, —NR$^{31}$C(=O)OR$^{32}$, —NR$^{31}$C(=O)NR$^{32}$R$^{33}$, —NR$^{31}$S(O)$_{0-2}$R$^{32}$, —C(=S)OR$^{31}$, —C(=O)SR$^{31}$, —NR$^{31}$C(=NR$^{32}$)NR$^{33}$R$^{32}$, —NR$^{31}$C(=NR$^{32}$)OR$^{33}$, —NR$^{31}$C(=NR$^{32}$)SR$^{33}$, —OC(=O)OR$^{33}$, —OC(=O)NR$^{31}$R$^{32}$, —OC(=O)SR$^{31}$, —SC(=O)OR$^{31}$, —P(O)OR$^{31}$OR$^{32}$, or —SC(=O)NR$^{31}$R$^{32}$, and wherein each of said alkyl, cycloalkyl, or heterocyclyl moiety is unsubstituted or is substituted with one or more alkyl, heteroalkyl, alkenyl, alkynyl, cycloalkyl, heterocycloalkyl, aryl, arylalkyl, heteroaryl, heteroarylalkyl, halo, —OH, —R$^{31}$, —CF$_3$, —OCF$_3$, —OR$^{31}$, —O-aryl, —NR$^{31}$R$^{32}$, —NR$^{34}$R$^{35}$, —C(O)R$^{31}$, —CO$_2$R$^{31}$, —C(=O)NR$^{34}$R$^{35}$, or —C(=O)NR$^{31}$R$^{32}$;

—(W$^2$)$_k$— is —NH—, —N(H)C(O)— or —N(H)S(O)$_2$—;

R$^2$ is hydrogen, halogen, —OR$^{31}$, —NR$^{31}$R$^{32}$, —NR$^{34}$R$^{35}$, —C(O)R$^{31}$, —CO$_2$R$^{31}$, —C(=O)NR$^{31}$R$^{32}$, —C(=O)NR$^{34}$R$^{35}$, —S(O)$_{0-2}$R$^{31}$, —SO$_2$NR$^{31}$R$^{32}$, —SO$_2$NR$^{34}$R$^{35}$, bicyclic aryl, substituted monocyclic aryl, heteroaryl, C$_{1-10}$alkyl, C$_{3-8}$cycloalkyl, C$_{1-10}$alkyl-C$_{3-8}$cycloalkyl, C$_{3-8}$cycloalkyl-C$_{1-10}$alkyl, C$_{2-10}$alkyl-monocyclic aryl, monocyclic aryl-C$_{2-10}$alkyl, C$_{1-10}$alkylbicycloaryl, bicycloaryl-C$_{1-10}$alkyl, substituted C$_{1-10}$alkylaryl, substituted aryl-C$_{1-10}$alkyl, C$_{1-10}$alkylheteroaryl, C$_{1-10}$alkylheterocyclyl, C$_{2-10}$-alkenyl, C$_{2-10}$alkynyl, heterocyclyl, heterocyclyl C$_{1-10}$alkyl, heterocyclyl-C$_{2-10}$alkenyl, heterocyclyl- $C_{2-10}$alkynyl, aryl-heterocyclyl, heteroaryl-$C_{1-10}$alkyl, heteroaryl-heteroalkyl, or heteroaryl-heterocyclyl, wherein each of said bicyclic aryl or heteroaryl moiety is unsubstituted, or wherein each of bicyclic aryl, heteroaryl moiety or monocyclic aryl moiety is substituted with one or more independent halo, —OH, —$R^{31}$, —$CF_3$, —$OCF_3$, —$OR^{31}$, —$NR^{31}R^{32}$, —$NR^{34}R^{35}$, —C(O)$R^{31}$, —$CO_2R^{31}$, —C(=O)$NR^{31}R^{32}$, —C(=O)$NR^{34}R^{35}$, —$NO_2$, —CN, —$S(O)_{0-2}R^{31}$, —$SO_2NR^{31}R^{32}$, —$SO_2NR^{34}R^{35}$, —$NR^{31}C(=O)R^{32}$, —$NR^{31}C(=O)OR^{32}$, —$NR^{31}C(=O)NR^{32}R^{33}$, —$NR^{31}S(O)_{0-2}R^{32}$, —C(=S)$OR^{31}$, —C(=O)$SR^{31}$, —$NR^{31}C(=NR^{32})NR^{33}R^{32}$, —$NR^{31}C(=NR^{32})OR^{33}$, —$NR^{31}C(=NR^{32})SR^{33}$, —OC(=O)$OR^{33}$, —OC(=O)$NR^{31}R^{32}$, —OC(=O)$SR^{31}$, —SC(=O)$OR^{31}$, —P(O)$OR^{31}OR^{32}$, or —SC(=O)$NR^{31}R^{32}$, and wherein each of said alkyl, cycloalkyl, heterocyclyl, or heteroalkyl moiety is unsubstituted or is substituted with one or more halo, —OH, —$R^{31}$, —$CF_3$, —$OCF_3$, —$OR^{31}$, —O-aryl, —$NR^{31}R^{32}$, —$NR^{34}R^{35}$, —C(O)$R^{31}$, —$CO_2R^{31}$, —C(=O)$NR^{34}R^{35}$, or —C(=O)$NR^{31}R^{32}$;

$R^{31}$, $R^{32}$, and $R^{33}$, in each instance, are independently H or $C_{1-10}$alkyl, wherein the $C_{1-10}$alkyl is unsubstituted; and $R^{34}$ and $R^{35}$ in —$NR^{34}R^{35}$, —C(=O)$NR^{34}R^{35}$, or —$SO_2NR^{34}R^{35}$, are taken together with the nitrogen atom to which they are attached to form a 3-10 membered saturated or unsaturated ring; wherein said ring is independently unsubstituted or is substituted by one or more —$NR^{31}R^{32}$, hydroxyl, halogen, oxo, aryl, heteroaryl, $C_{1-6}$alkyl, or O-aryl, and wherein said 3-10 membered saturated or unsaturated ring independently contains 0, 1, or 2 more heteroatoms in addition to the nitrogen.

The invention further provides a compound which is an mTor inhibitor, wherein the compound has the Formula I-A:

Formula I-A

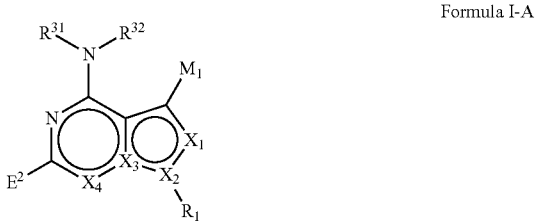

or a pharmaceutically acceptable salt thereof, wherein:

$X_1$ is N or C-$E^1$, $X_2$ is N, $X_3$ is C, and $X_4$ is C—$R^9$ or N; or $X_1$ is N or C-$E^1$, $X_2$ is C, $X_3$ is N, and $X_4$ is C—$R^9$ or N;

$R_1$ is —H, -L-$C_{1-10}$alkyl, -L-$C_{3-8}$cycloalkyl, -L-$C_{1-10}$alkyl-$C_{3-8}$cycloalkyl, -L-aryl, -L-heteroaryl, -L-$C_{1-10}$alkylaryl, -L-$C_{1-10}$alkylheteroaryl, -L-$C_{1-10}$alkylheterocyclyl, -L-$C_{2-10}$alkenyl, -L-$C_{2-10}$alkynyl, -L-$C_{2-10}$alkenyl-$C_{3-8}$cycloalkyl, -L-$C_{2-10}$alkynyl-$C_{3-8}$cycloalkyl, -L-heteroalkyl, -L-heteroalkylaryl, -L-heteroalkylheteroaryl, -L-heteroalkyl-heterocyclyl, -L-heteroalkyl-$C_{3-8}$cycloalkyl, -L-aralkyl, -L-heteroaralkyl, or -L-heterocyclyl, each of which is unsubstituted or is substituted by one or more independent $R^3$;

L is absent, —(C=O)—, —C(=O)O—, —C(=O)N($R^{31}$)—, —S—, —S(O)—, —$S(O)_2$—, —$S(O)_2N(R^{31})$—, or —N($R^{31}$)—;

$M_1$ is benzothiazolyl substituted with —$(W^2)_k$—$R^2$;

k is 0 or 1;

$E^1$ and $E^2$ are independently —$(W^1)_j$—$R^4$;

j, in each instance (i.e., in $E^1$ or j in $E^2$), is independently 0 or 1

$W^1$ is —O—, —$NR^7$—, —$S(O)_{0-2}$—, —C(O)—, —C(O)N($R^7$)—, —N($R^7$)C(O)—, —N($R^7$)S(O)—, —N($R^7$)S(O)$_2$—, —C(O)O—, —CH($R^7$)N(C(O)$OR^8$)—, —CH($R^7$)N(C(O)$R^8$)—, —CH($R^7$)N($SO_2R^8$)—, —CH($R^7$)N($R^8$)—, —CH($R^7$)C(O)N($R^8$)—, —CH($R^7$)N($R^8$)C(O)—, —CH($R^7$)N($R^8$)S(O)—, or —CH($R^7$)N($R^8$)$S(O)_2$—;

$W^2$ is —O—, —$NR^7$—, —$S(O)_{0-2}$—, —C(O)—, —C(O)N($R^7$)—, —N($R^7$)C(O)—, —N($R^7$)C(O)N($R^8$)—, —N($R^7$)S(O)—, —N($R^7$)S(O)$_2$—, —C(O)O—, —CH($R^7$)N(C(O)$OR^8$)—, —CH($R^7$)N(C(O)$R^8$)—, —CH($R^7$)N($SO_2R^8$)—, —CH($R^7$)N($R^8$)—, —CH($R^7$)C(O)N($R^8$)—, —CH($R^7$)N($R^8$)C(O)—, —CH($R^7$)N($R^8$)S(O)—, or —CH($R^7$)N($R^8$)$S(O)_2$—;

$R^2$ is hydrogen, halogen, —OH, —$R^{31}$, —$CF_3$, —$OCF_3$, —$OR^{31}$, —$NR^{31}R^{32}$, —$NR^{34}R^{35}$, —C(O)$R^{31}$, —$CO_2R^{31}$, —C(=O)$NR^{31}R^{32}$, —C(=O)$NR^{34}R^{35}$, —$NO_2$, —CN, —$S(O)_{0-2}R^{31}$, —$SO_2NR^{31}R^{32}$, —$SO_2NR^{34}R^{35}$, —$NR^{31}C(=O)R^{32}$, —$NR^{31}C(=O)OR^{32}$, —$NR^{31}C(=O)NR^{32}R^{33}$, —$NR^{31}S(O)_{0-2}R^{32}$, —C(=S)$OR^{31}$, —C(=O)$SR^{31}$, —$NR^{31}C(=NR^{32})NR^{33}R^{32}$, —$NR^{31}C(=NR^{32})OR^{33}$, —$NR^{31}C(=NR^{32})SR^{33}$, —OC(=O)$OR^{33}$, —OC(=O)$NR^{31}R^{32}$, —OC(=O)$SR^{31}$, —SC(=O)$OR^{31}$, —P(O)$OR^{31}OR^{32}$, —SC(=O)$NR^{31}R^{32}$, aryl (e.g. bicyclic aryl, unsubstituted aryl, or substituted monocyclic aryl), heteroaryl, $C_{1-10}$alkyl, $C_{3-8}$cycloalkyl, $C_{1-10}$alkyl-$C_{3-8}$cycloalkyl, $C_{3-8}$cycloalkyl-$C_{1-10}$alkyl, $C_{3-8}$cycloalkyl-$C_{2-10}$alkenyl, $C_{3-8}$cycloalkyl-$C_{2-10}$-alkynyl, $C_{1-10}$alkyl-$C_{2-10}$alkenyl, $C_{1-10}$alkyl-$C_{2-10}$alkynyl, $C_{1-10}$alkylaryl (e.g. $C_{2-10}$alkyl-monocyclic aryl, $C_{1-10}$alkyl-substituted monocyclic aryl, or $C_{1-10}$alkylbicycloaryl), $C_{1-10}$alkylheteroaryl, $C_{1-10}$alkylheterocyclyl, $C_{2-10}$alkenyl, $C_{2-10}$alkynyl, $C_{2-10}$alkenyl-$C_{1-10}$alkyl, $C_{2-10}$alkynyl-$C_{1-10}$alkyl, $C_{2-10}$-alkenylaryl, $C_{2-10}$alkenylheteroaryl, $C_{2-10}$alkenylheteroalkyl, $C_{2-10}$alkenylheterocycicyl, $C_{2-10}$alkenyl-$C_{3-8}$cycloalkyl, $C_{2-10}$alkynylaryl, $C_{2-10}$alkynylheteroaryl, $C_{2-10}$alkynylheteroalkyl, $C_{2-10}$alkynylheterocyclyl, $C_{2-10}$alkynyl-$C_{3-8}$cycloalkenyl, $C_{1-10}$alkoxy $C_{1-10}$alkyl, $C_{1-10}$alkoxy-$C_{2-10}$alkenyl, $C_{1-10}$alkoxy-$C_{2-10}$alkynyl, heterocyclyl, heteroalkyl, heterocyclyl-$C_{1-10}$alkyl, heterocyclyl-$C_{2-10}$alkenyl, heterocyclyl-$C_{2-10}$alkynyl, aryl-$C_{1-10}$alkyl (e.g. monocyclic aryl-$C_{2-10}$alkyl, substituted monocyclic aryl-$C_{1-10}$alkyl, or bicycloaryl-$C_{1-10}$alkyl), aryl-$C_{2-10}$alkenyl, aryl-$C_{2-10}$alkynyl, aryl-heterocyclyl, heteroaryl-$C_{1-10}$alkyl, heteroaryl-$C_{2-10}$alkenyl, heteroaryl-$C_{2-10}$alkynyl, heteroaryl-$C_{3-8}$cycloalkyl, heteroaryl-heteroalkyl, or heteroaryl-heterocyclyl, wherein each of said bicyclic aryl or heteroaryl moiety is unsubstituted, or wherein each of bicyclic aryl, heteroaryl moiety or monocyclic aryl moiety is substituted with one or more independent alkyl, heteroalkyl, alkenyl, alkynyl, cycloalkyl, heterocycloalkyl, aryl, arylalkyl, heteroaryl, heteroarylalkyl, halo, —OH, —$R^{31}$, —$CF_3$, —$OCF_3$, —$OR^{31}$, —$NR^{31}R^{32}$, —$NR^{34}R^{35}$, —C(O)$R^{31}$, —$CO_2R^{31}$, —C(=O)$NR^{31}R^{32}$, —C(=O)$NR^{34}R^{35}$, —$NO_2$, —CN, —$S(O)_{0-2}R^{31}$, —$SO_2NR^{31}R^{32}$, —$SO_2NR^{34}R^{35}$, —$NR^{31}C(=O)R^{32}$, —$NR^{31}C(=O)OR^{32}$, —$NR^{31}C(=O)NR^{32}R^{33}$, —$NR^{31}S(O)_{0-2}R^{32}$, —C(=S)$OR^{31}$, —C(=O)$SR^{31}$, —$NR^{31}C(=NR^{32})NR^{33}R^{32}$, —$NR^{31}C(=NR^{32})OR^{33}$, —$NR^{31}C(=NR^{32})SR^{33}$, —OC(=O)$OR^{33}$, —OC(=O)$NR^{31}R^{32}$, —OC(=O)$SR^{31}$, —SC(=O)$OR^{31}$, —P(O)$OR^{31}OR^{32}$, or —SC(=O)$NR^{31}R^{32}$, and wherein each of said alkyl, cycloalkyl, heterocyclyl, or heteroalkyl moiety is unsubstituted or is substituted with one or more alkyl, heteroalkyl, alkenyl, alkynyl, cycloalkyl, heterocycloalkyl, aryl, arylalkyl, heteroaryl, heteroarylalkyl, halo, —OH, —$R^{31}$, —$CF_3$, —$OCF_3$, —$OR^{31}$, —O-aryl, —$NR^{31}R^{32}$, —$NR^{34}R^{35}$, —C(O)$R^{31}$, —$CO_2R^{31}$, —C(=O)$NR^{34}R^{35}$, or —C(=O)$NR^{31}R^{32}$;

$R^3$ and $R^4$ are independently hydrogen, halogen, —OH, —$R^{31}$, —$CF_3$, —$OCF_3$, —$OR^{31}$, —$NR^{31}R^{32}$, —$NR^{34}R^{35}$, —$C(O)R^{31}$, —$CO_2R^{31}$, —$C(=O)NR^{31}R^{32}$, —$C(=O)NR^{34}R^{35}$, —$NO_2$, —CN, —$S(O)_{0-2}R^{31}$, —$SO_2NR^{31}R^{32}$, —$SO_2NR^{34}R^{35}$, —$NR^{31}C(=O)R^{32}$, —$NR^{31}C(=O)OR^{32}$, —$NR^{31}C(=O)NR^{32}R^{33}$, —$NR^{31}S(O)_{0-2}R^{32}$, —$C(=S)OR^{31}$, —$C(=O)SR^{31}$, —$NR^{31}C(=NR^{32})NR^{33}R^{32}$, —$NR^{31}C(=NR^{32})OR^{33}$, —$NR^{31}C(=NR^{32})SR^{33}$, —$OC(=O)OR^{33}$, —$OC(=O)NR^{31}R^{32}$, —$OC(=O)SR^{31}$, —$SC(=O)OR^{31}$, —$P(O)OR^{31}OR^{32}$, —$SC(=O)NR^{31}R^{32}$, aryl, heteroaryl, $C_{1-4}$alkyl, $C_{1-10}$alkyl, $C_{3-8}$cycloalkyl, $C_{1-10}$alkyl-$C_{3-8}$cycloalkyl, $C_{3-8}$cycloalkyl-$C_{1-10}$alkyl, $C_{3-8}$cycloalkyl-$C_{2-10}$alkenyl, $C_{3-8}$cycloalkyl-$C_{2-10}$alkynyl, $C_{1-10}$alkyl-$C_{2-10}$alkenyl, $C_{1-10}$alkyl-$C_{2-10}$alkynyl, $C_{1-10}$alkylaryl, $C_{1-10}$alkylheteroaryl, $C_{1-10}$alkylheterocyclyl, $C_{2-10}$alkenyl, $C_{2-10}$alkynyl, $C_{2-10}$alkenyl-$C_{1-10}$alkyl, $C_{2-10}$alkynyl-$C_{1-10}$alkyl, $C_{2-10}$alkenylaryl, $C_{2-10}$alkenylheteroaryl, $C_{2-10}$-alkenylheteroalkyl, $C_{2-10}$alkenylheterocyclyl, $C_{2-10}$alkenyl-$C_{3-8}$cycloalkyl, $C_{2-10}$alkynyl-$C_{3-8}$cycloalkyl, $C_{2-10}$alkynylaryl, $C_{2-10}$alkynylheteroaryl, $C_{2-10}$alkynylheteroalkyl, $C_{2-10}$alkynylheterocyclyl, $C_{2-10}$alkynyl-$C_{3-8}$cycloalkenyl, $C_{1-10}$alkoxy $C_{1-10}$alkyl, $C_{1-10}$alkoxy-$C_{2-10}$alkenyl, $C_{1-10}$alkoxy-$C_{2-10}$alkynyl, heterocyclyl, heterocyclyl-$C_{1-10}$alkyl, heterocyclyl-$C_{2-10}$alkenyl, heterocyclyl-$C_{2-10}$alkynyl, aryl-$C_{1-10}$alkyl, aryl-$C_{2-10}$alkenyl, aryl-$C_{2-10}$alkynyl, aryl-heterocyclyl, heteroaryl-$C_{1-10}$alkyl, heteroaryl-$C_{2-10}$alkenyl, heteroaryl-$C_{2-10}$alkynyl, heteroaryl-$C_{3-8}$cycloalkyl, heteroalkyl, heteroaryl-heteroalkyl, or heteroaryl-heterocyclyl, wherein each of said aryl or heteroaryl moiety is unsubstituted or is substituted with one or more independent halo, —OH, —$R^{31}$, —$CF_3$, —$OCF_3$, —$OR^{31}$, —$NR^{31}R^{32}$, —$NR^{34}R^{35}$, —$C(O)R^{31}$, —$CO_2R^{31}$, —$C(=O)NR^{31}R^{32}$, —$C(=O)NR^{34}R^{35}$, —$NO_2$, —CN, —$S(O)_{0-2}R^{31}$, —$SO_2NR^{31}R^{32}$, —$SO_2NR^{34}R^{35}$, —$NR^{31}C(=O)R^{32}$, —$NR^{31}C(=O)OR^{32}$, —$NR^{31}C(=O)NR^{32}R^{33}$, —$NR^{31}S(O)_{0-2}R^{32}$, —$C(=S)OR^{31}$, —$C(=O)SR^{31}$, —$NR^{31}C(=NR^{32})NR^{33}R^{32}$, —$NR^{31}C(=NR^{32})OR^{33}$, —$NR^{31}C(=NR^{32})SR^{33}$, —$OC(=O)OR^{33}$, —$OC(=O)NR^{31}R^{32}$, —$OC(=O)SR^{31}$, —$SC(=O)OR^{31}$, —$P(O)OR^{31}OR^{32}$, or —$SC(=O)NR^{31}R^{32}$, and wherein each of said alkyl, cycloalkyl, heterocyclyl, or heteroalkyl moiety is unsubstituted or is substituted with one or more halo, —OH, —$R^{31}$, —$CF_3$, —$OCF_3$, —$OR^{31}$, —O-aryl, —$NR^{31}R^{32}$, —$NR^{34}R^{35}$, —$C(O)R^{31}$, —$CO_2R^{31}$, —$C(=O)NR^{34}R^{35}$, or —$C(=O)NR^{31}R^{32}$;

$R^5$ is hydrogen, halogen, —OH, —$R^{31}$, —$CF_3$, —$OCF_3$, —$OR^{31}$, —$NR^{31}R^{32}$, —$NR^{34}R^{35}$, —$C(O)R^{31}$, —$CO_2R^{31}$, —$C(=O)NR^{31}R^{32}$, —$C(=O)NR^{34}R^{35}$, —$NO_2$, —CN, —$S(O)_{0-2}R^{31}$, —$SO_2NR^{31}R^{32}$, —$SO_2NR^{34}R^{35}$, —$NR^{31}C(=O)R^{32}$, —$NR^{31}C(=O)OR^{32}$, —$NR^{31}C(=O)NR^{32}R^{33}$, —$NR^{31}S(O)_{0-2}R^{32}$, —$C(=S)OR^{31}$, —$C(=O)SR^{31}$, —$NR^{31}C(=NR^{32})NR^{33}R^{32}$, —$NR^{31}C(=NR^{32})OR^{33}$, —$NR^{31}C(=NR^{32})SR^{33}$, —$OC(=O)OR^{33}$, —$OC(=O)NR^{31}R^{32}$, —$OC(=O)SR^{31}$, —$SC(=O)OR^{31}$, —$P(O)OR^{31}OR^{32}$, or —$SC(=O)NR^{31}R^{32}$;

$R^{31}$, $R^{32}$, and $R^{33}$, in each instance, are independently H or $C_{1-10}$alkyl, wherein the $C_{1-10}$alkyl is unsubstituted or is substituted with one or more aryl, heteroalkyl, heterocyclyl, or heteroaryl group, wherein each of said aryl, heteroalkyl, heterocyclyl, or heteroaryl group is unsubstituted or is substituted with one or more halo, —OH, —$C_{1-10}$alkyl, —$CF_3$, —O-aryl, —$OCF_3$, —$OC_{1-10}$alkyl, —$NH_2$, —$N(C_{1-10}$alkyl)($C_{1-10}$alkyl), —$NH(C_{1-10}$alkyl), —NH(aryl), —$NR^{34}R^{35}$, —$C(O)(C_{1-10}$alkyl), —$C(O)(C_{1-10}$alkyl-aryl), —C(O)(aryl), —$CO_2$—$C_{1-10}$alkyl, —$CO_2$—$C_{1-10}$alkylaryl, —$CO_2$-aryl, —$C(=O)N(C_{1-10}$alkyl)($C_{1-10}$alkyl), —$C(=O)NH(C_{1-10}$alkyl), —$C(=O)NR^{34}R^{35}$, —$C(=O)NH_2$, —$OCF_3$, —$O(C_{1-10}$alkyl), —O-aryl, —$N(aryl)(C_{1-10}$alkyl), —$NO_2$, —CN, —$S(O)_{0-2}C_{1-10}$alkyl, —$S(O)_{0-2}C_{1-10}$alkylaryl, —$S(O)_{0-2}$ aryl, —$SO_2N(aryl)$, —$SO_2N(C_{1-10}$alkyl)($C_{1-10}$alkyl), —$SO_2NH(C_{1-10}$alkyl) or —$SO_2NR^{34}R^{35}$;

$R^{34}$ and $R^{35}$ in —$NR^{34}R^{35}$, —$C(=O)NR^{34}R^{35}$, or —$SO_2NR^{34}R^{35}$, are taken together with the nitrogen atom to which they are attached to form a 3-10 membered saturated or unsaturated ring; wherein said ring is independently unsubstituted or is substituted by one or more —$NR^{31}R^{32}$, hydroxyl, halogen, oxo, aryl, heteroaryl, $C_{1-6}$alkyl, or O-aryl, and wherein said 3-10 membered saturated or unsaturated ring independently contains 0, 1, or 2 more heteroatoms in addition to the nitrogen atom;

$R^7$ and $R^8$ are each independently hydrogen, $C_{1-10}$alkyl, $C_{2-10}$alkenyl, aryl, heteroaryl, heterocyclyl or $C_{3-10}$cycloalkyl, each of which except for hydrogen is unsubstituted or is substituted by one or more independent $R^6$;

$R^6$ is halo, —$OR^{31}$, —SH, —$NH_2$, —$NR^{34}R^{35}$, —$NR^{31}R^{32}$, —$CO_2R^{31}$, —$CO_2$aryl, —$C(=O)NR^{31}R^{32}$, $C(=O)NR^{34}R^{35}$, —$NO_2$, —CN, —$S(O)_{0-2}C_{1-10}$alkyl, —$S(O)_{0-2}$aryl, —$SO_2NR^{34}R^{35}$, —$SO_2NR^{31}R^{32}$, $C_{1-10}$alkyl, $C_{2-10}$alkenyl, $C_{2-10}$alkynyl; aryl-$C_{1-10}$alkyl, aryl-$C_{2-10}$alkenyl, aryl-$C_{2-10}$alkynyl, heteroaryl-$C_{1-10}$alkyl, heteroaryl-$C_{2-10}$alkenyl, heteroaryl-$C_{2-10}$alkynyl, wherein each of said alkyl, alkenyl, alkynyl, aryl, heteroalkyl, heterocyclyl, or heteroaryl group is unsubstituted or is substituted with one or more independent halo, cyano, nitro, —$OC_{1-10}$alkyl, $C_{1-10}$alkyl, $C_{2-10}$alkenyl, $C_{2-10}$alkynyl, halo$C_{1-10}$alkyl, halo$C_{2-10}$alkenyl, halo$C_{2-10}$alkynyl, —COOH, —$C(=O)NR^{31}R^{32}$, —$C(=O)NR^{34}R^{35}$, —$SO_2NR^{34}R^{35}$, —$SO_2NR^{31}R^{32}$, —$NR^{31}R^{32}$, or —$NR^{34}R^{35}$; and $R^9$ is H, halo, —$OR^{31}$, —SH, —$NH_2$, —$NR^{34}R^{35}$, —$NR^{31}R^{32}$, —$CO_2R^{31}$, —$CO_2$aryl, —$C(=O)NR^{31}R^{32}$, $C(=O)NR^{34}R^{35}$, —$NO_2$, —CN, —$S(O)_{0-2}C_{1-10}$alkyl, —$S(O)_{0-2}$aryl, —$SO_2NR^{34}R^{35}$, —$SO_2NR^{31}R^{32}$, $C_{1-10}$alkyl, $C_{2-10}$alkenyl, $C_{2-10}$alkynyl; aryl-$C_{1-10}$alkyl, aryl-$C_{2-10}$alkenyl, aryl-$C_{2-10}$alkynyl, heteroaryl-$C_{1-10}$alkyl, heteroaryl-$C_{2-10}$alkenyl, heteroaryl-$C_{2-10}$alkynyl, wherein each of said alkyl, alkenyl, alkynyl, aryl, heteroalkyl, heterocyclyl, or heteroaryl group is unsubstituted or is substituted with one or more independent halo, cyano, nitro, —$OC_{1-10}$alkyl, $C_{1-10}$alkyl, $C_{2-10}$alkenyl, $C_{2-10}$alkynyl, halo$C_{1-10}$alkyl, halo$C_{2-10}$alkenyl, halo$C_{2-10}$alkynyl, —COOH, —$C(=O)NR^{31}R^{32}$, —$C(=O)NR^{34}R^{35}$, —$SO_2NR^{34}R^{35}$, —$SO_2NR^{31}R^{32}$, —$NR^{31}R^{32}$, or —$NR^{34}R^{35}$.

In some embodiments, $X_4$ is C—$R^9$.

The invention also provides an inhibitor as defined above, wherein the compound is of Formula I-B:

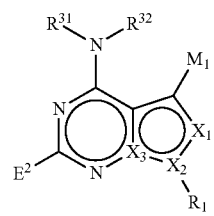

Formula I-B or a pharmaceutically acceptable salt thereof, and wherein the substituents are as defined above.

In various embodiments the compound of Formula I-B or its pharmaceutically acceptable salt thereof, is an inhibitor having the structure of Formula I-B1 or Formula I-B2:

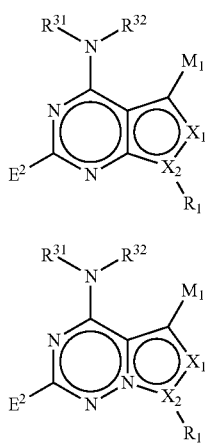

Formula I-B1

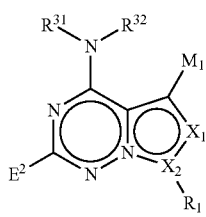

Formula I-B2 or a pharmaceutically acceptable salt thereof.

In various embodiments of Formula I-B1, $X_1$ is N and $X_2$ is N. In other embodiments, $X_1$ is C-$E^1$ and $X_2$ is N. In yet other embodiments, $X_1$ is NH and $X_2$ is C. In further embodiments, $X_1$ is CH-$E^1$ and $X_2$ is C.

In various embodiments of Formula I-B2, $X_1$ is N and $X_2$ is C. In further embodiments, $X_1$ is C-$E^1$ and $X_2$ is C.

In various embodiments, $X_1$ is C—$(W^1)_j$—$R^4$, where j is 0.

In another embodiment, $X_1$ is CH. In yet another embodiment, $X_1$ is C-halogen, where halogen is Cl, F, Br, or I.

In various embodiments of $X_1$, it is C—$(W^1)_j$—$R^4$. In various embodiments of $X_1$, j is 1, and $W^1$ is —O—. In various embodiments of $X_1$, j is 1, and $W^1$ is —N$R^7$—. In various embodiments of $X_1$, j is 1, and $W^1$ is —NH—. In various embodiments of $X_1$, j is 1, and $W^1$ is —S(O)$_{0-2}$—. In various embodiments of $X_1$, j is 1, and $W^1$ is —C(O)—. In various embodiments of $X_1$, j is 1, and $W^1$ is —C(O)N($R^7$)—. In various embodiments of $X_1$, j is 1, and $W^1$ is —N($R^7$)C(O)—. In various embodiments of $X_1$, j is 1, and $W^1$ is —N($R^7$)S(O)—. In various embodiments of $X_1$, j is 1, and $W^1$ is —N($R^7$)S(O)$_2$—. In various embodiments of $X_1$, j is 1, and $W^1$ is —C(O)O—. In various embodiments of $X_1$, j is 1, and $W^1$ is CH($R^7$)N(C(O)O$R^8$)—. In various embodiments of $X_1$, j is 1, and $W^1$ is —CH($R^7$)N(C(O)$R^8$)—. In various embodiments of $X_1$, j is 1, and $W^1$ is —CH($R^7$)N(SO$_2R^8$)—. In various embodiments of $X_1$, j is 1, and $W^1$ is —CH($R^7$)N($R^8$)—. In various embodiments of $X_1$, j is 1, and $W^1$ is —CH($R^7$)C(O)N($R^8$)—. In various embodiments of $X_1$, j is 1, and $W^1$ is —CH($R^7$)N($R^8$)C(O)—. In various embodiments of $X_1$, j is 1, and $W^1$ is —CH($R^7$)N($R^8$)S(O)—. In various embodiments of $X_1$, j is 1, and $W^1$ is —CH($R^7$)N($R^8$)S(O)$_2$—.

In another embodiment, $X_1$ is CH$_2$. In yet another embodiment, $X_1$ is CH-halogen, where halogen is Cl, F, Br, or I.

In another embodiment, $X_1$ is N.

In various embodiments, $X_2$ is N. In other embodiments, $X_2$ is C.

In various embodiments, $E^2$ is —$(W^1)_j$—$R^4$, where j is 0.

In another embodiment, $E^2$ is CH. In yet another embodiment, $E^2$ is C-halogen, where halogen is Cl, F, Br, or I.

In various embodiments of $E^2$, it is —$(W^1)_j$—$R^4$. In various embodiments of $E^2$, j is 1, and $W^1$ is —O—. In various embodiments of $E^2$, j is 1, and $W^1$ is —N$R^7$—. In various embodiments of $E^2$, j is 1, and $W^1$ is —NH—. In various embodiments of $E^2$, j is 1, and $W^1$ is —S(O)$_{0-2}$—. In various embodiments of $E^2$, j is 1, and $W^1$ is —C(O)—. In various embodiments of $E^2$, j is 1, and $W^1$ is —C(O)N($R^7$)—. In various embodiments of $E^2$, j is 1, and $W^1$ is —N($R^7$)C(O)—. In various embodiments of $E^2$, j is 1, and $W^1$ is —N($R^7$)S(O)—. In various embodiments of $E^2$, j is 1, and $W^1$ is —N($R^7$)S(O)$_2$—. In various embodiments of $E^2$, j is 1, and $W^1$ is —C(O)O—. In various embodiments of $E^2$, j is 1, and $W^1$ is CH($R^7$)N(C(O)O$R^8$)—. In various embodiments of $E^2$, j is 1, and $W^1$ is —CH($R^7$)N(C(O)$R^8$)—. In various embodiments of $E^2$, j is 1, and $W^1$ is —CH($R^7$)N(SO$_2R^8$)—. In various embodiments of $E^2$, j is 1, and $W^1$ is —CH($R^7$)N($R^8$)—. In various embodiments of $E^2$, j is 1, and $W^1$ is —CH($R^7$)C(O)N($R^8$)—. In various embodiments of $E^2$, j is 1, and $W^1$ is —CH($R^7$)N($R^8$)C(O)—. In various embodiments of $E^2$, j is 1, and $W^1$ is —CH($R^7$)N($R^8$)S(O)—. In various embodiments of $E^2$, j is 1, and $W^1$ is —CH($R^7$)N($R^8$)S(O)$_2$—.

In various embodiments of Formula I-A, I-B, I-B1 and I-B2, $M_1$ is:

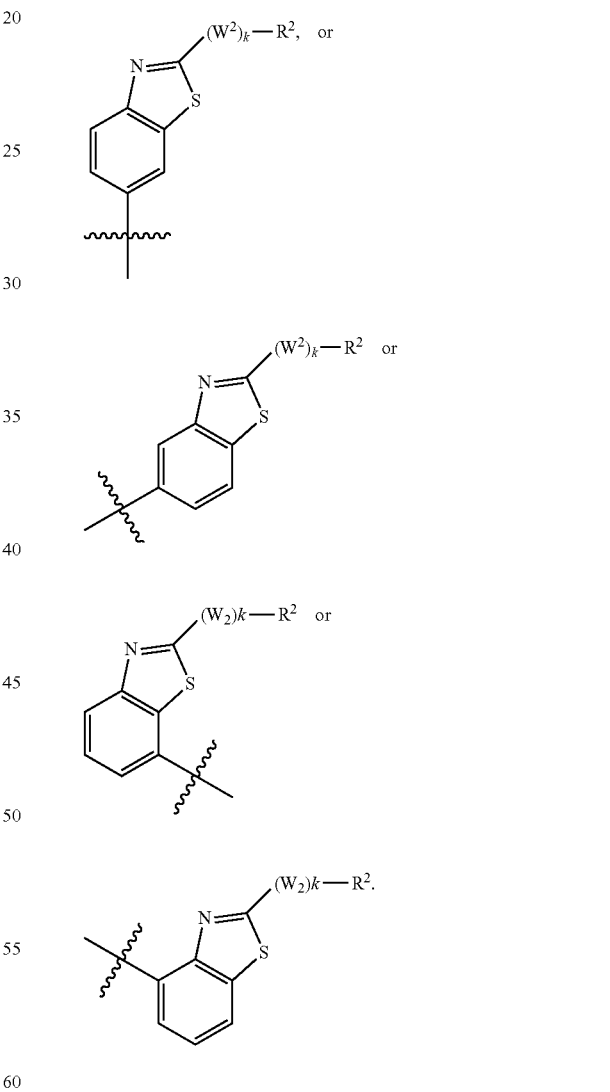

In some embodiments of the invention, $M_1$ is benzothiazolyl substituted with —$(W^2)_k$—$R^2$. $W^2$ can be —O—, —S(O)$_{0-2}$-(including but not limited to —S—, —S(O)—, and —S(O)$_2$—), —C(O)—, or —C(O)O—. In other embodiments, $W^1$ is —N$R^6$— or —CH($R^6$)N($R^7$)—, wherein $R^6$ and $R^7$ are each independently hydrogen, unsubstituted or substituted $C_1$-$C_{10}$alkyl (which includes but is not limited to —$CH_3$, —$CH_2CH_3$, n-propyl, isopropyl, n-butyl, tert-butyl, sec-butyl, pentyl, hexyl, and heptyl), unsubstituted or substituted $C_2$-$C_{10}$alkenyl (including but not limited to alkenyl such as, for example, vinyl, allyl, 1-methyl propen-1-yl, butenyl, or pentenyl). Additionally when $W^2$ is —$NR^6$— or —$CH(R^6)N(R^7)$—, $R^6$ and $R^7$ are each independently unsubstituted or substituted aryl (including phenyl and naphthtyl). In yet other embodiments, when $W^2$ is —$NR^6$— or —$CH(R^6)N(R^7)$—, $R^6$ and $R^7$ are each independently heteroaryl, wherein the heteroaryl is unsubstituted or substituted. $R^6$ and $R^7$ heteroaryl is monocyclic heteroaryl, and includes but is not limited to imidazolyl, pyrrolyl, oxazolyl, thiazolyl, and pyridinyl. In some other embodiments, when $W^2$ is —$NR^6$— or —$CH(R^6)N(R^7)$—, $R^6$ and $R^7$ are each independently unsubstituted or substituted heterocyclyl (which includes but is not limited to pyrrolidinyl, tetrahydrofuranyl, piperidinyl, tetrahydropyranyl, thiazolidinyl, imidazolidinyl, morpholinyl, and piperazinyl) or unsubstituted or substituted $C_{3-8}$cycloalkyl (including but not limited to cyclopropyl, cyclobutyl, and cyclopentyl). Non limiting exemplary $W^2$ include —NH—, —N(cyclopropyl), and —N(4-N-piperidinyl).

For example, exemplary mTor inhibitors of the invention have the Formulas:

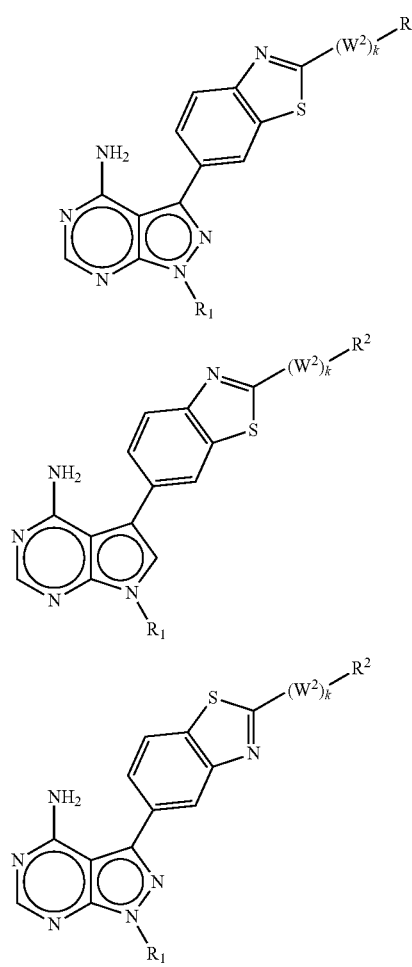

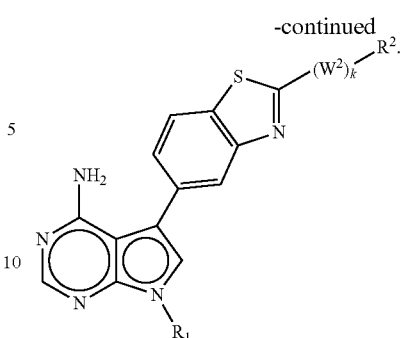

Reaction Schemes—mTor Inhibitor Compounds

The mTor inhibitor compounds disclosed herein may be prepared by the routes described below. Materials used herein are either commercially available or prepared by synthetic methods generally known in the art. These schemes are not limited to the compounds listed or by any particular substituents employed for illustratrative purposes. Numbering does not necessarily correspond to that of claims or other tables.

Scheme A

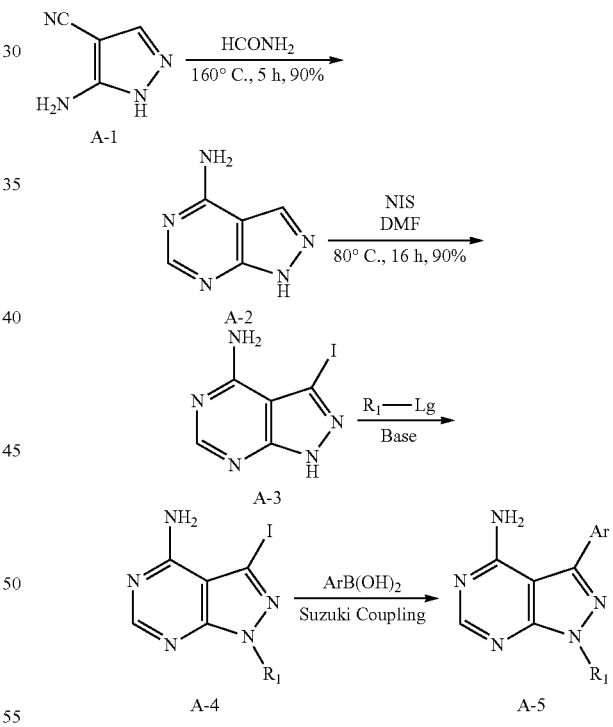

In one embodiment, compounds are synthesized by condensing a functionalized heterocycle A-1 with formamide, to provide a pyrazolopyrimidine A-2. The pyrazolopyrimidine is treated with N-iodosuccinimide, which introduces an iodo substituent in the pyrazole ring as in A-3. The $R_1$ substituent is introduced by reacting the pyrazolopyrimidine A3 with a compound of Formula $R_1$-Lg in the presence of a base such as potassium carbonate to produce a compound of Formula A-4. Other bases that are suitable for use in this step include but are not limited to sodium hydride and potassium t-butoxide. The compound of Formula $R_1$-Lg has a moiety $R_1$ as defined for $R_1$ of a compound of Formula I-A, and wherein -Lg is an appropriate leaving group such as halide (including bromo, iodo, and chloro), tosylate, or other suitable leaving group, The substituents corresponding to $M_1$ are thereafter introduced by reacting aryl or heteroaryl boronic acids with the compound of Formula A-4 to obtain compound A-5.

Scheme A-1

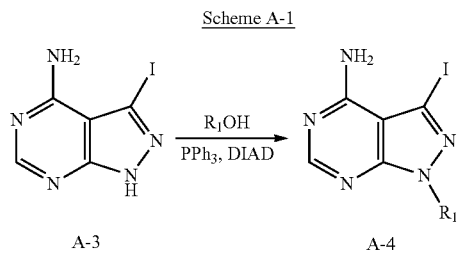

Alternatively, Mitsunobu chemistry can be used to obtain alkylated pyrazolopyrimidine A-4, as shown in Scheme A-1. Iodopyrazolopyrimidine A-3 is reacted with a suitable alcohol, in the presence of triphenylphosphine and diisopropylazodicarboxylate (DIAD) to produce pyrazolopyrimidine A-4.

Scheme B

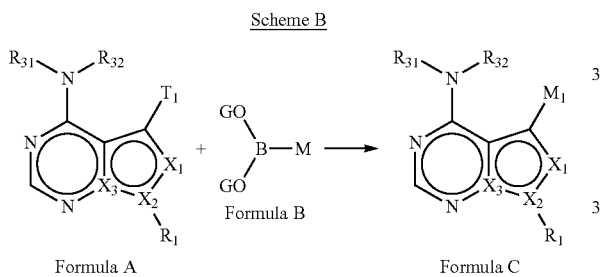

The compounds of the invention may be synthesized via a reaction scheme represented generally in Scheme B. The synthesis proceeds via coupling a compound of Formula A with a compound of Formula B to yield a compound of Formula C. The coupling step is typically catalyzed by using, e.g., a palladium catalyst, including but not limited to palladium tetrakis (triphenylphosphine). The coupling is generally performed in the presence of a suitable base, a nonlimiting example being sodium carbonate. One example of a suitable solvent for the reaction is aqueous dioxane.

A compound of Formula A for use in Scheme B has a structure of Formula A, wherein $T_1$ is triflate or halo (including bromo, chloro, and iodo), and wherein $R_1, X_1, X_2, X_3, R_{31}$ and $R_{32}$ are defined as for a compound of Formula I-A. For boronic acids and acid derivatives as depicted in Formula B, M is either $M_1$ or $M_2$. $M_1$ is defined as for a compound of Formula I-A. For example, $M_1$ can be a 5-benzoxazolyl or a 6-benzoxazolyl moiety, including but not limited to those $M_1$ moieties disclosed herein. $M_2$ is a moiety which is synthetically transformed to form $M_1$, after the $M_2$ moiety has been coupled to the bicyclic core of the compound of Formula A.

For a compound of Formula B, G is hydrogen or $R_{G1}$, wherein $R_{G1}$ is alkyl, alkenyl, or aryl. Alternatively, $B(OG)_2$ is taken together to form a 5- or 6-membered cyclic moiety. In some embodiments, the compound of Formula B is a compound having a structure of Formula E:

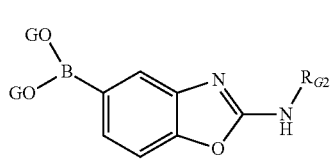

Formula E wherein G is H or $R_{G1}$; $R_{G1}$ is alkyl, alkenyl, or aryl. Alternatively,

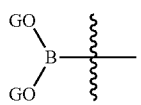

forms a 5- or 6-membered cyclic moiety; and $R_2$ is a $R_{G2}$ moiety, wherein the $R_{G2}$ moiety is H, acyl, or an amino protecting group including but not limited to tert-butyl carbamate (Boc), carbobenzyloxy (Cbz), benzyl (Bz), fluorenylmethyloxycarbonyl (FMOC), p-methoxybenzyl (PMB), and the like.

Scheme C

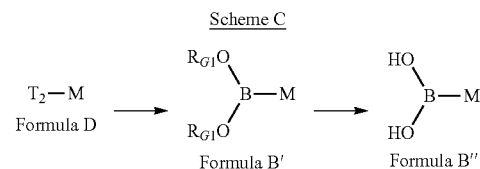

In some embodiments, a compound of Formula B is a compound of Formula B', wherein G is $R_{G1}$, or a compound of Formula B", wherein G is hydrogen. Scheme C depicts an exemplary scheme for synthesizing a compound of Formula B' or, optionally, Formula B" for use in Reaction Scheme C. This reaction proceeds via reacting a compound of Formula D with a trialkyl borate or a boronic acid derivative to produce a compound of Formula B'. The reaction is typically run a solvent such as dioxane or tetrahydrofuran. The trialkyl borate includes but is not limited to triisopropyl borate and the boronic acid derivative includes but is not limited to bis(pinacolato)diboron.

When the reaction is performed with trialkyl borate, a base such as n-butyllithium is first added to the compound of Formula D to generate an anion, prior to the addition of the borate. When the reaction is performed with a boronic acid derivative such as bis(pinacolato)diboron, a palladium catalyst and a base is used. Typical palladium catalysts include but is not limited to palladium chloride (diphenylphosphino)ferrocene). A suitable base includes but is not limited to potassium acetate.

A compound of Formula D for use in Scheme C is a compound wherein $T_2$ is halo or another leaving group, and M is as defined above in Scheme B. The compound of Formula B' may further be converted to a compound of Formula B" by treatment with an acid such as hydrochloric acid.

In one embodiment of a compound of Formula B, B', B", or E, the G groups are hydrogen. In another of a compound of Formula B, B', B", or E, the G groups are $R_{G1}$.

In some embodiments, no further synthetic transformation of $M_1$ moiety is performed after the coupling reaction when, e.g. $M_1$ is 2-N-acetyl-benzoxazol-5-yl.

Some exemplary compounds of Formula B that can be synthesized via Scheme C include but are not limited to compounds of the following formulae:

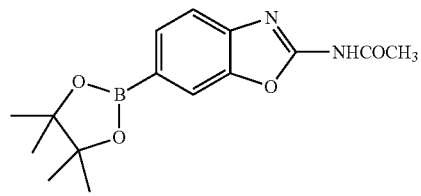
H-7

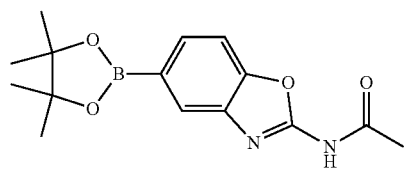
F-7

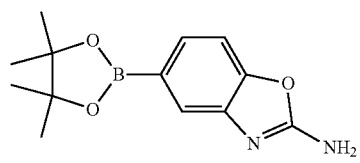
G-6

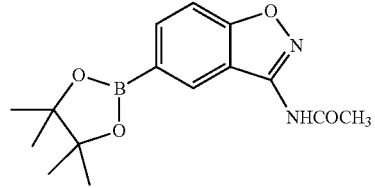
I-4

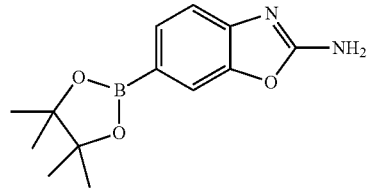
G-7

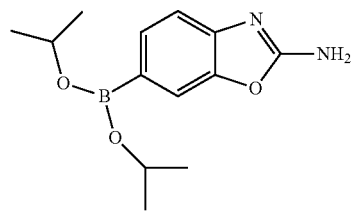
G-8

G-9

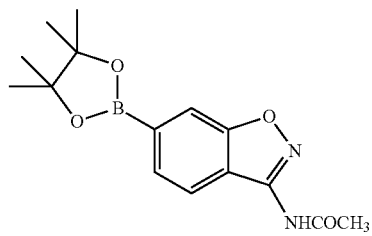
J-4

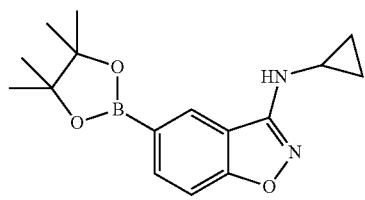
K-6

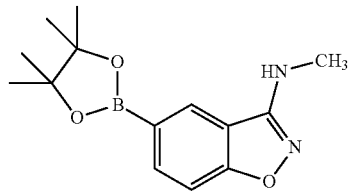
L-6

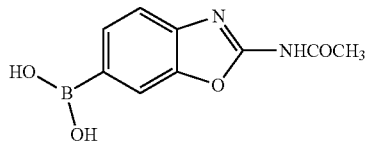
H-7-B

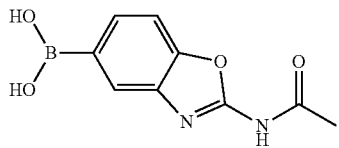
F-7-B

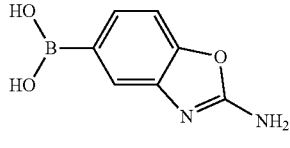
G-6-B

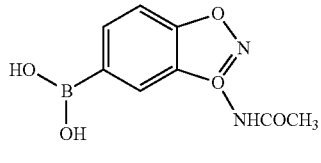
I-4-B

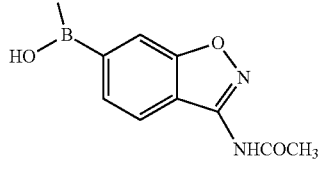
J-4-B

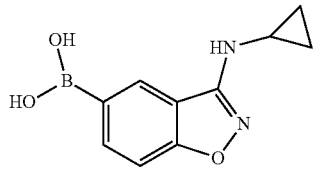
K-6-B

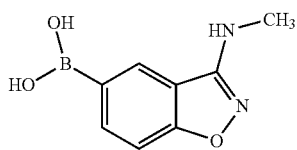

L-6-B

In other embodiments of the invention, a compound of Formula E is synthesized from a compound of Formula F, as shown in Scheme C-1:

Scheme C-1

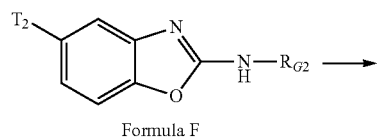

Scheme C-1 depicts an exemplary scheme for synthesizing a compound of Formula E. This reaction proceeds via reacting a compound of Formula F with a trialkyl borate or a boronic acid derivative to produce a compound of Formula E. The conditions of the reaction are as described above in Scheme C.

A compound of Formula F for use in Scheme C-1 is a compound wherein $T_2$ is halo (including Br, Cl, and I) or another leaving group (including but not limited to triflate, tosylate, and mesylate), and the $G_p$ moiety is H, acyl, or an amino protecting group including but not limited to tert-butyl carbamate (Boc), carbobenzyloxy (Cbz), benzyl (Bz), fluorenylmethyloxycarbonyl (FMOC), p-methoxybenzyl (PMB), and the like.

The compound of Formula E, wherein G is alkyl, may further be converted to a compound of Formula E, wherein G is hydrogen, by treatment with an acid such as hydrochloric acid Where desired, deprotection of a substituent (e.g., removal of Boc protection from an amino substituent) on the benzoxazolyl moiety (i.e. $M_1$ of Formula C) is performed after coupling the compound of Formula B to the compound of Formula A.

Some exemplary compounds with such protecting groups, include but are not limited to compounds of the following formulae:

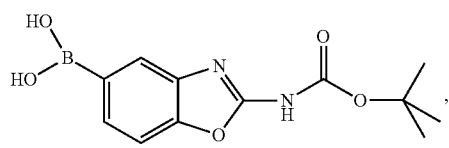

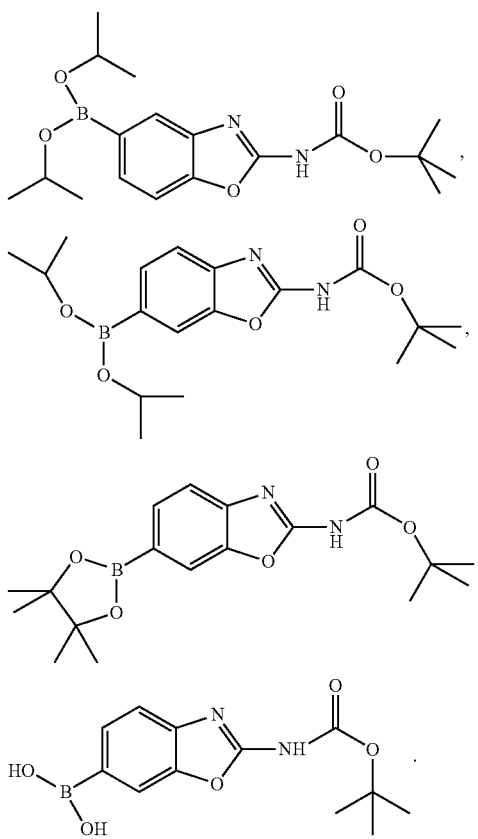

An exemplary transformation of $M_2$ to $M_1$ can be carried out via Scheme D as shown below.

Scheme D

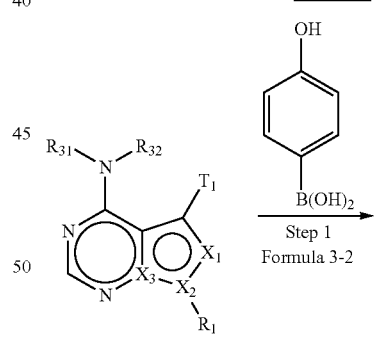

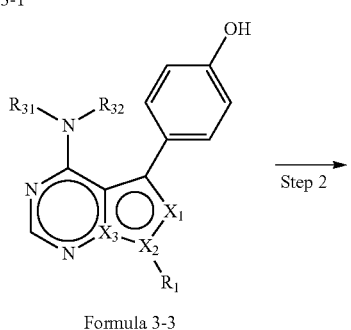

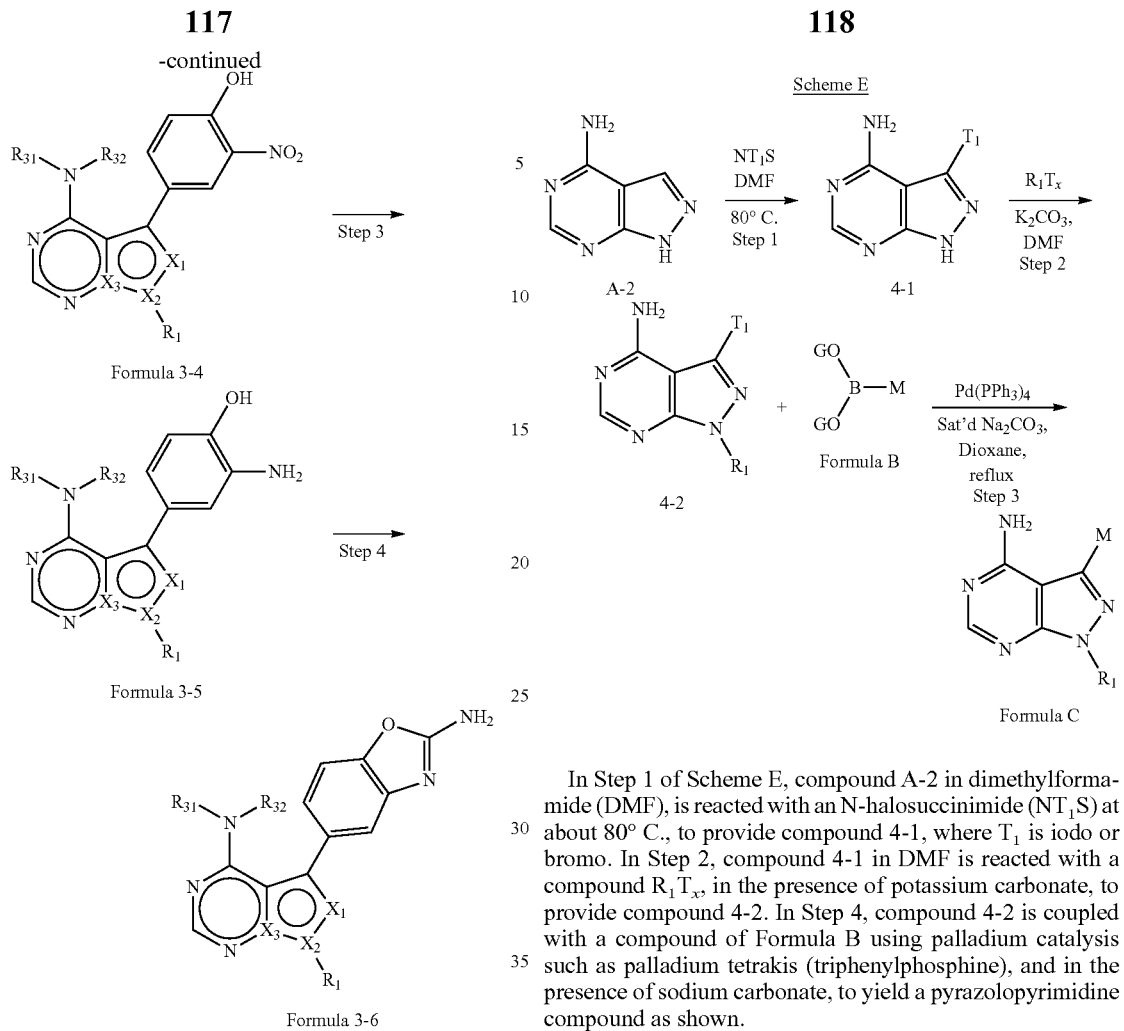

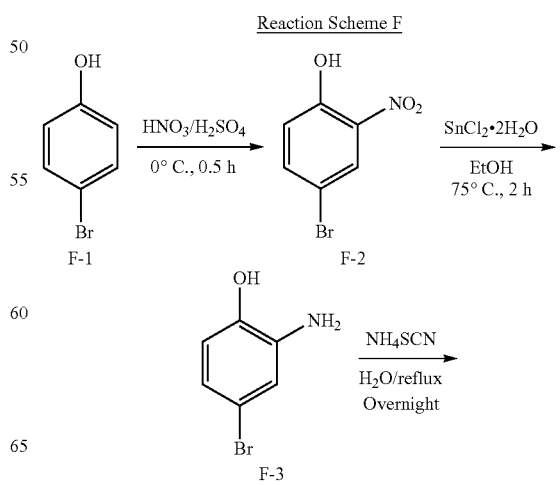

In Step 1, a compound of Formula 3-1 is reacted with boronic acid 3-2, in the presence of palladium tetrakis (triphenylphosphine) and a suitable base, such as sodium carbonate in an aqueous/organic solvent mixture to produce a compound of Formula 3-3. In Step 2, the compound of Formula 3-3 is reacted with about 2 equivalents of nitric acid in acetic acid as solvent to produce a compound of Formula 3-4. Two alternative transformations may be used to effect the next transformation of Step 3. In the first method, the compound of Formula 3-4 is treated with sodium dithionite and sodium hydroxide in water to produce a compound of Formula 3-5. Alternatively, the compound of Formula 3-4 is reduced using palladium on carbon in a suitable solvent under a hydrogen atmosphere to yield a compound of Formula 3-5.

In Step 4, compound 3-5 is reacted with about 1.2 equivalents of cyanogen bromide in a solvent such as methanol/tetrahydrofuran mixture to produce a compound of Formula 3-6. The compound of Formula 3-6 may be further transformed by other substitution or derivatization.

A compound of Formula 3-1 useful in the method of Scheme D is a compound having a structure of Formula 3-1, wherein $T_1$ is triflate or halo (including bromo, chloro, and iodo), and wherein $R_1$, $X_1$, $X_2$, $X_3$, $R_{31}$ and $R_{32}$ are defined as for a compound of Formula I-A.

Exemplary compounds having a pyrazolopyrimidine core can be synthesized via Scheme E.

In Step 1 of Scheme E, compound A-2 in dimethylformamide (DMF), is reacted with an N-halosuccinimide ($NT_1S$) at about 80° C., to provide compound 4-1, where $T_1$ is iodo or bromo. In Step 2, compound 4-1 in DMF is reacted with a compound $R_1T_x$, in the presence of potassium carbonate, to provide compound 4-2. In Step 4, compound 4-2 is coupled with a compound of Formula B using palladium catalysis such as palladium tetrakis (triphenylphosphine), and in the presence of sodium carbonate, to yield a pyrazolopyrimidine compound as shown.

A compound of Formula $R_1T_x$ suitable for use in Reaction Scheme E is the compound wherein $R_1$ is cycloalkyl or alkyl and $T_x$ is halo (including bromo, iodo, or chloro) or a leaving group, including but not limited to mesylate or tosylate.

Reaction Schemes F-M illustrate methods of synthesis of borane reagents useful in preparing intermediates of use in synthesis of the compounds of the invention as described in Reaction Schemes A, B, and E above, to introduce $M_1$ substituents.

-continued
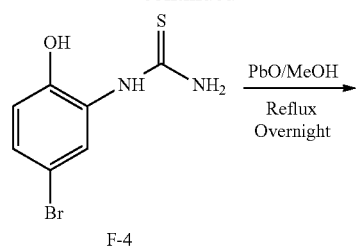
F-4
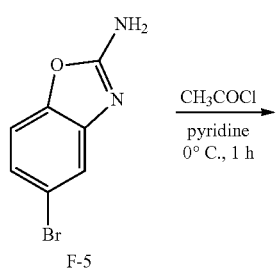
F-5
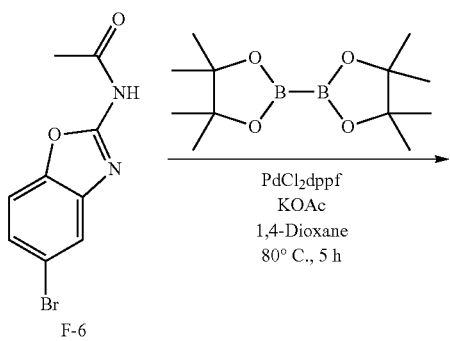
F-6
Reaction Scheme G
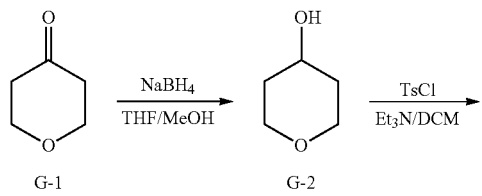
G-1   G-2
-continued
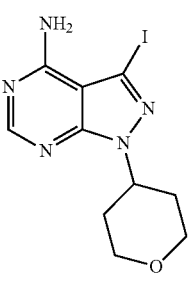
G-3 → G-4
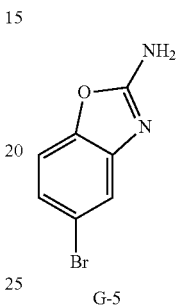
G-5
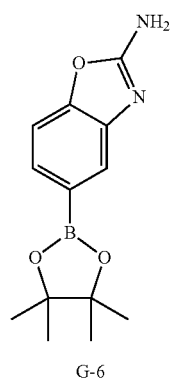
G-6
Reaction Scheme H
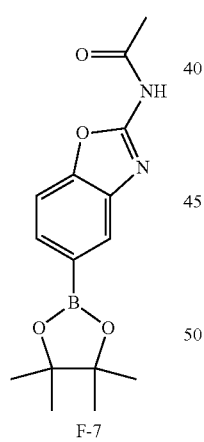
H-1
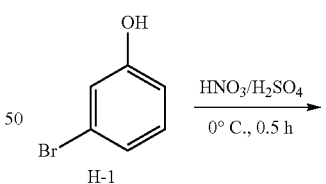
H-2
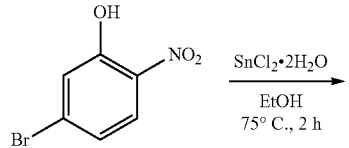
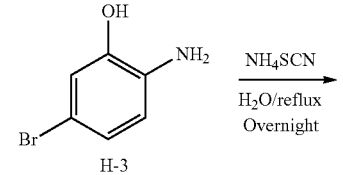
H-3

121
-continued
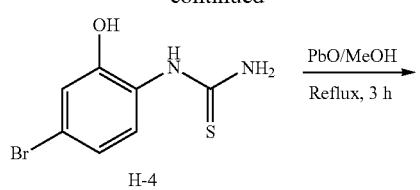
H-4
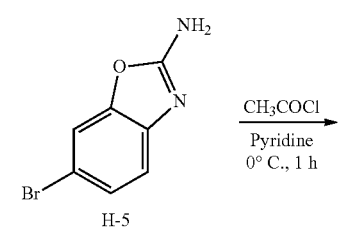
H-5
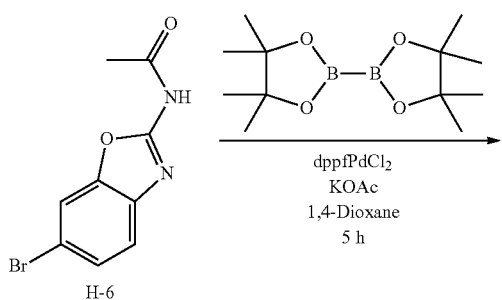
H-6
H-7
Reaction Scheme I
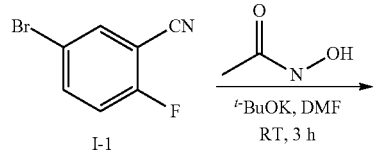
I-1
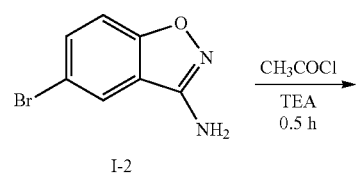
I-2
122
-continued
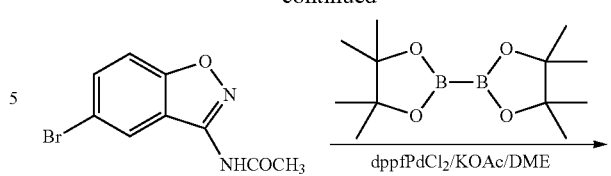
I-3
I-4
Reaction Scheme J
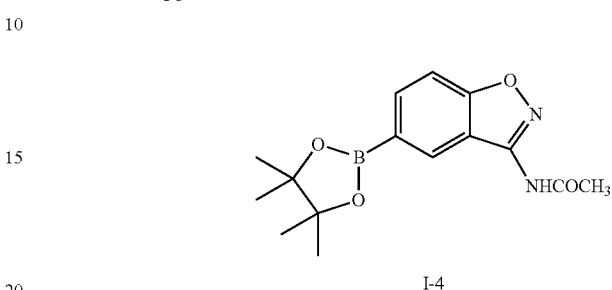
J-1
J-2
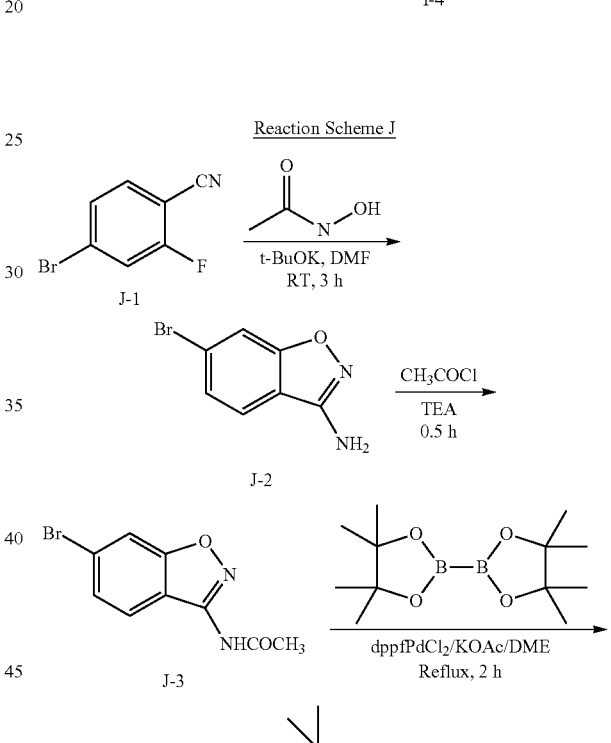
J-3
J-4
Reaction Scheme K
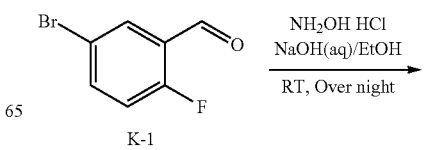
K-1

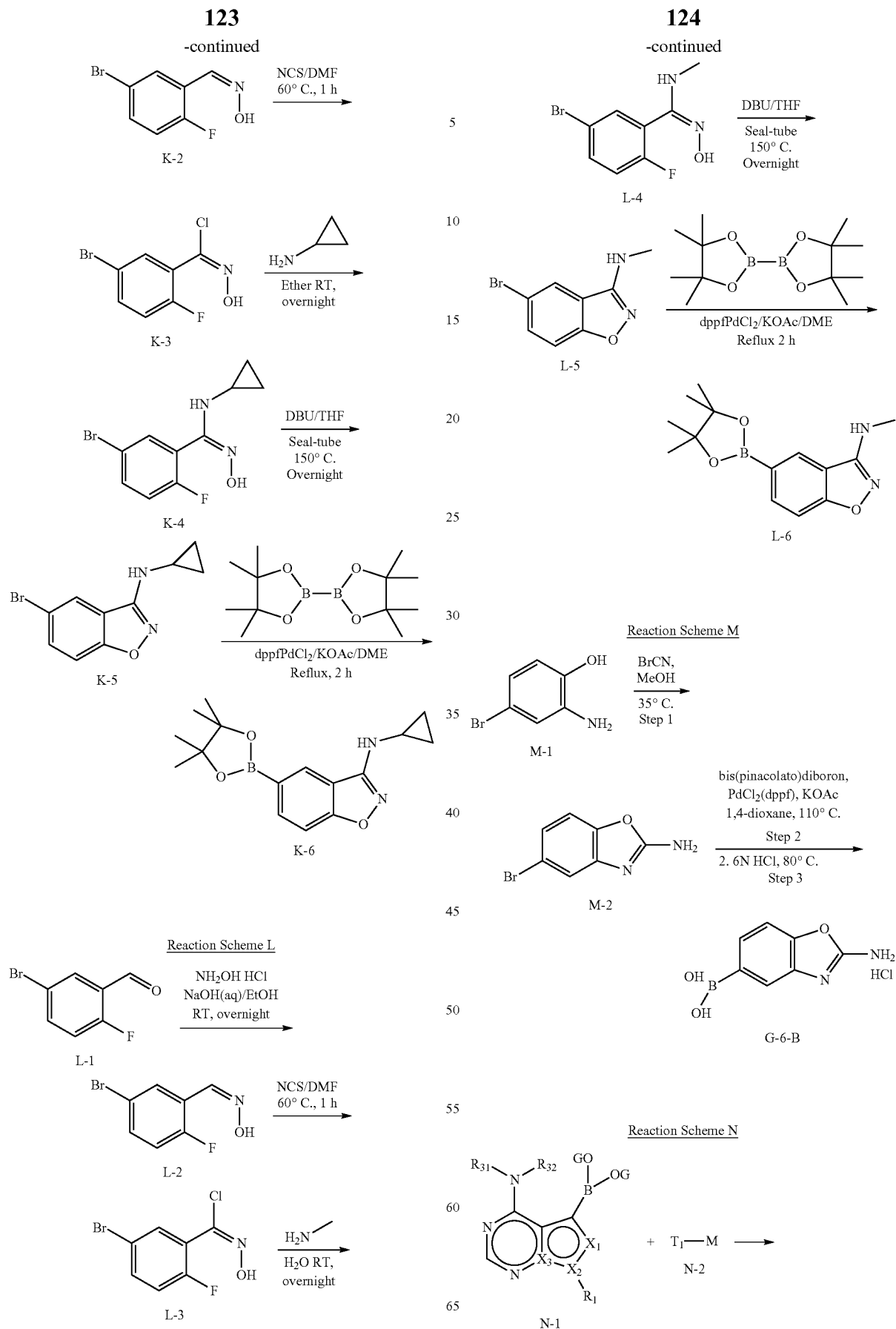

-continued

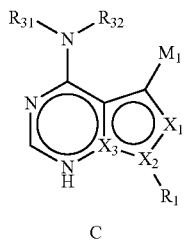

C

In an alternative method of synthesis, a compound of Formula N-1 and a compound of N-2 are coupled to produce a compound of Formula C. The coupling step is typically catalyzed by using, e.g., a palladium catalyst, including but not limited to palladium tetrakis (triphenylphosphine). The coupling is generally performed in the presence of a suitable base, a nonlimiting example being sodium carbonate. One example of a suitable solvent for the reaction is aqueous dioxane.

A compound of Formula N-1 for use in Scheme N has a structure of Formula N-1, wherein G is hydrogen or $R_{G1}$, wherein $R_{G1}$ is alkyl, alkenyl, or aryl. Alternatively, $B(OG)_2$ of the compound of Formula N-1 is taken together to form a 5- or 6-membered cyclic moiety. $R_1$, $X_1$, $X_2$, $X_3$, $R_{31}$ and $R_{32}$ of the compound of Formula N-1 are defined as for a compound of Formula I-A.

A compound of Formula N-2 for use in Scheme N has a structure of Formula N-2 wherein $T_1$ is triflate or halo (including bromo, chloro, and iodo). M of the compound of Formula N-2 is either $M_1$ or $M_2$. $M_1$ is defined as for a compound of Formula I. For example, $M_1$ can be a 5-benzoxazolyl or a 6-benzoxazolyl moiety, including but not limited to those $M_1$ moieties disclosed herein. $M_2$ is a moiety which is synthetically transformed to form $M_1$, after the $M_2$ moiety has been coupled to the bicyclic core of the compound of Formula N-1.

Scheme N-1

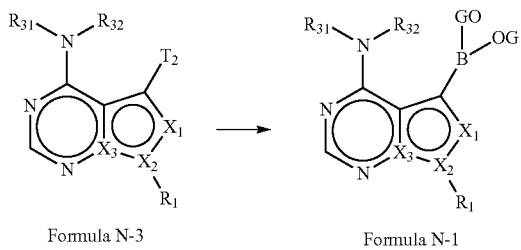

Formula N-3                    Formula N-1

A compound of Formula N-1 may be synthesized as shown in Scheme N-1. A compound of Formula N-1 is reacted with a trialkyl borate or a boronic acid derivative to produce a compound of Formula N-1. The reaction is typically run a solvent such as dioxane or tetrahydrofuran. The trialkyl borate includes but is not limited to triisopropyl borate and the boronic acid derivative includes but is not limited to bis(pinacolato)diboron.

When the reaction is performed with trialkyl borate, a base such as n-butyllithium is first added to the compound of Formula N-3 to generate an anion, prior to the addition of the borate. When the reaction is performed with a boronic acid derivative such as bis(pinacolato)diboron, a palladium catalyst and a base is used. Typical palladium catalysts include but is not limited to palladium chloride (diphenylphosphino)ferrocene). A suitable base includes but is not limited to potassium acetate.

A compound of Formula N-3 suitable for use in Scheme N-1 is a compound wherein $T_2$ is halo or another leaving group such as mesylate, tosylate, or triflate. $X_1$, $X_2$, $X_3$, $R_1$, $R_{31}$, and $R_{32}$ of the compound of Formula N-3 is as defined for a compound of Formula I-A.

In some embodiments of the invention, a compound of Formula A, B, B', B", C, C", D, E, E", 3-1, 3-2, 3-3, 3-4, 3-5, 3-6, N-1", N-3", 3-1", 3-3", 3-4", 3-5", 3-6", N-1", or N-3" is provided as its salt, including but not limited to hydrochloride, acetate, formate, nitrate, sulfate, and boronate.

In some embodiments of the invention, a palladium compound, including but not limited to palladium chloride (diphenylphosphino)ferrocene) and palladium tetrakis (triphenylphosphine), is used in the synthesis of a compound of Formula A, B, B', B", C, C", D, E, E", 3-1, 3-2, 3-3, 3-4, 3-5, 3-6, N-1", N-3", 3-1", 3-3", 3-4", 3-5", 3-6", N-1", or N-3". When a palladium compound is present in the synthesis of a compound of Formula A, B, B', B", C, C", D, E, E", 3-1, 3-2, 3-3, 3-4, 3-5, 3-6, N-1", N-3", 3-1", 3-3", 3-4", 3-5", 3-6", N-1", or N-3", it is present in an amount ranging from about 0.005 molar equivalents to about 0.5 molar equivalents, from about 0.05 molar equivalents to about 0.20 molar equivalents, from about 0.05 molar equivalents to about 0.25 molar equivalents, from about 0.07 molar equivalents to about 0.15 molar equivalents, or about 0.8 molar equivalents to about 0.1 molar equivalents of the compound of Formula A, B, B', B", C, D, E, 3-1, 3-2, 3-3, 3-4, 3-5, 3-6, N-1, or N-3. In some embodiments, a a palladium compound, including but not limited to palladium chloride (diphenylphosphino)ferrocene) and palladium tetrakis (triphenylphosphine) is present in the synthesis of a compound of Formula A, B, B', B", C, C", D, E, E", 3-1, 3-2, 3-3, 3-4, 3-5, 3-6, N-1", N-3", 3-1", 3-3", 3-4", 3-5", 3-6", N-1", or N-3" in about 0.07, about 0.08, about 0.09, about 0.10, about 0.11, about 0.12, about 0.13, about 0.14, or about 0.15 molar equivalents of a starting material of Formula A, B, B', B", C, C", D, E, E", 3-1, 3-2, 3-3, 3-4, 3-5, 3-6, N-1", N-3", 3-1", 3-3", 3-4", 3-5", 3-6", N-1", or N-3" that is used to synthesize a compound of Formula A, B, B', B", C, C", D, E, E", 3-1, 3-2, 3-3, 3-4, 3-5, 3-6, N-1", N-3", 3-1", 3-3", 3-4", 3-5", 3-6", N-1", or N-3".

In some embodiments of the above reaction schemes B, D, E, N or N-1, another embodiment of the compounds of Formula A, C, 3-1, 3-3, 3-4, 3-5, 3-6, A-2,4-1, 4-2, N-1 and N-3 is as shown in Schemes B'. D'. E', N' or N-1' below. In these alternative syntheses, producing a compound of Formula C, 3-1, 3-3, 3-4, 3-5, 3-6, A-2,4-1, 4-2, N-1 or N-3, use compounds that comprise an amino moiety having a $R_{G2}$ moiety present during one or more of the synthetic steps, wherein $R_{G2}$ is an amino protecting group including but not limited to tert-butyl carbamate (Boc), carbobenzyloxy (Cbz), benzyl (Bz), fluorenylmethyloxycarbonyl (FMOC), p-methoxybenzyl (PMB), and the like. These compounds include a compound of Formula A", C", 3-1", 3-3", 3-4", 3-5", 3-6", A-2", 4-1", 4-2", N-1" or N-3".

The $R_{G2}$ moiety is removed, using suitable methods, at any point desired, whereupon the compound of Formula C, 3-1, 3-3, 3-4, 3-5, 3-6, A-2,4-1, 4-2, N-1 or N-3 has a $R_{31}$ hydrogen replacing the $R_{G2}$ moiety on the amino moiety. This transformation is specifically illustrated for the conversion of a compound of Formula C" to a compound of C (i.e., as in Step 4 of Scheme E') and for the conversion of a compound of Formula 3-6″ to a compound of Formula 3-6 (ie., as in Step 5 of Scheme D′). This illustration is in no way limiting as to the choice of steps wherein a compound comprising a $NR_{31}R_{a2}$ moiety may be converted to a compound comprising a $NR_{31}R_{32}$ moiety wherein the $R_{32}$ moiety is hydrogen.
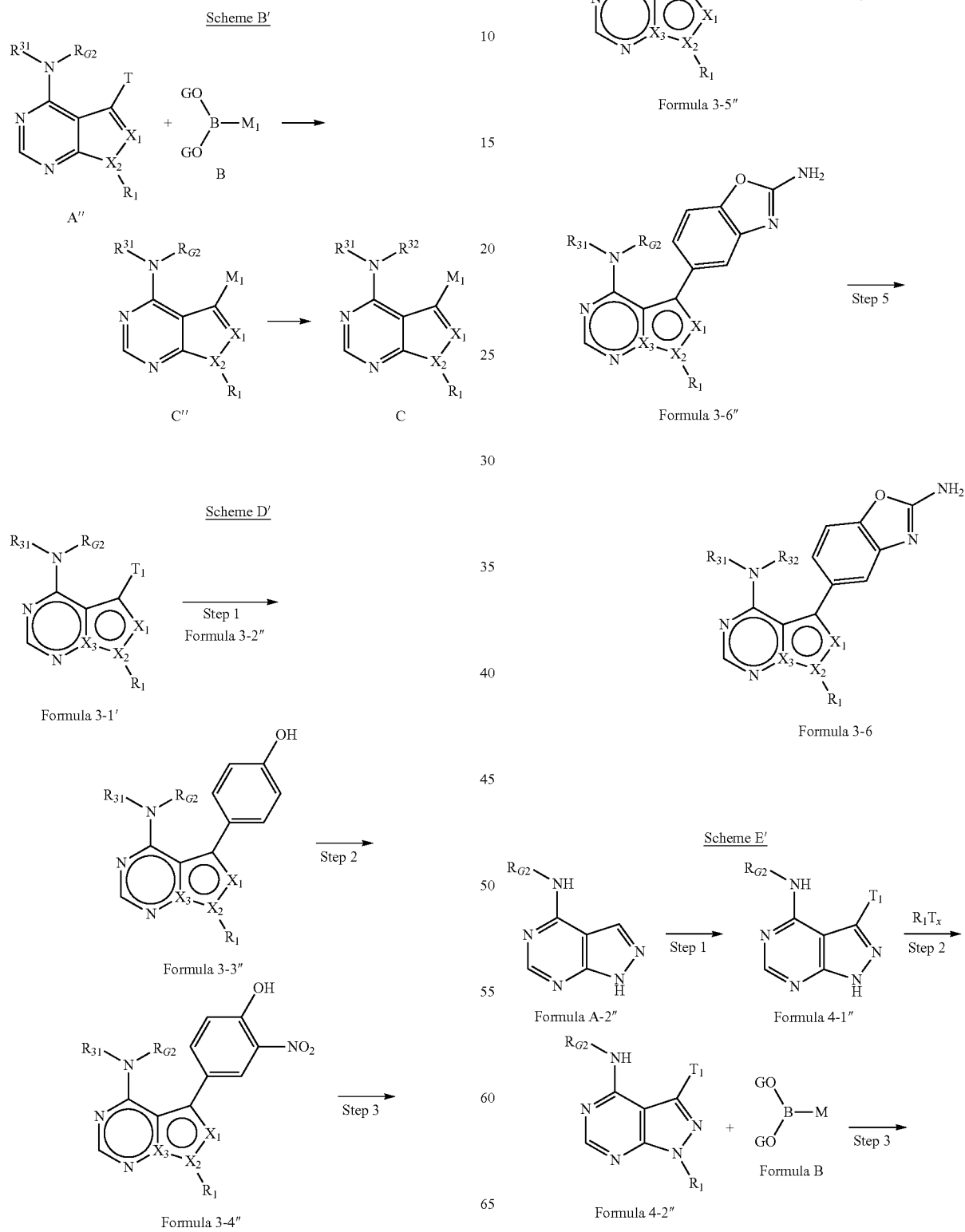

-continued

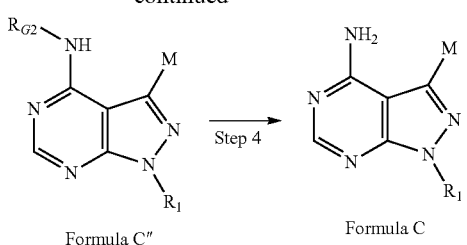

Formula C''    Formula C

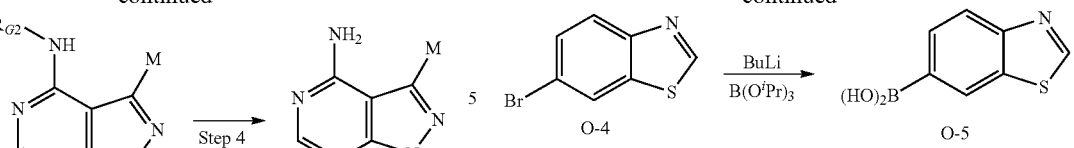

A compound of Formula O-1 is treated with, for example, nitric acid to produce a compound of Formula O-2. The compound of Formula O-2 is treated with a reducing agent such as stannous chloride to produce a compound of Formula O-3. The compound of 0-3 is treated with sodium nitrate in acid and cupric bromide to produce a compound of Formula O-4. The compound of 0-4 is treated a base such as butyl lithium and boron tris-isopropoxide to produce a compound of Formula O-5.

Scheme N' and N-1''

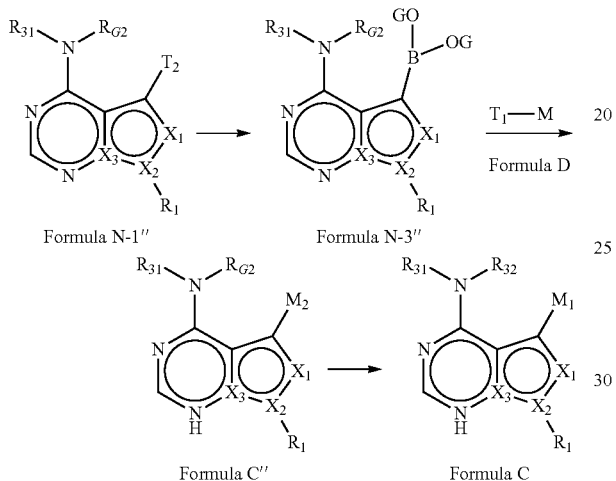

Formula C''    Formula C

Additionally, the invention encompasses methods of synthesis of the compounds of A, B, B', B'', C, E, 3-1, 3-2, 3-3, 3-4, 3-5, 3-6, N-1 or N-3, wherein one or more of M, $M_1$, or $R_1$ has a protecting group present during one or more steps of the synthesis. Protecting groups suitable for use for a M, $M_1$, or $R_1$ moiety are well known in the art, as well as the methods of incorporation and removal, and the reagents suitable for such transformations.

Compounds of the invention where $X_4$ is C—$R^9$ may be prepared by methods analogous to the ones described in the Schemes illustrated above.

Reaction Schemes O, P and Q illustrate methods of synthesis of borane reagents useful in preparing intermediates of use in synthesis of the compounds of the invention as described in Reaction Schemes 1 and 2 above, to introduce benzothiazolyl substituents.

Scheme O

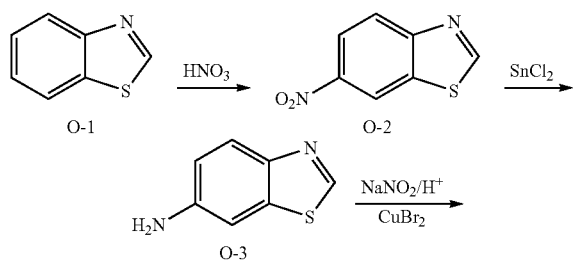

Scheme P (scheme showing synthesis from P-1 through P-5)

A compound of Formula P-1 is treated with, for example, potassium thiocyanate and bromine in acetic acid to produce a compound of Formula P-2. The compound of Formula P-2 is treated with an acetylating reagent such as acetyl chloride to produce a compound of Formula P-3. The compound of P-3 is reacted with, for example, bis(pinacolato)diboron (compound P-4) in the presence of a catalyst such as palladium chloride to produce a compound of Formula P-5.

Scheme Q

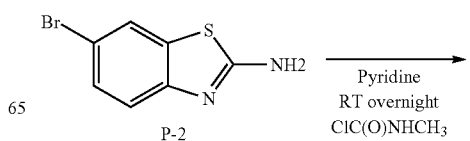

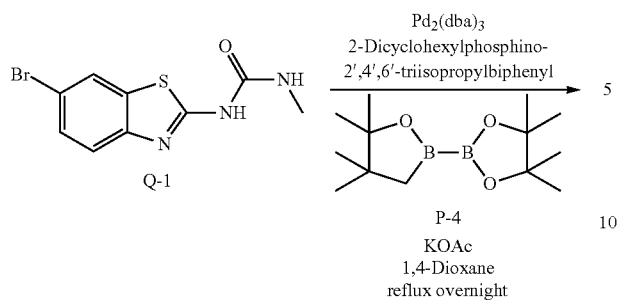

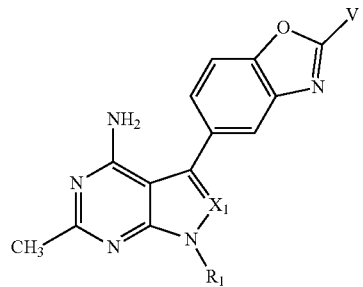

Subclass 2a

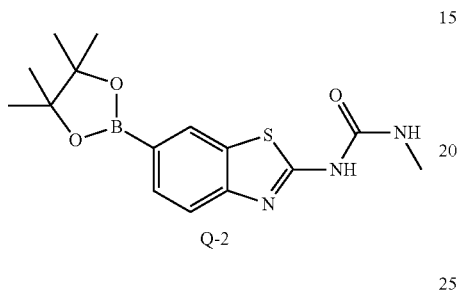

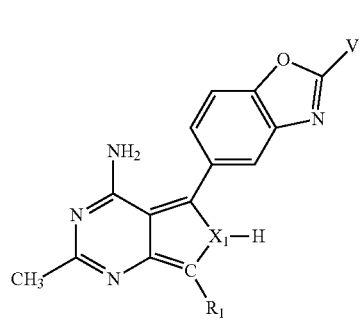

Subclass 2b

The compound of Formula P-2 is reacted with, for example, methyl carbamic acid chloride to produce a compound of Formula Q-1. The compound of Formula Q-1 is reacted with bis(pinacolato)diboron (compound P-4) in the presence of a catalyst such as $Pd_2(dba)_3$, 2-chlorohexylphosphino-2,4,6-triisopropylbiphenyl, a base such as potassium acetate, to produce the compound of Formula Q-2.

Some illustrative compounds of the invention which are mTor inhibitors are described below. The compounds of the invention are not limited in any way to the compounds illustrated herein.

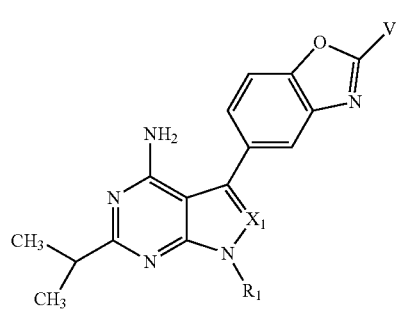

Subclass 3a

Subclass 1a

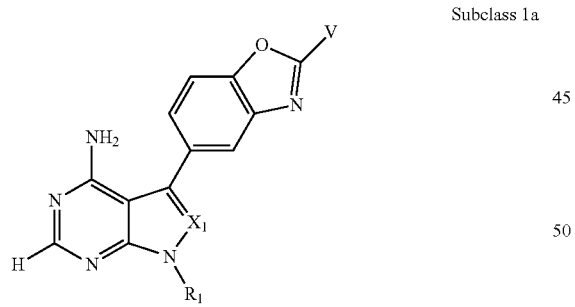

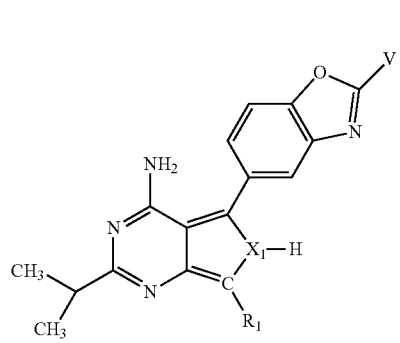

Subclass 3b

Subclass 1b

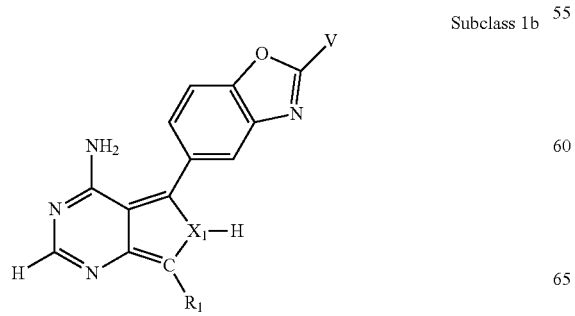

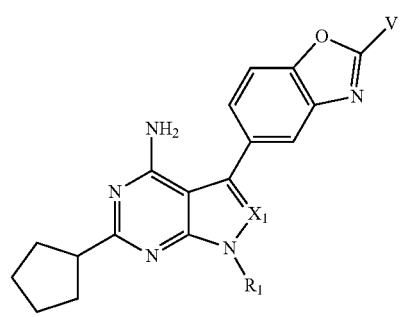

Subclass 4a

-continued
Subclass 4b
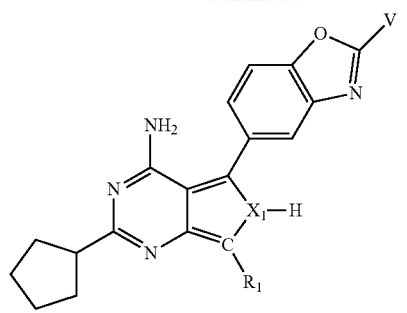
Subclass 5a
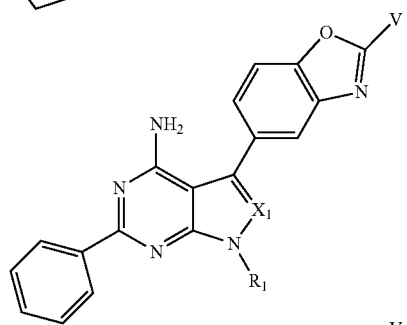
Subclass 5b
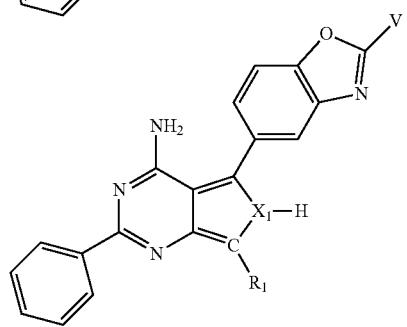
Subclass 6a
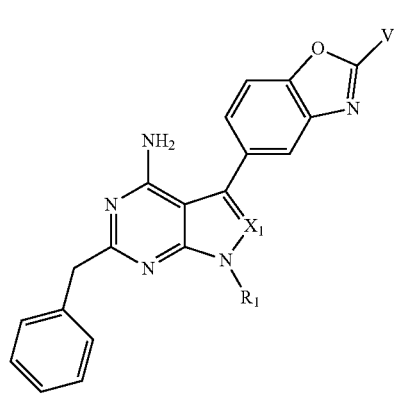
Subclass 6b
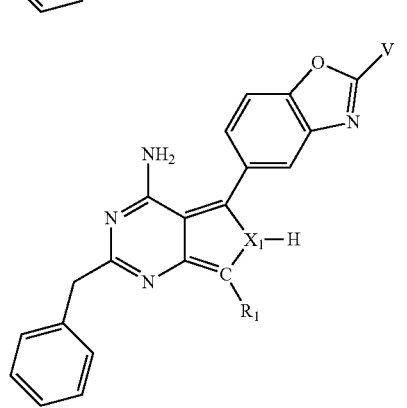
-continued
Subclass 7a
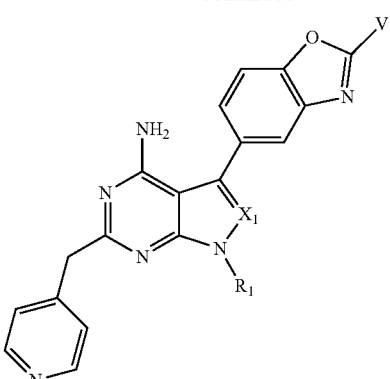
Subclass 7b
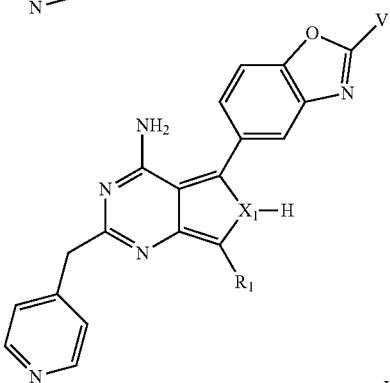
Subclass 8a
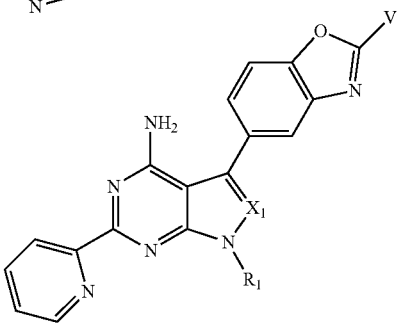
Subclass 8b
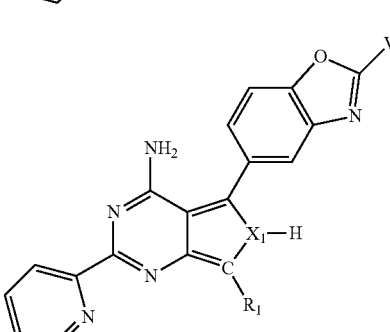
Subclass 9a
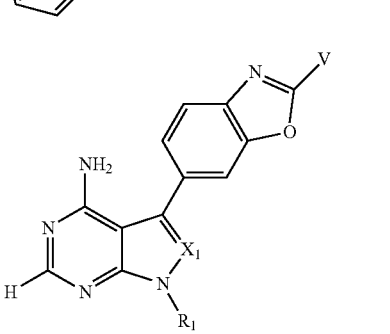

Subclass 9b
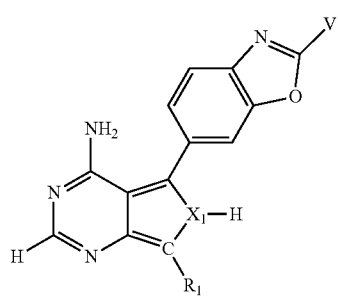
Subclass 10a
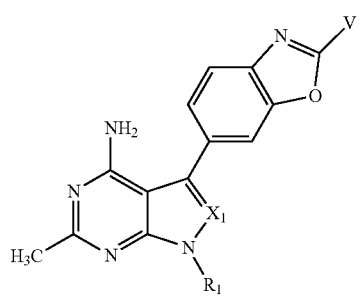
Subclass 10b
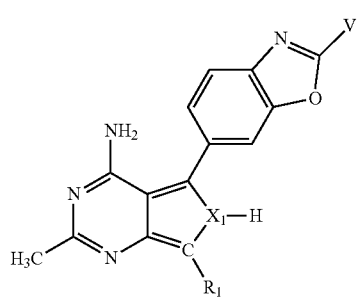
Subclass 11a
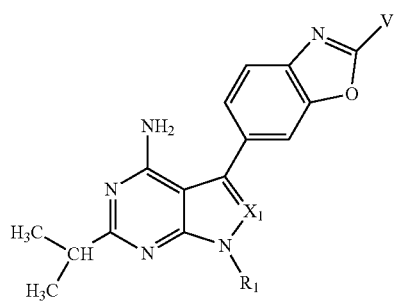
Subclass 11b
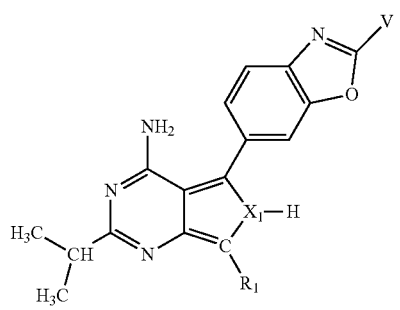
Subclass 12a
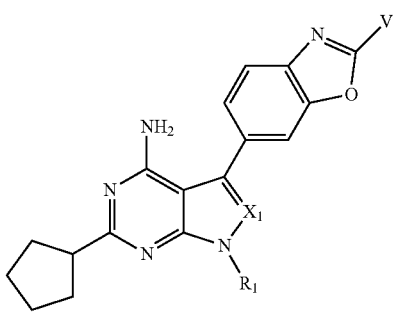
Subclass 12b
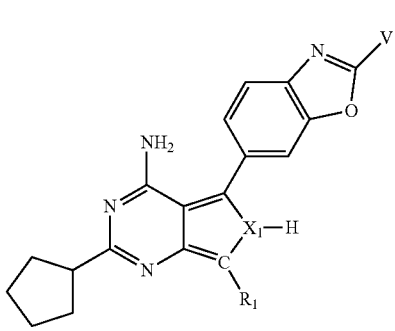
Subclass 13a
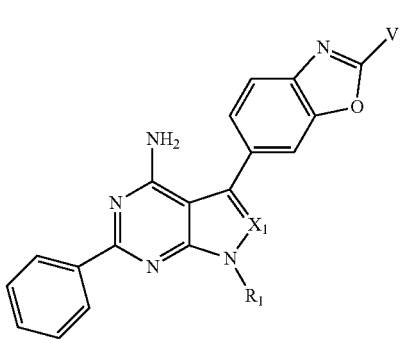
Subclass 13b
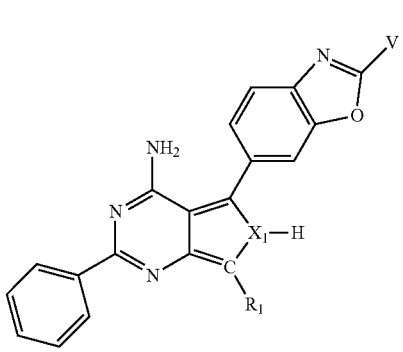
Subclass 14a
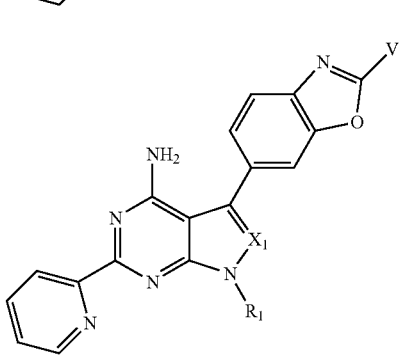

Illustrative compounds of the invention include those of subclass 1a, 1b, 2a, 2b, 3a, 3b, 4a, 4b, 5a, 5b, 6a, 6b, 7a, 7b, 8a, 8b, 9a, 9b, 10a, 10b, 11a, 11b, 12a, 12b, 13a, 13b, 14a, 14b, 15a, 15b, 16a, or 16b, where the substituents $R_1$, $X_1$, and V are as described below.

In some embodiments, when $R_1$ is H and $X_1$ is CH, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is H and $X_1$ is N, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is $CH_3$ and $X_1$ is CH, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is $CH_3$ and $X_1$ is N, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is Et and $X_1$ is CH, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is Et and $X_1$ is N, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is iPr and $X_1$ is CH, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is iPr and $X_1$ is N, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In one embodiment, $R_1$ is iPr, $X_1$ is N, and V is $NH_2$. In another embodiment, $R_1$ is iPr, $X_1$ is N, and V is NHCOMe. In other embodiments, when $R_1$ is cyclobutyl and $X_1$ is CH, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is cyclobutyl and $X_1$ is N, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is cyclopentyl and $X_1$ is CH, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is cyclopentyl and $X_1$ is N V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is phenyl and $X_1$ is CH, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is phenyl and $X_1$ is N, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is pyridin-2-yl and $X_1$ is CH, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is pyridin-2-yl and $X_1$ is N, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is N-methylaminocyclohex-4-yl and $X_1$ is CH, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is N-methylaminocyclohex-4-yl and $X_1$ is N, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is N-methylpiperidin-4-yl and $X_1$ is CH, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is N-methylpiperidin-4-yl and $X_1$ is N, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is N-methylaminocyclobut-3-yl and $X_1$ is CH, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is N-methylaminocyclobut-3-yl and $X_1$ is N, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is tert-butyl and $X_1$ is CH, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is tert-butyl and $X_1$ is N, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is 1-cyano-but-4-yl and $X_1$ is CH, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is 1-cyano-but-4-yl and $X_1$ is N, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is 1-cyano-prop-3-yl and $X_1$ is CH, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is 1-cyano-prop-3-yl and $X_1$ is N, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is 3-azetidinyl and $X_1$ is CH, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is 3-azetidinyl and $X_1$ is N, V is phenylamino, benzyl, phenyl, NHMe, $NH_2$, NHEt, NHCOH, NHCOMe, NHCOEt, NHCOiPr, NHCOOMe, CONHMe, or $NHSO_2Me$.

In other embodiments, when $R_1$ is

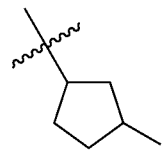 [SMILES: *C1CCC(C)C1]

and $X_1$ is CH, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

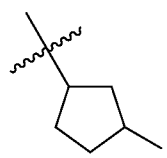 [SMILES: *C1CCC(C)C1]

and $X_1$ is N, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

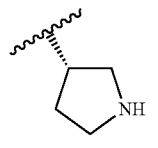 [SMILES: *[C@H]1CCNC1]

and $X_1$ is CH, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

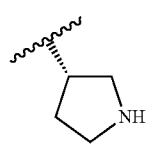 [SMILES: *[C@H]1CCNC1]

and $X_1$ is N, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

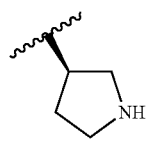

and $X_1$ is CH, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

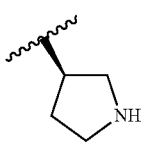 [SMILES: *[C@@H]1CCNC1]

and $X_1$ is N, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when $R_1$ is

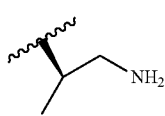 [SMILES: *[C@H](C)CN]

and $X_1$ is CH, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when $R_1$ is

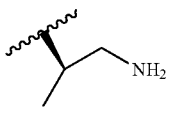 [SMILES: *[C@H](C)CN]

and $X_1$ is N, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when $R_1$ is

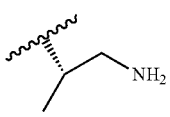

and $X_1$ is CH, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when $R_1$ is

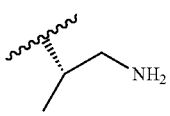

and $X_1$ is N, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when $R_1$ is

and $X_1$ is CH, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when $R_1$ is

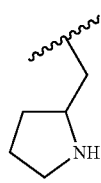

and $X_1$ is N, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when $R_1$ is

and $X_1$ is CH, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when $R_1$ is

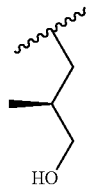

and $X_1$ is N, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when $R_1$ is

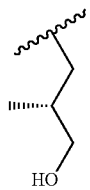 [SMILES: *C[C@@H](C)CO]

and $X_1$ is CH, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

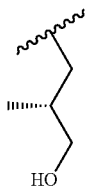

and $X_1$ is N, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

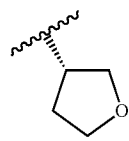 [SMILES: *[C@H]1CCOC1]

and $X_1$ is CH, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

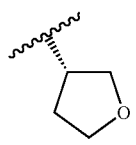 [SMILES: *[C@H]1CCOC1]

and $X_1$ is N, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

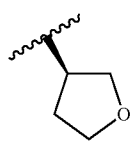 [SMILES: *[C@@H]1CCOC1]

and $X_1$ is CH, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

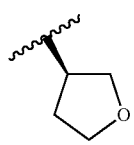 [SMILES: *[C@@H]1CCOC1]

and $X_1$ is N, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

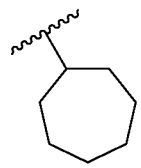 [SMILES: *C1CCCCCC1]

and $X_1$ is CH, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

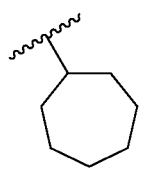 [SMILES: *C1CCCCCC1]

and $X_1$ is N, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

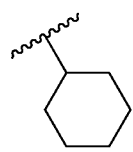 [SMILES: *C1CCCCC1]

and $X_1$ is CH, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

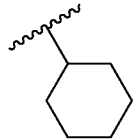 [SMILES: *C1CCCCC1]

and $X_1$ is N, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

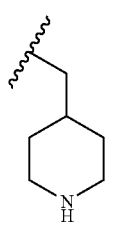 [SMILES: *CC1CCNCC1]

and $X_1$ is CH, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

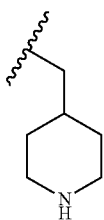 [SMILES: *CC1CCNCC1]

and $X_1$ is N, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when $R_1$ is

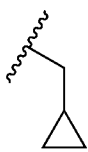 [SMILES: *CC1CC1]

and $X_1$ is CH, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when $R_1$ is

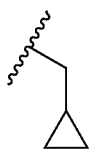 [SMILES: *CC1CC1]

and $X_1$ is N, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when $R_1$ is

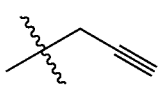 [SMILES: *CC#C]

and $X_1$ is CH, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when $R_1$ is

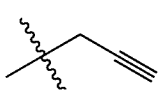 [SMILES: *CC#C]

and $X_1$ is N, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when $R_1$ is

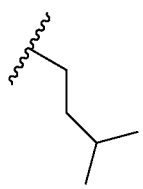 [SMILES: *CCC(C)C]

and $X_1$ is CH, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when $R_1$ is

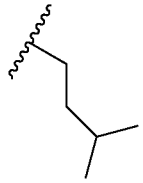 [SMILES: *CCC(C)C]

and $X_1$ is N, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when $R_1$ is

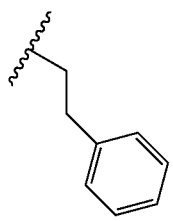 [SMILES: *CCc1ccccc1]

and $X_1$ is CH, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when $R_1$ is

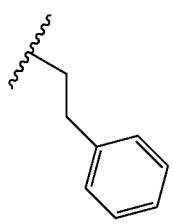 [SMILES: *CCc1ccccc1]

and $X_1$ is N, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when $R_1$ is

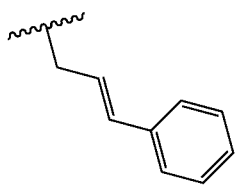 [SMILES: *C/C=C/c1ccccc1]

and X₁ is CH, V is phenylamino, benzyl, phenyl, NHMe, NH₂, NHEt, NHCOH, NHCOMe, NHCOEt, NHCOiPr, NHCOOMe, CONHMe, or NHSO₂Me. In other embodiments, when R₁ is

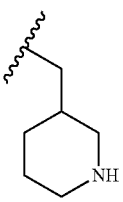

and X₁ is CH, V is phenylamino, benzyl, phenyl, NHMe, NH₂, NHEt, NHCOH, NHCOMe, NHCOEt, NHCOiPr, NHCOOMe, CONHMe, or NHSO₂Me. In other embodiments, when R₁ is

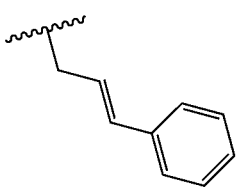 [SMILES: *C/C=C/c1ccccc1]

and X₁ is N, V is phenylamino, benzyl, phenyl, NHMe, NH₂, NHEt, NHCOH, NHCOMe, NHCOEt, NHCOiPr, NHCOOMe, CONHMe, or NHSO₂Me. In other embodiments, when R₁ is

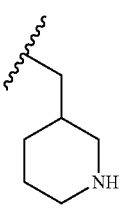

and X₁ is N, V is phenylamino, benzyl, phenyl, NHMe, NH₂, NHEt, NHCOH, NHCOMe, NHCOEt, NHCOiPr, NHCOOMe, CONHMe, or NHSO₂Me. In other embodiments, when R₁ is

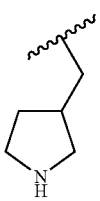 [SMILES: *CC1CCNC1]

and X₁ is CH, V is phenylamino, benzyl, phenyl, NHMe, NH₂, NHEt, NHCOH, NHCOMe, NHCOEt, NHCOiPr, NHCOOMe, CONHMe, or NHSO₂Me. In other embodiments, when R₁ is

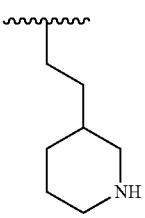

and X₁ is CH, V is phenylamino, benzyl, phenyl, NHMe, NH₂, NHEt, NHCOH, NHCOMe, NHCOEt, NHCOiPr, NHCOOMe, CONHMe, or NHSO₂Me. In other embodiments, when R₁ is

and X₁ is N, V is phenylamino, benzyl, phenyl, NHMe, NH₂, NHEt, NHCOH, NHCOMe, NHCOEt, NHCOiPr, NHCOOMe, CONHMe, or NHSO₂Me. In other embodiments, when R₁ is

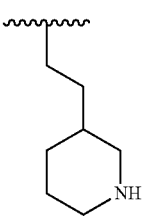

and X₁ is N, V is phenylamino, benzyl, phenyl, NHMe, NH₂, NHEt, NHCOH, NHCOMe, NHCOEt, NHCOiPr, NHCOOMe, CONHMe, or NHSO₂Me. In other embodiments, when R₁ is

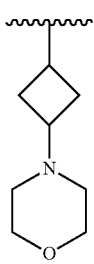

and $X_1$ is CH, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

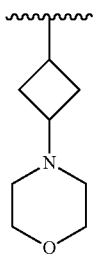

and $X_1$ is N, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

and $X_1$ is CH, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

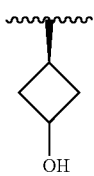

and $X_1$ is N, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

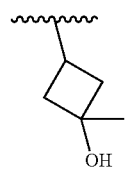 [SMILES: *C1CC(C)(O)C1]

and $X_1$ is CH, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

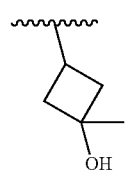 [SMILES: *C1CC(C)(O)C1]

and $X_1$ is N, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

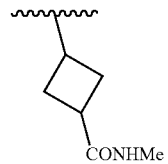

and $X_1$ is CH, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

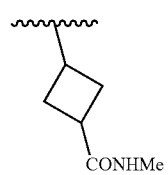

and $X_1$ is N, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

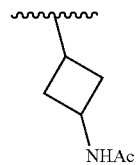 [SMILES: *C1CC(NC(C)=O)C1]

and $X_1$ is CH, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

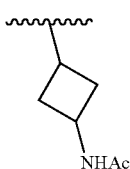 [SMILES: *C1CC(NC(C)=O)C1]

and $X_1$ is N, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when $R_1$ is

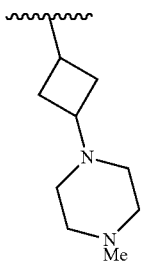 [SMILES: *C1CC(N2CCN(C)CC2)C1]

and $X_1$ is CH, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when $R_1$ is

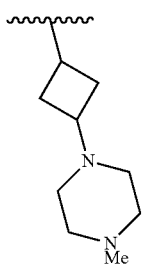 [SMILES: *C1CC(N2CCN(C)CC2)C1]

and $X_1$ is N, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when $R_1$ is

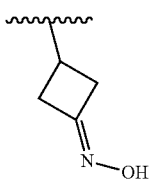 [SMILES: *C1CC(=NO)C1]

and $X_1$ is CH, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when $R_1$ is

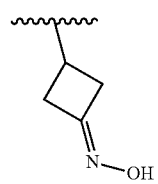 [SMILES: *C1CC(=NO)C1]

and $X_1$ is N, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when $R_1$ is

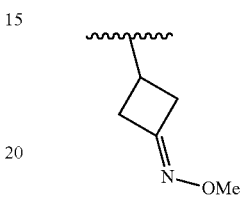

and $X_1$ is CH, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when $R_1$ is

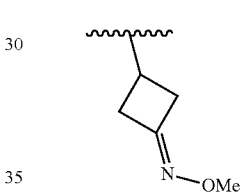

and $X_1$ is N, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when $R_1$ is

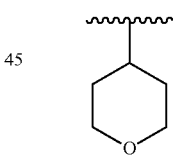

and $X_1$ is CH, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when $R_1$ is

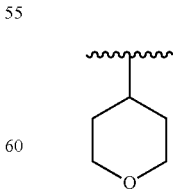

and $X_1$ is N, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when $R_1$ is

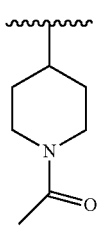

and $X_1$ is CH, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

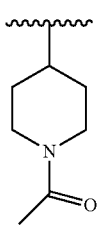

and $X_1$ is N, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

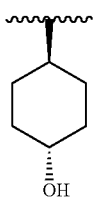

and $X_1$ is CH, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

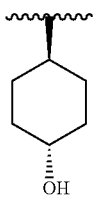

and $X_1$ is N, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

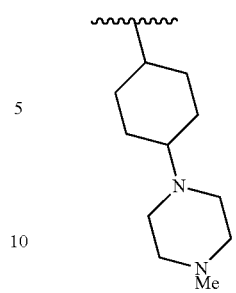

and $X_1$ is CH, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

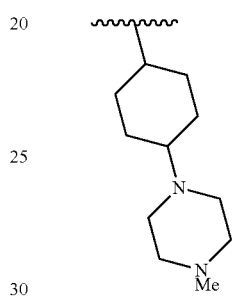

and $X_1$ is N, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

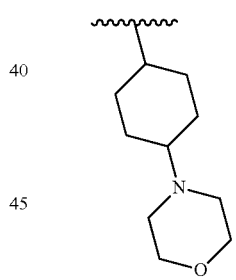

and $X_1$ is CH, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

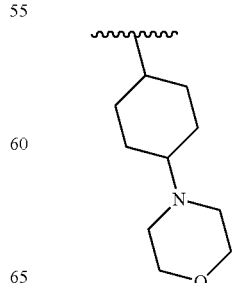

and $X_1$ is N, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when $R_1$ is

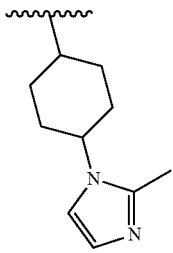 [SMILES: *C1CCC(n2ccnc2C)CC1]

and $X_1$ is CH, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when $R_1$ is

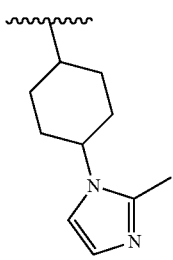 [SMILES: *C1CCC(n2ccnc2C)CC1]

and $X_1$ is N, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when $R_1$ is

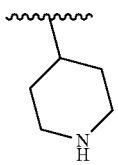 [SMILES: *C1CCNCC1]

and $X_1$ is CH, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when $R_1$ is

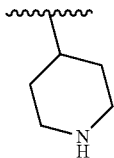

and $X_1$ is N, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when $R_1$ is

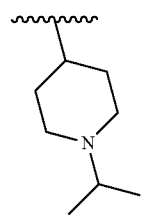

and $X_1$ is CH, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when $R_1$ is

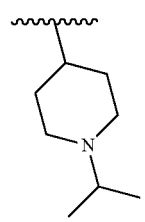 [SMILES: *C1CCN(C(C)C)CC1]

and $X_1$ is N, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when $R_1$ is

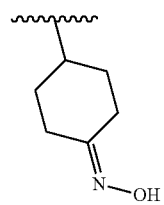 [SMILES: *C1CCC(=NO)CC1]

and $X_1$ is CH, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when $R_1$ is

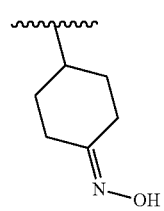 [SMILES: *C1CCC(=NO)CC1]

and $X_1$ is N, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when $R_1$ is

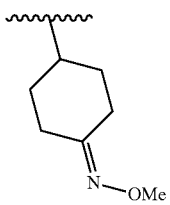 [SMILES: *C1CCC(=NOC)CC1]

and X₁ is CH, V is phenylamino, benzyl, phenyl, NHMe, NH₂, NHEt, NHCOH, NHCOMe, NHCOEt, NHCOiPr, NHCOOMe, CONHMe, or NHSO₂Me. In other embodiments, when R₁ is

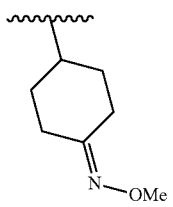 [SMILES: *C1CCC(=NOC)CC1]

and X₁ is N, V is phenylamino, benzyl, phenyl, NHMe, NHEt, NHCOH, NHCOMe, NHCOEt, NHCOiPr, NHCOOMe, CONHMe, or NHSO₂Me. In other embodiments, when R₁ is

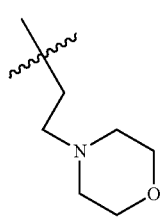 [SMILES: *CCN1CCOCC1]

and X₁ is CH, V is phenylamino, benzyl, phenyl, NHMe, NH₂, NHEt, NHCOH, NHCOMe, NHCOEt, NHCOiPr, NHCOOMe, CONHMe, or NHSO₂Me. In other embodiments, when R₁ is

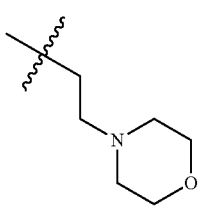 [SMILES: *CCN1CCOCC1]

and X₁ is N, V is phenylamino, benzyl, phenyl, NHMe, NH₂, NHEt, NHCOH, NHCOMe, NHCOEt, NHCOiPr, NHCOOMe, CONHMe, or NHSO₂Me. In other embodiments, when R₁ is

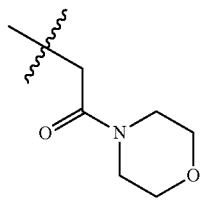 [SMILES: *CC(=O)N1CCOCC1]

and X₁ is CH, V is phenylamino, benzyl, phenyl, NHMe, NH₂, NHEt, NHCOH, NHCOMe, NHCOEt, NHCOiPr, NHCOOMe, CONHMe, or NHSO₂Me. In other embodiments, when R₁ is

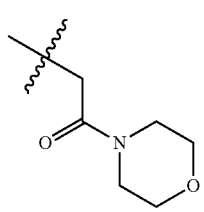 [SMILES: *CC(=O)N1CCOCC1]

and X₁ is N, V is phenylamino, benzyl, phenyl, NHMe, NHEt, NHCOH, NHCOMe, NHCOEt, NHCOiPr, NHCOOMe, CONHMe, or NHSO₂Me.

In other embodiments, when R₁ is

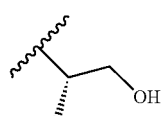

and X₁ is CH, V is phenylamino, benzyl, phenyl, NHMe, NH₂, NHEt, NHCOH, NHCOMe, NHCOEt, NHCOiPr, NHCOOMe, CONHMe, or NHSO₂Me. In other embodiments, when R₁ is

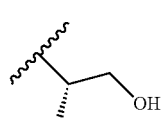

and X₁ is N, V is phenylamino, benzyl, phenyl, NHMe, NH₂, NHEt, NHCOH, NHCOMe, NHCOEt, NHCOiPr, NHCOOMe, CONHMe, or NHSO₂Me. In other embodiments, when R₁ is

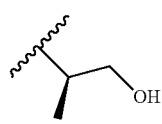 [SMILES: *[C@H](C)CO]

and X₁ is CH, V is phenylamino, benzyl, phenyl, NHMe, NH₂, NHEt, NHCOH, NHCOMe, NHCOEt, NHCOiPr, NHCOOMe, CONHMe, or NHSO₂Me. In other embodiments, when R₁ is

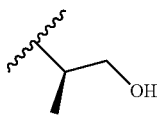

and $X_1$ is N, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when $R_1$ is

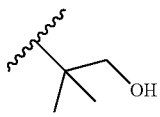 [SMILES: *C(C)(C)CO]

and $X_1$ is CH, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when $R_1$ is

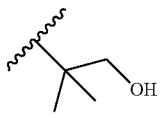

and $X_1$ is N, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when $R_1$ is

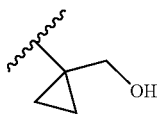 [SMILES: *C1(CO)CC1]

and $X_1$ is CH, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when $R_1$ is

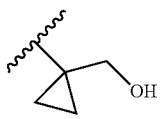

and $X_1$ is N, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when $R_1$ is

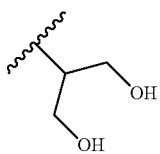 [SMILES: *C(CO)CO]

and $X_1$ is CH, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when $R_1$ is

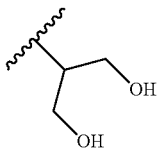 [SMILES: *C(CO)CO]

and $X_1$ is N, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when $R_1$ is

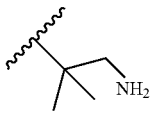 [SMILES: *C(C)(C)CN]

and $X_1$ is CH, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when $R_1$ is

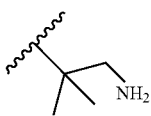 [SMILES: *C(C)(C)CN]

and $X_1$ is N, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when $R_1$ is

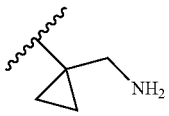

and $X_1$ is CH, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. In other embodiments, when $R_1$ is

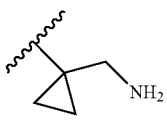 [SMILES: *C1(CN)CC1]

and $X_1$ is N, V is phenylamino, benzyl, phenyl, NHMe, NH$_2$, NHEt, NHCOH, NHCOMe, NHCOEt, NHCOiPr, NHCOOMe, CONHMe, or NHSO$_2$Me. and $X_1$ is CH, V is phenylamino, benzyl, phenyl, NHMe, NH$_2$, NHEt, NHCOH, NHCOMe, NHCOEt, NHCOiPr, NHCOOMe, CONHMe, or NHSO$_2$Me.

In other embodiments, when $R_1$ is

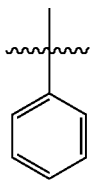 [SMILES: *c1ccccc1]

and $X_1$ is CH, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

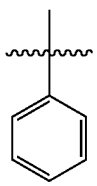 [SMILES: *c1ccccc1]

and $X_1$ is N, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

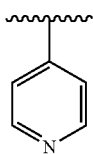

and $X_1$ is CH, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

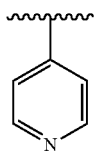

and $X_1$ is N, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

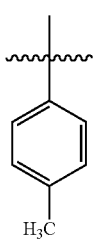

and $X_1$ is CH, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

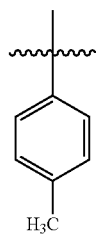

and $X_1$ is N, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

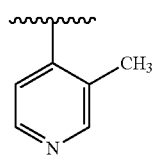 [SMILES: *c1ccncc1C]

and $X_1$ is CH, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

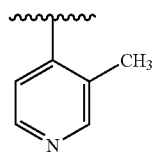 [SMILES: *c1ccncc1C]

and $X_1$ is N, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

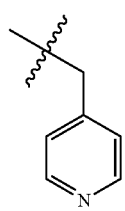

and $X_1$ is CH, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In other embodiments, when $R_1$ is

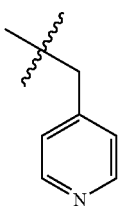 [SMILES: *Cc1ccncc1]

and X₁ is N, V is phenylamino, benzyl, phenyl, NHMe, NH₂, NHEt, NHCOH, NHCOMe, NHCOEt, NHCOiPr, NHCOOMe, CONHMe, or NHSO₂Me. In other embodiments, when R₁ is

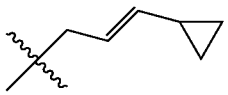 [SMILES: *C/C=C/C1CC1]

and X₁ is CH, V is phenylamino, benzyl, phenyl, NHMe, NH₂, NHEt, NHCOH, NHCOMe, NHCOEt, NHCOiPr, NHCOOMe, CONHMe, or NHSO₂Me. In other embodiments, when R₁ is

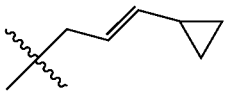 [SMILES: *C/C=C/C1CC1]

and X₁ is N, V is phenylamino, benzyl, phenyl, NHMe, NH₂, NHEt, NHCOH, NHCOMe, NHCOEt, NHCOiPr, NHCOOMe, CONHMe, or NHSO₂Me. In other embodiments, when R₁ is

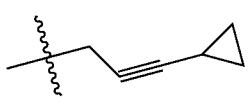 [SMILES: *CC#CC1CC1]

and X₁ is CH, V is phenylamino, benzyl, phenyl, NHMe, NH₂, NHEt, NHCOH, NHCOMe, NHCOEt, NHCOiPr, NHCOOMe, CONHMe, or NHSO₂Me. In other embodiments, when R₁ is

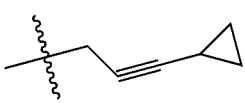 [SMILES: *CC#CC1CC1]

and X₁ is N, V is phenylamino, benzyl, phenyl, NHMe, NH₂, NHEt, NHCOH, NHCOMe, NHCOEt, NHCOiPr, NHCOOMe, CONHMe, or NHSO₂Me. In other embodiments, when R₁ is

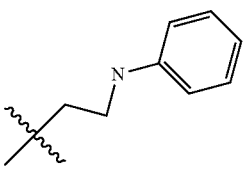 [SMILES: *CCNc1ccccc1]

and X₁ is CH, V is phenylamino, benzyl, phenyl, NHMe, NH₂, NHEt, NHCOH, NHCOMe, NHCOEt, NHCOiPr, NHCOOMe, CONHMe, or NHSO₂Me. In other embodiments, when R₁ is

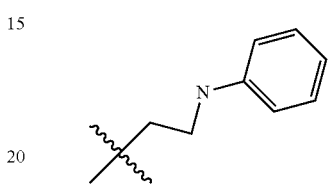

and X₁ is N, V is phenylamino, benzyl, phenyl, NHMe, NH₂, NHEt, NHCOH, NHCOMe, NHCOEt, NHCOiPr, NHCOOMe, CONHMe, or NHSO₂Me. In other embodiments, when R₁ is

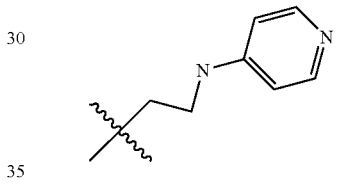

and X₁ is CH, V is phenylamino, benzyl, phenyl, NHMe, NH₂, NHEt, NHCOH, NHCOMe, NHCOEt, NHCOiPr, NHCOOMe, CONHMe, or NHSO₂Me. In other embodiments, when R₁ is

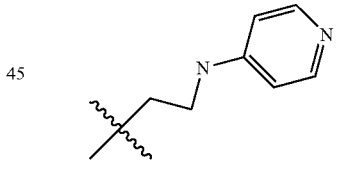

and X₁ is N, V is phenylamino, benzyl, phenyl, NHMe, NH₂, NHEt, NHCOH, NHCOMe, NHCOEt, NHCOiPr, NHCOOMe, CONHMe, or NHSO₂Me. In other embodiments, when R₁ is

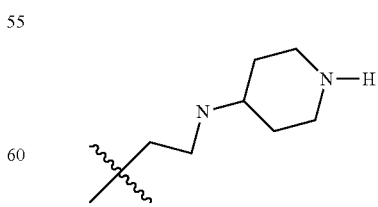

and X₁ is CH, V is phenylamino, benzyl, phenyl, NHMe, NH₂, NHEt, NHCOH, NHCOMe, NHCOEt, NHCOiPr, NHCOOMe, CONHMe, or NHSO₂Me. In other embodiments, when R₁ is

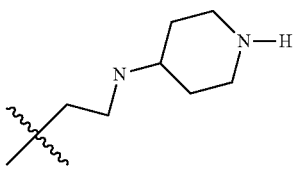 [SMILES: *CCNC1CCNCC1]

and $X_1$ is N, V is phenylamino, benzyl, phenyl, NHMe, $NH_2$, NHEt, NHCOH, NHCOMe, NHCOEt, NHCOiPr, NHCOOMe, CONHMe, or $NHSO_2Me$.

In the noted embodiments, pyridin-2-yl is

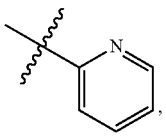 [SMILES: *c1ccccn1]

is

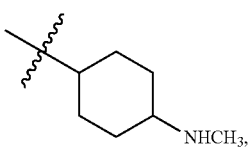

N-methylaminocyclohex-4-yl is

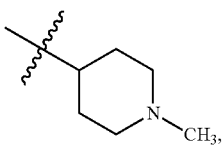 [SMILES: *C1CCN(C)CC1]

and N-methylaminocyclobut-3-yl is

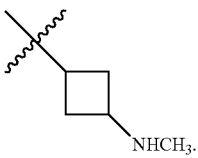

Illustrative compounds of the invention include those of subclass 1a, 1b, 2a, 2b, 3a, 3b, 4a, 4b, 5a, 5b, 6a, 6b, 7a, 7b, 8a, 8b, 9a, 9b, 10a, 10b, 11a, 11b, 12a, 12b, 13a, 13b, 14a, 14b, 15a, 15b, 16a, or 16b, where the substituents $R_1$, $X_1$, and V are as described below. In some embodiments, when $R_1$ is H and $X_1$ is CH, V is cyclopropanecarboxamido, cyclopropylamino, morpholinoethylamino, hydroxyethylamino, or N-morpholino. In other embodiments, when $R_1$ is H and $X_1$ is N, V is cyclopropanecarboxamido, cyclopropylamino, morpholinoethylamino, hydroxyethylamino, or N-morpholino. In some embodiments, when $R_1$ is $CH_3$ and $X_1$ is CH, V is cyclopropanecarboxamido, cyclopropylamino, morpholinoethylamino, hydroxyethylamino, or N-morpholino. In other embodiments, when $R_1$ is $CH_3$ and $X_1$ is N, V is cyclopropanecarboxamido, cyclopropylamino, morpholinoethylamino, hydroxyethylamino, or N-morpholino. In some embodiments, when $R_1$ is Et and $X_1$ is CH, V is cyclopropanecarboxamido, cyclopropylamino, morpholinoethylamino, hydroxyethylamino, or N-morpholino. In other embodiments, when $R_1$ is Et and $X_1$ is N, V is cyclopropanecarboxamido, cyclopropylamino, morpholinoethylamino, hydroxyethylamino, or N-morpholino. In some embodiments, when $R_1$ is iPr and $X_1$ is CH, V is cyclopropanecarboxamido, cyclopropylamino, morpholinoethylamino, hydroxyethylamino, or N-morpholino. In other embodiments, when $R_1$ is iPr and $X_1$ is N, V is cyclopropanecarboxamido, cyclopropylamino, morpholinoethylamino, hydroxyethylamino, or N-morpholino. In some embodiments, when $R_1$ is cyclobutyl and $X_1$ is CH, V is cyclopropanecarboxamido, cyclopropylamino, morpholinoethylamino, hydroxyethylamino, or N-morpholino. In other embodiments, when $R_1$ is cyclobutyl and $X_1$ is N, V is cyclopropanecarboxamido, cyclopropylamino, morpholinoethylamino, hydroxyethylamino, or N-morpholino. In some embodiments, when $R_1$ is cyclopentyl and $X_1$ is CH, V is cyclopropanecarboxamido, cyclopropylamino, morpholinoethylamino, hydroxyethylamino, or N-morpholino. In other embodiments, when $R_1$ is cyclopentyl and $X_1$ is N, V is cyclopropanecarboxamido, cyclopropylamino, morpholinoethylamino, hydroxyethylamino, or N-morpholino. In some embodiments, when $R_1$ is phenyl and $X_1$ is CH, V is cyclopropanecarboxamido, cyclopropylamino, morpholinoethylamino, hydroxyethylamino, or N-morpholino. In other embodiments, when $R_1$ is phenyl and $X_1$ is N, V is cyclopropanecarboxamido, cyclopropylamino, morpholinoethylamino, hydroxyethylamino, or N-morpholino. In some embodiments, when $R_1$ is pyridin-2-yl and $X_1$ is CH, V is cyclopropanecarboxamido, cyclopropylamino, morpholinoethylamino, hydroxyethylamino, or N-morpholino. In other embodiments, when $R_1$ is pyridin-2-yl and $X_1$ is N, V is cyclopropanecarboxamido, cyclopropylamino, morpholinoethylamino, hydroxyethylamino, or N-morpholino. In some embodiments, when $R_1$ is N-methylaminocyclohex-4-yl and $X_1$ is CH, V is cyclopropanecarboxamido, cyclopropylamino, morpholinoethylamino, hydroxyethylamino, or N-morpholino. In other embodiments, when $R_1$ is N-methylaminocyclohex-4-yl and $X_1$ is N, V is cyclopropanecarboxamido, cyclopropylamino, morpholinoethylamino, hydroxyethylamino, or N-morpholino. In some embodiments, when $R_1$ is N-methylpiperidin-4-yl and $X_1$ is CH, V is cyclopropanecarboxamido, cyclopropylamino, morpholinoethylamino, hydroxyethylamino, or N-morpholino. In other embodiments, when $R_1$ is N-methylpiperidin-4-yl and $X_1$ is N, V is cyclopropanecarboxamido, cyclopropylamino, morpholinoethylamino, hydroxyethylamino, or N-morpholino. In some embodiments, when $R_1$ is N-methylaminocyclobut-3-yl and $X_1$ is CH, V is cyclopropanecarboxamido, cyclopropylamino, morpholinoethylamino, hydroxyethylamino, or N-morpholino. In other embodiments, when $R_1$ is N-methylaminocyclobut-3-yl and $X_1$ is N, V is cyclopropanecarboxamido, cyclopropylamino, morpholinoethylamino, hydroxyethylamino, or N-morpholino. In other embodiments, when $R_1$ is tert-butyl and $X_1$ is CH, V is cyclopropanecarboxamido, cyclopropylamino, morpholinoethylamino, hydroxyethylamino, or N-morpholino. In other embodiments, when $R_1$ is tert-butyl and $X_1$ is N, V is cyclopropanecarboxamido, cyclopropylamino, morpholinoethylamino, hydroxyethylamino, or N-morpholino. In other embodiments, when $R_1$ is 1-cyanobut-4-yl and $X_1$ is CH, V is cyclopropanecarboxamido, cyclopropylamino, morpholinoethylamino, hydroxyethylamino, or N-morpholino. In other embodiments, when $R_1$ is 1-cyanobut-4-yl and $X_1$ is N, V is cyclopropanecarboxamido, cyclopropylamino, morpholinoethylamino, hydroxyethylamino, or N-morpholino. In other embodiments, when $R_1$ is 1-cyanoprop-3-yl and X₁ is CH, V is cyclopropanecarboxamido, cyclopropylamino, morpholinoethylamino, hydroxyethylamino, or N-morpholino. In other embodiments, when R₁ is 1-cyano-prop-3-yl and X₁ is N, V is cyclopropanecarboxamido, cyclopropylamino, morpholinoethylamino, hydroxyethylamino, or N-morpholino. In other embodiments, when R₁ is 3-azetidinyl and X₁ is CH, V is cyclopropanecarboxamido, cyclopropylamino, morpholinoethylamino, hydroxyethylamino, or N-morpholino. In other embodiments, when R₁ is 3-azetidinyl and X₁ is N, V is cyclopropanecarboxamido, cyclopropylamino, morpholinoethylamino, hydroxyethylamino, or N-morpholino. In other embodiments, when R₁ is

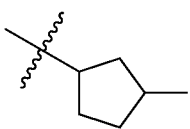 [SMILES: *C1CCC(C)C1]

and X₁ is CH, V is cyclopropanecarboxamido, cyclopropylamino, morpholinoethylamino, hydroxyethylamino, or N-morpholino. In other embodiments, when R₁ is

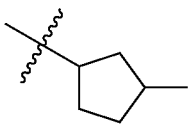 [SMILES: *C1CCC(C)C1]

and X₁ is N, V is cyclopropanecarboxamido, cyclopropylamino, morpholinoethylamino, hydroxyethylamino, or N-morpholino. In other embodiments, when R₁ is

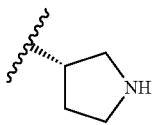 [SMILES: *[C@H]1CCNC1]

and X₁ is CH, V is cyclopropanecarboxamido, cyclopropylamino, morpholinoethylamino, hydroxyethylamino, or N-morpholino. In other embodiments, when R₁ is

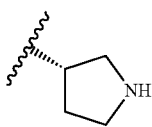 [SMILES: *[C@H]1CCNC1]

and X₁ is N, V is cyclopropanecarboxamido, cyclopropylamino, morpholinoethylamino, hydroxyethylamino, or N-morpholino. In other embodiments, when R₁ is

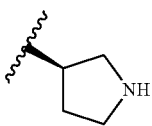 [SMILES: *[C@@H]1CCNC1]

and X₁ is CH, V is cyclopropanecarboxamido, cyclopropylamino, morpholinoethylamino, hydroxyethylamino, or N-morpholino. In other embodiments, when R₁ is

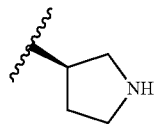 [SMILES: *[C@@H]1CCNC1]

and X₁ is N, V is cyclopropanecarboxamido, cyclopropylamino, morpholinoethylamino, hydroxyethylamino, or N-morpholino. In other embodiments, when R₁ is

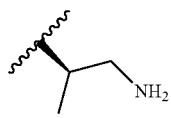 [SMILES: *[C@H](C)CN]

and X₁ is CH, V is cyclopropanecarboxamido, cyclopropylamino, morpholinoethylamino, hydroxyethylamino, or N-morpholino. In other embodiments, when R₁ is

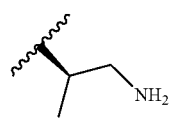 [SMILES: *[C@H](C)CN]

and X₁ is N, V is cyclopropanecarboxamido, cyclopropylamino, morpholinoethylamino, hydroxyethylamino, or N-morpholino. In other embodiments, when R₁ is

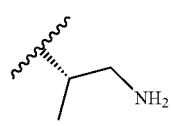 [SMILES: *[C@@H](C)CN]

and X₁ is CH, V is cyclopropanecarboxamido, cyclopropylamino, morpholinoethylamino, hydroxyethylamino, or N-morpholino. In other embodiments, when R₁ is

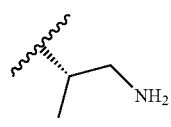 [SMILES: *[C@@H](C)CN]

and X₁ is N, V is cyclopropanecarboxamido, cyclopropylamino, morpholinoethylamino, hydroxyethylamino, or N-morpholino. In other embodiments, when R₁ is

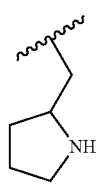 [SMILES: *CC1CCCN1]

and X₁ is CH, V is cyclopropanecarboxamido, cyclopropylamino, morpholinoethylamino, hydroxyethylamino, or N-morpholino. In other embodiments, when R₁ is

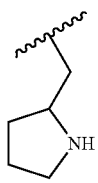

and $X_1$ is N, V is cyclopropanecarboxamido, cyclopropylamino, morpholinoethylamino, hydroxyethylamino, or N-morpholino. In other embodiments, when $R_1$ is

and $X_1$ is CH, V is cyclopropanecarboxamido, cyclopropylamino, morpholinoethylamino, hydroxyethylamino, or N-morpholino. In other embodiments, when $R_1$ is

and $X_1$ is N, V is cyclopropanecarboxamido, cyclopropylamino, morpholinoethylamino, hydroxyethylamino, or N-morpholino. In other embodiments, when $R_1$ is

and $X_1$ is CH, V is cyclopropanecarboxamido, cyclopropylamino, morpholinoethylamino, hydroxyethylamino, or N-morpholino. In other embodiments, when $R_1$ is

and $X_1$ is N, V is cyclopropanecarboxamido, cyclopropylamino, morpholinoethylamino, hydroxyethylamino, or N-morpholino. In other embodiments, when $R_1$ is

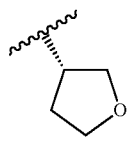 [SMILES: *[C@H]1CCOC1]

and $X_1$ is CH, V is cyclopropanecarboxamido, cyclopropylamino, morpholinoethylamino, hydroxyethylamino, or N-morpholino. In other embodiments, when $R_1$ is

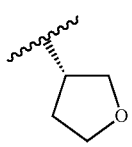

and $X_1$ is N, V is cyclopropanecarboxamido, cyclopropylamino, morpholinoethylamino, hydroxyethylamino, or N-morpholino. In other embodiments, when $R_1$ is

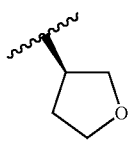 [SMILES: *[C@@H]1CCOC1]

and $X_1$ is CH, V is cyclopropanecarboxamido, cyclopropylamino, morpholinoethylamino, hydroxyethylamino, or N-morpholino. In other embodiments, when $R_1$ is

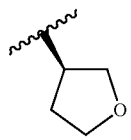 [SMILES: *[C@@H]1CCOC1]

and $X_1$ is N, V is cyclopropanecarboxamido, cyclopropylamino, morpholinoethylamino, hydroxyethylamino, or N-morpholino. In other embodiments, when $R_1$ is

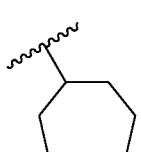

and $X_1$ is CH, V is cyclopropanecarboxamido, cyclopropylamino, morpholinoethylamino, hydroxyethylamino, or N-morpholino. In other embodiments, when $R_1$ is

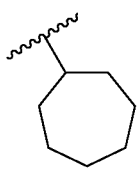 [SMILES: *C1CCCCCC1]

and $X_1$ is N, V is cyclopropanecarboxamido, cyclopropylamino, morpholinoethylamino, hydroxyethylamino, or N-morpholino. In other embodiments, when $R_1$ is

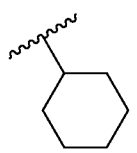

and $X_1$ is CH, V is cyclopropanecarboxamido, cyclopropylamino, morpholinoethylamino, hydroxyethylamino, or N-morpholino. In other embodiments, when $R_1$ is

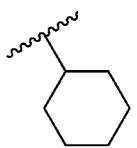 [SMILES: *C1CCCCC1]

and $X_1$ is N, V is cyclopropanecarboxamido, cyclopropylamino, morpholinoethylamino, hydroxyethylamino, or N-morpholino. In other embodiments, when $R_1$ is

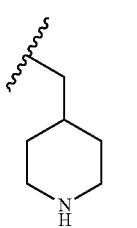 [SMILES: *CC1CCNCC1]

and $X_1$ is CH, V is cyclopropanecarboxamido, cyclopropylamino, morpholinoethylamino, hydroxyethylamino, or N-morpholino. In other embodiments, when $R_1$ is

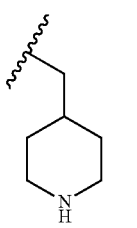 [SMILES: *CC1CCNCC1]

and $X_1$ is N, V is cyclopropanecarboxamido, cyclopropylamino, morpholinoethylamino, hydroxyethylamino, or N-morpholino. In other embodiments, when $R_1$ is

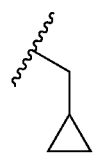 [SMILES: *CC1CC1]

and $X_1$ is CH, V is cyclopropanecarboxamido, cyclopropylamino, morpholinoethylamino, hydroxyethylamino, or N-morpholino. In other embodiments, when $R_1$ is

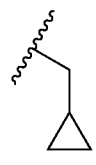 [SMILES: *CC1CC1]

and $X_1$ is N, V is cyclopropanecarboxamido, cyclopropylamino, morpholinoethylamino, hydroxyethylamino, or N-morpholino. In other embodiments, when $R_1$ is

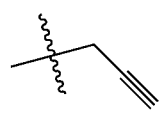 [SMILES: *CC#C]

and $X_1$ is CH, V is cyclopropanecarboxamido, cyclopropylamino, morpholinoethylamino, hydroxyethylamino, or N-morpholino. In other embodiments, when $R_1$ is

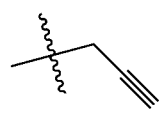 [SMILES: *CC#C]

and $X_1$ is N, V is cyclopropanecarboxamido, cyclopropylamino, morpholinoethylamino, hydroxyethylamino, or N-morpholino. In other embodiments, when $R_1$ is

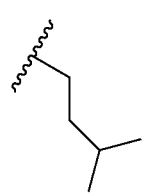 [SMILES: *CCC(C)C]

and $X_1$ is CH, V is cyclopropanecarboxamido, cyclopropylamino, morpholinoethylamino, hydroxyethylamino, or N-morpholino. In other embodiments, when $R_1$ is

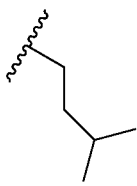 [SMILES: *CCC(C)C]

and $X_1$ is N, V is cyclopropanecarboxamido, cyclopropylamino, morpholinoethylamino, hydroxyethylamino, or N-morpholino. In other embodiments, when $R_1$ is

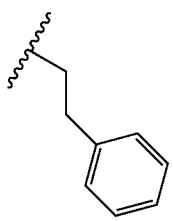 [SMILES: *CCc1ccccc1]

and $X_1$ is CH, V is cyclopropanecarboxamido, cyclopropylamino, morpholinoethylamino, hydroxyethylamino, or N-morpholino. In other embodiments, when $R_1$ is

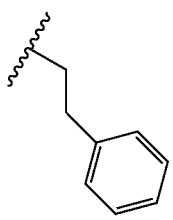 [SMILES: *CCc1ccccc1]

and $X_1$ is N, V is cyclopropanecarboxamido, cyclopropylamino, morpholinoethylamino, hydroxyethylamino, or N-morpholino. In other embodiments, when $R_1$ is

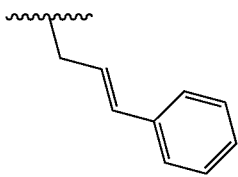 [SMILES: *C/C=C/c1ccccc1]

and $X_1$ is CH, V is cyclopropanecarboxamido, cyclopropylamino, morpholinoethylamino, hydroxyethylamino, or N-morpholino. In other embodiments, when $R_1$ is

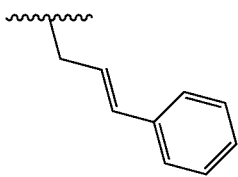 [SMILES: *C/C=C/c1ccccc1]

and $X_1$ is N, V is cyclopropanecarboxamido, cyclopropylamino, morpholinoethylamino, hydroxyethylamino, or N-morpholino. In other embodiments, when $R_1$ is

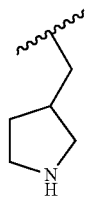 [SMILES: *CC1CCNC1]

and $X_1$ is CH, V is cyclopropanecarboxamido, cyclopropylamino, morpholinoethylamino, hydroxyethylamino, or N-morpholino. In other embodiments, when $R_1$ is

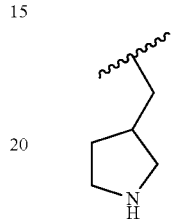

and $X_1$ is N, V is cyclopropanecarboxamido, cyclopropylamino, morpholinoethylamino, hydroxyethylamino, or N-morpholino. In other embodiments, when $R_1$ is

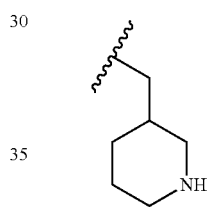

and $X_1$ is CH, V is cyclopropanecarboxamido, cyclopropylamino, morpholinoethylamino, hydroxyethylamino, or N-morpholino. In other embodiments, when $R_1$ is

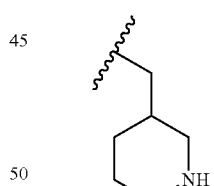

and $X_1$ is N, V is cyclopropanecarboxamido, cyclopropylamino, morpholinoethylamino, hydroxyethylamino, or N-morpholino. In other embodiments, when $R_1$ is

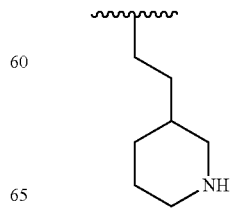

and X₁ is CH, V is cyclopropanecarboxamido, cyclopropylamino, morpholinoethylamino, hydroxyethylamino, or N-morpholino. In other embodiments, when R₁ is

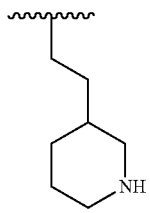 [SMILES: *CCC1CCCNC1]

and X₁ is N, V is cyclopropanecarboxamido, cyclopropylamino, morpholinoethylamino, hydroxyethylamino, or N-morpholino. In other embodiments, when R₁ is

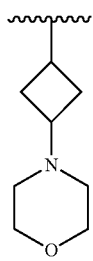 [SMILES: *C1CC(N2CCOCC2)C1]

and X₁ is CH, V is cyclopropanecarboxamido, cyclopropylamino, morpholinoethylamino, hydroxyethylamino, or N-morpholino. In other embodiments, when R₁ is

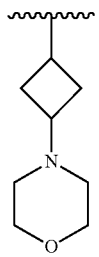 [SMILES: *C1CC(N2CCOCC2)C1]

and X₁ is N, V is cyclopropanecarboxamido, cyclopropylamino, morpholinoethylamino, hydroxyethylamino, or N-morpholino. In other embodiments, when R₁ is

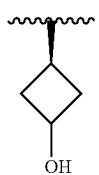

and X₁ is CH, V is cyclopropanecarboxamido, cyclopropylamino, morpholinoethylamino, hydroxyethylamino, or N-morpholino. In other embodiments, when R₁ is

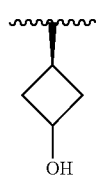

and X₁ is N, V is cyclopropanecarboxamido, cyclopropylamino, morpholinoethylamino, hydroxyethylamino, or N-morpholino. In other embodiments, when R₁ is

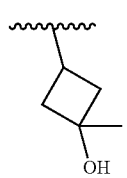 [SMILES: *C1CC(C)(O)C1]

and X₁ is CH, V is cyclopropanecarboxamido, cyclopropylamino, morpholinoethylamino, hydroxyethylamino, or N-morpholino. In other embodiments, when R₁ is

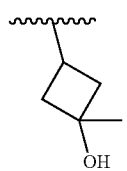 [SMILES: *C1CC(C)(O)C1]

and X₁ is N, V is cyclopropanecarboxamido, cyclopropylamino, morpholinoethylamino, hydroxyethylamino, or N-morpholino. In other embodiments, when R₁ is

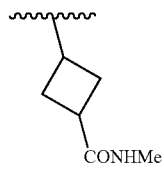

and X₁ is CH, V is cyclopropanecarboxamido, cyclopropylamino, morpholinoethylamino, hydroxyethylamino, or N-morpholino. In other embodiments, when R₁ is

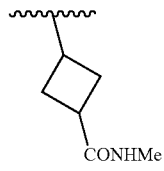

and X₁ is N, V is cyclopropanecarboxamido, cyclopropylamino, morpholinoethylamino, hydroxyethylamino, or N-morpholino. In other embodiments, when R₁ is

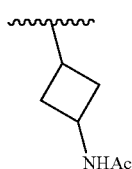 [SMILES: *C1CC(NC(C)=O)C1]

and X₁ is CH, V is cyclopropanecarboxamido, cyclopropylamino, morpholinoethylamino, hydroxyethylamino, or N-morpholino. In other embodiments, when R₁ is

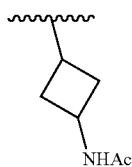 [SMILES: *C1CC(NC(C)=O)C1]

and X₁ is N, V is cyclopropanecarboxamido, cyclopropylamino, morpholinoethylamino, hydroxyethylamino, or N-morpholino. In other embodiments, when R₁ is

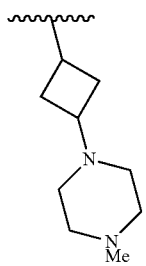 [SMILES: *C1CC(N2CCN(C)CC2)C1]

and X₁ is CH, V is cyclopropanecarboxamido, cyclopropylamino, morpholinoethylamino, hydroxyethylamino, or N-morpholino. In other embodiments, when R₁ is

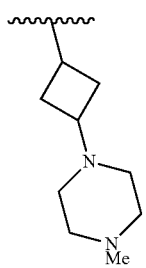 [SMILES: *C1CC(N2CCN(C)CC2)C1]

and X₁ is N, V is cyclopropanecarboxamido, cyclopropylamino, morpholinoethylamino, hydroxyethylamino, or N-morpholino. In other embodiments, when R₁ is

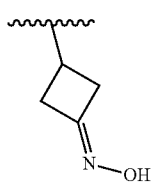 [SMILES: *C1CC(=NO)C1]

and X₁ is CH, V is cyclopropanecarboxamido, cyclopropylamino, morpholinoethylamino, hydroxyethylamino, or N-morpholino. In other embodiments, when R₁ is

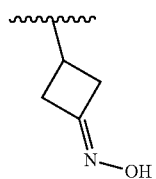 [SMILES: *C1CC(=NO)C1]

and X₁ is N, V is cyclopropanecarboxamido, cyclopropylamino, morpholinoethylamino, hydroxyethylamino, or N-morpholino. In other embodiments, when R₁ is

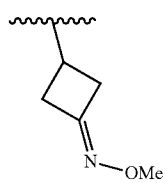 [SMILES: *C1CC(=NOC)C1]

and X₁ is CH, V is cyclopropanecarboxamido, cyclopropylamino, morpholinoethylamino, hydroxyethylamino, or N-morpholino. In other embodiments, when R₁ is

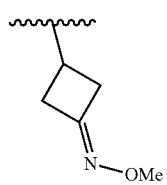 [SMILES: *C1CC(=NOC)C1]

and X₁ is N, V is cyclopropanecarboxamido, cyclopropylamino, morpholinoethylamino, hydroxyethylamino, or N-morpholino. In other embodiments, when R₁ is

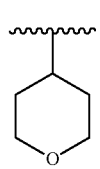

and X₁ is CH, V is cyclopropanecarboxamido, cyclopropylamino, morpholinoethylamino, hydroxyethylamino, or N-morpholino. In other embodiments, when R₁ is

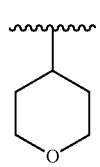

and X₁ is N, V is cyclopropanecarboxamido, cyclopropylamino, morpholinoethylamino, hydroxyethylamino, or N-morpholino. In other embodiments, when R₁ is

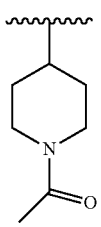

and $X_1$ is CH, V is cyclopropanecarboxamido, cyclopropylamino, morpholinoethylamino, hydroxyethylamino, or N-morpholino. In other embodiments, when $R_1$ is

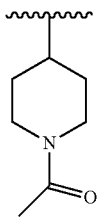

and $X_1$ is N, V is cyclopropanecarboxamido, cyclopropylamino, morpholinoethylamino, hydroxyethylamino, or N-morpholino. In other embodiments, when $R_1$ is

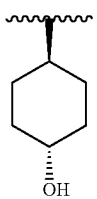

and $X_1$ is CH, V is cyclopropanecarboxamido, cyclopropylamino, morpholinoethylamino, hydroxyethylamino, or N-morpholino. In other embodiments, when $R_1$ is

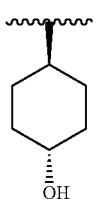

and $X_1$ is N, V is cyclopropanecarboxamido, cyclopropylamino, morpholinoethylamino, hydroxyethylamino, or N-morpholino. In other embodiments, when $R_1$ is

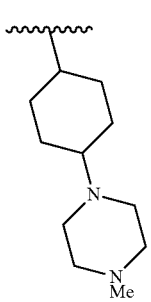 [SMILES: *C1CCC(N2CCN(C)CC2)CC1]

and $X_1$ is CH, V is cyclopropanecarboxamido, cyclopropylamino, morpholinoethylamino, hydroxyethylamino, or N-morpholino. In other embodiments, when $R_1$ is

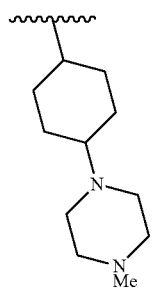 [SMILES: *C1CCC(N2CCN(C)CC2)CC1]

and $X_1$ is N, V is cyclopropanecarboxamido, cyclopropylamino, morpholinoethylamino, hydroxyethylamino, or N-morpholino. In other embodiments, when $R_1$ is

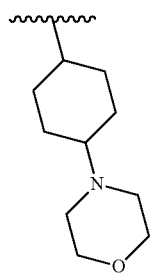 [SMILES: *C1CCC(N2CCOCC2)CC1]

and $X_1$ is CH, V is cyclopropanecarboxamido, cyclopropylamino, morpholinoethylamino, hydroxyethylamino, or N-morpholino. In other embodiments, when $R_1$ is

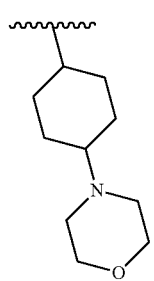 [SMILES: *C1CCC(N2CCOCC2)CC1]

and $X_1$ is N, V is cyclopropanecarboxamido, cyclopropylamino, morpholinoethylamino, hydroxyethylamino, or N-morpholino. In other embodiments, when $R_1$ is

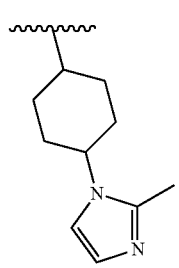 [SMILES: *C1CCC(n2ccnc2C)CC1]

and $X_1$ is CH, V is cyclopropanecarboxamido, cyclopropylamino, morpholinoethylamino, hydroxyethylamino, or N-morpholino. In other embodiments, when $R_1$ is

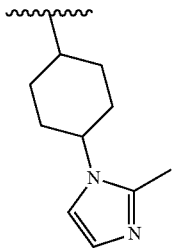 [SMILES: *C1CCC(n2ccnc2C)CC1]

and $X_1$ is N, V is cyclopropanecarboxamido, cyclopropylamino, morpholinoethylamino, hydroxyethylamino, or N-morpholino. In other embodiments, when $R_1$ is

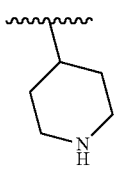 [SMILES: *C1CCNCC1]

and $X_1$ is CH, V is cyclopropanecarboxamido, cyclopropylamino, morpholinoethylamino, hydroxyethylamino, or N-morpholino. In other embodiments, when $R_1$ is

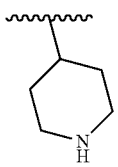 [SMILES: *C1CCNCC1]

and $X_1$ is N, V is cyclopropanecarboxamido, cyclopropylamino, morpholinoethylamino, hydroxyethylamino, or N-morpholino. In other embodiments, when $R_1$ is

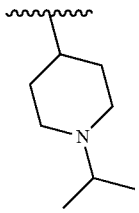

and $X_1$ is CH, V is cyclopropanecarboxamido, cyclopropylamino, morpholinoethylamino, hydroxyethylamino, or N-morpholino. In other embodiments, when $R_1$ is

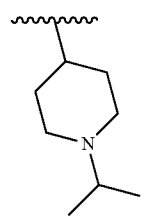

and $X_1$ is N, V is cyclopropanecarboxamido, cyclopropylamino, morpholinoethylamino, hydroxyethylamino, or N-morpholino. In other embodiments, when $R_1$ is

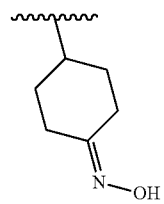 [SMILES: *C1CCC(=NO)CC1]

and $X_1$ is CH, V is cyclopropanecarboxamido, cyclopropylamino, morpholinoethylamino, hydroxyethylamino, or N-morpholino. In other embodiments, when $R_1$ is

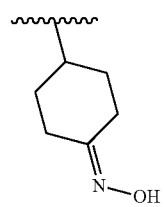 [SMILES: *C1CCC(=NO)CC1]

and $X_1$ is N, V is cyclopropanecarboxamido, cyclopropylamino, morpholinoethylamino, hydroxyethylamino, or N-morpholino. In other embodiments, when $R_1$ is

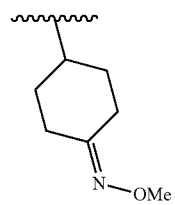 [SMILES: *C1CCC(=NOC)CC1]

and $X_1$ is CH, V is cyclopropanecarboxamido, cyclopropylamino, morpholinoethylamino, hydroxyethylamino, or N-morpholino. In other embodiments, when $R_1$ is

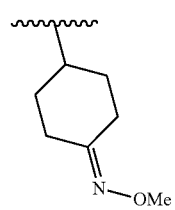 [SMILES: *C1CCC(=NOC)CC1]

and X₁ is N, V is cyclopropanecarboxamido, cyclopropylamino, morpholinoethylamino, hydroxyethylamino, or N-morpholino. In other embodiments, when R₁ is

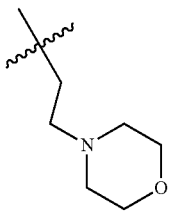 [SMILES: *CCN1CCOCC1]

and X₁ is CH, V is cyclopropanecarboxamido, cyclopropylamino, morpholinoethylamino, hydroxyethylamino, or N-morpholino. In other embodiments, when R₁ is

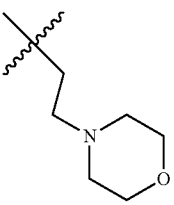 [SMILES: *CCN1CCOCC1]

and X₁ is N, V is cyclopropanecarboxamido, cyclopropylamino, morpholinoethylamino, hydroxyethylamino, or N-morpholino. In other embodiments, when R₁ is

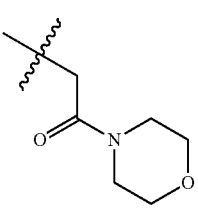 [SMILES: *CC(=O)N1CCOCC1]

and X₁ is CH, V is cyclopropanecarboxamido, cyclopropylamino, morpholinoethylamino, hydroxyethylamino, or N-morpholino. In other embodiments, when R₁ is

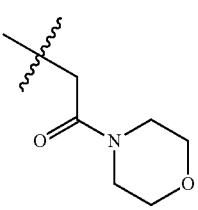 [SMILES: *CC(=O)N1CCOCC1]

and X₁ is N, V is cyclopropanecarboxamido, cyclopropylamino, morpholinoethylamino, hydroxyethylamino, or N-morpholino.

In other embodiments, when R₁ is

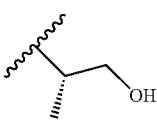 [SMILES: *[C@@H](C)CO]

and X₁ is CH, V is cyclopropanecarboxamido, cyclopropylamino, morpholinoethylamino, hydroxyethylamino, or N-morpholino. In other embodiments, when R₁ is

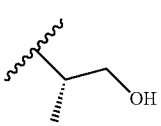

and X₁ is N, V is cyclopropanecarboxamido, cyclopropylamino, morpholinoethylamino, hydroxyethylamino, or N-morpholino. In other embodiments, when R₁ is

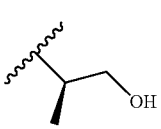

and X₁ is CH, V is cyclopropanecarboxamido, cyclopropylamino, morpholinoethylamino, hydroxyethylamino, or N-morpholino. In other embodiments, when R₁ is

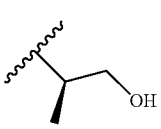 [SMILES: *[C@H](C)CO]

and X₁ is N, V is cyclopropanecarboxamido, cyclopropylamino, morpholinoethylamino, hydroxyethylamino, or N-morpholino. In other embodiments, when R₁ is

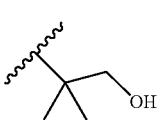 [SMILES: *C(C)(C)CO]

and X₁ is CH, V is cyclopropanecarboxamido, cyclopropylamino, morpholinoethylamino, hydroxyethylamino, or N-morpholino. In other embodiments, when R₁ is

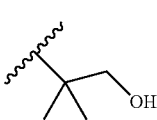 [SMILES: *C(C)(C)CO]

and X₁ is N, V is cyclopropanecarboxamido, cyclopropylamino, morpholinoethylamino, hydroxyethylamino, or N-morpholino. In other embodiments, when R₁ is

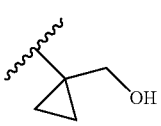 [SMILES: *C1(CO)CC1]

and X₁ is CH, V is cyclopropanecarboxamido, cyclopropylamino, morpholinoethylamino, hydroxyethylamino, or N-morpholino. In other embodiments, when R₁ is

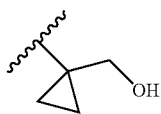 [SMILES: *C1(CO)CC1]

and $X_1$ is N, V is cyclopropanecarboxamido, cyclopropylamino, morpholinoethylamino, hydroxyethylamino, or N-morpholino. In other embodiments, when $R_1$ is

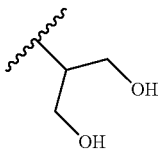 [SMILES: *C(CO)CO]

and $X_1$ is CH, V is cyclopropanecarboxamido, cyclopropylamino, morpholinoethylamino, hydroxyethylamino, or N-morpholino. In other embodiments, when $R_1$ is

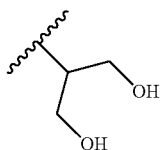 [SMILES: *C(CO)CO]

and $X_1$ is N, V is cyclopropanecarboxamido, cyclopropylamino, morpholinoethylamino, hydroxyethylamino, or N-morpholino. In other embodiments, when $R_1$ is

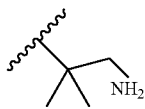

and $X_1$ is CH, V is cyclopropanecarboxamido, cyclopropylamino, morpholinoethylamino, hydroxyethylamino, or N-morpholino. In other embodiments, when $R_1$ is

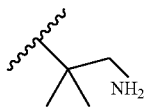 [SMILES: *C(C)(C)CN]

and $X_1$ is N, V is cyclopropanecarboxamido, cyclopropylamino, morpholinoethylamino, hydroxyethylamino, or N-morpholino In other embodiments, when $R_1$ is

and $X_1$ is CH, V is cyclopropanecarboxamido, cyclopropylamino, morpholinoethylamino, hydroxyethylamino, or N-morpholino. In other embodiments, when $R_1$ is

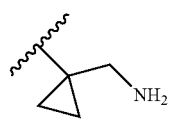 [SMILES: *C1(CN)CC1]

and $X_1$ is N, V is cyclopropanecarboxamido, cyclopropylamino, morpholinoethylamino, hydroxyethylamino, or N-morpholino. and $X_1$ is CH, V is cyclopropanecarboxamido, cyclopropylamino, morpholinoethylamino, hydroxyethylamino, or N-morpholino.

In other embodiments, when $R_1$ is

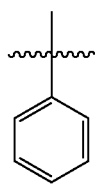

and $X_1$ is CH, V is cyclopropanecarboxamido, cyclopropylamino, morpholinoethylamino, hydroxyethylamino, or N-morpholino. In other embodiments, when $R_1$ is

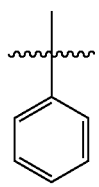

and $X_1$ is N, V is cyclopropanecarboxamido, cyclopropylamino, morpholinoethylamino, hydroxyethylamino, or N-morpholino. In other embodiments, when $R_1$ is

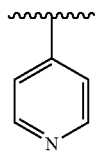

and $X_1$ is CH, V is cyclopropanecarboxamido, cyclopropylamino, morpholinoethylamino, hydroxyethylamino, or N-morpholino. In other embodiments, when $R_1$ is

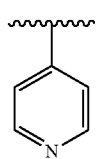

and $X_1$ is N, V is cyclopropanecarboxamido, cyclopropylamino, morpholinoethylamino, hydroxyethylamino, or N-morpholino. In other embodiments, when $R_1$ is

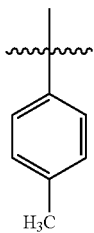

and X₁ is CH, V is cyclopropanecarboxamido, cyclopropylamino, morpholinoethylamino, hydroxyethylamino, or N-morpholino. In other embodiments, when R₁ is

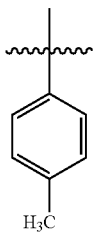

and X₁ is N, V is cyclopropanecarboxamido, cyclopropylamino, morpholinoethylamino, hydroxyethylamino, or N-morpholino. In other embodiments, when R₁ is

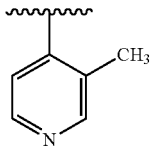 [SMILES: *c1ccncc1C]

and X₁ is CH, V is cyclopropanecarboxamido, cyclopropylamino, morpholinoethylamino, hydroxyethylamino, or N-morpholino. In other embodiments, when R₁ is

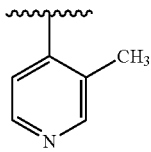

and X₁ is N, V is cyclopropanecarboxamido, cyclopropylamino, morpholinoethylamino, hydroxyethylamino, or N-morpholino. In other embodiments, when R₁ is

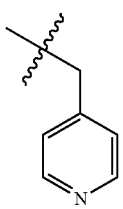 [SMILES: *Cc1ccncc1]

and X₁ is CH, V is cyclopropanecarboxamido, cyclopropylamino, morpholinoethylamino, hydroxyethylamino, or N-morpholino. In other embodiments, when R₁ is

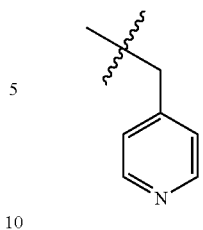

and X₁ is N, V is cyclopropanecarboxamido, cyclopropylamino, morpholinoethylamino, hydroxyethylamino, or N-morpholino. In other embodiments, when R₁ is

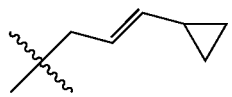 [SMILES: *C/C=C/C1CC1]

and X₁ is CH, V is cyclopropanecarboxamido, cyclopropylamino, morpholinoethylamino, hydroxyethylamino, or N-morpholino. In other embodiments, when R₁ is

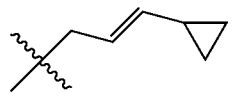 [SMILES: *C/C=C/C1CC1]

and X₁ is N, V is cyclopropanecarboxamido, cyclopropylamino, morpholinoethylamino, hydroxyethylamino, or N-morpholino. In other embodiments, when R₁ is

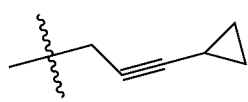 [SMILES: *CC#CC1CC1]

and X₁ is CH, V is cyclopropanecarboxamido, cyclopropylamino, morpholinoethylamino, hydroxyethylamino, or N-morpholino. In other embodiments, when R₁ is

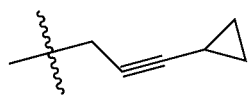 [SMILES: *CC#CC1CC1]

and X₁ is N, V is cyclopropanecarboxamido, cyclopropylamino, morpholinoethylamino, hydroxyethylamino, or N-morpholino. In other embodiments, when R₁ is

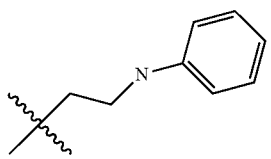 [SMILES: *CCNc1ccccc1]

and $X_1$ is CH, V is cyclopropanecarboxamido, cyclopropylamino, morpholinoethylamino, hydroxyethylamino, or N-morpholino. In other embodiments, when $R_1$ is

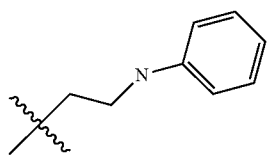 [SMILES: *CCNc1ccccc1]

and $X_1$ is N, V is cyclopropanecarboxamido, cyclopropylamino, morpholinoethylamino, hydroxyethylamino, or N-morpholino. In other embodiments, when $R_1$ is

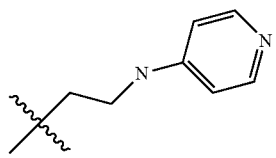 [SMILES: *CCNc1ccncc1]

and $X_1$ is CH, V is cyclopropanecarboxamido, cyclopropylamino, morpholinoethylamino, hydroxyethylamino, or N-morpholino. In other embodiments, when $R_1$ is

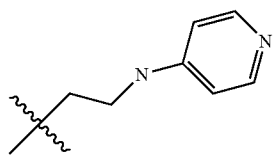 [SMILES: *CCNc1ccncc1]

and $X_1$ is N, V is cyclopropanecarboxamido, cyclopropylamino, morpholinoethylamino, hydroxyethylamino, or N-morpholino. In other embodiments, when $R_1$ is

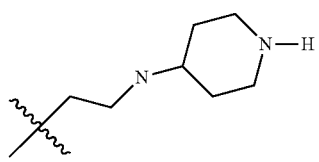 [SMILES: *CCNC1CCNCC1]

and $X_1$ is CH, V is cyclopropanecarboxamido, cyclopropylamino, morpholinoethylamino, hydroxyethylamino, or N-morpholino. In other embodiments, when $R_1$ is

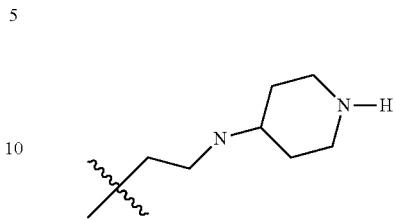

and $X_1$ is N, V is cyclopropanecarboxamido, cyclopropylamino, morpholinoethylamino, hydroxyethylamino, or N-morpholino.

In the noted embodiments, cyclopropanecarboxamido is

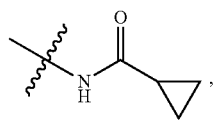 [SMILES: *NC(=O)C1CC1]

cyclopropylamino is

2-morpholinoethylamino is

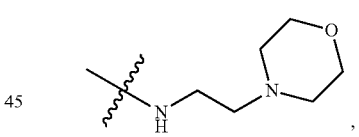

hydroxyethylamino is

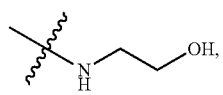 [SMILES: *NCCO]

and N-morpholino is

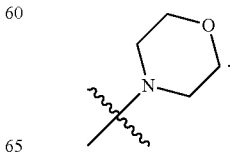

TABLE 1

Biological activity of several illustrative mTor inhibitor compounds of the invention.

| Structure | mTOR IC$_{50}$ (nM) | PI3K α IC$_{50}$ (nM) | PI3K β IC$_{50}$ (nM) | PI3K γ IC$_{50}$ (nM) | PI3K δ IC$_{50}$ (nM) | PC3 EC50 (nM) |
|---|---|---|---|---|---|---|
| 1 | ++++ | +++ | ++ | ++++ | +++ | ++++ |
| 2 | ++++ | ++ | + | +++ | +++ | +++ |
| 3 | ++ | + | ++ | ++ | ++ | |
| 4 | +++ | ++ | ++ | +++ | +++ | ++ |

TABLE 1-continued

Biological activity of several illustrative mTor inhibitor compounds of the invention.

| | Structure | mTOR $IC_{50}$ (nM) | PI3K α $IC_{50}$ (nM) | PI3K β $IC_{50}$ (nM) | PI3K γ $IC_{50}$ (nM) | PI3K δ $IC_{50}$ (nM) | PC3 $EC50$ (nM) |
|---|---|---|---|---|---|---|---|
| 5 | 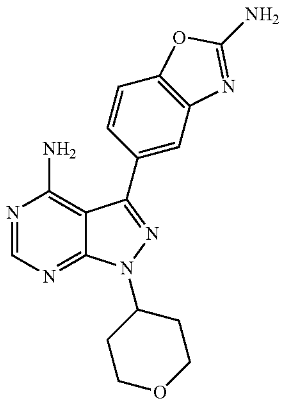 [SMILES: Nc1nc2cc(-c3nn(C4CCOCC4)c4ncnc(N)c34)ccc2o1] | ++++ | +++ | ++ | ++++ | +++ | ++++ |
| 6 | 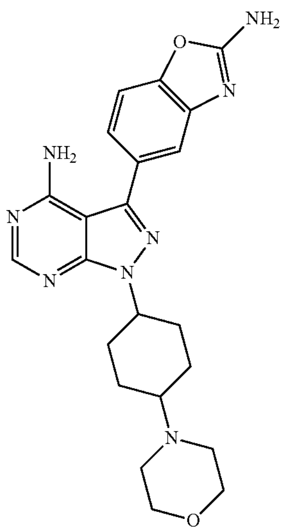 [SMILES: Nc1nc2cc(-c3nn(C4CCC(N5CCOCC5)CC4)c4ncnc(N)c34)ccc2o1] | ++++ | ++ | + | ++ | +++ | +++ |
| 7 | 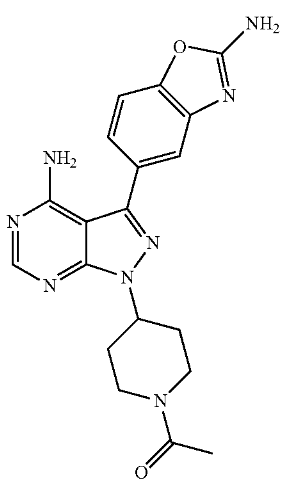 [SMILES: CC(=O)N1CCC(n2nc(-c3ccc4oc(N)nc4c3)c3c(N)ncnc32)CC1] | ++++ | +++ | ++ | ++ | +++ | ++ |

TABLE 1-continued

Biological activity of several illustrative mTor inhibitor compounds of the invention.

| | Structure | mTOR IC$_{50}$ (nM) | PI3K α IC$_{50}$ (nM) | PI3K β IC$_{50}$ (nM) | PI3K γ IC$_{50}$ (nM) | PI3K δ IC$_{50}$ (nM) | PC3 EC50 (nM) |
|---|---|---|---|---|---|---|---|
| 8 | 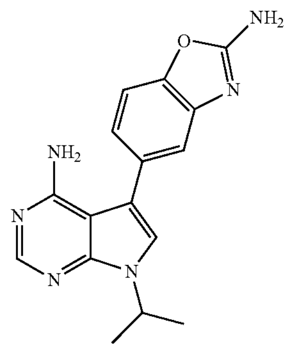 [SMILES: CC(C)n1cc(-c2ccc3oc(N)nc3c2)c2c(N)ncnc21] | ++++ | +++ | + | +++ | +++ | ++++ |
| 9 | 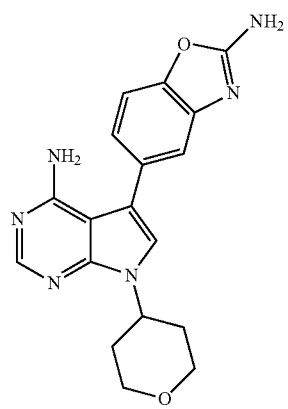 [SMILES: Nc1nc2cc(-c3cn(C4CCOCC4)c4ncnc(N)c34)ccc2o1] | ++++ | ++ | + | +++ | +++ | ++++ |
| 10 | 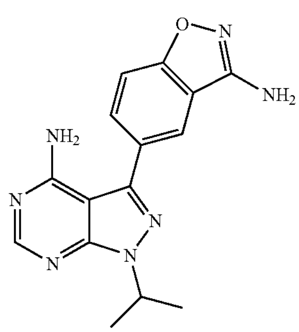 [SMILES: CC(C)n1nc(-c2ccc3onc(N)c3c2)c2c(N)ncnc21] | ++ | | | | | + |
| 11 | 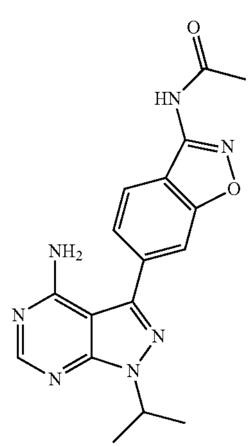 [SMILES: CC(=O)Nc1noc2cc(-c3nn(C(C)C)c4ncnc(N)c34)ccc12] | +++ | | | | | + |

TABLE 1-continued

Biological activity of several illustrative mTor inhibitor compounds of the invention.

| | Structure | mTOR IC$_{50}$ (nM) | PI3K α IC$_{50}$ (nM) | PI3K β IC$_{50}$ (nM) | PI3K γ IC$_{50}$ (nM) | PI3K δ IC$_{50}$ (nM) | PC3 EC50 (nM) |
|---|---|---|---|---|---|---|---|
| 12 | 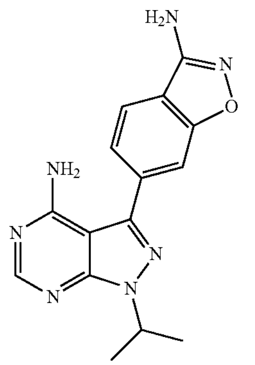 [SMILES: CC(C)n1nc(-c2ccc3c(N)noc3c2)c2c(N)ncnc21] | +++ | | | | | + |
| 13 | 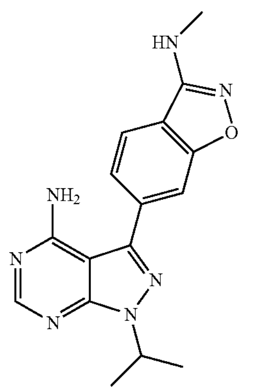 [SMILES: CNc1noc2cc(-c3nn(C(C)C)c4ncnc(N)c34)ccc12] | ++ | ++ | | +++ | +++ | |
| 14 | 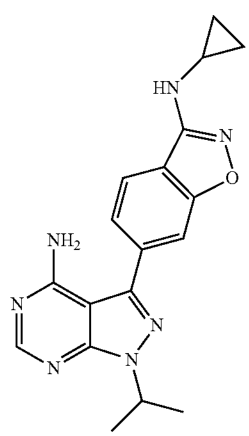 [SMILES: CC(C)n1nc(-c2ccc3c(NC4CC4)noc3c2)c2c(N)ncnc21] | ++ | ++ | | +++ | ++ | |
| 15 | 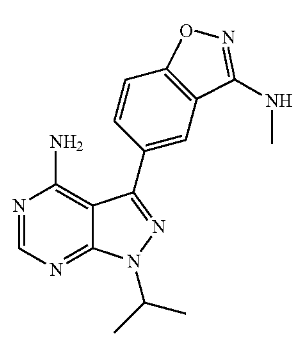 [SMILES: CNc1noc2ccc(-c3nn(C(C)C)c4ncnc(N)c34)cc12] | + | + | | + | + | |

TABLE 1-continued

Biological activity of several illustrative mTor inhibitor compounds of the invention.

| | Structure | mTOR IC$_{50}$ (nM) | PI3K α IC$_{50}$ (nM) | PI3K β IC$_{50}$ (nM) | PI3K γ IC$_{50}$ (nM) | PI3K δ IC$_{50}$ (nM) | PC3 EC50 (nM) |
|---|---|---|---|---|---|---|---|
| 16 | 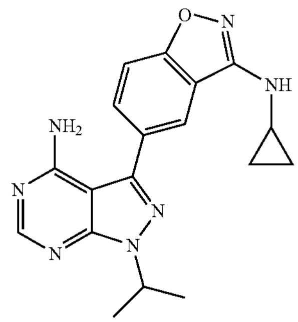 [SMILES: CC(C)n1nc(-c2ccc3onc(NC4CC4)c3c2)c2c(N)ncnc21] | + | + | | ++ | + | |
| 17 | 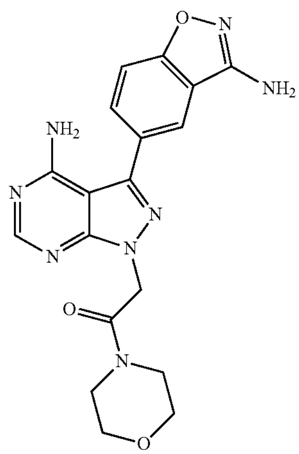 [SMILES: Nc1noc2ccc(-c3nn(CC(=O)N4CCOCC4)c4ncnc(N)c34)cc12] | + | + | | + | + | |
| 18 | 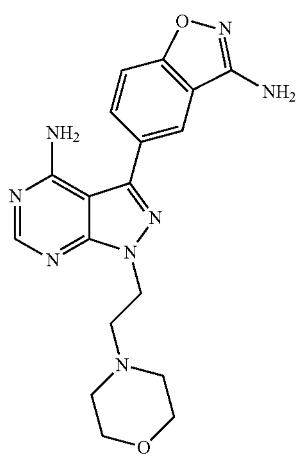 [SMILES: Nc1noc2ccc(-c3nn(CCN4CCOCC4)c4ncnc(N)c34)cc12] | + | + | | + | + | |
| 19 | 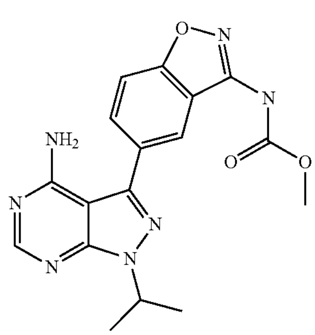 [SMILES: COC(=O)Nc1noc2ccc(-c3nn(C(C)C)c4ncnc(N)c34)cc12] | ++ | + | + | | + | |

TABLE 1-continued

Biological activity of several illustrative mTor inhibitor compounds of the invention.

| Structure | mTOR IC$_{50}$ (nM) | PI3K α IC$_{50}$ (nM) | PI3K β IC$_{50}$ (nM) | PI3K γ IC$_{50}$ (nM) | PI3K δ IC$_{50}$ (nM) | PC3 EC50 (nM) |
|---|---|---|---|---|---|---|
| 20 | ++ | ++ | + |  | ++ |  |
| 21 | +++ | + | + | + | + |  |
| 22 | ++++ | ++++ | ++ | +++ | +++ | ++ |
| 23 | ++++ | ++ | + | ++ | ++ |  |

TABLE 1-continued

Biological activity of several illustrative mTor inhibitor compounds of the invention.

| Structure | mTOR IC$_{50}$ (nM) | PI3K α IC$_{50}$ (nM) | PI3K β IC$_{50}$ (nM) | PI3K γ IC$_{50}$ (nM) | PI3K δ IC$_{50}$ (nM) | PC3 EC50 (nM) |
|---|---|---|---|---|---|---|
| 24 | | + | + | + | + | |
| 25 | | +++ | ++ | ++++ | +++ | |
| 26 | | ++++ | +++ | ++++ | +++ | |

TABLE 1-continued

Biological activity of several illustrative mTor inhibitor compounds of the invention.

| | Structure | mTOR IC$_{50}$ (nM) | PI3K α IC$_{50}$ (nM) | PI3K β IC$_{50}$ (nM) | PI3K γ IC$_{50}$ (nM) | PI3K δ IC$_{50}$ (nM) | PC3 EC50 (nM) |
|---|---|---|---|---|---|---|---|
| 27 | 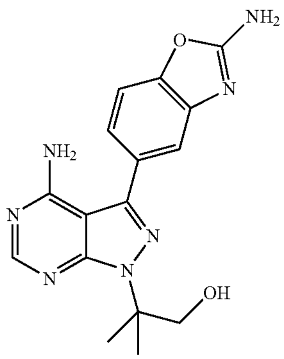 [SMILES: CC(C)(CO)n1nc(-c2ccc3oc(N)nc3c2)c2c(N)ncnc21] | | ++ | + | + | +++ | |

Table 1 shows the biological activity in mTOR and PI3K kinase assays of several compounds of the invention. The scale utilized in Table 1 is as follows: ++++ less than 100 nM; +++ less than 1.0 μM; ++ less than 10 μM; and + greater than 10 μM.

In other embodiments, the present invention provides the following compounds:

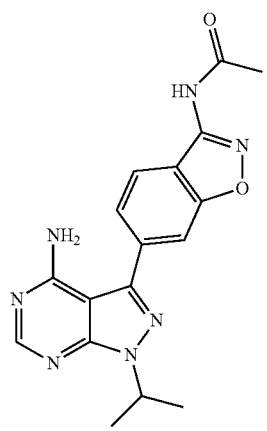

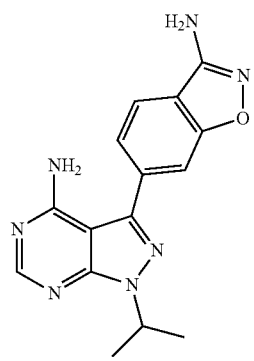

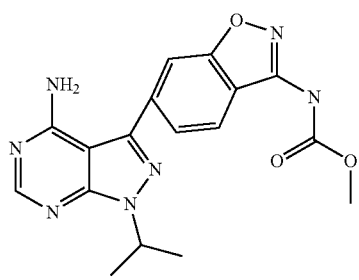

-continued

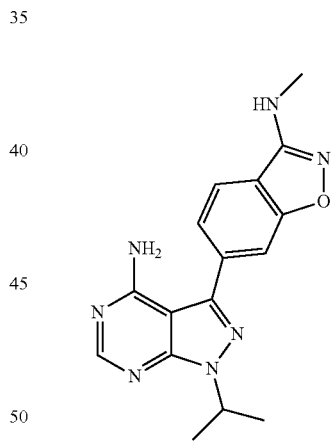

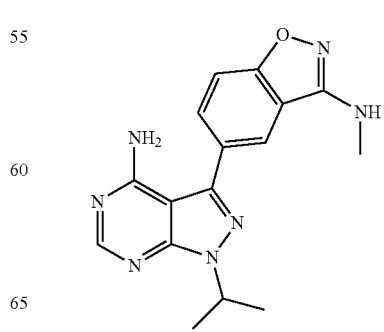

207
-continued
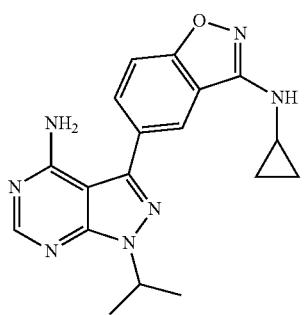
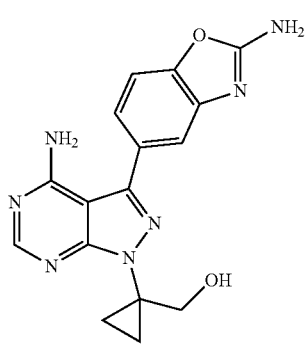
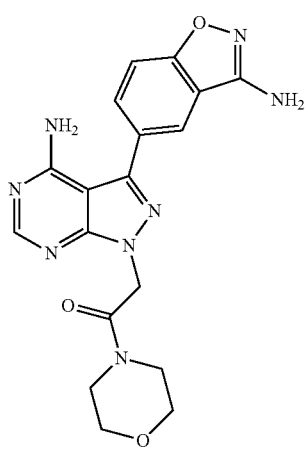
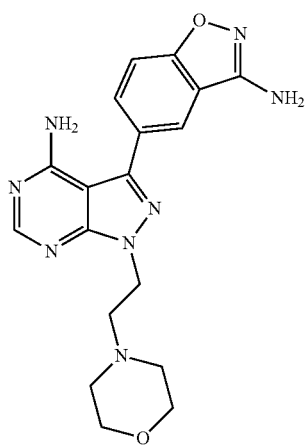
208
-continued
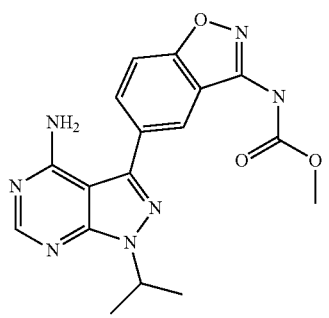
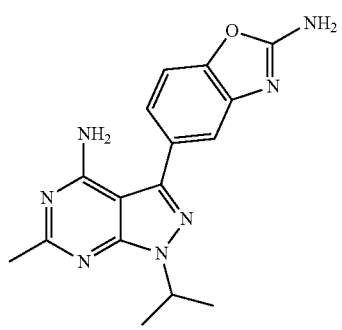
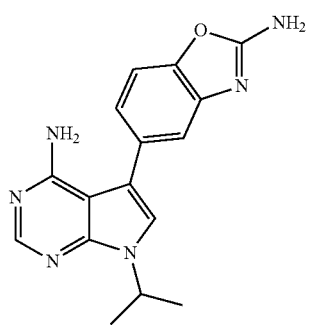
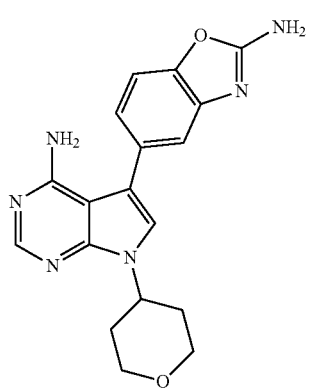

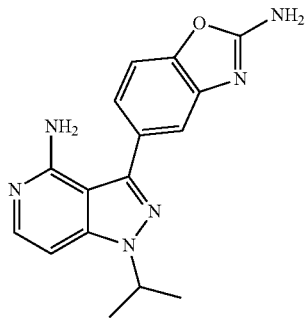

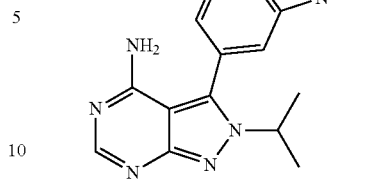

Any of the compounds shown above may show a biological activity in an mTOR or PI3K inhibition assay of between about 0.5 nM and 25 μM (IC50).

Additional compounds which are mTor inhibitors of the invention are shown in Table 2.

TABLE 2

In vitro IC$_{50}$ values for Illustrative mTor Inhibitor Compounds of the Invention.

| # | Structure | mTORC IC$_{50}$ (nM) | PI3K α IC$_{50}$ (nM) | PI3K β IC$_{50}$ (nM) | PI3K γ IC$_{50}$ (nM) | PI3K δ IC$_{50}$ (nM) | PC3 proliferation (nM) |
|---|---|---|---|---|---|---|---|
| 1 | 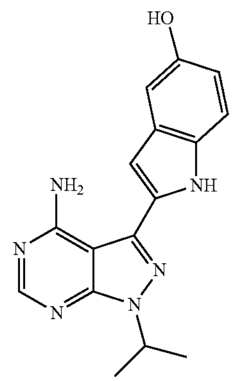 | ++++ | + | + | ++ | ++ | +++ |
| 2 | 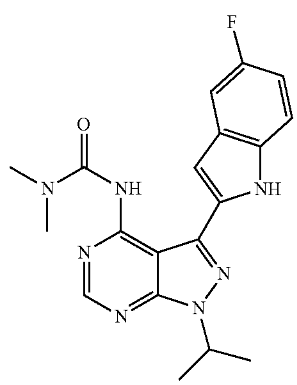 [SMILES: CC(C)n1nc(-c2cc3cc(F)ccc3[nH]2)c2c(NC(=O)N(C)C)ncnc21] | + | − | − | − | − | − |

TABLE 2-continued

In vitro IC$_{50}$ values for Illustrative mTor Inhibitor Compounds of the Invention.

| # | Structure | mTORC IC$_{50}$ (nM) | PI3K α IC$_{50}$ (nM) | PI3K β IC$_{50}$ (nM) | PI3K γ IC$_{50}$ (nM) | PI3K δ IC$_{50}$ (nM) | PC3 proliferation (nM) |
|---|---|---|---|---|---|---|---|
| 3 | (5-fluoro-1H-indol-2-yl substituted 4-amino-1-isopropyl-1H-pyrazolo[3,4-d]pyrimidine) | ++ | + | − | − | − | − |
| 4 | (5-cyano-1H-indol-2-yl substituted 4-amino-1-isopropyl-1H-pyrazolo[3,4-d]pyrimidine) | + | + | | | | − |
| 5 | (5-methoxy-1H-indol-2-yl substituted 4-amino-1-isopropyl-1H-pyrazolo[3,4-d]pyrimidine) | + | + | | | | + |
| 6 | (1-methyl-1H-indol-3-yl substituted 4-amino-1-isopropyl-1H-pyrazolo[3,4-d]pyrimidine) | + | + | | | | + |

TABLE 2-continued

In vitro IC$_{50}$ values for Illustrative mTor Inhibitor Compounds of the Invention.

| # | Structure | mTORC IC$_{50}$ (nM) | PI3K α IC$_{50}$ (nM) | PI3K β IC$_{50}$ (nM) | PI3K γ IC$_{50}$ (nM) | PI3K δ IC$_{50}$ (nM) | PC3 proliferation (nM) |
|---|---|---|---|---|---|---|---|
| 7 | 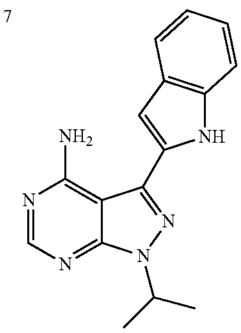 | +++ | + | | | | + |
| 8 | 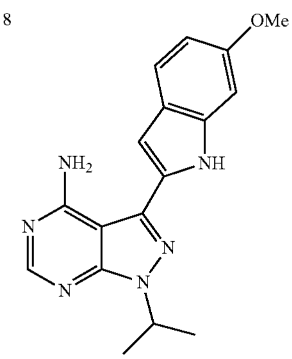 | + | + | | | | + |
| 9 | 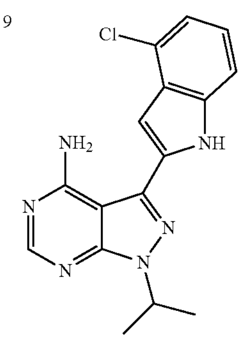 | ++++ | + | | | | + |
| 10 | 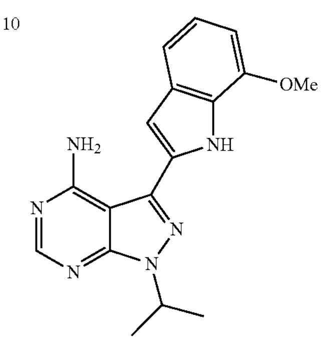 | +++++ | + | + | + | + | + |

TABLE 2-continued

In vitro IC$_{50}$ values for Illustrative mTor Inhibitor Compounds of the Invention.

| # | Structure | mTORC IC$_{50}$ (nM) | PI3K α IC$_{50}$ (nM) | PI3K β IC$_{50}$ (nM) | PI3K γ IC$_{50}$ (nM) | PI3K δ IC$_{50}$ (nM) | PC3 proliferation (nM) |
|---|---|---|---|---|---|---|---|
| 11 | 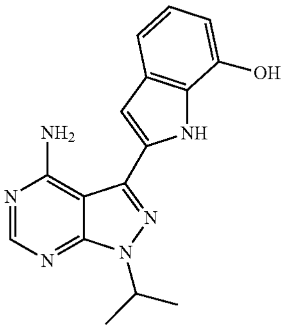 [SMILES: CC(C)n1nc(-c2cc3cccc(O)c3[nH]2)c2c(N)ncnc21] | +++++++ | + | + | ++ | ++ | ++++ |
| 12 | 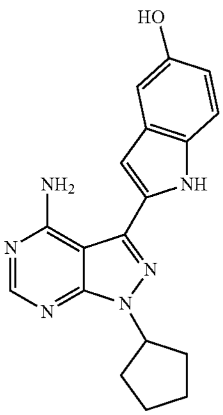 [SMILES: Nc1ncnc2c1c(-c1cc3cc(O)ccc3[nH]1)nn2C1CCCC1] | ++++++ | + | + | ++ | + | ++++ |
| 13 | 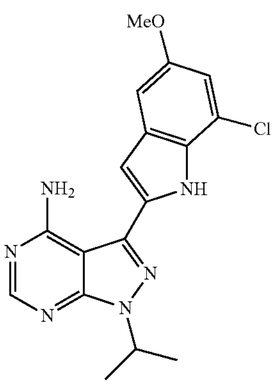 [SMILES: COc1cc(Cl)c2[nH]c(-c3nn(C(C)C)c4ncnc(N)c34)cc2c1] | | + | + | | | + |
| 14 | 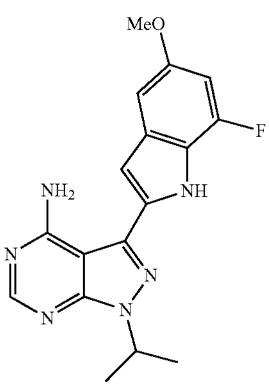 [SMILES: COc1cc(F)c2[nH]c(-c3nn(C(C)C)c4ncnc(N)c34)cc2c1] | | + | + | | | − |

TABLE 2-continued

In vitro IC$_{50}$ values for Illustrative mTor Inhibitor Compounds of the Invention.

| # | Structure | mTORC IC$_{50}$ (nM) | PI3K α IC$_{50}$ (nM) | PI3K β IC$_{50}$ (nM) | PI3K γ IC$_{50}$ (nM) | PI3K δ IC$_{50}$ (nM) | PC3 proliferation (nM) |
|---|---|---|---|---|---|---|---|
| 15 | 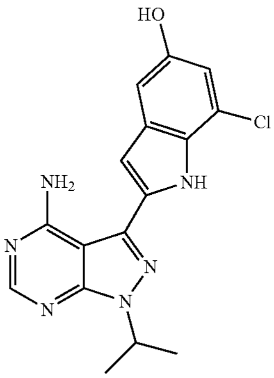 [SMILES: CC(C)n1nc(-c2cc3cc(O)cc(Cl)c3[nH]2)c2c(N)ncnc21] | +++++++ | + | + | ++++ | ++++ | ++++ |
| 16 | 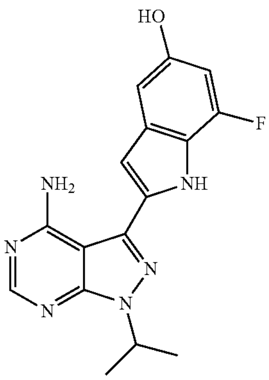 [SMILES: CC(C)n1nc(-c2cc3cc(O)cc(F)c3[nH]2)c2c(N)ncnc21] | +++++++ | + | + | ++ | +++ | ++ |
| 17 | 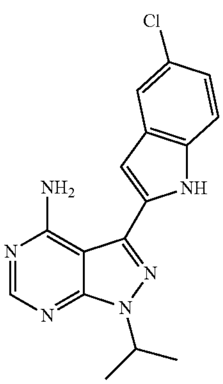 | | + | + | | | + |
| 18 | 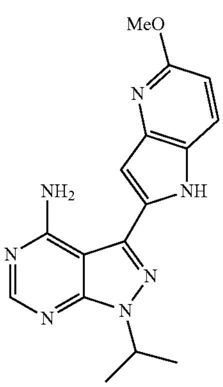 [SMILES: COc1ccc2[nH]c(-c3nn(C(C)C)c4ncnc(N)c34)cc2n1] | | + | * | | | * |

TABLE 2-continued

In vitro IC$_{50}$ values for Illustrative mTor Inhibitor Compounds of the Invention.

| # | Structure | mTORC IC$_{50}$ (nM) | PI3K α IC$_{50}$ (nM) | PI3K β IC$_{50}$ (nM) | PI3K γ IC$_{50}$ (nM) | PI3K δ IC$_{50}$ (nM) | PC3 proliferation (nM) |
|---|---|---|---|---|---|---|---|
| 19 | 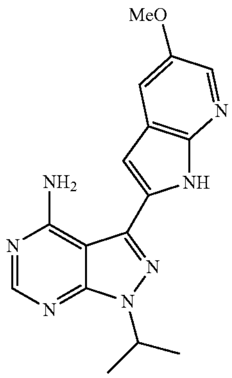 [SMILES: COc1cnc2[nH]c(-c3nn(C(C)C)c4ncnc(N)c34)cc2c1] | + | + | | | | − |
| 20 | 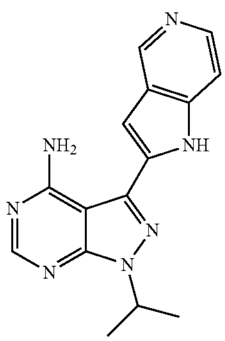 [SMILES: CC(C)n1nc(-c2cc3cnccc3[nH]2)c2c(N)ncnc21] | + | + | | | | − |
| 21 | 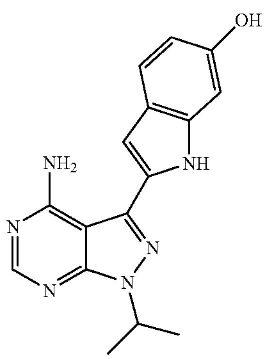 [SMILES: CC(C)n1nc(-c2cc3ccc(O)cc3[nH]2)c2c(N)ncnc21] | ++++ | ++ | + | ++ | ++ | + |
| 22 | 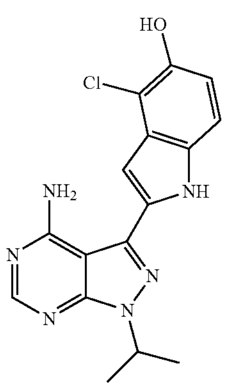 [SMILES: CC(C)n1nc(-c2cc3c(Cl)c(O)ccc3[nH]2)c2c(N)ncnc21] | +++++++ | + | + | − | + | ++ |

TABLE 2-continued
In vitro IC$_{50}$ values for Illustrative mTor Inhibitor Compounds of the Invention.
| # | Structure | mTORC IC$_{50}$ (nM) | PI3K α IC$_{50}$ (nM) | PI3K β IC$_{50}$ (nM) | PI3K γ IC$_{50}$ (nM) | PI3K δ IC$_{50}$ (nM) | PC3 proliferation (nM) |
|---|---|---|---|---|---|---|---|
| 23 | 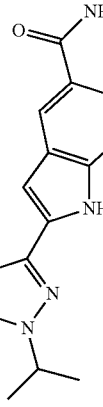 | + | + | | | | − |
| 24 | 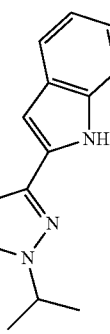 | + | + | | | | + |
| 25 | 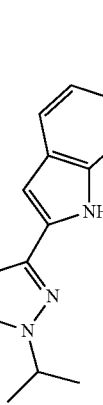 | ++ | + | | | | + |

TABLE 2-continued

In vitro IC$_{50}$ values for Illustrative mTor Inhibitor Compounds of the Invention.

| # | Structure | mTORC IC$_{50}$ (nM) | PI3K α IC$_{50}$ (nM) | PI3K β IC$_{50}$ (nM) | PI3K γ IC$_{50}$ (nM) | PI3K δ IC$_{50}$ (nM) | PC3 proliferation (nM) |
|---|---|---|---|---|---|---|---|
| 26 | 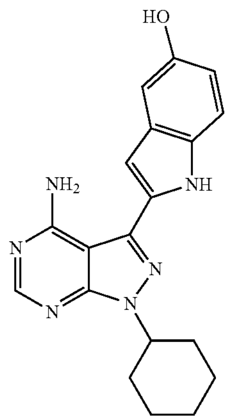 [SMILES: Nc1ncnc2c1c(-c1cc3cc(O)ccc3[nH]1)nn2C1CCCCC1] | ++++++ | + | + | ++ | +++ | ++ |
| 27 | 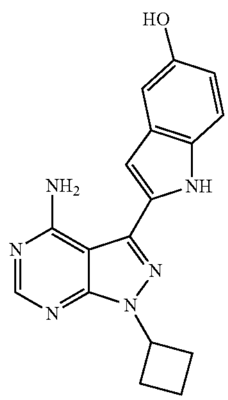 [SMILES: Nc1ncnc2c1c(-c1cc3cc(O)ccc3[nH]1)nn2C1CCC1] | +++++ | | | | | ++ |
| 28 | 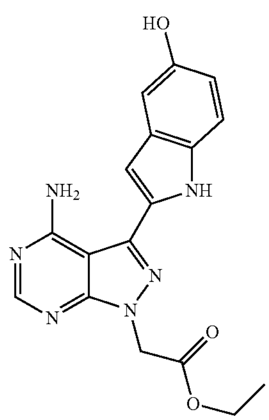 [SMILES: CCOC(=O)Cn1nc(-c2cc3cc(O)ccc3[nH]2)c2c(N)ncnc21] | ++ | + | + | − | + | + |

TABLE 2-continued

In vitro IC$_{50}$ values for Illustrative mTor Inhibitor Compounds of the Invention.

| # | Structure | mTORC IC$_{50}$ (nM) | PI3K α IC$_{50}$ (nM) | PI3K β IC$_{50}$ (nM) | PI3K γ IC$_{50}$ (nM) | PI3K δ IC$_{50}$ (nM) | PC3 proliferation (nM) |
|---|---|---|---|---|---|---|---|
| 29 | 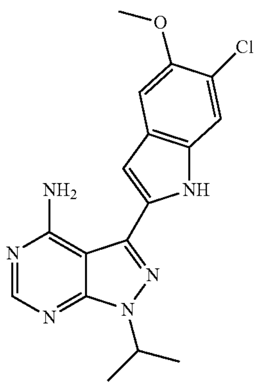 [SMILES: COc1cc2cc(-c3nn(C(C)C)c4ncnc(N)c34)[nH]c2cc1Cl] | + | | | | | − |
| 30 | 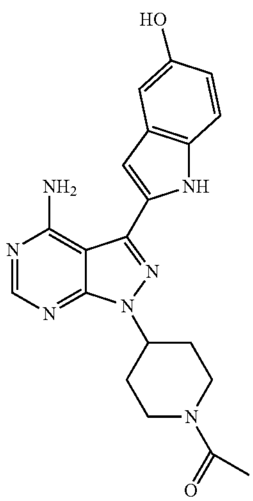 [SMILES: CC(=O)N1CCC(n2nc(-c3cc4cc(O)ccc4[nH]3)c3c(N)ncnc32)CC1] | +++++ | + | + | − | + | + |
| 31 | 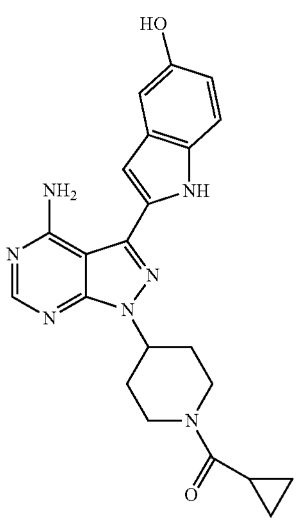 [SMILES: Nc1ncnc2c1c(-c1cc3cc(O)ccc3[nH]1)nn2C1CCN(C(=O)C2CC2)CC1] | +++++ | + | + | − | ++ | + |

TABLE 2-continued

In vitro IC$_{50}$ values for Illustrative mTor Inhibitor Compounds of the Invention.

| # | Structure | mTORC IC$_{50}$ (nM) | PI3K α IC$_{50}$ (nM) | PI3K β IC$_{50}$ (nM) | PI3K γ IC$_{50}$ (nM) | PI3K δ IC$_{50}$ (nM) | PC3 proliferation (nM) |
|---|---|---|---|---|---|---|---|
| 32 | 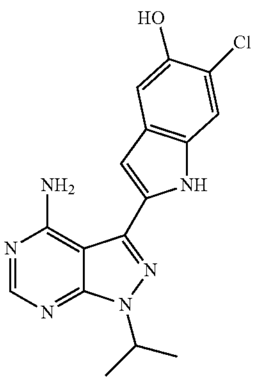 [SMILES: CC(C)n1nc(-c2cc3cc(O)c(Cl)cc3[nH]2)c2c(N)ncnc21] | ++ | + | − | + | + | + |
| 33 | 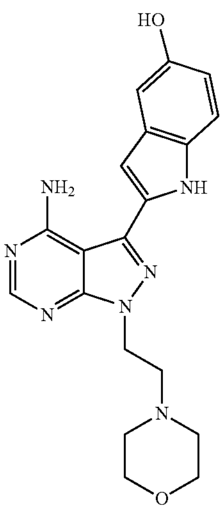 [SMILES: Nc1ncnc2c1c(-c1cc3cc(O)ccc3[nH]1)nn2CCN1CCOCC1] | ++ | + | − | + | + | + |
| 34 | 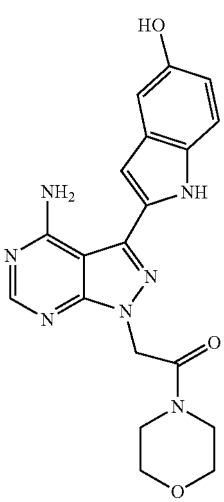 [SMILES: Nc1ncnc2c1c(-c1cc3cc(O)ccc3[nH]1)nn2CC(=O)N1CCOCC1] | + | + | − | + | + | − |

TABLE 2-continued

In vitro IC$_{50}$ values for Illustrative mTor Inhibitor Compounds of the Invention.

| # | Structure | mTORC IC$_{50}$ (nM) | PI3K α IC$_{50}$ (nM) | PI3K β IC$_{50}$ (nM) | PI3K γ IC$_{50}$ (nM) | PI3K δ IC$_{50}$ (nM) | PC3 proliferation (nM) |
|---|---|---|---|---|---|---|---|
| 35 | 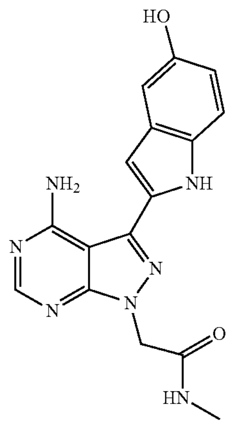 [SMILES: CNC(=O)Cn1nc(-c2cc3cc(O)ccc3[nH]2)c2c(N)ncnc21] | + | + | − | + | + | − |
| 36 | 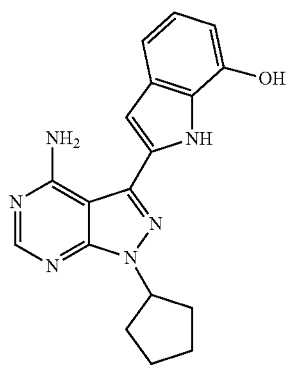 [SMILES: Nc1ncnc2c1c(-c1cc3cccc(O)c3[nH]1)nn2C1CCCC1] | ++++++ | + | − | +++ | ++ | +++ |
| 37 | 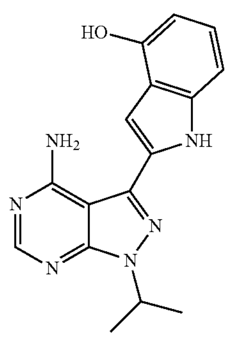 [SMILES: CC(C)n1nc(-c2cc3c(O)cccc3[nH]2)c2c(N)ncnc21] | + | ++ | − | ++ | ++ | − |
| 38 | 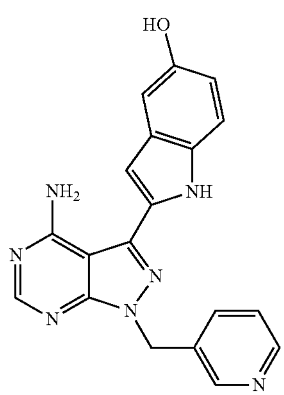 [SMILES: Nc1ncnc2c1c(-c1cc3cc(O)ccc3[nH]1)nn2Cc1cccnc1] | ++ | + | − | + | + | + |

TABLE 2-continued

In vitro IC$_{50}$ values for Illustrative mTor Inhibitor Compounds of the Invention.

| # | Structure | mTORC IC$_{50}$ (nM) | PI3K α IC$_{50}$ (nM) | PI3K β IC$_{50}$ (nM) | PI3K γ IC$_{50}$ (nM) | PI3K δ IC$_{50}$ (nM) | PC3 proliferation (nM) |
|---|---|---|---|---|---|---|---|
| 39 | 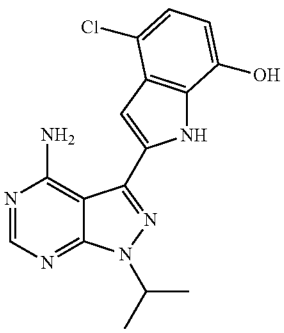 [SMILES: CC(C)n1nc(-c2cc3c(Cl)ccc(O)c3[nH]2)c2c(N)ncnc21] | ++++++ | + | − | + | + | + |
| 40 | 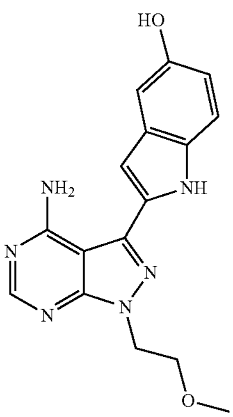 [SMILES: COCCn1nc(-c2cc3cc(O)ccc3[nH]2)c2c(N)ncnc21] | +++ | + | − | + | + | + |
| 41 | 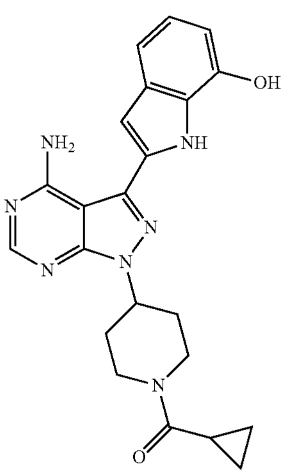 [SMILES: Nc1ncnc2c1c(-c1cc3cccc(O)c3[nH]1)nn2C1CCN(C(=O)C2CC2)CC1] | ++++++ | + | + | ++++ | + | + |

TABLE 2-continued

In vitro IC$_{50}$ values for Illustrative mTor Inhibitor Compounds of the Invention.

| # | Structure | mTORC IC$_{50}$ (nM) | PI3K α IC$_{50}$ (nM) | PI3K β IC$_{50}$ (nM) | PI3K γ IC$_{50}$ (nM) | PI3K δ IC$_{50}$ (nM) | PC3 proliferation (nM) |
|---|---|---|---|---|---|---|---|
| 42 | 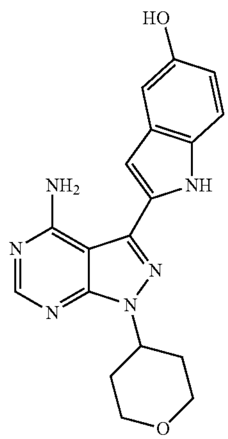 [SMILES: Nc1ncnc2c1c(-c1cc3cc(O)ccc3[nH]1)nn2C1CCOCC1] | +++++++ | + | + | − | +++ | + |
| 43 | 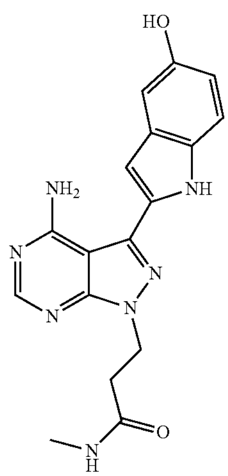 [SMILES: CNC(=O)CCn1nc(-c2cc3cc(O)ccc3[nH]2)c2c(N)ncnc21] | + | + | + | − | + | − |
| 44 | 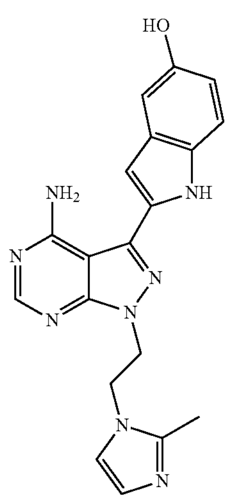 [SMILES: Cc1nccn1CCn1nc(-c2cc3cc(O)ccc3[nH]2)c2c(N)ncnc21] | +++ | + | + | − | + | − |

TABLE 2-continued

In vitro IC$_{50}$ values for Illustrative mTor Inhibitor Compounds of the Invention.

| # | Structure | mTORC IC$_{50}$ (nM) | PI3K α IC$_{50}$ (nM) | PI3K β IC$_{50}$ (nM) | PI3K γ IC$_{50}$ (nM) | PI3K δ IC$_{50}$ (nM) | PC3 proliferation (nM) |
|---|---|---|---|---|---|---|---|
| 45 | 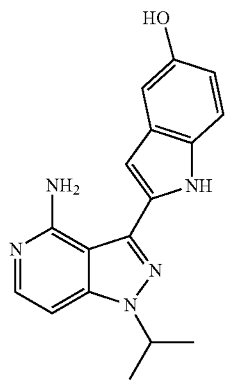 [SMILES: CC(C)n1nc(-c2cc3cc(O)ccc3[nH]2)c2c(N)nccc21] | + | | | | | |
| 46 | 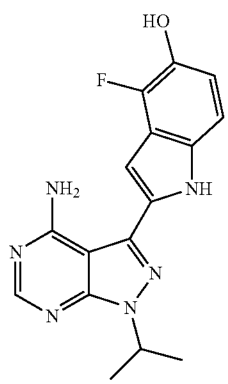 [SMILES: CC(C)n1nc(-c2cc3c(F)c(O)ccc3[nH]2)c2c(N)ncnc21] | − | | | | | |
| 47 | 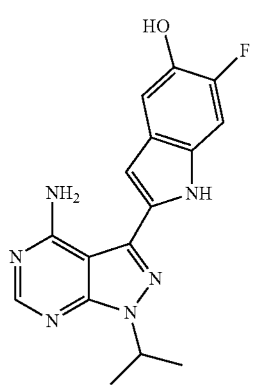 [SMILES: CC(C)n1nc(-c2cc3cc(O)c(F)cc3[nH]2)c2c(N)ncnc21] | − | | | | | |

TABLE 2-continued
In vitro IC$_{50}$ values for Illustrative mTor Inhibitor Compounds of the Invention.
| # | Structure | mTORC IC$_{50}$ (nM) | PI3K α IC$_{50}$ (nM) | PI3K β IC$_{50}$ (nM) | PI3K γ IC$_{50}$ (nM) | PI3K δ IC$_{50}$ (nM) | PC3 proliferation (nM) |
|---|---|---|---|---|---|---|---|
| 48 | 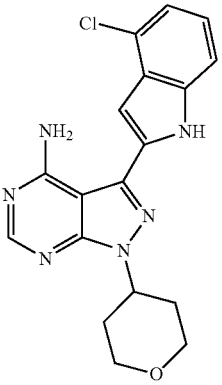 [SMILES: Nc1ncnc2c1c(-c1cc3c(Cl)cccc3[nH]1)nn2C1CCOCC1] | ++++ | + | + | + | + | |
| 49 | 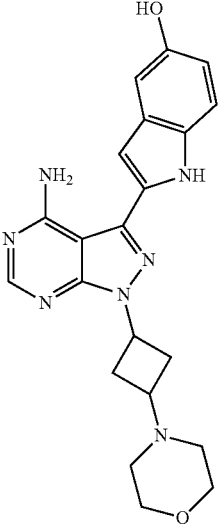 [SMILES: Nc1ncnc2c1c(-c1cc3cc(O)ccc3[nH]1)nn2C1CC(N2CCOCC2)C1] | ++++++ | + | + | ++ | ++ | |
| 50 | 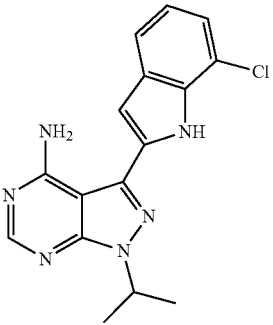 [SMILES: CC(C)n1nc(-c2cc3cccc(Cl)c3[nH]2)c2c(N)ncnc21] | ++++ | + | + | ++ | ++ | |

TABLE 2-continued

In vitro IC$_{50}$ values for Illustrative mTor Inhibitor Compounds of the Invention.

| # | Structure | mTORC IC$_{50}$ (nM) | PI3K α IC$_{50}$ (nM) | PI3K β IC$_{50}$ (nM) | PI3K γ IC$_{50}$ (nM) | PI3K δ IC$_{50}$ (nM) | PC3 proliferation (nM) |
|---|---|---|---|---|---|---|---|
| 51 | 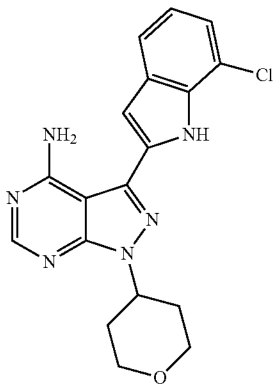 [SMILES: Nc1ncnc2c1c(-c1cc3cccc(Cl)c3[nH]1)nn2C1CCOCC1] | ++++ | + | + | ++ | ++ | |
| 52 | 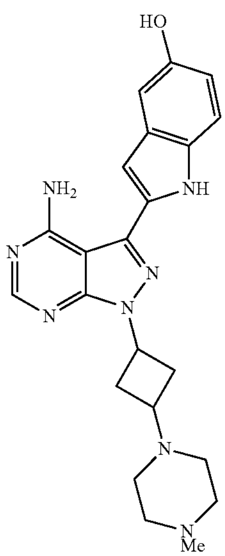 [SMILES: CN1CCN(C2CC(n3nc(-c4cc5cc(O)ccc5[nH]4)c4c(N)ncnc43)C2)CC1] | ++ | + | + | + | ++ | |
| 53 | 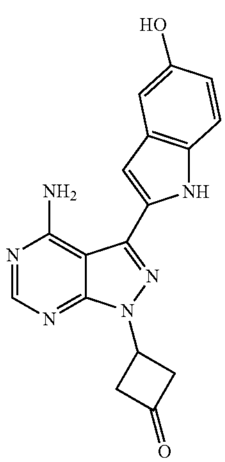 [SMILES: Nc1ncnc2c1c(-c1cc3cc(O)ccc3[nH]1)nn2C1CC(=O)C1] | +++ | + | + | + | − | |

TABLE 2-continued

In vitro IC$_{50}$ values for Illustrative mTor Inhibitor Compounds of the Invention.

| # | Structure | mTORC IC$_{50}$ (nM) | PI3K α IC$_{50}$ (nM) | PI3K β IC$_{50}$ (nM) | PI3K γ IC$_{50}$ (nM) | PI3K δ IC$_{50}$ (nM) | PC3 proliferation (nM) |
|---|---|---|---|---|---|---|---|
| 54 | 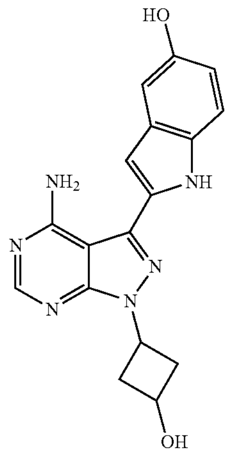 [SMILES: Nc1ncnc2c1c(-c1cc3cc(O)ccc3[nH]1)nn2C1CC(O)C1] | +++++ | + | + | + | − | |
| 55 | 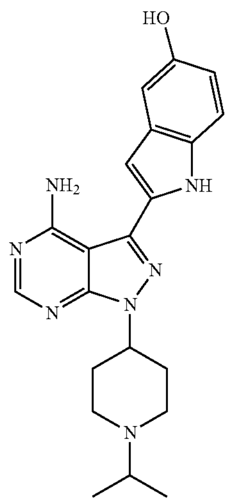 [SMILES: CC(C)N1CCC(n2nc(-c3cc4cc(O)ccc4[nH]3)c3c(N)ncnc32)CC1] | ++ | + | + | + | − | |
| 56 | 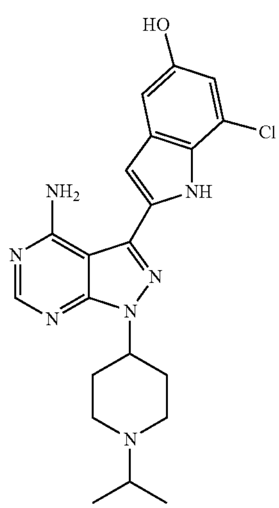 [SMILES: CC(C)N1CCC(n2nc(-c3cc4cc(O)cc(Cl)c4[nH]3)c3c(N)ncnc32)CC1] | + | + | + | + | − | |

TABLE 2-continued
In vitro IC$_{50}$ values for Illustrative mTor Inhibitor Compounds of the Invention.
| # | Structure | mTORC IC$_{50}$ (nM) | PI3K α IC$_{50}$ (nM) | PI3K β IC$_{50}$ (nM) | PI3K γ IC$_{50}$ (nM) | PI3K δ IC$_{50}$ (nM) | PC3 proliferation (nM) |
|---|---|---|---|---|---|---|---|
| 57 | 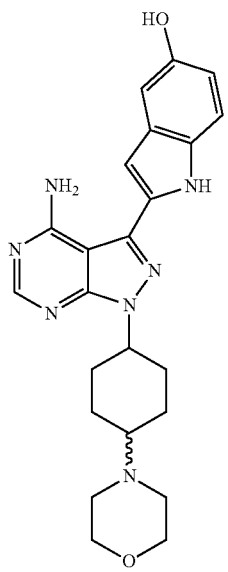 [SMILES: Nc1ncnc2c1c(-c1cc3cc(O)ccc3[nH]1)nn2C1CCC(N2CCOCC2)CC1] | +++++ | + | + | + | − | |
| 58 | 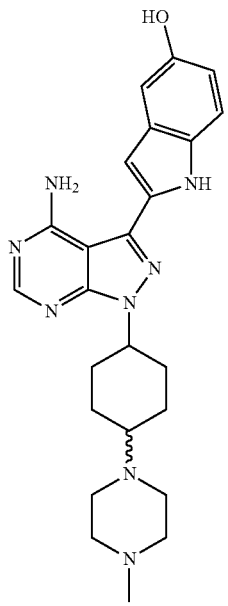 [SMILES: CN1CCN(C2CCC(n3nc(-c4cc5cc(O)ccc5[nH]4)c4c(N)ncnc43)CC2)CC1] | | + | + | + | + | − |

TABLE 2-continued
In vitro IC$_{50}$ values for Illustrative mTor Inhibitor Compounds of the Invention.
| # | Structure | mTORC IC$_{50}$ (nM) | PI3K α IC$_{50}$ (nM) | PI3K β IC$_{50}$ (nM) | PI3K γ IC$_{50}$ (nM) | PI3K δ IC$_{50}$ (nM) | PC3 proliferation (nM) |
|---|---|---|---|---|---|---|---|
| 59 | 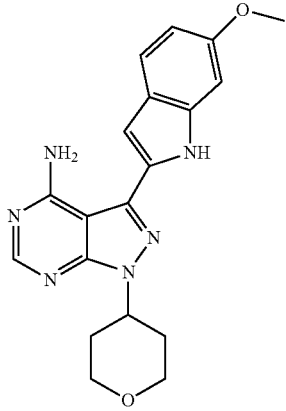 [SMILES: COc1ccc2cc(-c3nn(C4CCOCC4)c4ncnc(N)c34)[nH]c2c1] | + | + | + | + | − | |
| 60 | 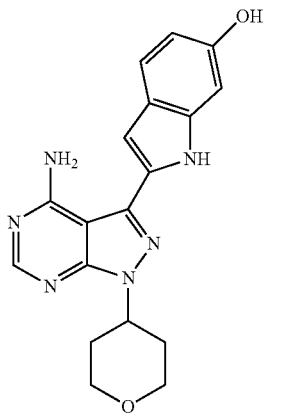 [SMILES: Nc1ncnc2c1c(-c1cc3ccc(O)cc3[nH]1)nn2C1CCOCC1] | +++ | + | + | +++ | − | |
| 61 | 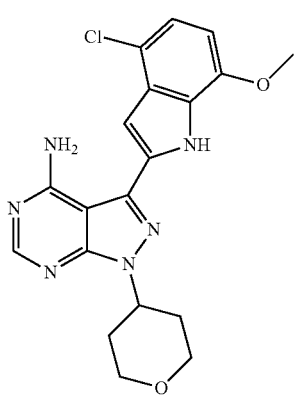 [SMILES: COc1ccc(Cl)c2cc(-c3nn(C4CCOCC4)c4ncnc(N)c34)[nH]c12] | +++++ | + | + | + | + | |

TABLE 2-continued

In vitro IC$_{50}$ values for Illustrative mTor Inhibitor Compounds of the Invention.

| # | Structure | mTORC IC$_{50}$ (nM) | PI3K α IC$_{50}$ (nM) | PI3K β IC$_{50}$ (nM) | PI3K γ IC$_{50}$ (nM) | PI3K δ IC$_{50}$ (nM) | PC3 proliferation (nM) |
|---|---|---|---|---|---|---|---|
| 62 | 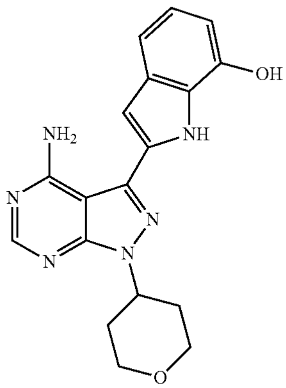 [SMILES: Nc1ncnc2c1c(-c1cc3cccc(O)c3[nH]1)nn2C1CCOCC1] | +++++++ | + | + | + | +++ | |
| 63 | 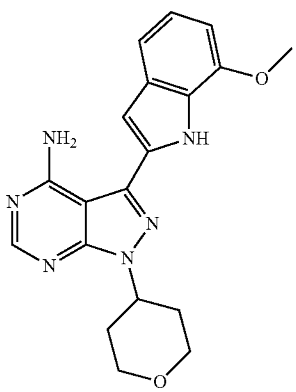 [SMILES: COc1cccc2cc(-c3nn(C4CCOCC4)c4ncnc(N)c34)[nH]c12] | +++++++ | ++ | + | +++++ | +++++ | |
| 64 | 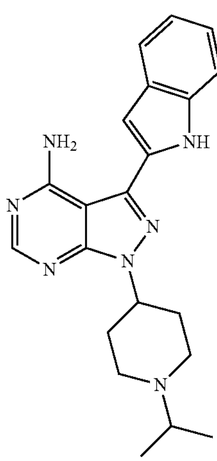 | +++++ | + | + | ++ | ++ | |

TABLE 2-continued

In vitro IC$_{50}$ values for Illustrative mTor Inhibitor Compounds of the Invention.

| # | Structure | mTORC IC$_{50}$ (nM) | PI3K α IC$_{50}$ (nM) | PI3K β IC$_{50}$ (nM) | PI3K γ IC$_{50}$ (nM) | PI3K δ IC$_{50}$ (nM) | PC3 proliferation (nM) |
|---|---|---|---|---|---|---|---|
| 65 | | ++++++ | ++++ | + | +++++ | +++++ | |
| 66 | | + | + | + | + | + | |
| 67 | | + | + | + | + | + | |

US 9,295,673 B2
251                                                                                                                        252
TABLE 2-continued
In vitro IC$_{50}$ values for Illustrative mTor Inhibitor Compounds of the Invention.
| # | Structure | mTORC IC$_{50}$ (nM) | PI3K α IC$_{50}$ (nM) | PI3K β IC$_{50}$ (nM) | PI3K γ IC$_{50}$ (nM) | PI3K δ IC$_{50}$ (nM) | PC3 proliferation (nM) |
|---|---|---|---|---|---|---|---|
| 68 | 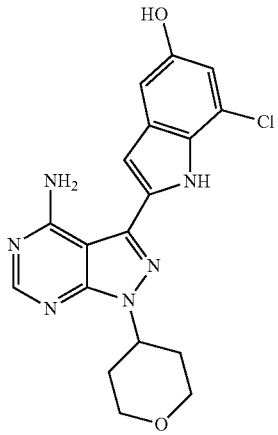 [SMILES: Nc1ncnc2c1c(-c1cc3cc(O)cc(Cl)c3[nH]1)nn2C1CCOCC1] | +++++++ | ++ | + | ++++ | +++++ | |
| 69 | 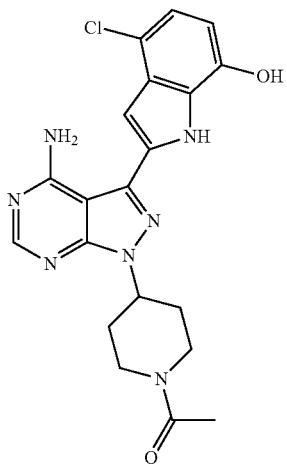 [SMILES: CC(=O)N1CCC(n2nc(-c3cc4c(Cl)ccc(O)c4[nH]3)c3c(N)ncnc32)CC1] | +++++++ | + | + | + | ++ | |
| 70 | 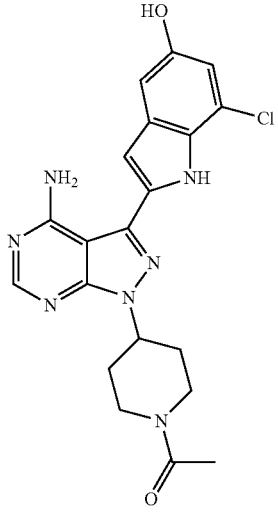 [SMILES: CC(=O)N1CCC(n2nc(-c3cc4cc(O)cc(Cl)c4[nH]3)c3c(N)ncnc32)CC1] | +++++++ | ++ | + | +++ | +++++ | |

TABLE 2-continued

In vitro IC$_{50}$ values for Illustrative mTor Inhibitor Compounds of the Invention.

| # | Structure | mTORC IC$_{50}$ (nM) | PI3K α IC$_{50}$ (nM) | PI3K β IC$_{50}$ (nM) | PI3K γ IC$_{50}$ (nM) | PI3K δ IC$_{50}$ (nM) | PC3 proliferation (nM) |
|---|---|---|---|---|---|---|---|
| 71 | 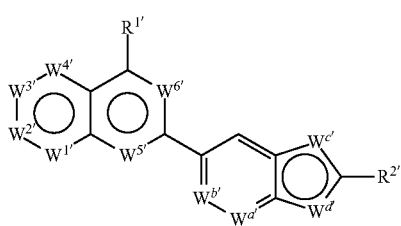 | +++ | + | + | + | + | |

In Table 2 above, a +++++++ indicates an IC50 of 5 nM or less; a ++++++ indicates an IC50 of 10 nM or less; a +++++ indicates an IC50 of 25 nM or less; an ++++ indicates an IC50 of 50 nm or less, a +++ indicates an IC50 of 100 nM or less, a ++ indicates an IC50 of 500 nM or less, and a + indicates an IC50 of more than 500 nM.

Exemplary PI3Kα Inhibitor Compounds

In one aspect, the present invention provides a PI3Kα inhibitor which is a compound of Formula I:

Formula II

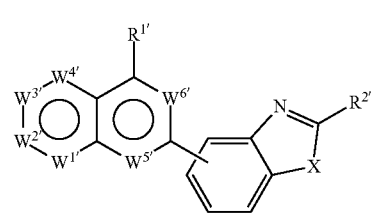

or its pharmaceutically acceptable salts thereof, wherein:
$W^{1'}$ is N, $NR^{3'}$, or $CR^{3'}$; $W^{2'}$ is N, $NR^{4'}$, $CR^{4'}$, or C=O; $W^{3'}$ is N, $NR^{5'}$ or $CR^{5'}$; $W^{4'}$ is N, wherein no more than two N atoms and no more than two C=O groups are adjacent;
$W^{5'}$ is N;
$W^{6'}$ is N or $CR^{8'}$;
$W^{a'}$ and $W^{b'}$ are independently N or $CR^{9'}$;
one of $W^{c'}$ and $W^{d'}$ is N, and the other is O, $NR^{10'}$, or S;
$R^{1'}$ and $R^{2'}$ are independently hydrogen, alkyl, heteroalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, halo, cyano, hydroxy, nitro, phosphate, urea, carbonate, or NR'R" wherein R' and R" are taken together with nitrogen to form a cyclic moiety;
$R^{3'}$ and $R^{4'}$ are independently hydrogen, alkyl, heteroalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, halo, cyano, hydroxy, nitro, phosphate, urea, carbonate, or NR'R" wherein R' and R" are taken together with nitrogen to form a cyclic moiety; or $R^{3'}$ and $R^{4'}$ taken together form a cyclic moiety;
$R^{5'}$, $R^{6'}$, $R^{7'}$ and $R^{8'}$ are independently hydrogen, alkyl, heteroalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, halo, cyano, hydroxy, nitro, phosphate, urea, carbonate, or NR'R" wherein R' and R" are taken together with nitrogen to form a cyclic moiety;
$R^{9'}$ is alkyl or halo; and
$R^{10'}$ is hydrogen, alkyl, heteroalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, halo, cyano, hydroxy, nitro, phosphate, urea, carbonate, or NR'R" wherein R' and R" are taken together with nitrogen to form a cyclic moiety.

For example, the present invention provides a PI3Kα inhibitor which is a compound of Formula I:

Formula II

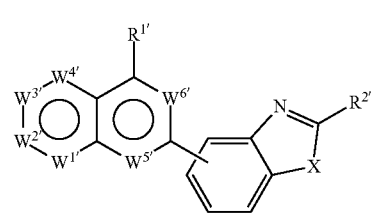

or its pharmaceutically acceptable salts thereof, wherein:
X is O or S or N;
$W^{1'}$ is N, $N^{3'}$, $CR^{3'}$, or C=O, $W^{2'}$ is $N^{4'}$, $CR^{4'}$, or C=O, $W^{3'}$ is N, $NR^{5'}$ or $CR^{5'}$, $W^{4'}$ is N, C=O or $CR^{6'}$, wherein no more than two N atoms and no more than two C=O groups are adjacent;

W[5'] is N or CR[7'];

W[6'] is N or CR[8'];

R[1'] and R[2'] are independently hydrogen, alkyl, heteroalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, halo, cyano, hydroxy, nitro, phosphate, urea, carbonate, or NR'R" wherein R' and R" are taken together with nitrogen to form a cyclic moiety;

R[3'] and R[4'] are independently hydrogen, alkyl, heteroalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, halo, cyano, hydroxy, nitro, phosphate, urea, carbonate, or NR'R" wherein R' and R" are taken together with nitrogen to form a cyclic moiety;

or R[3'] and R[4'] taken together form a cyclic moiety; and

R[5'], R[6'], R[7'] and R[8'] are independently hydrogen, alkyl, heteroalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, halo, cyano, hydroxy, nitro, phosphate, urea, carbonate, or NR'R" wherein R' and R" are taken together with nitrogen to form a cyclic moiety.

In some embodiments, the compound of Formula II exists as a tautomer, and such tautomers are contemplated by the present invention.

In some embodiments, the compound of Formula II has the formula:

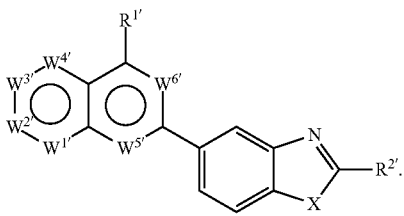

For example, a compound of Formula II is:

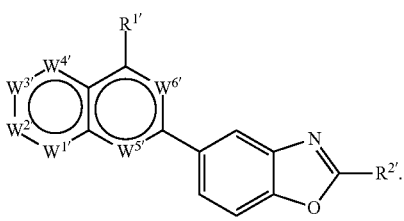

In some embodiments of the compound of Formula II, W[1'] is CR[3'], W[2'] is CR[4'], W[3'] is CR[5'], W[4'] is N, W[5'] is CR[7'], and W[6'] is CR[8']; W[1'] is N, W[2'] is CR[4'], W[3'] is CR[5'], W[4'] is N, W[5'] is CR[7'], and W[6'] is CR[8']; or W[1'] is CR[3'], W[2'] is N, W[3'] is CR[5'], W[4'] is N, W[5'] is CR[7'], and W[6'] is CR[8']. Formulas for such embodiments are shown below:

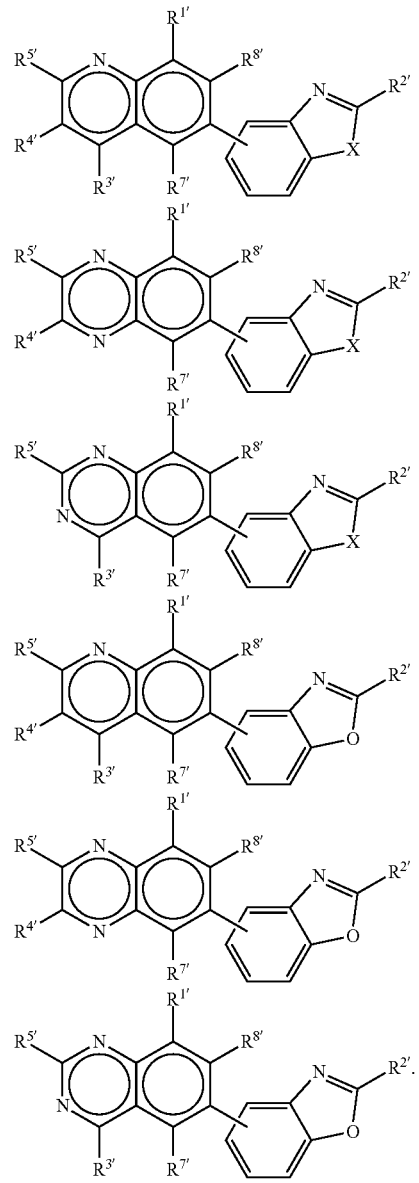

In some embodiments, X is O. In other embodiments, X is S.

In some embodiments, R[1] is hydrogen. In other embodiments, R[1] is alkyl, heteroalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, halo, cyano, hydroxy, nitro, phosphate, urea, carbonate, or NR'R", wherein R' and R" are taken together with nitrogen to form a cyclic moiety.

In some embodiments, R[2'] is hydrogen. In other embodiments, R[2'] is, for example, unsubstituted or substituted alkyl (including but not limited to $CH_3$, —$CH_2CH_3$, n-propyl, isopropyl, n-butyl, tert-butyl, sec-butyl, pentyl, hexyl, and heptyl). In other embodiments, R[2'] is unsubstituted or substituted alkenyl (including but not limited to unsubstituted or substituted $C_2$-$C_5$alkenyl such as, for example, vinyl, allyl, 1-methyl propen-1-yl, butenyl, or pentenyl) or substituted or unsubstituted alkynyl (including but not limited to unsubstituted or substituted $C_2$-$C_5$alkynyl such as acetylenyl, propargyl, butynyl, or pentynyl). Alternatively, R[2'] is unsubstituted or substituted aryl (including but not limited to monocyclic or bicyclic aryl) or unsubstituted or substituted arylalkyl (including but not limited to monocyclic or bicyclic aryl linked to alkyl wherein alkyl includes but is not limited to $CH_3$, —$CH_2CH_3$, n-propyl, isopropyl, n-butyl, sec-butyl, and pentyl). In some other embodiments, $R^{2'}$ is unsubstituted or substituted heteroaryl, including but not limited to monocyclic and bicyclic heteroaryl. Monocyclic heteroaryl $R^{2'}$ includes but is not limited to pyrrolyl, thienyl, furyl, pyridinyl, pyranyl, pyrimidinyl, pyrazinyl, pyridazinyl, imidazolyl, thiazolyl, pyrazolyl, and oxazolyl. Bicyclic heteroaryl $R^{2'}$ includes but is not limited to benzothiophenyl, benzofuryl, indolyl, quinolinyl, isoquinolinyl, benzimidazolyl, benzoxazolyl, benzothiazolyl, quinazolinyl, azaindolyl, pyrazolopyrimidinyl, purinyl, pyrrolo[1,2-b]pyridazinyl, pyrrolopyrimidinyl, indazolyl, pyrazolylpyridinyl, imidazo[1,2-a]pyridinyl, and pyrrolo[1,2-f][1,2,4]triazinyl. The present invention also provides compounds wherein $R^{2'}$ is unsubstituted or substituted heteroarylalkyl, including but not limited to monocyclic and bicyclic heteroaryl as described above, that are linked to alkyl, which in turn includes but is not limited to $CH_3$, —$CH_2CH_3$, n-propyl, isopropyl, n-butyl, sec-butyl, and pentyl. In some embodiments, $R^{2'}$ is unsubstituted or substituted cycloalkyl (including but not limited to cyclopropyl, cyclobutyl, and cyclopentyl) or unsubstituted or substituted heteroalkyl (non-limiting examples include ethoxymethyl, methoxymethyl, and diethylaminomethyl). In some further embodiments, $R^{2'}$ is unsubstituted or substituted heterocycloalkyl which includes but is not limited to pyrrolidinyl, tetrahydrofuranyl, piperidinyl, tetrahydropyranyl, thiazolidinyl, imidazolidinyl, morpholinyl, and piperazinyl. In yet other embodiments of the compounds of Formula II, $R^{2'}$ is unsubstituted or substituted alkoxy including but not limited to $C_1$-$C_4$alkoxy such as methoxy, ethoxy, propoxy or butoxy. $R^{2'}$ can also be unsubstituted or substituted heterocycloalkyloxy, including but not limited to 4-NH piperidin-1-yl-oxy, 4-methyl piperidin-1-yl-oxy, 4-ethyl piperidin-1-yl-oxy, 4-isopropyl-piperidin-1-yl-oxy, and pyrrolidin-3-yl-oxy. In other embodiments, $R^{2'}$ is unsubstituted or substituted amino, wherein the substituted amino includes but is not limited to dimethylamino, diethylamino, di-isopropyl amino, N-methyl N-ethyl amino, and dibutylamino. In some embodiments, $R^{2'}$ is unsubstituted or substituted acyl, unsubstituted or substituted acyloxy, unsubstituted or substituted $C_1$-$C_4$acyloxy, unsubstituted or substituted alkoxycarbonyl, unsubstituted or substituted amido, or unsubstituted or substituted sulfonamido. In other embodiments, $R^{2'}$ is halo, which is —I, —F, —Cl, or —Br. In some embodiments, $R^{2'}$ is selected from the group consisting of cyano, hydroxy, nitro, phosphate, urea, and carbonate. Also contemplated are $R^{2'}$ being —$CH_3$, —$CH_2CH_3$, n-propyl, isopropyl, n-butyl, tert-butyl, sec-butyl, pentyl, hexyl, heptyl, —$OCH_3$, —$OCH_2CH_3$, or —$CF_3$.

In some embodiments of the compound of Formula II, $W^{1'}$ is $CR^{3'}$. $R^{3'}$ can be, for example, hydrogen, unsubstituted or substituted alkyl (including but not limited to $CH_3$, —$CH_2CH_3$, n-propyl, isopropyl, n-butyl, tert-butyl, sec-butyl, pentyl, hexyl, and heptyl). In other embodiments, $R^{3'}$ is unsubstituted or substituted alkenyl (including but not limited to unsubstituted or substituted $C_2$-$C_5$alkenyl such as, for example, vinyl, allyl, 1-methyl propen-1-yl, butenyl, or pentenyl) or unsubstituted or substituted alkynyl (including but not limited to unsubstituted or substituted $C_2$-$C_5$alkynyl such as acetylenyl, propargyl, butynyl, or pentynyl). Alternatively, $R^{3'}$ is unsubstituted or substituted aryl (including but not limited to monocyclic or bicyclic aryl) or unsubstituted or substituted arylalkyl (including but not limited to monocyclic or bicyclic aryl linked to alkyl wherein alkyl includes but is not limited to $CH_3$, —$CH_2CH_3$, n-propyl, isopropyl, n-butyl, sec-butyl, and pentyl). In some other embodiments, $R^{3'}$ is unsubstituted or substituted heteroaryl, including but not limited to monocyclic and bicyclic heteroaryl. Monocyclic heteroaryl $R^{3'}$ includes but is not limited to pyrrolyl, thienyl, furyl, pyridinyl, pyranyl, pyrimidinyl, pyrazinyl, pyridazinyl, imidazolyl, thiazolyl, pyrazolyl, and oxazolyl. Bicyclic heteroaryl $R^{3'}$ includes but is not limited to benzothiophenyl, benzofuryl, indolyl, quinolinyl, isoquinolinyl, benzimidazolyl, benzoxazolyl, benzothiazolyl, quinazolinyl, azaindolyl, pyrazolopyrimidinyl, purinyl, pyrrolo[1,2-b]pyridazinyl, pyrrolopyrimidinyl, indazolyl, pyrazolylpyridinyl, imidazo[1,2-a]pyridinyl, and pyrrolo[1,2-f][1,2,4]triazinyl. The present invention also provides compounds of Formula II wherein $R^{3'}$ is unsubstituted or substituted heteroarylalkyl, including but not limited to monocyclic and bicyclic heteroaryl as described above, that are linked to alkyl, which in turn includes but is not limited to $CH_3$, —$CH_2CH_3$, n-propyl, isopropyl, n-butyl, sec-butyl, and pentyl. In some embodiments, $R^{3'}$ is unsubstituted or substituted cycloalkyl (including but not limited to cyclopropyl, cyclobutyl, and cyclopentyl) or unsubstituted or substituted heteroalkyl (non-limiting examples include ethoxymethyl, methoxymethyl, and diethylaminomethyl). In some further embodiments, $R^{3'}$ is unsubstituted or substituted heterocycloalkyl which includes but is not limited to pyrrolidinyl, tetrahydrofuranyl, piperidinyl, tetrahydropyranyl, thiazolidinyl, imidazolidinyl, morpholinyl, and piperazinyl. In yet other embodiments of the compounds of Formula II, $R^{3'}$ is unsubstituted or substituted alkoxy including but not limited to $C_1$-$C_4$alkoxy such as methoxy, ethoxy, propoxy or butoxy. $R^{3'}$ can also be unsubstituted or substituted heterocycloalkyloxy, including but not limited to 4-NH piperidin-1-yl-oxy, 4-methyl piperidin-1-yl-oxy, 4-ethyl piperidin-1-yl-oxy, 4-isopropyl-piperidin-1-yl-oxy, and pyrrolidin-3-yl-oxy. In other embodiments, $R^{3'}$ is unsubstituted or substituted amino, wherein the substituted amino includes but is not limited to dimethylamino, diethylamino, di-isopropyl amino, N-methyl N-ethyl amino, and dibutylamino. In some embodiments, $R^{3'}$ is unsubstituted or substituted acyl, unsubstituted or substituted acyloxy, unsubstituted or substituted $C_1$-$C_4$acyloxy, unsubstituted or substituted alkoxycarbonyl, unsubstituted or substituted amido, or unsubstituted or substituted sulfonamido. In other embodiments, $R^{3'}$ is halo, which is —I, —F, —Cl, or —Br. In some embodiments, $R^{3'}$ is selected from the group consisting of cyano, hydroxy, nitro, phosphate, urea, and carbonate. Also contemplated are $R^{3'}$ being —$CH_3$, —$CH_2CH_3$, n-propyl, isopropyl, n-butyl, tert-butyl, sec-butyl, pentyl, hexyl, heptyl, —$OCH_3$, —$OCH_2CH_3$, or —$CF_3$.

$R^{3'}$ of the compounds of Formula II can also be NR'R" wherein R' and R" are taken together with the nitrogen to form a cyclic moiety having from 3 to 8 ring atoms. The cyclic moiety so formed may further include one or more heteroatoms which are selected from the group consisting of S, O, and N. The cyclic moiety so formed is unsubstituted or substituted, including but not limited to morpholinyl, azetidinyl, pyrrolidinyl, piperidinyl, piperazinyl, isothiazolidinyl 1,2, dioxide, and thiomorpholinyl. Further non-limiting exemplary cyclic moieties are the following:

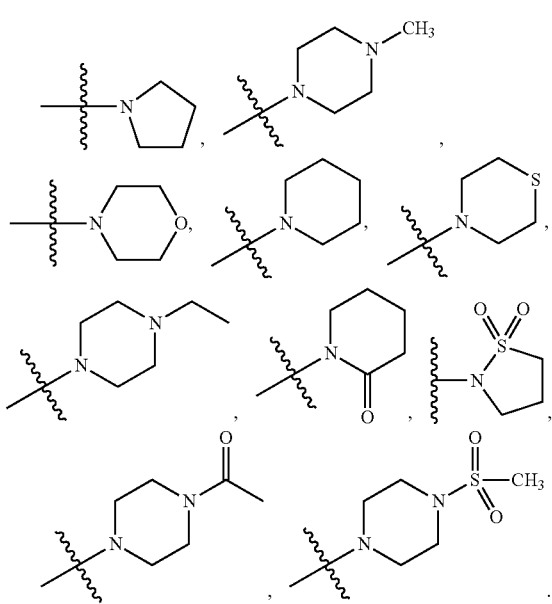

The invention also provides compounds of Formula II, wherein when R³' is a member of the group consisting of alkyl, alkenyl, alkynyl, cycloalkyl, heteroalkyl, heterocycloalkyl, heterocycloalkyloxy, aryl, arylalkyl, heteroaryl, heteroarylalkyl, acyl, alkoxy, amido, amino, sulfonamido, acyloxy, alkoxycarbonyl, and NR'R" (wherein R' and R" are taken together with nitrogen to form a cyclic moiety), then R³' is optionally substituted with one or more of the following substituents: alkyl, alkenyl, alkynyl, cycloalkyl, heteroalkyl, heterocycloalkyl, heterocycloalkyloxy, aryl, arylalkyl, heteroaryl, heteroarylalkyl, acyl, heterocycloalkyloxy, alkoxy, amido, amino, sulfonamido, acyloxy, alkoxycarbonyl, halo, cyano, hydroxy, nitro, phosphate, urea, carbonate, or NR'R" wherein R' and R" are taken together with nitrogen to form a cyclic moiety. Each of the above substituents may be further substituted with one or more substituents chosen from the group consisting of alkyl, alkoxy, amido, amino, sulfonamido, acyloxy, alkoxycarbonyl, halo, cyano, hydroxy, nitro, oxo, phosphate, urea, and carbonate.

For example, the invention provides compounds wherein when R³' is alkyl, the alkyl is substituted with NR'R" wherein R' and R" are taken together with the nitrogen to form a cyclic moiety. The cyclic moiety so formed can be unsubstituted or substituted. Non-limiting exemplary cyclic moieties includes but are not limited to morpholinyl, azetidinyl, pyrrolidinyl, piperidinyl, piperazinyl, and thiomorpholinyl. In other examples of the compounds of Formula II, when R³' is alkyl, the alkyl is substituted with heterocycloalkyl, which includes oxetanyl, azetidinyl, tetrahydrofuranyl, pyrrolyl, tetrahydropyranyl, piperidinyl, morpholinyl, and piperazinyl. All of the above listed heterocycloaklyl substituents can be unsubstituted or substituted.

In yet other examples of the compounds of Formula II, when R³' is alkyl, the alkyl is substituted with a 5, 6, 7, 8, 9, or 10 membered monocyclic or bicyclic heteroaryl, which is unsubstituted or substituted. The monocyclic heteroaryl includes but is not limited to pyrrolyl, thienyl, furyl, pyridinyl, pyranyl, pyrimidinyl, pyrazinyl, pyridazinyl, imidazolyl, thiazolyl, pyrazolyl, and oxazolyl. The bicyclic heteroaryl includes but is not limited to benzothiophenyl, benzofuryl, indolyl, quinolinyl, isoquinolinyl, benzimidazolyl, benzoxazolyl, benzothiazolyl, quinazolinyl, azaindolyl, pyrazolopyrimidinyl, purinyl, pyrrolo[1,2-b]pyridazinyl, pyrrolopyrimidinyl, indazolyl, pyrazolylpyridinyl, imidazo[1,2-a]pyridinyl, and pyrrolo[1,2-f][1,2,4]triazinyl.

In other embodiments of the compound of Formula II, R³' is —NHR³''', —N(CH₃)R³''', —N(CH₂CH₃)R³''', —N(CH(CH₃)₂)R³''', or —OR³''', wherein R³''' is unsubstituted or substituted heterocycloalkyl (nonlimiting examples thereof include 4-NH piperidin-1-yl, 4-methyl piperidin-1-yl, 4-ethyl piperidin-1-yl, 4-isopropyl-piperidin-1-yl, and pyrrolidin-3-yl), unsubstituted or substituted monocyclic aryl, or unsubstituted or substituted monocyclic heteroaryl (including but not limited to pyrrolyl, thienyl, furyl, pyridinyl, pyranyl, pyrimidinyl, pyrazinyl, pyridazinyl, imidazolyl, thiazolyl, pyrazolyl, and oxazolyl). In one example, R³' is —O-aryl, i.e. phenoxy. In another example, R³' is —O-(4-methyl)piperidin-1-yl or —O-(4-isopropyl)piperidin-1-yl.

In some embodiments of the compound of Formula II, R³' is one of the following moieties:

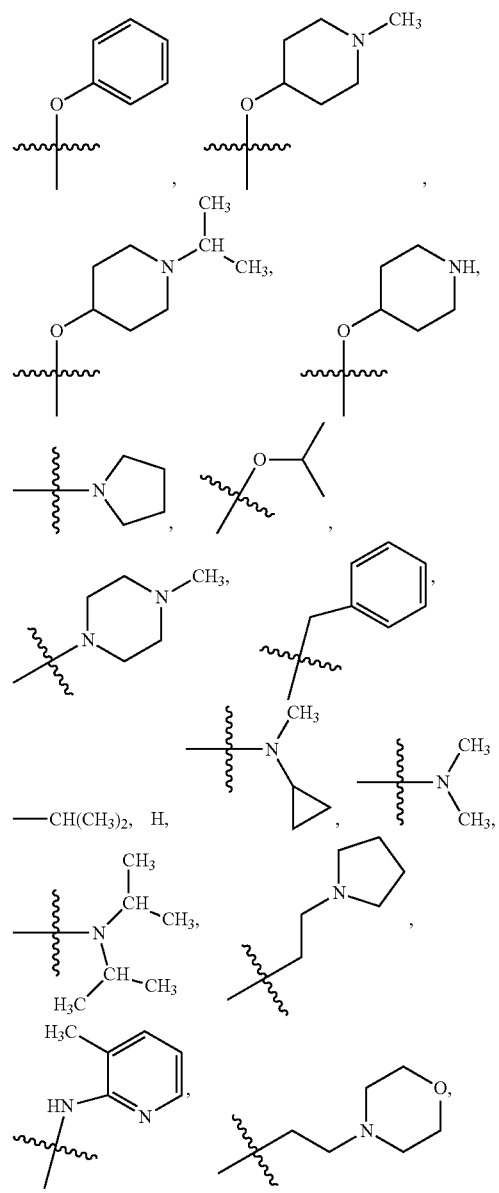

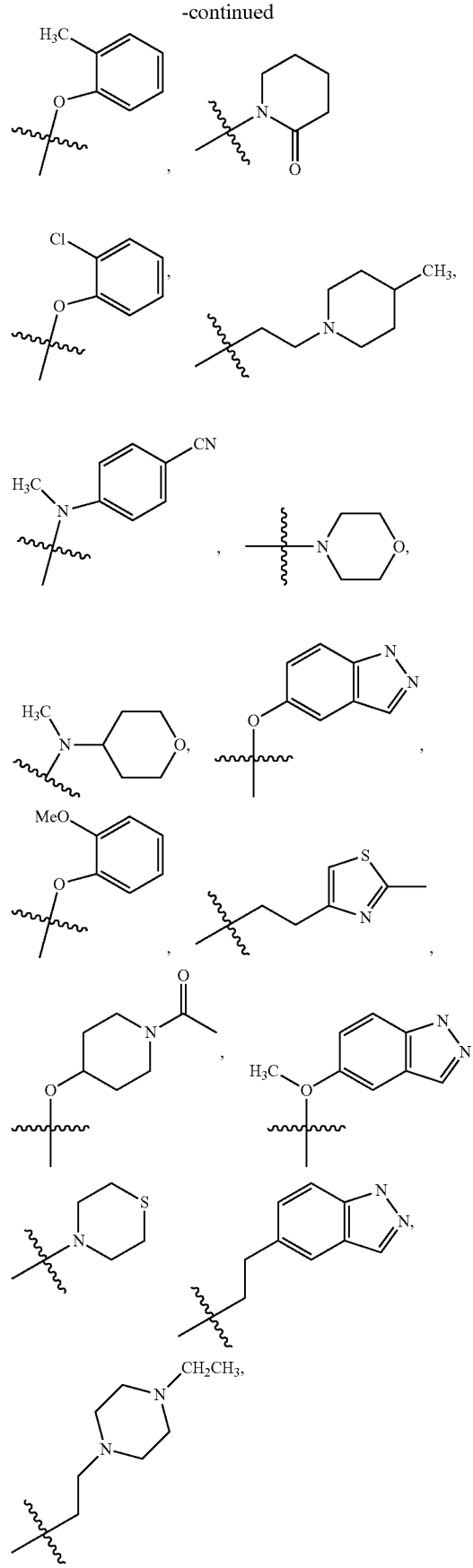
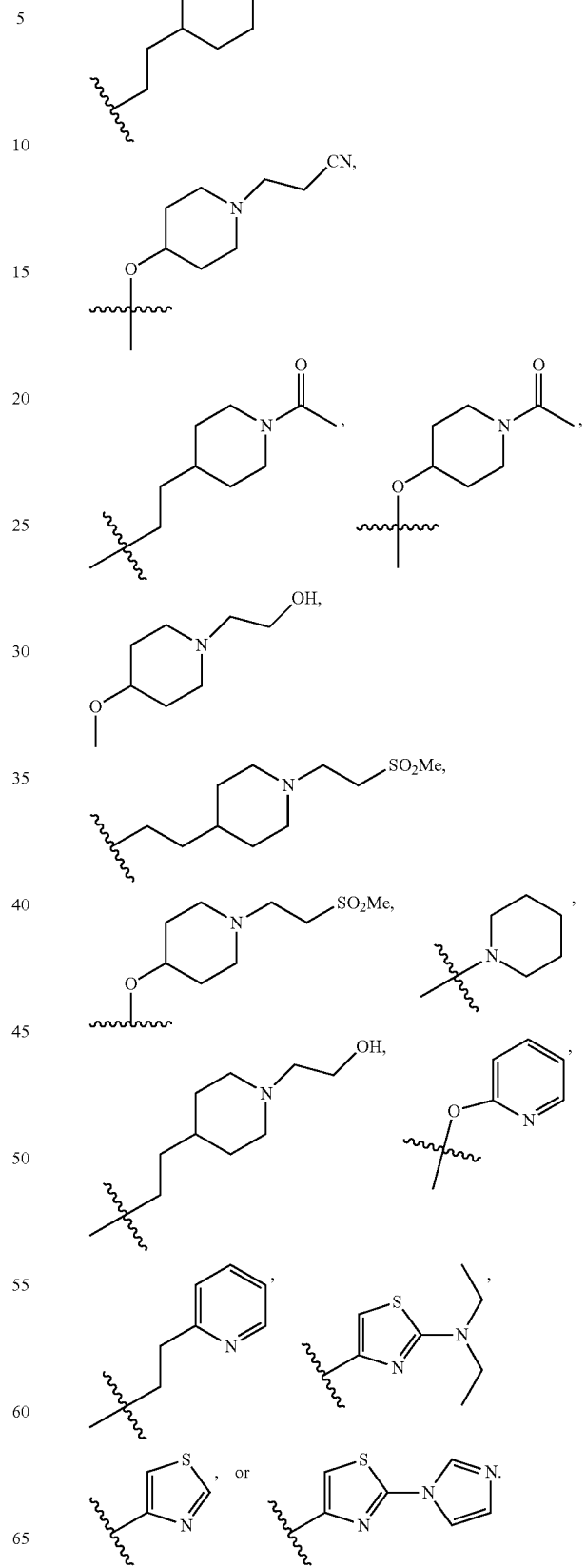

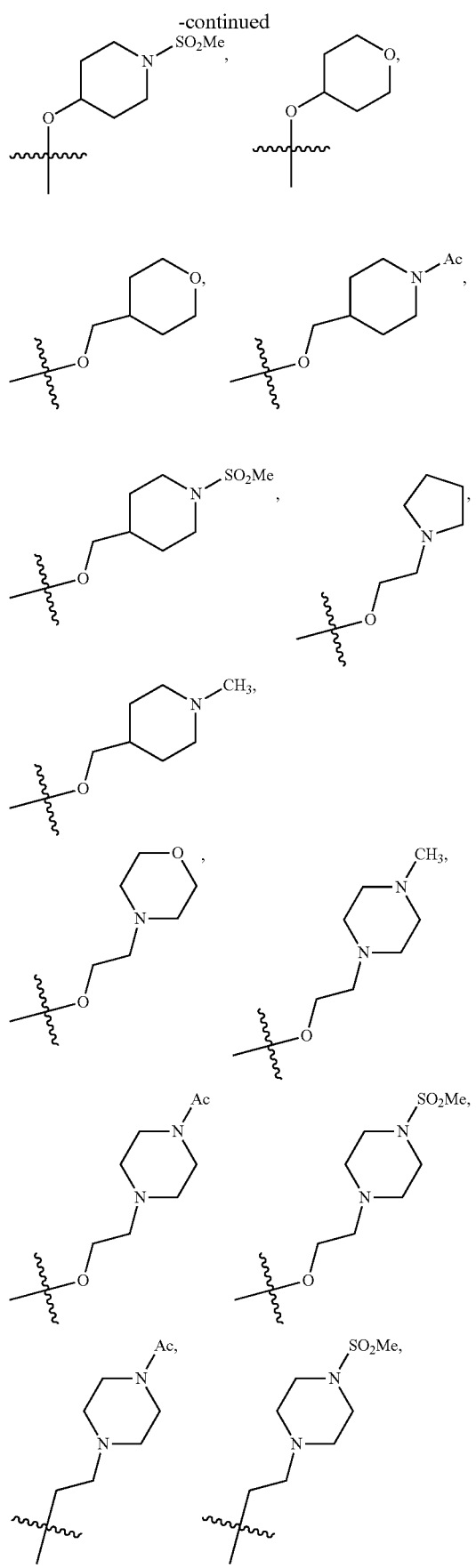
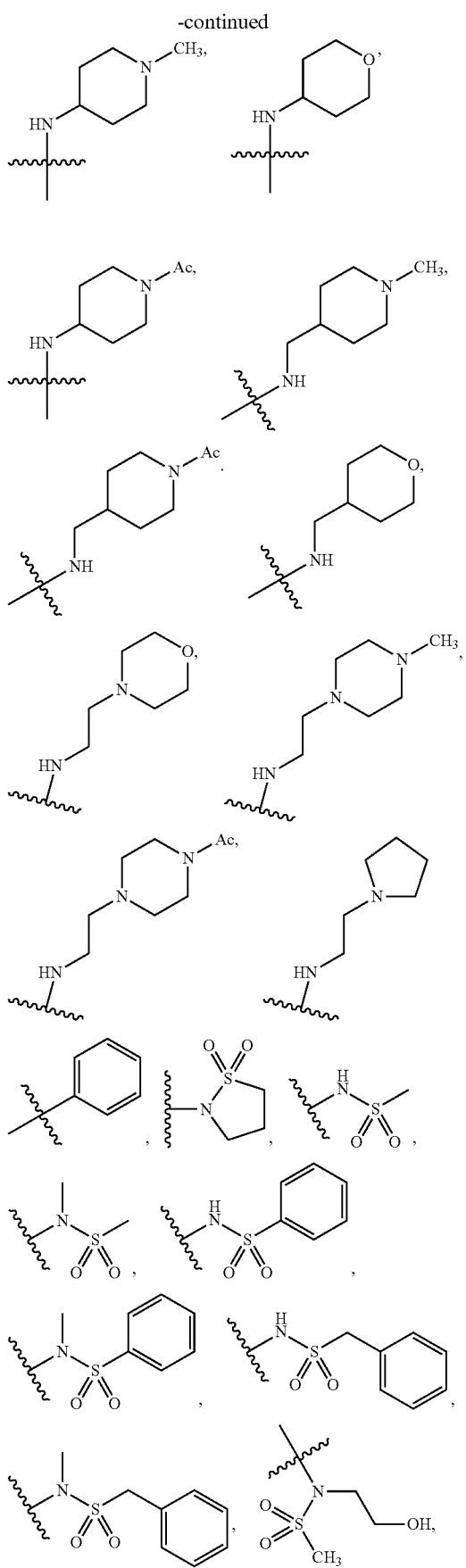

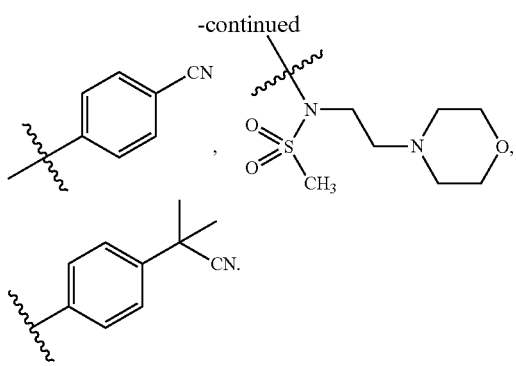

In some embodiments of the compound of Formula II, $W^{1'}$ is $NR^{3'}$, wherein $R^{3'}$ is hydrogen, unsubstituted or substituted $C_1$-$C_{10}$alkyl (which includes but is not limited to —$CH_3$, —$CH_2CH_3$, n-propyl, isopropyl, n-butyl, tert-butyl, sec-butyl, pentyl, hexyl, and heptyl), or unsubstituted or substituted $C_3$-$C_7$cycloalkyl (which includes but is not limited to cyclopropyl, cyclobutyl, cyclopentyl, and cyclohexyl). In other embodiments of the compound of Formula II, $R^{3'}$ is unsubstituted or substituted heterocycloalkyl (which includes but is not limited to oxetanyl, tetrahydrofuranyl, pyrrolidinyl, tetrahydropyranyl, piperidinyl, and piperazinyl), or unsubstituted or substituted $C_2$-$C_{10}$heteroalkyl (which includes but is not limited to methoxyethoxy, methoxymethyl, and diethylaminoethyl). Alternatively, $R^{3'}$ is unsubstituted or substituted monocyclic heteroaryl (which includes but is not limited to pyrrolyl, thienyl, furyl, pyridinyl, pyranyl, pyrimidinyl, pyrazinyl, pyridazinyl, imidazolyl, thiazolyl, pyrazolyl, and oxazolyl) or unsubstituted or substituted monocyclic aryl.

In still other embodiments, $W^{1'}$ is C=O.

In some embodiments of the compound of Formula II, $W^{2'}$ is $CR^{4'}$. $R^{4'}$ can be, for example, hydrogen, or unsubstituted or substituted alkyl (including but not limited to $CH_3$, —$CH_2CH_3$, n-propyl, isopropyl, n-butyl, tert-butyl, sec-butyl, pentyl, hexyl, and heptyl). In other embodiments, $R^{4'}$ is unsubstituted or substituted alkenyl (including but not limited to unsubstituted or substituted $C_2$-$C_5$alkenyl such as, for example, vinyl, allyl, 1-methyl propen-1-yl, butenyl, or pentenyl) or unsubstituted or substituted alkynyl (including but not limited to unsubstituted or substituted $C_2$-$C_5$alkynyl such as acetylenyl, propargyl, butynyl, or pentynyl). Alternatively, $R^{4'}$ is unsubstituted or substituted aryl (including but not limited to monocyclic or bicyclic aryl) or unsubstituted or substituted arylalkyl (including but not limited to monocyclic or bicyclic aryl linked to alkyl wherein alkyl includes but is not limited to $CH_3$, —$CH_2CH_3$, n-propyl, isopropyl, n-butyl, sec-butyl, and pentyl). In some other embodiments, $R^{4'}$ is unsubstituted or substituted heteroaryl, including but not limited to monocyclic and bicyclic heteroaryl. Monocyclic heteroaryl $R^{4'}$ includes but is not limited to pyrrolyl, thienyl, furyl, pyridinyl, pyranyl, pyrimidinyl, pyrazinyl, pyridazinyl, imidazolyl, thiazolyl, pyrazolyl, and oxazolyl. Bicyclic heteroaryl $R^{4'}$ includes but is not limited to benzothiophenyl, benzofuryl, indolyl, quinolinyl, isoquinolinyl, benzimidazolyl, benzoxazolyl, benzothiazolyl, quinazolinyl, azaindolyl, pyrazolopyrimidinyl, purinyl, pyrrolo[1,2-b]pyridazinyl, pyrrolopyrimidinyl, indazolyl, pyrazolylpyridinyl, imidazo[1,2-a]pyridinyl, and pyrrolo[1,2-f][1,2,4]triazinyl.

The present invention also provides compounds of Formula II wherein $R^{4'}$ is unsubstituted or substituted heteroarylalkyl, including but not limited to monocyclic and bicyclic heteroaryl as described above, that are linked to alkyl, which in turn includes but is not limited to $CH_3$, —$CH_2CH_3$, n-propyl, isopropyl, n-butyl, sec-butyl, and pentyl. In some embodiments, $R^{4'}$ is unsubstituted or substituted cycloalkyl (including but not limited to cyclopropyl, cyclobutyl, and cyclopentyl) or unsubstituted or substituted heteroalkyl (non-limiting examples include ethoxymethyl, methoxymethyl, and diethylaminomethyl). In some further embodiments, $R^{4'}$ is unsubstituted or substituted heterocycloalkyl which includes but is not limited to pyrrolidinyl, tetrahydrofuranyl, piperidinyl, tetrahydropyranyl, thiazolidinyl, imidazolidinyl, morpholinyl, and piperazinyl. In yet other embodiments of the compounds of Formula II, $R^{4'}$ is unsubstituted or substituted alkoxy including but not limited to $C_1$-$C_4$alkoxy such as methoxy, ethoxy, propoxy or butoxy. $R^{4'}$ can also be unsubstituted or substituted heterocycloalkyloxy, including but not limited to 4-NH piperidin-1-yl-oxy, 4-methyl piperidin-1-yl-oxy, 4-ethyl piperidin-1-yl-oxy, 4-isopropyl-piperidin-1-yl-oxy, and pyrrolidin-3-yl-oxy. In other embodiments, $R^{4'}$ is unsubstituted or substituted amino, wherein the substituted amino includes but is not limited to dimethylamino, diethylamino, di-isopropyl amino, N-methyl N-ethyl amino, and dibutylamino. In some embodiments, $R^{4'}$ is unsubstituted or substituted acyl, unsubstituted or substituted acyloxy, unsubstituted or substituted $C_1$-$C_4$acyloxy, unsubstituted or substituted alkoxycarbonyl, unsubstituted or substituted amido, or unsubstituted or substituted sulfonamido. In some embodiments, $R^{4'}$ is halo, which is —I, —F, —Cl, or —Br. In some embodiments, $R^{4'}$ is selected from the group consisting of cyano, hydroxy, nitro, phosphate, urea, or carbonate. Also contemplated are $R^{4'}$ being —$CH_3$, —$CH_2CH_3$, n-propyl, isopropyl, n-butyl, tert-butyl, sec-butyl, pentyl, hexyl, heptyl, —$OCH_3$, —$OCH_2CH_3$, or —$CF_3$.

$R^{4'}$ of the compounds of Formula II, can also be NR'R" wherein R' and R" are taken together with the nitrogen to form a cyclic moiety having from 3 to 8 ring atoms. The cyclic moiety so formed may further include one or more heteroatoms which are selected from the group consisting of S, O, and N. The cyclic moiety so formed is unsubstituted or substituted, including but not limited to morpholinyl, azetidinyl, pyrrolidinyl, piperidinyl, piperazinyl, isothiazolidinyl 1,2, dioxide, and thiomorpholinyl. Further non-limiting exemplary cyclic moieties are the following:

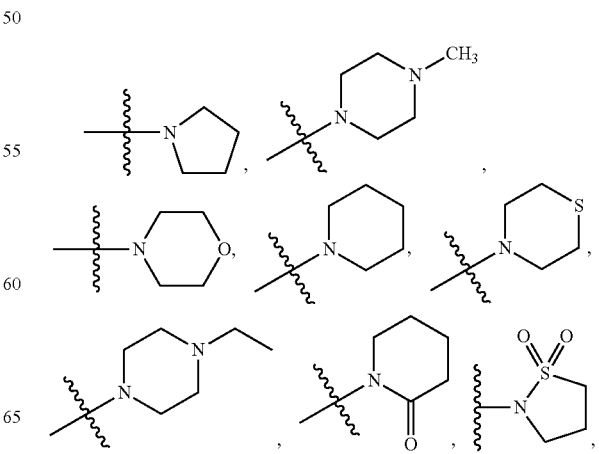

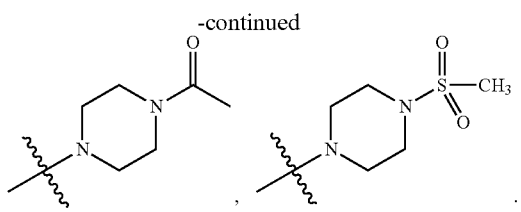

The invention also provides compounds of Formula II, wherein when $R^{4'}$ is a member of the group consisting of alkyl, alkenyl, alkynyl, cycloalkyl, heteroalkyl, heterocycloalkyl, heterocycloalkyloxy, aryl, arylalkyl, heteroaryl, heteroarylalkyl, acyl, alkoxy, amido, amino, sulfonamido, acyloxy, alkoxycarbonyl, and NR'R" (wherein R' and R" are taken together with nitrogen to form a cyclic moiety), then $R^{4'}$ is optionally substituted with one or more of the following substituents: alkyl, alkenyl, alkynyl, cycloalkyl, heteroalkyl, heterocycloalkyl, heterocycloalkyloxy, aryl, arylalkyl, heteroaryl, heteroarylalkyl, acyl, alkoxy, amido, amino, sulfonamido, acyloxy, alkoxycarbonyl, halo, cyano, hydroxy, nitro, phosphate, urea, carbonate, or NR'R" wherein R' and R" are taken together with nitrogen to form a cyclic moiety. Each of the above substituents may be further substituted with one or more substituents chosen from the group consisting of alkyl, alkoxy, amido, amino, sulfonamido, acyloxy, alkoxycarbonyl, halo, cyano, hydroxy, nitro, oxo, phosphate, urea, and carbonate.

For example, the invention provides compounds wherein when $R^{4'}$ is alkyl, the alkyl is substituted with NR'R" wherein R' and R" are taken together with the nitrogen to form a cyclic moiety. The cyclic moiety so formed can be unsubstituted or substituted. Non-limiting exemplary cyclic moieties includes but are not limited to morpholinyl, azetidinyl, pyrrolidinyl, piperidinyl, piperazinyl, isothiazolidinyl 1,2, dioxide, and thiomorpholinyl. In other examples of the compounds of Formula II, when $R^{4'}$ is alkyl, the alkyl is substituted with heterocycloalkyl, which includes oxetanyl, azetidinyl, tetrahydrofuranyl, pyrrolyl, tetrahydropyranyl, piperidinyl, morpholinyl, and piperazinyl. All of the above listed heterocycloaklyl substituents can be unsubstituted or substituted.

In yet other examples of the compounds of Formula II, when $R^{4'}$ is alkyl, the alkyl is substituted with a 5, 6, 7, 8, 9, or 10 membered monocyclic or bicyclic heteroaryl, which is unsubstituted or substituted. The monocyclic heteroaryl includes but is not limited to pyrrolyl, thienyl, furyl, pyridinyl, pyranyl, pyrimidinyl, pyrazinyl, pyridazinyl, imidazolyl, thiazolyl, pyrazolyl, and oxazolyl. The bicyclic heteroaryl includes but is not limited benzothiophenyl, benzofuryl, indolyl, quinolinyl, isoquinolinyl, benzimidazolyl, benzoxazolyl, benzothiazolyl, quinazolinyl, azaindolyl, pyrazolopyrimidinyl, purinyl, pyrrolo[1,2-b]pyridazinyl, pyrrolopyrimidinyl, indazolyl, pyrazolylpyridinyl, imidazo[1,2-a]pyridinyl, and pyrrolo[1,2-f][1,2,4]triazinyl.

In some embodiments of the compound of Formula II, $W^{2'}$ is $NR^{4'}$, wherein $R^{4'}$ is hydrogen, unsubstituted or substituted $C_1$-$C_{10}$alkyl (which includes but is not limited to —$CH_3$, —$CH_2CH_3$, n-propyl, isopropyl, n-butyl, tert-butyl, sec-butyl, pentyl, hexyl, and heptyl), or unsubstituted or substituted $C_3$-$C_7$cycloalkyl (which includes but is not limited to cyclopropyl, cyclobutyl, cyclopentyl, and cyclohexyl). In other embodiments of the compound of Formula II, $R^{4'}$ is unsubstituted or substituted heterocycloalkyl (which includes but is not limited to oxetanyl, tetrahydrofuranyl, pyrrolidinyl, tetrahydropyranyl, piperidinyl, and piperazinyl), or unsubstituted or substituted $C_2$-$C_{10}$heteroalkyl (which includes but is not limited to methoxyethoxy, methoxymethyl, and diethylaminoethyl). Alternatively, $R^{4'}$ is unsubstituted or substituted monocyclic heteroaryl (which includes but is not limited to pyrrolyl, thienyl, furyl, pyridinyl, pyranyl, pyrimidinyl, pyrazinyl, pyridazinyl, imidazolyl, thiazolyl, pyrazolyl, and oxazolyl) or unsubstituted or substituted monocyclic aryl.

In some embodiments $R^{3'}$ and $R^{4'}$ taken together form a cyclic moiety. Such a moiety may have, for example, from 3 to 8 ring atoms. The cyclic moiety so formed may further include one or more heteroatoms which are selected from the group consisting of S, O, and N. The cyclic moiety so formed is unsubstituted or substituted. In some embodiments, the substituent is $C_1$-$C_{10}$alkyl (which includes but is not limited to —$CH_3$, —$CH_2CH_3$, n-propyl, isopropyl, n-butyl, tert-butyl, sec-butyl, pentyl, hexyl, and heptyl), or $C_3$-$C_7$cycloalkyl (which includes but is not limited to cyclopropyl, cyclobutyl, cyclopentyl, and cyclohexyl); heterocycloalkyl (which includes but is not limited to oxetanyl, tetrahydrofuranyl, pyrrolidinyl, tetrahydropyranyl, piperidinyl, and piperazinyl), $C_2$-$C_{10}$heteroalkyl (which includes but is not limited to methoxyethoxy, methoxymethyl, and diethylaminoethyl); monocyclic heteroaryl (which includes but is not limited to pyrrolyl, thienyl, furyl, pyridinyl, pyranyl, pyrimidinyl, pyrazinyl, pyridazinyl, imidazolyl, thiazolyl, pyrazolyl, and oxazolyl) or unsubstituted or substituted monocyclic aryl. The cyclic moiety may have one or more substituents, which may be the same or different.

In some embodiments, the cyclic moiety formed by $R^{3'}$ and $R^{4'}$ is substituted with at least one of the following substituents:

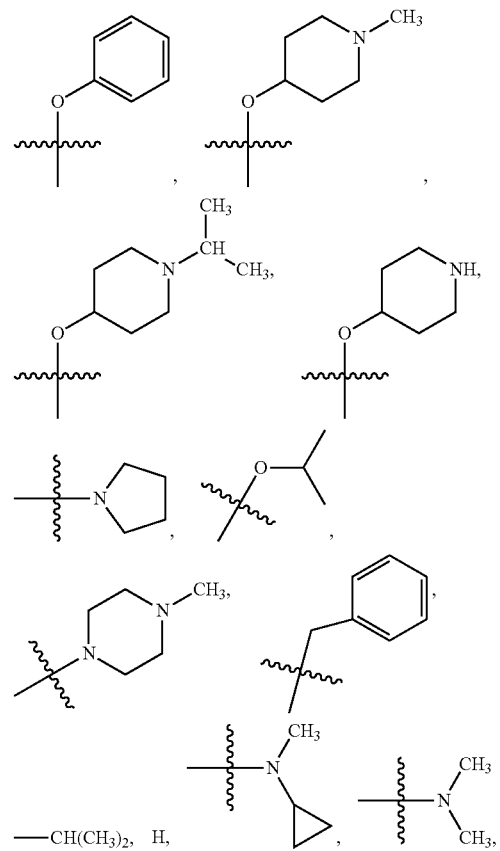

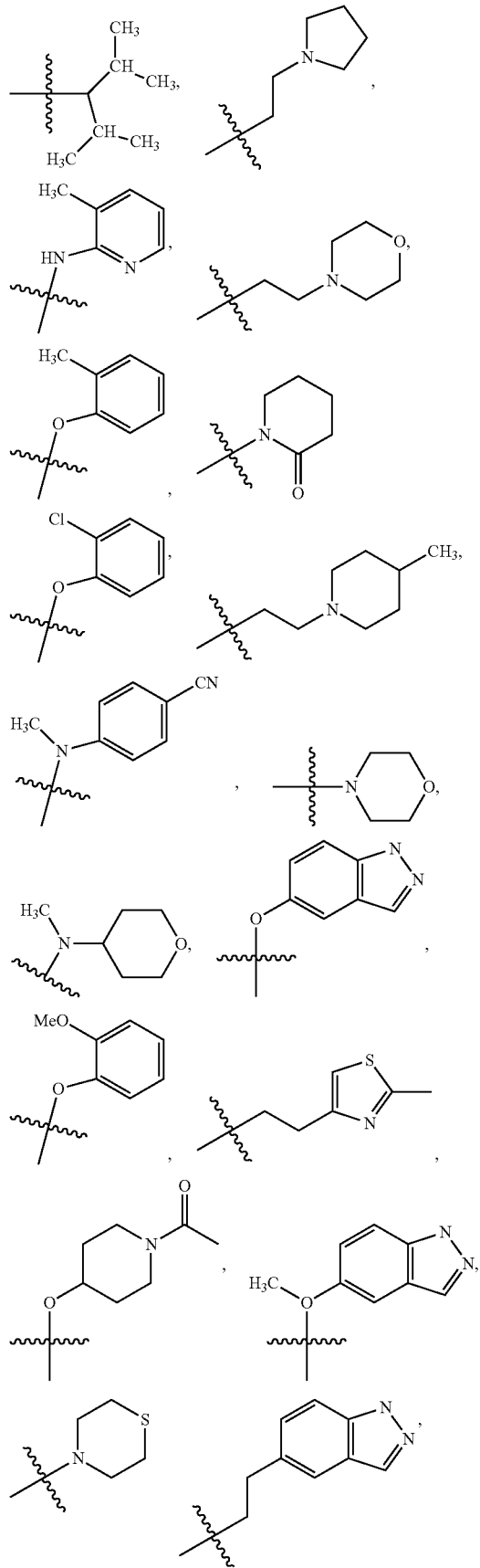
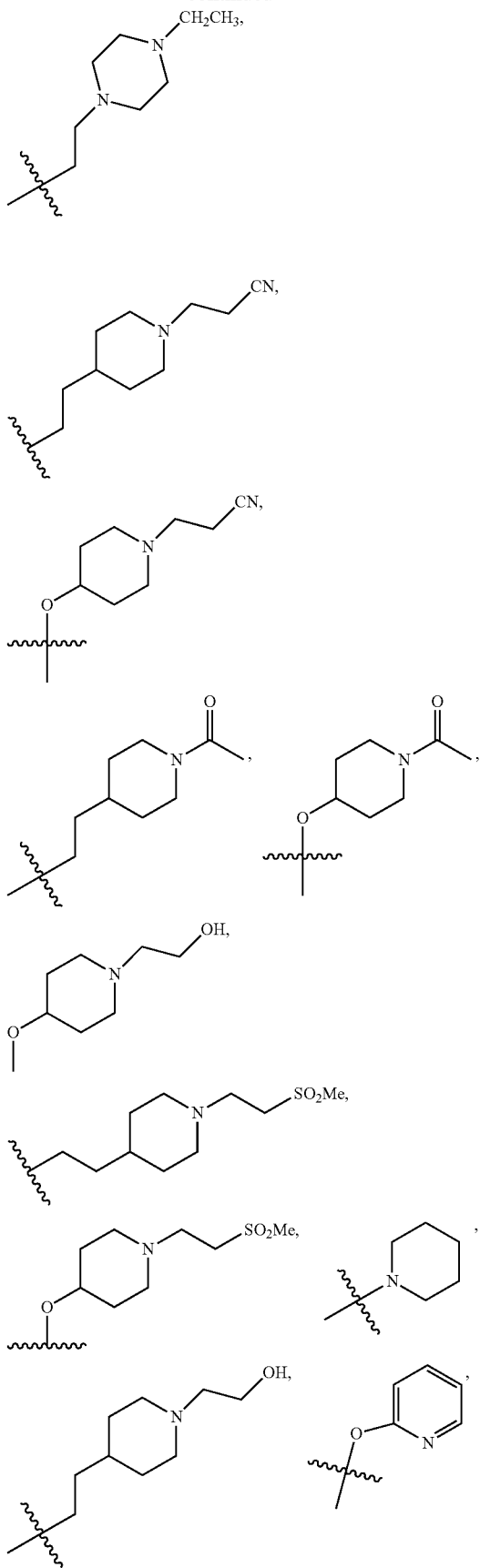

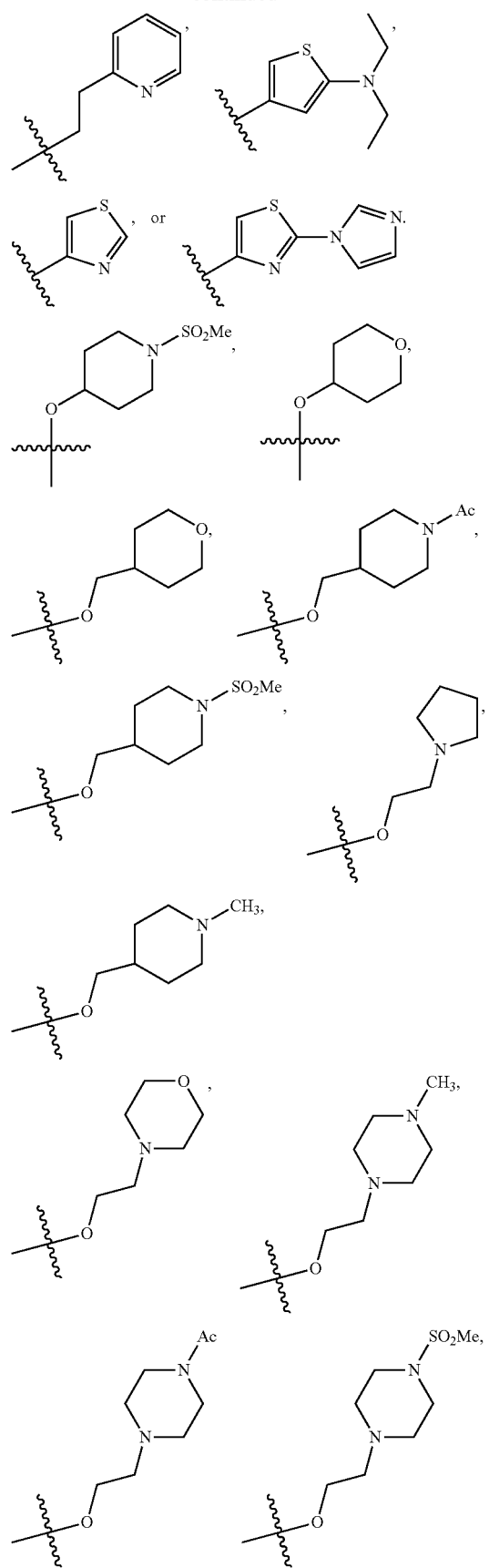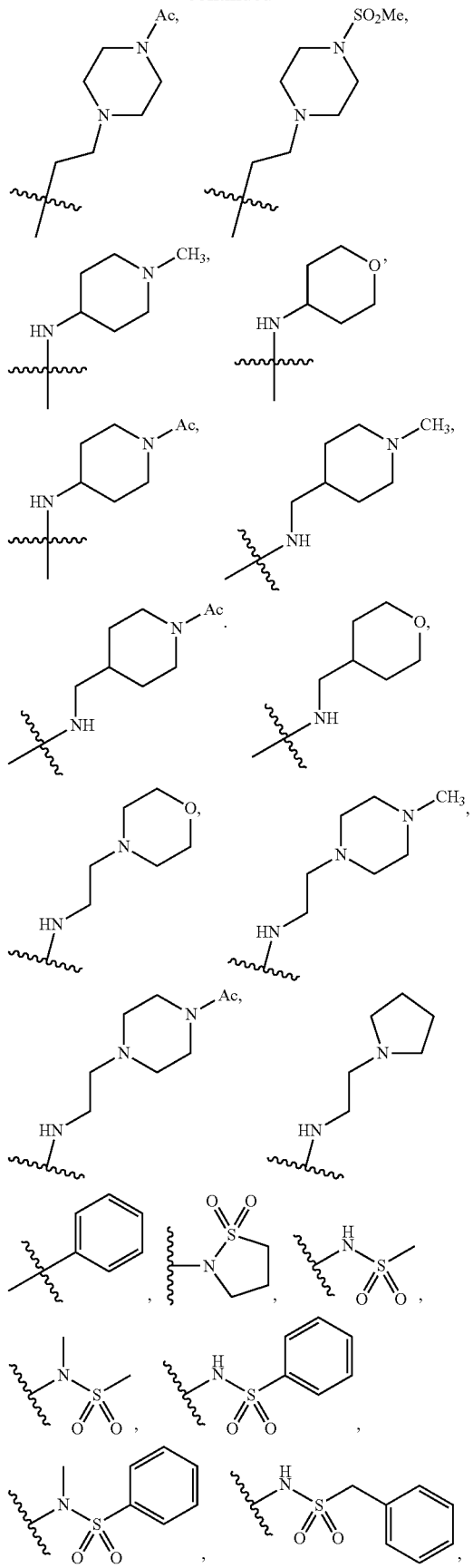

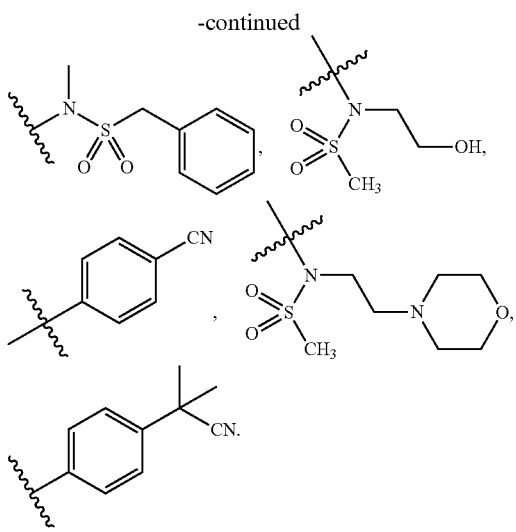

In some embodiments of the compound of Formula II, $W^{3'}$ is $CR^{5'}$. $R^{5'}$ can be, for example, hydrogen, or unsubstituted or substituted alkyl (including but not limited to $CH_3$, —$CH_2CH_3$, n-propyl, isopropyl, n-butyl, tert-butyl, sec-butyl, pentyl, hexyl, and heptyl). In one embodiment, $R^{5'}$ is H. In other embodiments, $R^{5'}$ is unsubstituted or substituted alkenyl (including but not limited to unsubstituted or substituted $C_2$-$C_5$alkenyl such as, for example, vinyl, allyl, 1-methyl propen-1-yl, butenyl, or pentenyl) or unsubstituted or substituted alkynyl (including but not limited to unsubstituted or substituted $C_2$-$C_5$alkynyl such as acetylenyl, propargyl, butynyl, or pentynyl). Alternatively, $R^{5'}$ is unsubstituted or substituted aryl (including but not limited to monocyclic or bicyclic aryl) or unsubstituted or substituted arylalkyl (including but not limited to monocyclic or bicyclic aryl linked to alkyl wherein alkyl includes but is not limited to $CH_3$, —$CH_2CH_3$, n-propyl, isopropyl, n-butyl, sec-butyl, and pentyl). In some other embodiments, $R^{5'}$ is unsubstituted or substituted heteroaryl, including but not limited to monocyclic and bicyclic heteroaryl. Monocyclic heteroaryl $R^{5'}$ includes but is not limited to pyrrolyl, thienyl, furyl, pyridinyl, pyranyl, pyrimidinyl, pyrazinyl, pyridazinyl, imidazolyl, thiazolyl, pyrazolyl, and oxazolyl. Bicyclic heteroaryl $R^{5'}$ includes but is not limited to benzothiophenyl, benzofuryl, indolyl, quinolinyl, isoquinolinyl, benzimidazolyl, benzoxazolyl, benzothiazolyl, quinazolinyl, azaindolyl, pyrazolopyrimidinyl, purinyl, pyrrolo[1,2-b]pyridazinyl, pyrrolopyrimidinyl, indazolyl, pyrazolylpyridinyl, imidazo[1,2-a]pyridinyl, and pyrrolo[1,2-f][1,2,4]triazinyl.

In some embodiments of the compound of Formula II, $W^{3'}$ is N or $NR^{5'}$, wherein $R^{5'}$ is hydrogen, unsubstituted or substituted $C_1$-$C_{10}$alkyl (which includes but is not limited to —$CH_3$, —$CH_2CH_3$, n-propyl, isopropyl, n-butyl, tert-butyl, sec-butyl, pentyl, hexyl, and heptyl), or unsubstituted or substituted $C_3$-$C_7$cycloalkyl (which includes but is not limited to cyclopropyl, cyclobutyl, cyclopentyl, and cyclohexyl). In other embodiments of the compound of Formula II, $R^{5'}$ is unsubstituted or substituted heterocycloalkyl (which includes but is not limited to oxetanyl, tetrahydrofuranyl, pyrrolidinyl, tetrahydropyranyl, piperidinyl, and piperazinyl), or unsubstituted or substituted $C_2$-$C_{10}$heteroalkyl (which includes but is not limited to methoxyethoxy, methoxymethyl, and diethylaminoethyl). Alternatively, $R^{5'}$ is unsubstituted or substituted monocyclic heteroaryl (which includes but is not limited to pyrrolyl, thienyl, furyl, pyridinyl, pyranyl, pyrimidinyl, pyrazinyl, pyridazinyl, imidazolyl, thiazolyl, pyrazolyl, and oxazolyl) or unsubstituted or substituted monocyclic aryl.

In some embodiments of the compound of Formula II, $W^{4'}$ is $CR^{6'}$. $R^{6'}$ can be, for example, hydrogen, or unsubstituted or substituted alkyl (including but not limited to $CH_3$, —$CH_2CH_3$, n-propyl, isopropyl, n-butyl, tert-butyl, sec-butyl, pentyl, hexyl, and heptyl). In one embodiment, $R^{6'}$ is H. In other embodiments, $R^{6'}$ is unsubstituted or substituted alkenyl (including but not limited to unsubstituted or substituted $C_2$-$C_5$alkenyl such as, for example, vinyl, allyl, 1-methyl propen-1-yl, butenyl, or pentenyl) or unsubstituted or substituted alkynyl (including but not limited to unsubstituted or substituted $C_2$-$C_5$alkynyl such as acetylenyl, propargyl, butynyl, or pentynyl). Alternatively, $R^{6'}$ is unsubstituted or substituted aryl (including but not limited to monocyclic or bicyclic aryl) or unsubstituted or substituted arylalkyl (including but not limited to monocyclic or bicyclic aryl linked to alkyl wherein alkyl includes but is not limited to $CH_3$, —$CH_2CH_3$, n-propyl, isopropyl, n-butyl, sec-butyl, and pentyl). In some other embodiments, $R^{6'}$ is unsubstituted or substituted heteroaryl, including but not limited to monocyclic and bicyclic heteroaryl. Monocyclic heteroaryl $R^{6'}$ includes but is not limited to pyrrolyl, thienyl, furyl, pyridinyl, pyranyl, pyrimidinyl, pyrazinyl, pyridazinyl, imidazolyl, thiazolyl, pyrazolyl, and oxazolyl. Bicyclic heteroaryl $R^{6'}$ includes but is not limited to benzothiophenyl, benzofuryl, indolyl, quinolinyl, isoquinolinyl, benzimidazolyl, benzoxazolyl, benzothiazolyl, quinazolinyl, azaindolyl, pyrazolopyrimidinyl, purinyl, pyrrolo[1,2-b]pyridazinyl, pyrrolopyrimidinyl, indazolyl, pyrazolylpyridinyl, imidazo[1,2-a]pyridinyl, and pyrrolo[1,2-f][1,2,4]triazinyl.

In some embodiments of the compound of Formula II, $W^{4'}$ is N or $NR^{6'}$, wherein $R^{6'}$ is hydrogen, unsubstituted or substituted $C_1$-$C_{10}$alkyl (which includes but is not limited to —$CH_3$, —$CH_2CH_3$, n-propyl, isopropyl, n-butyl, tert-butyl, sec-butyl, pentyl, hexyl, and heptyl), or unsubstituted or substituted $C_3$-$C_7$cycloalkyl (which includes but is not limited to cyclopropyl, cyclobutyl, cyclopentyl, and cyclohexyl). In other embodiments of the compound of Formula II, $R^6$ is unsubstituted or substituted heterocycloalkyl (which includes but is not limited to oxetanyl, tetrahydrofuranyl, pyrrolidinyl, tetrahydropyranyl, piperidinyl, and piperazinyl), or unsubstituted or substituted $C_2$-$C_{10}$heteroalkyl (which includes but is not limited to methoxyethoxy, methoxymethyl, and diethylaminoethyl). Alternatively, $R^{6'}$ is unsubstituted or substituted monocyclic heteroaryl (which includes but is not limited to pyrrolyl, thienyl, furyl, pyridinyl, pyranyl, pyrimidinyl, pyrazinyl, pyridazinyl, imidazolyl, thiazolyl, pyrazolyl, and oxazolyl) or unsubstituted or substituted monocyclic aryl.

In other embodiments, $W^{4'}$ is C=O.

In some embodiments of the compound of Formula II, $W^{5'}$ is N. In other embodiments of the compound of Formula II, $W^{5'}$ is $CR^{7'}$. $R^{7'}$ can be, for example, hydrogen, or unsubstituted or substituted alkyl (including but not limited to $CH_3$, —$CH_2CH_3$, n-propyl, isopropyl, n-butyl, tert-butyl, sec-butyl, pentyl, hexyl, and heptyl). In one embodiment, $R^{7'}$ is H. In other embodiments, $R^{7'}$ is unsubstituted or substituted alkenyl (including but not limited to unsubstituted or substituted $C_2$-$C_5$alkenyl such as, for example, vinyl, allyl, 1-methyl propen-1-yl, butenyl, or pentenyl) or unsubstituted or substituted alkynyl (including but not limited to unsubstituted or substituted $C_2$-$C_5$alkynyl such as acetylenyl, propargyl, butynyl, or pentynyl). Alternatively, $R^{7'}$ is unsubstituted or substituted aryl (including but not limited to monocyclic or bicyclic aryl) or unsubstituted or substituted arylalkyl (including but not limited to monocyclic or bicyclic aryl linked to alkyl wherein alkyl includes but is not limited to $CH_3$, $-CH_2CH_3$, n-propyl, isopropyl, n-butyl, sec-butyl, and pentyl). In some other embodiments, $R^{7'}$ is unsubstituted or substituted heteroaryl, including but not limited to monocyclic and bicyclic heteroaryl. Monocyclic heteroaryl $R^{7'}$ includes but is not limited to pyrrolyl, thienyl, furyl, pyridinyl, pyranyl, pyrimidinyl, pyrazinyl, pyridazinyl, imidazolyl, thiazolyl, pyrazolyl, and oxazolyl. Bicyclic heteroaryl $R^{7'}$ includes but is not limited to benzothiophenyl, benzofuryl, indolyl, quinolinyl, isoquinolinyl, benzimidazolyl, benzoxazolyl, benzothiazolyl, quinazolinyl, azaindolyl, pyrazolopyrimidinyl, purinyl, pyrrolo[1,2-b]pyridazinyl, pyrrolopyrimidinyl, indazolyl, pyrazolylpyridinyl, imidazo[1,2-a]pyridinyl, and pyrrolo[1,2-f][1,2,4]triazinyl.

In some embodiments of the compound of Formula II, $W^{6'}$ is N. In other embodiments of the compound of Formula II, $W^{6'}$ is $CR^{8'}$. $R^{8'}$ can be, for example, hydrogen, or unsubstituted or substituted alkyl (including but not limited to $CH_3$, $-CH_2CH_3$, n-propyl, isopropyl, n-butyl, tert-butyl, sec-butyl, pentyl, hexyl, and heptyl). In one embodiment, $R^{8'}$ is H. In other embodiments, $R^{8'}$ is unsubstituted or substituted alkenyl (including but not limited to unsubstituted or substituted $C_2$-$C_5$alkenyl such as, for example, vinyl, allyl, 1-methyl propen-1-yl, butenyl, or pentenyl) or unsubstituted or substituted alkynyl (including but not limited to unsubstituted or substituted $C_2$-$C_5$alkynyl such as acetylenyl, propargyl, butynyl, or pentynyl). Alternatively, $R^{8'}$ is unsubstituted or substituted aryl (including but not limited to monocyclic or bicyclic aryl) or unsubstituted or substituted arylalkyl (including but not limited to monocyclic or bicyclic aryl linked to alkyl wherein alkyl includes but is not limited to $CH_3$, $-CH_2CH_3$, n-propyl, isopropyl, n-butyl, sec-butyl, and pentyl). In some other embodiments, $R^{8'}$ is unsubstituted or substituted heteroaryl, including but not limited to monocyclic and bicyclic heteroaryl. Monocyclic heteroaryl $R^{8'}$ includes but is not limited to pyrrolyl, thienyl, furyl, pyridinyl, pyranyl, pyrimidinyl, pyrazinyl, pyridazinyl, imidazolyl, thiazolyl, pyrazolyl, and oxazolyl. Bicyclic heteroaryl $R^{8'}$ includes but is not limited to benzothiophenyl, benzofuryl, indolyl, quinolinyl, isoquinolinyl, benzimidazolyl, benzoxazolyl, benzothiazolyl, quinazolinyl, azaindolyl, pyrazolopyrimidinyl, purinyl, pyrrolo[1,2-b]pyridazinyl, pyrrolopyrimidinyl, indazolyl, pyrazolylpyridinyl, imidazo[1,2-a]pyridinyl, and pyrrolo[1,2-f][1,2,4]triazinyl.

In some embodiments, the compound of Formula II has the formula:

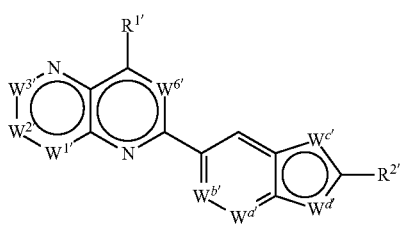

In other embodiments, the compound of Formula II is:

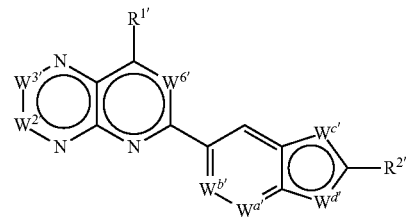

For example, the compound of Formula II is:

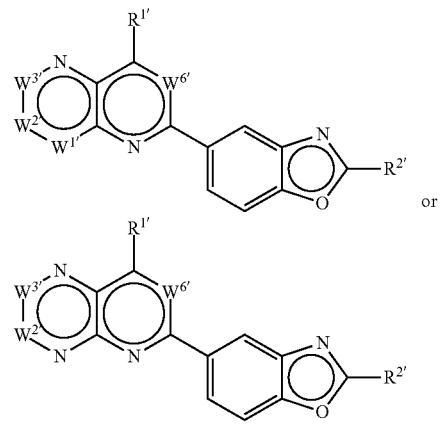

or

In some embodiments, the compound of Formula II is:

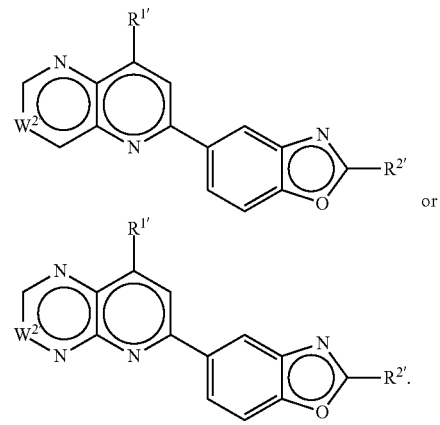

or

In another aspect, the invention provides compounds of Subformula IIa.

Subformula IIa

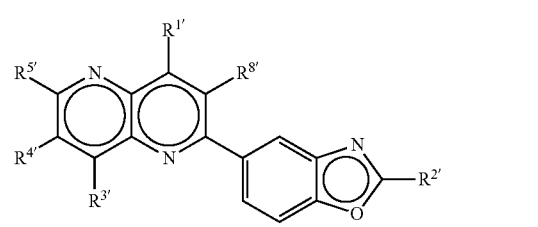

In one embodiment, $R^{1'}$, $R^{3'}$, $R^{4'}$, $R^{5'}$, and $R^{8'}$ are hydrogen. In another embodiment, $R^{1'}$, $R^{3'}$, $R^{5'}$, and $R^{8'}$ are hydrogen and $R^{4'}$ is alkyl, heteroalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, halo, cyano, hydroxy, nitro, phosphate, urea, carbonate, or NR'R" wherein R' and R" are taken together with nitrogen to form a cyclic moiety. $R^{4'}$ can be, for example, hydrogen, unsubstituted or substituted alkyl (including but not limited to $CH_3$, —$CH_2CH_3$, n-propyl, isopropyl, n-butyl, tert-butyl, sec-butyl, pentyl, hexyl, and heptyl). In other embodiments, $R^{4'}$ is unsubstituted or substituted alkenyl (including but not limited to unsubstituted or substituted $C_2$-$C_5$alkenyl such as, for example, vinyl, allyl, 1-methyl propen-1-yl, butenyl, or pentenyl) or unsubstituted or substituted alkynyl (including but not limited to unsubstituted or substituted $C_2$-$C_5$alkynyl such as acetylenyl, propargyl, butynyl, or pentynyl). Alternatively, $R^{4'}$ is unsubstituted or substituted aryl (including but not limited to monocyclic or bicyclic aryl) or unsubstituted or substituted arylalkyl (including but not limited to monocyclic or bicyclic aryl linked to alkyl wherein alkyl includes but is not limited to $CH_3$, —$CH_2CH_3$, n-propyl, isopropyl, n-butyl, sec-butyl, and pentyl). In some other embodiments, $R^{4'}$ is unsubstituted or substituted heteroaryl, including but not limited to monocyclic and bicyclic heteroaryl. Monocyclic heteroaryl $R^{4'}$ includes but is not limited to pyrrolyl, thienyl, furyl, pyridinyl, pyranyl, pyrimidinyl, pyrazinyl, pyridazinyl, imidazolyl, thiazolyl, pyrazolyl, and oxazolyl. Bicyclic heteroaryl $R^{4'}$ includes but is not limited to benzothiophenyl, benzofuryl, indolyl, quinolinyl, isoquinolinyl, benzimidazolyl, benzoxazolyl, benzothiazolyl, quinazolinyl, azaindolyl, pyrazolopyrimidinyl, purinyl, pyrrolo[1,2-b]pyridazinyl, pyrrolopyrimidinyl, indazolyl, pyrazolylpyridinyl, imidazo[1,2-a]pyridinyl, and pyrrolo[1,2-f][1, 2, 4]triazinyl.

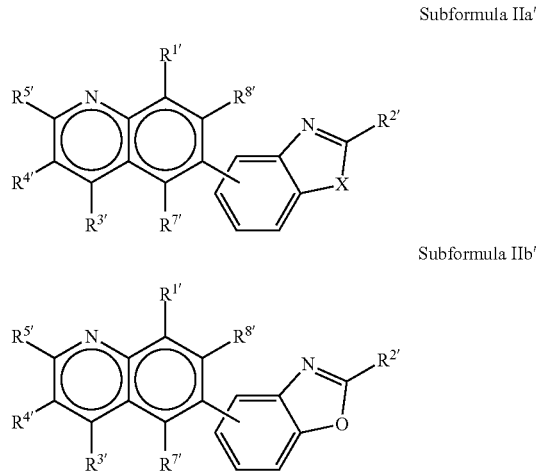

Subformula IIa'

Subformula IIb'

In another aspect, the invention provides compounds of Subformula IIa' and IIb', where $W^{1'}$ is $CR^{3'}$, $W^{2'}$ is $CR^{4'}$, $W^{3'}$ is $CR^{5'}$, $W^{4'}$ is N, $W^{5'}$ is $CR^{7'}$, and $W^{6'}$ is $CR^{8'}$. In one embodiment, $R^{1'}$, $R^{3'}$, $R^{4'}$, $R^{5'}$, $R^{7'}$ and $R^{8'}$ are hydrogen. In another embodiment, $R^{1'}$, $R^{4'}$, $R^{5'}$, $R^{7'}$ and $R^{8'}$ are hydrogen and $R^{3'}$ is alkyl, heteroalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, halo, cyano, hydroxy, nitro, phosphate, urea, carbonate, or NR'R" wherein R' and R" are taken together with nitrogen to form a cyclic moiety. $R^{3'}$ can be, for example, hydrogen, unsubstituted or substituted alkyl (including but not limited to $CH_3$, —$CH_2CH_3$, n-propyl, isopropyl, n-butyl, tert-butyl, sec-butyl, pentyl, hexyl, and heptyl). In other embodiments, $R^{3'}$ is unsubstituted or substituted alkenyl (including but not limited to unsubstituted or substituted $C_2$-$C_5$alkenyl such as, for example, vinyl, allyl, 1-methyl propen-1-yl, butenyl, or pentenyl) or unsubstituted or substituted alkynyl (including but not limited to unsubstituted or substituted $C_2$-$C_5$alkynyl such as acetylenyl, propargyl, butynyl, or pentynyl). Alternatively, $R^{3'}$ is unsubstituted or substituted aryl (including but not limited to monocyclic or bicyclic aryl) or unsubstituted or substituted arylalkyl (including but not limited to monocyclic or bicyclic aryl linked to alkyl wherein alkyl includes but is not limited to $CH_3$, —$CH_2CH_3$, n-propyl, isopropyl, n-butyl, sec-butyl, and pentyl). In some other embodiments, $R^{3'}$ is unsubstituted or substituted heteroaryl, including but not limited to monocyclic and bicyclic heteroaryl. Monocyclic heteroaryl $R^{3'}$ includes but is not limited to pyrrolyl, thienyl, furyl, pyridinyl, pyranyl, pyrimidinyl, pyrazinyl, pyridazinyl, imidazolyl, thiazolyl, pyrazolyl, and oxazolyl. Bicyclic heteroaryl $R^{3'}$ includes but is not limited to benzothiophenyl, benzofuryl, indolyl, quinolinyl, isoquinolinyl, benzimidazolyl, benzoxazolyl, benzothiazolyl, quinazolinyl, azaindolyl, pyrazolopyrimidinyl, purinyl, pyrrolo[1,2-b]pyridazinyl, pyrrolopyrimidinyl, indazolyl, pyrazolylpyridinyl, imidazo[1,2-a]pyridinyl, and pyrrolo[1,2-f][1,2,4]triazinyl. The present invention also provides compounds of Formula II wherein $R^{3'}$ is unsubstituted or substituted heteroarylalkyl, including but not limited to monocyclic and bicyclic heteroaryl as described above, that are linked to alkyl, which in turn includes but is not limited to $CH_3$, —$CH_2CH_3$, n-propyl, isopropyl, n-butyl, sec-butyl, and pentyl. In some embodiments, $R^{3'}$ is unsubstituted or substituted cycloalkyl (including but not limited to cyclopropyl, cyclobutyl, and cyclopentyl) or unsubstituted or substituted heteroalkyl (non-limiting examples include ethoxymethyl, methoxymethyl, and diethylaminomethyl). In some further embodiments, $R^{3'}$ is unsubstituted or substituted heterocycloalkyl which includes but is not limited to pyrrolidinyl, tetrahydrofuranyl, piperidinyl, tetrahydropyranyl, thiazolidinyl, imidazolidinyl, morpholinyl, and piperazinyl. In yet other embodiments of the compounds of Formula II, $R^{3'}$ is unsubstituted or substituted alkoxy including but not limited to $C_1$-$C_4$alkoxy such as methoxy, ethoxy, propoxy or butoxy. $R^{3'}$ can also be unsubstituted or substituted heterocycloalkyloxy, including but not limited to 4-NH piperidin-1-yl-oxy, 4-methyl piperidin-1-yl-oxy, 4-ethyl piperidin-1-yl-oxy, 4-isopropyl-piperidin-1-yl-oxy, and pyrrolidin-3-yl-oxy. In other embodiments, $R^{3'}$ is unsubstituted or substituted amino, wherein the substituted amino includes but is not limited to dimethylamino, diethylamino, di-isopropyl amino, N-methyl N-ethyl amino, and dibutylamino. In some embodiments, $R^{3'}$ is unsubstituted or substituted acyl, unsubstituted or substituted acyloxy, unsubstituted or substituted $C_1$-$C_4$acyloxy, unsubstituted or substituted alkoxycarbonyl, unsubstituted or substituted amido, or unsubstituted or substituted sulfonamido. In other embodiments, $R^{3'}$ is halo, which is —I, —F, —Cl, or —Br. In some embodiments, $R^{3'}$ is selected from the group consisting of cyano, hydroxy, nitro, phosphate, urea, and carbonate. Also contemplated are $R^{3'}$ being —$CH_3$, —$CH_2CH_3$, n-propyl, isopropyl, n-butyl, tert-butyl, sec-butyl, pentyl, hexyl, heptyl, —$OCH_3$, —$OCH_2CH_3$, or —$CF_3$. In some embodiments $R^{3'}$ can also be NR'R" wherein R' and R" are taken together with the nitrogen to form a cyclic moiety having from 3 to 8 ring atoms. The cyclic moiety so formed may further include one or more heteroatoms which are selected from the group consisting of S, O, and N. The cyclic moiety so formed is unsubstituted or substituted, including but not limited to morpholinyl, azetidinyl, pyrrolidinyl, piperidinyl, piperazinyl, isothiazolidinyl 1,2, dioxide, and thiomorpholinyl. Further non-limiting exemplary cyclic moieties are the following:

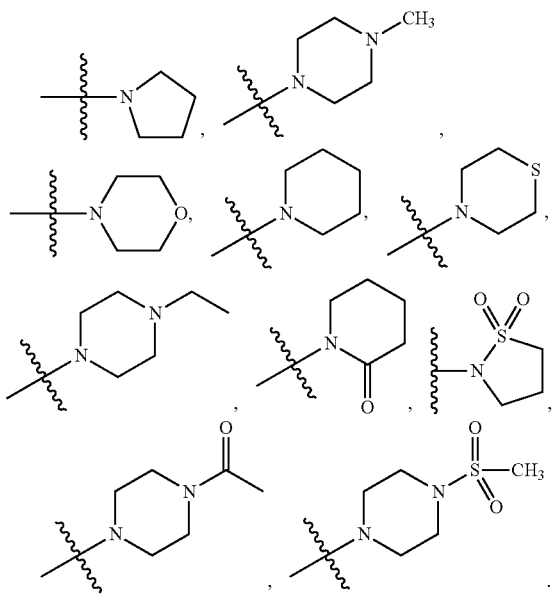

In another aspect, the invention provides compounds of Subformula IIb:

Subformula IIb

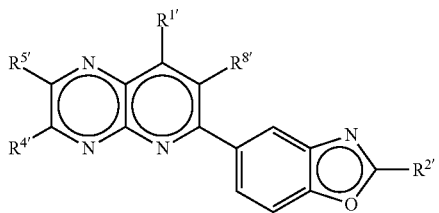

In one embodiment, $R^{1'}$, $R^{4'}$, $R^{5'}$ and $R^{8'}$ are hydrogen. In another embodiment, $R^{1'}$, $R^{5'}$, and $R^{8'}$ are hydrogen and $R^{4'}$ is alkyl, heteroalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, halo, cyano, hydroxy, nitro, phosphate, urea, carbonate, or NR'R" wherein R' and R" are taken together with nitrogen to form a cyclic moiety. $R^{4'}$ can be, for example, hydrogen, unsubstituted or substituted alkyl (including but not limited to $CH_3$, —$CH_2CH_3$, n-propyl, isopropyl, n-butyl, tert-butyl, sec-butyl, pentyl, hexyl, and heptyl). In other embodiments, $R^{4'}$ is unsubstituted or substituted alkenyl (including but not limited to unsubstituted or substituted $C_2$-$C_5$alkenyl such as, for example, vinyl, allyl, 1-methyl propen-1-yl, butenyl, or pentenyl) or unsubstituted or substituted alkynyl (including but not limited to unsubstituted or substituted $C_2$-$C_5$alkynyl such as acetylenyl, propargyl, butynyl, or pentynyl). Alternatively, $R^{4'}$ is unsubstituted or substituted aryl (including but not limited to monocyclic or bicyclic aryl) or unsubstituted or substituted arylalkyl (including but not limited to monocyclic or bicyclic aryl linked to alkyl wherein alkyl includes but is not limited to $CH_3$, —$CH_2CH_3$, n-propyl, isopropyl, n-butyl, sec-butyl, and pentyl). In some other embodiments, $R^{4'}$ is unsubstituted or substituted heteroaryl, including but not limited to monocyclic and bicyclic heteroaryl. Monocyclic heteroaryl $R^{4'}$ includes but is not limited to pyrrolyl, thienyl, furyl, pyridinyl, pyranyl, pyrimidinyl, pyrazinyl, pyridazinyl, imidazolyl, thiazolyl, pyrazolyl, and oxazolyl. Bicyclic heteroaryl $R^{4'}$ includes but is not limited to benzothiophenyl, benzofuryl, indolyl, quinolinyl, isoquinolinyl, benzimidazolyl, benzoxazolyl, benzothiazolyl, quinazolinyl, azaindolyl, pyrazolopyrimidinyl, purinyl, pyrrolo[1,2-b]pyridazinyl, pyrrolopyrimidinyl, indazolyl, pyrazolylpyridinyl, imidazo[1,2-a]pyridinyl, and pyrrolo[1,2-f][1, 2, 4]triazinyl.

In another aspect, the invention provides compounds of Subformula IIc and IId, where $W^{1'}$ is N, $W^{2'}$ is $CR^{4'}$, $W^{3'}$ is $CR^{5'}$, $W^{4'}$ is N, $W^{5'}$ is $CR^{7'}$, and $W^{6'}$ is $CR^{8'}$:

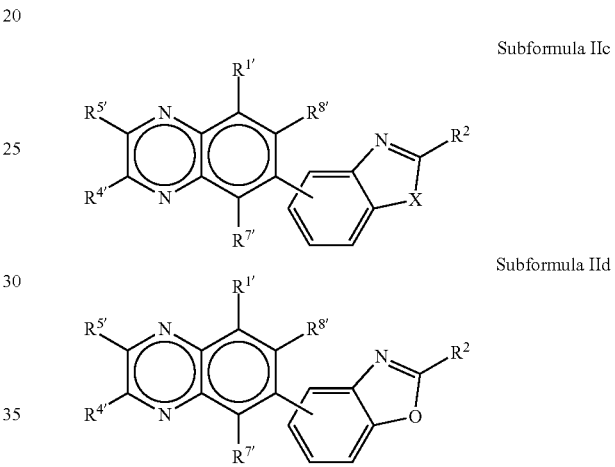

In one embodiment, $R^{1'}$, $R^{4'}$, $R^{5'}$, $R^{7'}$ and $R^{8'}$ are hydrogen. In another embodiment, $R^{1'}$, $R^{5'}$, $R^{7'}$ and $R^{8'}$ are hydrogen and $R^{4'}$ is alkyl, heteroalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, halo, cyano, hydroxy, nitro, phosphate, urea, carbonate, or NR'R" wherein R' and R" are taken together with nitrogen to form a cyclic moiety. $R^{4'}$ can be, for example, hydrogen, unsubstituted or substituted alkyl (including but not limited to $CH_3$, —$CH_2CH_3$, n-propyl, isopropyl, n-butyl, tert-butyl, sec-butyl, pentyl, hexyl, and heptyl). In other embodiments, $R^{4'}$ is unsubstituted or substituted alkenyl (including but not limited to unsubstituted or substituted $C_2$-$C_5$alkenyl such as, for example, vinyl, allyl, 1-methyl propen-1-yl, butenyl, or pentenyl) or unsubstituted or substituted alkynyl (including but not limited to unsubstituted or substituted $C_2$-$C_5$alkynyl such as acetylenyl, propargyl, butynyl, or pentynyl). Alternatively, $R^{4'}$ is unsubstituted or substituted aryl (including but not limited to monocyclic or bicyclic aryl) or unsubstituted or substituted arylalkyl (including but not limited to monocyclic or bicyclic aryl linked to alkyl wherein alkyl includes but is not limited to $CH_3$, —$CH_2CH_3$, n-propyl, isopropyl, n-butyl, sec-butyl, and pentyl). In some other embodiments, $R^{4'}$ is unsubstituted or substituted heteroaryl, including but not limited to monocyclic and bicyclic heteroaryl. Monocyclic heteroaryl $R^{4'}$ includes but is not limited to pyrrolyl, thienyl, furyl, pyridinyl, pyranyl, pyrimidinyl, pyrazinyl, pyridazinyl, imidazolyl, thiazolyl, pyrazolyl, and oxazolyl. Bicyclic heteroaryl $R^{4'}$ includes but is not limited to benzothiophenyl, benzofuryl, indolyl, quinolinyl, isoquinolinyl, benzimidazolyl, benzoxazolyl, benzothiazolyl, quinazolinyl, azaindolyl, pyrazolopyrimidinyl, purinyl, pyrrolo[1,2-b]pyridazinyl, pyrrolopyrimidinyl, indazolyl, pyrazolylpyridinyl, imidazo[1,2-a]pyridinyl, and pyrrolo[1,2-f][1, 2, 4]triazinyl. The present invention also provides compounds of Formula II wherein $R^{4'}$ is unsubstituted or substituted heteroarylalkyl, including but not limited to monocyclic and bicyclic heteroaryl as described above, that are linked to alkyl, which in turn includes but is not limited to $CH_3$, —$CH_2CH_3$, n-propyl, isopropyl, n-butyl, sec-butyl, and pentyl. In some embodiments, $R^{4'}$ is unsubstituted or substituted cycloalkyl (including but not limited to cyclopropyl, cyclobutyl, and cyclopentyl) or unsubstituted or substituted heteroalkyl (non-limiting examples include ethoxymethyl, methoxymethyl, and diethylaminomethyl). In some further embodiments, $R^{4'}$ is unsubstituted or substituted heterocycloalkyl which includes but is not limited to pyrrolidinyl, tetrahydrofuranyl, piperidinyl, tetrahydropyranyl, thiazolidinyl, imidazolidinyl, morpholinyl, and piperazinyl. In yet other embodiments of the compounds of Formula II, $R^{4'}$ is unsubstituted or substituted alkoxy including but not limited to $C_1$-$C_4$alkoxy such as methoxy, ethoxy, propoxy or butoxy. $R^{3'}$ can also be unsubstituted or substituted heterocycloalkyloxy, including but not limited to 4-NH piperidin-1-yl-oxy, 4-methyl piperidin-1-yl-oxy, 4-ethyl piperidin-1-yl-oxy, 4-isopropyl-piperidin-1-yl-oxy, and pyrrolidin-3-yl-oxy. In other embodiments, $R^{4'}$ is unsubstituted or substituted amino, wherein the substituted amino includes but is not limited to dimethylamino, diethylamino, di-isopropyl amino, N-methyl N-ethyl amino, and dibutylamino. In some embodiments, $R^{4'}$ is unsubstituted or substituted acyl, unsubstituted or substituted acyloxy, unsubstituted or substituted $C_1$-$C_4$acyloxy, unsubstituted or substituted alkoxycarbonyl, unsubstituted or substituted amido, or unsubstituted or substituted sulfonamido. In other embodiments, $R^{4'}$ is halo, which is —I, —F, —Cl, or —Br. In some embodiments, $R^{4'}$ is selected from the group consisting of cyano, hydroxy, nitro, phosphate, urea, and carbonate. Also contemplated are $R^{4'}$ being —$CH_3$, —$CH_2CH_3$, n-propyl, isopropyl, n-butyl, tert-butyl, sec-butyl, pentyl, hexyl, heptyl, —$OCH_3$, —$OCH_2CH_3$, or —$CF_3$. In some embodiments $R^{4'}$ can also be NR'R" wherein R' and R" are taken together with the nitrogen to form a cyclic moiety having from 3 to 8 ring atoms. The cyclic moiety so formed may further include one or more heteroatoms which are selected from the group consisting of S, O, and N. The cyclic moiety so formed is unsubstituted or substituted, including but not limited to morpholinyl, azetidinyl, pyrrolidinyl, piperidinyl, piperazinyl, isothiazolidinyl 1,2, dioxide, and thiomorpholinyl. Further non-limiting exemplary cyclic moieties are the following:

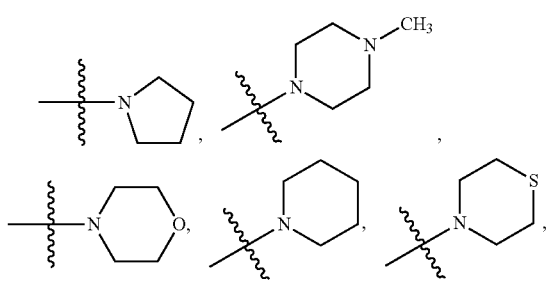

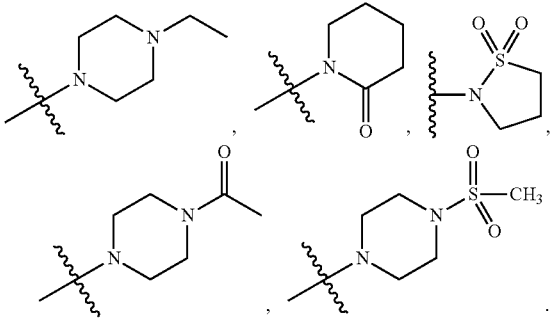

In another aspect, the invention provides compounds of Subformula IIe and IIf, where $W^{1'}$ is $CR^{3'}$, $W^{2'}$ is N, $W^{3'}$ is $CR^{5'}$, $W^{4'}$ is N, $W^{5'}$ is $CR^{7'}$, and $W^{6'}$ is $CR^{8'}$:

Subformula IIe

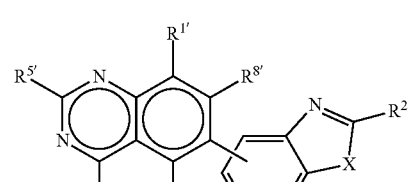

Subformula IIf

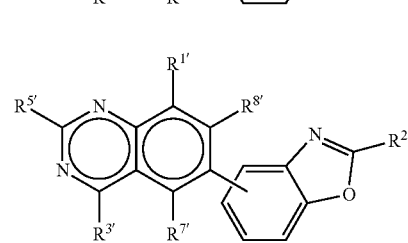

In one embodiment, $R^{1'}$, $R^{3'}$, $R^{5'}$, $R^{7'}$ and $R^{8'}$ are hydrogen. In another embodiment, $R^{1'}$, $R^{5'}$, $R^{7'}$ and $R^{8'}$ are hydrogen and $R^{3'}$ is alkyl, heteroalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, halo, cyano, hydroxy, nitro, phosphate, urea, carbonate, or NR'R" wherein R' and R" are taken together with nitrogen to form a cyclic moiety. $R^{3'}$ can be, for example, hydrogen, unsubstituted or substituted alkyl (including but not limited to $CH_3$, —$CH_2CH_3$, n-propyl, isopropyl, n-butyl, tert-butyl, sec-butyl, pentyl, hexyl, and heptyl). In other embodiments, $R^{3'}$ is unsubstituted or substituted alkenyl (including but not limited to unsubstituted or substituted $C_2$-$C_5$alkenyl such as, for example, vinyl, allyl, 1-methyl propen-1-yl, butenyl, or pentenyl) or unsubstituted or substituted alkynyl (including but not limited to unsubstituted or substituted $C_2$-$C_5$alkynyl such as acetylenyl, propargyl, butynyl, or pentynyl). Alternatively, $R^{3'}$ is unsubstituted or substituted aryl (including but not limited to monocyclic or bicyclic aryl) or unsubstituted or substituted arylalkyl (including but not limited to monocyclic or bicyclic aryl linked to alkyl wherein alkyl includes but is not limited to $CH_3$, —$CH_2CH_3$, n-propyl, isopropyl, n-butyl, sec-butyl, and pentyl). In some other embodiments, $R^{3'}$ is unsubstituted or substituted heteroaryl, including but not limited to monocyclic and bicyclic heteroaryl. Monocyclic heteroaryl $R^{3'}$ includes but is not limited to pyrrolyl, thienyl, furyl, pyridinyl, pyranyl, pyrimidinyl, pyrazinyl, pyridazinyl, imidazolyl, thiazolyl, pyrazolyl, and oxazolyl. Bicyclic heteroaryl $R^{3'}$ includes but is not limited to benzothiophenyl, benzofuryl, indolyl, quinolinyl, isoquinolinyl, benzimidazolyl, benzoxazolyl, benzothiazolyl, quinazolinyl, azaindolyl, pyrazolopyrimidinyl, purinyl, pyrrolo[1,2-b]pyridazinyl, pyrrolopyrimidinyl, indazolyl, pyrazolylpyridinyl, imidazo[1,2-a]pyridinyl, and pyrrolo[1,2-f][1, 2, 4]triazinyl. The present invention also provides compounds of Formula II wherein $R^{3'}$ is unsubstituted or substituted heteroarylalkyl, including but not limited to monocyclic and bicyclic heteroaryl as described above, that are linked to alkyl, which in turn includes but is not limited to $CH_3$, —$CH_2CH_3$, n-propyl, isopropyl, n-butyl, sec-butyl, and pentyl. In some embodiments, $R^{3'}$ is unsubstituted or substituted cycloalkyl (including but not limited to cyclopropyl, cyclobutyl, and cyclopentyl) or unsubstituted or substituted heteroalkyl (non-limiting examples include ethoxymethyl, methoxymethyl, and diethylaminomethyl). In some further embodiments, $R^{3'}$ is unsubstituted or substituted heterocycloalkyl which includes but is not limited to pyrrolidinyl, tetrahydrofuranyl, piperidinyl, tetrahydropyranyl, thiazolidinyl, imidazolidinyl, morpholinyl, and piperazinyl. In yet other embodiments of the compounds of Formula II, $R^{3'}$ is unsubstituted or substituted alkoxy including but not limited to $C_1$-$C_4$alkoxy such as methoxy, ethoxy, propoxy or butoxy. $R^{3'}$ can also be unsubstituted or substituted heterocycloalkyloxy, including but not limited to 4-NH piperidin-1-yl-oxy, 4-methyl piperidin-1-yl-oxy, 4-ethyl piperidin-1-yl-oxy, 4-isopropyl-piperidin-1-yl-oxy, and pyrrolidin-3-yl-oxy. In other embodiments, $R^{3'}$ is unsubstituted or substituted amino, wherein the substituted amino includes but is not limited to dimethylamino, diethylamino, di-isopropyl amino, N-methyl N-ethyl amino, and dibutylamino. In some embodiments, $R^{3'}$ is unsubstituted or substituted acyl, unsubstituted or substituted acyloxy, unsubstituted or substituted $C_1$-$C_4$acyloxy, unsubstituted or substituted alkoxycarbonyl, unsubstituted or substituted amido, or unsubstituted or substituted sulfonamido. In other embodiments, $R^{3'}$ is halo, which is —I, —F, —Cl, or —Br. In some embodiments, $R^{3'}$ is selected from the group consisting of cyano, hydroxy, nitro, phosphate, urea, and carbonate. Also contemplated are $R^{3'}$ being —$CH_3$, —$CH_2CH_3$, n-propyl, isopropyl, n-butyl, tert-butyl, sec-butyl, pentyl, hexyl, heptyl, —$OCH_3$, —$OCH_2CH_3$, or —$CF_3$. In some embodiments $R^{3'}$ can also be NR'R" wherein R' and R" are taken together with the nitrogen to form a cyclic moiety having from 3 to 8 ring atoms. The cyclic moiety so formed may further include one or more heteroatoms which are selected from the group consisting of S, O, and N. The cyclic moiety so formed is unsubstituted or substituted, including but not limited to morpholinyl, azetidinyl, pyrrolidinyl, piperidinyl, piperazinyl, isothiazolidinyl 1,2, dioxide, and thiomorpholinyl. Further non-limiting exemplary cyclic moieties are the following:

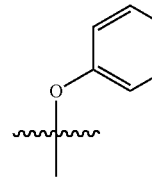

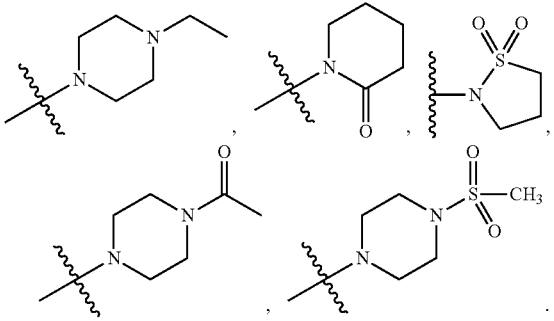

In some embodiments, the substituents $R^{3'}$, $R^{4'}$, $R^{5'}$, $R^{6'}$ or $R^8$ may be any of the substituents shown in Table 1:

TABLE 1

$R^{3'}$, $R^{4'}$, $R^{5'}$, $R^{6'}$, $R^8$ moieties of the compounds of Formula II, each independently includes but is not limited to the following:

| Subclass # | R |
|---|---|
| R-1 | 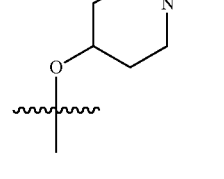 |
| R-2 | 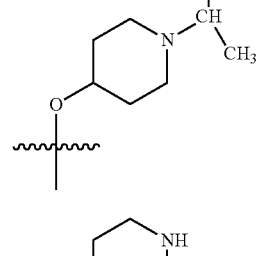 |
| R-3 | 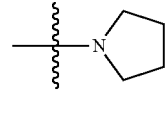 [SMILES: *N1CCCC1] |
| R-4 |  |
| R-5 | |
| R-6 | |

TABLE 1-continued

R³', R⁴', R⁵', R⁶', R⁸' moieties of the compounds of Formula II, each independently includes but is not limited to the following:

| Sub-class # | R |
|---|---|
| R-7 | *N-piperazinyl-N'-methyl* |
| R-8 | *benzyl (CH₂-phenyl)* |
| R-9 | —CH(CH₃)₂ |
| R-10 | *N(CH₃)(cyclopropyl)* |
| R-11 | *N(CH₃)₂* |
| R-12 | *N(CH(CH₃)₂)₂* |
| R-13 | *pyrrolidinyl-propyl* |
| R-14 | *3-methyl-2-pyridyl-NH–* |
| R-15 | *morpholino-propyl* |
| R-16 | *2-methylphenoxy* |
| R-17 | *2-chlorophenoxy* |
| R-18 | *4-methylpiperazinyl-propyl* |
| R-19 | *N(CH₃)(4-cyanophenyl)* |
| R-20 | *morpholino* |
| R-21 | *N(CH₃)(tetrahydropyran-4-yl)* |
| R-22 | *indazol-5-yloxy* |
| R-23 | *2-methoxyphenoxy* |
| R-24 | *2-methylthiazol-4-yl-propyl* |

TABLE 1-continued
R³', R⁴', R⁵', R⁶', R⁸' moieties of the compounds of Formula II, each independently includes but is not limited to the following:
| Subclass # | R |
|---|---|
| R-25 | 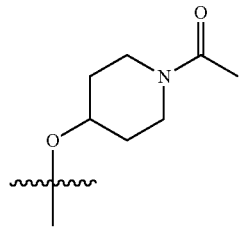 [SMILES: *OC1CCN(C(C)=O)CC1] |
| R-26 | 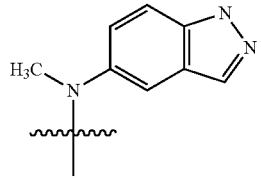 [SMILES: *N(C)c1ccc2[nH]ncc2c1] |
| R-27 | 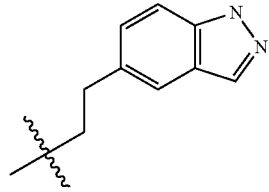 [SMILES: *CCc1ccc2[nH]ncc2c1] |
| R-28 | 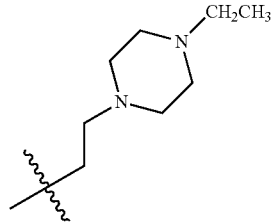 [SMILES: *CCN1CCN(CC)CC1] |
| R-29 | 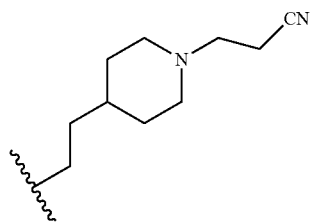 [SMILES: *CCC1CCN(CCC#N)CC1] |
| R-30 | 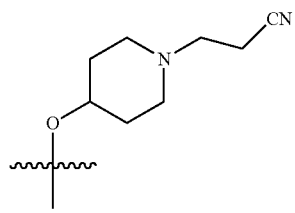 [SMILES: *OC1CCN(CCC#N)CC1] |
| R-31 | 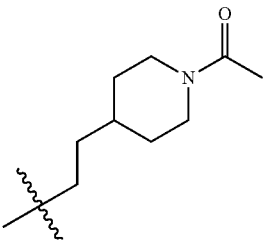 [SMILES: *CCC1CCN(C(C)=O)CC1] |
| R-32 | 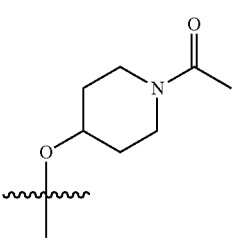 [SMILES: *OC1CCN(C(C)=O)CC1] |
| R-33 | 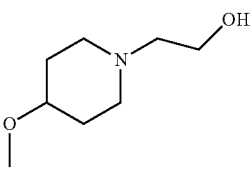 |
| R-34 | 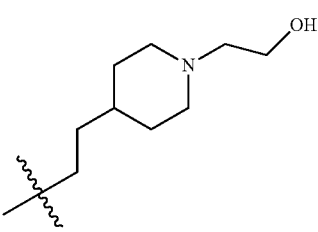 [SMILES: *CCC1CCN(CCO)CC1] |
| R-35 | 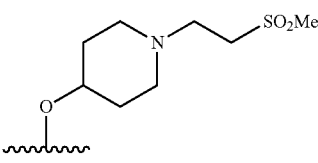 [SMILES: *OC1CCN(CCS(C)(=O)=O)CC1] |
| R-36 | 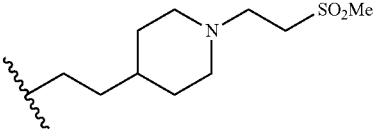 [SMILES: *CCC1CCN(CCS(C)(=O)=O)CC1] |
| R-37 | 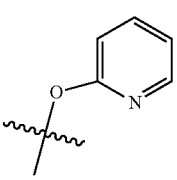 [SMILES: *Oc1ccccn1] |

TABLE 1-continued

R³', R⁴', R⁵', R⁶', R⁸' moieties of the compounds of Formula II, each independently includes but is not limited to the following:

| Subclass # | R |
|---|---|
| R-38 | 2-(pyridin-2-yl)ethyl |
| R-39 | thiazol-4-yl |
| R-40 | H |
| R-41 | 2-(diethylamino)thiazol-4-yl |
| R-42 | 2-(1H-imidazol-1-yl)thiazol-4-yl |
| R-43 | piperidin-1-yl |
| R-44 | 2-oxopiperidin-1-yl |
| R-45 | thiomorpholin-4-yl |
| R-46 | 4-ethylpiperazin-1-yl |
| R-47 | (1-(methylsulfonyl)piperidin-4-yl)oxy |
| R-48 | (tetrahydro-2H-pyran-4-yl)oxy |
| R-49 | ((tetrahydro-2H-pyran-4-yl)methoxy) |
| R-50 | ((1-acetylpiperidin-4-yl)methoxy) |
| R-51 | ((1-(methylsulfonyl)piperidin-4-yl)methoxy) |
| R-52 | 2-(pyrrolidin-1-yl)ethoxy |
| R-53 | ((1-methylpiperidin-4-yl)methoxy) |
| R-54 | 2-(4-acetylpiperazin-1-yl)ethoxy |

TABLE 1-continued
R³', R⁴', R⁵', R⁶', R⁸' moieties of the compounds of Formula II, each independently includes but is not limited to the following:
| Sub-class # | R |
|---|---|
| R-55 | 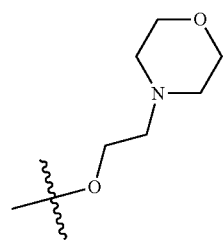 [SMILES: *OCCN1CCOCC1] |
| R-56 | 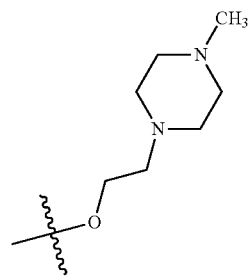 [SMILES: *OCCN1CCN(C)CC1] |
| R-57 | 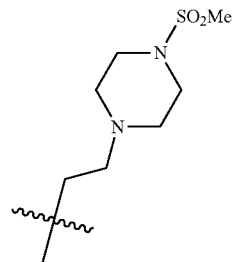 [SMILES: *CCN1CCN(S(C)(=O)=O)CC1] |
| R-58 | 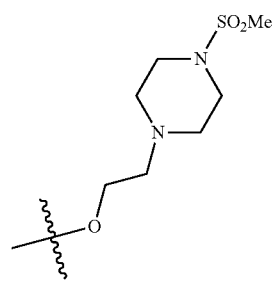 [SMILES: *OCCN1CCN(S(C)(=O)=O)CC1] |
| R-59 | 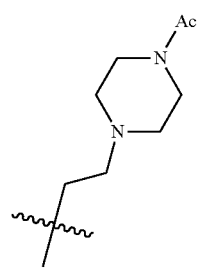 [SMILES: *CCN1CCN(C(C)=O)CC1] |
| R-60 | 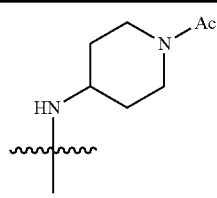 |
| R-61 | 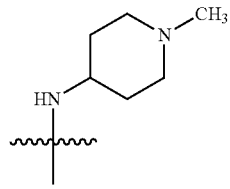 [SMILES: *NC1CCN(C)CC1] |
| R-62 | 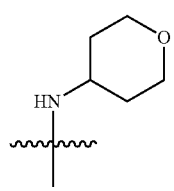 [SMILES: *NC1CCOCC1] |
| R-63 | 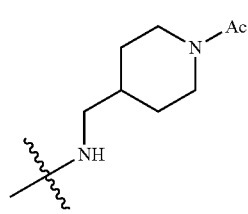 [SMILES: *NCC1CCN(C(C)=O)CC1] |
| R-64 | 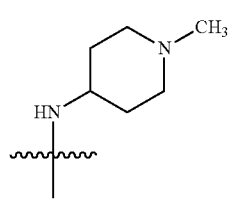 [SMILES: *NC1CCN(C)CC1] |
| R-65 | 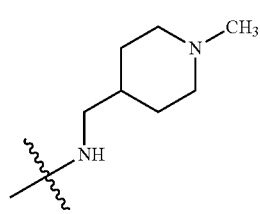 [SMILES: *NCC1CCN(C)CC1] |
| R-66 | 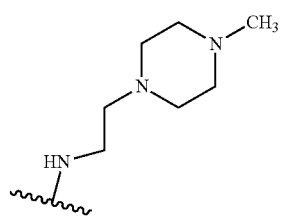 [SMILES: *NCCN1CCN(C)CC1] |

TABLE 1-continued
R³', R⁴', R⁵', R⁶', R⁸' moieties of the compounds of Formula II, each independently includes but is not limited to the following:
| Subclass # | R |
|---|---|
| R-67 | 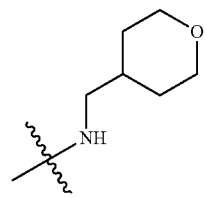 [SMILES: *NCC1CCOCC1] |
| R-68 | 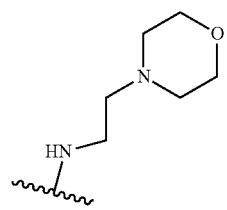 [SMILES: *NCCN1CCOCC1] |
| R-69 | 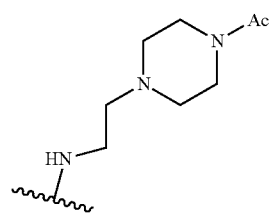 [SMILES: *NCCN1CCN(C(C)=O)CC1] |
| R-70 | 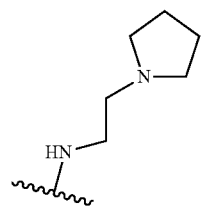 [SMILES: *NCCN1CCCC1] |
| R-71 | 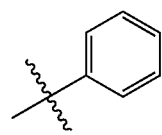 [SMILES: *c1ccccc1] |
| R-72 | 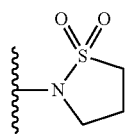 [SMILES: *N1CCCS1(=O)=O] |
| R-73 | 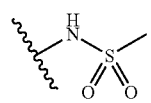 |
| R-74 | 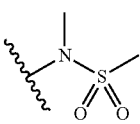 [SMILES: *N(C)S(C)(=O)=O] |
| R-75 | 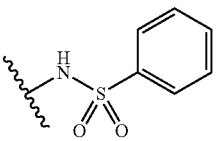 [SMILES: *NS(=O)(=O)c1ccccc1] |
| R-76 | 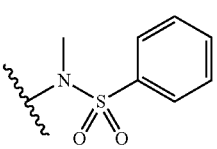 [SMILES: *N(C)S(=O)(=O)c1ccccc1] |
| R-77 | 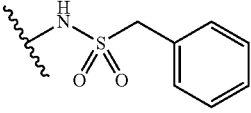 [SMILES: *NS(=O)(=O)Cc1ccccc1] |
| R-78 | 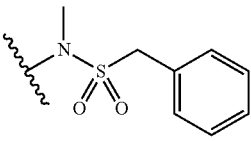 [SMILES: *N(C)S(=O)(=O)Cc1ccccc1] |
| R-79 | 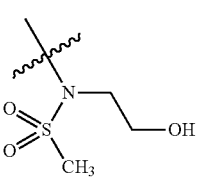 |
| R-80 | 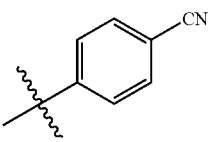 [SMILES: *c1ccc(C#N)cc1] |
| R-81 | 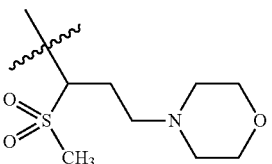 |
In another aspect, the invention provides a PI3Kα inhibitor which is a compound of Formula III:

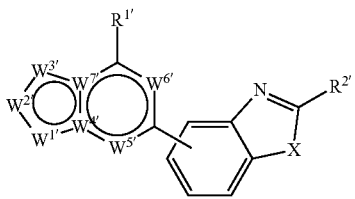

or its pharmaceutically acceptable salts thereof, where:

X is O or S or N;

$W^{1'}$ is S, N, $NR^{3'}$ or $CR^{3'}$, $W^{2'}$ is N or $CR^{4'}$, $W^{3'}$ is S, N or $CR^{5'}$, $W^{4'}$ is N or C, and $W^{7'}$ is N or C, wherein no more than two N atoms and no more than two C=O groups are adjacent;

$W^{5'}$ is N or $CR^{7'}$;

$W^{6'}$ is N or $CR^{8'}$;

$R^{1'}$ and $R^{2'}$ are independently hydrogen, alkyl, heteroalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, halo, cyano, hydroxy, nitro, phosphate, urea, carbonate, or NR'R" wherein R' and R" are taken together with nitrogen to form a cyclic moiety;

$R^{3'}$ and $R^{4'}$ are independently hydrogen, alkyl, heteroalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, halo, cyano, hydroxy, nitro, phosphate, urea, carbonate, or NR'R" wherein R' and R" are taken together with nitrogen to form a cyclic moiety; or $R^{3'}$ and $R^{4'}$ taken together form a cyclic moiety; and $R^{5'}$, $R^{7'}$ and $R^{8'}$ are independently hydrogen, alkyl, heteroalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, halo, cyano, hydroxy, nitro, phosphate, urea, carbonate, or NR'R" wherein R' and R" are taken together with nitrogen to form a cyclic moiety.

In some embodiments, the compound of Formula III exists as a tautomer, and such tautomers are contemplated by the present invention.

In some embodiments, the PI3Kα inhibitor is a compound of Formula III which has the Formula:

Formula III

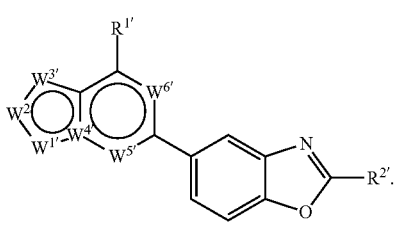

In yet other embodiments, $W^{1'}$ is $CR^{3'}$, $W^{2'}$ is $CR^{4'}$, $W^{3'}$ is N, $W^{4'}$ is N, $W^{5'}$ is $CR^{7'}$, and $W^{6'}$ is $CR^{8'}$. In other embodiments, $W^{1'}$ is $CR^{3'}$, $W^{2'}$ is $CR^{4'}$, $W^{3'}$ is N, $W^{4'}$ is N, $W^{5'}$ is $CR^{7'}$, and $W^{6'}$ is $CR^{8'}$. In other embodiments, $W^{1'}$ is $CR^{3'}$, $W^{2'}$ is $CR^{4'}$, $W^{3'}$ is N, $W^{4'}$ is N, $W^{5'}$ is N, and $W^{6'}$ is $CR^{8'}$. In still other embodiments, $W^{1'}$ is $NR^{3'}$, $W^{2'}$ is $CR^{4'}$, $W^{3'}$ is N, $W^{4'}$ is C, $W^{5'}$ is $CR^{7'}$, and $W^{6'}$ is $CR^{8'}$. In other embodiments, $W^{1'}$ is S, $W^{2'}$ is $CR^{4'}$, $W^{3'}$ is N, $W^{4'}$ is C, $W^{5'}$ is $CR^{7'}$, and $W^{6'}$ is $CR^{8'}$. In other embodiments, $W^{1'}$ is $CR^{3'}$, $W^{2'}$ is $CR^{4'}$, $W^{3'}$ is S, $W^{4'}$ is C, $W^{5'}$ is N, and $W^{6'}$ is N.

In other embodiments, an inhibitor of Formula III is a compound according to one of the formulas:

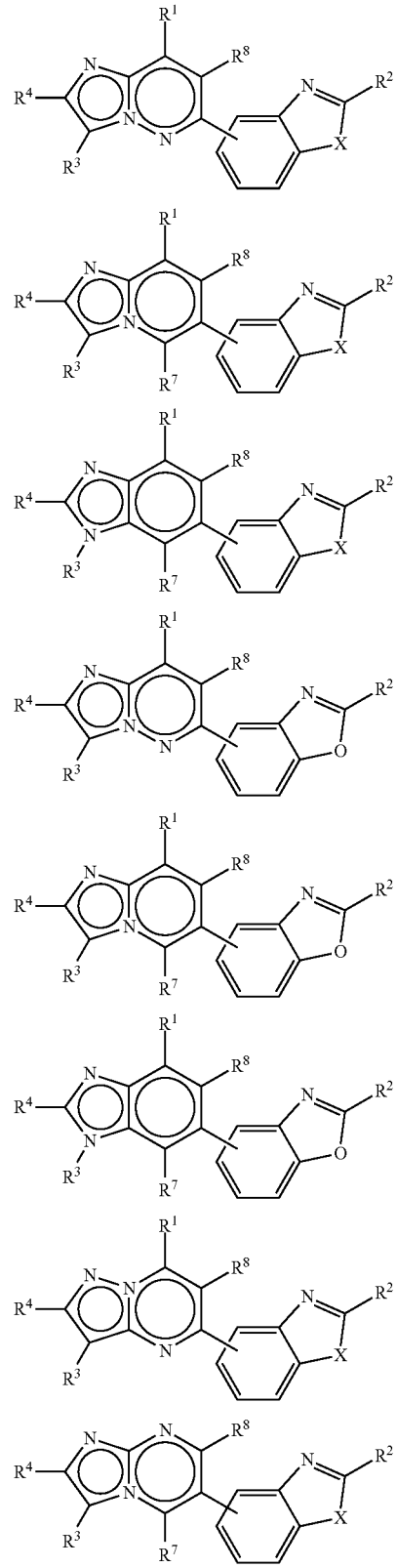

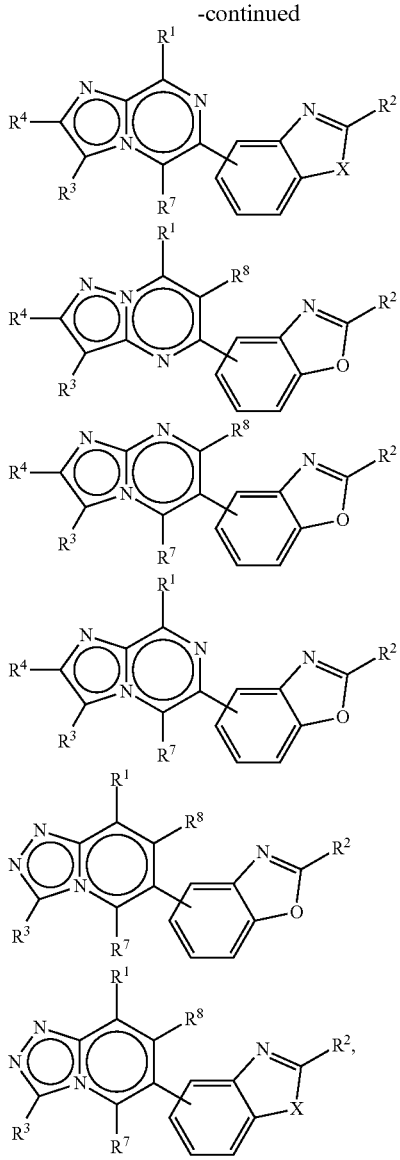

wherein for each of the above formulas, each respective R variable includes a 'prime' (').

In some embodiments, X is O. In other embodiments, X is S.

In some embodiments, $R^{1'}$ is hydrogen. In other embodiments, $R^{1'}$ is alkyl, heteroalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, halo, cyano, hydroxy, nitro, phosphate, urea, carbonate, or NR'R", wherein R' and R" are taken together with nitrogen to form a cyclic moiety.

In some embodiments, $R^{2'}$ is hydrogen. In other embodiments, $R^{2'}$ is, for example, unsubstituted or substituted alkyl (including but not limited to $CH_3$, $-CH_2CH_3$, n-propyl, isopropyl, n-butyl, tert-butyl, sec-butyl, pentyl, hexyl, and heptyl). In other embodiments, $R^{2'}$ is unsubstituted or substituted alkenyl (including but not limited to unsubstituted or substituted $C_2-C_5$alkenyl such as, for example, vinyl, allyl, 1-methyl propen-1-yl, butenyl, or pentenyl) or substituted alkynyl (including but not limited to unsubstituted or substituted $C_2-C_5$alkynyl such as acetylenyl, propargyl, butynyl, or pentynyl). Alternatively, $R^{2'}$ is unsubstituted or substituted aryl (including but not limited to monocyclic or bicyclic aryl) or unsubstituted or substituted arylalkyl (including but not limited to monocyclic or bicyclic aryl linked to alkyl wherein alkyl includes but is not limited to $CH_3$, $-CH_2CH_3$, n-propyl, isopropyl, n-butyl, sec-butyl, and pentyl). In some other embodiments, $R^{2'}$ is unsubstituted or substituted heteroaryl, including but not limited to monocyclic and bicyclic heteroaryl. Monocyclic heteroaryl $R^{2'}$ includes but is not limited to pyrrolyl, thienyl, furyl, pyridinyl, pyranyl, pyrimidinyl, pyrazinyl, pyridazinyl, imidazolyl, thiazolyl, pyrazolyl, and oxazolyl. Bicyclic heteroaryl $R^{2'}$ includes but is not limited to benzothiophenyl, benzofuryl, indolyl, quinolinyl, isoquinolinyl, benzimidazolyl, benzoxazolyl, benzothiazolyl, quinazolinyl, azaindolyl, pyrazolopyrimidinyl, purinyl, pyrrolo[1,2-b]pyridazinyl, pyrrolopyrimidinyl, indazolyl, pyrazolylpyridinyl, imidazo[1,2-a]pyridinyl, and pyrrolo[1,2-f][1,2,4]triazinyl. The present invention also provides compounds wherein $R^{2'}$ is unsubstituted or substituted heteroarylalkyl, including but not limited to monocyclic and bicyclic heteroaryl as described above, that are linked to alkyl, which in turn includes but is not limited to $CH_3$, $-CH_2CH_3$, n-propyl, isopropyl, n-butyl, sec-butyl, and pentyl. In some embodiments, $R^{2'}$ is unsubstituted or substituted cycloalkyl (including but not limited to cyclopropyl, cyclobutyl, and cyclopentyl) or unsubstituted or substituted heteroalkyl (non-limiting examples include ethoxymethyl, methoxymethyl, and diethylaminomethyl). In some further embodiments, $R^{2'}$ is unsubstituted or substituted heterocycloalkyl which includes but is not limited to pyrrolidinyl, tetrahydrofuranyl, piperidinyl, tetrahydropyranyl, thiazolidinyl, imidazolidinyl, morpholinyl, and piperazinyl. In yet other embodiments of the compounds of Formula III, $R^{2'}$ is unsubstituted or substituted alkoxy including but not limited to $C_1-C_4$alkoxy such as methoxy, ethoxy, propoxy or butoxy. $R^{2'}$ can also be unsubstituted or substituted heterocycloalkyloxy, including but not limited to 4-NH piperidin-1-yl-oxy, 4-methyl piperidin-1-yl-oxy, 4-ethyl piperidin-1-yl-oxy, 4-isopropyl-piperidin-1-yl-oxy, and pyrrolidin-3-yl-oxy. In other embodiments, $R^{2'}$ is unsubstituted or substituted amino, wherein the substituted amino includes but is not limited to dimethylamino, diethylamino, di-isopropyl amino, N-methyl N-ethyl amino, and dibutylamino. In some embodiments, $R^{2'}$ is unsubstituted or substituted acyl, unsubstituted or substituted acyloxy, unsubstituted or substituted $C_1-C_4$acyloxy, unsubstituted or substituted alkoxycarbonyl, unsubstituted or substituted amido, or unsubstituted or substituted sulfonamido. In other embodiments, $R^{2'}$ is halo, which is $-I$, $-F$, $-Cl$, or $-Br$. In some embodiments, $R^{2'}$ is selected from the group consisting of cyano, hydroxy, nitro, phosphate, urea, and carbonate. Also contemplated are $R^{2'}$ being $-CH_3$, $-CH_2CH_3$, n-propyl, isopropyl, n-butyl, tert-butyl, sec-butyl, pentyl, hexyl, heptyl, $-OCH_3$, $-OCH_2CH_3$, or $-CF_3$.

In some embodiments of the compound of Formula III, $W^{1'}$ is $CR^3$. $R^{3'}$ can be, for example, hydrogen, unsubstituted or substituted alkyl (including but not limited to $CH_3$, $-CH_2CH_3$, n-propyl, isopropyl, n-butyl, tert-butyl, sec-butyl, pentyl, hexyl, and heptyl). In other embodiments, $R^{3'}$ is unsubstituted or substituted alkenyl (including but not limited to unsubstituted or substituted $C_2-C_5$alkenyl such as, for example, vinyl, allyl, 1-methyl propen-1-yl, butenyl, or pentenyl) or unsubstituted or substituted alkynyl (including but not limited to unsubstituted or substituted $C_2-C_5$alkynyl such as acetylenyl, propargyl, butynyl, or pentynyl). Alternatively, $R^{3'}$ is unsubstituted or substituted aryl (including but not limited to monocyclic or bicyclic aryl) or unsubstituted or substituted arylalkyl (including but not limited to monocyclic or bicyclic aryl linked to alkyl wherein alkyl includes but is not limited to $CH_3$, $-CH_2CH_3$, n-propyl, isopropyl, n-butyl, sec-butyl, and pentyl). In some other embodiments, $R^{3'}$ is unsubstituted or substituted heteroaryl, including but not limited to monocyclic and bicyclic heteroaryl. Monocyclic heteroaryl $R^{3'}$ includes but is not limited to pyrrolyl, thienyl, furyl, pyridinyl, pyranyl, pyrimidinyl, pyrazinyl, pyridazinyl, imidazolyl, thiazolyl, pyrazolyl, and oxazolyl. Bicyclic heteroaryl $R^{3'}$ includes but is not limited to benzothiophenyl, benzofuryl, indolyl, quinolinyl, isoquinolinyl, benzimidazolyl, benzoxazolyl, benzothiazolyl, quinazolinyl, azaindolyl, pyrazolopyrimidinyl, purinyl, pyrrolo[1,2-b]pyridazinyl, pyrrolopyrimidinyl, indazolyl, pyrazolylpyridinyl, imidazo[1,2-a]pyridinyl, and pyrrolo[1,2-f][1,2,4]triazinyl. The present invention also provides compounds of Formula III wherein $R^{3'}$ is unsubstituted or substituted heteroarylalkyl, including but not limited to monocyclic and bicyclic heteroaryl as described above, that are linked to alkyl, which in turn includes but is not limited to $CH_3$, $-CH_2CH_3$, n-propyl, isopropyl, n-butyl, sec-butyl, and pentyl. In some embodiments, $R^{3'}$ is unsubstituted or substituted cycloalkyl (including but not limited to cyclopropyl, cyclobutyl, and cyclopentyl) or unsubstituted or substituted heteroalkyl (non-limiting examples include ethoxymethyl, methoxymethyl, and diethylaminomethyl). In some further embodiments, $R^{3'}$ is unsubstituted or substituted heterocycloalkyl which includes but is not limited to pyrrolidinyl, tetrahydrofuranyl, piperidinyl, tetrahydropyranyl, thiazolidinyl, imidazolidinyl, morpholinyl, and piperazinyl. In yet other embodiments of the compounds of Formula III, $R^{3'}$ is unsubstituted or substituted alkoxy including but not limited to $C_1$-$C_4$alkoxy such as methoxy, ethoxy, propoxy or butoxy. $R^{3'}$ can also be unsubstituted or substituted heterocycloalkyloxy, including but not limited to 4-NH piperidin-1-yl-oxy, 4-methyl piperidin-1-yl-oxy, 4-ethyl piperidin-1-yl-oxy, 4-isopropyl-piperidin-1-yl-oxy, and pyrrolidin-3-yl-oxy. In other embodiments, $R^{3'}$ is unsubstituted or substituted amino, wherein the substituted amino includes but is not limited to dimethylamino, diethylamino, di-isopropyl amino, N-methyl N-ethyl amino, and dibutylamino. In some embodiments, $R^{3'}$ is unsubstituted or substituted acyl, unsubstituted or substituted acyloxy, unsubstituted or substituted $C_1$-$C_4$acyloxy, unsubstituted or substituted alkoxycarbonyl, unsubstituted or substituted amido, or unsubstituted or substituted sulfonamido. In other embodiments, $R^{3'}$ is halo, which is —I, —F, —Cl, or —Br. In some embodiments, $R^{3'}$ is selected from the group consisting of cyano, hydroxy, nitro, phosphate, urea, and carbonate. Also contemplated are $R^{3'}$ being —$CH_3$, —$CH_2CH_3$, n-propyl, isopropyl, n-butyl, tert-butyl, sec-butyl, pentyl, hexyl, heptyl, —$OCH_3$, —$OCH_2CH_3$, or —$CF_3$.

$R^{3'}$ of the compounds of Formula III, can also be NR'R" wherein R' and R" are taken together with the nitrogen to form a cyclic moiety having from 3 to 8 ring atoms. The cyclic moiety so formed may further include one or more heteroatoms which are selected from the group consisting of S, O, and N. The cyclic moiety so formed is unsubstituted or substituted, including but not limited to morpholinyl, azetidinyl, pyrrolidinyl, piperidinyl, piperazinyl, isothiazolidinyl 1,2, dioxide, and thiomorpholinyl. Further non-limiting exemplary cyclic moieties are the following:

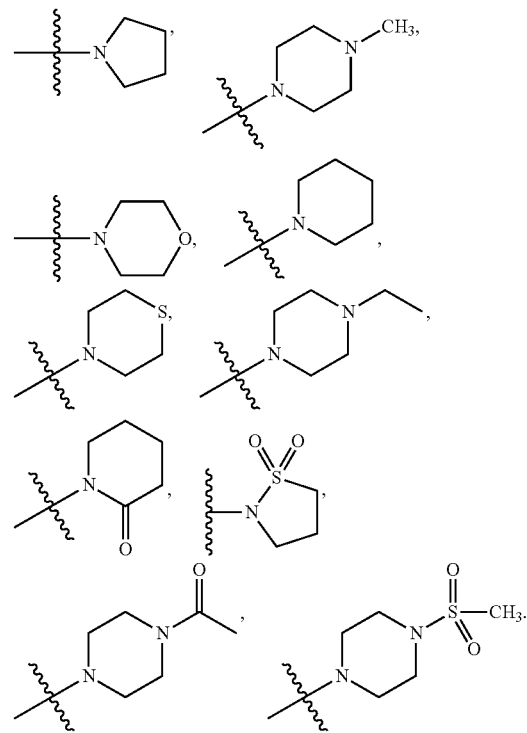

The invention also provides compounds of Formula III, wherein when $R^{3'}$ is a member of the group consisting of alkyl, alkenyl, alkynyl, cycloalkyl, heteroalkyl, heterocycloalkyl, heterocycloalkyloxy, aryl, arylalkyl, heteroaryl, heteroarylalkyl, acyl, alkoxy, amido, amino, sulfonamido, acyloxy, alkoxycarbonyl, and NR'R" (wherein R' and R" are taken together with nitrogen to form a cyclic moiety), then $R^{3'}$ is optionally substituted with one or more of the following substituents: alkyl, alkenyl, alkynyl, cycloalkyl, heteroalkyl, heterocycloalkyl, heterocycloalkyloxy, aryl, arylalkyl, heteroaryl, heteroarylalkyl, acyl, heterocycloalkyloxy, alkoxy, amido, amino, sulfonamido, acyloxy, alkoxycarbonyl, halo, cyano, hydroxy, nitro, phosphate, urea, carbonate, or NR'R" wherein R' and R" are taken together with nitrogen to form a cyclic moiety. Each of the above substituents may be further substituted with one or more substituents chosen from the group consisting of alkyl, alkoxy, amido, amino, sulfonamido, acyloxy, alkoxycarbonyl, halo, cyano, hydroxy, nitro, oxo, phosphate, urea, and carbonate.

For example, the invention provides compounds wherein when $R^{3'}$ is alkyl, the alkyl is substituted with NR'R" wherein R' and R" are taken together with the nitrogen to form a cyclic moiety. The cyclic moiety so formed can be unsubstituted or substituted. Non-limiting exemplary cyclic moieties includes but are not limited to morpholinyl, azetidinyl, pyrrolidinyl, piperidinyl, piperazinyl, and thiomorpholinyl. In other examples of the compounds of Formula III, when $R^{3'}$ is alkyl, the alkyl is substituted with heterocycloalkyl, which includes oxetanyl, azetidinyl, tetrahydrofuranyl, pyrrolyl, tetrahydropyranyl, piperidinyl, morpholinyl, and piperazinyl. All of the above listed heterocycloaklyl substituents can be unsubstituted or substituted.

In yet other examples of the compounds of Formula III, when $R^{3'}$ is alkyl, the alkyl is substituted with a 5, 6, 7, 8, 9, or 10 membered monocyclic or bicyclic heteroaryl, which is unsubstituted or substituted. The monocyclic heteroaryl includes but is not limited to pyrrolyl, thienyl, furyl, pyridinyl, pyranyl, pyrimidinyl, pyrazinyl, pyridazinyl, imidazolyl, thiazolyl, pyrazolyl, and oxazolyl. The bicyclic heteroaryl includes but is not limited to benzothiophenyl, benzofuryl, indolyl, quinolinyl, isoquinolinyl, benzimidazolyl, benzoxazolyl, benzothiazolyl, quinazolinyl, azaindolyl, pyrazolopyrimidinyl, purinyl, pyrrolo[1,2-b]pyridazinyl, pyrrolopyrimidinyl, indazolyl, pyrazolylpyridinyl, imidazo[1,2-a]pyridinyl, and pyrrolo[1,2-f][1,2,4]triazinyl.

In other embodiments of the compound of Formula III, $R^{3'}$ is —$NHR^{3''}$, —$N(CH_3)R^{3''}$, —$N(CH_2CH_3)R^{3''}$, —$N(CH(CH_3)_2)R^{3''}$, or —$OR^{3''}$, wherein $R^{3''}$ is unsubstituted or substituted heterocycloalkyl (nonlimiting examples thereof include 4-NH piperidin-1-yl, 4-methyl piperidin-1-yl, 4-ethyl piperidin-1-yl, 4-isopropyl-piperidin-1-yl, and pyrrolidin-3-yl), unsubstituted or substituted monocyclic aryl, or unsubstituted or substituted monocyclic heteroaryl (including but not limited to pyrrolyl, thienyl, furyl, pyridinyl, pyranyl, pyrimidinyl, pyrazinyl, pyridazinyl, imidazolyl, thiazolyl, pyrazolyl, and oxazolyl). In one example, $R^{3'}$ is —O-aryl, i.e. phenoxy. In another example, $R^{3'}$ is —O-(4-methyl)piperidin-1-yl or —O-(4-isopropyl)piperidin-1-yl.

In some embodiments of the compound of Formula III, $R^{3'}$ is one of the following moieties:

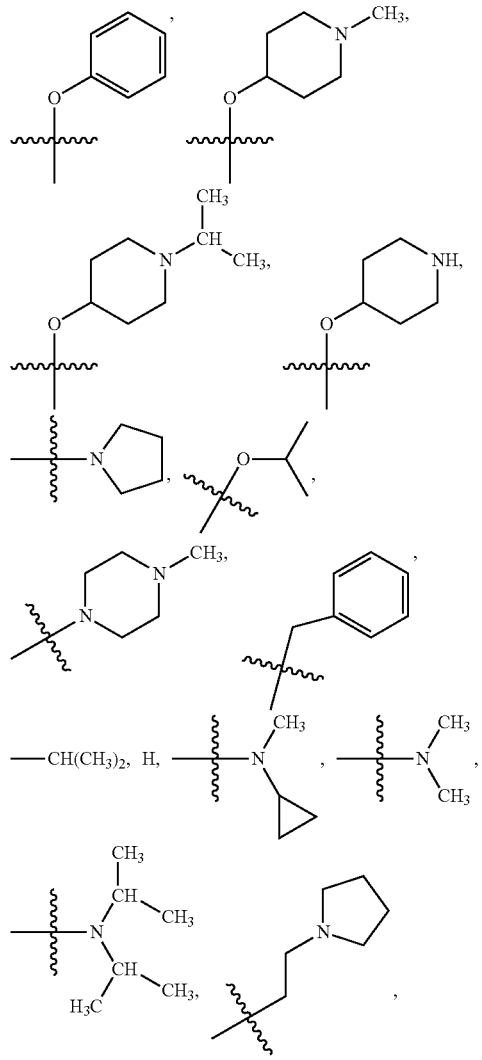
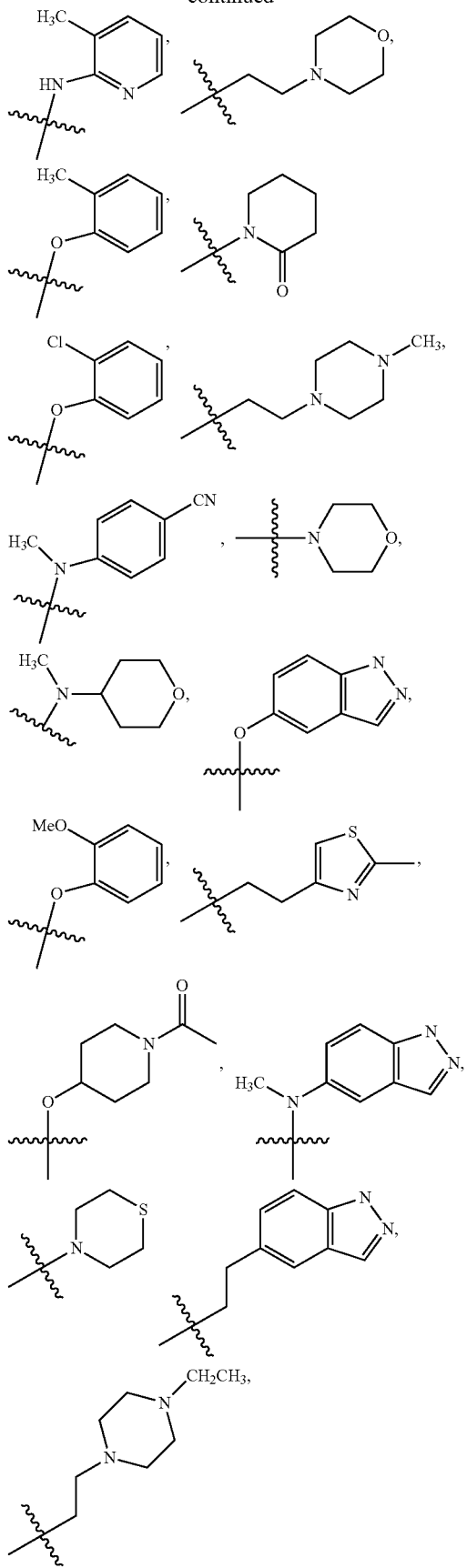

-continued

-continued

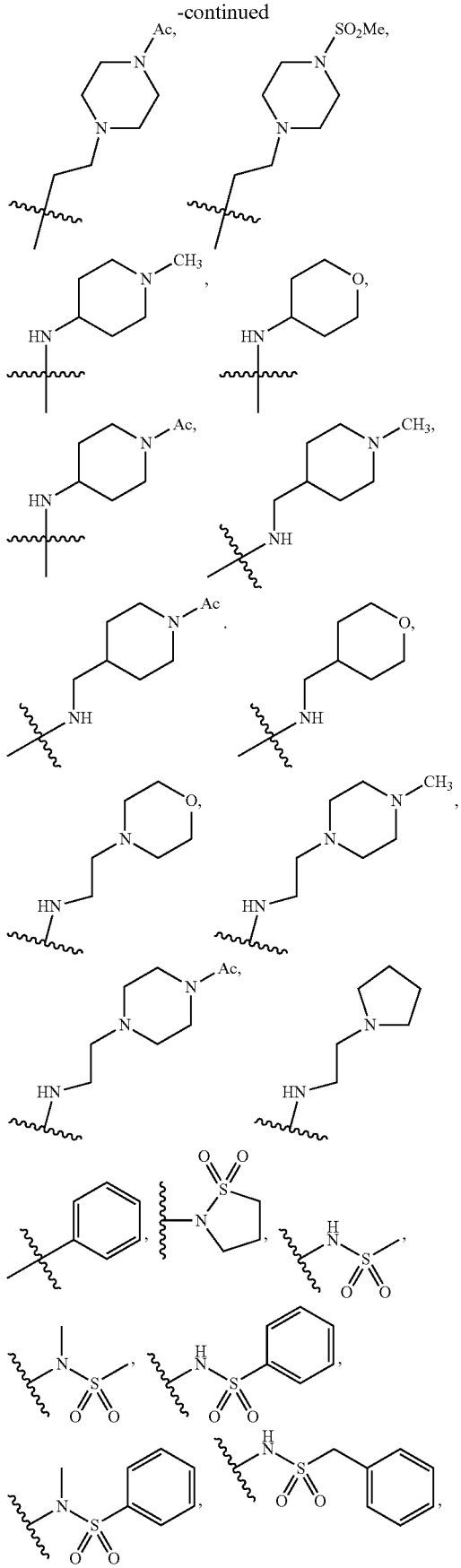

-continued

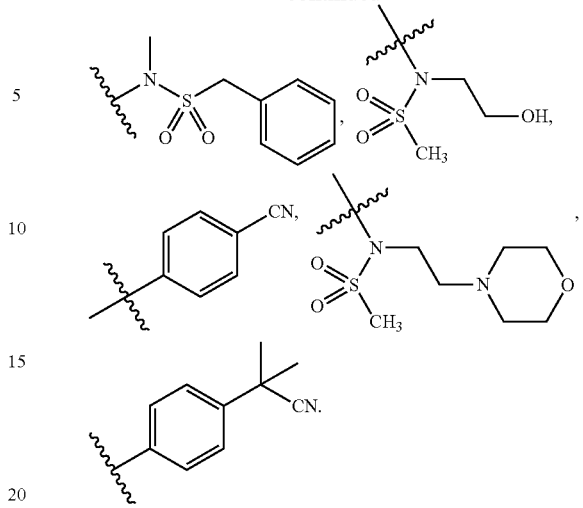

In some embodiments of the compound of Formula III, $W^{1'}$ is $NR^{3'}$, wherein $R^{3'}$ is hydrogen, unsubstituted or substituted $C_1$-$C_{10}$alkyl (which includes but is not limited to —$CH_3$, —$CH_2CH_3$, n-propyl, isopropyl, n-butyl, tert-butyl, sec-butyl, pentyl, hexyl, and heptyl), or unsubstituted or substituted $C_3$-$C_7$cycloalkyl (which includes but is not limited to cyclopropyl, cyclobutyl, cyclopentyl, and cyclohexyl). In other embodiments of the compound of Formula III, $R^{3'}$ is unsubstituted or substituted heterocycloalkyl (which includes but is not limited to oxetanyl, tetrahydrofuranyl, pyrrolidinyl, tetrahydropyranyl, piperidinyl, and piperazinyl), or unsubstituted or substituted $C_2$-$C_{10}$heteroalkyl (which includes but is not limited to methoxyethoxy, methoxymethyl, and diethylaminoethyl). Alternatively, $R^{3'}$ is unsubstituted or substituted monocyclic heteroaryl (which includes but is not limited to pyrrolyl, thienyl, furyl, pyridinyl, pyranyl, pyrimidinyl, pyrazinyl, pyridazinyl, imidazolyl, thiazolyl, pyrazolyl, and oxazolyl) or unsubstituted or substituted monocyclic aryl.

In other embodiments, $W^{1'}$ is N. In still other embodiments, $W^{1'}$ is S.

In some embodiments of the compound of Formula III, $W^{2'}$ is $CR^{4'}$. $R^{4'}$ can be, for example, hydrogen, or unsubstituted or substituted alkyl (including but not limited to $CH_3$, —$CH_2CH_3$, n-propyl, isopropyl, n-butyl, tert-butyl, sec-butyl, pentyl, hexyl, and heptyl). In other embodiments, $R^{4'}$ is unsubstituted or substituted alkenyl (including but not limited to unsubstituted or substituted $C_2$-$C_5$alkenyl such as, for example, vinyl, allyl, 1-methyl propen-1-yl, butenyl, or pentenyl) or unsubstituted or substituted alkynyl (including but not limited to unsubstituted or substituted $C_2$-$C_5$alkynyl such as acetylenyl, propargyl, butynyl, or pentynyl). Alternatively, $R^{4'}$ is unsubstituted or substituted aryl (including but not limited to monocyclic or bicyclic aryl) or unsubstituted or substituted arylalkyl (including but not limited to monocyclic or bicyclic aryl linked to alkyl wherein alkyl includes but is not limited to $CH_3$, —$CH_2CH_3$, n-propyl, isopropyl, n-butyl, sec-butyl, and pentyl). In some other embodiments, $R^{4'}$ is unsubstituted or substituted heteroaryl, including but not limited to monocyclic and bicyclic heteroaryl. Monocyclic heteroaryl $R^{4'}$ includes but is not limited to pyrrolyl, thienyl, furyl, pyridinyl, pyranyl, pyrimidinyl, pyrazinyl, pyridazinyl, imidazolyl, thiazolyl, pyrazolyl, and oxazolyl. Bicyclic heteroaryl $R^{4'}$ includes but is not limited to benzothiophenyl, benzofuryl, indolyl, quinolinyl, isoquinolinyl, benzimidazolyl, benzoxazolyl, benzothiazolyl, quinazolinyl, azaindolyl, pyrazolopyrimidinyl, purinyl, pyrrolo[1,2-b]pyridazinyl, pyrrolopyrimidinyl, indazolyl, pyrazolylpyridinyl, imidazo[1,2-a]pyridinyl, and pyrrolo[1,2-f][1,2,4]triazinyl.

The present invention also provides compounds of Formula III wherein $R^{4'}$ is unsubstituted or substituted heteroarylalkyl, including but not limited to monocyclic and bicyclic heteroaryl as described above, that are linked to alkyl, which in turn includes but is not limited to $CH_3$, $—CH_2CH_3$, n-propyl, isopropyl, n-butyl, sec-butyl, and pentyl. In some embodiments, $R^{4'}$ is unsubstituted or substituted cycloalkyl (including but not limited to cyclopropyl, cyclobutyl, and cyclopentyl) or unsubstituted or substituted heteroalkyl (non-limiting examples include ethoxymethyl, methoxymethyl, and diethylaminomethyl). In some further embodiments, $R^{4'}$ is unsubstituted or substituted heterocycloalkyl which includes but is not limited to pyrrolidinyl, tetrahydrofuranyl, piperidinyl, tetrahydropyranyl, thiazolidinyl, imidazolidinyl, morpholinyl, and piperazinyl. In yet other embodiments of the compounds of Formula III, $R^{4'}$ is unsubstituted or substituted alkoxy including but not limited to $C_1$-$C_4$alkoxy such as methoxy, ethoxy, propoxy or butoxy. $R^{4'}$ can also be unsubstituted or substituted heterocycloalkyloxy, including but not limited to 4-NH piperidin-1-yl-oxy, 4-methyl piperidin-1-yl-oxy, 4-ethyl piperidin-1-yl-oxy, 4-isopropyl-piperidin-1-yl-oxy, and pyrrolidin-3-yl-oxy. In other embodiments, $R^{4'}$ is unsubstituted or substituted amino, wherein the substituted amino includes but is not limited to dimethylamino, diethylamino, di-isopropyl amino, N-methyl N-ethyl amino, and dibutylamino. In some embodiments, $R^{4'}$ is unsubstituted or substituted acyl, unsubstituted or substituted acyloxy, unsubstituted or substituted $C_1$-$C_4$acyloxy, unsubstituted or substituted alkoxycarbonyl, unsubstituted or substituted amido, or unsubstituted or substituted sulfonamido. In some embodiments, $R^{4'}$ is halo, which is —I, —F, —Cl, or —Br. In some embodiments, $R^{4'}$ is selected from the group consisting of cyano, hydroxy, nitro, phosphate, urea, or carbonate. Also contemplated are $R^{4'}$ being $—CH_3$, $—CH_2CH_3$, n-propyl, isopropyl, n-butyl, tert-butyl, sec-butyl, pentyl, hexyl, heptyl, $—OCH_3$, $—OCH_2CH_3$, or $—CF_3$.

$R^{4'}$ of the compounds of Formula III, can also be NR'R" wherein R' and R" are taken together with the nitrogen to form a cyclic moiety having from 3 to 8 ring atoms. The cyclic moiety so formed may further include one or more heteroatoms which are selected from the group consisting of S, O, and N. The cyclic moiety so formed is unsubstituted or substituted, including but not limited to morpholinyl, azetidinyl, pyrrolidinyl, piperidinyl, piperazinyl, isothiazolidinyl 1,2, dioxide, and thiomorpholinyl. Further non-limiting exemplary cyclic moieties are the following:

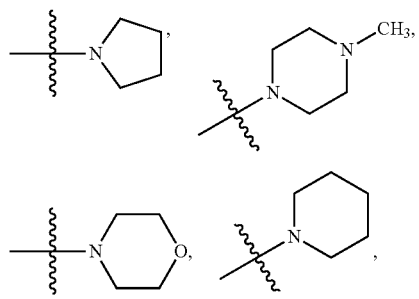

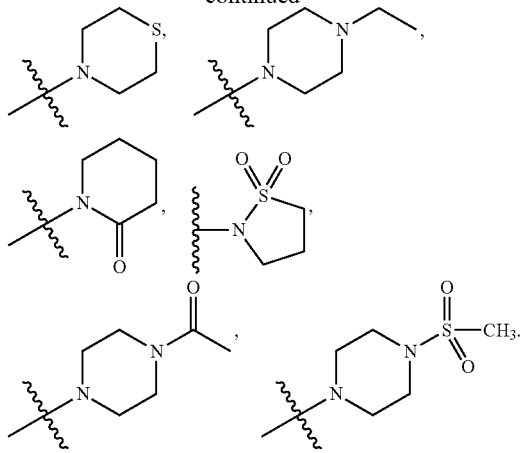

The invention also provides compounds of Formula III, wherein when $R^{4'}$ is a member of the group consisting of alkyl, alkenyl, alkynyl, cycloalkyl, heteroalkyl, heterocycloalkyl, heterocycloalkyloxy, aryl, arylalkyl, heteroaryl, heteroarylalkyl, acyl, alkoxy, amido, amino, sulfonamido, acyloxy, alkoxycarbonyl, and NR'R" (wherein R' and R" are taken together with nitrogen to form a cyclic moiety), then $R^{4'}$ is optionally substituted with one or more of the following substituents: alkyl, alkenyl, alkynyl, cycloalkyl, heteroalkyl, heterocycloalkyl, heterocycloalkyloxy, aryl, arylalkyl, heteroaryl, heteroarylalkyl, acyl, alkoxy, amido, amino, sulfonamido, acyloxy, alkoxycarbonyl, halo, cyano, hydroxy, nitro, phosphate, urea, carbonate, or NR'R" wherein R' and R" are taken together with nitrogen to form a cyclic moiety. Each of the above substituents may be further substituted with one or more substituents chosen from the group consisting of alkyl, alkoxy, amido, amino, sulfonamido, acyloxy, alkoxycarbonyl, halo, cyano, hydroxy, nitro, oxo, phosphate, urea, and carbonate.

For example, the invention provides compounds wherein when $R^{4'}$ is alkyl, the alkyl is substituted with NR'R" wherein R' and R" are taken together with the nitrogen to form a cyclic moiety. The cyclic moiety so formed can be unsubstituted or substituted. Non-limiting exemplary cyclic moieties includes but are not limited to morpholinyl, azetidinyl, pyrrolidinyl, piperidinyl, piperazinyl, isothiazolidinyl 1,2, dioxide, and thiomorpholinyl. In other examples of the compounds of Formula III, when $R^{4'}$ is alkyl, the alkyl is substituted with heterocycloalkyl, which includes oxetanyl, azetidinyl, tetrahydrofuranyl, pyrrolyl, tetrahydropyranyl, piperidinyl, morpholinyl, and piperazinyl. All of the above listed heterocycloaklyl substituents can be unsubstituted or substituted.

In yet other examples of the compounds of Formula III, when $R^{4'}$ is alkyl, the alkyl is substituted with a 5, 6, 7, 8, 9, or 10 membered monocyclic or bicyclic heteroaryl, which is unsubstituted or substituted. The monocyclic heteroaryl includes but is not limited to pyrrolyl, thienyl, furyl, pyridinyl, pyranyl, pyrimidinyl, pyrazinyl, pyridazinyl, imidazolyl, thiazolyl, pyrazolyl, and oxazolyl. The bicyclic heteroaryl includes but is not limited benzothiophenyl, benzofuryl, indolyl, quinolinyl, isoquinolinyl, benzimidazolyl, benzoxazolyl, benzothiazolyl, quinazolinyl, azaindolyl, pyrazolopyrimidinyl, purinyl, pyrrolo[1,2-b]pyridazinyl, pyrrolopyrimidinyl, indazolyl, pyrazolylpyridinyl, imidazo[1,2-a]pyridinyl, and pyrrolo[1,2-f][1,2,4]triazinyl. In some embodiments of the compound of Formula III, $W^{2'}$ is N.

In some embodiments $R^{3'}$ and $R^{4'}$ taken together form a cyclic moiety. Such a moiety may have, for example, from 3 to 8 ring atoms. The cyclic moiety so formed may further include one or more heteroatoms which are selected from the group consisting of S, O, and N. The cyclic moiety so formed is unsubstituted or substituted. In some embodiments, the substituent is $C_1$-$C_{10}$alkyl (which includes but is not limited to —$CH_3$, —$CH_2CH_3$, n-propyl, isopropyl, n-butyl, tert-butyl, sec-butyl, pentyl, hexyl, and heptyl), or $C_3$-$C_7$cycloalkyl (which includes but is not limited to cyclopropyl, cyclobutyl, cyclopentyl, and cyclohexyl); heterocycloalkyl (which includes but is not limited to oxetanyl, tetrahydrofuranyl, pyrrolidinyl, tetrahydropyranyl, piperidinyl, and piperazinyl), $C_2$-$C_{10}$heteroalkyl (which includes but is not limited to methoxyethoxy, methoxymethyl, and diethylaminoethyl); monocyclic heteroaryl (which includes but is not limited to pyrrolyl, thienyl, furyl, pyridinyl, pyranyl, pyrimidinyl, pyrazinyl, pyridazinyl, imidazolyl, thiazolyl, pyrazolyl, and oxazolyl) or unsubstituted or substituted monocyclic aryl. The cyclic moiety may have one or more substituents, which may be the same or different.

In some embodiments, the cyclic moiety formed by $R^{3'}$ and $R^{4'}$ is substituted with at least one of the following substituents:

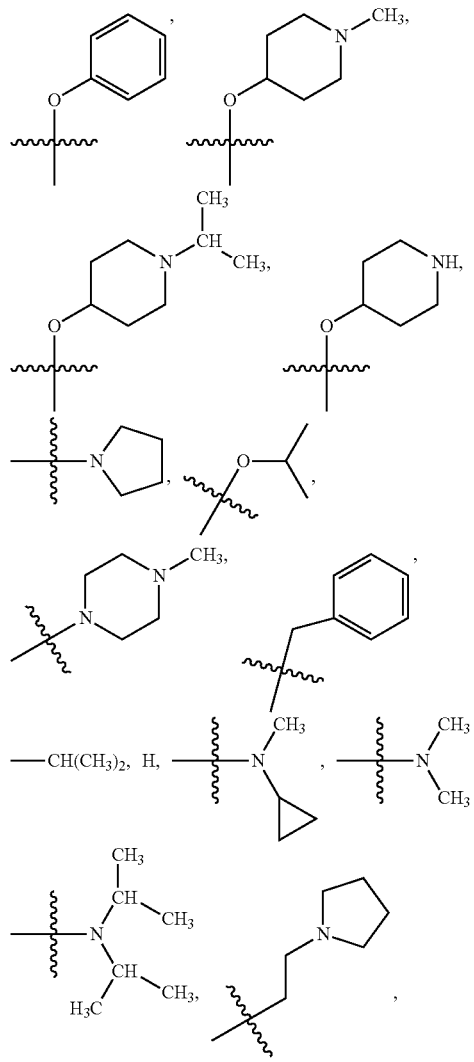

-continued

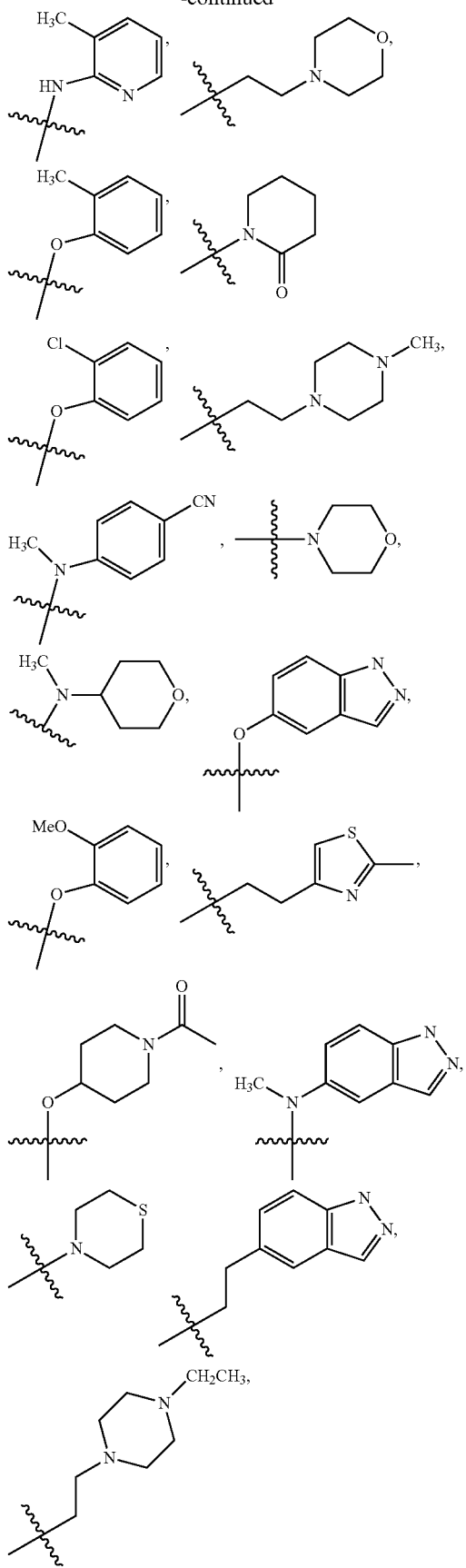

311
-continued
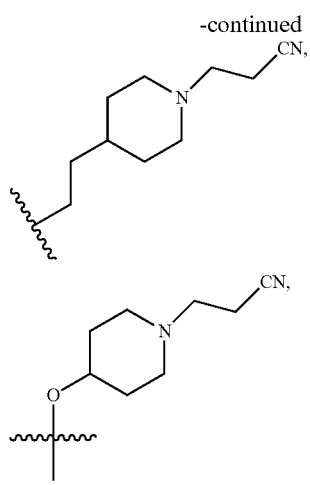
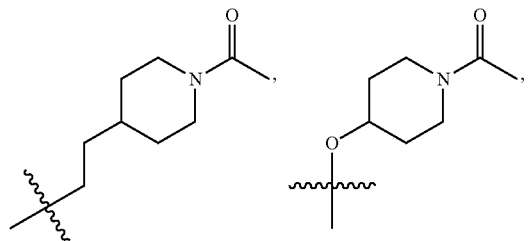
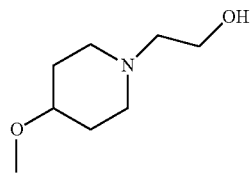
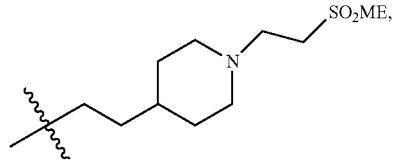
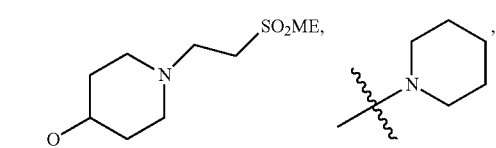
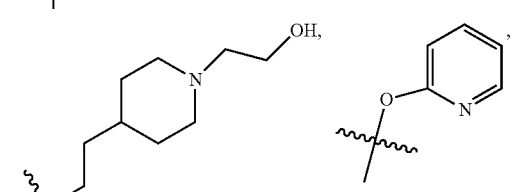
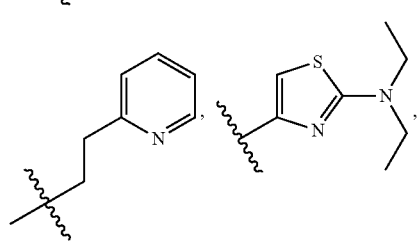
312
-continued
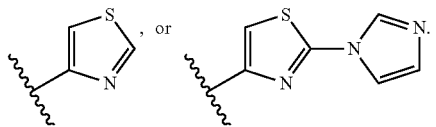
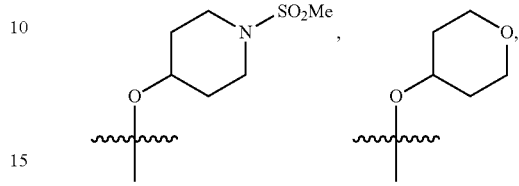
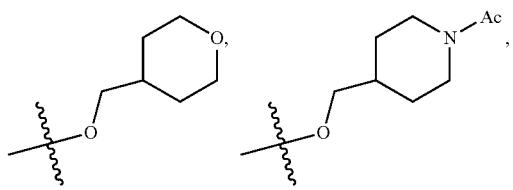
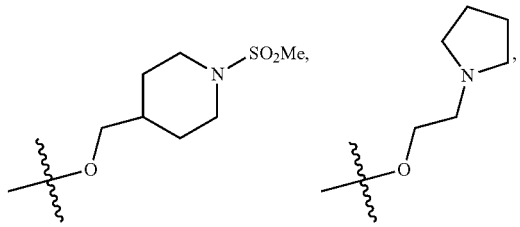
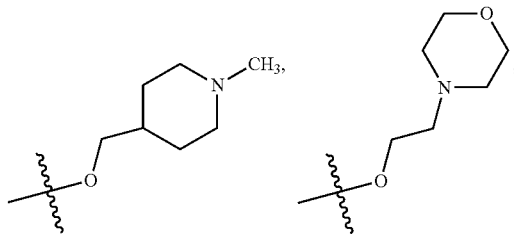
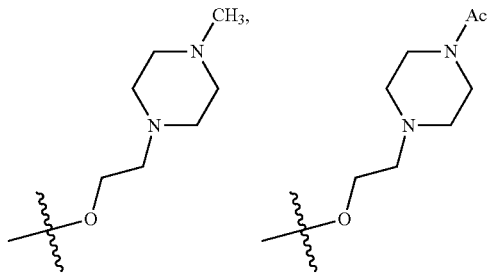
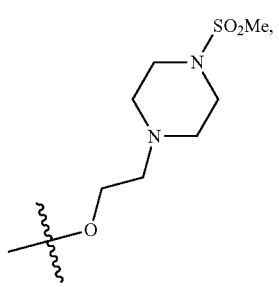

-continued

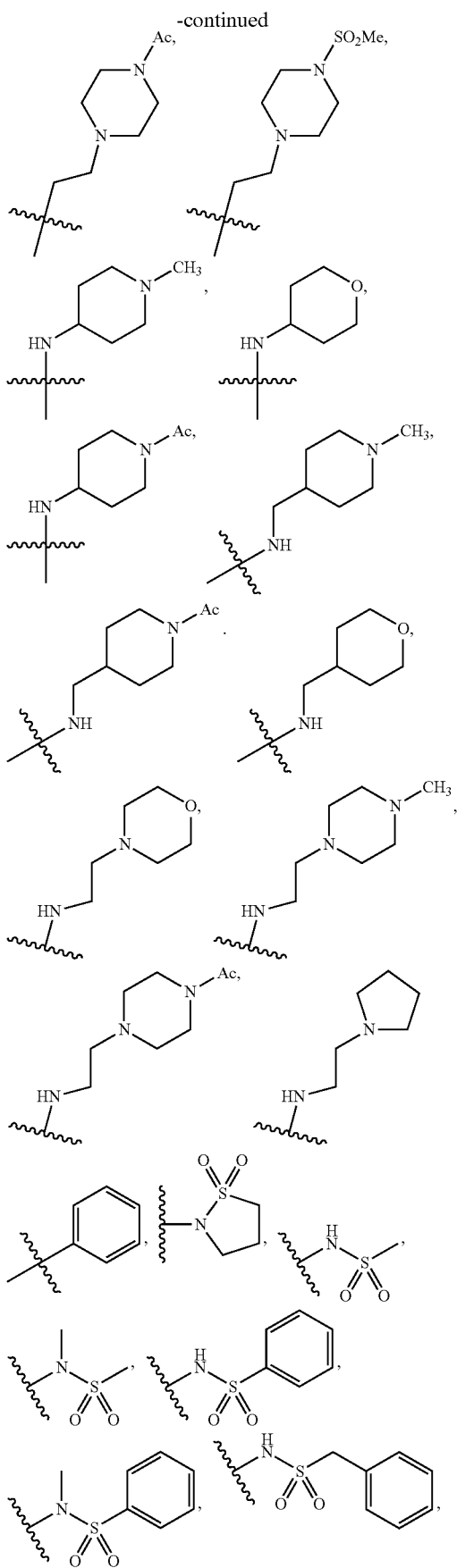

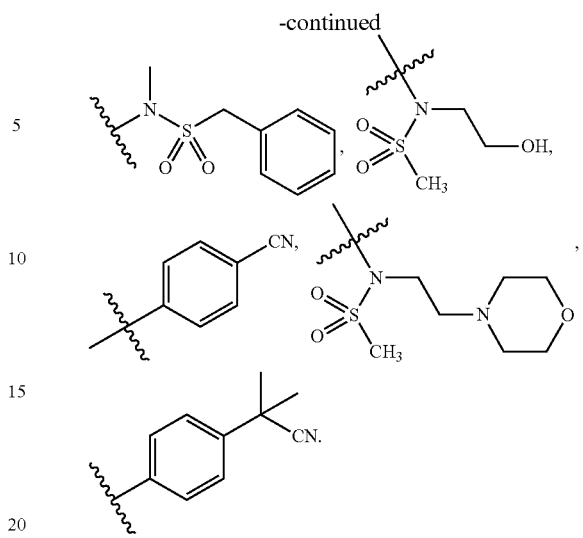

In some embodiments of the compound of Formula III, $W^{3'}$ is $CR^{5'}$. $R^{5'}$ can be, for example, hydrogen, or unsubstituted or substituted alkyl (including but not limited to $CH_3$, —$CH_2CH_3$, n-propyl, isopropyl, n-butyl, tert-butyl, sec-butyl, pentyl, hexyl, and heptyl). In one embodiment, $R^{5'}$ is H. In other embodiments, $R^{5'}$ is unsubstituted or substituted alkenyl (including but not limited to unsubstituted or substituted $C_2$-$C_5$alkenyl such as, for example, vinyl, allyl, 1-methyl propen-1-yl, butenyl, or pentenyl) or unsubstituted or substituted alkynyl (including but not limited to unsubstituted or substituted $C_2$-$C_5$alkynyl such as acetylenyl, propargyl, butynyl, or pentynyl). Alternatively, $R^{5'}$ is unsubstituted or substituted aryl (including but not limited to monocyclic or bicyclic aryl) or unsubstituted or substituted arylalkyl (including but not limited to monocyclic or bicyclic aryl linked to alkyl wherein alkyl includes but is not limited to $CH_3$, —$CH_2CH_3$, n-propyl, isopropyl, n-butyl, sec-butyl, and pentyl). In some other embodiments, $R^{5'}$ is unsubstituted or substituted heteroaryl, including but not limited to monocyclic and bicyclic heteroaryl. Monocyclic heteroaryl $R^{5'}$ includes but is not limited to pyrrolyl, thienyl, furyl, pyridinyl, pyranyl, pyrimidinyl, pyrazinyl, pyridazinyl, imidazolyl, thiazolyl, pyrazolyl, and oxazolyl. Bicyclic heteroaryl $R^{5'}$ includes but is not limited to benzothiophenyl, benzofuryl, indolyl, quinolinyl, isoquinolinyl, benzimidazolyl, benzoxazolyl, benzothiazolyl, quinazolinyl, azaindolyl, pyrazolopyrimidinyl, purinyl, pyrrolo[1,2-b]pyridazinyl, pyrrolopyrimidinyl, indazolyl, pyrazolylpyridinyl, imidazo[1,2-a]pyridinyl, and pyrrolo[1,2-f][1, 2, 4]triazinyl. In some embodiments of the compound of Formula III, $W^{3'}$ is N. In other embodiments, $W^{3'}$ is S.

In some embodiments of the compound of Formula III, $W^{4'}$ is C. In other embodiments, $W^{4'}$ is N.

In some embodiments of the compound of Formula III, $W^{5'}$ is N. In other embodiments of the compound of Formula III, $W^{5'}$ is $CR^{7'}$. $R^{7'}$ can be, for example, hydrogen, or unsubstituted or substituted alkyl (including but not limited to $CH_3$, —$CH_2CH_3$, n-propyl, isopropyl, n-butyl, tert-butyl, sec-butyl, pentyl, hexyl, and heptyl). In one embodiment, $R^{7'}$ is H. In other embodiments, $R^{7'}$ is unsubstituted or substituted alkenyl (including but not limited to unsubstituted or substituted $C_2$-$C_5$alkenyl such as, for example, vinyl, allyl, 1-methyl propen-1-yl, butenyl, or pentenyl) or unsubstituted or substituted alkynyl (including but not limited to unsubstituted or substituted $C_2$-$C_5$alkynyl such as acetylenyl, propargyl, butynyl, or pentynyl). Alternatively, $R^{7'}$ is unsubstituted or substituted aryl (including but not limited to monocyclic or bicyclic aryl) or unsubstituted or substituted arylalkyl (including but not limited to monocyclic or bicyclic aryl linked to alkyl wherein alkyl includes but is not limited to CH$_3$, —CH$_2$CH$_3$, n-propyl, isopropyl, n-butyl, sec-butyl, and pentyl). In some other embodiments, R$^{7'}$ is unsubstituted or substituted heteroaryl, including but not limited to monocyclic and bicyclic heteroaryl. Monocyclic heteroaryl R$^{7'}$ includes but is not limited to pyrrolyl, thienyl, furyl, pyridinyl, pyranyl, pyrimidinyl, pyrazinyl, pyridazinyl, imidazolyl, thiazolyl, pyrazolyl, and oxazolyl. Bicyclic heteroaryl R$^{7'}$ includes but is not limited to benzothiophenyl, benzofuryl, indolyl, quinolinyl, isoquinolinyl, benzimidazolyl, benzoxazolyl, benzothiazolyl, quinazolinyl, azaindolyl, pyrazolopyrimidinyl, purinyl, pyrrolo[1,2-b]pyridazinyl, pyrrolopyrimidinyl, indazolyl, pyrazolylpyridinyl, imidazo[1,2-a]pyridinyl, and pyrrolo[1,2-f][1,2,4]triazinyl.

In some embodiments of the compound of Formula III, W$^{6'}$ is N. In other embodiments of the compound of Formula III, W$^{6'}$ is CR$^{8'}$. R$^{8'}$ can be, for example, hydrogen, or unsubstituted or substituted alkyl (including but not limited to CH$_3$, —CH$_2$CH$_3$, n-propyl, isopropyl, n-butyl, tert-butyl, sec-butyl, pentyl, hexyl, and heptyl). In one embodiment, R$^{8'}$ is H. In other embodiments, R$^{8'}$ is unsubstituted or substituted alkenyl (including but not limited to unsubstituted or substituted C$_2$-C$_5$alkenyl such as, for example, vinyl, allyl, 1-methyl propen-1-yl, butenyl, or pentenyl) or unsubstituted or substituted alkynyl (including but not limited to unsubstituted or substituted C$_2$-C$_5$alkynyl such as acetylenyl, propargyl, butynyl, or pentynyl). Alternatively, R$^{8'}$ is unsubstituted or substituted aryl (including but not limited to monocyclic or bicyclic aryl) or unsubstituted or substituted arylalkyl (including but not limited to monocyclic or bicyclic aryl linked to alkyl wherein alkyl includes but is not limited to CH$_3$, —CH$_2$CH$_3$, n-propyl, isopropyl, n-butyl, sec-butyl, and pentyl). In some other embodiments, R$^{8'}$ is unsubstituted or substituted heteroaryl, including but not limited to monocyclic and bicyclic heteroaryl. Monocyclic heteroaryl R$^{8'}$ includes but is not limited to pyrrolyl, thienyl, furyl, pyridinyl, pyranyl, pyrimidinyl, pyrazinyl, pyridazinyl, imidazolyl, thiazolyl, pyrazolyl, and oxazolyl. Bicyclic heteroaryl R$^{8'}$ includes but is not limited to benzothiophenyl, benzofuryl, indolyl, quinolinyl, isoquinolinyl, benzimidazolyl, benzoxazolyl, benzothiazolyl, quinazolinyl, azaindolyl, pyrazolopyrimidinyl, purinyl, pyrrolo[1,2-b]pyridazinyl, pyrrolopyrimidinyl, indazolyl, pyrazolylpyridinyl, imidazo[1,2-a]pyridinyl, and pyrrolo[1,2-f][1, 2, 4]triazinyl.

In some embodiments of the compound of Formula III, W$^{7'}$ is C. In other embodiments, W$^{7'}$ is N.

The invention also provides compounds of Formula III which are defined as defined by the following subclasses:

Subclass IIIa

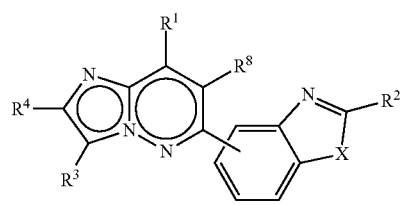

Subclass IIIb

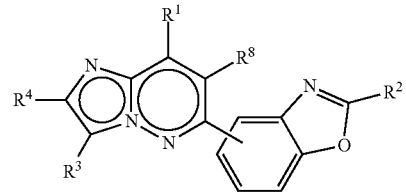

Subclass IIIc

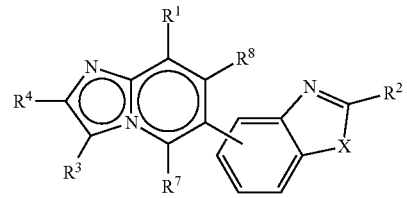

Subclass IIId

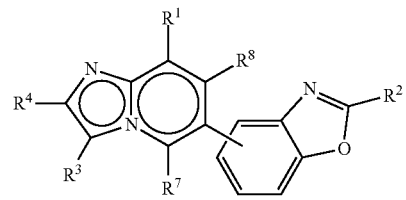

Subclass IIIe

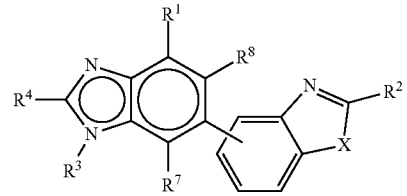

Subclass IIIf

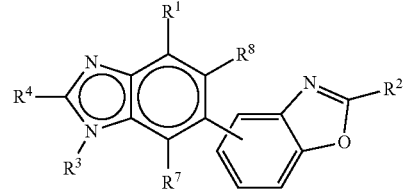

Subclass IIIg

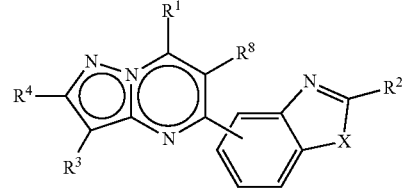

Subclass IIIh

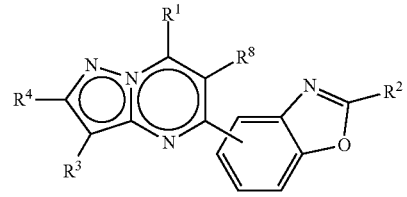

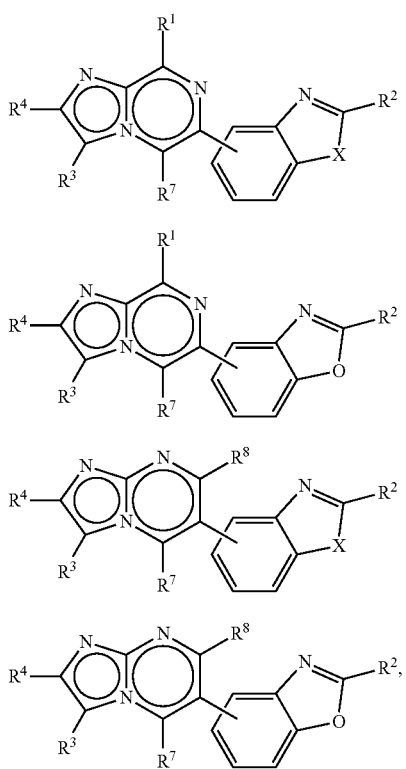

wherein for each of the above formulas, each respective R variable includes a 'prime' (').

In some embodiments of compounds of Subclasses IIIa-IIIj, $R^{1'}$ is hydrogen. In other embodiments of compounds of Subclasses IIIa-IIIl, $R^{2'}$ is $NH_2$ of NHCO(alkyl). In other embodiments of compounds of Subclasses IIIa-IIIl, $R^{4'}$ is hydrogen. In other embodiments of compounds of Subclasses IIIc-IIIf and IIIi-IIIl, $R^{7'}$ is hydrogen. In other embodiments of compounds of Subclasses IIIa-IIIh and IIIk-IIIl, $R^{8'}$ is hydrogen.

In some embodiments of compounds of Subclasses IIIa through IIIl, $R^{3'}$ is alkyl, heteroalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, halo, cyano, hydroxy, nitro, phosphate, urea, carbonate, or NR'R" wherein R' and R" are taken together with nitrogen to form a cyclic moiety. $R^{3'}$ can be, for example, hydrogen, unsubstituted or substituted alkyl (including but not limited to $CH_3$, —$CH_2CH_3$, n-propyl, isopropyl, n-butyl, tert-butyl, sec-butyl, pentyl, hexyl, and heptyl). In other embodiments, $R^{3'}$ is unsubstituted or substituted alkenyl (including but not limited to unsubstituted or substituted $C_2$-$C_5$alkenyl such as, for example, vinyl, allyl, 1-methyl propen-1-yl, butenyl, or pentenyl) or unsubstituted or substituted alkynyl (including but not limited to unsubstituted or substituted $C_2$-$C_5$alkynyl such as acetylenyl, propargyl, butynyl, or pentynyl). Alternatively, $R^{3'}$ is unsubstituted or substituted aryl (including but not limited to monocyclic or bicyclic aryl) or unsubstituted or substituted arylalkyl (including but not limited to monocyclic or bicyclic aryl linked to alkyl wherein alkyl includes but is not limited to $CH_3$, —$CH_2CH_3$, n-propyl, isopropyl, n-butyl, sec-butyl, and pentyl). In some other embodiments, $R^{3'}$ is unsubstituted or substituted heteroaryl, including but not limited to monocyclic and bicyclic heteroaryl. Monocyclic heteroaryl $R^{3'}$ includes but is not limited to pyrrolyl, thienyl, furyl, pyridinyl, pyranyl, pyrimidinyl, pyrazinyl, pyridazinyl, imidazolyl, thiazolyl, pyrazolyl, and oxazolyl. Bicyclic heteroaryl $R^{3'}$ includes but is not limited to benzothiophenyl, benzofuryl, indolyl, quinolinyl, isoquinolinyl, benzimidazolyl, benzoxazolyl, benzothiazolyl, quinazolinyl, azaindolyl, pyrazolopyrimidinyl, purinyl, pyrrolo[1,2-b]pyridazinyl, pyrrolopyrimidinyl, indazolyl, pyrazolylpyridinyl, imidazo[1,2-a]pyridinyl, and pyrrolo[1,2-f][1,2,4]triazinyl. The present invention also provides compounds of Formula II wherein $R^{3'}$ is unsubstituted or substituted heteroarylalkyl, including but not limited to monocyclic and bicyclic heteroaryl as described above, that are linked to alkyl, which in turn includes but is not limited to $CH_3$, —$CH_2CH_3$, n-propyl, isopropyl, n-butyl, sec-butyl, and pentyl. In some embodiments, $R^{3'}$ is unsubstituted or substituted cycloalkyl (including but not limited to cyclopropyl, cyclobutyl, and cyclopentyl) or unsubstituted or substituted heteroalkyl (non-limiting examples include ethoxymethyl, methoxymethyl, and diethylaminomethyl). In some further embodiments, $R^{3'}$ is unsubstituted or substituted heterocycloalkyl which includes but is not limited to pyrrolidinyl, tetrahydrofuranyl, piperidinyl, tetrahydropyranyl, thiazolidinyl, imidazolidinyl, morpholinyl, and piperazinyl. In yet other embodiments of the compounds of Formula II, $R^{3'}$ is unsubstituted or substituted alkoxy including but not limited to $C_1$-$C_4$alkoxy such as methoxy, ethoxy, propoxy or butoxy. $R^{3'}$ can also be unsubstituted or substituted heterocycloalkyloxy, including but not limited to 4-NH piperidin-1-yl-oxy, 4-methyl piperidin-1-yl-oxy, 4-ethyl piperidin-1-yl-oxy, 4-isopropyl-piperidin-1-yl-oxy, and pyrrolidin-3-yl-oxy. In other embodiments, $R^{3'}$ is unsubstituted or substituted amino, wherein the substituted amino includes but is not limited to dimethylamino, diethylamino, di-isopropyl amino, N-methyl N-ethyl amino, and dibutylamino. In some embodiments, $R^{3'}$ is unsubstituted or substituted acyl, unsubstituted or substituted acyloxy, unsubstituted or substituted $C_1$-$C_4$acyloxy, unsubstituted or substituted alkoxycarbonyl, unsubstituted or substituted amido, or unsubstituted or substituted sulfonamido. In other embodiments, $R^{3'}$ is halo, which is —I, —F, —Cl, or —Br. In some embodiments, $R^{3'}$ is selected from the group consisting of cyano, hydroxy, nitro, phosphate, urea, and carbonate. Also contemplated are $R^{3'}$ being —$CH_3$, —$CH_2CH_3$, n-propyl, isopropyl, n-butyl, tert-butyl, sec-butyl, pentyl, hexyl, heptyl, —$OCH_3$, —$OCH_2CH_3$, or —$CF_3$. In some embodiments $R^{3'}$ can also be NR'R" wherein R' and R" are taken together with the nitrogen to form a cyclic moiety having from 3 to 8 ring atoms. The cyclic moiety so formed may further include one or more heteroatoms which are selected from the group consisting of S, O, and N. The cyclic moiety so formed is unsubstituted or substituted, including but not limited to morpholinyl, azetidinyl, pyrrolidinyl, piperidinyl, piperazinyl, isothiazolidinyl 1,2, dioxide, and thiomorpholinyl. Further non-limiting exemplary cyclic moieties are the following:

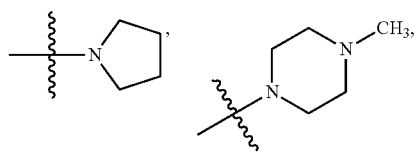

-continued

[chemical structures: morpholine, piperidine, thiomorpholine, N-ethylpiperazine, piperidinone, isothiazolidine 1,1-dioxide, acetylpiperazine, methylsulfonylpiperazine]

The invention further provides a PI3Kα inhibitor which is a compound of Formula IV:

[structure of Formula IV]

or its pharmaceutically acceptable salts thereof, wherein
W$^{1'}$ is CR$^{3'}$, W$^{2'}$ is C-benzoxazolyl substituted with R$^{2'}$ and W$^{3'}$ is S;
W$^{1'}$ is CR$^{3'}$, W$^{2'}$ is C-benzoxazolyl substituted with R$^{2'}$ and W$^{3'}$ is CR$^{5'}$;
W$^{1'}$ is N or NR$^{3'}$, W$^{2'}$ is CR$^{4'}$, and W$^{3'}$ is C-benzoxazolyl substituted with R$^{2'}$;
W$^{1'}$ is CR$^{3'}$, W$^{2'}$ is CR$^{4'}$, and W$^{3'}$ is C-benzoxazolyl substituted with R$^{2'}$; or
W$^{1'}$ is N or NR$^{3'}$, W$^{2'}$ is NR$^{4'}$, and W$^{3'}$ is C-benzoxazolyl substituted with R$^{2'}$;
X is N;
R$^{1'}$ and R$^{2'}$ are independently hydrogen, alkyl, heteroalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, halo, cyano, hydroxy, nitro, phosphate, urea, carbonate, or NR'R" wherein R' and R" are taken together with nitrogen to form a cyclic moiety;
R$^{3'}$ and R$^{4'}$ are independently hydrogen, alkyl, heteroalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, halo, cyano, hydroxy, nitro, phosphate, urea, carbonate, or NR'R" wherein R' and R" are taken together with nitrogen to form a cyclic moiety;
R$^{5'}$, R$^{6'}$, R$^{7'}$ and R$^{8'}$ are independently hydrogen, alkyl, heteroalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, halo, cyano, hydroxy, nitro, phosphate, urea, carbonate, or NR'R" wherein R' and R" are taken together with nitrogen to form a cyclic moiety.

In some embodiments of the compound of Formula IV, the compound is:

[chemical structure]

and wherein W$^{1'}$ is CR$^{3'}$ or NR$^{3'}$ and W$^{2'}$ is CR$^{4'}$.

In another aspect, the invention provides a PI3Kα inhibitor which is a compound of Formula V:

[structure of Formula V]

Formula V or its pharmaceutically acceptable salts thereof, wherein:
W$^{1'}$ is N, NR$^{3'}$, CR$^{3'}$, or C=O; W$^{2'}$ is N, NR$^{4'}$, CR$^{4'}$, or C=O; W$^{3'}$ is N, NR$^{5'}$ or CR$^{5'}$; W$^{4'}$ is N, C=O or CR$^{6'}$, wherein no more than two N atoms and no more than two C=O groups are adjacent;
W$^{5'}$ is N or CR$^{7'}$;
W$^{6'}$ is N or CR$^{8'}$;
W$^{a'}$ and W$^{b'}$ are independently N or CR$^{9'}$;
one of W$^{c'}$ and W$^{d'}$ is N, and the other is O, NR$^{10'}$, or S;
R$^{1'}$ and R$^{2'}$ are independently hydrogen, alkyl, heteroalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, halo, cyano, hydroxy, nitro, phosphate, urea, carbonate, or NR'R" wherein R' and R" are taken together with nitrogen to form a cyclic moiety;
R$^{3'}$ and R$^{4'}$ are independently hydrogen, alkyl, heteroalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, halo, cyano, hydroxy, nitro, phosphate, urea, carbonate, or NR'R" wherein R' and R" are taken together with nitrogen to form a cyclic moiety;
or R$^{3'}$ and R$^{4'}$ taken together form a cyclic moiety;
R$^{5'}$, R$^{6'}$, R$^{7'}$ and R$^{8'}$ are independently hydrogen, alkyl, heteroalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, halo, cyano, hydroxy, nitro, phosphate, urea, carbonate, or NR'R" wherein R' and R" are taken together with nitrogen to form a cyclic moiety;

$R^{9'}$ is alkyl or halo; and $R^{10'}$ is hydrogen, alkyl, heteroalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, halo, cyano, hydroxy, nitro, phosphate, urea, carbonate, or NR'R" wherein R' and R" are taken together with nitrogen to form a cyclic moiety.

In some embodiments of the compound of Formula IV, $W^{1'}$ is $CR^{3'}$, $W^{2'}$ is $CR^{4'}$, $W^{3'}$ is $CR^{5'}$, $W^{4'}$ is N, $W^{5'}$ is $CR^{7'}$, and $W^{6'}$ is $CR^{8'}$; $W^{1'}$ is N, $W^{2'}$ is $CR^{4'}$, $W^{3'}$ is $CR^{5'}$, $W^{4'}$ is N, $W^{5'}$ is $CR^{7'}$, and $W^{6'}$ is $CR^{8'}$; or $W^{1'}$ is $CR^{3'}$, $W^{2'}$ is N, $W^{3'}$ is $CR^{5'}$, $W^{4'}$ is N, $W^{5'}$ is $CR^{7'}$, and $W^{6'}$ is $CR^{8'}$. In some embodiments of the compound of Formula IV, $W^{b'}$ is N. In other embodiments, $W^{a'}$ is $CR^{9'}$ and $R^{9'}$ is alkyl.

The invention also provides a PI3Kα inhibitor which is a compound of Formula VI:

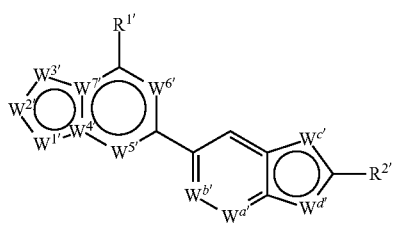

Formula VI or its pharmaceutically acceptable salts thereof, wherein $W^{1'}$ is S, N, $NR^{3'}$ or $CR^{3'}$, $W^{2'}$ is N or $CR^{4'}$, $W^{3'}$ is S, N or $CR^{5'}$, $W^{4'}$ is N or C, and $W^{7'}$ is N or C, wherein no more than two N atoms and no more than two C=O groups are adjacent;

$W^{5'}$ is N or $CR^{7'}$;

$W^{6'}$ is N or $CR^{8'}$;

$W^{a'}$ and $W^{b'}$ are independently N or $CR^{9'}$;

one of $W^{c'}$ and $W^{d'}$ is N, and the other is O, $NR^{10'}$, or S;

$R^{1'}$ and $R^{2'}$ are independently hydrogen, alkyl, heteroalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, halo, cyano, hydroxy, nitro, phosphate, urea, carbonate, or NR'R" wherein R' and R" are taken together with nitrogen to form a cyclic moiety;

$R^{3'}$ and $R^{4'}$ are independently hydrogen, alkyl, heteroalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, halo, cyano, hydroxy, nitro, phosphate, urea, carbonate, or NR'R" wherein R' and R" are taken together with nitrogen to form a cyclic moiety; or $R^{3'}$ and $R^{4'}$ taken together form a cyclic moiety;

$R^{5'}$, $R^{7'}$ and $R^{8'}$ are independently hydrogen, alkyl, heteroalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, halo, cyano, hydroxy, nitro, phosphate, urea, carbonate, or NR'R" wherein R' and R" are taken together with nitrogen to form a cyclic moiety;

$R^{9'}$ is alkyl or halo; and $R^{10'}$ is hydrogen, alkyl, heteroalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, halo, cyano, hydroxy, nitro, phosphate, urea, carbonate, or NR'R" wherein R' and R" are taken together with nitrogen to form a cyclic moiety.

In some embodiments of the compound of Formula VI, $W^{1'}$ is $CR^{3'}$, $W^{2'}$ is $CR^{4'}$, $W^{3'}$ is N, $W^{4'}$ is N, $W^{5'}$ is $CR^{7'}$, and $W^{6'}$ is $CR^{8'}$. In other embodiments, $W^{1'}$ is $CR^{3'}$, $W^{2'}$ is $CR^{4'}$, $W^{3'}$ is N, $W^{4'}$ is N, $W^{5'}$ is $CR^{7'}$, and $W^{6'}$ is $CR^{8'}$. In other embodiments, $W^{1'}$ is $CR^{3'}$, $W^{2'}$ is $CR^{4'}$, $W^{3'}$ is N, $W^{4'}$ is N, $W^{5'}$ is N, and $W^{6'}$ is $CR^{8'}$. In still other embodiments, $W^{1'}$ is $NR^{3'}$, $W^{2'}$ is $CR^{4'}$, $W^{3'}$ is N, $W^{4'}$ is C, $W^{5'}$ is $CR^{7'}$, and $W^{6'}$ is $CR^{8'}$. In other embodiments, $W^{1'}$ is S, $W^{2'}$ is $CR^{4'}$, $W^{3'}$ is N, $W^{4'}$ is C, $W^{5'}$ is $CR^{7'}$, and $W^{6'}$ is $CR^{8'}$. In other embodiments, $W^{1'}$ is $CR^{3'}$, $W^{2'}$ is $CR^{4'}$, $W^{3'}$ is S, $W^{4'}$ is C, $W^{5'}$ is N, and $W^{6'}$ is N.

In some embodiments of the compound of Formula VI, $W^{b'}$ is N. In other embodiments, $W^{a'}$ is $CR^{9'}$ and $R^{9'}$ is alkyl.

The invention further provides PI3Kα inhibitors which are compounds of Formula VI-A and VI-B:

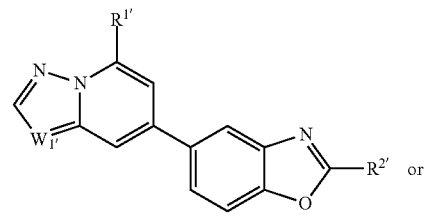

Formula VI-A

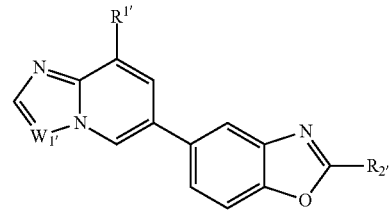

Formula VI-B or its pharmaceutically acceptable salts thereof, wherein $W^{1'}$ is $CR^{3'}$;

$R^{1'}$ and $R^{2'}$ are independently hydrogen, alkyl, heteroalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, halo, cyano, hydroxy, nitro, phosphate, urea, carbonate, or NR'R" wherein R' and R" are taken together with nitrogen to form a cyclic moiety;

and $R^{3'}$ is hydrogen, alkyl, heteroalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, halo, cyano, hydroxy, nitro, phosphate, urea, carbonate, or NR'R" wherein R' and R" are taken together with nitrogen to form a cyclic moiety.

Also provided herein are PI3Kα inhibitors which are compounds of Formula VI-C and VI-D:

Formula VI-C

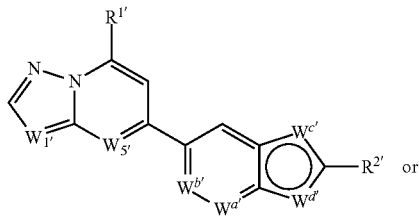

Formula VI-D

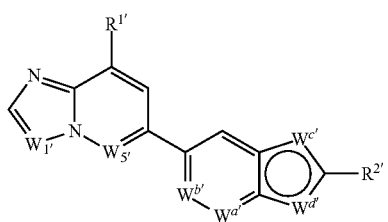

or its pharmaceutically acceptable salts thereof, wherein
W$^{1'}$ is CR$^{3'}$;
W$^{5'}$ is N or CR$^{7'}$;
W$^{a'}$ and W$^{b'}$ are independently N or CR$^{9'}$;
one of W$^{c'}$ and W$^{d'}$ is N, and the other is O, NR$^{10'}$, or S;
R$^{1'}$ and R$^{2'}$ are independently hydrogen, alkyl, heteroalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, halo, cyano, hydroxy, nitro, phosphate, urea, carbonate, or NR'R" wherein R' and R" are taken together with nitrogen to form a cyclic moiety;
R$^{3'}$ is hydrogen, alkyl, heteroalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, halo, cyano, hydroxy, nitro, phosphate, urea, carbonate, or NR'R" wherein R' and R" are taken together with nitrogen to form a cyclic moiety;
R$^{7'}$ is hydrogen, alkyl, heteroalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, halo, cyano, hydroxy, nitro, phosphate, urea, carbonate, or NR'R" wherein R' and R" are taken together with nitrogen to form a cyclic moiety;
R$^{9'}$ is alkyl or halo; and
R$^{10'}$ is hydrogen, alkyl, heteroalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, halo, cyano, hydroxy, nitro, phosphate, urea, carbonate, or NR'R" wherein R' and R" are taken together with nitrogen to form a cyclic moiety.

In some embodiments of the compound of Formula V-C or V-D, W$^{b'}$ is N. In other embodiments, is CR$^{9'}$ and R$^{9'}$ is alkyl.

Also provided herein is a PI3Kα inhibitor which is a compound of Formula VII:

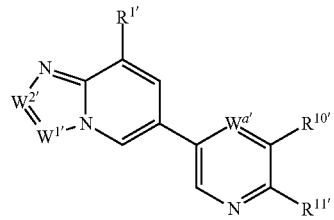

or its pharmaceutically acceptable salts thereof, wherein
W$^{1'}$ is CR$^{3'}$; W$^{2'}$ is CR$^{4'}$;
W$^{a'}$ is CH or N;
R$^{1'}$ is hydrogen, alkyl, heteroalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, halo, cyano, hydroxy, nitro, phosphate, urea, carbonate, or NR'R" wherein R' and R" are taken together with nitrogen to form a cyclic moiety;
R$^{3'}$ is alkyl, heteroalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, halo, cyano, hydroxy, nitro, phosphate, urea, carbonate, or NR'R" wherein R' and R" are taken together with nitrogen to form a cyclic moiety;
R$^{4'}$ is hydrogen, alkyl, heteroalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, halo, cyano, hydroxy, nitro, phosphate, urea, carbonate, or NR'R" wherein R' and R" are taken together with nitrogen to form a cyclic moiety;
or R$^{3'}$ and R$^{4'}$ taken together form a cyclic moiety; and
R$^{10'}$ and R$^{11'}$ are independently hydrogen, alkyl, heteroalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, halo, cyano, hydroxy, nitro, phosphate, urea, carbonate, or NR'R" wherein R' and R" are taken together with nitrogen to form a cyclic moiety.

The invention further provides a PI3Kα inhibitor which is a compound of Formula VIII:

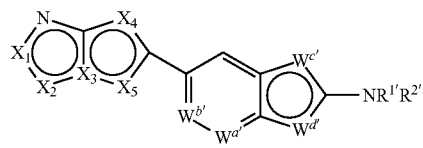

or a pharmaceutically acceptable salt thereof, wherein
X$_1$ is CR$^{3'}$, NR$^{3'}$, or S;
X$_2$ is CR$^{4'}$, NR$^{4'}$, CR$^{4'}$═CR$^{5'}$, or CR$^{4'}$═NR$^{5'}$;
X$_3$ and X$_4$ are independently C or N;
X$_5$ is CR$^{6'}$, NR$^{6'}$, or S;
X$_4$ is CR$^{7'}$, NR$^{7'}$, CR$^{7'}$═CR$^{8'}$, or CR$^{7'}$═NR$^{8'}$;
W$^{a'}$ and W$^{b'}$ are independently N or CR$^{9'}$;
one of W$^{c'}$ and W$^{d'}$ is N, and the other is O, NR$^{10'}$, or S;
R$^{1'}$ and R$^{2'}$ are independently hydrogen, alkyl, heteroalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, halo, cyano, nitro, phosphate, urea, carbonate, or NR'R" wherein R' and R" are taken together with nitrogen to form a cyclic moiety;

$R^{3'}$ and $R^{4'}$ are independently hydrogen, alkyl, heteroalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, halo, cyano, hydroxy, nitro, phosphate, urea, carbonate, or NR'R" wherein R' and R" are taken together with nitrogen to form a cyclic moiety; or $R^{3'}$ and $R^{4'}$ taken together form a cyclic moiety;

$R^{5'}$, $R^{6'}$, $R^{7'}$, and $R^{8'}$ are independently hydrogen, alkyl, heteroalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, halo, cyano, hydroxy, nitro, phosphate, urea, carbonate, or NR'R" wherein R' and R" are taken together with nitrogen to form a cyclic moiety;

$R^{9'}$ is alkyl or halo; and $R^{10'}$ is hydrogen, alkyl, heteroalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, halo, cyano, hydroxy, nitro, phosphate, urea, carbonate, or NR'R" wherein R' and R" are taken together with nitrogen to form a cyclic moiety.

In some embodiments of the compound of Formula VIII, $W^{b'}$ is N. In other embodiments, $W^{a'}$ is $CR^{9'}$ and $R^{9'}$ is alkyl.

In some embodiments, the mTor inhibitor is a compound as described in U.S. Pat. No. 7,651,687 or 7,585,868; or as described International Patent Applications WO 2007/079164, WO 2007/061737, WO 2007/106503, WO 2007/134828 or WO2011/025889 which are hereby incorporated by reference in their entirety.

In other embodiments, the mTor inhibitor is NVP-BEZ235 (Novartis), BGT226 (Novartis), XL765 (Sanofi-Aventis, Exelixis), GDC0980 (Genentech), SF1126 (Semafore), PKI587 (Wyeth), PF04691502 (Pfizer), or GSK2126458 (GlaxoSmithKline). In still other embodiments, the mTor inhibitor is CC223 (Celgene), OSI027 (OSI Pharmaceuticals), AZD8055 (Astra Zeneca), AZD2014 (Astra Zeneca), or Palomid 529 (Paloma Pharmaceuticals).

Structures of exemplary mTor inhibitors are shown below:

| mTor inhibitor | Structure |
|---|---|
| NVP-BEZ235 | 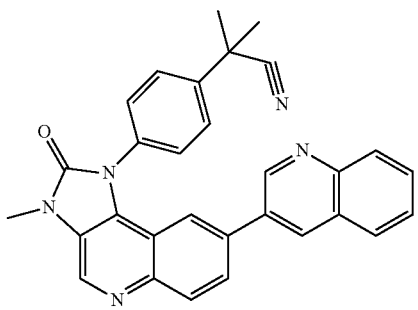 [SMILES: Cn1c(=O)n(-c2ccc(C(C)(C)C#N)cc2)c2c3cc(-c4cnc5ccccc5c4)ccc3ncc21] |
| XL765 | 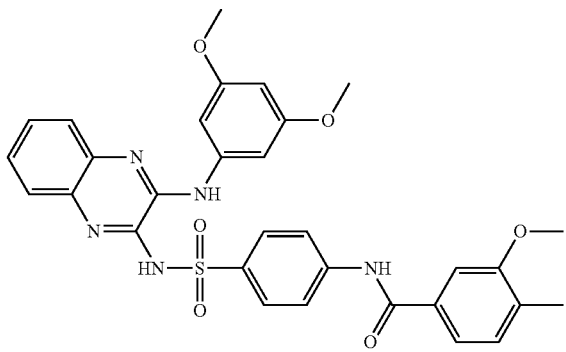 [SMILES: COc1cc(Nc2nc3ccccc3nc2NS(=O)(=O)c2ccc(NC(=O)c3ccc(C)c(OC)c3)cc2)cc(OC)c1] |
| GDC0980 | 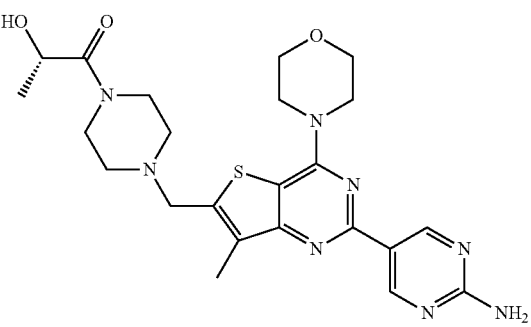 [SMILES: Cc1c(CN2CCN(C(=O)[C@H](C)O)CC2)sc2c(N3CCOCC3)nc(-c3cnc(N)nc3)nc12] |

| mTor inhibitor | Structure |
|---|---|
| SF1126 | 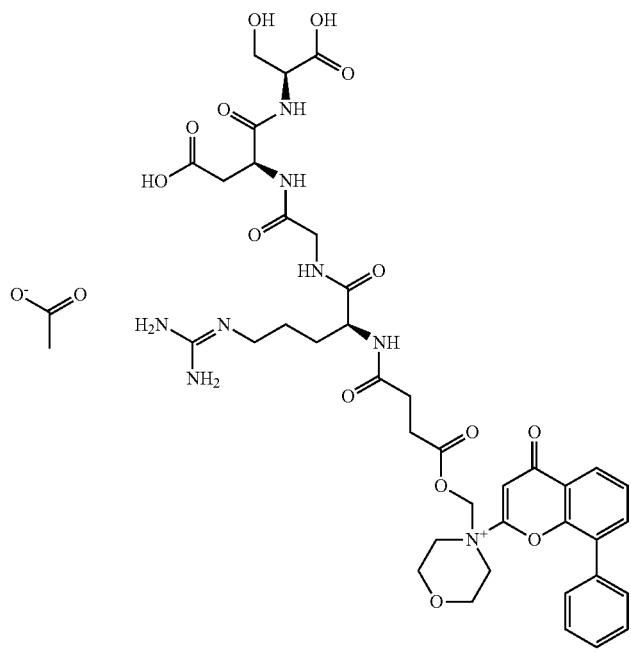 |
| PKI587 | 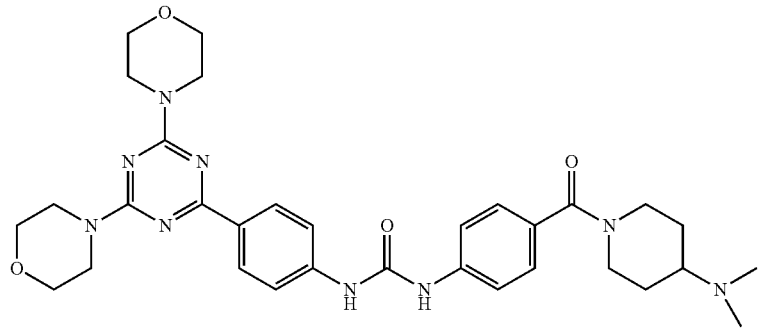 [SMILES: CN(C)C1CCN(C(=O)c2ccc(NC(=O)Nc3ccc(-c4nc(N5CCOCC5)nc(N5CCOCC5)n4)cc3)cc2)CC1] |
| PF04691502 | 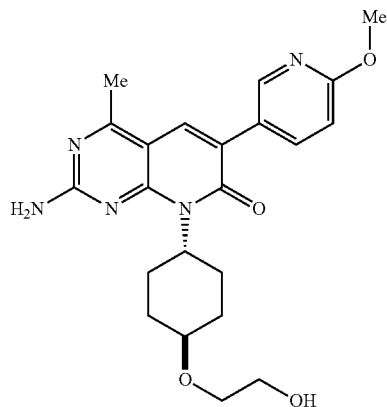 [SMILES: COc1ccc(-c2cc3c(C)nc(N)nc3n([C@H]3CC[C@H](OCCO)CC3)c2=O)cn1] |

-continued
| mTor inhibitor | Structure |
|---|---|
| GSK2126458 | 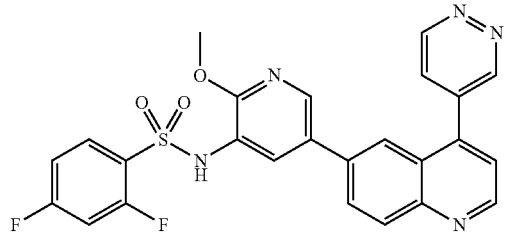 [SMILES: COc1ncc(-c2ccc3nccc(-c4ccnnc4)c3c2)cc1NS(=O)(=O)c1ccc(F)cc1F] |
| OSI027 | 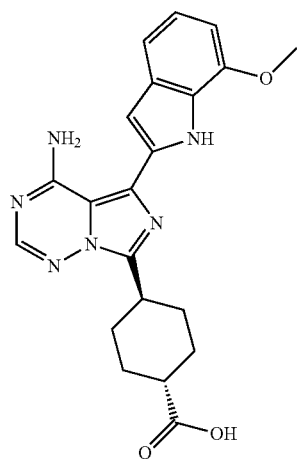 [SMILES: COc1cccc2cc(-c3nc([C@H]4CC[C@H](C(=O)O)CC4)n4ncnc(N)c34)[nH]c12] |
| AZD8055 | 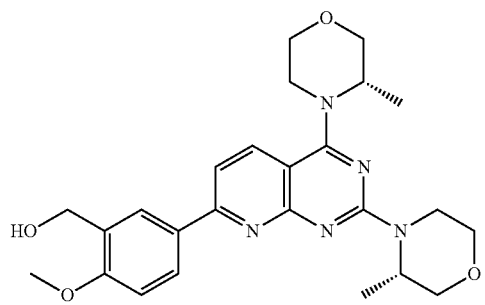 [SMILES: COc1ccc(-c2ccc3c(N4CCOC[C@@H]4C)nc(N4CCOC[C@@H]4C)nc3n2)cc1CO] |
| P529 | 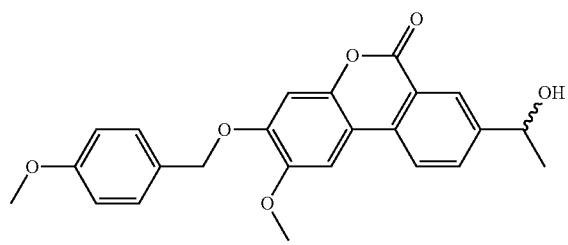 [SMILES: COc1ccc(COc2cc3oc(=O)c4cc(C(C)O)ccc4c3cc2OC)cc1] |

Reaction Schemes —PI3Kα Inhibitor Compounds

In general, compounds of the invention may be prepared by the following reaction scheme:

Scheme A':

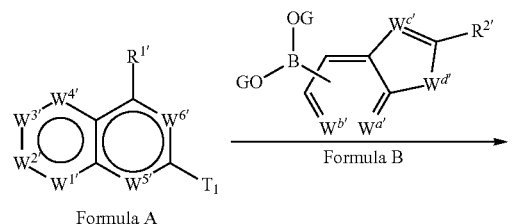

Formula A

Formula B

Formula C

For example, compounds of the invention may be prepared by the following reaction schemes:

Scheme A'':

Formula A

Formula B

Formula C

Scheme B':

Formula A

Formula B

Formula C

The compounds of the invention may be synthesized via a reaction scheme represented generally in Schemes A', A'' and B'. The synthesis proceeds via coupling a compound of Formula A with a compound of Formula B to yield a compound of Formula C. The coupling step is typically catalyzed by using a palladium catalyst, including but not limited to palladium tetrakis (triphenylphosphine). The coupling is generally performed in the presence of a suitable base, a nonlimiting example being sodium carbonate. One example of a suitable solvent for the reaction is aqueous dioxane.

A compound of Formula A for use in Scheme A' or A'' has a structure of Formula A, wherein $T_1$ is halo including bromo, chloro, fluoro, and iodo, and wherein the remaining substituents are defined for Formulas I and II of compounds of the invention. For boronic acids and acid derivatives as depicted in Formula B, X is either O or S, and the benzoxazole or benzothiazole moiety can be attached at the 4-, 5-, 6- or 7-position.

For a compound of Formula B, G is hydrogen or $R_{G1}$, wherein $R_{G1}$ is alkyl, alkenyl, or aryl. Alternatively, $B(OG)_2$ is taken together to form a 5- or 6-membered cyclic moiety. In some embodiments, the compound of Formula B is a compound having a structure of Formula E:

Formula E wherein G is H or $R_{G1}$; $R_{G1}$ is alkyl, alkenyl, or aryl. Alternatively, $B(OG)_2$ is taken together to form a 5- or 6-membered cyclic moiety; and $R_{G2}$ is H, tert-butyl carbamate, or acyl.

Scheme C':

Formula D  Formula B'  Formula B''

Scheme C' depicts an exemplary scheme for synthesizing a compound of Formula B' or, optionally, Formula B'' for use in Reaction Scheme C'. M is a heterocyclic moiety such as a benzoxazolyl or benzothiazolyl moiety as described by Formula B. This reaction proceeds via reacting a compound of Formula D with a trialkyl borate or a boronic acid derivative to produce a compound of Formula B'. The trialkyl borate includes but is not limited to triisopropyl borate and the boronic acid derivative includes but is not limited to bis(pinacolato)diboron. The reaction typically is run in the presence of a base, a nonlimiting example being potassium acetate. The reaction may be run in a solvent such as dioxane or tetrahydrofuran.

A compound of Formula D for use in Scheme C' is a compound wherein $T_2$ is halo or another leaving group, and M is as defined above. The compound of Formula B' may further be converted to a compound of Formula B" by treatment with an acid such as hydrochloric acid.

Some exemplary compounds of Formula B that can be synthesized via Scheme C' include but are not limited to compounds of the following formulae:

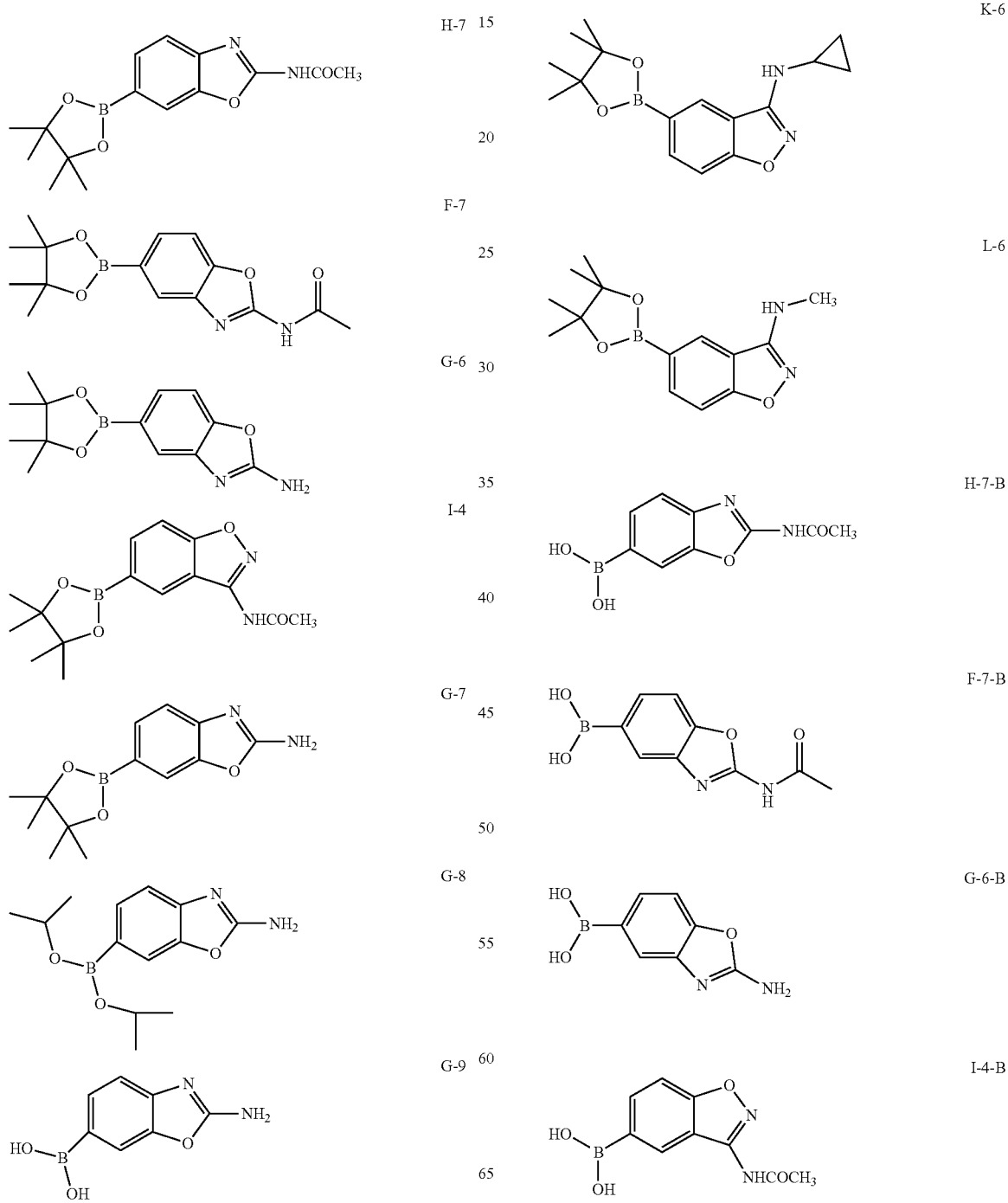

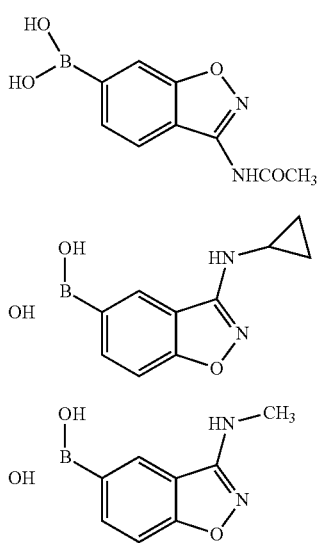

J-4-B

K-6-B

L-6-B

Where desired, deprotection of a substituent (e.g., removal of Boc protection from an amino substituent) on the benzoxazolyl moiety (i.e. $M_1$ of Formula C) is performed after coupling the compound of Formula B to the compound of Formula A.

Some exemplary compounds with such protecting groups, include but are not limited to compounds of the following formulae:

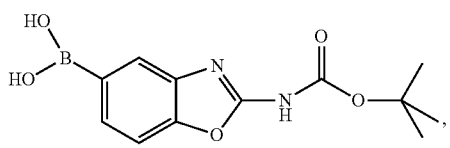

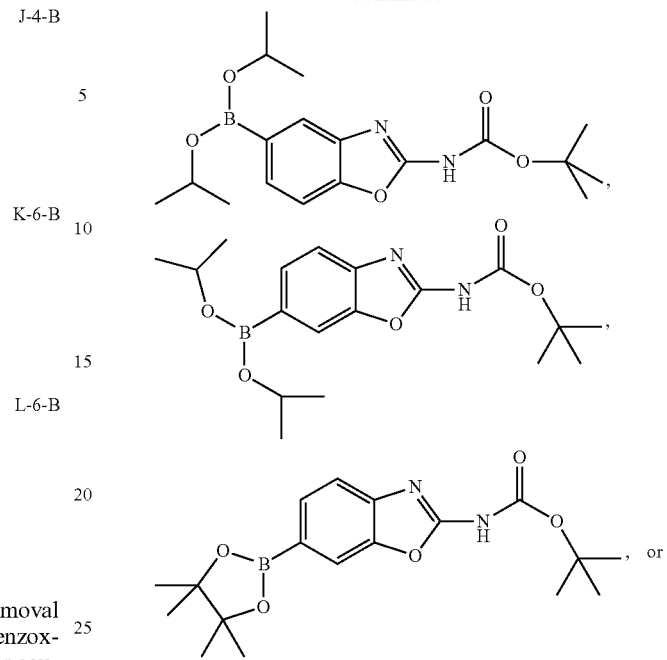

, or

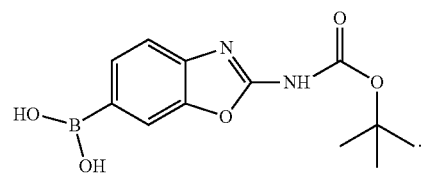

The following Reaction Schemes illustrate the preparation of several compounds of the invention.

Scheme D': Synthesis of 5-(7-(3-(4-isopropylpiperazin-1-yl)azetidin-1-yl)-1,5-naphthyridin-2-yl)benzo[d]oxazol-2-amine

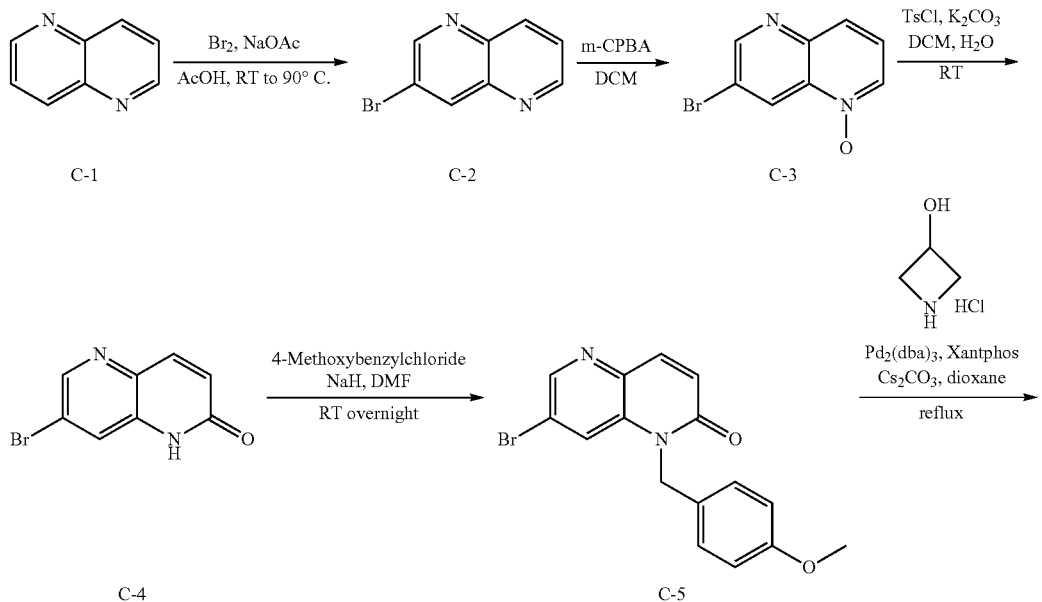

-continued
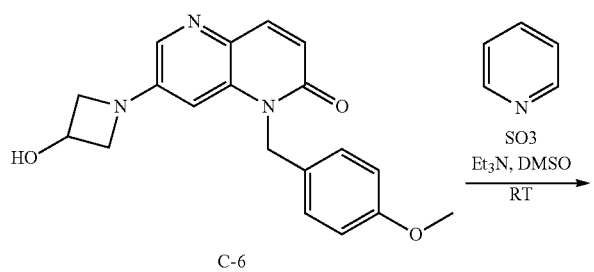
C-6
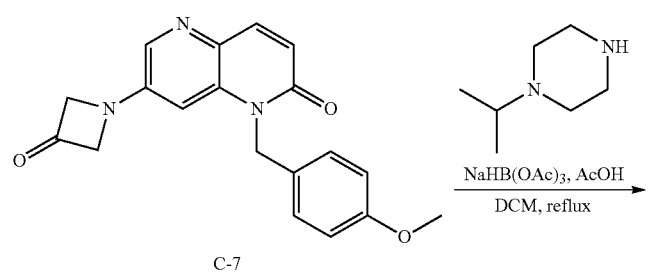
C-7
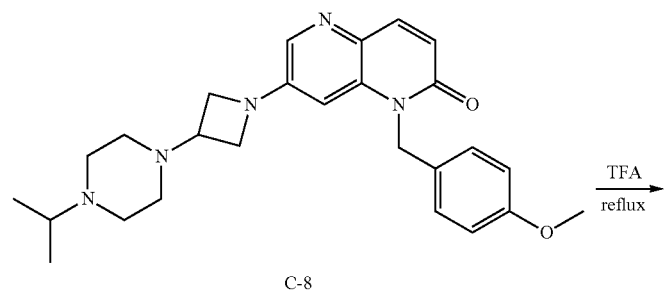
C-8
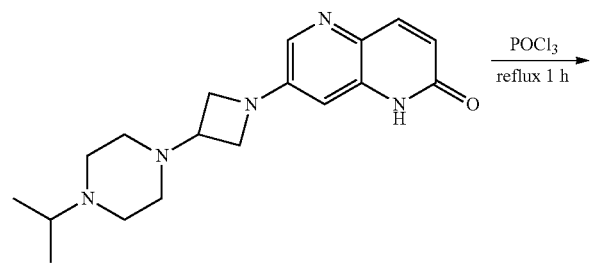
C-9
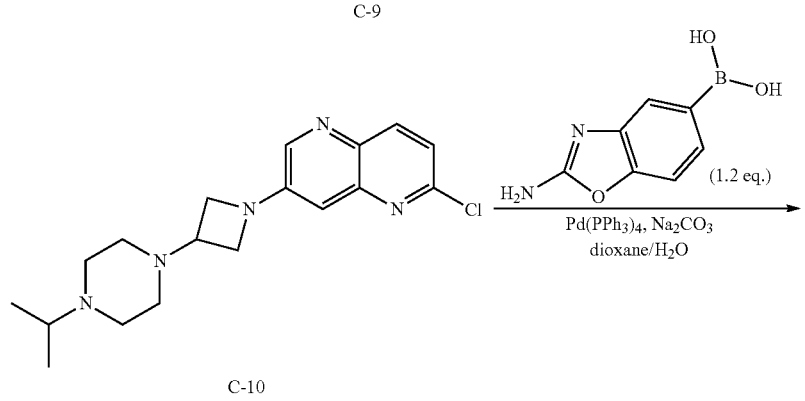
C-10

-continued
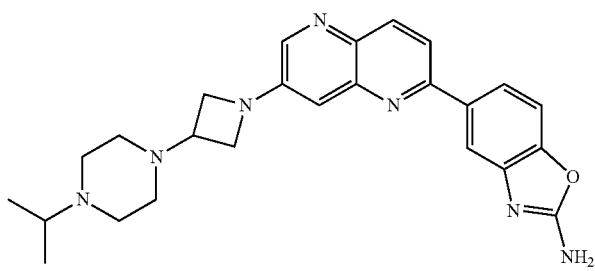
72
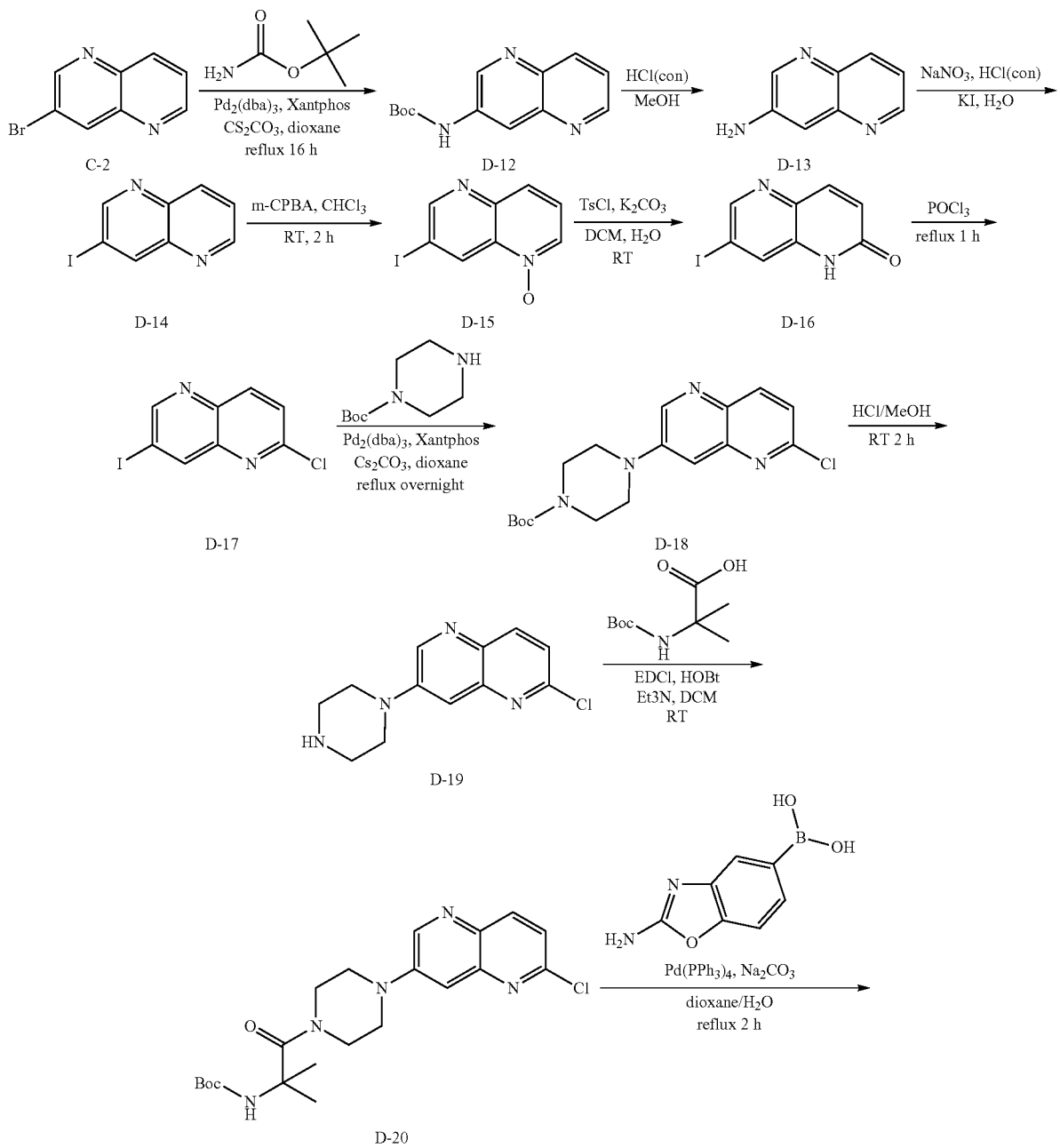
Scheme E′: Synthesis of 2-amino-1-(4-(6-(2-aminobenzo[d]oxazol-5-yl)-1,5-naphthyridin-3-yl)piperazin-1-yl)-2-methylpropan-1-one

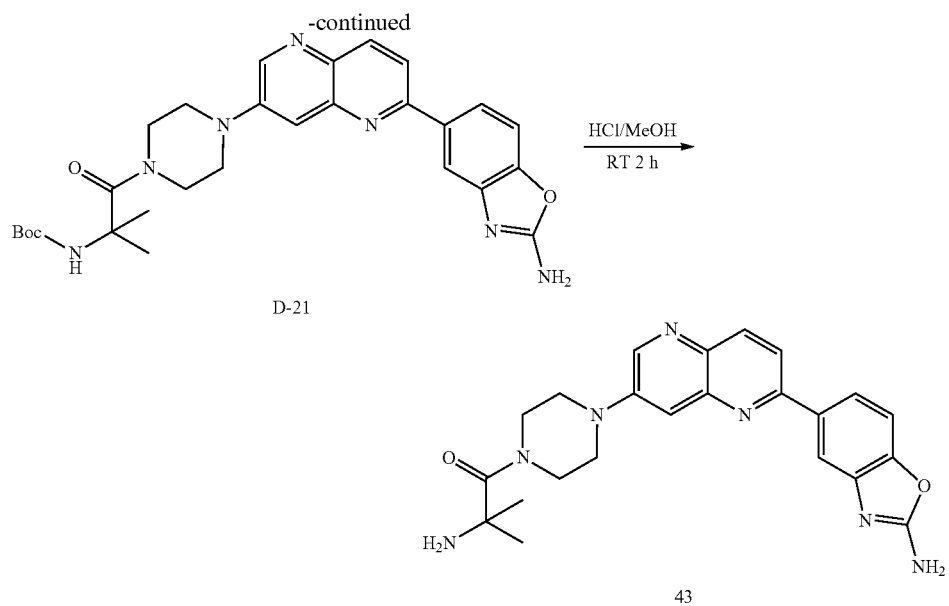
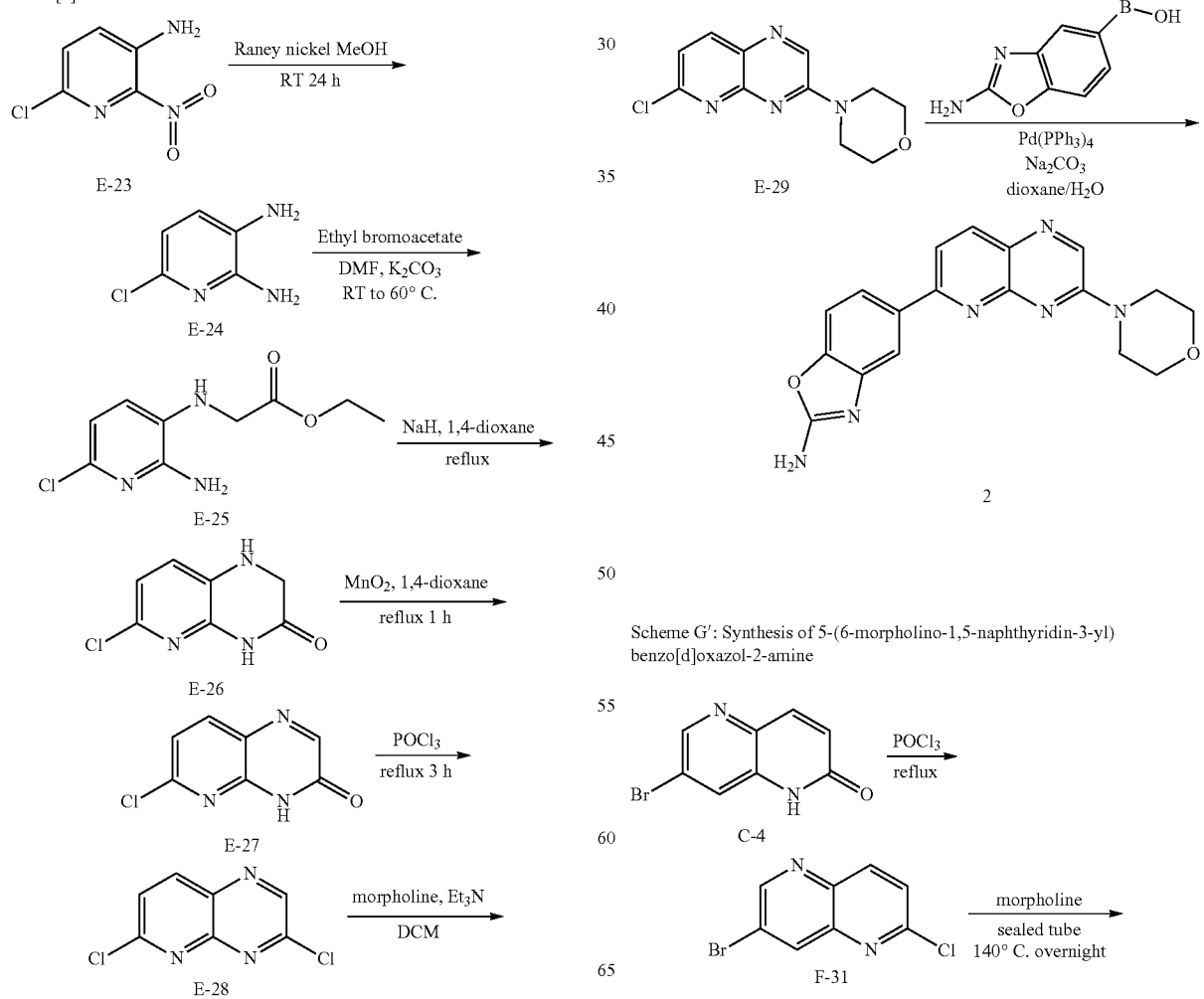
Scheme F': Synthesis of 5-(3-morpholinopyrido[2,3-b]pyrazin-6-yl)benzo[d]oxazol-2-amine
Scheme G': Synthesis of 5-(6-morpholino-1,5-naphthyridin-3-yl)benzo[d]oxazol-2-amine 343
-continued
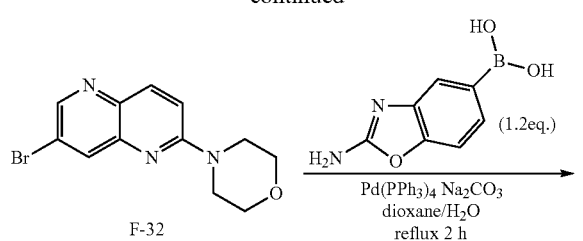
F-32
73
Reaction Scheme H':
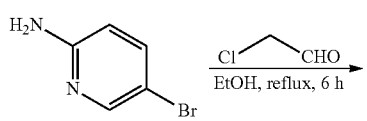
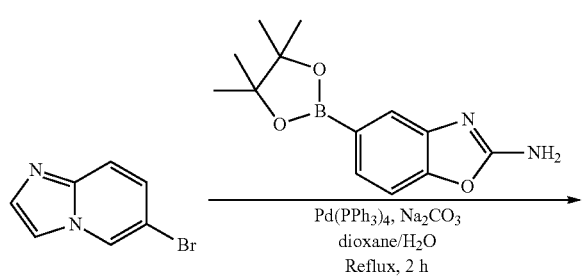
344
-continued
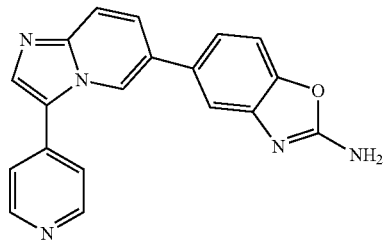
Reaction Scheme I':
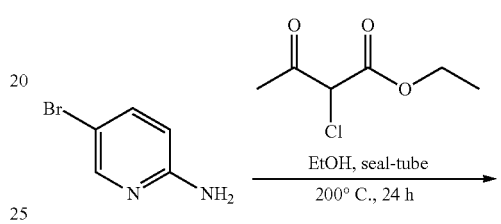
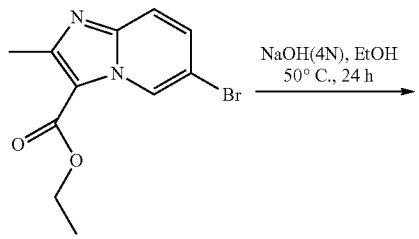
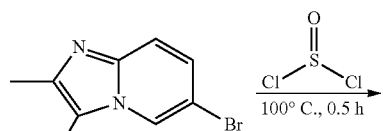
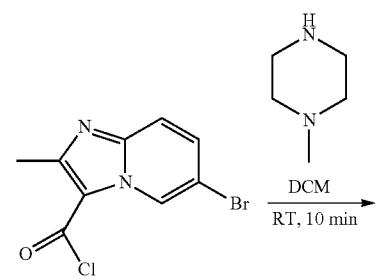
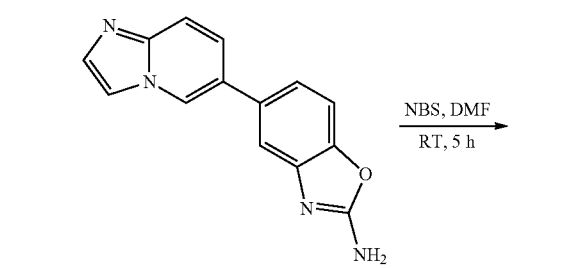
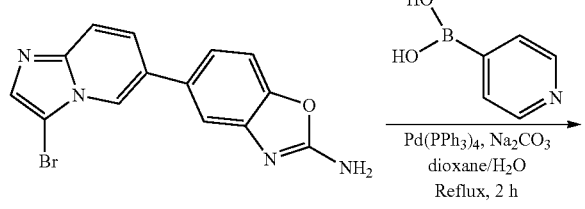
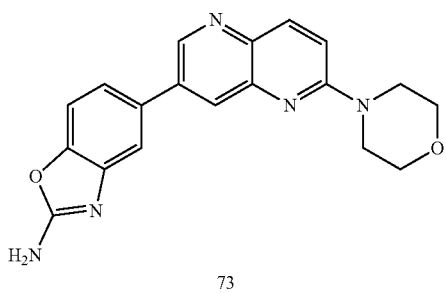
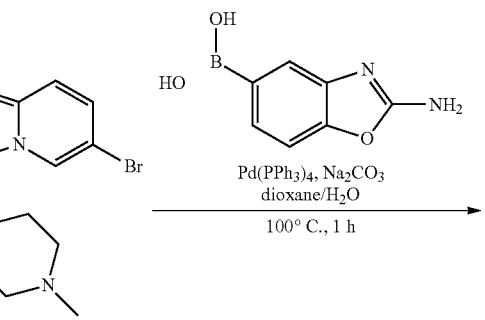

345 -continued
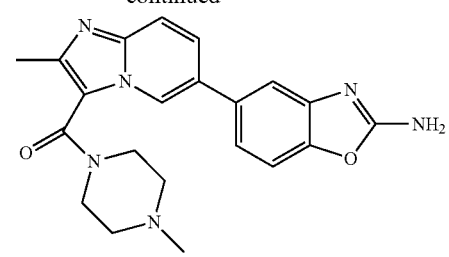
346 -continued
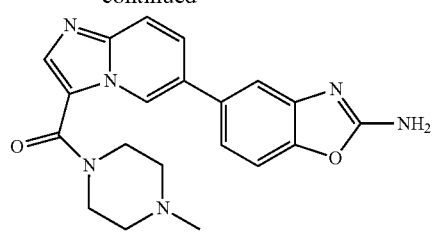
Reaction Scheme J':
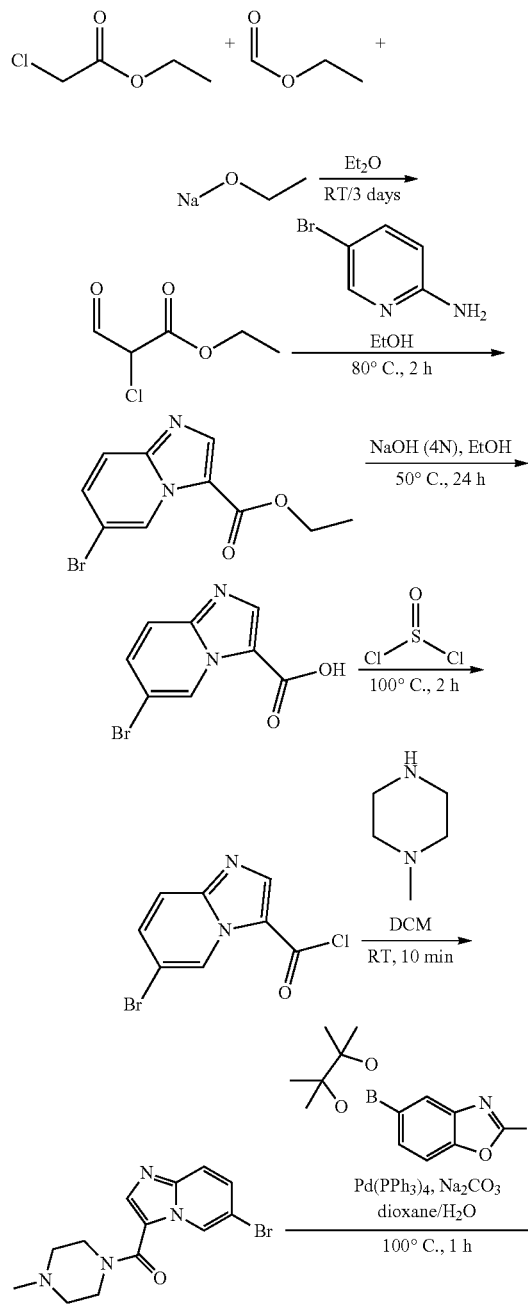
Reaction Scheme K':
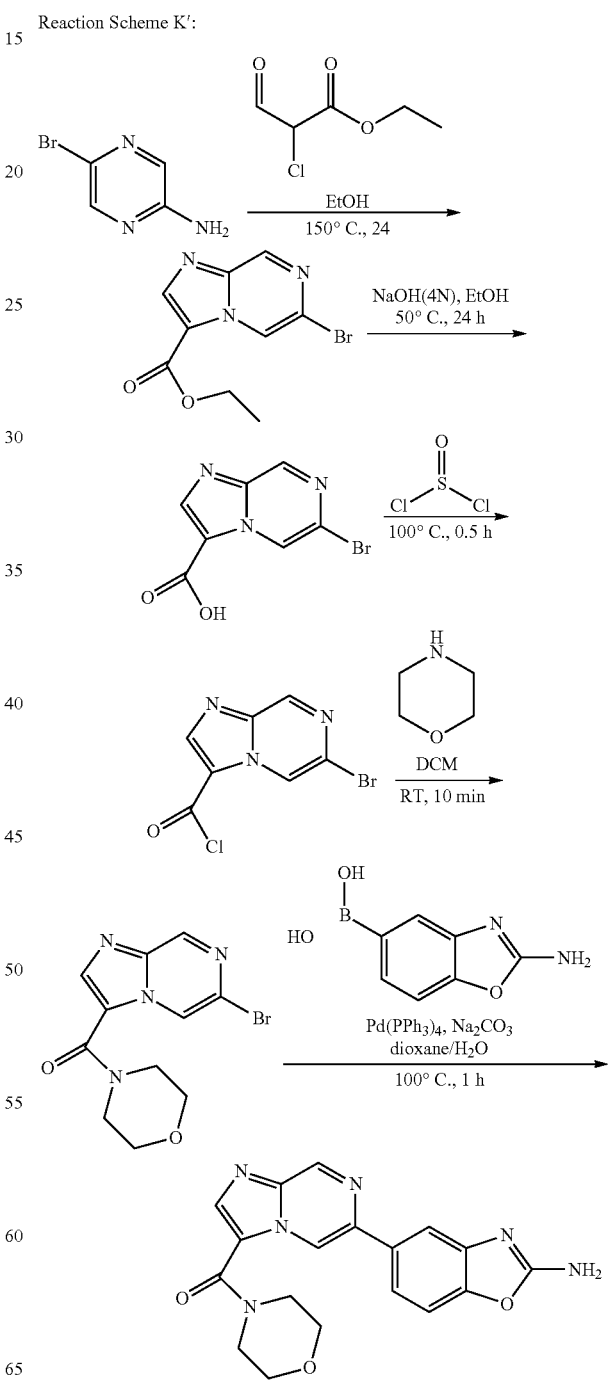

Reaction Scheme L':
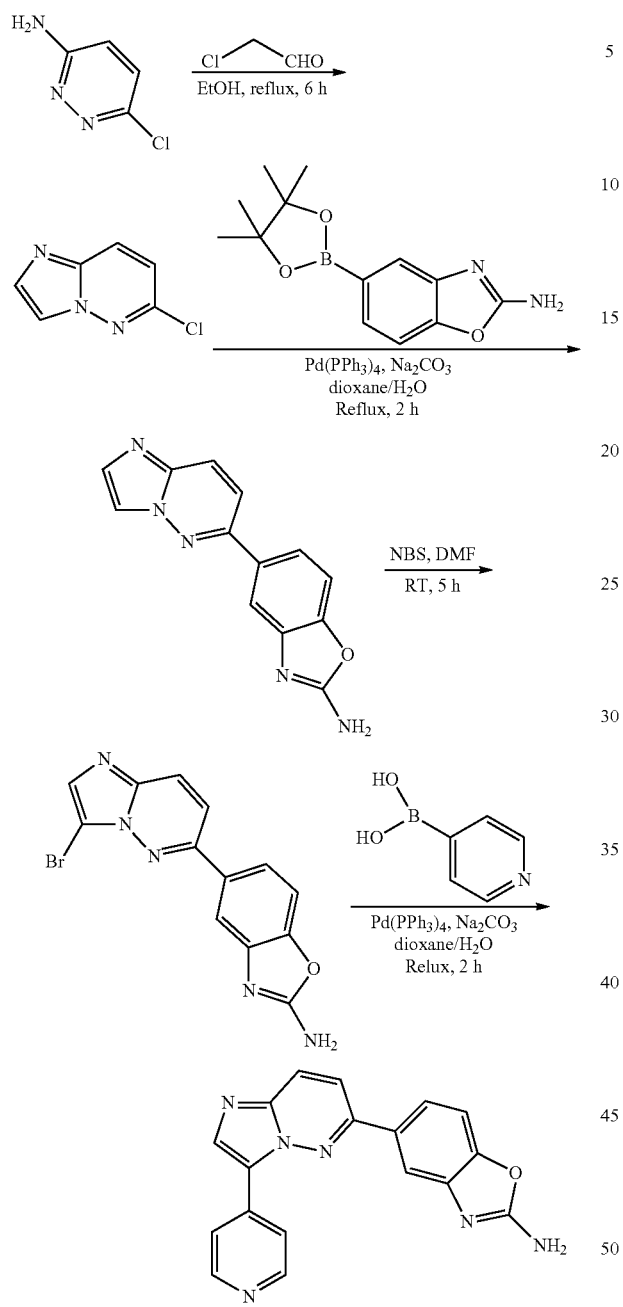
Reaction Scheme M':
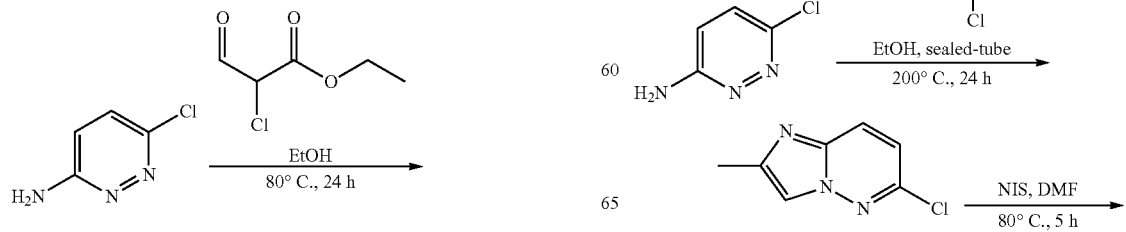
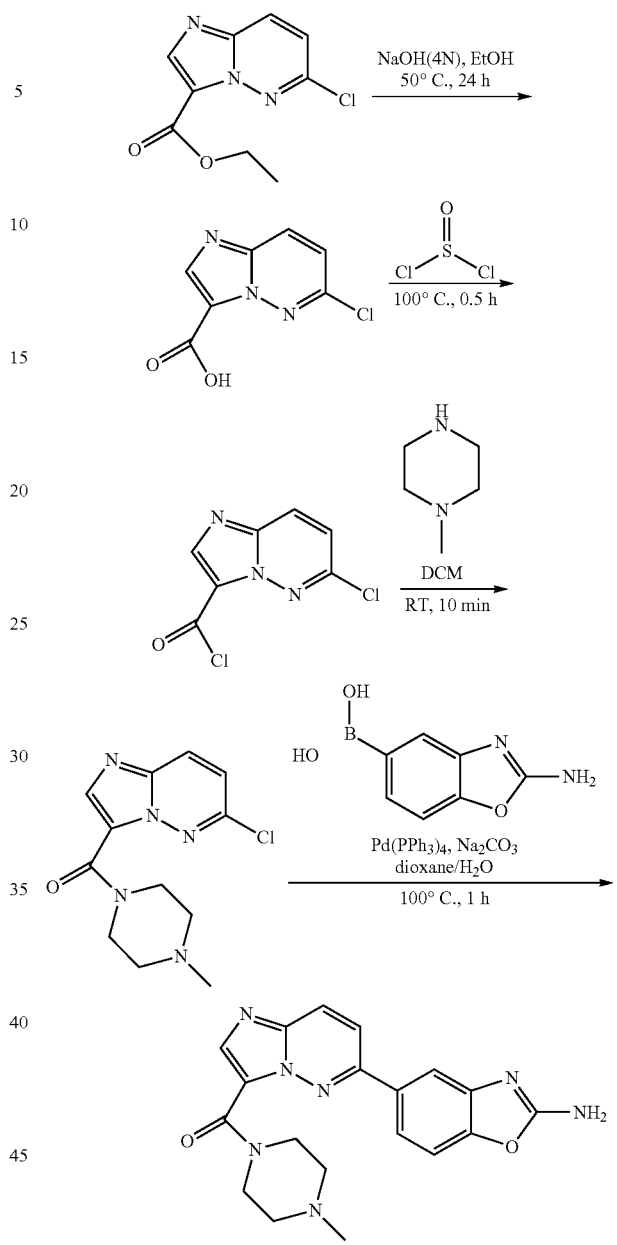
Reaction Scheme N':

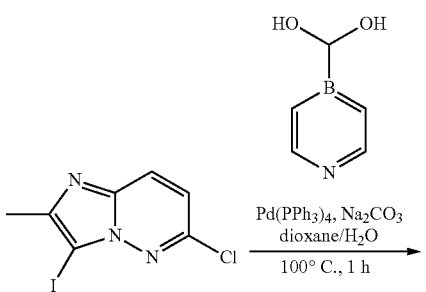
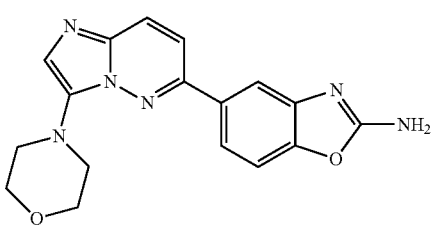
Reaction Scheme P':
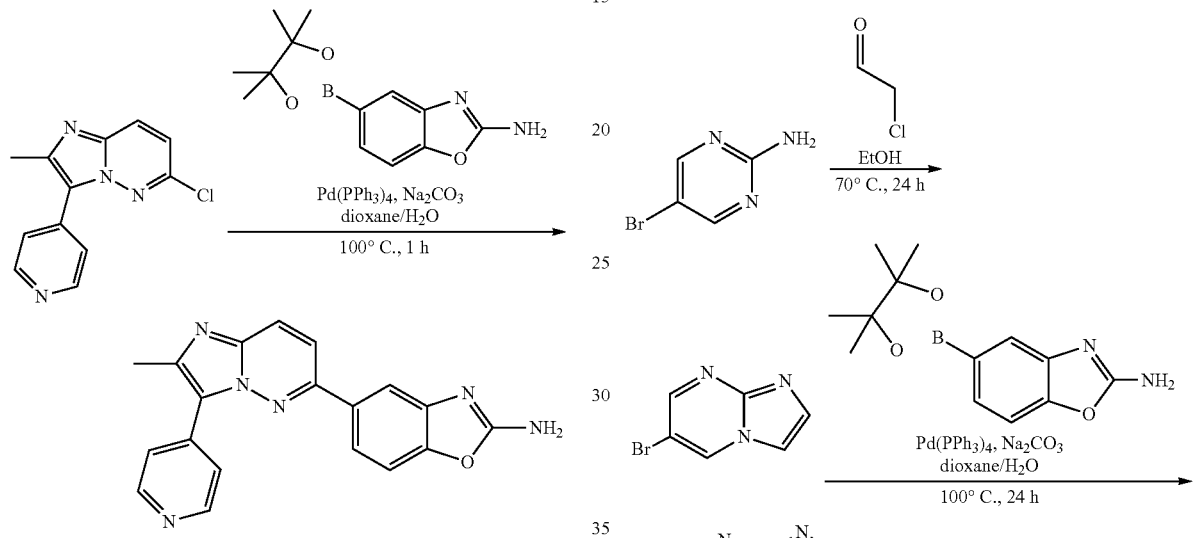
Reaction Scheme O':
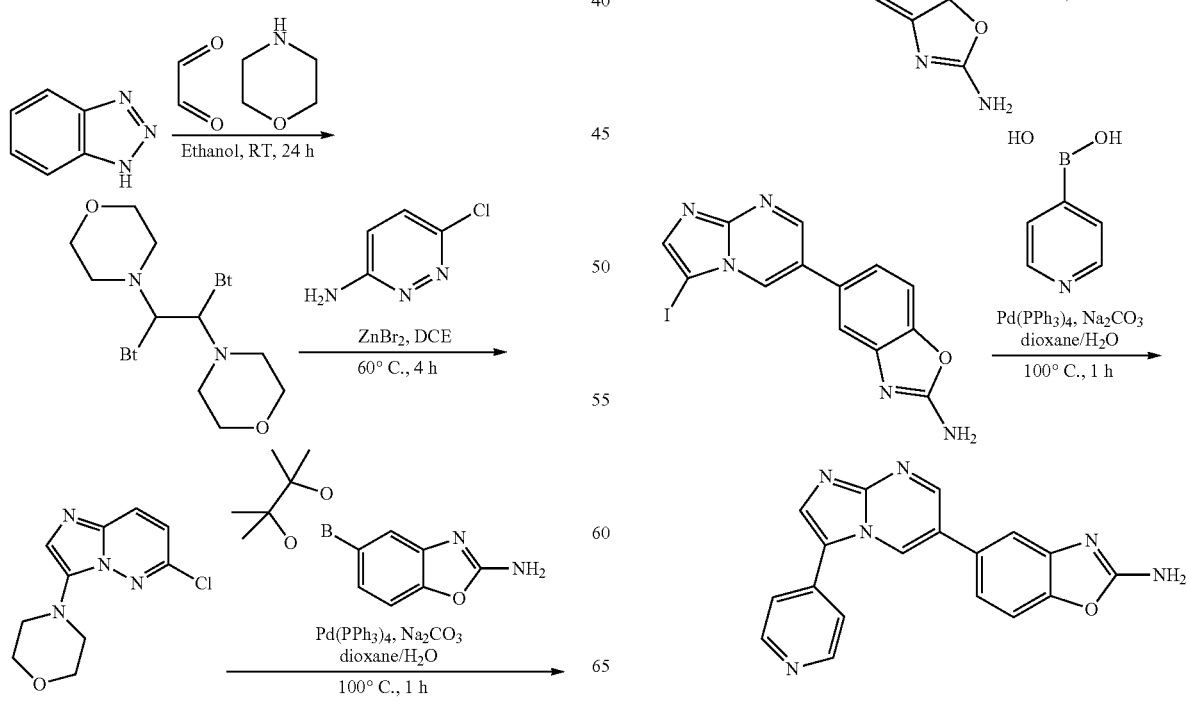

Reaction Scheme Q':
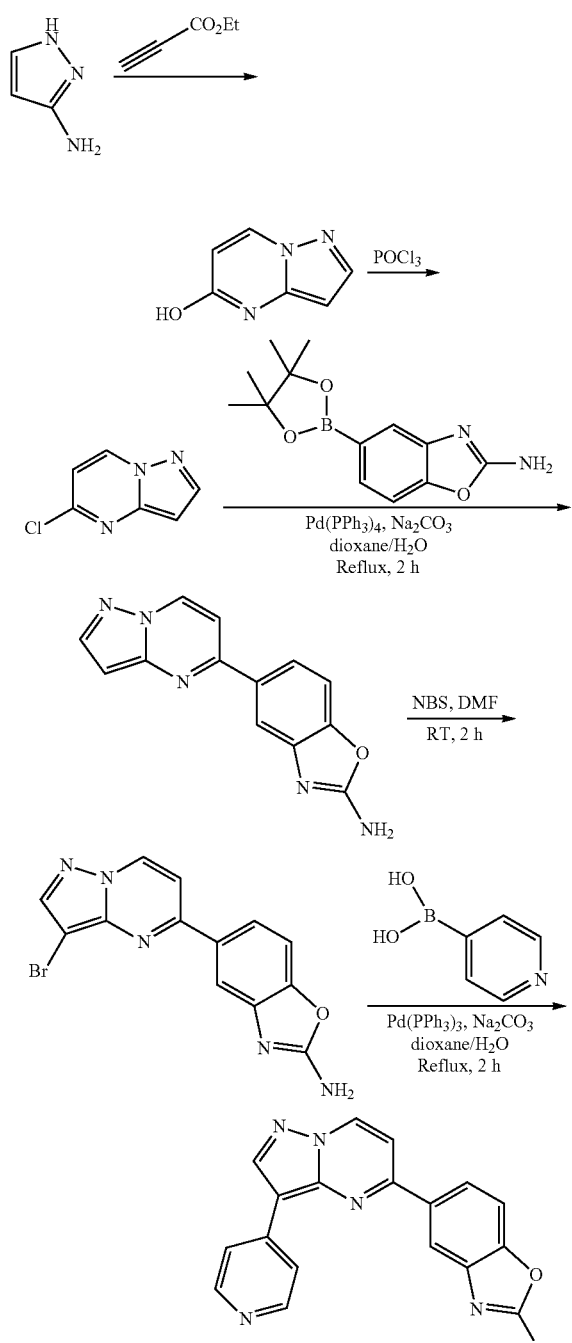
Reaction Scheme R':
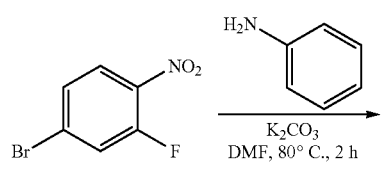
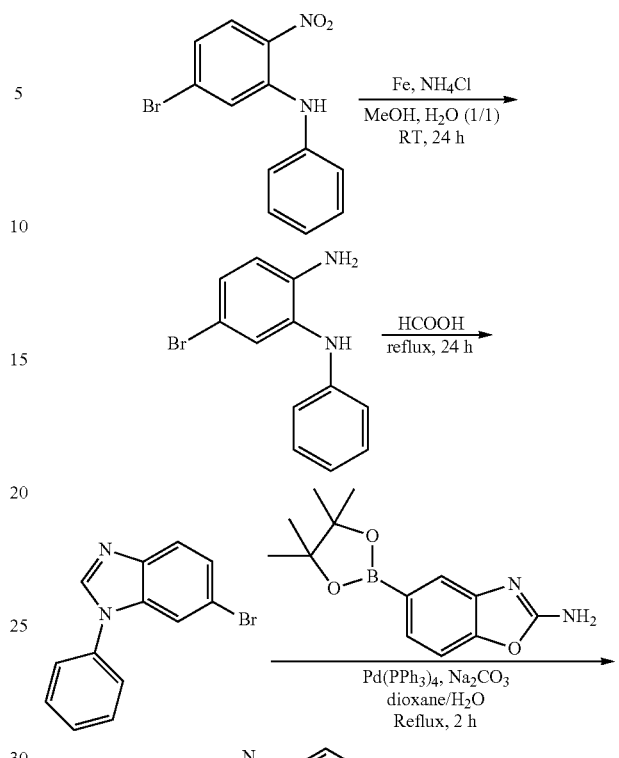
Reaction Scheme S':
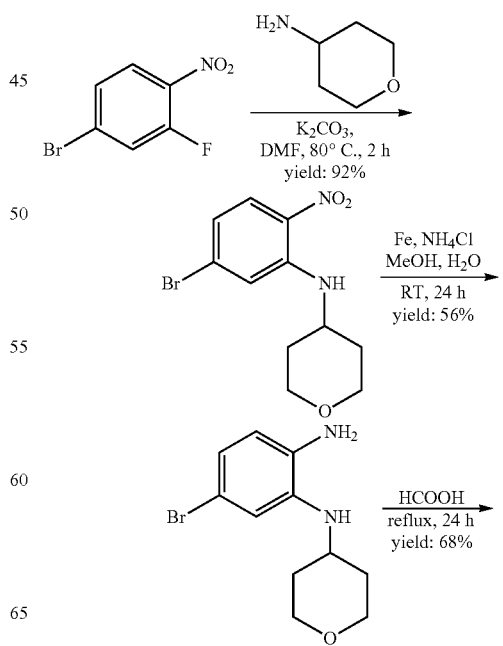

-continued
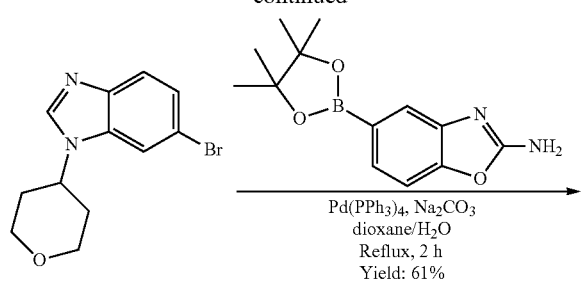
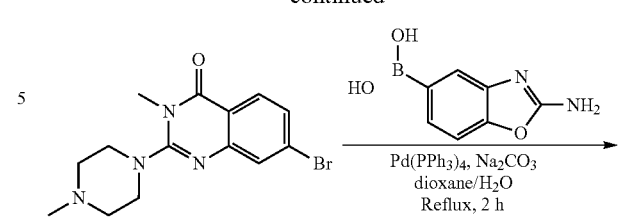
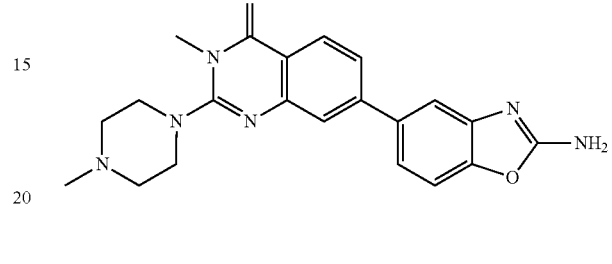
Reaction Scheme T':
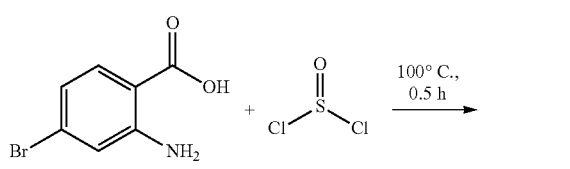
Reaction Scheme U':
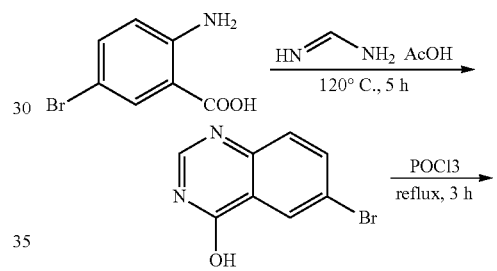
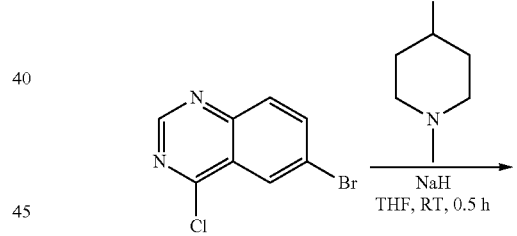
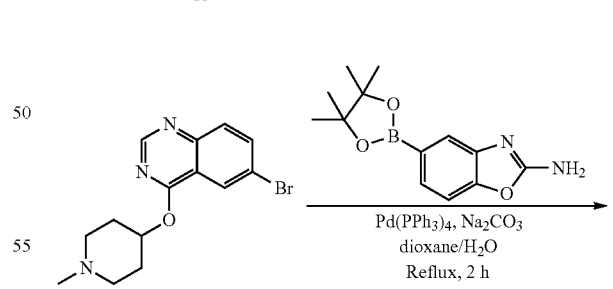
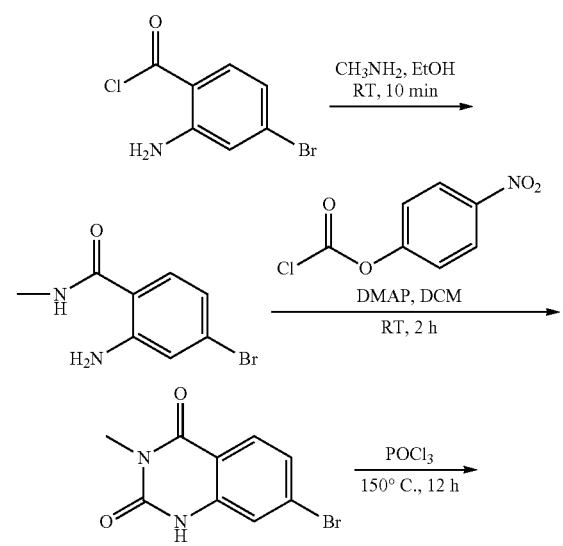
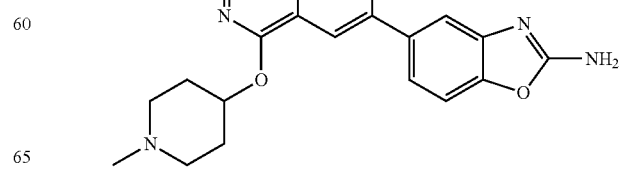
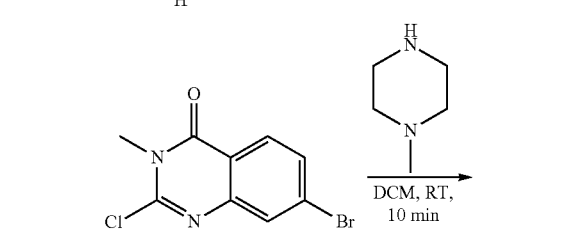

Reaction Scheme V':
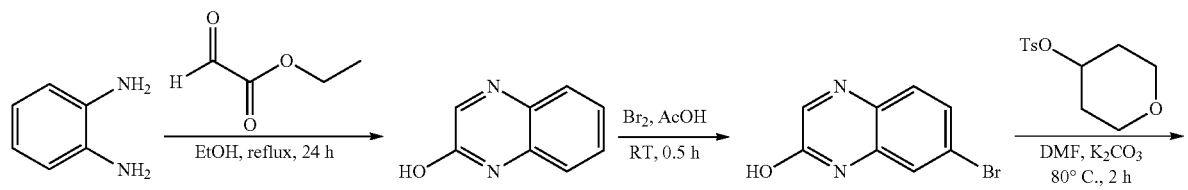
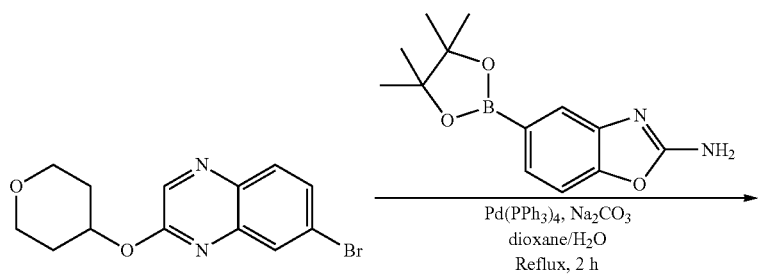
Reaction Scheme W':
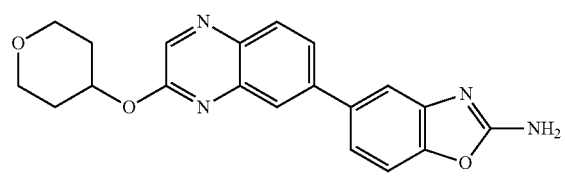
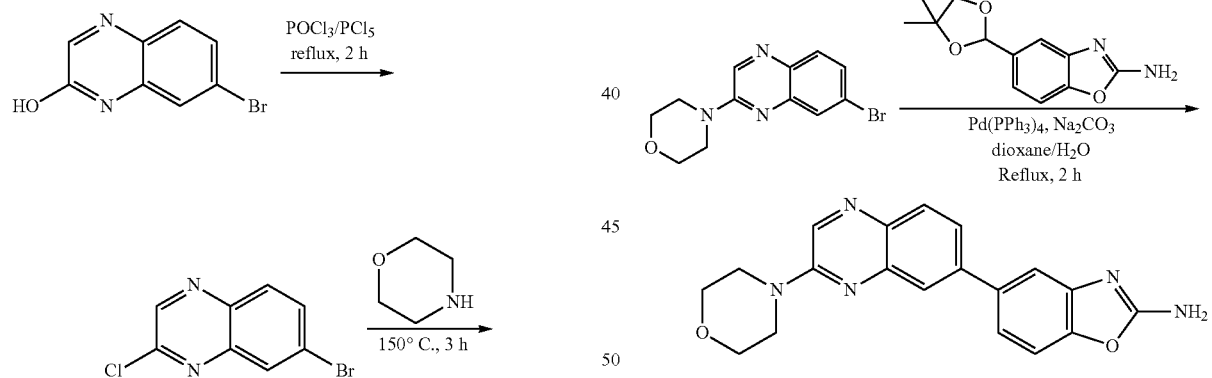
Reaction Scheme X':
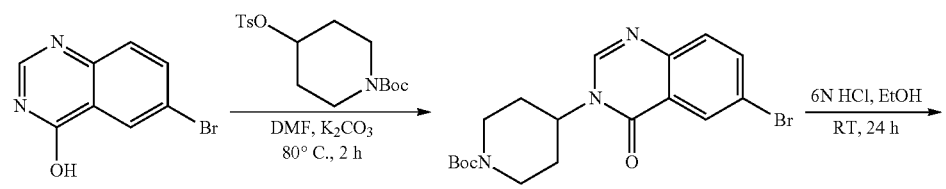

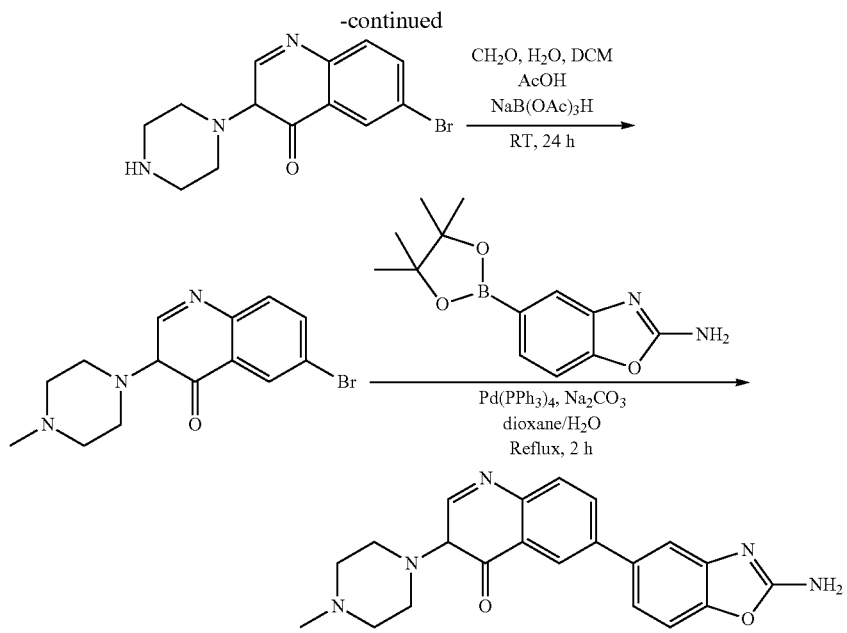
Reaction Scheme Y':
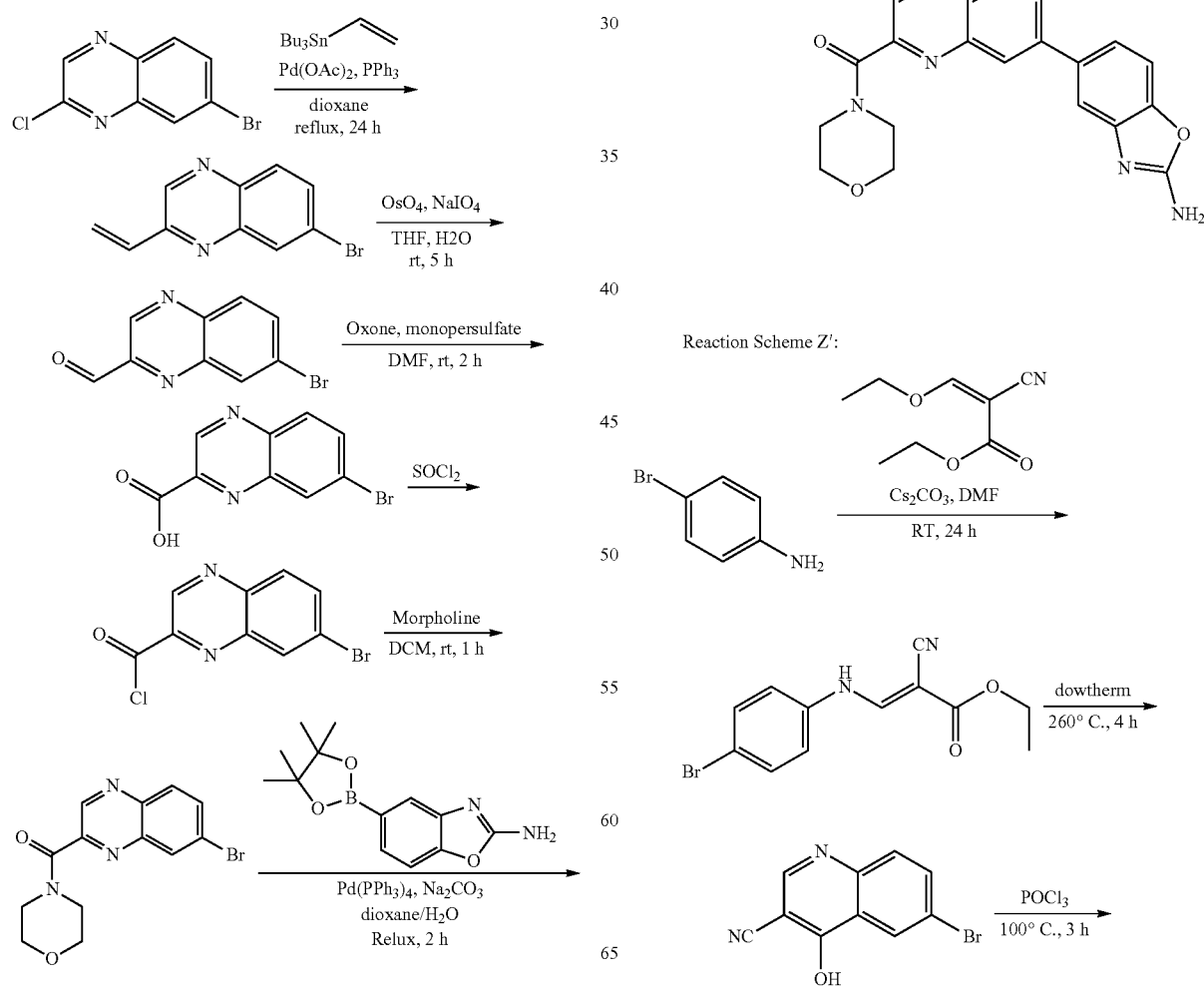
Reaction Scheme Z':

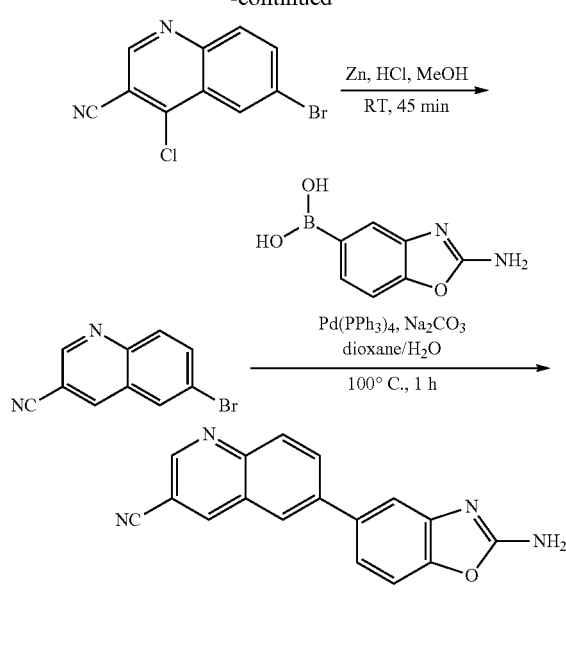
Reaction scheme AA':
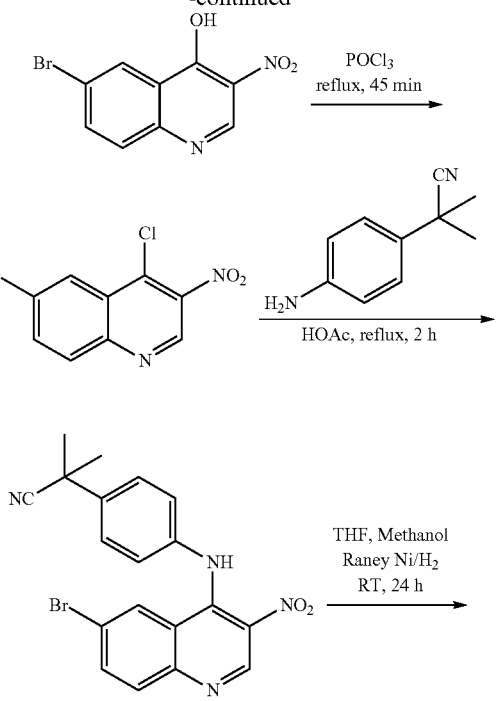
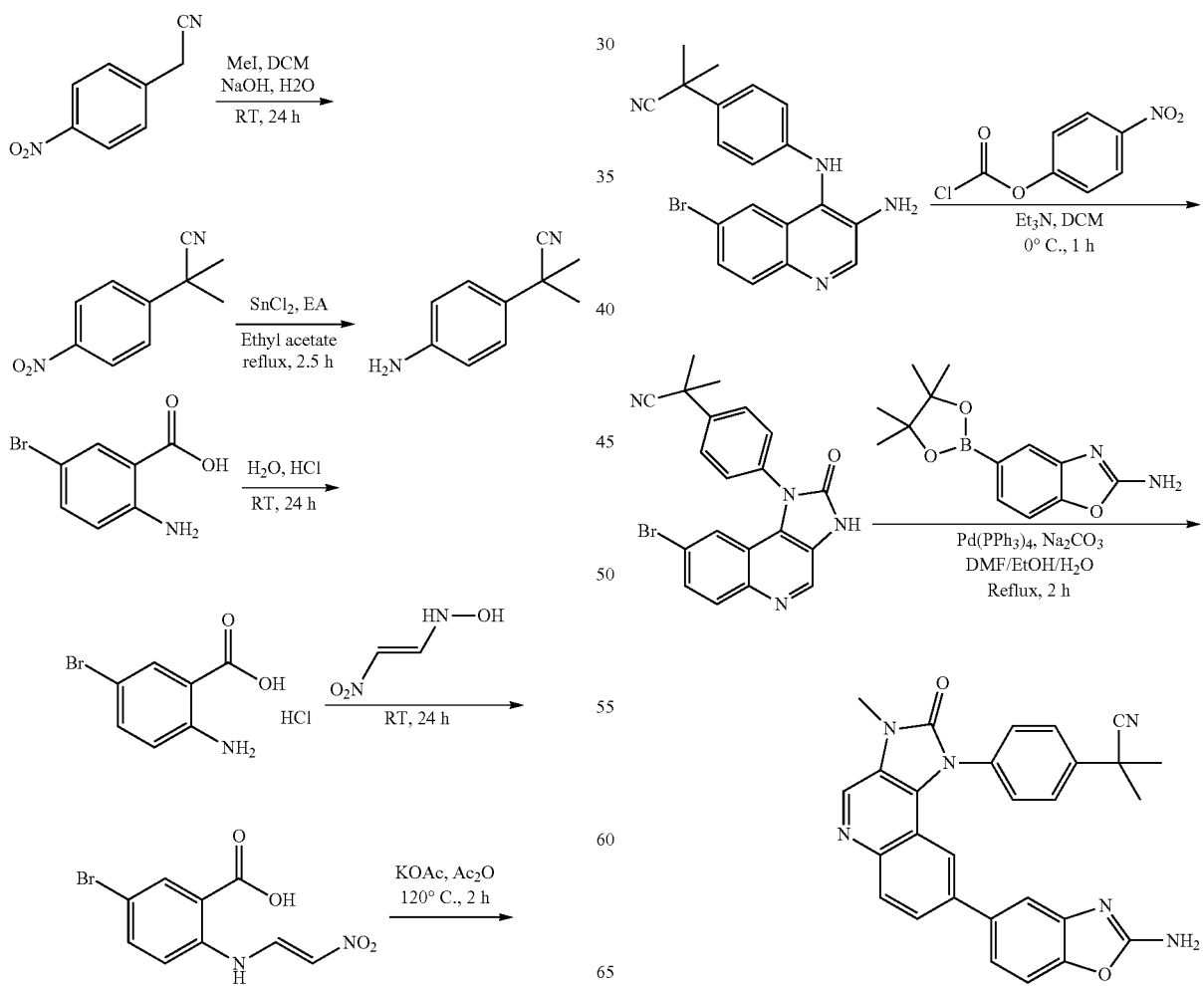

Reaction Scheme AB':
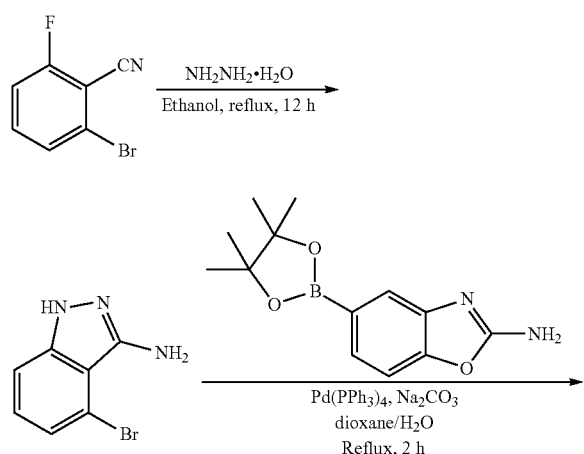
Reaction Scheme AD':
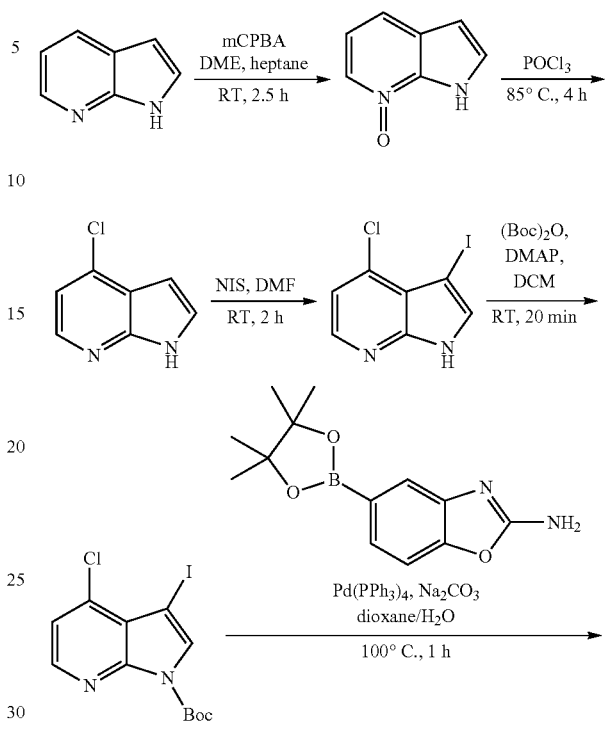
Reaction Scheme AC':
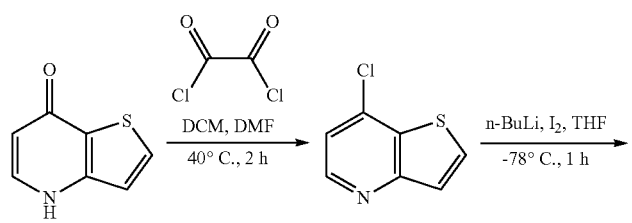
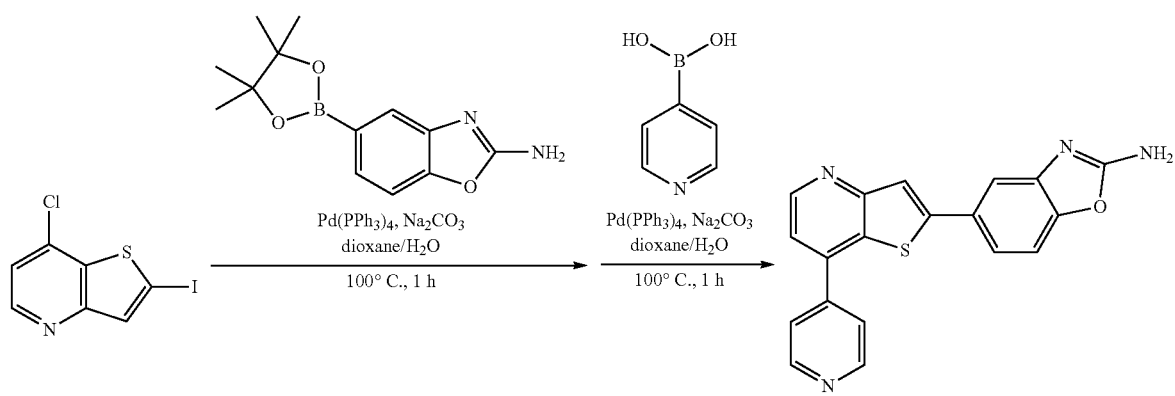

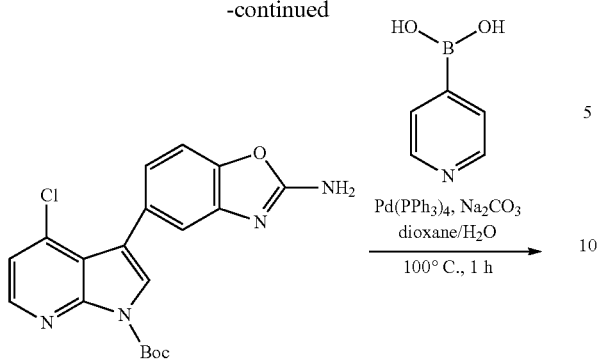
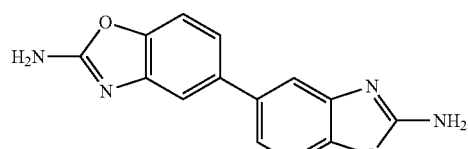
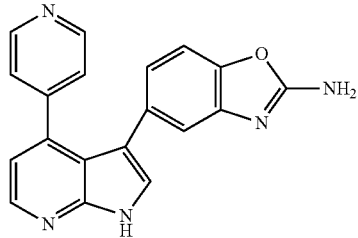
Reaction Scheme AE′:
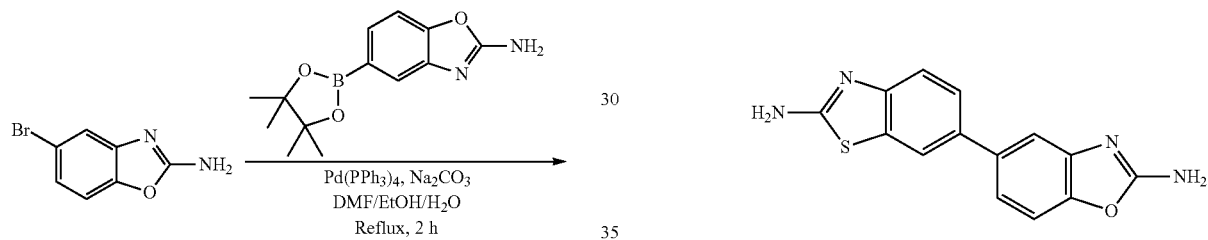
Reaction Scheme AF′:
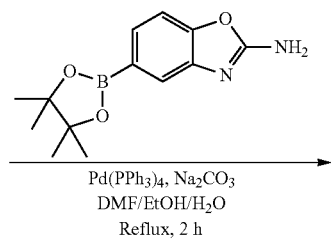
Reaction Scheme AG′:
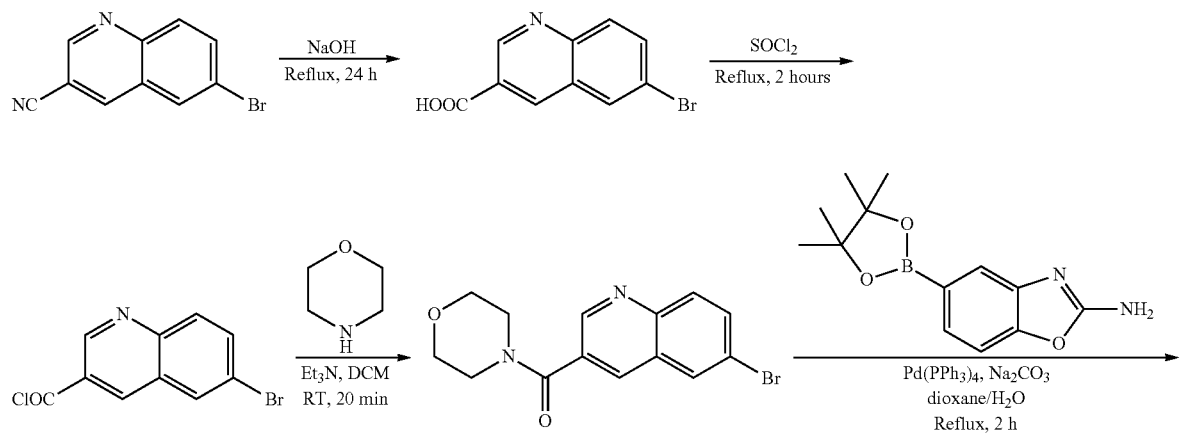
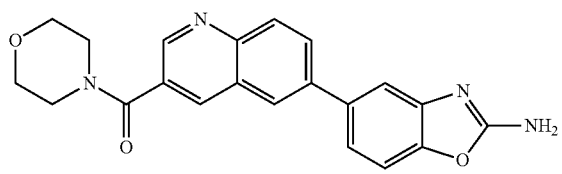

Reaction Scheme AH′:
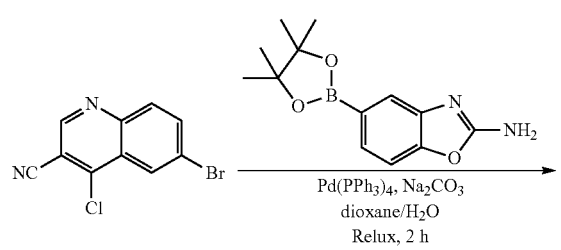
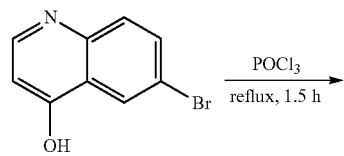
Reaction Scheme AI′:
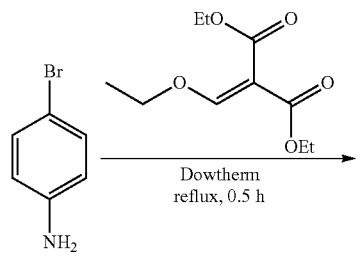
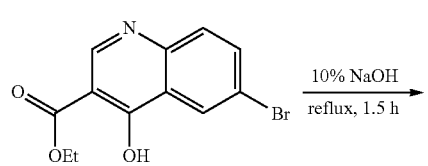
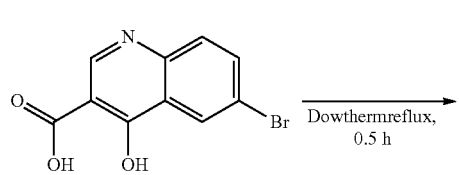
Reaction Scheme AJ′:
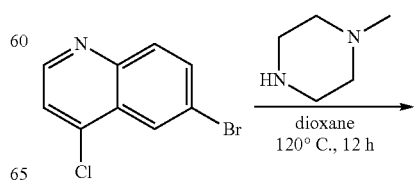

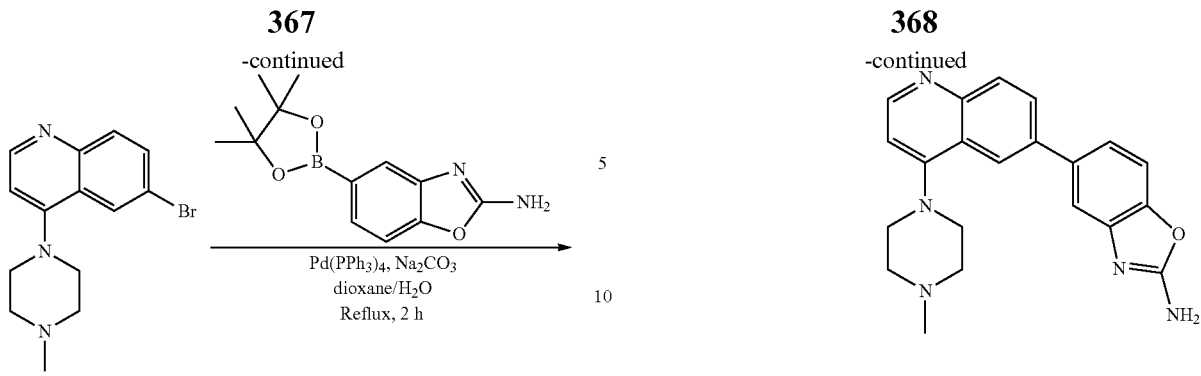

Table 3 shows exemplary PI3Kα inhibitors of the invention.

TABLE 3

In Vitro IC$_{50}$ data for selected compounds of the invention.

| # | Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | PC3 proliferation (nM)* | T47D proliferation (nM) | Mass Characterization |
|---|---|---|---|---|---|---|---|---|---|
| 1 | 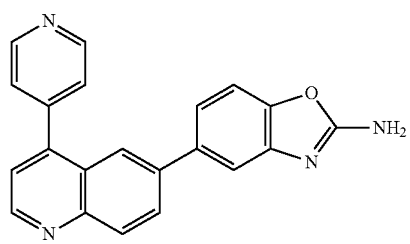 [SMILES: Nc1nc2cc(-c3ccc4nccc(-c5ccncc5)c4c3)ccc2o1] | +++ | ++++ | +++ | ++++ | ++++ | +++ | +++ | Calcd: 388.1 Found: 389.0 [M + H]$^+$ |
| 2 | 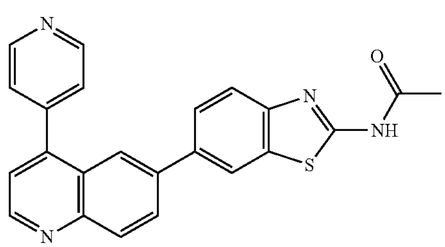 [SMILES: CC(=O)Nc1nc2ccc(-c3ccc4nccc(-c5ccncc5)c4c3)cc2s1] | + | +++ | + | + | +++ | ++ | | Calcd: 396.10 Found: 397.0 [M + H]$^+$ |
| 3 | 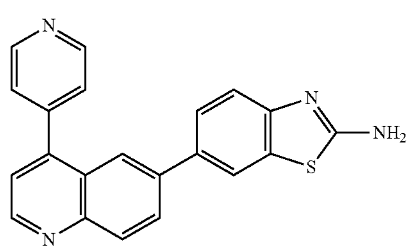 | +++ | ++++ | + | +++ | +++ | | | Calcd: 354.09 Found: 355.0 [M + H]$^+$ |
| 4 | 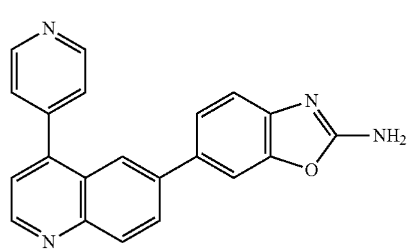 [SMILES: Nc1nc2ccc(-c3ccc4nccc(-c5ccncc5)c4c3)cc2o1] | +++ | ++++ | ++++ | ++++ | ++++ | ++++ | | Calcd: 338.12 Found: 339.0 [M + H]$^+$ |

TABLE 3-continued

In Vitro IC$_{50}$ data for selected compounds of the invention.

| | Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | PC3 proliferation (nM)* | T47D proliferation (nM) | Mass Characterization |
|---|---|---|---|---|---|---|---|---|---|
| 5 | 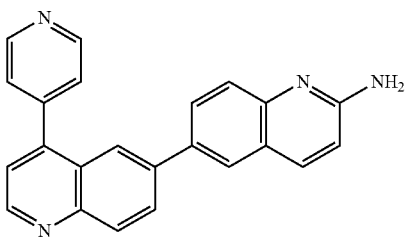 [SMILES: Nc1ccc2cc(-c3ccc4nccc(-c5ccncc5)c4c3)ccc2n1] | +++ | +++ | + | ++ | +++ | | | Calcd: 348.14 Found: 349.0 [M + H]$^+$ |
| 6 | 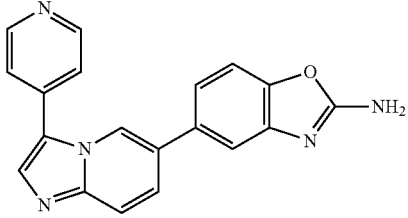 [SMILES: Nc1nc2cc(-c3ccc4ncc(-c5ccncc5)n4c3)ccc2o1] | ++ | ++++ | ++ | +++ | ++++ | ++ | +++ | Calcd: 327.11 Found: 328.0 [M + H]$^+$ |
| 7 | 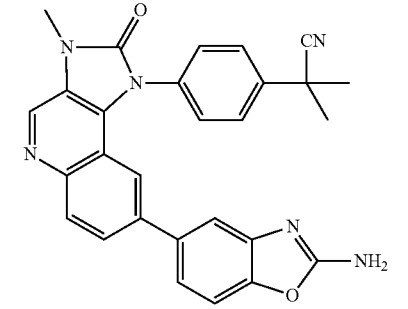 [SMILES: Cn1c(=O)n(-c2ccc(C(C)(C)C#N)cc2)c2c3cc(-c4ccc5oc(N)nc5c4)ccc3ncc21] | ++++ | ++++ | ++++ | ++++ | ++++ | ++++ | | Calcd: 474.18 Found: 475.0 M + H]$^+$ |
| 8 | 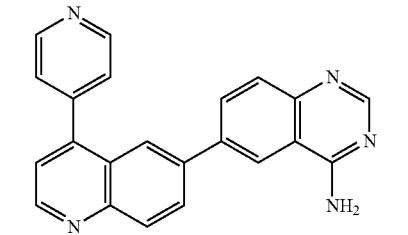 [SMILES: Nc1ncnc2ccc(-c3ccc4nccc(-c5ccncc5)c4c3)cc12] | + | ++ | + | | +++ | | | Calcd: 349.13 Found: 350.0 [M + H]$^+$ |
| 9 | 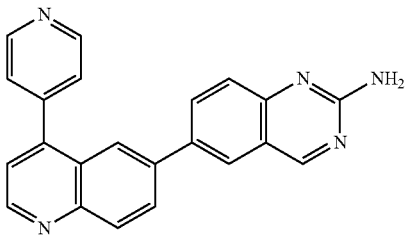 [SMILES: Nc1ncc2cc(-c3ccc4nccc(-c5ccncc5)c4c3)ccc2n1] | + | +++ | ++ | | +++ | | | Calcd: 349.13 Found: 350.0 [M + H]$^+$ |

TABLE 3-continued

In Vitro IC$_{50}$ data for selected compounds of the invention.

| | Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | PC3 proliferation (nM)* | T47D proliferation (nM) | Mass Characterization |
|---|---|---|---|---|---|---|---|---|---|
| 10 | 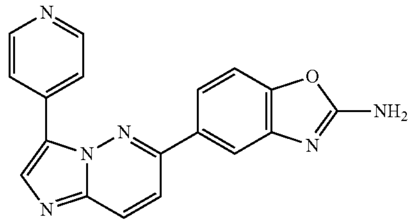 [SMILES: Nc1nc2cc(-c3ccc4ncc(-c5ccncc5)n4n3)ccc2o1] | +++ | ++++ | +++ | | ++++ | +++ | +++ | Calcd: 328.11 Found: 329.0 [M + H]$^+$ |
| 11 | 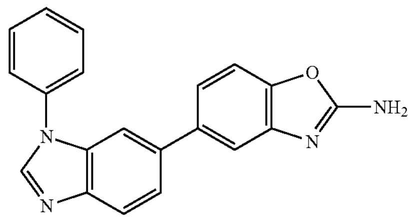 [SMILES: Nc1nc2cc(-c3ccc4ncn(-c5ccccc5)c4c3)ccc2o1] | + | ++++ | ++ | | +++ | + | | Calcd: 326.12 Found: 327.0 [M + H]$^+$ |
| 12 | 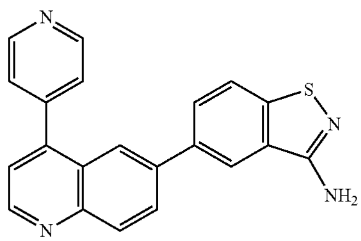 [SMILES: Nc1nsc2ccc(-c3ccc4nccc(-c5ccncc5)c4c3)cc12] | | + | + | + | + | | | Calcd: 354.09 Found: 355.0 [M + H]$^+$ |
| 13 | 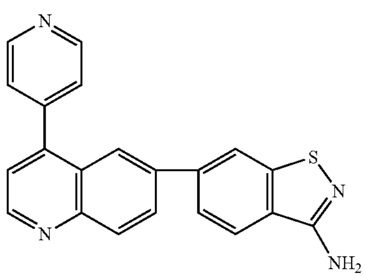 [SMILES: Nc1nsc2cc(-c3ccc4nccc(-c5ccncc5)c4c3)ccc12] | | ++++ | +++ | +++ | +++ | | | Calcd: 354.09 Found: 355.0 [M + H]$^+$ |
| 14 | 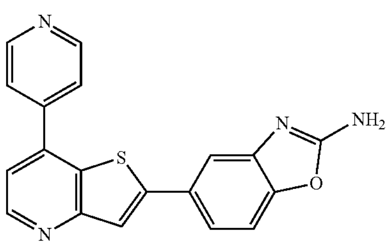 [SMILES: Nc1nc2cc(-c3cc4nccc(-c5ccncc5)c4s3)ccc2o1] | | ++ | + | + | ++ | | | Calcd: 344.09 Found: 345.0 [M + H]$^+$ |
| 15 | 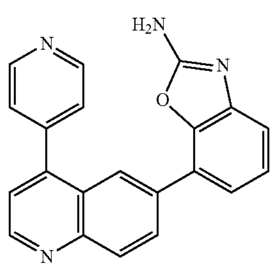 [SMILES: Nc1nc2cccc(-c3ccc4nccc(-c5ccncc5)c4c3)c2o1] | ++++ | ++++ | ++++ | +++ | +++ | | | Calcd: 338.12 Found: 339.0 [M + H]$^+$ |

TABLE 3-continued

In Vitro IC$_{50}$ data for selected compounds of the invention.

| | Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | PC3 proliferation (nM)* | T47D proliferation (nM) | Mass Characterization |
|---|---|---|---|---|---|---|---|---|---|
| 16 | 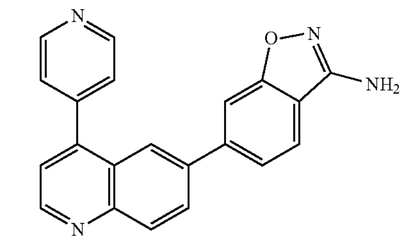 [SMILES: Nc1noc2cc(-c3ccc4nccc(-c5ccncc5)c4c3)ccc12] | | ++++ | ++ | ++ | +++ | | +++ | Calcd: 338.12 Found: 339.0 [M + H]$^+$ |
| 17 | 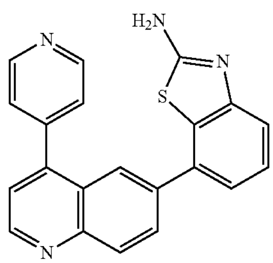 | | ++++ | +++ | +++ | ++++ | | | Calcd: 354.09 Found: 355.0 [M + H]$^+$ |
| 18 | 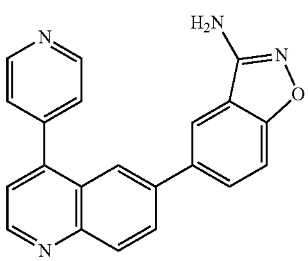 [SMILES: Nc1noc2ccc(-c3ccc4nccc(-c5ccncc5)c4c3)cc12] | | ++ | + | + | ++ | | | Calcd: 338.12 Found: 339.0 [M + H]$^+$ |
| 19 | 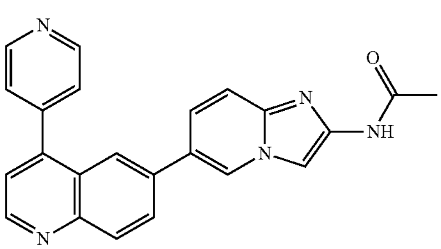 [SMILES: CC(=O)Nc1cn2cc(-c3ccc4nccc(-c5ccncc5)c4c3)ccc2n1] | | + | + | + | + | | | Calcd: 379.14 Found: 380.0 [M + H]$^+$ |
| 20 | 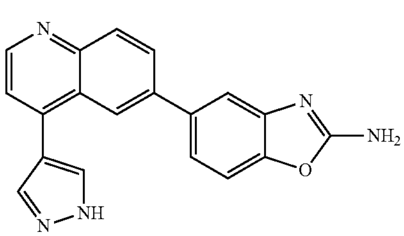 [SMILES: Nc1nc2cc(-c3ccc4nccc(-c5cn[nH]c5)c4c3)ccc2o1] | | ++++ | ++++ | ++++ | | | | Calcd: 327.11 Found: 328.0 [M + H]$^+$ |

TABLE 3-continued

In Vitro IC$_{50}$ data for selected compounds of the invention.

| | Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | PC3 proliferation (nM)* | T47D proliferation (nM) | Mass Characterization |
|---|---|---|---|---|---|---|---|---|---|
| 21 | 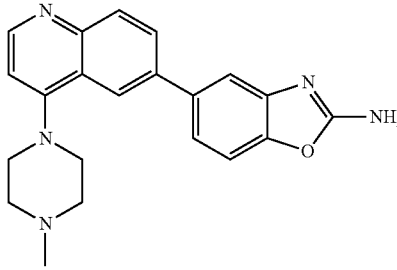 [SMILES: CN1CCN(c2ccnc3ccc(-c4ccc5oc(N)nc5c4)cc23)CC1] | | +++ | ++ | ++ | ++ | | | Calcd: 359.17 Found: 360.0 [M + H]$^+$ |
| 22 | 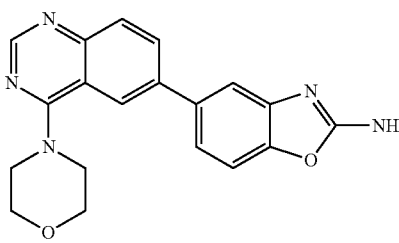 | +++ | ++++ | ++++ | ++++ | ++++ | | | Calcd: 347.14 Found: 348.0 [M + H]$^+$ |
| 23 | 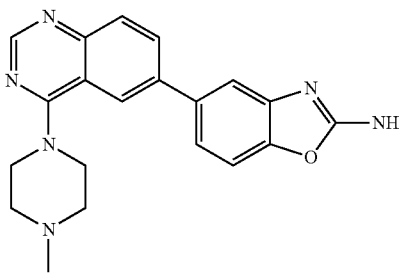 | | ++++ | +++ | ++ | ++++ | | | Calcd: 360.17 Found: 361.0 [M + H]$^+$ |
| 24 | 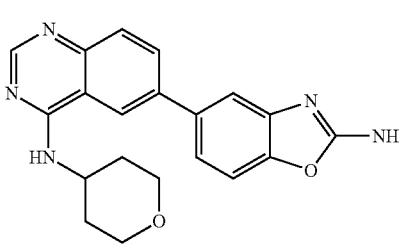 | | ++++ | +++ | ++++ | ++++ | | | Calcd: 361.15 Found: 362.0 [M + H]$^+$ |
| 25 | 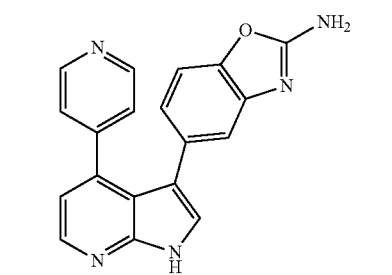 [SMILES: Nc1nc2cc(-c3c[nH]c4nccc(-c5ccncc5)c34)ccc2o1] | | ++ | + | + | ++ | | | |

TABLE 3-continued

In Vitro IC$_{50}$ data for selected compounds of the invention.

| | Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | PC3 proliferation (nM)* | T47D proliferation (nM) | Mass Characterization |
|---|---|---|---|---|---|---|---|---|---|
| 26 | 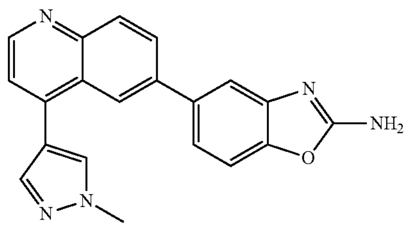 [SMILES: Cn1cc(-c2ccnc3ccc(-c4ccc5oc(N)nc5c4)cc23)cn1] | +++ | ++++ | | ++++ | ++++ | | | Calcd: 341.13 Found: 342.2 [M + H]$^+$ |
| 27 | 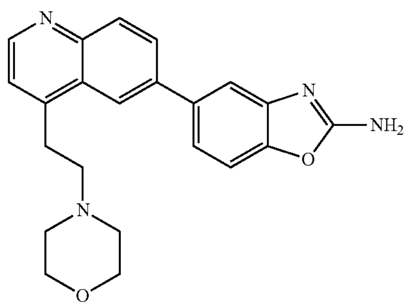 [SMILES: Nc1nc2cc(-c3ccc4nccc(CCN5CCOCC5)c4c3)ccc2o1] | | | +++ | ++ | ++++ | | | Calcd: 374.17 Found: 375.2 [M + H]$^+$ |
| 28 | 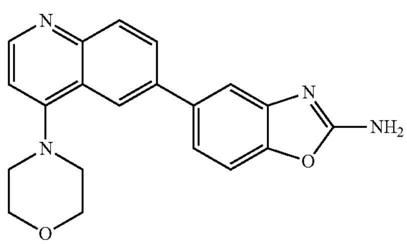 [SMILES: Nc1nc2cc(-c3ccc4nccc(N5CCOCC5)c4c3)ccc2o1] | | | ++++ | +++ | ++++ | | | Calcd: 346.14 Found: 347.2 [M + H]$^+$ |
| 29 | 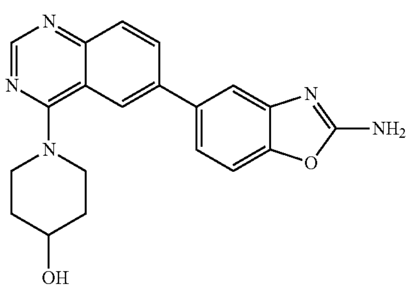 [SMILES: Nc1nc2cc(-c3ccc4ncnc(N5CCC(O)CC5)c4c3)ccc2o1] | | | ++++ | ++++ | ++++ | | | Calcd: 361.15 Found: 362.0 [M + H]$^+$ |
| 30 | 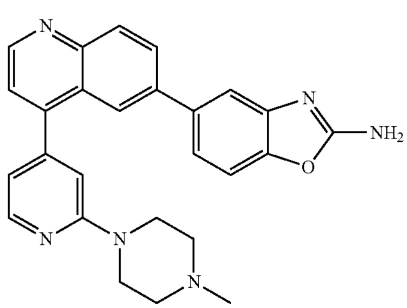 [SMILES: CN1CCN(c2cc(-c3ccnc4ccc(-c5ccc6oc(N)nc6c5)cc34)ccn2)CC1] | | | ++++ | ++++ | ++++ | | | Calcd: 436.20 Found: 437.2 [M + H]$^+$ |

TABLE 3-continued

In Vitro IC$_{50}$ data for selected compounds of the invention.

| | Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | PC3 proliferation (nM)* | T47D proliferation (nM) | Mass Characterization |
|---|---|---|---|---|---|---|---|---|---|
| 31 | 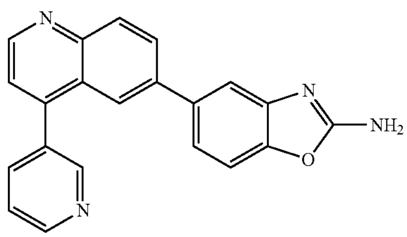 [SMILES: Nc1nc2cc(-c3ccc4nccc(-c5cccnc5)c4c3)ccc2o1] | | ++++ | | ++++ | ++++ | | | Calcd: 338.12 Found: 339.2 [M + H]$^+$ |
| 32 | 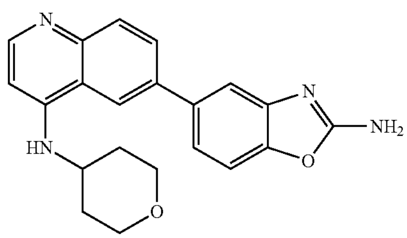 [SMILES: Nc1nc2cc(-c3ccc4nccc(NC5CCOCC5)c4c3)ccc2o1] | | ++ | | + | ++ | | | Calcd: 360.16 Found: 361.2 [M + H]$^+$ |
| 33 | 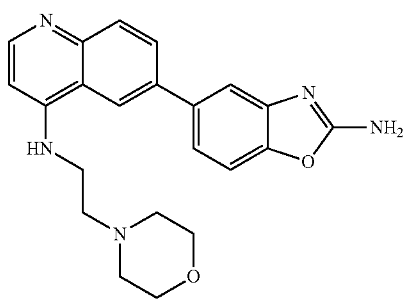 [SMILES: Nc1nc2cc(-c3ccc4nccc(NCCN5CCOCC5)c4c3)ccc2o1] | | ++++ | | +++ | +++ | | | Calcd: 389.19 Found: 390.2 [M + H]$^+$ |
| 34 | 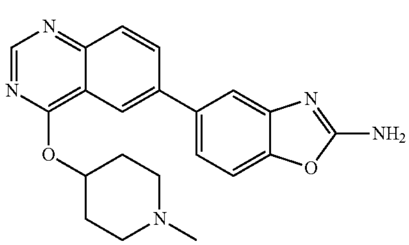 [SMILES: CN1CCC(Oc2ncnc3ccc(-c4ccc5oc(N)nc5c4)cc23)CC1] | | ++++ | | +++ | ++++ | | | Calcd: 375.7 Found: 376.0 [M + H]$^+$ |
| 35 | 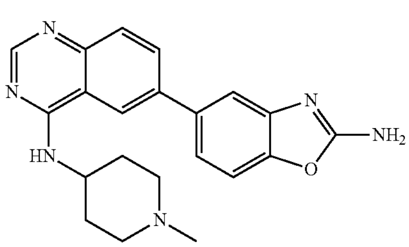 | ++ | ++++ | ++++ | ++++ | | ++ | | Calcd: 374.19 Found: 375.0 [M + H]$^+$ |

TABLE 3-continued

In Vitro IC$_{50}$ data for selected compounds of the invention.

| | Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | PC3 proliferation (nM)* | T47D proliferation (nM) | Mass Characterization |
|---|---|---|---|---|---|---|---|---|---|
| 36 | 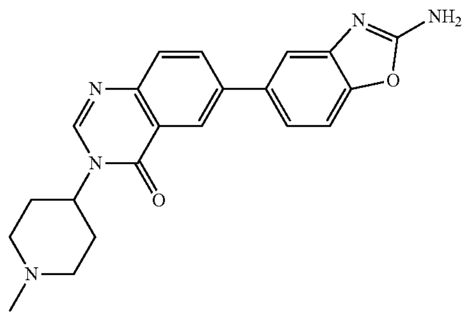 [SMILES: CN1CCC(n2cnc3ccc(-c4ccc5oc(N)nc5c4)cc3c2=O)CC1] | ++ | ++++ | | ++ | + | | ++ | Calcd: 375.17 Found: 376.0 [M + H]$^+$ |
| 37 | 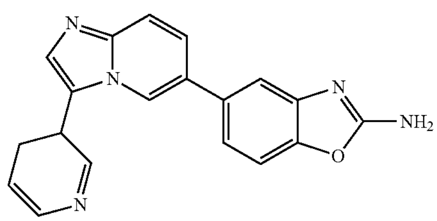 [SMILES: Nc1nc2cc(-c3ccc4ncc(C5C=NC=CC5)n4c3)ccc2o1] | | ++++ | | ++++ | ++++ | | | Calcd: 327.11 Found: 328.0 [M + H]$^+$ |
| 38 | 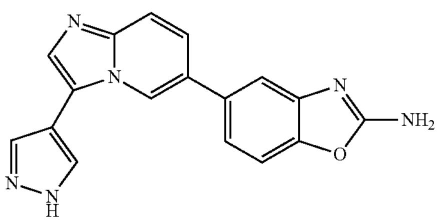 [SMILES: Nc1nc2cc(-c3ccc4ncc(-c5cn[nH]c5)n4c3)ccc2o1] | | ++++ | | ++++ | ++++ | | | Calcd: 316.11 Found: 317.0 [M + H]$^+$ |
| 39 | 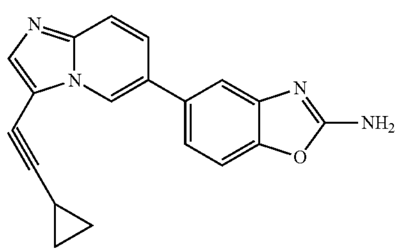 [SMILES: Nc1nc2cc(-c3ccc4ncc(C#CC5CC5)n4c3)ccc2o1] | | ++++ | | ++++ | ++++ | | | Calcd: 314.12 Found: 315.0 [M + H]$^+$ |
| 40 | 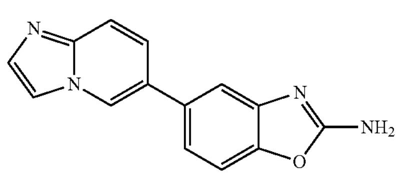 [SMILES: Nc1nc2cc(-c3ccc4nccn4c3)ccc2o1] | ++ | ++ | | + | ++ | | | Calcd: 250.09 Found: 251.0 [M + H]$^+$ |
| 41 | 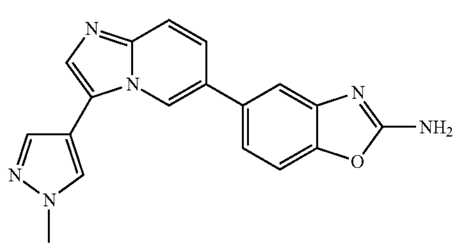 [SMILES: Cn1cc(-c2cnc3ccc(-c4ccc5oc(N)nc5c4)cn23)cn1] | ++ | ++++ | | +++ | +++ | | ++ | Calcd: 330.12 Found: 331.0 [M + H]$^+$ |

TABLE 3-continued

In Vitro IC$_{50}$ data for selected compounds of the invention.

| Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | PC3 proliferation (nM)* | T47D proliferation (nM) | Mass Characterization |
|---|---|---|---|---|---|---|---|---|
| 42 | + | ++++ | | +++ | +++ | | ++ | Calcd: 425.20 Found: 426.0 [M + H]$^+$ |
| 43 | | ++++ | | ++++ | ++++ | | | |
| 44 | ++ | ++++ | | ++ | ++ | | | Calcd: 376.16 Found: 377.0 [M + H]$^+$ |
| 45 | | ++++ | | ++++ | ++++ | | | Calcd: 406.18 Found: 407.0 [M + H]$^+$ |

TABLE 3-continued

In Vitro IC$_{50}$ data for selected compounds of the invention.

| | Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | PC3 proliferation (nM)* | T47D proliferation (nM) | Mass Characterization |
|---|---|---|---|---|---|---|---|---|---|
| 46 | 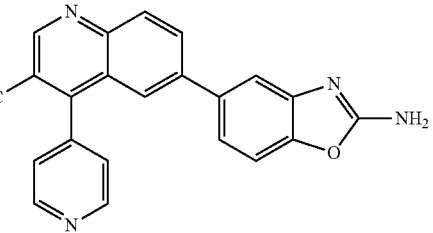 | ++++ | ++++ | | ++++ | ++++ | | | Calcd: 363.11 Found: 364.0 [M + H]$^+$ |
| 47 | 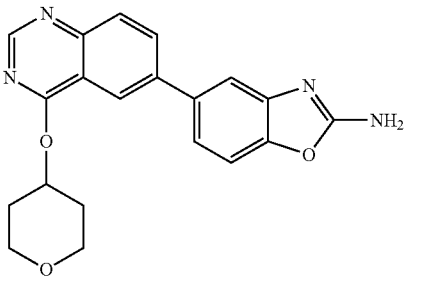 [SMILES: Nc1nc2cc(-c3ccc4ncnc(OC5CCOCC5)c4c3)ccc2o1] | ++++ | ++++ | +++ | +++ | +++ | | +++ | Calcd: 362.14 Found: 363.0 [M + H]$^+$ |
| 48 | 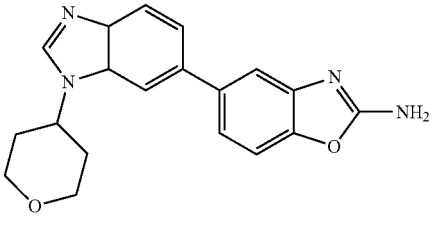 [SMILES: Nc1nc2cc(C3=CC4C(C=C3)N=CN4C3CCOCC3)ccc2o1] | | ++ | + | + | + | | | Calcd: 334.14 Found: 335.0 [M + H]$^+$ |
| 49 | 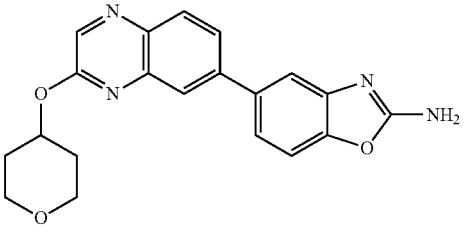 [SMILES: Nc1nc2cc(-c3ccc4ncc(OC5CCOCC5)nc4c3)ccc2o1] | ++ | ++++ | ++ | +++ | ++ | | | Calcd: 362.14 Found: 363.0 [M + H]$^+$ |
| 50 | 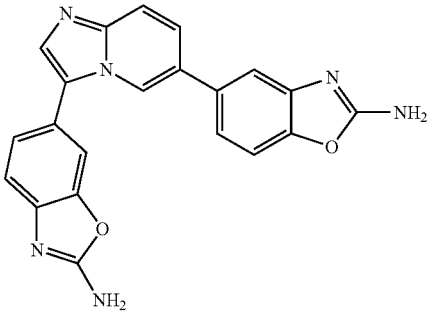 [SMILES: Nc1nc2cc(-c3ccc4ncc(-c5ccc6nc(N)oc6c5)n4c3)ccc2o1] | + | ++++ | ++ | ++++ | ++ | | | Calcd: 382.12 Found: 383.0 [M + H]$^+$ |

TABLE 3-continued

In Vitro IC$_{50}$ data for selected compounds of the invention.

| Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | PC3 proliferation (nM)* | T47D proliferation (nM) | Mass Characterization |
|---|---|---|---|---|---|---|---|---|
| 51 | | ++++ | +++ | +++ | +++ | | | Calcd: 412.16 Found: 413.0 [M + H]$^+$ |
| 52 | ++ | ++++ | | ++++ | ++++ | | | Calcd: 412.16 Found: 413.0 [M + H]$^+$ |
| 53 | | ++ | + | + | + | | | Calcd: 335.14 Found: 336.0 [M + H]$^+$ |
| 54 | ++ | ++++ | ++ | ++ | ++ | | ++ | Calcd: 363.13 Found: 364.2 [M + H]$^+$ |

TABLE 3-continued

In Vitro IC$_{50}$ data for selected compounds of the invention.

| Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | PC3 proliferation (nM)* | T47D proliferation (nM) | Mass Characterization |
|---|---|---|---|---|---|---|---|---|
| 55 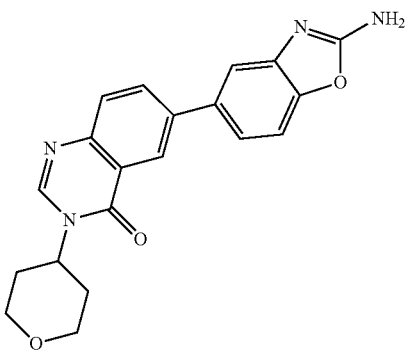 [SMILES: Nc1nc2cc(-c3ccc4ncn(C5CCOCC5)c(=O)c4c3)ccc2o1] | + | +++ | | + | + | | | Calcd: 342.12 Found: 363.0 [M + H]$^+$ |
| 56 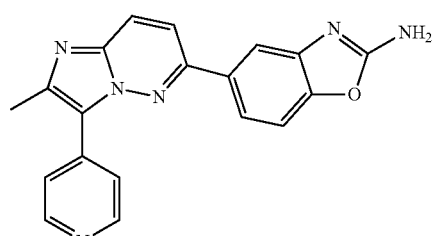 | +++ | ++++ | +++ | + | ++++ | | ++ | Calcd: 342.12 Found: 343.0 [M + H]$^+$ |
| 57 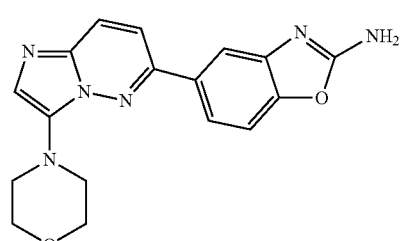 | | +++ | +++ | + | ++ | | | Calcd: 336.13 Found: 337.0 [M + H]$^+$ |
| 58 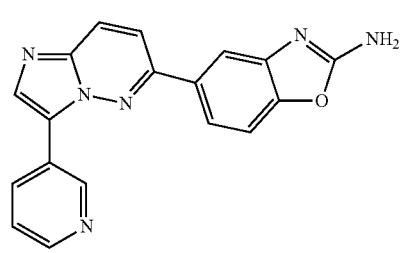 [SMILES: Nc1nc2cc(-c3ccc4ncc(-c5cccnc5)n4n3)ccc2o1] | | ++++ | ++++ | ++++ | ++++ | | | Calcd: 328.11 Found: 329.0 [M + H]$^+$ |
| 59 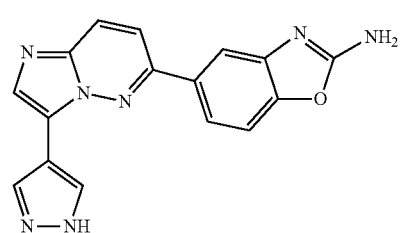 [SMILES: Nc1nc2cc(-c3ccc4ncc(-c5cn[nH]c5)n4n3)ccc2o1] | | ++++ | ++++ | +++ | ++++ | | | Calcd: 317.10 Found: 318.0 [M + H]$^+$ |

TABLE 3-continued

In Vitro IC$_{50}$ data for selected compounds of the invention.

| Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | PC3 proliferation (nM)* | T47D proliferation (nM) | Mass Characterization |
|---|---|---|---|---|---|---|---|---|
| 60 | +++ | ++++ | ++ | +++ | ++++ | | | Calcd: 402.18 Found: 403.0 [M + H]$^+$ |
| 61 | | + | + | + | + | | | Calcd: 328.11 Found: 329.0 [M + H]$^+$ |
| 62 | ++++ | ++++ | ++++ | ++++ | ++++ | | | Calcd: 328.11 Found: 329.0 [M + H]$^+$ |
| 63 | | ++ | + | + | + | | | Calcd: 362.14 Found: 363.2 [M + H]$^+$ |
| 64 | ++ | ++++ | +++ | + | ++++ | | ++ | Calcd: 347.14 Found: 348.0 [M + H]$^+$ |

TABLE 3-continued

In Vitro IC$_{50}$ data for selected compounds of the invention.

| | Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | PC3 proliferation (nM)* | T47D proliferation (nM) | Mass Characterization |
|---|---|---|---|---|---|---|---|---|---|
| 65 | 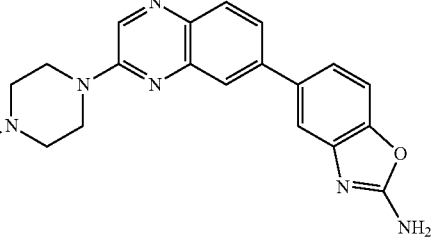 | + | ++++ | ++++ | ++ | +++ | | ++ | Calcd: 360.17 Found: 361.2 [M + H]$^+$ |
| 66 | 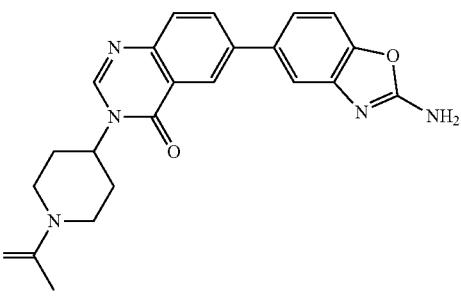 | | ++ | | + | + | | | Calcd: 403.16 Found: 404.2 [M + H]$^+$ |
| 67 | 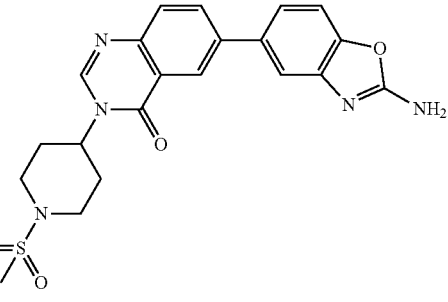 | | +++ | | + | + | | | Calcd: 439.13 Found: 440.0 [M + H]$^+$ |
| 68 | 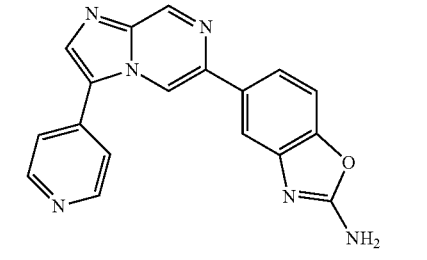 [SMILES: Nc1nc2cc(-c3cn4c(-c5ccncc5)cnc4cn3)ccc2o1] | | ++++ | ++ | ++ | +++ | | | Calcd: 328.11 Found: 329.0 [M + H]$^+$ |
| 69 | 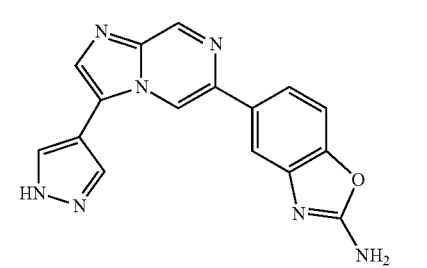 [SMILES: Nc1nc2cc(-c3cn4c(-c5cn[nH]c5)cnc4cn3)ccc2o1] | | +++ | ++ | ++ | +++ | | | Calcd: 317.10 Found: 318.0 [M + H]$^+$ |

TABLE 3-continued

In Vitro IC$_{50}$ data for selected compounds of the invention.

| | Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | PC3 proliferation (nM)* | T47D proliferation (nM) | Mass Characterization |
|---|---|---|---|---|---|---|---|---|---|
| 70 | 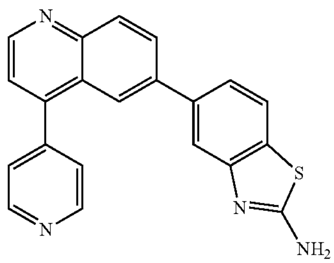 [SMILES: Nc1nc2cc(-c3ccc4nccc(-c5ccncc5)c4c3)ccc2s1] | | ++++ | ++++ | ++++ | ++++ | | | Calcd: 354.09 Found: 355.0 [M + H]$^+$ |
| 71 | 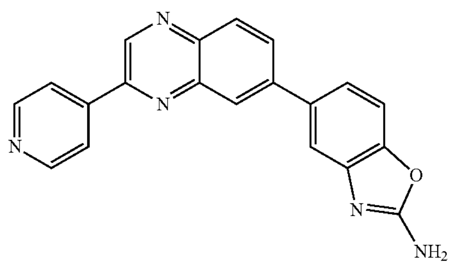 [SMILES: Nc1nc2cc(-c3ccc4ncc(-c5ccncc5)nc4c3)ccc2o1] | | ++++ | ++ | +++ | ++++ | | | Calcd: 339.11 Found: 340.0 [M + H]$^+$ |
| 72 | 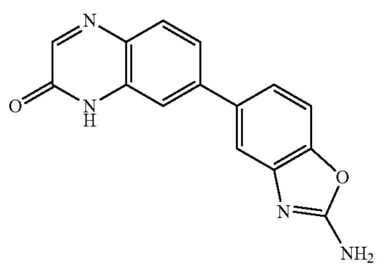 [SMILES: Nc1nc2cc(-c3ccc4ncc(=O)[nH]c4c3)ccc2o1] | +++ | ++++ | +++ | + | ++++ | | | Calcd: 278.08 Found: 279.0 [M + H]$^+$ |
| 73 | 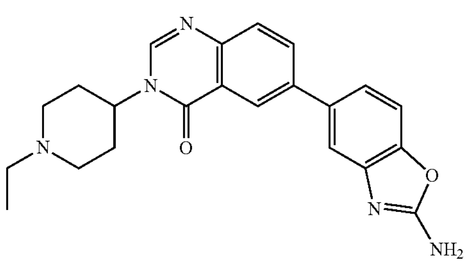 [SMILES: CCN1CCC(n2cnc3ccc(-c4ccc5oc(N)nc5c4)cc3c2=O)CC1] | | +++ | ++ | + | + | | | Calcd: 389.19 Found: 390.2 [M + H]$^+$ |
| 74 | 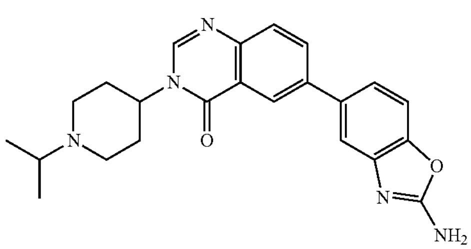 [SMILES: CC(C)N1CCC(n2cnc3ccc(-c4ccc5oc(N)nc5c4)cc3c2=O)CC1] | ++ | ++++ | ++ | + | ++ | ++ | | Calcd: 403.20 Found: 404.2 [M + H]$^+$ |

TABLE 3-continued

In Vitro IC$_{50}$ data for selected compounds of the invention.

| | Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | PC3 proliferation (nM)* | T47D proliferation (nM) | Mass Characterization |
|---|---|---|---|---|---|---|---|---|---|
| 75 | 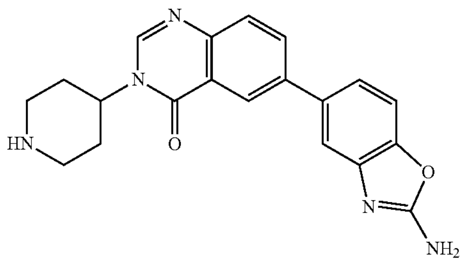 [SMILES: Nc1nc2cc(-c3ccc4ncn(C5CCNCC5)c(=O)c4c3)ccc2o1] | | ++++ | ++ | + | ++ | | | Calcd: 361.15 Found: 362.0 [M + H]$^+$ |
| 76 | 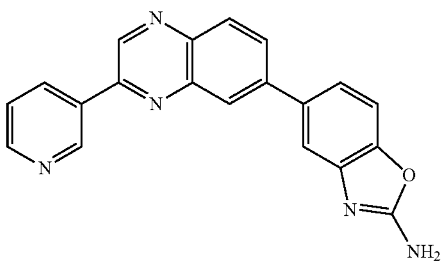 [SMILES: Nc1nc2cc(-c3ccc4ncc(-c5cccnc5)nc4c3)ccc2o1] | ++ | ++++ | + | + | +++ | | ++ | Calcd: 339.11 Found: 340.0 [M + H]$^+$ |
| 77 | 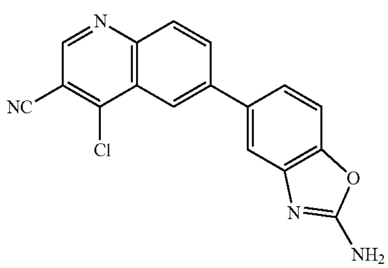 | +++ | | | | | | | Calcd: 320.05 Found: 321.0 [M + H]$^+$ |
| 78 | 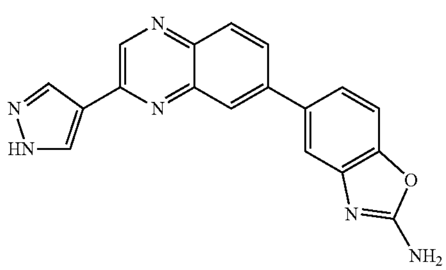 [SMILES: Nc1nc2cc(-c3ccc4ncc(-c5cn[nH]c5)nc4c3)ccc2o1] | | ++++ | +++ | +++ | ++++ | | | Calcd: 328.11 Found: 329.0 [M + H]$^+$ |
| 79 | 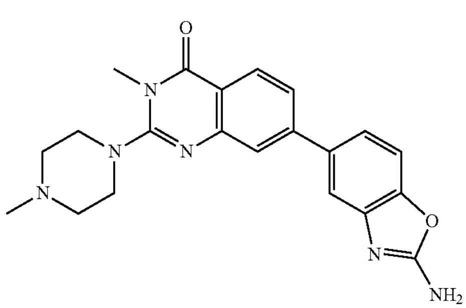 [SMILES: CN1CCN(c2nc3cc(-c4ccc5oc(N)nc5c4)ccc3c(=O)n2C)CC1] | | ++ | + | + | + | | | Calcd: 390.18 Found: 391.2 [M + H]$^+$ |

TABLE 3-continued

In Vitro IC$_{50}$ data for selected compounds of the invention.

| | Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | PC3 proliferation (nM)* | T47D proliferation (nM) | Mass Characterization |
|---|---|---|---|---|---|---|---|---|---|
| 80 | 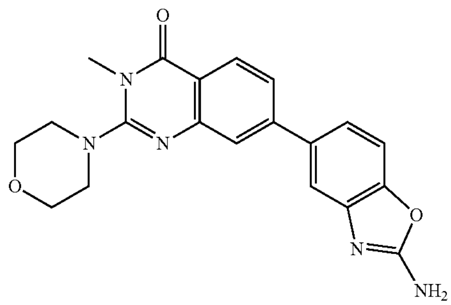 [SMILES: Cn1c(N2CCOCC2)nc2cc(-c3ccc4oc(N)nc4c3)ccc2c1=O] | | +++ | + | + | + | | | Calcd: 377.15 Found: 378.0 [M + H]$^+$ |
| 81 | 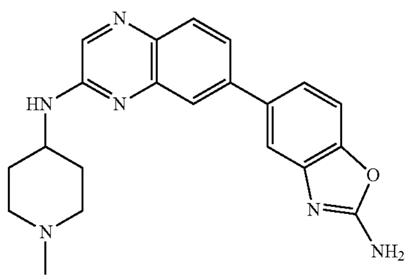 [SMILES: CN1CCC(Nc2cnc3ccc(-c4ccc5oc(N)nc5c4)cc3n2)CC1] | | ++++ | +++ | ++++ | +++ | | | Calcd: 374.19 Found: 375.2 [M + H]$^+$ |
| 82 | 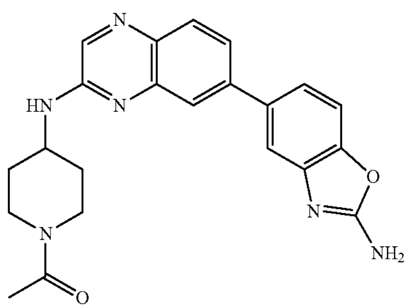 [SMILES: CC(=O)N1CCC(Nc2cnc3ccc(-c4ccc5oc(N)nc5c4)cc3n2)CC1] | | ++++ | ++ | ++++ | ++++ | | | Calcd: 402.18 Found: 403.2 [M + H]$^+$ |
| 83 | 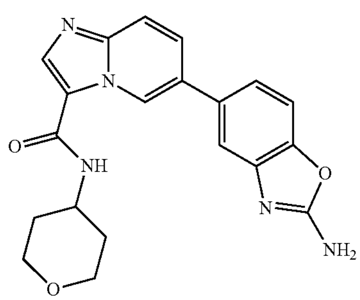 [SMILES: Nc1nc2cc(-c3ccc4ncc(C(=O)NC5CCOCC5)n4c3)ccc2o1] | | ++++ | ++ | ++++ | ++++ | | | Calcd: 377.15 Found: 378.0 [M + H]$^+$ |
| 84 | 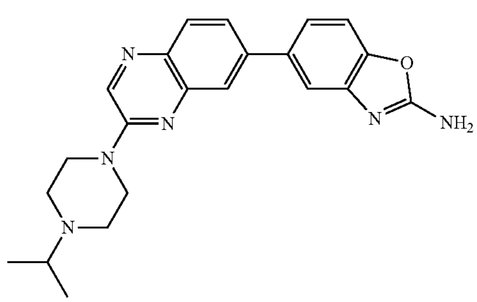 [SMILES: CC(C)N1CCN(c2cnc3ccc(-c4ccc5oc(N)nc5c4)cc3n2)CC1] | | ++++ | ++++ | +++ | ++++ | ++ | | Calcd: 388.20 Found: 389.2 [M + H]$^+$ |

TABLE 3-continued

In Vitro IC$_{50}$ data for selected compounds of the invention.

| Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | PC3 proliferation (nM)* | T47D proliferation (nM) | Mass Characterization |
|---|---|---|---|---|---|---|---|---|
| 85 | | ++++ | ++++ | ++++ | ++++ | | | Calcd: 388.16 Found: 389.0 [M + H]$^+$ |
| 86 | | ++++ | +++ | +++ | ++++ | | | Calcd: 424.13 Found: 425.0 [M + H]$^+$ |
| 87 | | ++++ | +++ | ++++ | ++++ | | | Calcd: 438.15 Found: 439.0 [M + H]$^+$ |
| 88 | | ++++ | ++++ | ++ | +++ | | ++ | Calcd: 346.15 Found: 347.2 [M + H]$^+$ |

TABLE 3-continued
In Vitro IC$_{50}$ data for selected compounds of the invention.
| Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | PC3 proliferation (nM)* | T47D proliferation (nM) | Mass Characterization |
|---|---|---|---|---|---|---|---|---|
| 89 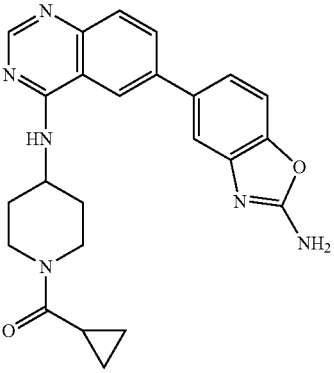 [SMILES: Nc1nc2cc(-c3ccc4ncnc(NC5CCN(C(=O)C6CC6)CC5)c4c3)ccc2o1] | | ++++ | ++ | ++++ | ++++ | | | Calcd: 428.20 Found: 429.2 [M + H]$^+$ |
| 90 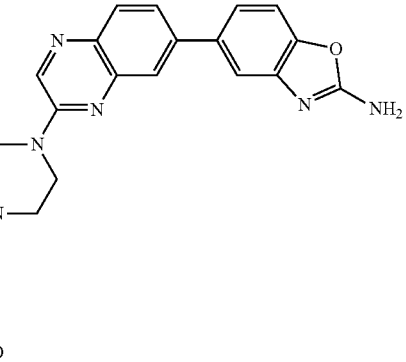 | | ++++ | +++ | ++ | +++ | | +++ | Calcd: 452.16 Found: 453.0 [M + H]$^+$ |
| 91 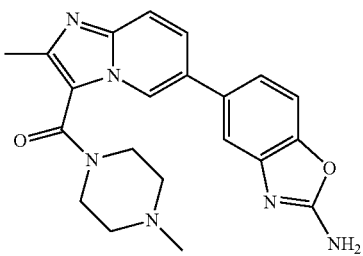 [SMILES: Cc1nc2ccc(-c3ccc4oc(N)nc4c3)cn2c1C(=O)N1CCN(C)CC1] | | + | + | + | + | | | Calcd: 390.18 Found: 391.0 [M + H]$^+$ |
| 92 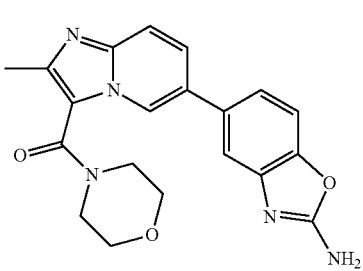 [SMILES: Cc1nc2ccc(-c3ccc4oc(N)nc4c3)cn2c1C(=O)N1CCOCC1] | | + | + | + | + | | | Calcd: 377.15 Found: 378.0 [M + H]$^+$ |

TABLE 3-continued

In Vitro IC$_{50}$ data for selected compounds of the invention.

| | Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | PC3 proliferation (nM)* | T47D proliferation (nM) | Mass Characterization |
|---|---|---|---|---|---|---|---|---|---|
| 93 | 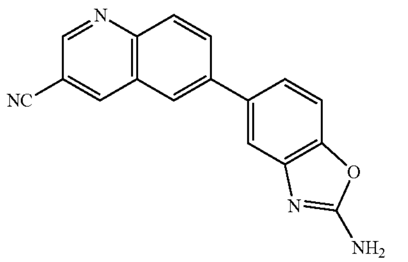 [SMILES: N#Cc1cnc2ccc(-c3ccc4oc(N)nc4c3)cc2c1] | ++ | +++ | + | + | +++ | | | Calcd: 286.09 Found: 287.0 [M + H]$^+$ |
| 94 | 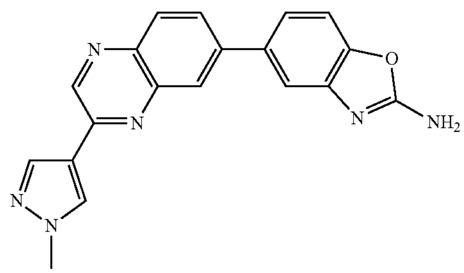 [SMILES: Cn1cc(-c2cnc3ccc(-c4ccc5oc(N)nc5c4)cc3n2)cn1] | | ++++ | +++ | ++ | ++++ | | | Calcd: 342.12 Found: 343.0 [M + H]$^+$ |
| 95 | 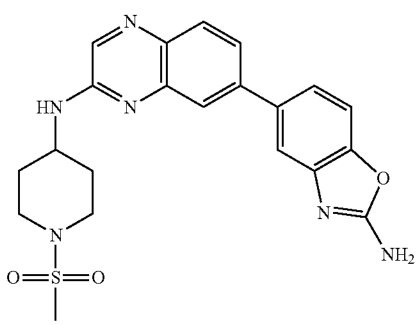 [SMILES: CS(=O)(=O)N1CCC(Nc2cnc3ccc(-c4ccc5oc(N)nc5c4)cc3n2)CC1] | | ++++ | ++ | ++++ | ++++ | | | Calcd: 438.15 Found: 439.0 [M + H]$^+$ |
| 96 | 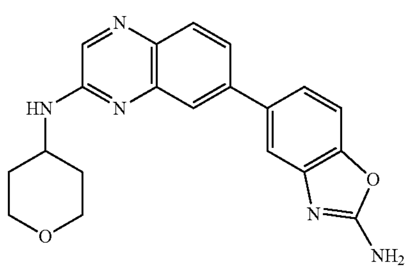 [SMILES: Nc1nc2cc(-c3ccc4ncc(NC5CCOCC5)nc4c3)ccc2o1] | | ++++ | ++ | +++ | ++++ | | +++ | Calcd: 361.15 Found: 362.0 [M + H]$^+$ |
| 97 | 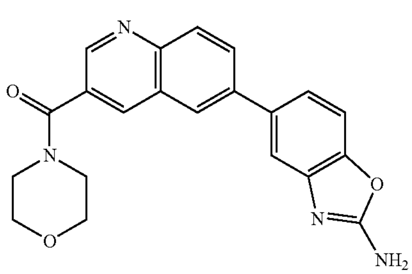 [SMILES: Nc1nc2cc(-c3ccc4ncc(C(=O)N5CCOCC5)cc4c3)ccc2o1] | ++ | + | + | + | | | | Calcd: 374.14 Found: 375.0 [M + H]$^+$ |

TABLE 3-continued

In Vitro IC$_{50}$ data for selected compounds of the invention.

| Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | PC3 proliferation (nM)* | T47D proliferation (nM) | Mass Characterization |
|---|---|---|---|---|---|---|---|---|
| 98 | | ++++ | + | + | ++++ | | | Calcd: 395.11 Found: 396.0 [M + H]$^+$ |
| 99 | | ++++ | ++ | +++ | +++ | | ++ | Calcd: 361.15 Found: 362.2 [M + H]$^+$ |
| 100 | | ++++ | ++++ | ++ | +++ | | +++ | Calcd: 390.18 Found: 391.0 [M + H]$^+$ |
| 101 | | ++++ | ++ | +++ | ++ | | ++ | Calcd: 402.22 Found: 403.0 [M + H]$^+$ |

TABLE 3-continued

In Vitro IC$_{50}$ data for selected compounds of the invention.

| | Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | PC3 proliferation (nM)* | T47D proliferation (nM) | Mass Characterization |
|---|---|---|---|---|---|---|---|---|---|
| 102 | 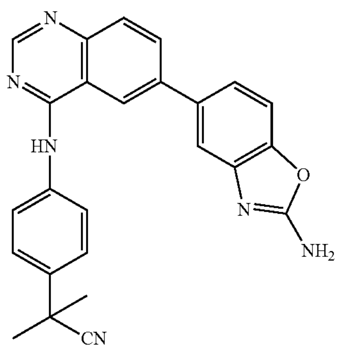 [SMILES: CC(C)(C#N)c1ccc(Nc2ncnc3ccc(-c4ccc5oc(N)nc5c4)cc23)cc1] | | ++++ | +++ | +++ | ++++ | | | Calcd: 420.17 Found: 421.0 [M + H]$^+$ |
| 103 | 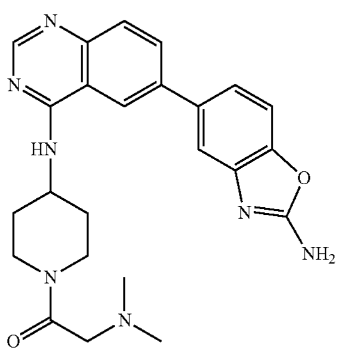 [SMILES: CN(C)CC(=O)N1CCC(Nc2ncnc3ccc(-c4ccc5oc(N)nc5c4)cc23)CC1] | | ++++ | +++ | +++ | +++ | | ++ | Calcd: 445.22 Found: 446.0 [M + H]$^+$ |
| 104 | 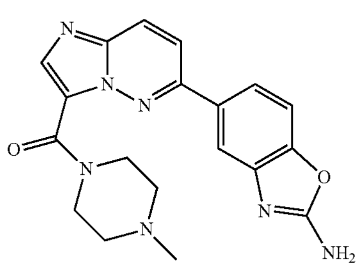 [SMILES: CN1CCN(C(=O)c2cnc3ccc(-c4ccc5oc(N)nc5c4)nn23)CC1] | | ++ | + | + | ++ | | | Calcd: 377.16 Found: 378.0 [M + H]$^+$ |
| 105 | 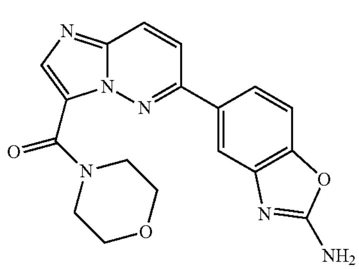 | | +++ | ++ | + | +++ | | | Calcd: 364.13 Found: 365.0 [M + H]$^+$ |

TABLE 3-continued

In Vitro IC$_{50}$ data for selected compounds of the invention.

| | Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | PC3 proliferation (nM)* | T47D proliferation (nM) | Mass Characterization |
|---|---|---|---|---|---|---|---|---|---|
| 106 | 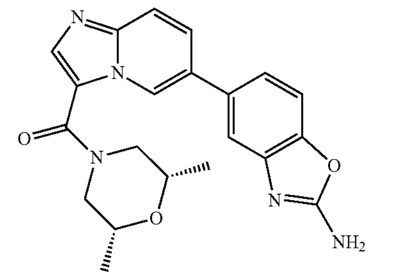 [SMILES: C[C@@H]1CN(C(=O)c2cnc3ccc(-c4ccc5oc(N)nc5c4)cn23)C[C@H](C)O1] | | ++ | + | + | ++ | | | Calcd: 391.16 Found: 392.0 [M + H]$^+$ |
| 107 | 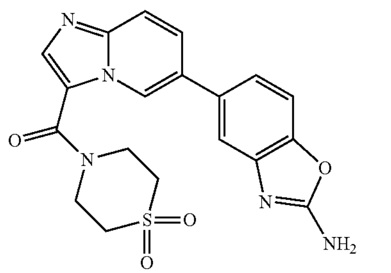 [SMILES: Nc1nc2cc(-c3ccc4ncc(C(=O)N5CCS(=O)(=O)CC5)n4c3)ccc2o1] | | +++ | + | + | ++ | | | Calcd: 411.10 Found: 412.0 [M + H]$^+$ |
| 108 | 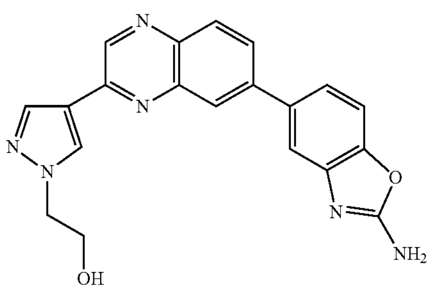 [SMILES: Nc1nc2cc(-c3ccc4ncc(-c5cnn(CCO)c5)nc4c3)ccc2o1] | | ++++ | ++ | + | ++++ | | +++ | Calcd: 372.13 Found: 373.2 [M + H]$^+$ |
| 109 | 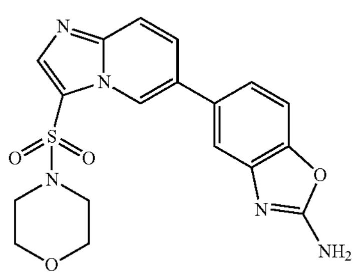 [SMILES: Nc1nc2cc(-c3ccc4ncc(S(=O)(=O)N5CCOCC5)n4c3)ccc2o1] | | + | + | + | + | | | Calcd: 399.10 Found: 400.0 [M + H]$^+$ |
| 110 | 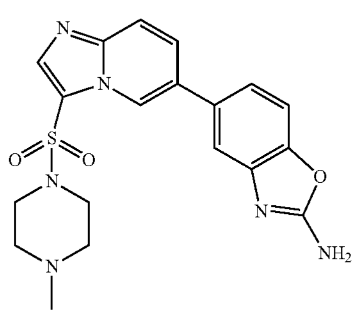 [SMILES: CN1CCN(S(=O)(=O)c2cnc3ccc(-c4ccc5oc(N)nc5c4)cn23)CC1] | | + | + | + | + | | | Calcd: 412.13 Found: 413.0 [M + H]$^+$ |

TABLE 3-continued

In Vitro IC$_{50}$ data for selected compounds of the invention.

| Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | PC3 proliferation (nM)* | T47D proliferation (nM) | Mass Characterization |
|---|---|---|---|---|---|---|---|---|
| 111 | | ++++ | ++ | + | + | | | Calcd: 362.15 Found: 363.0 [M + H]$^+$ |
| 112 | | ++++ | + | ++ | +++ | | +++ | Calcd: 440.13 Found: 441.0 [M + H]$^+$ |
| 113 | | ++++ | + | + | +++ | | ++ | Calcd: 404.16 Found: 405.2 [M + H]$^+$ |
| 114 | | ++++ | + | + | +++ | | | Calcd: 363.12 Found: 364.0 [M + H]$^+$ |
| 115 | | ++++ | ++++ | + | ++ | | ++ | Calcd: 376.15 Found: 377.0 [M + H]$^+$ |

TABLE 3-continued

In Vitro IC$_{50}$ data for selected compounds of the invention.

| | Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | PC3 proliferation (nM)* | T47D proliferation (nM) | Mass Characterization |
|---|---|---|---|---|---|---|---|---|---|
| 116 | 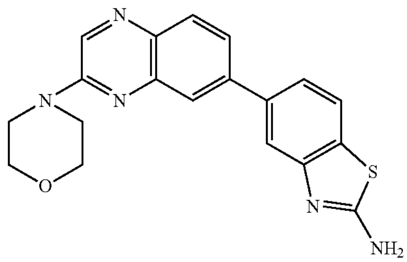 [SMILES: Nc1nc2cc(-c3ccc4ncc(N5CCOCC5)nc4c3)ccc2s1] | | ++++ | +++ | + | +++ | | +++ | Calcd: 363.12 Found: 364.0 [M + H]$^+$ |
| 117 | 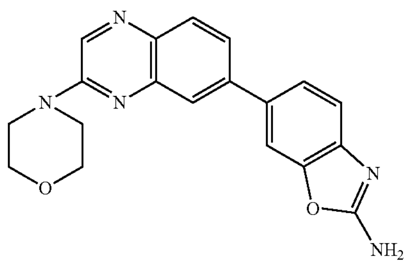 [SMILES: Nc1nc2ccc(-c3ccc4ncc(N5CCOCC5)nc4c3)cc2o1] | | ++++ | +++ | + | +++ | | ++ | Calcd: 347.14 Found: 348.2 [M + H]$^+$ |
| 118 | 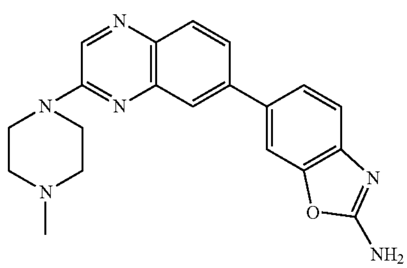 | | +++ | ++++ | + | ++ | | | Calcd: 360.17 Found: 361.0 [M + H]$^+$ |
| 119 | 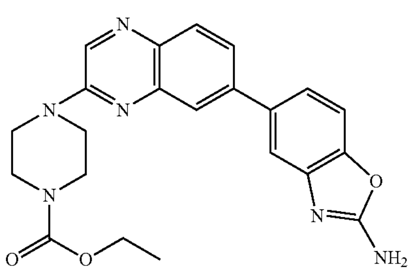 [SMILES: CCOC(=O)N1CCN(c2cnc3ccc(-c4ccc5oc(N)nc5c4)cc3n2)CC1] | ++ | ++++ | ++ | ++ | ++ | | ++ | Calcd: 418.18 Found: 419.0 [M + H]$^+$ |
| 120 | 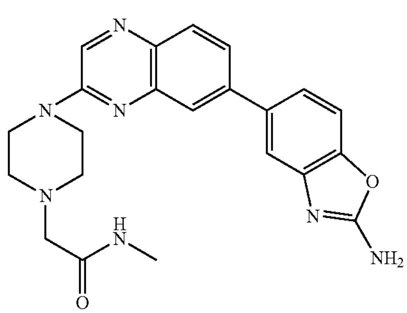 [SMILES: CNC(=O)CN1CCN(c2cnc3ccc(-c4ccc5oc(N)nc5c4)cc3n2)CC1] | | ++++ | +++ | ++ | + | | +++ | Calcd: 417.19 Found: 418.0 [M + H]$^+$ |

TABLE 3-continued

In Vitro IC$_{50}$ data for selected compounds of the invention.

| | Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | PC3 proliferation (nM)* | T47D proliferation (nM) | Mass Characterization |
|---|---|---|---|---|---|---|---|---|---|
| 121 | 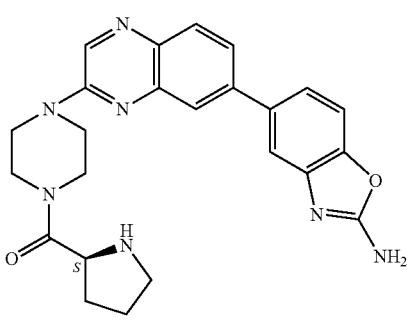 | + | ++++ | ++++ | ++++ | ++++ | | +++ | Calcd: 443.21 Found: 444.2 [M + H]$^+$ |
| 122 | 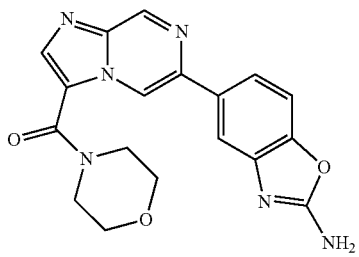 [SMILES: Nc1nc2cc(-c3cn4c(C(=O)N5CCOCC5)cnc4cn3)ccc2o1] | | + | + | + | + | | | Calcd: 364.13 Found: 365.0 [M + H]$^+$ |
| 123 | 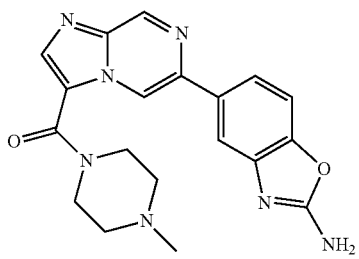 [SMILES: CN1CCN(C(=O)c2cnc3cnc(-c4ccc5oc(N)nc5c4)cn23)CC1] | | ++ | + | + | + | | | Calcd: 377.16 Found: 378.2 [M + H]$^+$ |
| 124 | 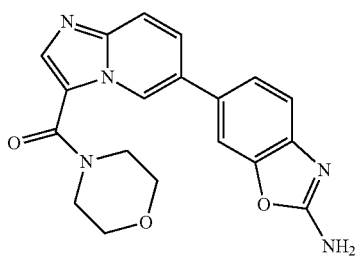 [SMILES: Nc1nc2ccc(-c3ccc4ncc(C(=O)N5CCOCC5)n4c3)cc2o1] | | +++ | +++ | + | +++ | | | Calcd: 363.13 Found: 364.0 [M + H]$^+$ |
| 125 | 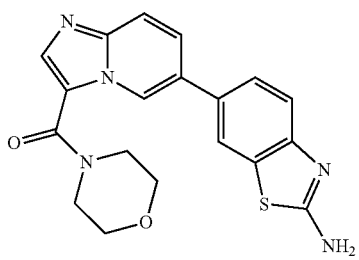 [SMILES: Nc1nc2ccc(-c3ccc4ncc(C(=O)N5CCOCC5)n4c3)cc2s1] | | +++ | + | ++ | +++ | | | Calcd: 379.11 Found: 380.0 [M + H]$^+$ |

TABLE 3-continued

In Vitro IC$_{50}$ data for selected compounds of the invention.

| | Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | PC3 proliferation (nM)* | T47D proliferation (nM) | Mass Characterization |
|---|---|---|---|---|---|---|---|---|---|
| 126 | 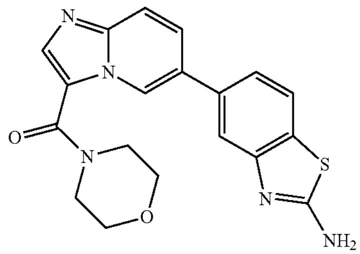 [SMILES: Nc1nc2cc(-c3ccc4ncc(C(=O)N5CCOCC5)n4c3)ccc2s1] | | +++ | ++ | + | +++ | | | Calcd: 379.11 Found: 380.0 [M + H]$^+$ |
| 127 | 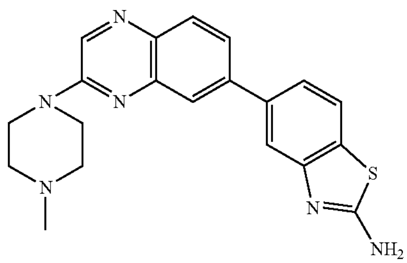 [SMILES: CN1CCN(c2cnc3ccc(-c4ccc5sc(N)nc5c4)cc3n2)CC1] | | +++ | ++++ | + | ++ | | | Calcd: 376.15 Found: 377.2 [M + H]$^+$ |
| 128 | 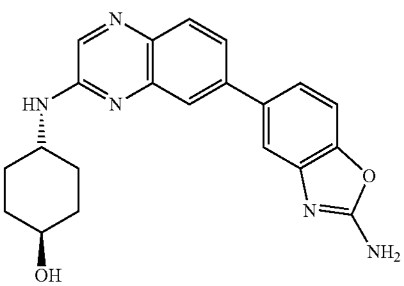 | | ++++ | ++ | ++++ | ++++ | | | Calcd: 375.17 Found: 376.2 [M + H]$^+$ |
| 129 | 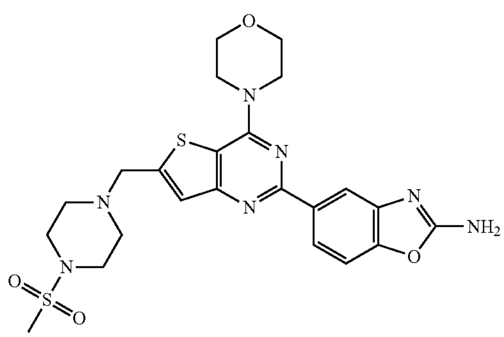 [SMILES: CS(=O)(=O)N1CCN(Cc2cc3nc(-c4ccc5oc(N)nc5c4)nc(N4CCOCC4)c3s2)CC1] | +++ | ++++ | +++ | +++ | ++++ | +++ | | Calcd: 529.16 Found: 530.0 [M + H]$^+$ |
| 130 | 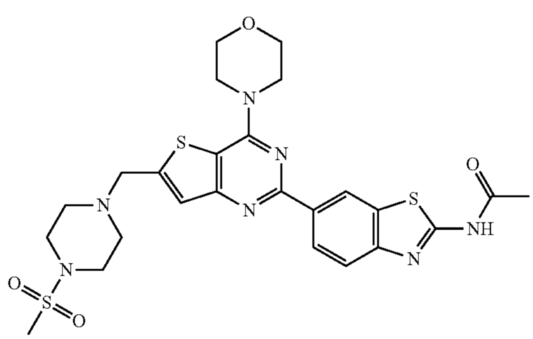 [SMILES: CC(=O)Nc1nc2ccc(-c3nc(N4CCOCC4)c4sc(CN5CCN(S(C)(=O)=O)CC5)cc4n3)cc2s1] | | + | + | + | + | | | Calcd: 587.14 Found: 588.0 [M + H]$^+$ |

TABLE 3-continued

In Vitro IC$_{50}$ data for selected compounds of the invention.

| | Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | PC3 proliferation (nM)* | T47D proliferation (nM) | Mass Characterization |
|---|---|---|---|---|---|---|---|---|---|
| 131 | 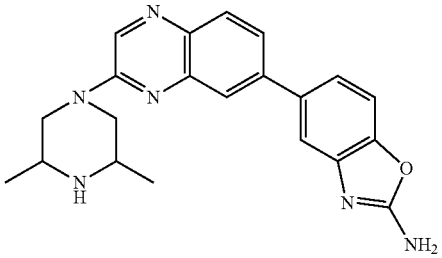 [SMILES: CC1CN(c2cnc3ccc(-c4ccc5oc(N)nc5c4)cc3n2)CC(C)N1] | | +++ | +++ | +++ | +++ | | | Calcd: 374.19 Found: 375.2 [M + H]$^+$ |
| 132 | 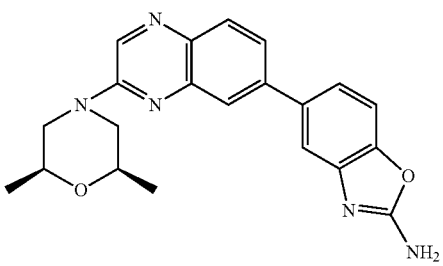 [SMILES: C[C@@H]1CN(c2cnc3ccc(-c4ccc5oc(N)nc5c4)cc3n2)C[C@H](C)O1] | | +++ | + | + | ++ | | | Calcd: 375.17 Found: 376.2 [M + H]$^+$ |
| 133 | 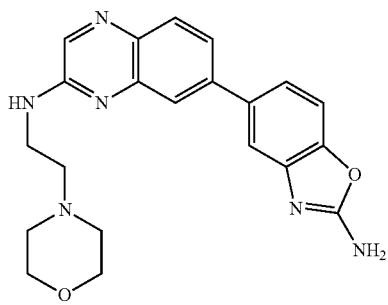 [SMILES: Nc1nc2cc(-c3ccc4ncc(NCCN5CCOCC5)nc4c3)ccc2o1] | + | ++++ | +++ | +++ | +++ | | ++ | Calcd: 390.18 Found: 390.2 [M]$^+$ |
| 134 | 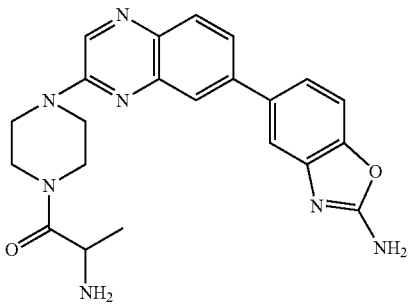 [SMILES: CC(N)C(=O)N1CCN(c2cnc3ccc(-c4ccc5oc(N)nc5c4)cc3n2)CC1] | | ++++ | +++ | +++ | ++ | | +++ | Calcd: 417.19 Found: 418.0 [M + H]$^+$ |
| 135 | 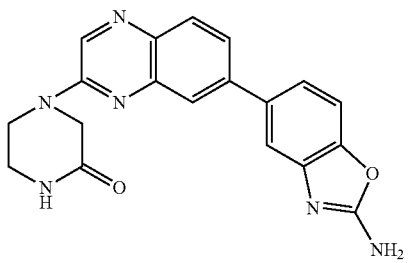 [SMILES: Nc1nc2cc(-c3ccc4ncc(N5CCNC(=O)C5)nc4c3)ccc2o1] | + | ++++ | +++ | + | +++ | | +++ | Calcd: 360.13 Found: 361.0 [M + H]$^+$ |

US 9,295,673 B2

423                                                                     424

TABLE 3-continued

In Vitro IC$_{50}$ data for selected compounds of the invention.

| Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | PC3 proliferation (nM)* | T47D proliferation (nM) | Mass Characterization |
|---|---|---|---|---|---|---|---|---|
| 136 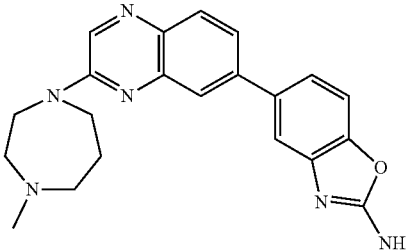 | | +++ | +++ | + | ++ | | | Calcd: 374.19 Found: 375.2 [M + H]$^+$ |
| 137 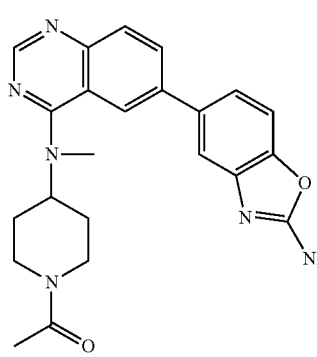 | + | ++++ | +++ | +++ | +++ | | +++ | Calcd: 416.20 Found: 417.2 [M + H]$^+$ |
| 138 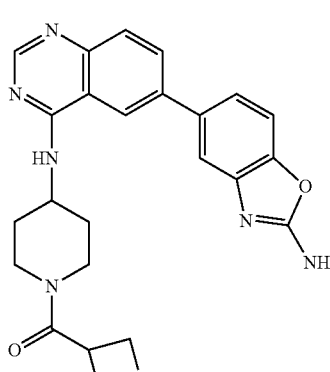 | | ++++ | +++ | ++++ | +++ | + | | Calcd: 457.22 Found: 458.2 [M + H]$^+$ |
| 139 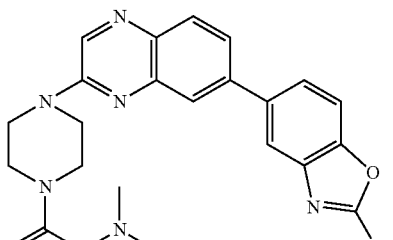 | + | ++++ | +++ | +++ | +++ | | +++ | Calcd: 431.21 Found: 432.2 [M + H]$^+$ |

TABLE 3-continued

In Vitro IC$_{50}$ data for selected compounds of the invention.

| Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | PC3 proliferation (nM)* | T47D proliferation (nM) | Mass Characterization |
|---|---|---|---|---|---|---|---|---|
| 140 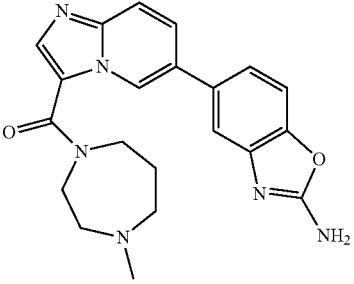 [SMILES: CN1CCCN(C(=O)c2cnc3ccc(-c4ccc5oc(N)nc5c4)cn23)CC1] | | +++ | ++ | + | + | | | Calcd: 390.18 Found: 391.2 [M + H]$^+$ |
| 141 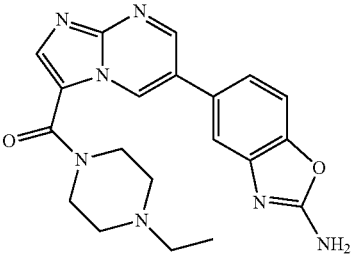 | | +++ | + | + | ++ | | | Calcd: 390.18 Found: 391.2 [M + H]$^+$ |
| 142 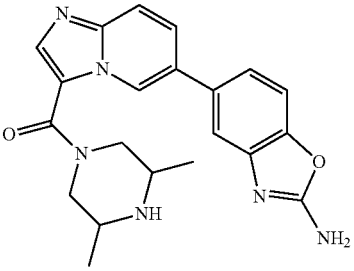 [SMILES: CC1CN(C(=O)c2cnc3ccc(-c4ccc5oc(N)nc5c4)cn23)CC(C)N1] | | ++ | + | + | + | | | Calcd: 390.18 Found: 391.2 [M + H]$^+$ |
| 143 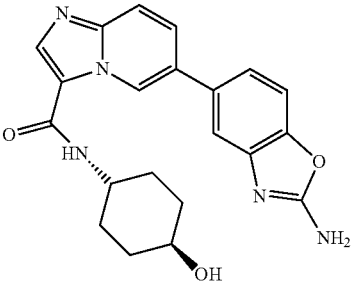 | + | ++++ | ++ | ++++ | ++++ | | +++ | Calcd: 391.16 Found: 392.2 [M + H]$^+$ |
| 144 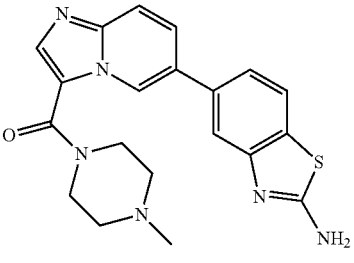 [SMILES: CN1CCN(C(=O)c2cnc3ccc(-c4ccc5sc(N)nc5c4)cn23)CC1] | | +++ | ++ | + | + | | | Calcd: 392.14 Found: 393.0 [M + H]$^+$ |

TABLE 3-continued

In Vitro IC$_{50}$ data for selected compounds of the invention.

| | Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | PC3 proliferation (nM)* | T47D proliferation (nM) | Mass Characterization |
|---|---|---|---|---|---|---|---|---|---|
| 145 | 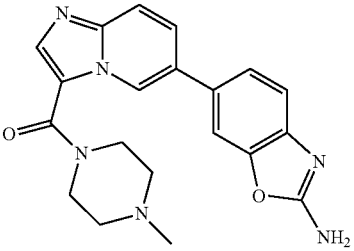 | | +++ | ++ | + | ++ | | | Calcd: 376.16 Found: 377.2 [M + H]$^+$ |
| 146 | 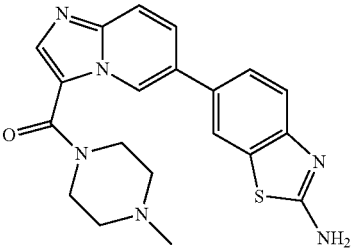 | | ++ | ++ | + | + | | | Calcd: 392.14 Found: 393.0 [M + H]$^+$ |
| 147 | 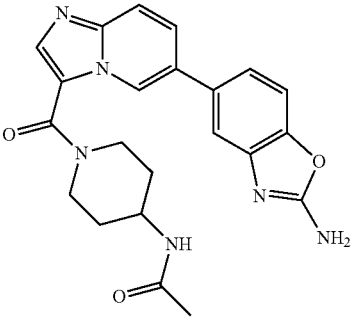 [SMILES: CC(=O)NC1CCN(C(=O)c2cnc3ccc(-c4ccc5oc(N)nc5c4)cn23)CC1] | | +++ | ++ | ++ | ++ | | | Calcd: 418.18 Found: 419.2 [M + H]$^+$ |
| 148 | 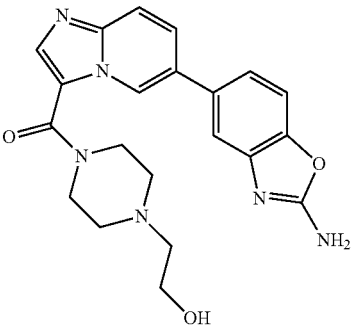 [SMILES: Nc1nc2cc(-c3ccc4ncc(C(=O)N5CCN(CCO)CC5)n4c3)ccc2o1] | | ++++ | + | + | ++ | | ++ | Calcd: 406.18 Found: 407.2 [M + H]$^+$ |
| 149 | 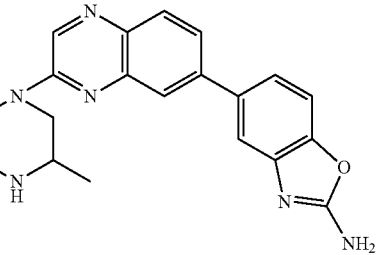 | | ++++ | ++++ | ++ | +++ | + | | Calcd: 360.17 Found: 361.0 [M + H]$^+$ |

TABLE 3-continued

In Vitro IC$_{50}$ data for selected compounds of the invention.

| | Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | PC3 proliferation (nM)* | T47D proliferation (nM) | Mass Characterization |
|---|---|---|---|---|---|---|---|---|---|
| 150 | 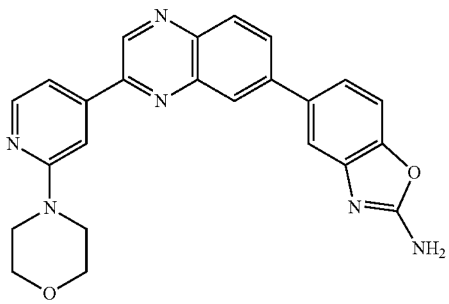 [SMILES: Nc1nc2cc(-c3ccc4ncc(-c5ccnc(N6CCOCC6)c5)nc4c3)ccc2o1] | | +++ | + | + | + | | | Calcd: 424.16 Found: 425.0 [M + H]$^+$ |
| 151 | 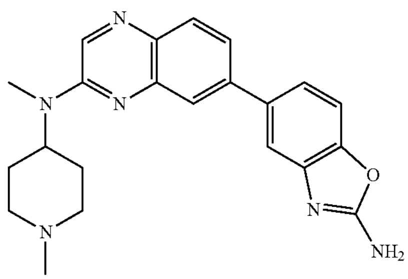 [SMILES: CN1CCC(N(C)c2cnc3ccc(-c4ccc5oc(N)nc5c4)cc3n2)CC1] | | ++++ | ++ | +++ | ++ | | ++ | Calcd: 388.20 Found: 389.0 [M + H]$^+$ |
| 152 | 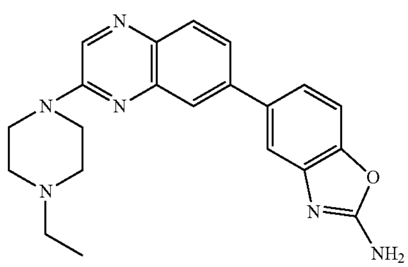 [SMILES: CCN1CCN(c2cnc3ccc(-c4ccc5oc(N)nc5c4)cc3n2)CC1] | | ++++ | ++++ | ++ | +++ | | ++ | Calcd: 374.19 Found: 375.0 [M + H]$^+$ |
| 153 | 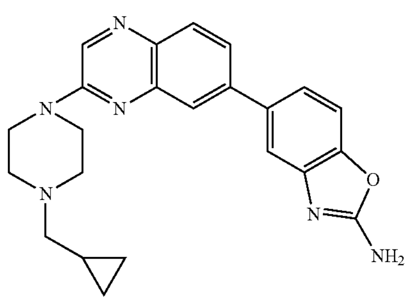 [SMILES: Nc1nc2cc(-c3ccc4ncc(N5CCN(CC6CC6)CC5)nc4c3)ccc2o1] | | ++++ | ++++ | +++ | +++ | | +++ | Calcd: 400.20 Found: 401.0 [M + H]$^+$ |
| 154 | 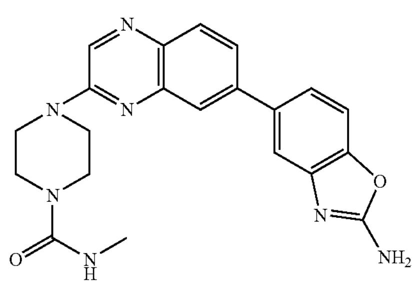 [SMILES: CNC(=O)N1CCN(c2cnc3ccc(-c4ccc5oc(N)nc5c4)cc3n2)CC1] | | ++++ | +++ | ++ | ++++ | | +++ | Calcd: 403.18 Found: 404.0 [M + H]$^+$ |

TABLE 3-continued

In Vitro IC$_{50}$ data for selected compounds of the invention.

| | Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | PC3 proliferation (nM)* | T47D proliferation (nM) | Mass Characterization |
|---|---|---|---|---|---|---|---|---|---|
| 155 | 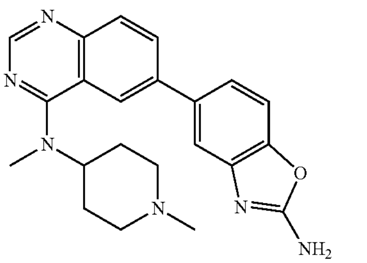 [SMILES: CN1CCC(N(C)c2ncnc3ccc(-c4ccc5oc(N)nc5c4)cc23)CC1] | | ++++ | ++++ | +++ | ++++ | | | Calcd: 388.20 Found: 389.0 [M + H]$^+$ |
| 156 | 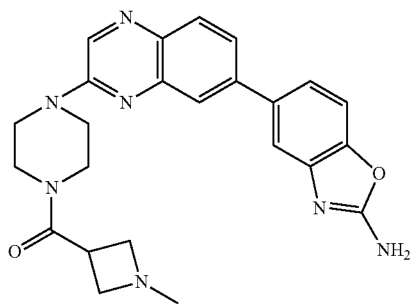 [SMILES: CN1CC(C(=O)N2CCN(c3cnc4ccc(-c5ccc6oc(N)nc6c5)cc4n3)CC2)C1] | + | ++++ | +++ | +++ | +++ | | +++ | Calcd: 443.21 Found: 444.0 [M + H]$^+$ |
| 157 | 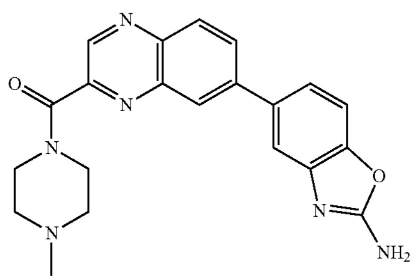 [SMILES: CN1CCN(C(=O)c2cnc3ccc(-c4ccc5oc(N)nc5c4)cc3n2)CC1] | | ++ | + | + | + | | | Calcd: 388.16 Found: 389.0 [M + H]$^+$ |
| 158 | 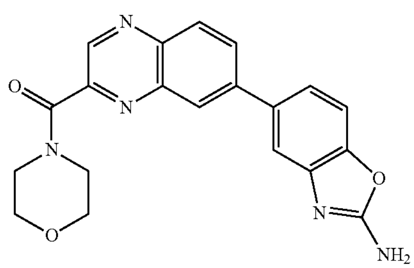 [SMILES: Nc1nc2cc(-c3ccc4ncc(C(=O)N5CCOCC5)nc4c3)ccc2o1] | | ++ | + | + | + | | | Calcd: 375.13 Found: 376.0 [M + H]$^+$ |
| 159 | 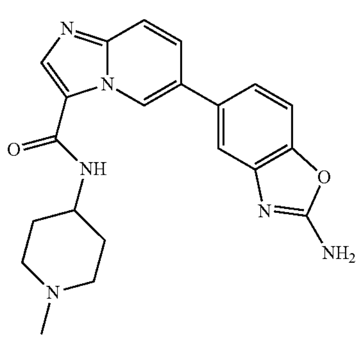 [SMILES: CN1CCC(NC(=O)c2cnc3ccc(-c4ccc5oc(N)nc5c4)cn23)CC1] | | ++++ | +++ | ++++ | +++ | | ++ | Calcd: 390.18 Found: 391.0 [M + H]$^+$ |

TABLE 3-continued

In Vitro IC$_{50}$ data for selected compounds of the invention.

| Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | PC3 proliferation (nM)* | T47D proliferation (nM) | Mass Characterization |
|---|---|---|---|---|---|---|---|---|
| 160 | | ++++ | ++ | + | + | | ++ | Calcd: 404.20 Found: 405.0 [M + H]$^+$ |
| 161 | | +++ | ++ | ++ | ++ | | | Calcd: 416.20 Found: 417.0 [M + H]$^+$ |
| 162 | | +++ | + | + | ++ | | | Calcd: 377.15 Found: 378.0 [M + H]$^+$ |
| 163 | | +++ | ++ | ++ | ++ | | | Calcd: 446.21 Found: 447.0 [M + H]$^+$ |

TABLE 3-continued

In Vitro IC$_{50}$ data for selected compounds of the invention.

| Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | PC3 proliferation (nM)* | T47D proliferation (nM) | Mass Characterization |
|---|---|---|---|---|---|---|---|---|
| 164 | | +++ | +++ | + | + | | | Calcd: 377.15 Found: 378.0 [M + H]$^+$ |
| 165 | | +++ | ++ | ++ | + | +++ | | Calcd: 404.20 Found: 405.0 [M + H]$^+$ |
| 166 | | +++ | ++ | + | ++ | | | Calcd: 404.20 Found: 405.2 [M + H]$^+$ |
| 167 | | ++ | + | + | + | | | Calcd: 424.16 Found: 425.0 [M + H]$^+$ |

TABLE 3-continued

In Vitro IC$_{50}$ data for selected compounds of the invention.

| Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | PC3 proliferation (nM)* | T47D proliferation (nM) | Mass Characterization |
|---|---|---|---|---|---|---|---|---|
| 168 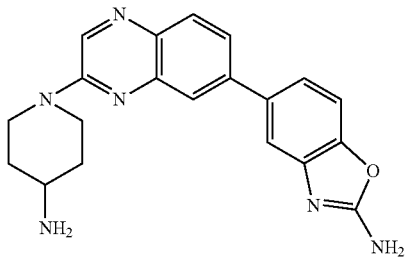 [SMILES: Nc1nc2cc(-c3ccc4ncc(N5CCC(N)CC5)nc4c3)ccc2o1] | | ++++ | +++ | ++ | + | | ++ | Calcd: 360.17 Found: 361.0 [M + H]$^+$ |
| 169 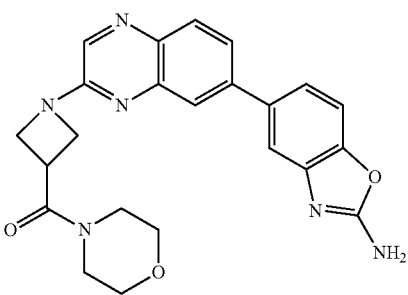 [SMILES: Nc1nc2cc(-c3ccc4ncc(N5CC(C(=O)N6CCOCC6)C5)nc4c3)ccc2o1] | ++ | ++++ | +++ | +++ | +++ | | +++ | Calcd: 430.18 Found: 431.0 [M + H]$^+$ |
| 170 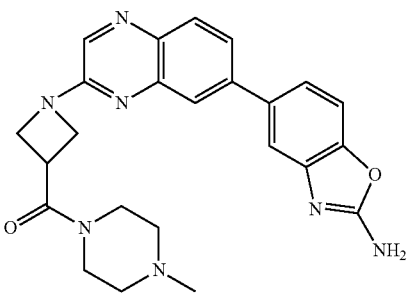 [SMILES: CN1CCN(C(=O)C2CN(c3cnc4ccc(-c5ccc6oc(N)nc6c5)cc4n3)C2)CC1] | ++ | ++++ | +++ | +++ | ++ | | +++ | Calcd: 443.21 Found: 444.2 [M + H]$^+$ |
| 171 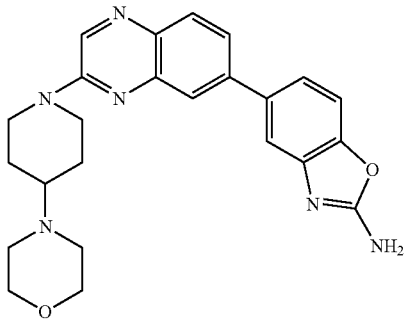 [SMILES: Nc1nc2cc(-c3ccc4ncc(N5CCC(N6CCOCC6)CC5)nc4c3)ccc2o1] | + | ++++ | +++ | +++ | +++ | | +++ | Calcd: 430.21 Found: 431.0 [M + H]$^+$ |
| 172 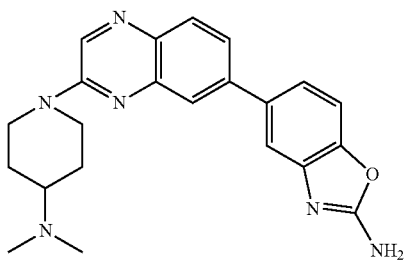 [SMILES: CN(C)C1CCN(c2cnc3ccc(-c4ccc5oc(N)nc5c4)cc3n2)CC1] | | ++++ | ++++ | ++++ | +++ | | | Calcd: 388.20 Found: 389.0 [M + H]$^+$ |

TABLE 3-continued

In Vitro IC$_{50}$ data for selected compounds of the invention.

| | Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | PC3 proliferation (nM)* | T47D proliferation (nM) | Mass Characterization |
|---|---|---|---|---|---|---|---|---|---|
| 173 | 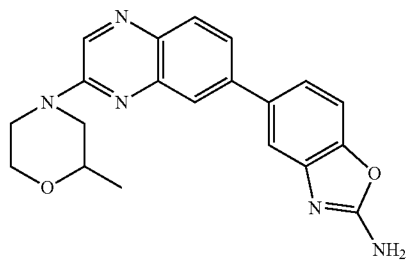 | | ++++ | +++ | ++ | ++++ | | ++ | Calcd: 361.15 Found: 362.0 [M + H]$^+$ |
| 174 | 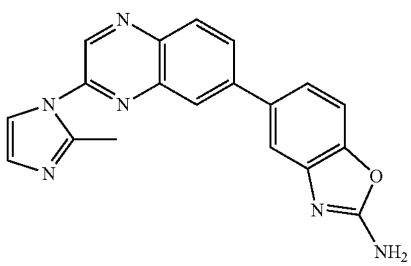 [SMILES: Cc1nccn1-c1cnc2ccc(-c3ccc4oc(N)nc4c3)cc2n1] | | ++++ | +++ | ++ | ++++ | | ++ | Calcd: 342.12 Found: 343.0 [M + H]$^+$ |
| 175 | 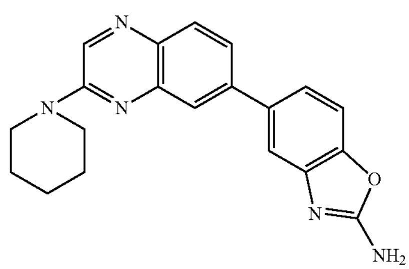 | | ++++ | + | + | ++ | | + | Calcd: 345.16 Found: 346.0 [M + H]$^+$ |
| 176 | 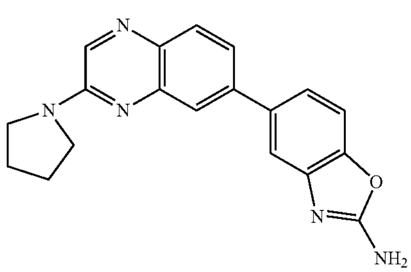 [SMILES: Nc1nc2cc(-c3ccc4ncc(N5CCCC5)nc4c3)ccc2o1] | | ++++ | +++ | +++ | ++++ | | +++ | Calcd: 331.14 Found: 332.0 [M + H]$^+$ |
| 177 | 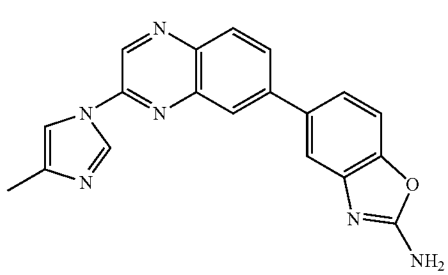 [SMILES: Cc1cn(-c2cnc3ccc(-c4ccc5oc(N)nc5c4)cc3n2)cn1] | | ++++ | + | + | +++ | | + | Calcd: 343.12 Found: 343.0 [M]$^+$ |

TABLE 3-continued

In Vitro IC$_{50}$ data for selected compounds of the invention.

| | Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | PC3 proliferation (nM)* | T47D proliferation (nM) | Mass Characterization |
|---|---|---|---|---|---|---|---|---|---|
| 178 | 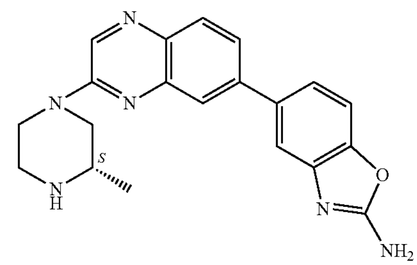 | | ++++ | ++++ | +++ | +++ | | | Calcd: 360.17 Found: 361.0 [M + H]$^+$ |
| 179 | 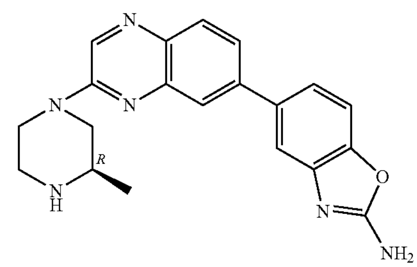 | | ++++ | +++ | ++ | ++ | | ++ | Calcd: 360.17 Found: 361.0 [M + H]$^+$ |
| 180 | 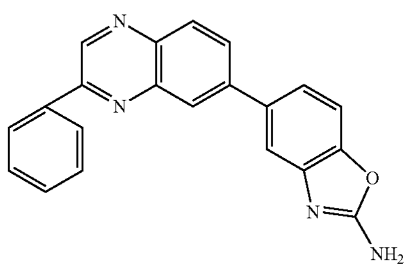 [SMILES: Nc1nc2cc(-c3ccc4ncc(-c5ccccc5)nc4c3)ccc2o1] | | +++ | + | + | + | | | Calcd: 338.12 Found: 339.0 [M + H]$^+$ |
| 181 | 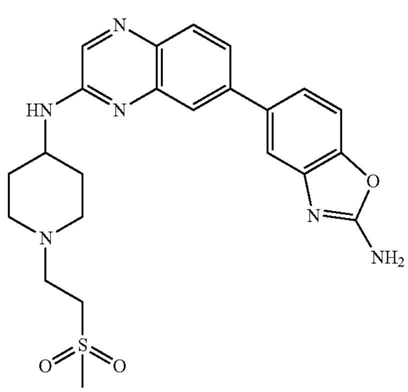 [SMILES: CS(=O)(=O)CCN1CCC(Nc2cnc3ccc(-c4ccc5oc(N)nc5c4)cc3n2)CC1] | | ++++ | ++ | +++ | ++++ | | ++ | Calcd: 466.18 Found: 467.0 [M + H]$^+$ |
| 182 | 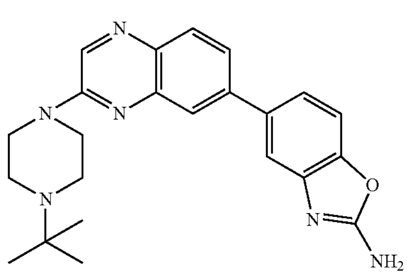 [SMILES: CC(C)(C)N1CCN(c2cnc3ccc(-c4ccc5oc(N)nc5c4)cc3n2)CC1] | | ++++ | +++ | +++ | +++ | | ++ | Calcd: 402.22 Found: 403.2 [M + H]$^+$ |

TABLE 3-continued

In Vitro IC$_{50}$ data for selected compounds of the invention.

| | Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | PC3 proliferation (nM)* | T47D proliferation (nM) | Mass Characterization |
|---|---|---|---|---|---|---|---|---|---|
| 183 | 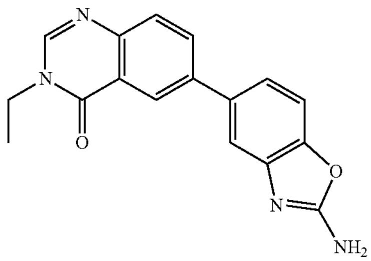 [SMILES: CCn1cnc2ccc(-c3ccc4oc(N)nc4c3)cc2c1=O] | | ++++ | ++ | ++ | ++++ | | ++ | Calcd: 306.11 Found: 307.0 [M + H]$^+$ |
| 184 | 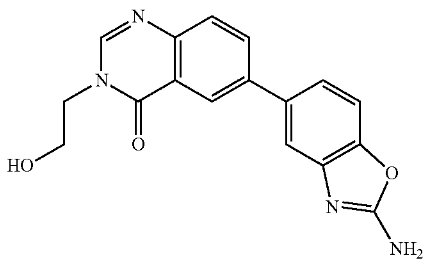 [SMILES: Nc1nc2cc(-c3ccc4ncn(CCO)c(=O)c4c3)ccc2o1] | | ++++ | ++ | + | +++ | | ++ | Calcd: 322.11 Found: 323.0 [M + H]$^+$ |
| 185 | 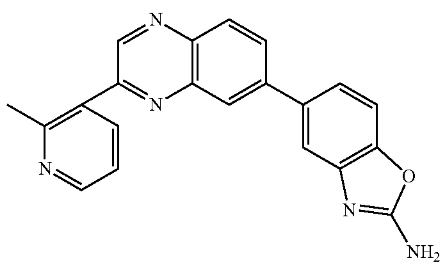 [SMILES: Cc1ncccc1-c1cnc2ccc(-c3ccc4oc(N)nc4c3)cc2n1] | | +++ | + | + | + | | | Calcd: 353.13 Found: 354.0 [M + H]$^+$ |
| 186 | 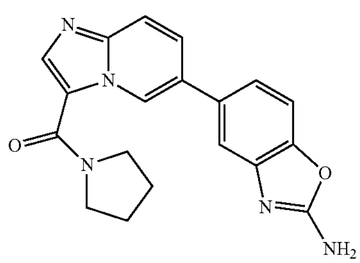 [SMILES: Nc1nc2cc(-c3ccc4ncc(C(=O)N5CCCC5)n4c3)ccc2o1] | | ++++ | ++ | +++ | ++++ | | ++ | Calcd: 347.14 Found: 348.0 [M + H]$^+$ |
| 187 | 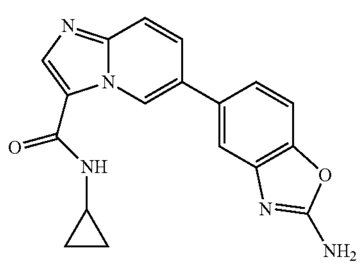 [SMILES: Nc1nc2cc(-c3ccc4ncc(C(=O)NC5CC5)n4c3)ccc2o1] | | ++++ | ++ | +++ | ++++ | | +++ | Calcd: 333.12 Found: 334.0 [M + H]$^+$ |

TABLE 3-continued

In Vitro IC$_{50}$ data for selected compounds of the invention.

| Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | PC3 proliferation (nM)* | T47D proliferation (nM) | Mass Characterization |
|---|---|---|---|---|---|---|---|---|
| 188 | | ++++ | +++ | +++ | ++++ | | +++ | Calcd: 321.12 Found: 322.0 [M + H]$^+$ |
| 189 | | ++++ | +++ | +++ | +++ | | +++ | Calcd: 337.12 Found: 338.0 [M + H]$^+$ |
| 190 | | ++++ | + | +++ | ++++ | | + | Calcd: 370.12 Found: 371.0 [M + H]$^+$ |
| 191 | | ++++ | ++ | ++ | ++ | | | Calcd: 418.21 Found: 419.0 [M + H]$^+$ |
| 192 | | ++++ | +++ | +++ | +++ | | | Calcd: 403.18 Found: 404.0 [M + H]$^+$ |

TABLE 3-continued

In Vitro IC$_{50}$ data for selected compounds of the invention.

| Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | PC3 proliferation (nM)* | T47D proliferation (nM) | Mass Characterization |
|---|---|---|---|---|---|---|---|---|
| 193 | | ++++ | +++ | ++ | ++++ | | | Calcd: 404.16 Found: 405.0 [M + H]$^+$ |
| 194 | | ++++ | + | + | ++++ | | | Calcd: 353.13 Found: 354.0 [M + H]$^+$ |
| 195 | | +++ | ++ | + | ++++ | | | Calcd: 339.11 Found: 340.0 [M + H]$^+$ |
| 196 | | +++ | ++ | + | ++ | | | Calcd: 361.15 Found: 362.0 [M + H]$^+$ |
| 197 | | ++++ | ++ | ++ | ++++ | | | Calcd: 333.12 Found: 334.0 [M + H]$^+$ |

TABLE 3-continued
In Vitro IC$_{50}$ data for selected compounds of the invention.
| | Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | PC3 proliferation (nM)* | T47D proliferation (nM) | Mass Characterization |
|---|---|---|---|---|---|---|---|---|---|
| 198 | 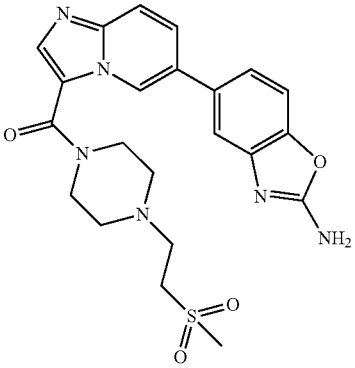 [SMILES: CS(=O)(=O)CCN1CCN(C(=O)c2cnc3ccc(-c4ccc5oc(N)nc5c4)cn23)CC1] | | ++++ | ++ | ++ | +++ | | | Calcd: 468.16 Found: 469.0 [M + H]$^+$ |
| 199 | 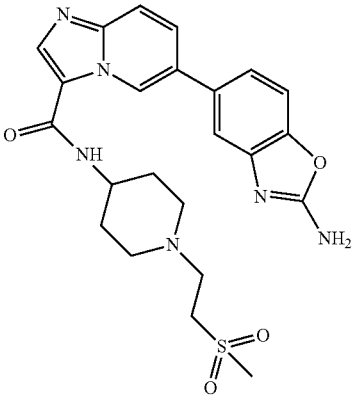 [SMILES: CS(=O)(=O)CCN1CCC(NC(=O)c2cnc3ccc(-c4ccc5oc(N)nc5c4)cn23)CC1] | | ++++ | ++ | ++++ | ++++ | | | Calcd: 482.17 Found: 483.0 [M + H]$^+$ |
| 200 | 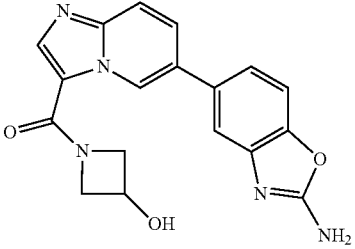 [SMILES: Nc1nc2cc(-c3ccc4ncc(C(=O)N5CC(O)C5)n4c3)ccc2o1] | | ++++ | ++ | ++ | ++++ | | ++ | Calcd: 349.12 Found: 350.0 [M + H]$^+$ |
| 201 | 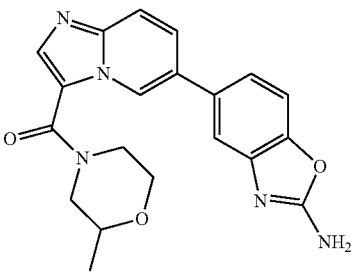 [SMILES: CC1CN(C(=O)c2cnc3ccc(-c4ccc5oc(N)nc5c4)cn23)CCO1] | | ++++ | ++ | + | ++ | | ++ | Calcd: 377.15 Found: 378.0 [M + H]$^+$ |

TABLE 3-continued

In Vitro IC$_{50}$ data for selected compounds of the invention.

| Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | PC3 proliferation (nM)* | T47D proliferation (nM) | Mass Characterization |
|---|---|---|---|---|---|---|---|---|
| 202 | | ++++ | ++ | ++ | +++ | | +++ | Calcd: 363.13 Found: 364.0 [M + H]$^+$ |
| 203 | | ++++ | ++++ | +++ | ++++ | | | Calcd: 391.18 Found: 392.0 [M + H]$^+$ |
| 204 | | ++++ | +++ | + | + | | | Calcd: 376.16 Found: 377.0 [M + H]$^+$ |
| 205 | | ++++ | + | + | + | | | Calcd: 332.13 Found: 333.0 [M + H]$^+$ |
| 206 | | ++++ | + | + | +++ | | | Calcd: 320.13 Found: 321.0 [M + H]$^+$ |

TABLE 3-continued

In Vitro IC₅₀ data for selected compounds of the invention.

| | Structure | mTORC IC₅₀ (nM) | PI3K α IC₅₀ (nM) | PI3K β IC₅₀ (nM) | PI3K δ IC₅₀ (nM) | PI3K γ IC₅₀ (nM) | PC3 proliferation (nM)* | T47D proliferation (nM) | Mass Characterization |
|---|---|---|---|---|---|---|---|---|---|
| 207 | 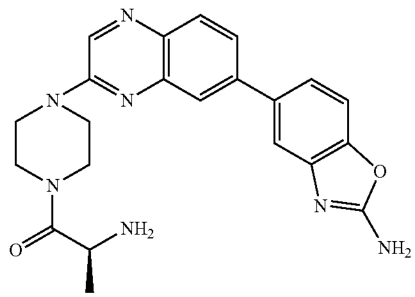 [SMILES: C[C@H](N)C(=O)N1CCN(c2cnc3ccc(-c4ccc5oc(N)nc5c4)cc3n2)CC1] | | ++++ | ++++ | +++ | ++++ | | +++ | Calcd: 417.19 Found: 418.0 [M + H]⁺ |
| 208 | 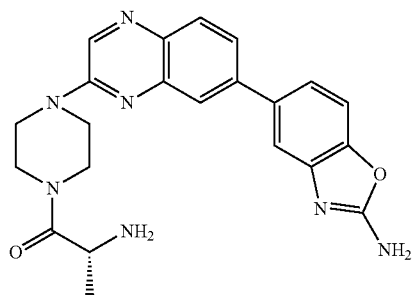 [SMILES: C[C@@H](N)C(=O)N1CCN(c2cnc3ccc(-c4ccc5oc(N)nc5c4)cc3n2)CC1] | | ++++ | +++ | +++ | ++ | | ++ | Calcd: 417.19 Found: 418.0 [M + H]⁺ |
| 209 | 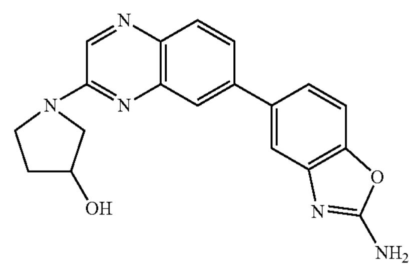 [SMILES: Nc1nc2cc(-c3ccc4ncc(N5CCC(O)C5)nc4c3)ccc2o1] | | ++++ | +++ | ++ | ++++ | | ++ | Calcd: 347.14 Found: 348.0 [M + H]⁺ |
| 210 | 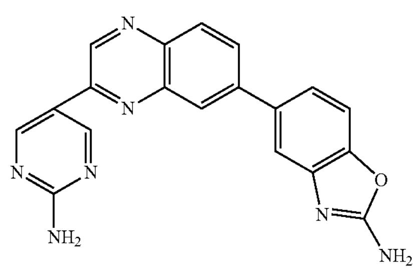 [SMILES: Nc1ncc(-c2cnc3ccc(-c4ccc5oc(N)nc5c4)cc3n2)cn1] | | +++ | + | + | + | | | Calcd: 355.12 Found: 356.0 [M + H]⁺ |
| 211 | 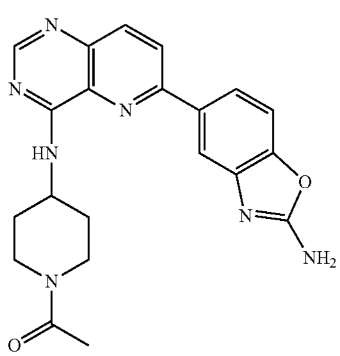 [SMILES: CC(=O)N1CCC(Nc2ncnc3ccc(-c4ccc5oc(N)nc5c4)nc23)CC1] | | ++++ | ++++ | ++++ | ++++ | | +++ | Calcd: 403.18 Found: 404.0 [M + H]⁺ |

TABLE 3-continued

In Vitro IC$_{50}$ data for selected compounds of the invention.

| | Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | PC3 proliferation (nM)* | T47D proliferation (nM) | Mass Characterization |
|---|---|---|---|---|---|---|---|---|---|
| 212 | 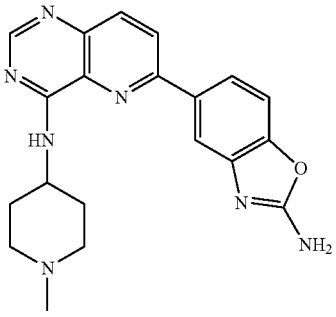 [SMILES: CN1CCC(Nc2ncnc3ccc(-c4ccc5oc(N)nc5c4)nc23)CC1] | | ++++ | +++ | +++ | +++ | | +++ | Calcd: 375.18 Found: 376.0 [M + H]$^+$ |
| 213 | 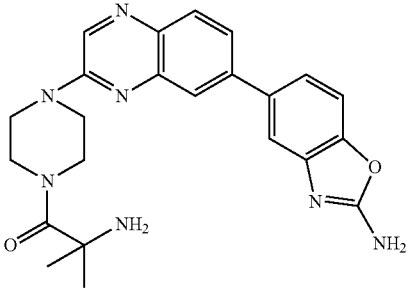 [SMILES: CC(C)(N)C(=O)N1CCN(c2cnc3ccc(-c4ccc5oc(N)nc5c4)cc3n2)CC1] | | ++++ | +++ | +++ | + | | +++ | Calcd: 431.21 Found: 432.0 [M + H]$^+$ |
| 214 | 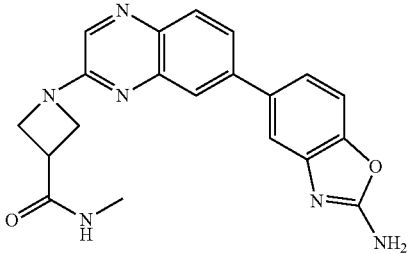 [SMILES: CNC(=O)C1CN(c2cnc3ccc(-c4ccc5oc(N)nc5c4)cc3n2)C1] | | ++++ | ++++ | ++ | +++ | | | Calcd: 374.15 Found: 375.0 [M + H]$^+$ |
| 215 | 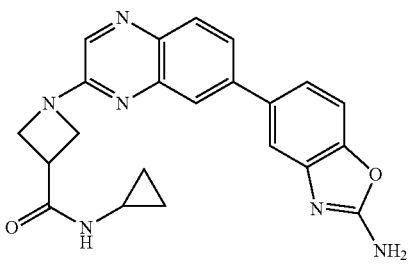 [SMILES: Nc1nc2cc(-c3ccc4ncc(N5CC(C(=O)NC6CC6)C5)nc4c3)ccc2o1] | | ++++ | +++ | ++ | +++ | | | Calcd: 400.16 Found: 401.0 [M + H]$^+$ |
| 216 | 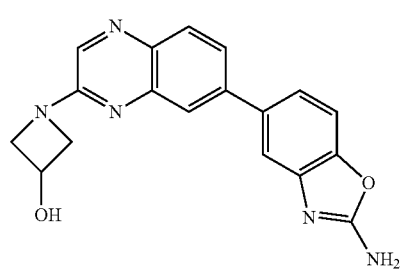 [SMILES: Nc1nc2cc(-c3ccc4ncc(N5CC(O)C5)nc4c3)ccc2o1] | | ++++ | +++ | ++ | ++++ | | | Calcd: 333.12 Found: 334.0 [M + H]$^+$ |

TABLE 3-continued

In Vitro IC$_{50}$ data for selected compounds of the invention.

| | Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | PC3 proliferation (nM)* | T47D proliferation (nM) | Mass Characterization |
|---|---|---|---|---|---|---|---|---|---|
| 217 | 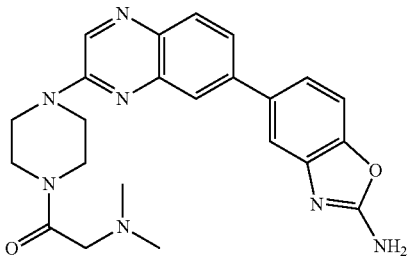 [SMILES: CN(C)CC(=O)N1CCN(c2cnc3ccc(-c4ccc5oc(N)nc5c4)cc3n2)CC1] | | ++++ | +++ | +++ | +++ | | | Calcd: 431.21 Found: 432.0 [M + H]$^+$ |
| 218 | 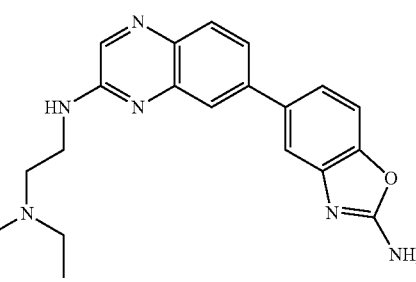 | | +++ | +++ | +++ | ++ | | | Calcd: 376.20 Found: 377.2 [M + H]$^+$ |
| 219 | 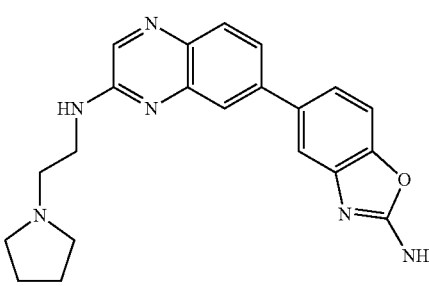 | | +++ | +++ | +++ | +++ | | | Calcd: 374.19 Found: 375.0 [M + H]$^+$ |
| 220 | 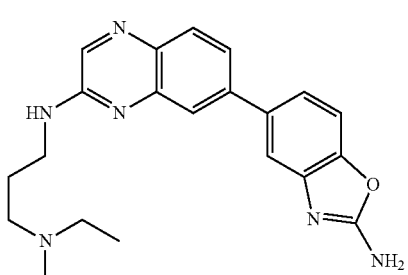 | | ++++ | +++ | ++++ | +++ | | | Calcd: 390.22 Found: 391.2 [M + H]$^+$ |
| 221 | 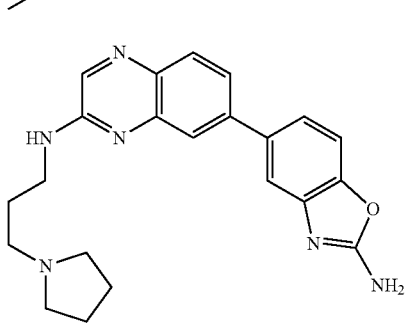 | | ++++ | +++ | ++++ | ++++ | | | Calcd: 388.20 Found: 389.0 [M + H]$^+$ |

TABLE 3-continued

In Vitro IC$_{50}$ data for selected compounds of the invention.

| | Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | PC3 proliferation (nM)* | T47D proliferation (nM) | Mass Characterization |
|---|---|---|---|---|---|---|---|---|---|
| 222 | 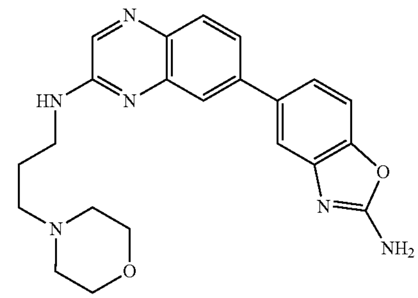 [SMILES: Nc1nc2cc(-c3ccc4ncc(NCCCN5CCOCC5)nc4c3)ccc2o1] | | ++++ | +++ | ++++ | +++ | | | Calcd: 404.20 Found: 405.0 [M + H]$^+$ |
| 223 | 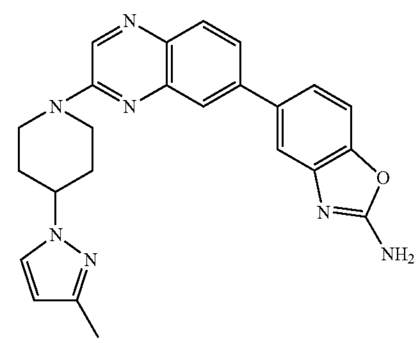 [SMILES: Cc1ccn(C2CCN(c3cnc4ccc(-c5ccc6oc(N)nc6c5)cc4n3)CC2)n1] | | ++++ | + | + | +++ | | | Calcd: 425.20 Found: 426.0 [M + H]$^+$ |
| 224 | 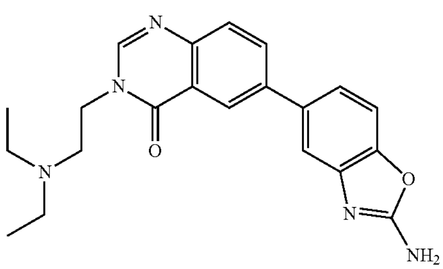 [SMILES: CCN(CC)CCn1cnc2ccc(-c3ccc4oc(N)nc4c3)cc2c1=O] | | ++ | + | + | + | | | Calcd: 377.19 Found: 378.0 [M + H]$^+$ |
| 225 | 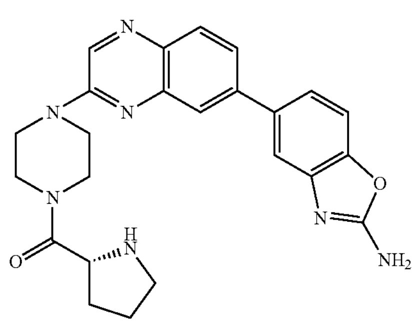 [SMILES: Nc1nc2cc(-c3ccc4ncc(N5CCN(C(=O)[C@H]6CCCN6)CC5)nc4c3)ccc2o1] | | ++++ | ++++ | ++++ | ++++ | | | Calcd: 443.21 Found: 444.0 [M + H]$^+$ |

TABLE 3-continued

In Vitro IC$_{50}$ data for selected compounds of the invention.

| Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | PC3 proliferation (nM)* | T47D proliferation (nM) | Mass Characterization |
|---|---|---|---|---|---|---|---|---|
| 226 | | +++ | + | ++ | ++ | | | Calcd: 429.19 Found: 430.2 [M + H]$^+$ |
| 227 | | ++++ | +++ | ++++ | ++ | | | Calcd: 443.24 Found: 444.0 [M + H]$^+$ |
| 228 | | | | | | | | Calcd: 347.14 Found: 348.0 [M + H]$^+$ |
| 229 | | +++ | +++ | + | ++ | | | Calcd: 328.11 Found: 329.0 [M + H]$^+$ |
| 230 | | ++ | +++ | ++ | +++ | | | Calcd: 328.11 Found: 329.0 [M + H]$^+$ |

TABLE 3-continued

In Vitro IC$_{50}$ data for selected compounds of the invention.

| Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | PC3 proliferation (nM)* | T47D proliferation (nM) | Mass Characterization |
|---|---|---|---|---|---|---|---|---|
| 231 | ++ | ++++ | +++ | ++++ | ++++ | ++ | +++ | Calcd: 324.07 Found: 325.0 [M + H]$^+$ |
| 232 | ++ | +++ | +++ | ++ | ++++ | | | Calcd: 282.06 Found: 283.0 [M + H]$^+$ |
| 233 | + | + | + | + | ++ | | | Calcd: 227.08 Found: 228.0 [M + H]$^+$ |
| 234 | +++ | ++++ | +++ | ++++ | ++++ | ++++ | +++ | Calcd: 307.11 Found: 308.0 [M + H]$^+$ |
| 235 | ++ | ++ | + | ++ | ++ | | | Calcd: 274.05 Found: 275.0 [M + H]$^+$ |
| 236 | + | + | + | | + | | | Calcd: 265.10 Found: 266.0 [M + H]$^+$ |
| 237 | +++ | ++ | ++ | | ++ | | | Calcd: 285.12 Found: 286.0 [M + H]$^+$ |
| 238 | | +++ | +++ | ++ | +++ | | | Calcd: 257.09 Found: 258.0 [M + H]$^+$ |

TABLE 3-continued

In Vitro IC$_{50}$ data for selected compounds of the invention.

| | Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | PC3 proliferation (nM)* | T47D proliferation (nM) | Mass Characterization |
|---|---|---|---|---|---|---|---|---|---|
| 239 | 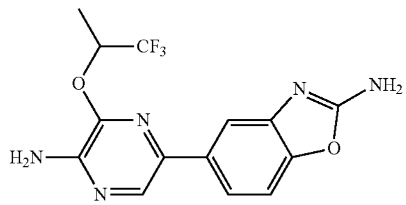 | | ++ | +++ | ++ | ++ | | | Calcd: 339.09 Found: 340.0 [M + H]$^+$ |
| 240 | 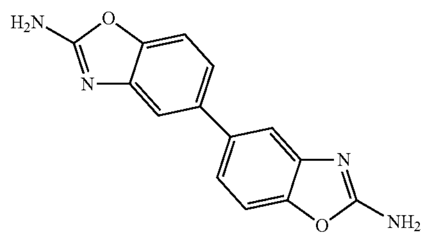 [SMILES: Nc1nc2cc(-c3ccc4oc(N)nc4c3)ccc2o1] | ++ | +++ | | ++ | ++++ | | | Calcd: 266.08 Found: 267.0 [M + H]$^+$ |
| 241 | 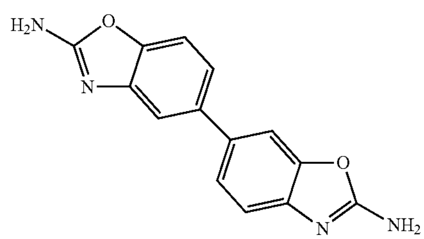 [SMILES: Nc1nc2cc(-c3ccc4nc(N)oc4c3)ccc2o1] | ++ | +++ | | +++ | ++++ | | | Calcd: 266.08 Found: 267.0 [M + H]$^+$ |
| 242 | 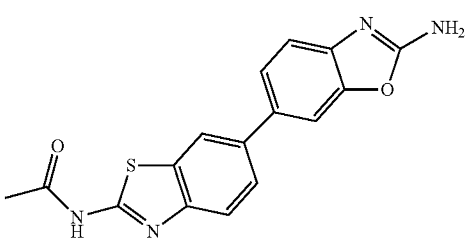 [SMILES: CC(=O)Nc1nc2ccc(-c3ccc4nc(N)oc4c3)cc2s1] | ++++ | ++++ | | + | ++++ | | | Calcd: 324.07 Found: 325.0 [M + H]$^+$ |
| 243 | 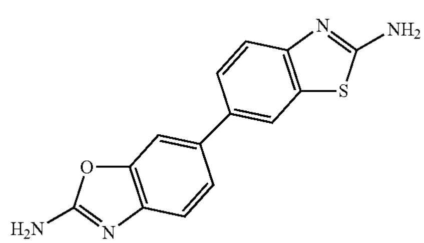 [SMILES: Nc1nc2ccc(-c3ccc4nc(N)sc4c3)cc2o1] | +++ | ++++ | | + | ++++ | | | Calcd: 282.06 Found: 283.0 [M + H]$^+$ |
| 244 | 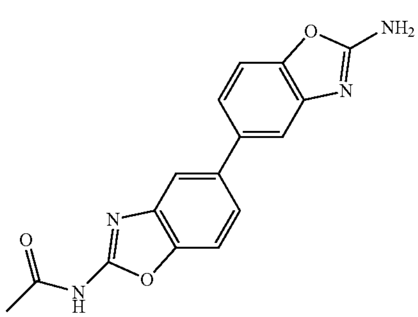 [SMILES: CC(=O)Nc1nc2cc(-c3ccc4oc(N)nc4c3)ccc2o1] | + | + | | + | + | | | Calcd: 308.09 Found: 309.0 [M + H]$^+$ |

TABLE 3-continued

In Vitro IC$_{50}$ data for selected compounds of the invention.

| Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | PC3 proliferation (nM)* | T47D proliferation (nM) | Mass Characterization |
|---|---|---|---|---|---|---|---|---|
| 245 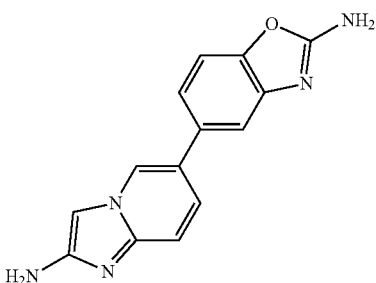 | | +++ | ++ | + | +++ | | | Calcd: 265.10 Found: 266.0 |
| 246 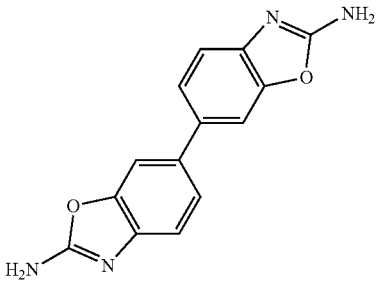 [SMILES: Nc1nc2ccc(-c3ccc4nc(N)oc4c3)cc2o1] | | + | + | + | + | | | Calcd: 266.08 Found: 267.0 [M + H]$^+$ |
| 247 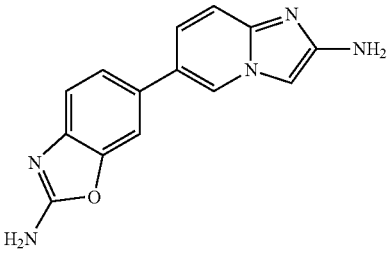 [SMILES: Nc1cn2cc(-c3ccc4nc(N)oc4c3)ccc2n1] | | + | ++ | + | ++ | | | Calcd: 265.10 Found: 266.2 [M + H]$^+$ |
| 248 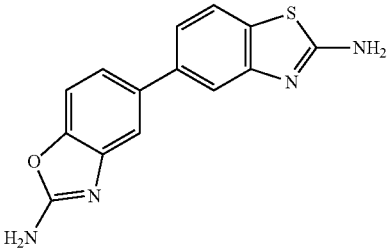 [SMILES: Nc1nc2cc(-c3ccc4sc(N)nc4c3)ccc2o1] | | ++ | +++ | ++ | +++ | | ++ | Calcd: 282.06 Found: 283.0 [M + H]$^+$ |
| 249 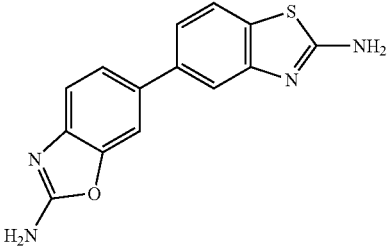 [SMILES: Nc1nc2ccc(-c3ccc4sc(N)nc4c3)cc2o1] | | ++++ | ++++ | +++ | ++++ | | | Calcd: 282.06 Found: 283.0 [M + H]$^+$ |

TABLE 3-continued

In Vitro IC$_{50}$ data for selected compounds of the invention.

| | Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | PC3 proliferation (nM)* | T47D proliferation (nM) | Mass Characterization |
|---|---|---|---|---|---|---|---|---|---|
| 250 | 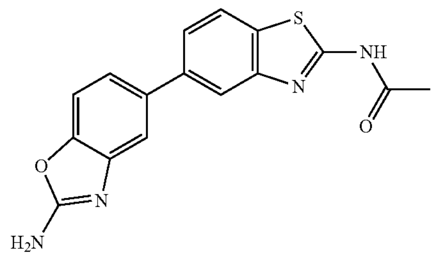 [SMILES: CC(=O)Nc1nc2cc(-c3ccc4oc(N)nc4c3)ccc2s1] | | + | + | + | ++++ | | | Calcd: 324.07 Found: 325.0 [M + H]$^+$ |
| 251 | 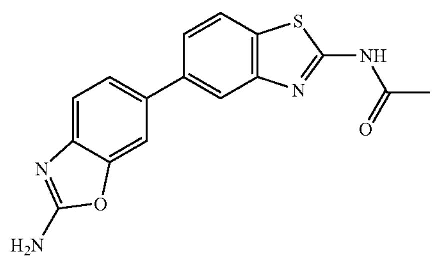 [SMILES: CC(=O)Nc1nc2cc(-c3ccc4nc(N)oc4c3)ccc2s1] | | ++++ | ++++ | ++++ | ++++ | | | Calcd: 324.07 Found: 325.0 [M + H]$^+$ |
| 252 | 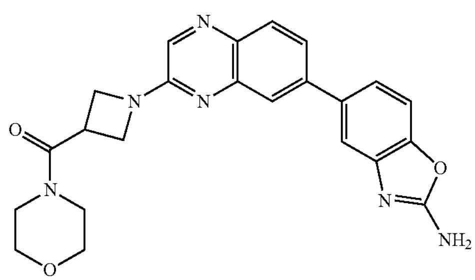 [SMILES: Nc1nc2cc(-c3ccc4ncc(N5CC(C(=O)N6CCOCC6)C5)nc4c3)ccc2o1] | | + | ++ | ++ | ++ | | | |
| 253 | 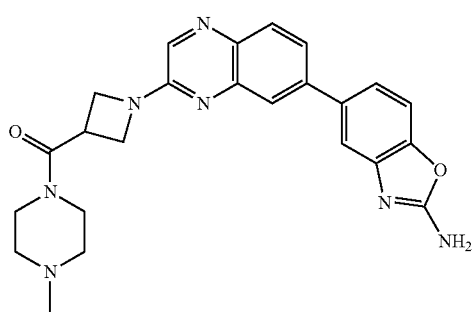 [SMILES: CN1CCN(C(=O)C2CN(c3cnc4ccc(-c5ccc6oc(N)nc6c5)cc4n3)C2)CC1] | | + | ++ | ++ | ++ | | | |
| 254 | 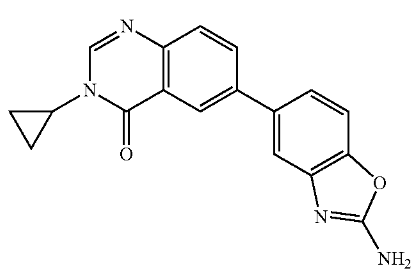 [SMILES: Nc1nc2cc(-c3ccc4ncn(C5CC5)c(=O)c4c3)ccc2o1] | | +++ | + | + | +++ | | | Calcd: 318.11 Found: 319.0 [M + H]$^+$ |

TABLE 3-continued

In Vitro IC$_{50}$ data for selected compounds of the invention.

| | Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | PC3 proliferation (nM)* | T47D proliferation (nM) | Mass Characterization |
|---|---|---|---|---|---|---|---|---|---|
| 255 | 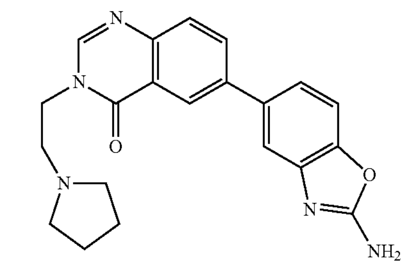 [SMILES: Nc1nc2cc(-c3ccc4ncn(CCN5CCCC5)c(=O)c4c3)ccc2o1] | | ++ | ++ | ++ | ++ | | | Calcd: 375.17 Found: 376.0 [M + H]$^+$ |
| 256 | 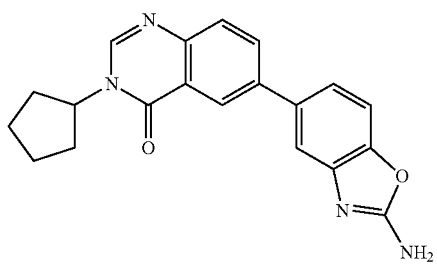 [SMILES: Nc1nc2cc(-c3ccc4ncn(C5CCCC5)c(=O)c4c3)ccc2o1] | | ++ | + | + | + | | | Calcd: 346.14 Found: 347.0 [M + H]$^+$ |
| 257 | 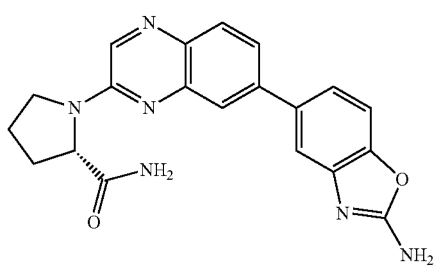 [SMILES: NC(=O)[C@@H]1CCCN1c1cnc2ccc(-c3ccc4oc(N)nc4c3)cc2n1] | | ++++ | + | + | + | | ++ | Calcd: 374.15 Found: 375.0 [M + H]$^+$ |
| 258 | 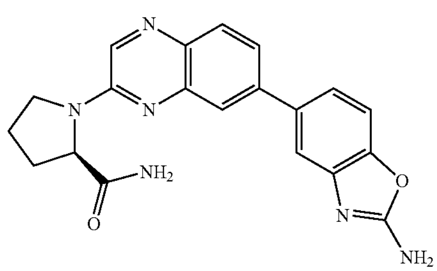 [SMILES: NC(=O)[C@H]1CCCN1c1cnc2ccc(-c3ccc4oc(N)nc4c3)cc2n1] | | ++++ | ++++ | + | ++++ | | +++ | Calcd: 390.14 Found: 391.0 [M + H]$^+$ |
| 259 | 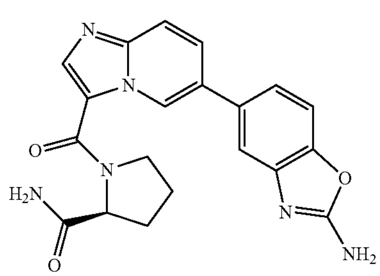 [SMILES: NC(=O)[C@@H]1CCCN1C(=O)c1cnc2ccc(-c3ccc4oc(N)nc4c3)cn12] | | +++ | + | + | ++ | | | Calcd: 390.14 Found: 391.0 [M + H]$^+$ |

TABLE 3-continued

In Vitro IC$_{50}$ data for selected compounds of the invention.

| | Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | PC3 proliferation (nM)* | T47D proliferation (nM) | Mass Characterization |
|---|---|---|---|---|---|---|---|---|---|
| 260 | 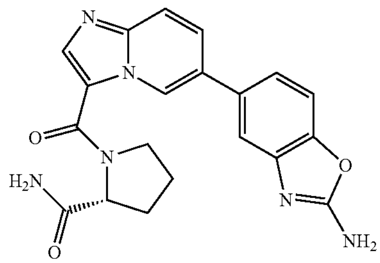 [SMILES: NC(=O)[C@H]1CCCN1C(=O)c1cnc2ccc(-c3ccc4oc(N)nc4c3)cn12] | | +++ | + | + | ++ | | | Calcd: 390.14 Found: 391.0 [M + H]$^+$ |
| 261 | 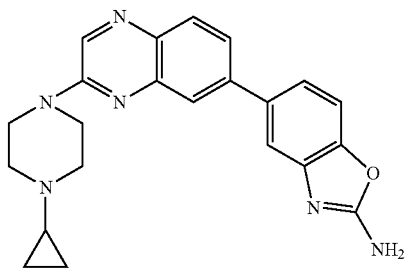 [SMILES: Nc1nc2cc(-c3ccc4ncc(N5CCN(C6CC6)CC5)nc4c3)ccc2o1] | | ++++ | +++ | + | +++ | | ++ | Calcd: 386.19 Found: 387.0 [M + H]$^+$ |
| 262 | 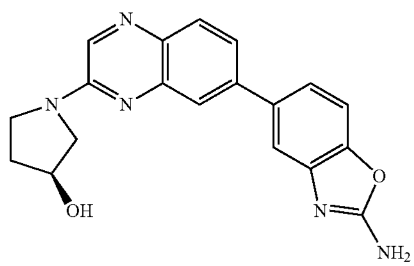 | ++ | ++++ | +++ | + | +++ | | ++ | Calcd: 347.14 Found: 348.0 [M + H]$^+$ |
| 263 | 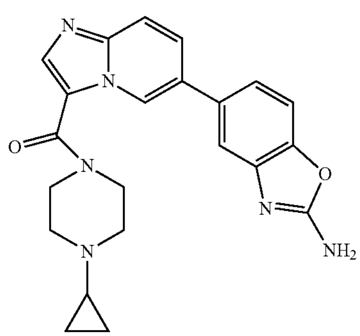 [SMILES: Nc1nc2cc(-c3ccc4ncc(C(=O)N5CCN(C6CC6)CC5)n4c3)ccc2o1] | | ++++ | ++ | ++ | ++ | | ++ | Calcd: 402.18 Found: 403.0 [M + H]$^+$ |
| 264 | 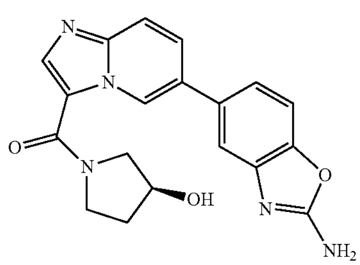 [SMILES: Nc1nc2cc(-c3ccc4ncc(C(=O)N5CC[C@H](O)C5)n4c3)ccc2o1] | | ++++ | ++ | ++ | +++ | | +++ | Calcd: 363.13 Found: 364.0 [M + H]$^+$ |

TABLE 3-continued

In Vitro IC$_{50}$ data for selected compounds of the invention.

| Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | PC3 proliferation (nM)* | T47D proliferation (nM) | Mass Characterization |
|---|---|---|---|---|---|---|---|---|
| 265 | | ++++ | ++ | ++ | ++++ | | +++ | Calcd: 363.13 Found: 364.0 [M + H]$^+$ |
| 266 | | ++++ | ++ | +++ | +++ | | ++ | Calcd: 418.18 Found: 419.2 [M + H]$^+$ |
| 267 | ++ | ++++ | ++ | +++ | +++ | +++ | +++ | Calcd: 443.21 Found: 444.2 [M + H]$^+$ |
| 268 | | ++++ | ++ | ++ | +++ | | +++ | Calcd: 443.21 Found: 444.2 [M + H]$^+$ |

TABLE 3-continued

In Vitro IC$_{50}$ data for selected compounds of the invention.

| | Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | PC3 proliferation (nM)* | T47D proliferation (nM) | Mass Characterization |
|---|---|---|---|---|---|---|---|---|---|
| 269 | 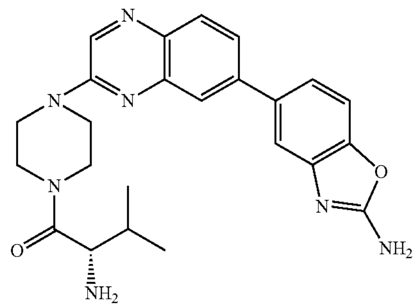 [SMILES: CC(C)[C@H](N)C(=O)N1CCN(c2cnc3ccc(-c4ccc5oc(N)nc5c4)cc3n2)CC1] | | ++++ | +++ | +++ | ++ | | ++ | Calcd: 445.22 Found: 446.2 [M + H]$^+$ |
| 270 | 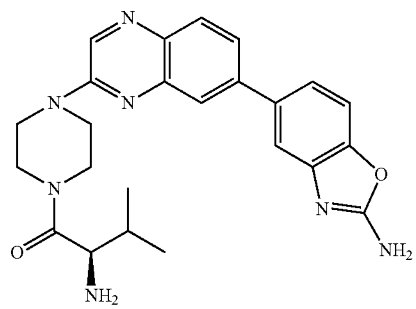 [SMILES: CC(C)[C@@H](N)C(=O)N1CCN(c2cnc3ccc(-c4ccc5oc(N)nc5c4)cc3n2)CC1] | ++ | ++++ | +++ | +++ | +++ | | +++ | Calcd: 445.22 Found: 446.2 [M + H]$^+$ |
| 271 | 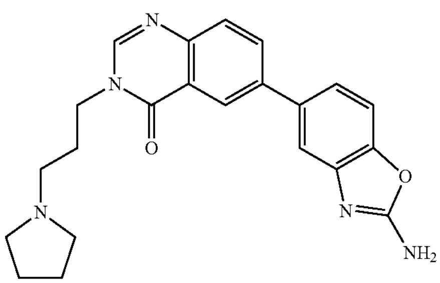 [SMILES: Nc1nc2cc(-c3ccc4ncn(CCCN5CCCC5)c(=O)c4c3)ccc2o1] | | +++ | ++ | ++ | + | | | Calcd: 389.19 Found: 390.2 [M + H]$^+$ |
| 272 | 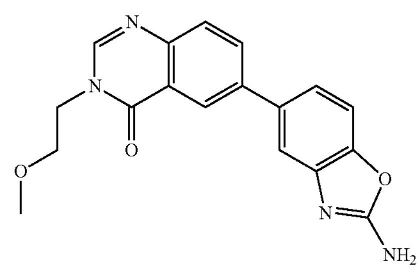 [SMILES: COCCn1cnc2ccc(-c3ccc4oc(N)nc4c3)cc2c1=O] | | +++ | ++ | + | ++ | | | Calcd: 336.12 Found: 337.0 [M + H]$^+$ |
| 273 | 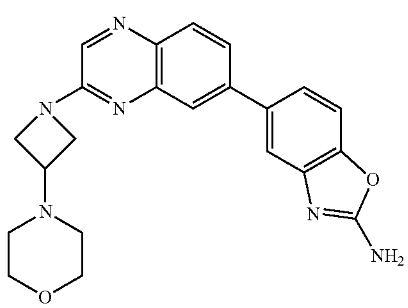 | +++ | ++++ | + | + | ++ | | +++ | Calcd: 402.18 Found: 403.0 [M + H]$^+$ |

TABLE 3-continued

In Vitro IC$_{50}$ data for selected compounds of the invention.

| Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | PC3 proliferation (nM)* | T47D proliferation (nM) | Mass Characterization |
|---|---|---|---|---|---|---|---|---|
| 274 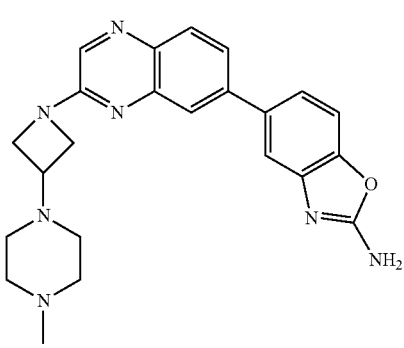 [SMILES: CN1CCN(C2CN(c3cnc4ccc(-c5ccc6oc(N)nc6c5)cc4n3)C2)CC1] | ++ | ++++ | ++ | ++ | ++ | | +++ | Calcd: 415.21 Found: 416.2 [M + H]$^+$ |
| 275 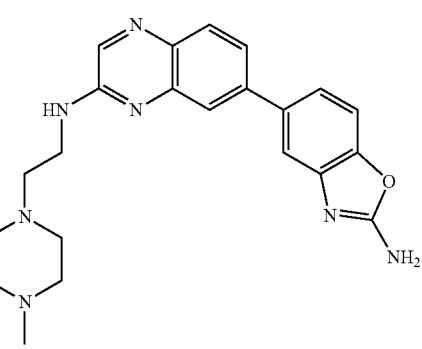 | | ++++ | +++ | +++ | +++ | | +++ | Calcd: 403.21 Found: 404.0 [M + H]$^+$ |
| 276 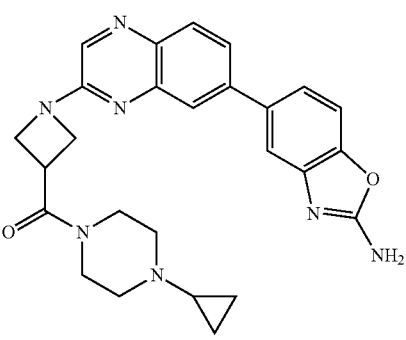 [SMILES: Nc1nc2cc(-c3ccc4ncc(N5CC(C(=O)N6CCN(C7CC7)CC6)C5)nc4c3)ccc2o1] | ++ | ++++ | ++ | +++ | +++ | | +++ | Calcd: 469.22 Found: 470.2 [M + H]$^+$ |
| 277 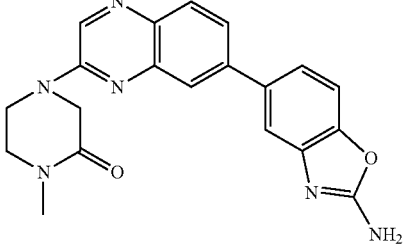 | ++ | ++++ | +++ | ++ | +++ | | +++ | Calcd: 374.15 Found: 375.0 [M + H]$^+$ |

TABLE 3-continued

In Vitro IC$_{50}$ data for selected compounds of the invention.

| Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | PC3 proliferation (nM)* | T47D proliferation (nM) | Mass Characterization |
|---|---|---|---|---|---|---|---|---|
| 278 | | ++++ | +++ | ++ | +++ | | +++ | Calcd: 457.22 Found: 458.2 [M + H]$^+$ |
| 279 | | ++++ | ++ | ++ | ++ | | +++ | Calcd: 459.24 Found: 460.2 [M + H]$^+$ |
| 280 | | ++ | + | + | + | | | Calcd: 404.20 Found: 405.2 [M + H]$^+$ |
| 281 | | +++ | + | ++ | + | | | Calcd: 391.20 Found: 392.2 [M + H]$^+$ |
| 282 | | + | + | + | + | | + | Calcd: 364.13 Found: 365.0 [M + H]$^+$ |

TABLE 3-continued

In Vitro IC$_{50}$ data for selected compounds of the invention.

| | Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | PC3 proliferation (nM)* | T47D proliferation (nM) | Mass Characterization |
|---|---|---|---|---|---|---|---|---|---|
| 283 | 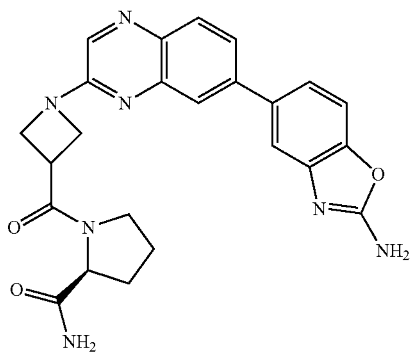 [SMILES: NC(=O)[C@@H]1CCCN1C(=O)C1CN(c2cnc3ccc(-c4ccc5oc(N)nc5c4)cc3n2)C1] | | ++++ | + | + | +++ | | ++ | Calcd: 457.19 Found: 458.0 [M + H]$^+$ |
| 284 | 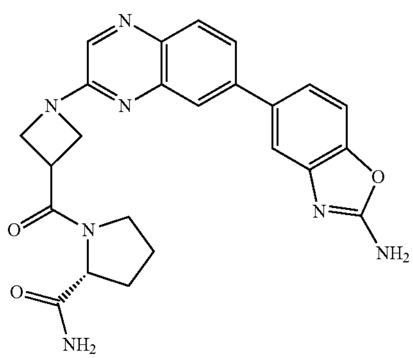 [SMILES: NC(=O)[C@H]1CCCN1C(=O)C1CN(c2cnc3ccc(-c4ccc5oc(N)nc5c4)cc3n2)C1] | | ++++ | ++ | ++ | +++ | | ++ | Calcd: 457.19 Found: 458.0 [M + H]$^+$ |
| 285 | 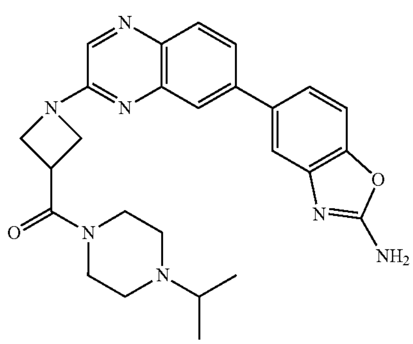 [SMILES: CC(C)N1CCN(C(=O)C2CN(c3cnc4ccc(-c5ccc6oc(N)nc6c5)cc4n3)C2)CC1] | | ++++ | ++ | +++ | +++ | | +++ | Calcd: 471.24 Found: 472.2 [M + H]$^+$ |
| 286 | 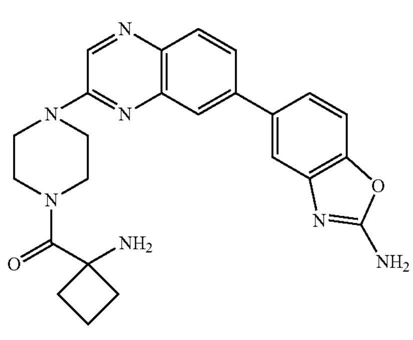 [SMILES: Nc1nc2cc(-c3ccc4ncc(N5CCN(C(=O)C6(N)CCC6)CC5)nc4c3)ccc2o1] | | ++++ | +++ | +++ | ++++ | | +++ | Calcd: 443.21 Found: 444.2 [M + H]$^+$ |

TABLE 3-continued

In Vitro IC$_{50}$ data for selected compounds of the invention.

| Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | PC3 proliferation (nM)* | T47D proliferation (nM) | Mass Characterization |
|---|---|---|---|---|---|---|---|---|
| 287 | | ++++ | ++ | +++ | +++ | | ++ | Calcd: 483.24 Found: 484.2 [M + H]$^+$ |
| 288 | | +++ | +++ | +++ | ++ | | ++ | Calcd: 420.19 Found: 421.2 [M + H]$^+$ |
| 289 | | +++ | ++ | + | +++ | | | Calcd: 391.16 Found: 392.0 [M + H]$^+$ |
| 290 | | +++ | + | + | + | | | Calcd: 405.18 Found: 406.2 [M + H]$^+$ |

TABLE 3-continued
In Vitro IC$_{50}$ data for selected compounds of the invention.
| Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | PC3 proliferation (nM)* | T47D proliferation (nM) | Mass Characterization |
|---|---|---|---|---|---|---|---|---|
| 291 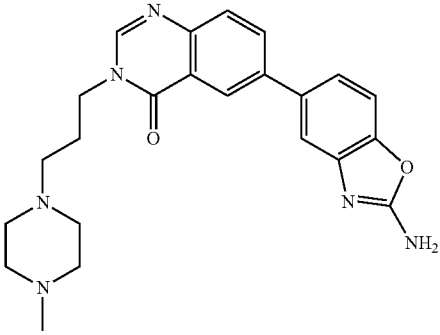 [SMILES: CN1CCN(CCCn2cnc3ccc(-c4ccc5oc(N)nc5c4)cc3c2=O)CC1] | | +++ | + | + | + | | | Calcd: 418.21 Found: 419.0 [M + H]$^+$ |
| 292 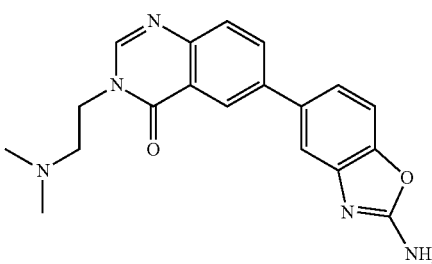 | | ++ | + | + | + | | | Calcd: 349.15 Found: 350.0 [M + H]$^+$ |
| 293 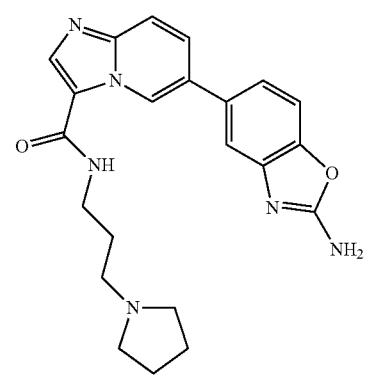 [SMILES: Nc1nc2cc(-c3ccc4ncc(C(=O)NCCCN5CCCC5)n4c3)ccc2o1] | | ++++ | +++ | ++++ | +++ | | +++ | Calcd: 404.20 Found: 405.0 [M + H]$^+$ |
| 294 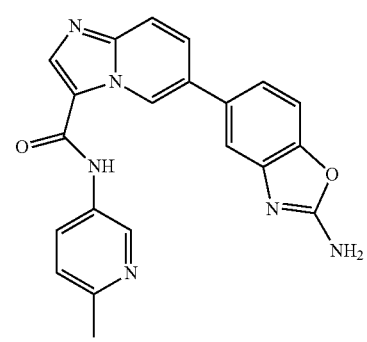 [SMILES: Cc1ccc(NC(=O)c2cnc3ccc(-c4ccc5oc(N)nc5c4)cn23)cn1] | | ++++ | + | ++ | ++++ | | ++ | Calcd: 384.13 Found: 385.0 [M + H]$^+$ |

TABLE 3-continued

In Vitro IC$_{50}$ data for selected compounds of the invention.

| | Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | PC3 proliferation (nM)* | T47D proliferation (nM) | Mass Characterization |
|---|---|---|---|---|---|---|---|---|---|
| 295 | 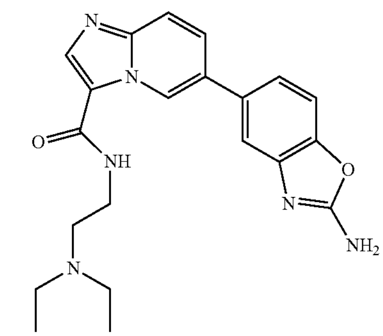 [SMILES: CCN(CC)CCNC(=O)c1cnc2ccc(-c3ccc4oc(N)nc4c3)cn12] | | +++ | +++ | +++ | +++ | | | Calcd: 392.20 Found: 393.0 [M + H]$^+$ |
| 296 | 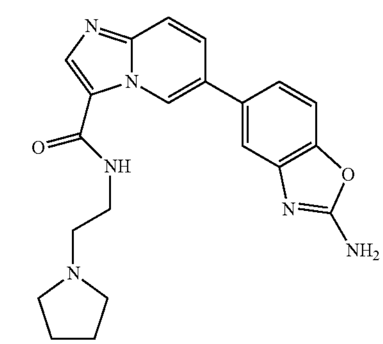 [SMILES: Nc1nc2cc(-c3ccc4ncc(C(=O)NCCN5CCCC5)n4c3)ccc2o1] | | +++ | ++ | +++ | + | | | Calcd: 390.18 Found: 391.0 [M + H]$^+$ |
| 297 | 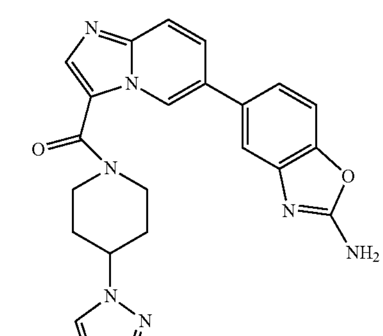 | | +++ | + | + | ++ | | | Calcd: 441.19 Found: 442.0 [M + H]$^+$ |
| 298 | 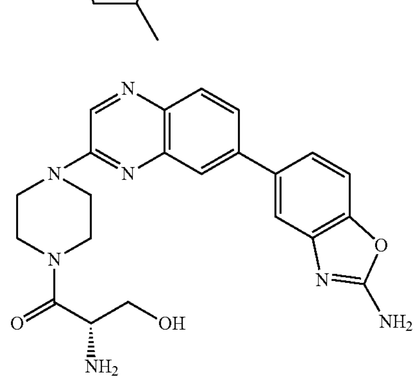 | ++ | ++++ | +++ | ++ | ++ | | ++ | Calcd: 433.19 Found: 434.0 [M + H]$^+$ |

TABLE 3-continued
In Vitro IC$_{50}$ data for selected compounds of the invention.
| Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | PC3 proliferation (nM)* | T47D proliferation (nM) | Mass Characterization |
|---|---|---|---|---|---|---|---|---|
| 299 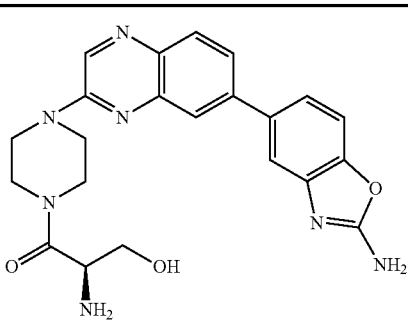 | | ++++ | +++ | ++++ | ++++ | | +++ | Calcd: 433.19 Found: 434.0 [M + H]$^+$ |
| 300 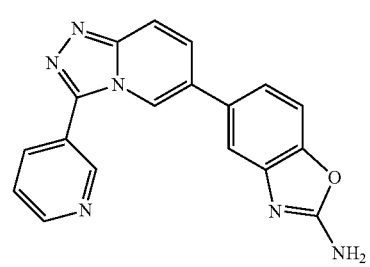 [SMILES: Nc1nc2cc(-c3ccc4nnc(-c5cccnc5)n4c3)ccc2o1] | | ++ | ++ | + | + | | | Calcd: 328.11 Found: 329.0 [M + H]$^+$ |
| 301 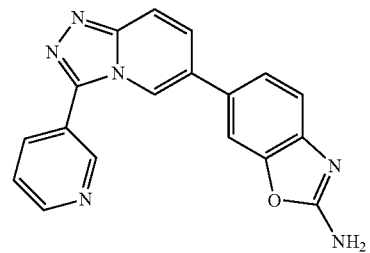 [SMILES: Nc1nc2ccc(-c3ccc4nnc(-c5cccnc5)n4c3)cc2o1] | | ++ | ++ | + | + | | | Calcd: 328.11 Found: 329.0 [M + H]$^+$ |
| 302 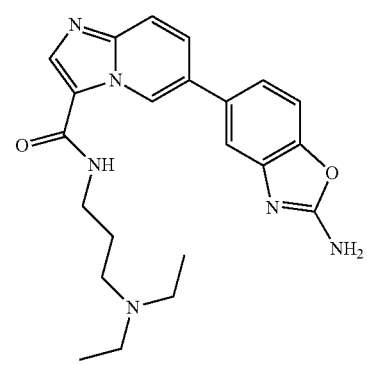 [SMILES: CCN(CC)CCCNC(=O)c1cnc2ccc(-c3ccc4oc(N)nc4c3)cn12] | | +++ | ++ | ++++ | ++ | | | Calcd: 406.21 Found: 407.2 [M + H]$^+$ |

TABLE 3-continued

In Vitro IC$_{50}$ data for selected compounds of the invention.

| | Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | PC3 proliferation (nM)* | T47D proliferation (nM) | Mass Characterization |
|---|---|---|---|---|---|---|---|---|---|
| 303 | 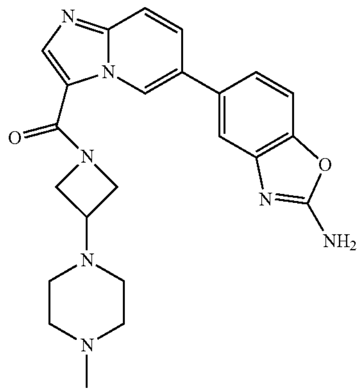 [SMILES: CN1CCN(C2CN(C(=O)c3cnc4ccc(-c5ccc6oc(N)nc6c5)cn34)C2)CC1] | ++ | ++++ | + | ++ | + | | +++ | Calcd: 431.21 Found: 432.2 [M + H]$^+$ |
| 304 | 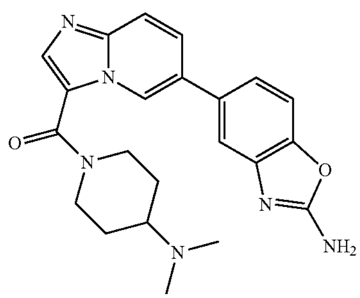 [SMILES: CN(C)C1CCN(C(=O)c2cnc3ccc(-c4ccc5oc(N)nc5c4)cn23)CC1] | | +++ | + | + | + | | | Calcd: 404.20 Found: 405.2 [M + H]$^+$ |
| 305 | 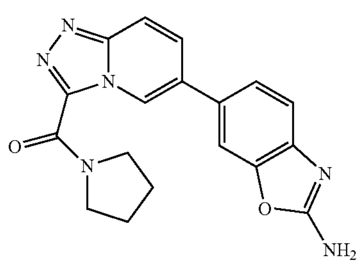 [SMILES: Nc1nc2ccc(-c3ccc4nnc(C(=O)N5CCCC5)n4c3)cc2o1] | | ++ | + | + | + | | | Calcd: 348.13 Found: 349.0 [M + H]$^+$ |
| 306 | 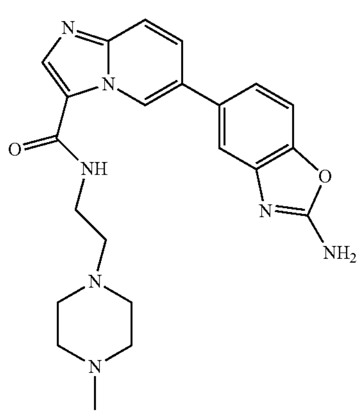 [SMILES: CN1CCN(CCNC(=O)c2cnc3ccc(-c4ccc5oc(N)nc5c4)cn23)CC1] | | ++++ | +++ | +++ | +++ | | | Calcd: 419.21 Found: 420.0 [M + H]$^+$ |

TABLE 3-continued

In Vitro IC₅₀ data for selected compounds of the invention.

| | Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | PC3 proliferation (nM)* | T47D proliferation (nM) | Mass Characterization |
|---|---|---|---|---|---|---|---|---|---|
| 307 | 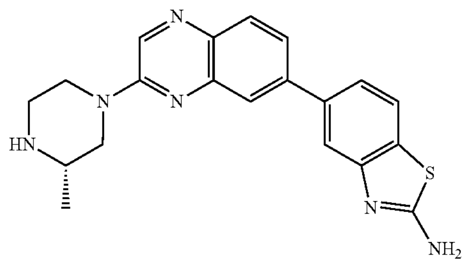 [SMILES: C[C@H]1CN(c2cnc3ccc(-c4ccc5sc(N)nc5c4)cc3n2)CCN1] | | +++ | +++ | + | + | | | Calcd: 376.15 Found: 377.0 [M + H]⁺ |
| 308 | 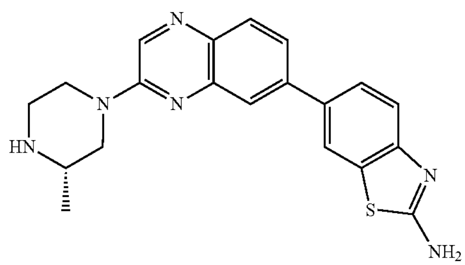 | | +++ | +++ | + | ++ | | | Calcd: 376.15 Found: 377.0 [M + H]⁺ |
| 309 | 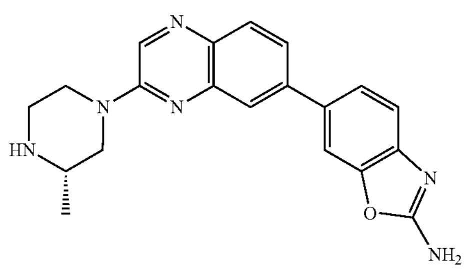 | | +++ | +++ | + | ++ | | | Calcd: 360.17 Found: 361.0 [M + H]⁺ |
| 310 | 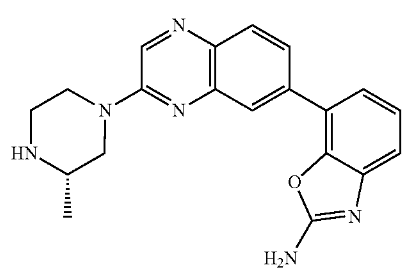 [SMILES: C[C@H]1CN(c2cnc3ccc(-c4cccc5nc(N)oc45)cc3n2)CCN1] | | + | + | + | + | | | Calcd: 360.17 Found: 361.2 [M + H]⁺ |
| 311 | 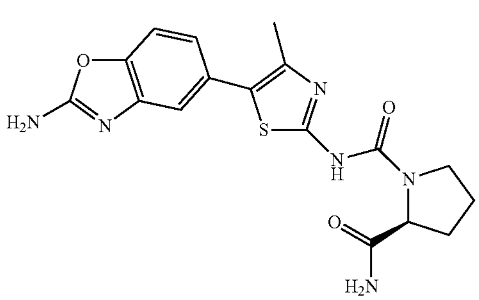 [SMILES: Cc1nc(NC(=O)N2CCC[C@H]2C(N)=O)sc1-c1ccc2oc(N)nc2c1] | | +++ | + | + | + | | | Calcd: 386.12 Found: 387.0 [M + H]⁺ |

TABLE 3-continued

In Vitro IC$_{50}$ data for selected compounds of the invention.

| | Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | PC3 proliferation (nM)* | T47D proliferation (nM) | Mass Characterization |
|---|---|---|---|---|---|---|---|---|---|
| 312 | 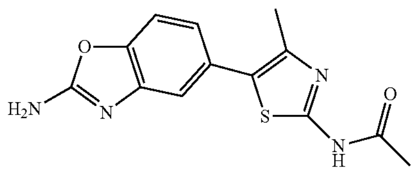 [SMILES: CC(=O)Nc1nc(C)c(-c2ccc3oc(N)nc3c2)s1] | | +++ | ++ | +++ | ++++ | | | Calcd: 288.07 Found: 289.0 [M + H]$^+$ |
| 313 | 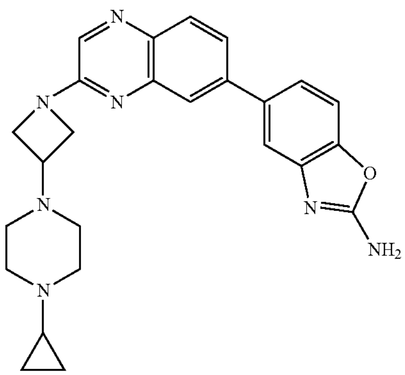 [SMILES: Nc1nc2cc(-c3ccc4ncc(N5CC(N6CCN(C7CC7)CC6)C5)nc4c3)ccc2o1] | ++ | ++++ | ++ | ++ | ++ | | | Calcd: 441.23 Found: 442.2 [M + H]$^+$ |
| 314 | 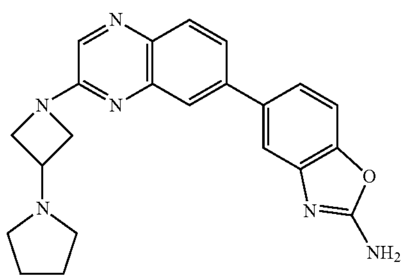 [SMILES: Nc1nc2cc(-c3ccc4ncc(N5CC(N6CCCC6)C5)nc4c3)ccc2o1] | | +++ | ++ | ++ | ++ | | | Calcd: 386.19 Found: 387.2 [M + H]$^+$ |
| 315 | 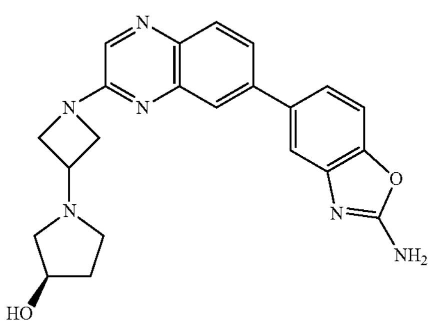 [SMILES: Nc1nc2cc(-c3ccc4ncc(N5CC(N6CC[C@@H](O)C6)C5)nc4c3)ccc2o1] | +++ | ++++ | ++ | ++ | ++ | | | Calcd: 402.18 Found: 403.2 [M + H]$^+$ |
| 316 | 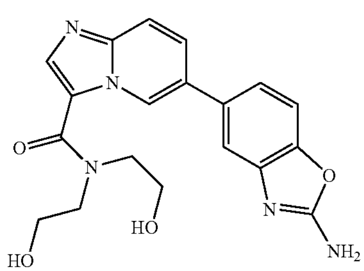 [SMILES: Nc1nc2cc(-c3ccc4ncc(C(=O)N(CCO)CCO)n4c3)ccc2o1] | | +++ | ++ | + | ++ | | | Calcd: 381.14 Found: 382.0 [M + H]$^+$ |

TABLE 3-continued

In Vitro IC$_{50}$ data for selected compounds of the invention.

| | Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | PC3 proliferation (nM)* | T47D proliferation (nM) | Mass Characterization |
|---|---|---|---|---|---|---|---|---|---|
| 317 | 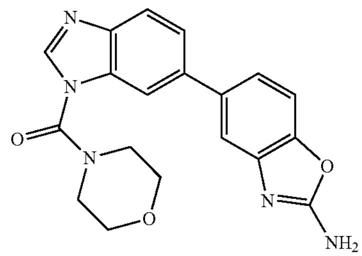 [SMILES: Nc1nc2cc(-c3ccc4ncn(C(=O)N5CCOCC5)c4c3)ccc2o1] | | + | + | + | + | | | Calcd: 363.13 Found: 364.0 [M + H]$^+$ |
| 318 | 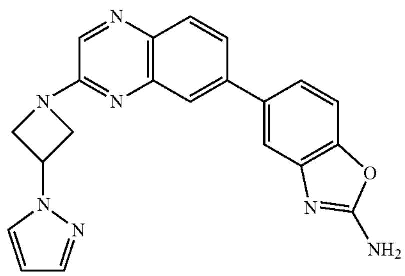 [SMILES: Nc1nc2cc(-c3ccc4ncc(N5CC(n6cccn6)C5)nc4c3)ccc2o1] | +++ | ++++ | ++ | + | +++ | | | Calcd: 383.15 Found: 384.2 [M + H]$^+$ |
| 319 | 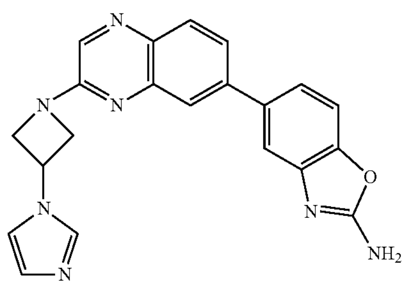 [SMILES: Nc1nc2cc(-c3ccc4ncc(N5CC(n6ccnc6)C5)nc4c3)ccc2o1] | | ++++ | +++ | ++ | +++ | | | Calcd: 383.15 Found: 384.2 [M + H]$^+$ |
| 320 | 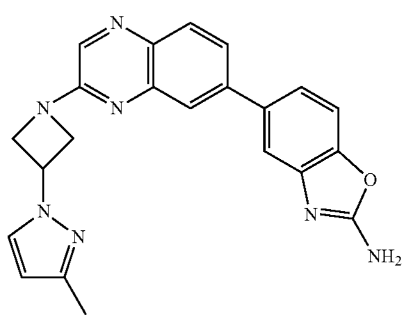 [SMILES: Cc1ccn(C2CN(c3cnc4ccc(-c5ccc6oc(N)nc6c5)cc4n3)C2)n1] | + | ++++ | ++ | ++ | ++ | | | Calcd: 397.17 Found: 398.0 [M + H]$^+$ |
| 321 | 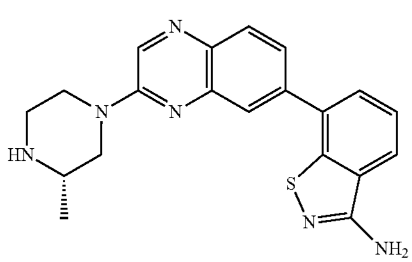 [SMILES: C[C@H]1CN(c2cnc3ccc(-c4cccc5c(N)nsc45)cc3n2)CCN1] | | + | + | + | + | | | Calcd: 376.15 Found: 377.0 [M + H]$^+$ |

TABLE 3-continued

In Vitro IC$_{50}$ data for selected compounds of the invention.

| | Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | PC3 proliferation (nM)* | T47D proliferation (nM) | Mass Characterization |
|---|---|---|---|---|---|---|---|---|---|
| 322 | 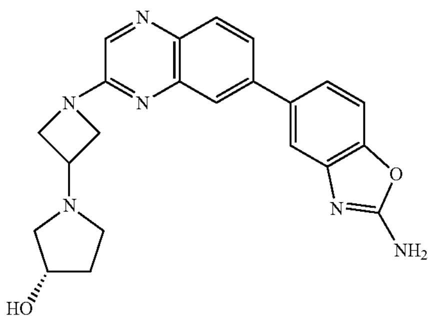 [SMILES: Nc1nc2cc(-c3ccc4ncc(N5CC(N6CC[C@H](O)C6)C5)nc4c3)ccc2o1] | + | ++++ | +++ | ++ | +++ | | | Calcd: 402.18 Found: 403.2 [M + H]$^+$ |
| 323 | 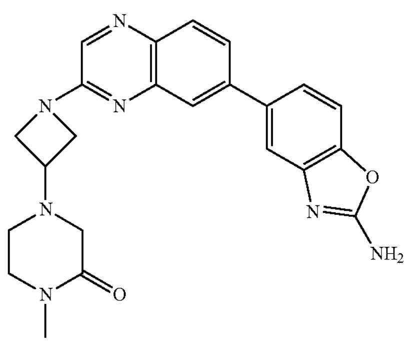 [SMILES: CN1CCN(C2CN(c3cnc4ccc(-c5ccc6oc(N)nc6c5)cc4n3)C2)CC1=O] | + | ++++ | ++ | ++ | +++ | | | Calcd: 429.19 Found: 430.2 [M + H]$^+$ |
| 324 | 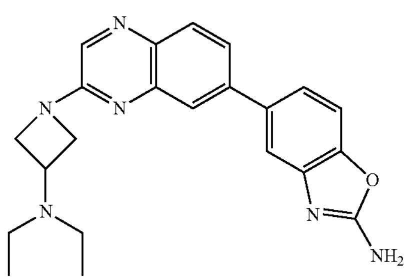 [SMILES: CCN(CC)C1CN(c2cnc3ccc(-c4ccc5oc(N)nc5c4)cc3n2)C1] | + | ++++ | ++ | ++ | +++ | | | Calcd: 388.20 Found: 389.2 [M + H]$^+$ |
| 325 | 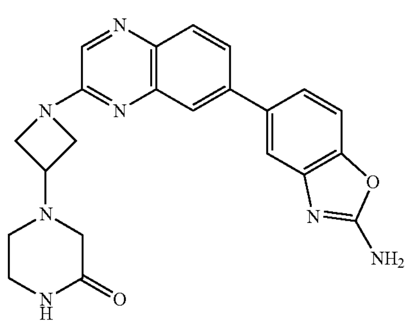 [SMILES: Nc1nc2cc(-c3ccc4ncc(N5CC(N6CCNC(=O)C6)C5)nc4c3)ccc2o1] | | ++++ | +++ | ++ | ++++ | | | Calcd: 415.18 Found: 416.2 [M + H]$^+$ |

TABLE 3-continued
In Vitro IC$_{50}$ data for selected compounds of the invention.
| | Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | PC3 proliferation (nM)* | T47D proliferation (nM) | Mass Characterization |
|---|---|---|---|---|---|---|---|---|---|
| 326 | 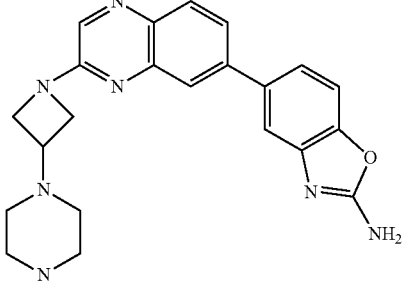 | + | ++++ | +++ | +++ | +++ | | | Calcd: 401.20 Found: 402.2 [M + H]$^+$ |
| 327 | 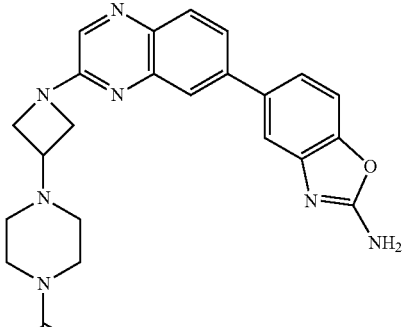 | + | ++++ | ++ | +++ | +++ | | | Calcd: 443.21 Found: 444.2 [M + H]$^+$ |
| 328 | 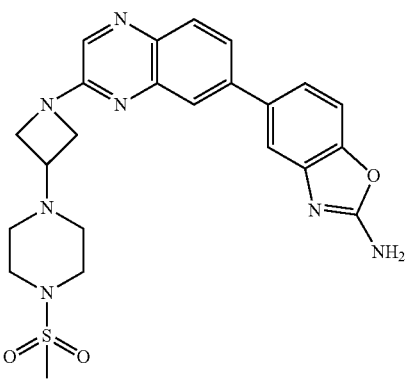 [SMILES: CS(=O)(=O)N1CCN(C2CN(c3cnc4ccc(-c5ccc6oc(N)nc6c5)cc4n3)C2)CC1] | + | ++++ | ++ | ++ | ++ | | | Calcd: 479.17 Found: 480.2 [M + H]$^+$ |
| 329 | 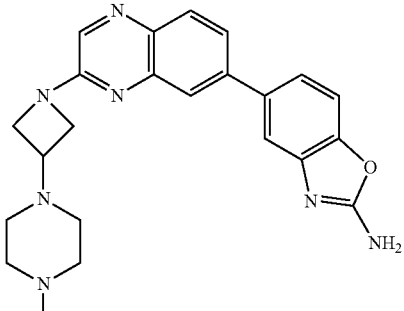 | + | ++++ | +++ | +++ | ++ | | | Calcd: 429.23 Found: 430.2 [M + H]$^+$ |

//

TABLE 3-continued

In Vitro IC$_{50}$ data for selected compounds of the invention.

| | Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | PC3 proliferation (nM)* | T47D proliferation (nM) | Mass Characterization |
|---|---|---|---|---|---|---|---|---|---|
| 330 | 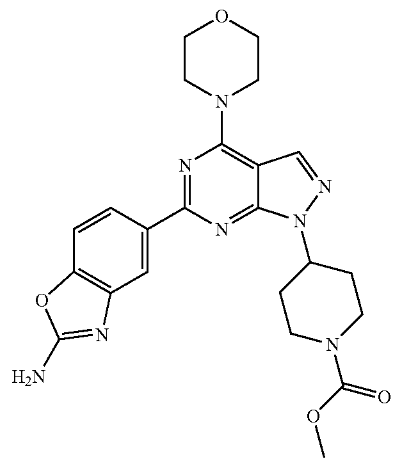 [SMILES: COC(=O)N1CCC(n2ncc3c(N4CCOCC4)nc(-c4ccc5oc(N)nc5c4)nc32)CC1] | +++ | +++ | ++ | + | + | | | Calcd: 478.21 Found: 479.2 [M + H]$^+$ |
| 331 | 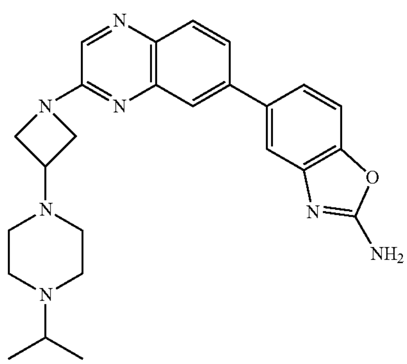 [SMILES: CC(C)N1CCN(C2CN(c3cnc4ccc(-c5ccc6oc(N)nc6c5)cc4n3)C2)CC1] | + | ++++ | ++ | ++ | ++ | | | Calcd: 443.24 Found: 444.2 [M + H]$^+$ |
| 332 | 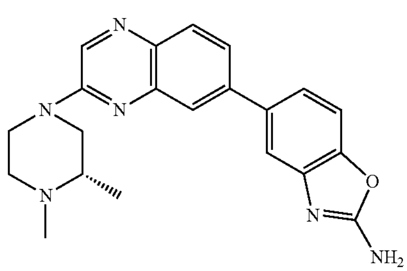 [SMILES: C[C@H]1CN(c2cnc3ccc(-c4ccc5oc(N)nc5c4)cc3n2)CCN1C] | +++ | ++++ | ++ | +++ | | | | Calcd: 374.19 Found: 375.2 [M + H]$^+$ |
| 333 | 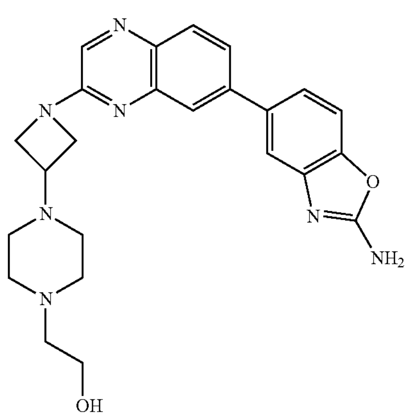 [SMILES: Nc1nc2cc(-c3ccc4ncc(N5CC(N6CCN(CCO)CC6)C5)nc4c3)ccc2o1] | + | ++++ | ++ | +++ | ++ | | +++ | Calcd: 445.22 Found: 446.2 [M + H]$^+$ |

TABLE 3-continued
In Vitro IC$_{50}$ data for selected compounds of the invention.
| | Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | PC3 proliferation (nM)* | T47D proliferation (nM) | Mass Characterization |
|---|---|---|---|---|---|---|---|---|---|
| 334 | 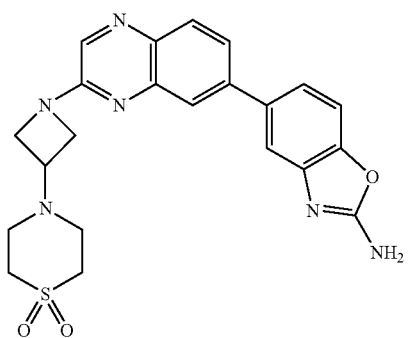 [SMILES: Nc1nc2cc(-c3ccc4ncc(N5CC(N6CCS(=O)(=O)CC6)C5)nc4c3)ccc2o1] | | ++++ | ++ | ++ | ++ | | +++ | Calcd: 450.15 Found: 451.0 [M + H]$^+$ |
| 335 | 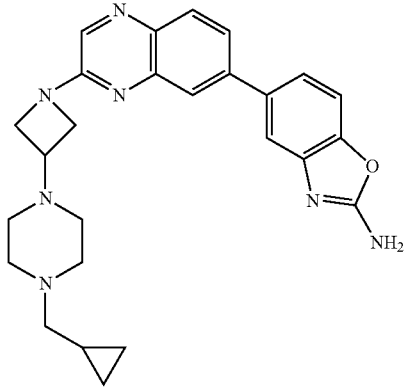 [SMILES: Nc1nc2cc(-c3ccc4ncc(N5CC(N6CCN(CC7CC7)CC6)C5)nc4c3)ccc2o1] | + | ++++ | ++ | ++ | + | | +++ | Calcd: 455.24 Found: 456.2 [M + H]$^+$ |
| 336 | 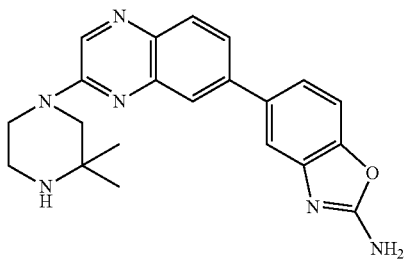 [SMILES: CC1(C)CN(c2cnc3ccc(-c4ccc5oc(N)nc5c4)cc3n2)CCN1] | | +++ | +++ | ++ | + | | | Calcd: 374.19 Found: 375.2 [M + H]$^+$ |
| 337 | 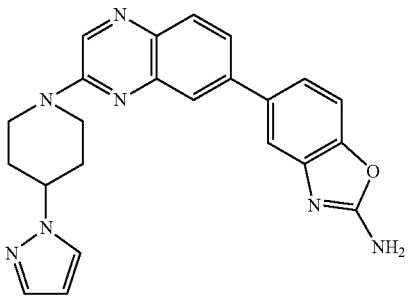 [SMILES: Nc1nc2cc(-c3ccc4ncc(N5CCC(n6cccn6)CC5)nc4c3)ccc2o1] | | ++++ | + | + | +++ | | | Calcd: 411.18 Found: 412.2 [M + H]$^+$ |

TABLE 3-continued

In Vitro IC$_{50}$ data for selected compounds of the invention.

| | Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | PC3 proliferation (nM)* | T47D proliferation (nM) | Mass Characterization |
|---|---|---|---|---|---|---|---|---|---|
| 338 | 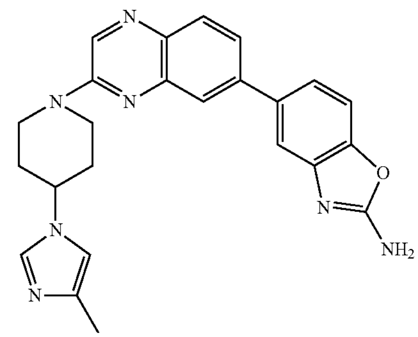 [SMILES: Cc1cn(C2CCN(c3cnc4ccc(-c5ccc6oc(N)nc6c5)cc4n3)CC2)cn1] | | ++++ | ++ | ++ | ++ | | ++ | Calcd: 425.20 Found: 426.2 [M + H]$^+$ |
| 339 | 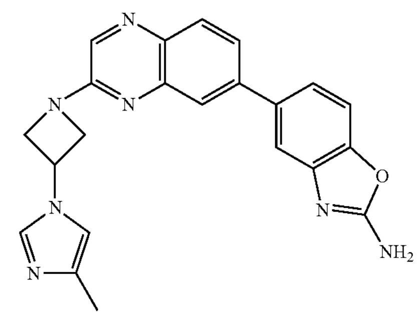 [SMILES: Cc1cn(C2CN(c3cnc4ccc(-c5ccc6oc(N)nc6c5)cc4n3)C2)cn1] | | ++++ | +++ | +++ | +++ | | | Calcd: 397.17 Found: 398.2 [M + H]$^+$ |
| 340 | 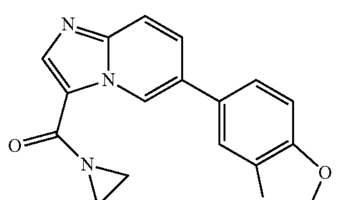 | | +++ | + | + | +++ | | | Calcd: 319.11 Found: 320.2 [M + H]$^+$ |
| 341 | 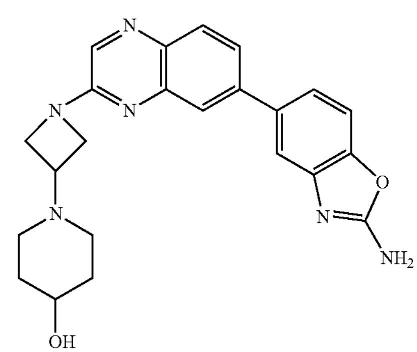 [SMILES: Nc1nc2cc(-c3ccc4ncc(N5CC(N6CCC(O)CC6)C5)nc4c3)ccc2o1] | | +++ | + | ++ | ++ | | ++ | Calcd: 416.20 Found: 417.2 [M + H]$^+$ |

TABLE 3-continued

In Vitro IC$_{50}$ data for selected compounds of the invention.

| Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | PC3 proliferation (nM)* | T47D proliferation (nM) | Mass Characterization |
|---|---|---|---|---|---|---|---|---|
| 342 | | + | + | + | + | | | Calcd: 360.17 Found: 361.2 [M + H]$^+$ |
| 343 | | + | ++ | + | + | | | Calcd: 360.17 Found: 361.2 [M + H]$^+$ |
| 344 | | ++++ | ++ | +++ | ++ | | | Calcd: 425.20 Found: 426.2 [M + H]$^+$ |
| 345 | ++ | ++++ | +++ | +++ | +++ | | | Calcd: 411.18 Found: 412.2 [M + H]$^+$ |

TABLE 3-continued

In Vitro IC$_{50}$ data for selected compounds of the invention.

| | Structure | mTOR C IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | PC3 proliferation (nM)* | T47D proliferation (nM) | Mass Characterization |
|---|---|---|---|---|---|---|---|---|---|
| 346 | 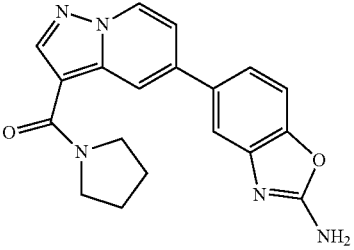 [SMILES: Nc1nc2cc(-c3ccn4ncc(C(=O)N5CCCC5)c4c3)ccc2o1] | | ++++ | ++ | + | +++ | | | Calcd: 347.14 Found: 348.2 [M + H]$^+$ |
| 347 | 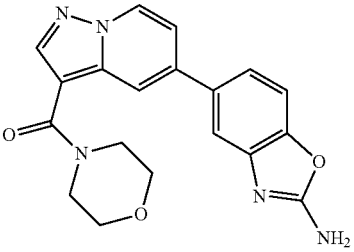 [SMILES: Nc1nc2cc(-c3ccn4ncc(C(=O)N5CCOCC5)c4c3)ccc2o1] | | +++ | ++ | + | +++ | | | Calcd: 363.13 Found: 364.2 [M + H]$^+$ |
| 348 | 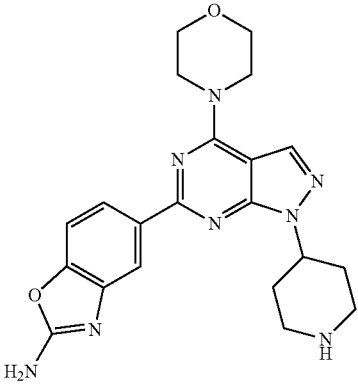 [SMILES: Nc1nc2cc(-c3nc(N4CCOCC4)c4cnn(C5CCNCC5)c4n3)ccc2o1] | +++ | +++ | ++++ | ++ | +++ | | | Calcd: 420.20 Found: 421.2 [M + H]$^+$ |
| 349 | 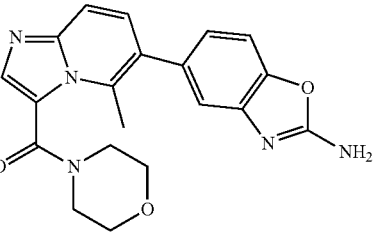 | | + | + | + | + | | | Calcd: 377.15 Found: 378.2 [M + H]$^+$ |
| 350 | 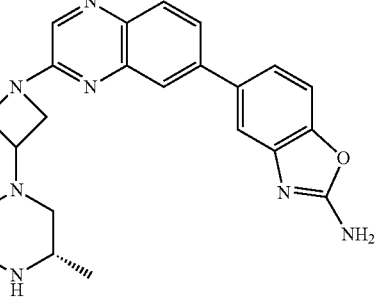 | + | ++++ | ++ | ++ | + | | | Calcd: 415.21 Found: 416.2 [M + H]$^+$ |

TABLE 3-continued

In Vitro IC$_{50}$ data for selected compounds of the invention.

| | Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | PC3 proliferation (nM)* | T47D proliferation (nM) | Mass Characterization |
|---|---|---|---|---|---|---|---|---|---|
| 351 | 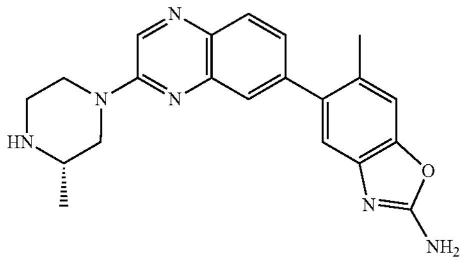 | | ++ | +++ | + | + | | | Calcd: 374.19 Found: 375.0 [M + H]$^+$ |
| 352 | 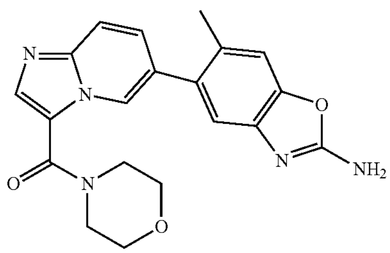 [SMILES: Cc1cc2oc(N)nc2cc1-c1ccc2ncc(C(=O)N3CCOCC3)n2c1] | | + | + | + | + | | | Calcd: 377.15 Found: 378.2 [M + H]$^+$ |
| 353 | 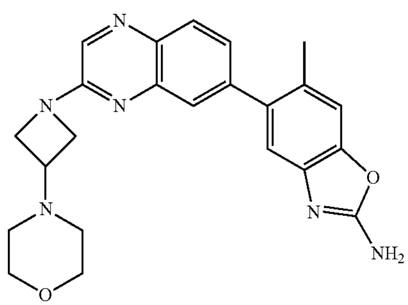 [SMILES: Cc1cc2oc(N)nc2cc1-c1ccc2ncc(N3CC(N4CCOCC4)C3)nc2c1] | + | ++ | + | + | + | | | Calcd: 416.20 Found: 417.2 [M + H]$^+$ |
| 354 | 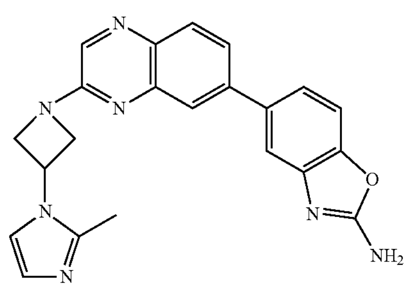 [SMILES: Cc1nccn1C1CN(c2cnc3ccc(-c4ccc5oc(N)nc5c4)cc3n2)C1] | ++ | ++++ | ++ | ++ | ++ | | +++ | Calcd: 397.17 Found: 398.0 [M + H]$^+$ |
| 355 | 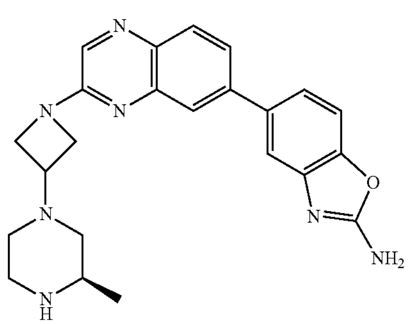 [SMILES: C[C@@H]1CN(C2CN(c3cnc4ccc(-c5ccc6oc(N)nc6c5)cc4n3)C2)CCN1] | ++++ | ++ | +++ | ++ | | +++ | | Calcd: 415.21 Found: 416.2 [M + H]$^+$ |

TABLE 3-continued

In Vitro IC$_{50}$ data for selected compounds of the invention.

| | Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | PC3 proliferation (nM)* | T47D proliferation (nM) | Mass Characterization |
|---|---|---|---|---|---|---|---|---|---|
| 356 | 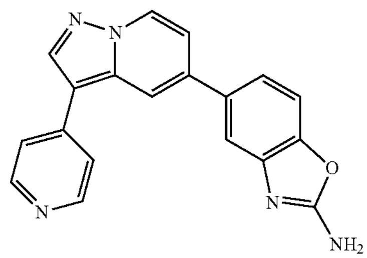 [SMILES: Nc1nc2cc(-c3ccn4ncc(-c5ccncc5)c4c3)ccc2o1] | | ++++ | ++++ | ++++ | ++++ | | +++ | Calcd: 327.11 Found: 328.2 [M + H]$^+$ |
| 357 | 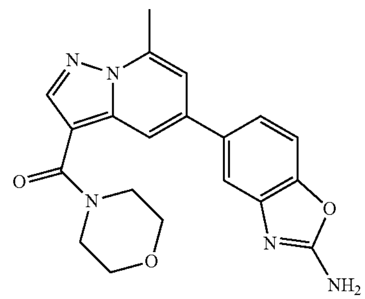 [SMILES: Cc1cc(-c2ccc3oc(N)nc3c2)cc2c(C(=O)N3CCOCC3)cnn12] | | +++ | ++ | ++ | +++ | | | Calcd: 377.15 Found: 378.2 [M + H]$^+$ |
| 358 | 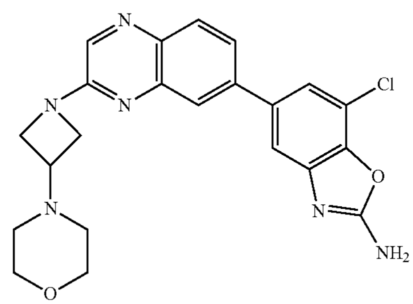 [SMILES: Nc1nc2cc(-c3ccc4ncc(N5CC(N6CCOCC6)C5)nc4c3)cc(Cl)c2o1] | | ++++ | +++ | +++ | +++ | | | Calcd: 436.14 Found: 437.0 [M + H]$^+$ |
| 359 | 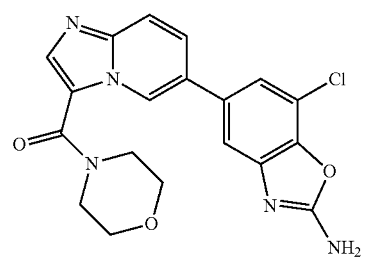 [SMILES: Nc1nc2cc(-c3ccc4ncc(C(=O)N5CCOCC5)n4c3)cc(Cl)c2o1] | | ++++ | +++ | ++ | ++++ | | | Calcd: 397.09 Found: 398.0 [M + H]$^+$ |
| 360 | 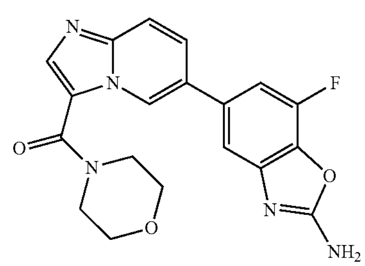 [SMILES: Nc1nc2cc(-c3ccc4ncc(C(=O)N5CCOCC5)n4c3)cc(F)c2o1] | | ++++ | +++ | ++ | ++++ | | | Calcd: 381.12 Found: 382.0 [M + H]$^+$ |

TABLE 3-continued
In Vitro IC$_{50}$ data for selected compounds of the invention.
| | Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | PC3 proliferation (nM)* | T47D proliferation (nM) | Mass Characterization |
|---|---|---|---|---|---|---|---|---|---|
| 361 | 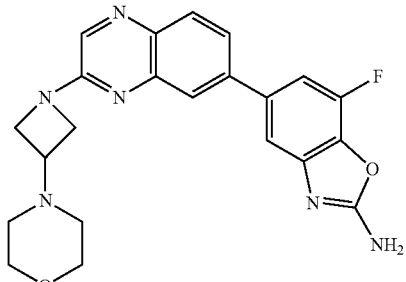 | | ++++ | +++ | ++ | +++ | | | Calcd: 420.17 Found: 421.0 [M + H]$^+$ |
| 362 | 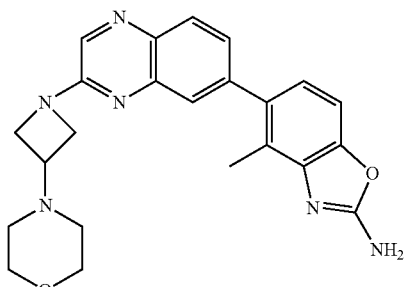 | | + | + | + | + | | | Calcd: 416.20 Found: 417.0 [M + H]$^+$ |
| 363 | 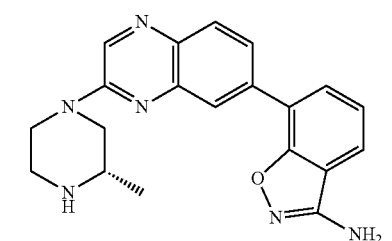 | | + | + | + | + | | | |
| 364 | 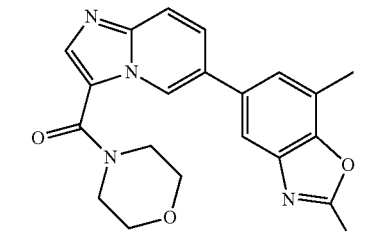 | | +++ | ++ | + | +++ | | | Calcd: 377.15 Found: 378.0 [M + H]$^+$ |
| 365 | 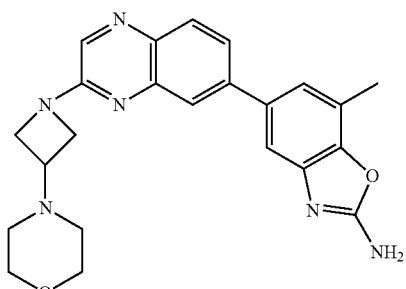 | | ++ | ++ | ++ | ++ | | | Calcd: 416.20 Found: 417.0 [M + H]$^+$ |

TABLE 3-continued

In Vitro IC$_{50}$ data for selected compounds of the invention.

| | Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | PC3 proliferation (nM)* | T47D proliferation (nM) | Mass Characterization |
|---|---|---|---|---|---|---|---|---|---|
| 366 | 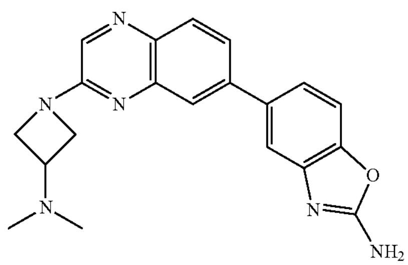 [SMILES: CN(C)C1CN(c2cnc3ccc(-c4ccc5oc(N)nc5c4)cc3n2)C1] | | ++++ | ++ | + | ++ | | | Calcd: 360.17 Found: 361.0 [M + H]$^+$ |
| 367 | 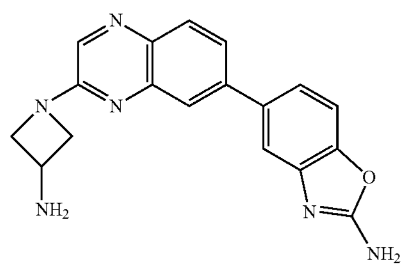 [SMILES: Nc1nc2cc(-c3ccc4ncc(N5CC(N)C5)nc4c3)ccc2o1] | | +++ | +++ | ++ | +++ | | | Calcd: 332.14 Found: 333.0 [M + H]$^+$ |
| 368 | 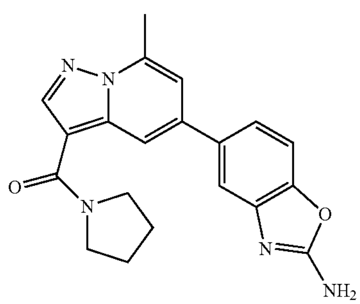 [SMILES: Cc1cc(-c2ccc3oc(N)nc3c2)cc2c(C(=O)N3CCCC3)cnn12] | | ++++ | ++ | +++ | +++ | | | Calcd: 361.15 Found: 362.0 [M + H]$^+$ |
| 369 | 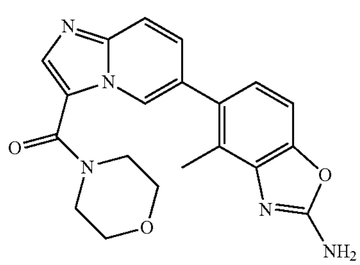 [SMILES: Cc1c(-c2ccc3ncc(C(=O)N4CCOCC4)n3c2)ccc2oc(N)nc12] | | + | + | + | + | | | Calcd: 377.15 Found: 378.0 [M + H]$^+$ |
| 370 | 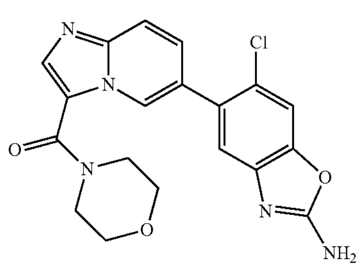 [SMILES: Nc1nc2cc(-c3ccc4ncc(C(=O)N5CCOCC5)n4c3)c(Cl)cc2o1] | | ++ | + | + | + | | | Calcd: 397.09 Found: 398.0 [M + H]$^+$ |

TABLE 3-continued

In Vitro IC$_{50}$ data for selected compounds of the invention.

| Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | PC3 proliferation (nM)* | T47D proliferation (nM) | Mass Characterization |
|---|---|---|---|---|---|---|---|---|
| 371 | | +++ | ++ | + | + | | | Calcd: 436.14 Found: 437.0 [M + H]$^+$ |
| 372 | | +++ | ++ | ++ | ++ | | | Calcd: 381.12 Found: 382.2 [M + H]$^+$ |
| 373 | + | ++++ | ++ | ++ | ++ | | | Calcd: 420.17 Found: 421.2 [M + H]$^+$ |
| 374 | | +++ | ++++ | ++ | + | | | Calcd: 374.19 Found: 375.2 [M + H]$^+$ |
| 375 | | +++ | ++ | +++ | +++ | | | Calcd: 416.20 Found: 417.2 [M + H]$^+$ |

TABLE 3-continued

In Vitro IC$_{50}$ data for selected compounds of the invention.

| | Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | PC3 proliferation (nM)* | T47D proliferation (nM) | Mass Characterization |
|---|---|---|---|---|---|---|---|---|---|
| 376 | 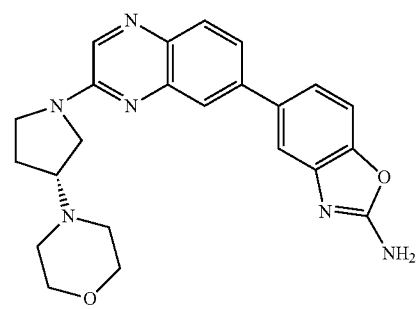 [SMILES: Nc1nc2cc(-c3ccc4ncc(N5CC[C@@H](N6CCOCC6)C5)nc4c3)ccc2o1] | | ++++ | ++ | ++ | ++++ | | | Calcd: 416.20 Found: 417.2 [M + H]$^+$ |
| 377 | 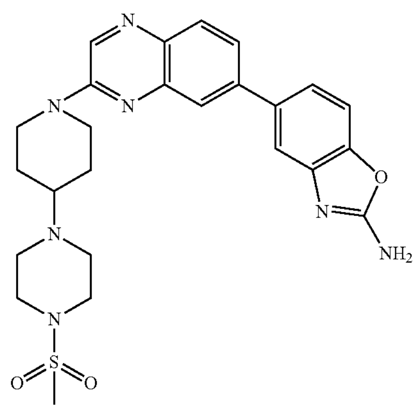 [SMILES: CS(=O)(=O)N1CCN(C2CCN(c3cnc4ccc(-c5ccc6oc(N)nc6c5)cc4n3)CC2)CC1] | ++ | ++++ | ++ | ++ | +++ | | | Calcd: 507.21 Found: 508.2 [M + H]$^+$ |
| 378 | 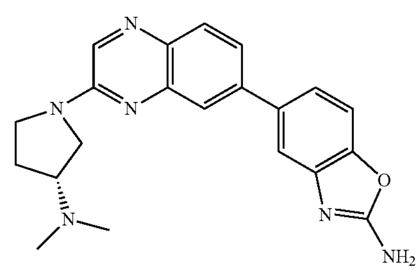 [SMILES: CN(C)[C@@H]1CCN(c2cnc3ccc(-c4ccc5oc(N)nc5c4)cc3n2)C1] | +++ | ++++ | ++++ | ++ | ++ | | | Calcd: 374.19 Found: 375.2 [M + H]$^+$ |
| 379 | 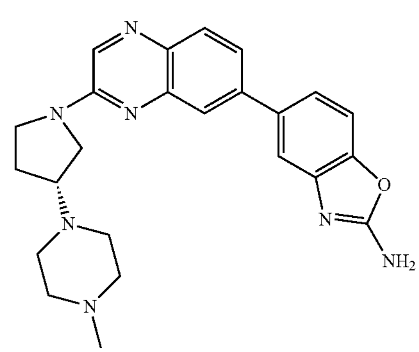 [SMILES: CN1CCN([C@@H]2CCN(c3cnc4ccc(-c5ccc6oc(N)nc6c5)cc4n3)C2)CC1] | ++ | ++++ | +++ | ++ | + | | | Calcd: 429.23 Found: 430.2 [M + H]$^+$ |

TABLE 3-continued

In Vitro IC$_{50}$ data for selected compounds of the invention.

| | Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | PC3 proliferation (nM)* | T47D proliferation (nM) | Mass Characterization |
|---|---|---|---|---|---|---|---|---|---|
| 380 | 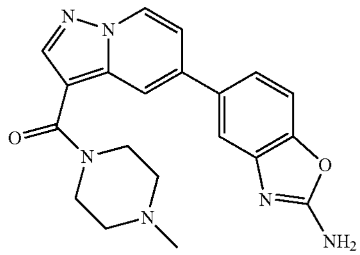 [SMILES: CN1CCN(C(=O)c2cnn3ccc(-c4ccc5oc(N)nc5c4)cc23)CC1] | | +++ | ++ | + | ++ | | | Calcd: 376.16 Found: 377.0 [M + H]$^+$ |
| 381 | 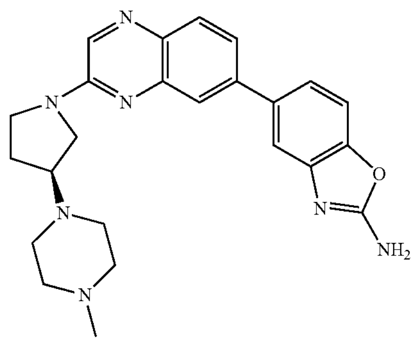 [SMILES: CN1CCN([C@H]2CCN(c3cnc4ccc(-c5ccc6oc(N)nc6c5)cc4n3)C2)CC1] | | ++++ | +++ | ++ | ++ | | | Calcd: 429.23 Found: 430.2 [M + H]$^+$ |
| 382 | 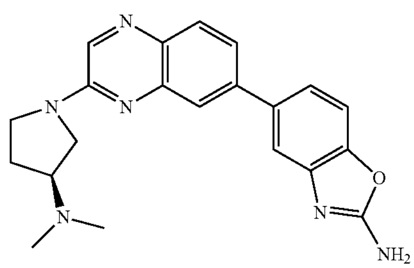 [SMILES: CN(C)[C@H]1CCN(c2cnc3ccc(-c4ccc5oc(N)nc5c4)cc3n2)C1] | | ++++ | +++ | ++ | +++ | | | Calcd: 374.19 Found: 375.2 [M + H]$^+$ |
| 383 | 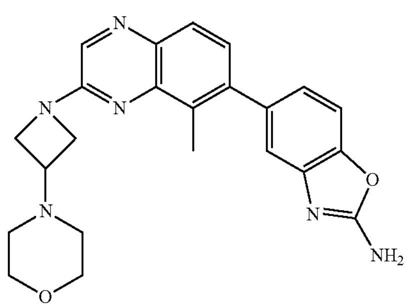 [SMILES: Cc1c(-c2ccc3oc(N)nc3c2)ccc2ncc(N3CC(N4CCOCC4)C3)nc12] | | +++ | + | + | + | | | Calcd: 416.20 Found: 417.2 [M + H]$^+$ |
| 384 | 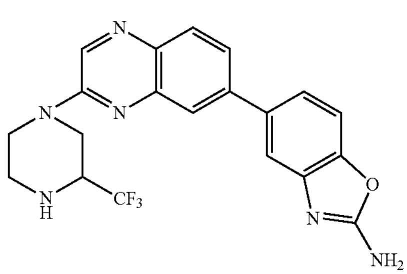 [SMILES: Nc1nc2cc(-c3ccc4ncc(N5CCNC(C(F)(F)F)C5)nc4c3)ccc2o1] | +++ | ++++ | +++ | ++ | +++ | | | Calcd: 414.14 Found: 415.2 [M + H]$^+$ |

TABLE 3-continued

In Vitro IC$_{50}$ data for selected compounds of the invention.

| | Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | PC3 proliferation (nM)* | T47D proliferation (nM) | Mass Characterization |
|---|---|---|---|---|---|---|---|---|---|
| 385 | 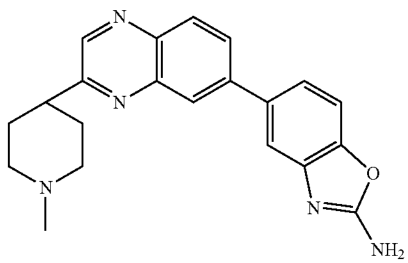 | | ++++ | ++ | + | + | | | Calcd: 359.17 Found: 360.2 [M + H]$^+$ |
| 386 | 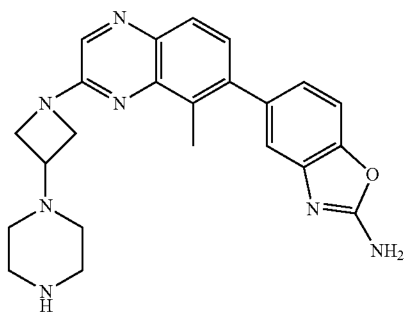 [SMILES: Cc1c(-c2ccc3oc(N)nc3c2)ccc2ncc(N3CC(N4CCNCC4)C3)nc12] | | ++++ | + | + | | | | Calcd: 415.21 Found: 416.2 [M + H]$^+$ |
| 387 | 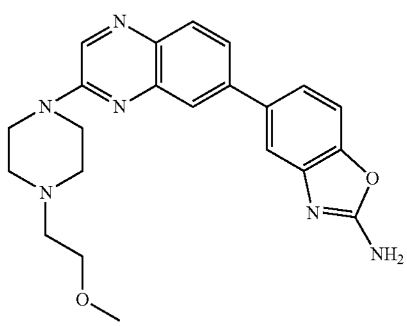 [SMILES: COCCN1CCN(c2cnc3ccc(-c4ccc5oc(N)nc5c4)cc3n2)CC1] | | ++++ | +++ | + | +++ | | | Calcd: 404.20 Found: 405.2 [M + H]$^+$ |
| 388 | 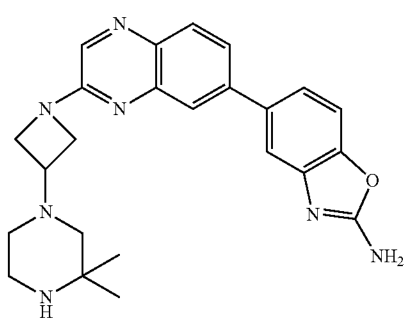 [SMILES: CC1(C)CN(C2CN(c3cnc4ccc(-c5ccc6oc(N)nc6c5)cc4n3)C2)CCN1] | ++++ | ++++ | +++ | +++ | +++ | | | Calcd: 429.23 Found: 430.2 [M + H]$^+$ |
| 389 | 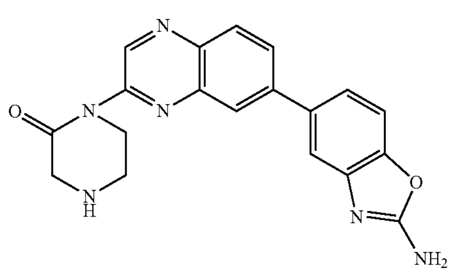 | | +++ | + | + | ++ | | | Calcd: 360.13 Found: 361.0 [M + H]$^+$ |

… TABLE 3-continued
In Vitro IC₅₀ data for selected compounds of the invention.
| | Structure | mTORC IC₅₀ (nM) | PI3K α IC₅₀ (nM) | PI3K β IC₅₀ (nM) | PI3K δ IC₅₀ (nM) | PI3K γ IC₅₀ (nM) | PC3 proliferation (nM)* | T47D proliferation (nM) | Mass Characterization |
|---|---|---|---|---|---|---|---|---|---|
| 390 | 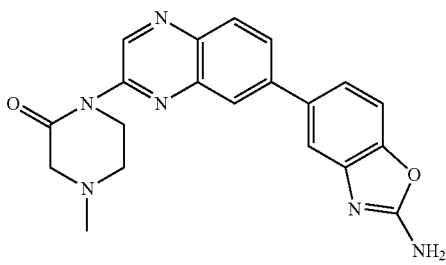 | | ++ | | | + | | | Calcd: 374.15 Found: 375.2 [M + H]⁺ |
| 391 | 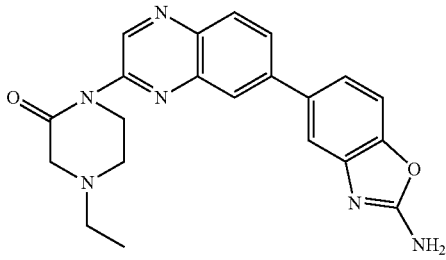 [SMILES: CCN1CCN(c2cnc3ccc(-c4ccc5oc(N)nc5c4)cc3n2)C(=O)C1] | | ++ | + | + | + | | | Calcd: 388.16 Found: 389.2 [M + H]⁺ |
| 392 | 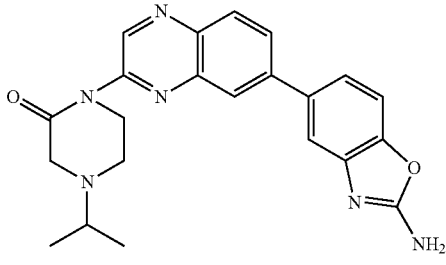 [SMILES: CC(C)N1CCN(c2cnc3ccc(-c4ccc5oc(N)nc5c4)cc3n2)C(=O)C1] | | + | + | + | + | | | Calcd: 402.18 Found: 403.2 [M + H]⁺ |
| 393 | 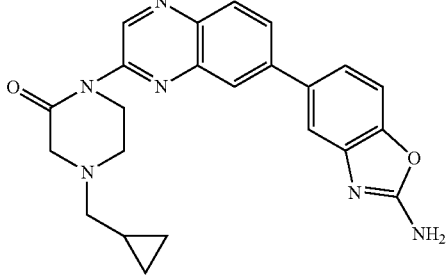 | | ++ | + | + | + | | | Calcd: 414.18 Found: 415.2 [M + H]⁺ |
| 394 | 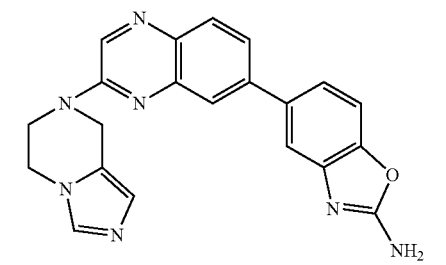 [SMILES: Nc1nc2cc(-c3ccc4ncc(N5CCn6cncc6C5)nc4c3)ccc2o1] | | ++++ | ++++ | +++ | ++++ | | | Calcd: 383.15 Found: 384.2 [M + H]⁺ |

TABLE 3-continued

In Vitro IC$_{50}$ data for selected compounds of the invention.

| Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | PC3 proliferation (nM)* | T47D proliferation (nM) | Mass Characterization |
|---|---|---|---|---|---|---|---|---|
| 395 | | ++++ | + | + | ++++ | | | Calcd: 428.16 Found: 429.2 [M + H]$^+$ |
| 396 | | ++++ | ++++ | + | ++ | | | Calcd: 359.17 Found: 360.2 [M + H]$^+$ |
| 397 | | ++++ | +++ | +++ | ++++ | | | Calcd: 341.13 Found: 342.2 [M + H]$^+$ |
| 398 | | +++ | ++ | ++ | ++ | | | Calcd: 446.21 Found: 447.2 [M + H]$^+$ |
| 399 | | + | + | + | + | | | Calcd: 365.13 Found: 366.2 [M + H]$^+$ |

TABLE 3-continued

In Vitro IC$_{50}$ data for selected compounds of the invention.

| Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | PC3 proliferation (nM)* | T47D proliferation (nM) | Mass Characterization |
|---|---|---|---|---|---|---|---|---|
| 400 | | ++++ | ++ | + | ++ | | | Calcd: 364.13 Found: 365.2 [M + H]$^+$ |
| 401 | | + | + | + | ++ | | | Calcd: 325.10 Found: 326.0 [M + H]$^+$ |
| 402 | | + | + | + | + | | | Calcd: 345.07 Found: 346.0 [M + H]$^+$ |
| 403 | | ++ | + | + | + | | | Calcd: 375.18 Found: 376.2 [M + H]$^+$ |

TABLE 3-continued

In Vitro IC$_{50}$ data for selected compounds of the invention.

| Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | PC3 proliferation (nM)* | T47D proliferation (nM) | Mass Characterization |
|---|---|---|---|---|---|---|---|---|
| 404 | | + | + | + | + | | | Calcd: 417.19 Found: 418.2 [M + H]$^+$ |
| 405 | | + | + | + | + | | | Calcd: 441.11 Found: 442.0 [M + H]$^+$ |
| 406 | | ++ | ++ | + | + | | | Calcd: 377.15 Found: 378.2 [M + H]$^+$ |
| 407 | | + | ++ | + | + | | | Calcd: 439.16 Found: 440.2 [M + H]$^+$ |

TABLE 3-continued

In Vitro IC$_{50}$ data for selected compounds of the invention.

| | Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | PC3 proliferation (nM)* | T47D proliferation (nM) | Mass Characterization |
|---|---|---|---|---|---|---|---|---|---|
| 408 | 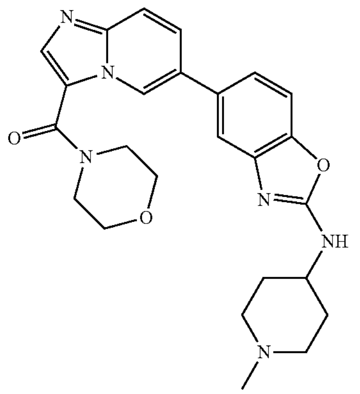 [SMILES: CN1CCC(Nc2nc3cc(-c4ccc5ncc(C(=O)N6CCOCC6)n5c4)ccc3o2)CC1] | | + | + | + | + | | | Calcd: 460.22 Found: 461.2 [M + H]$^+$ |
| 409 | 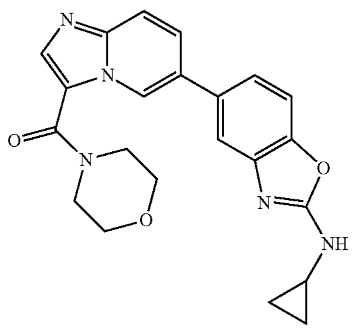 [SMILES: O=C(c1cnc2ccc(-c3ccc4oc(NC5CC5)nc4c3)cn12)N1CCOCC1] | | ++ | + | + | + | | | Calcd: 403.16 Found: 404.2 [M + H]$^+$ |
| 410 | 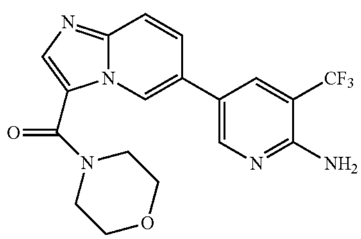 [SMILES: Nc1ncc(-c2ccc3ncc(C(=O)N4CCOCC4)n3c2)cc1C(F)(F)F] | | ++ | + | + | + | | | Calcd: 391.13 Found: 392.0 [M + H]$^+$ |
| 411 | 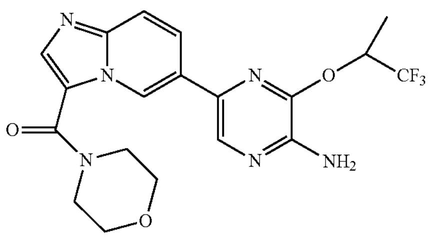 [SMILES: CC(Oc1nc(-c2ccc3ncc(C(=O)N4CCOCC4)n3c2)cnc1N)C(F)(F)F] | | ++++ | ++ | ++ | +++ | | | Calcd: 436.15 Found: 437.2 [M + H]$^+$ |
| 412 | 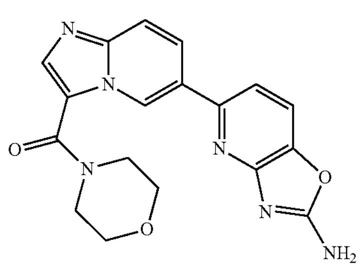 [SMILES: Nc1nc2nc(-c3ccc4ncc(C(=O)N5CCOCC5)n4c3)ccc2o1] | | ++ | + | + | + | | | Calcd: 364.13 Found: 365.0 [M + H]$^+$ |

TABLE 3-continued

In Vitro IC$_{50}$ data for selected compounds of the invention.

| Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | PC3 proliferation (nM)* | T47D proliferation (nM) | Mass Characterization |
|---|---|---|---|---|---|---|---|---|
| 413 | | ++++ | +++ | ++ | +++ | | | Calcd: 396.15 Found: 397.2 [M + H]$^+$ |
| 414 | | ++ | + | + | + | | | Calcd: 353.15 Found: 354.2 [M + H]$^+$ |
| 415 | | ++ | + | + | + | | | Calcd: 357.10 Found: 358.0 [M + H]$^+$ |
| 416 | | ++++ | ++ | ++ | +++ | | | Calcd: 431.13 Found: 432.0 [M + H]$^+$ |
| 417 | +++ | ++++ | ++++ | ++++ | ++++ | | | Calcd: 529.12 Found: 530.0 [M + H]$^+$ |

TABLE 3-continued

In Vitro IC$_{50}$ data for selected compounds of the invention.

| Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | PC3 proliferation (nM)* | T47D proliferation (nM) | Mass Characterization |
|---|---|---|---|---|---|---|---|---|
| 418 | ++++ | ++++ | ++++ | ++++ | ++++ | | | Calcd: 435.08 Found: 436.0 [M + H]$^+$ |
| 419 | +++ | ++++ | ++++ | ++++ | ++++ | | | Calcd: 533.07 Found: 534.0 [M + H]$^+$ |
| 420 | ++++ | + | +++ | +++ | | | | Calcd: 493.14 Found: 494.2 [M + H]$^+$ |
| 421 | ++++ | +++ | ++++ | ++++ | | | | Calcd: 511.13 Found: 512.0 [M + H]$^+$ |

TABLE 3-continued

In Vitro IC$_{50}$ data for selected compounds of the invention.

| Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | PC3 proliferation (nM)* | T47D proliferation (nM) | Mass Characterization |
|---|---|---|---|---|---|---|---|---|
| 422 | | ++++ | ++ | +++ | ++++ | | | Calcd: 511.13 Found: 512.0 [M + H]$^+$ |
| 423 | | ++++ | +++ | ++++ | ++++ | | | Calcd: 511.13 Found: 512.0 [M + H]$^+$ |
| 424 | | +++ | + | ++ | +++ | | | Calcd: 463.51 Found: 464.0 [M + H]$^+$ |
| 425 | | ++++ | + | +++ | ++++ | | | Calcd: 499.49 Found: 500.0 [M + H]$^+$ |

TABLE 3-continued

In Vitro IC$_{50}$ data for selected compounds of the invention.

| | Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | PC3 proliferation (nM)* | T47D proliferation (nM) | Mass Characterization |
|---|---|---|---|---|---|---|---|---|---|
| 426 | 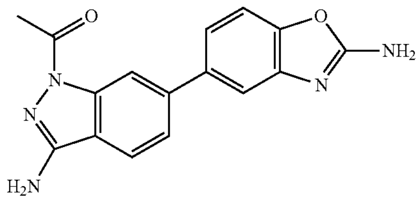 [SMILES: CC(=O)n1nc(N)c2ccc(-c3ccc4oc(N)nc4c3)cc21] | | + | + | + | + | | | Calcd: 307.11 Found: 308.0 [M + H]$^+$ |
| 427 | 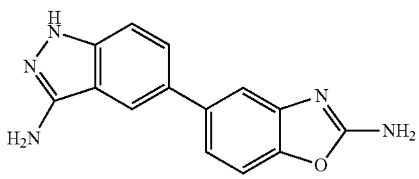 [SMILES: Nc1nc2cc(-c3ccc4[nH]nc(N)c4c3)ccc2o1] | | + | + | + | + | | | Calcd: 265.27 Found: 266.0 [M + H]$^+$ |
| 428 | 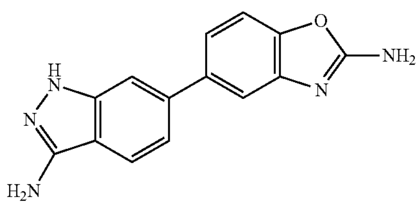 [SMILES: Nc1nc2cc(-c3ccc4c(N)n[nH]c4c3)ccc2o1] | | ++ | ++ | + | +++ | | | Calcd: 265.10 Found: 266.0 [M + H]$^+$ |
| 429 | 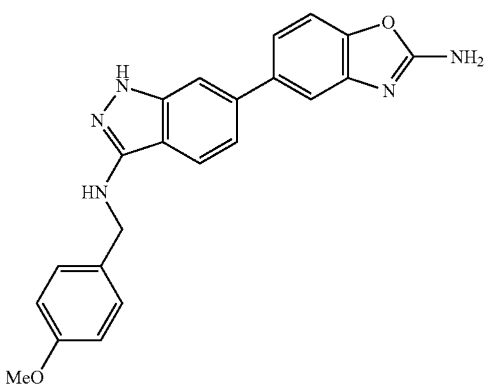 [SMILES: COc1ccc(CNc2n[nH]c3cc(-c4ccc5oc(N)nc5c4)ccc23)cc1] | | + | + | + | + | | | Calcd: 385.15 Found: 386.2 [M + H]$^+$ |
| 430 | 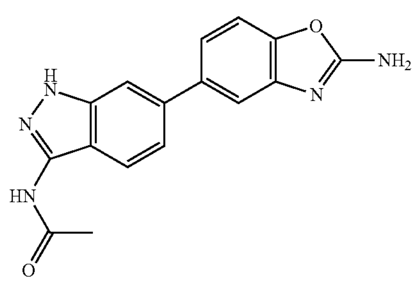 [SMILES: CC(=O)Nc1n[nH]c2cc(-c3ccc4oc(N)nc4c3)ccc12] | | ++ | ++ | + | ++ | | | Calcd: 307.11 Found: 308.0 [M + H]$^+$ |
| 431 | 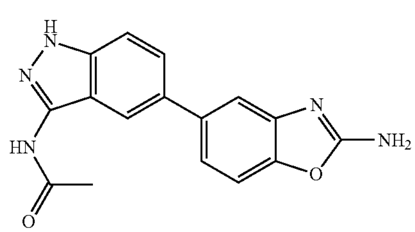 [SMILES: CC(=O)Nc1n[nH]c2ccc(-c3ccc4oc(N)nc4c3)cc12] | | + | + | + | + | | | Calcd: 307.11 Found: 308.0 [M + H]$^+$ |

TABLE 3-continued

In Vitro IC$_{50}$ data for selected compounds of the invention.

| | Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | PC3 proliferation (nM)* | T47D proliferation (nM) | Mass Characterization |
|---|---|---|---|---|---|---|---|---|---|
| 432 | 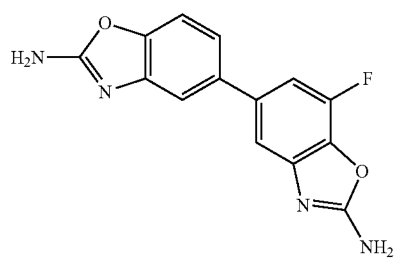 [SMILES: Nc1nc2cc(-c3cc(F)c4oc(N)nc4c3)ccc2o1] | | ++ | +++ | + | ++++ | | | Calcd: 284.07 Found: 285.0 [M + H]$^+$ |
| 433 | 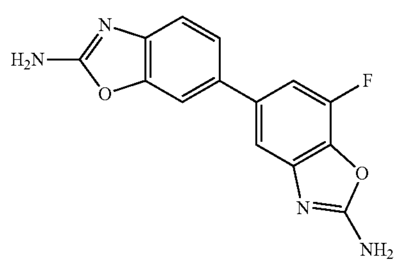 | | +++ | +++ | ++ | ++++ | | | Calcd: 284.07 Found: 285.2 [M + H]$^+$ |
| 434 | 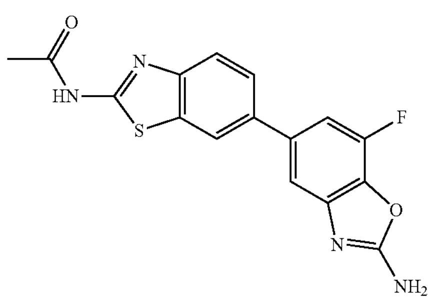 [SMILES: CC(=O)Nc1nc2ccc(-c3cc(F)c4oc(N)nc4c3)cc2s1] | | ++++ | ++++ | ++++ | ++++ | | | Calcd: 342.06 Found: 343.0 [M + H]$^+$ |
| 435 | 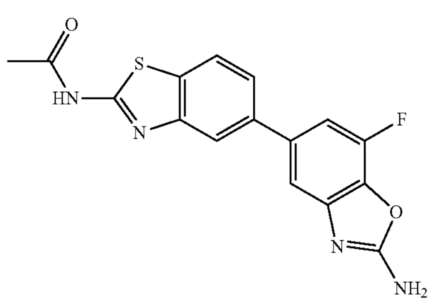 [SMILES: CC(=O)Nc1nc2cc(-c3cc(F)c4oc(N)nc4c3)ccc2s1] | | ++ | ++ | + | ++++ | | | Calcd: 342.06 Found: 343.0 [M + H]$^+$ |
| 436 | 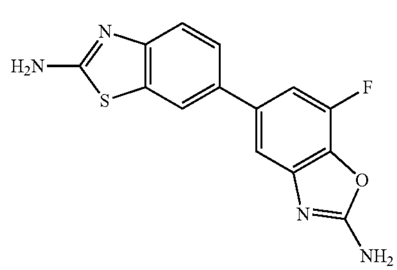 [SMILES: Nc1nc2cc(-c3ccc4nc(N)sc4c3)cc(F)c2o1] | | ++++ | ++++ | +++ | ++++ | | | Calcd: 300.05 Found: 301.1 [M + H]$^+$ |

TABLE 3-continued

In Vitro IC₅₀ data for selected compounds of the invention.

| | Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | PC3 proliferation (nM)* | T47D proliferation (nM) | Mass Characterization |
|---|---|---|---|---|---|---|---|---|---|
| 437 | 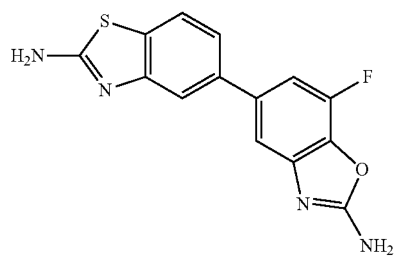 | | ++ | +++ | + | +++ | | | Calcd: 300.05 Found: 301.2 [M + H]⁺ |
| 438 | 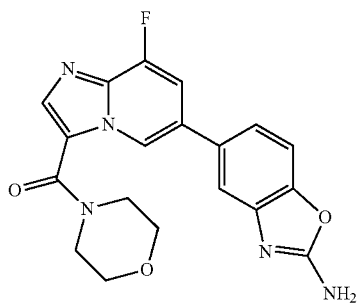 [SMILES: Nc1nc2cc(-c3cc(F)c4ncc(C(=O)N5CCOCC5)n4c3)ccc2o1] | | ++ | + | + | + | | | Calcd: 381.12 Found: 382.2 [M + H]⁺ |
| 439 | 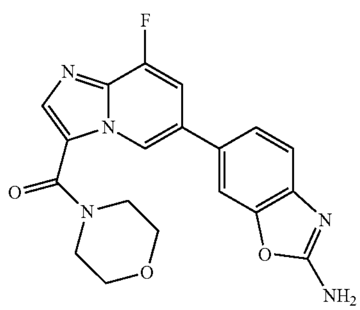 [SMILES: Nc1nc2ccc(-c3cc(F)c4ncc(C(=O)N5CCOCC5)n4c3)cc2o1] | | ++ | + | + | + | | | Calcd: 381.12 Found: 382.2 [M + H]⁺ |
| 440 | 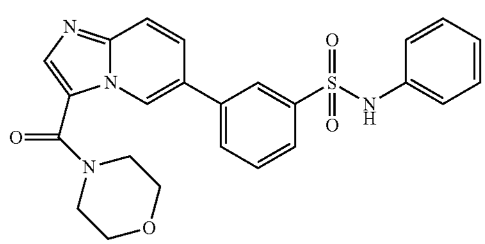 [SMILES: O=C(c1cnc2ccc(-c3cccc(S(=O)(=O)Nc4ccccc4)c3)cn12)N1CCOCC1] | | + | + | + | + | | | Calcd: 462.14 Found: 463.0 [M + H]⁺ |
| 441 | 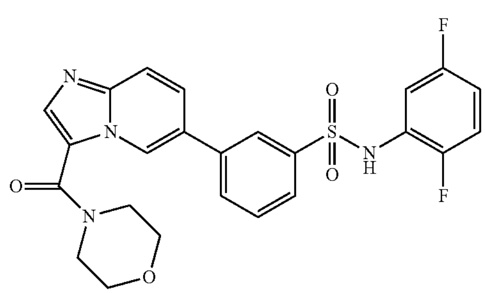 [SMILES: O=C(c1cnc2ccc(-c3cccc(S(=O)(=O)Nc4cc(F)ccc4F)c3)cn12)N1CCOCC1] | | + | + | + | + | | | |

TABLE 3-continued

In Vitro IC$_{50}$ data for selected compounds of the invention.

| Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | PC3 proliferation (nM)* | T47D proliferation (nM) | Mass Characterization |
|---|---|---|---|---|---|---|---|---|
| 442 | | + | + | + | + | | | Calcd: 400.12 Found: 401.0 [M + H]$^+$ |
| 443 | | + | + | + | + | | | Calcd: 400.12 Found: 401.2 [M + H]$^+$ |
| 444 | | ++ | + | + | + | | | Calcd: 492.15 Found: 493.0 [M + H]$^+$ |
| 445 | | + | + | + | + | | | Calcd: 430.13 Found: 431.0 [M + H]$^+$ |
| 446 | | +++ | + | + | + | | | Calcd: 376.16 Found: 377.2 [M + H]$^+$ |
| 447 | | ++ | + | + | + | | | Calcd: 463.13 Found: 464.0 [M + H]$^+$ |

TABLE 3-continued

In Vitro IC$_{50}$ data for selected compounds of the invention.

| Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | PC3 proliferation (nM)* | T47D proliferation (nM) | Mass Characterization |
|---|---|---|---|---|---|---|---|---|
| 448 | | +++ | + | + | ++ | | | Calcd: 377.40 Found: 378.2 [M + H]$^+$ |
| 449 | | +++ | +++ | + | ++++ | | | Calcd: 377.15 Found: 378.2 [M + H]$^+$ |
| 450 | | ++ | + | + | + | | | Calcd: 401.12 Found: 402.2 [M + H]$^+$ |
| 451 | ++++ | +++ | ++++ | ++++ | +++ | | | Calcd: 497.95 Found: 498.0 [M]$^+$ |
| 452 | ++++ | +++ | ++++ | ++++ | ++ | | | Calcd: 515.08 Found: 516.0 [M + H]$^+$ |

TABLE 3-continued

In Vitro IC$_{50}$ data for selected compounds of the invention.

| | Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | PC3 proliferation (nM)* | T47D proliferation (nM) | Mass Characterization |
|---|---|---|---|---|---|---|---|---|---|
| 453 | 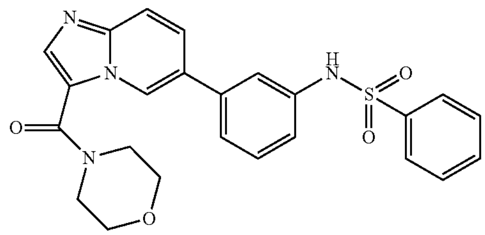 [SMILES: O=C(c1cnc2ccc(-c3cccc(NS(=O)(=O)c4ccccc4)c3)cn12)N1CCOCC1] | | ++ | + | + | ++ | | | Calcd: 462.14 Found: 463.0 [M + H]$^+$ |
| 454 | 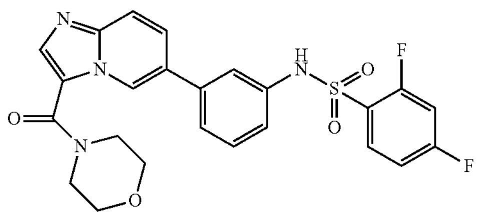 [SMILES: O=C(c1cnc2ccc(-c3cccc(NS(=O)(=O)c4ccc(F)cc4F)c3)cn12)N1CCOCC1] | | ++ | + | ++ | ++ | | | Calcd: 498.12 Found: 499.0 [M + H]$^+$ |
| 455 | 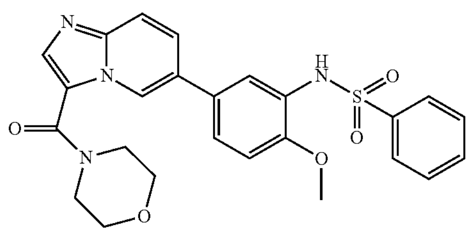 [SMILES: COc1ccc(-c2ccc3ncc(C(=O)N4CCOCC4)n3c2)cc1NS(=O)(=O)c1ccccc1] | | ++ | + | + | ++ | | | Calcd: 492.15 Found: 493.2 [M + H]$^+$ |
| 456 | 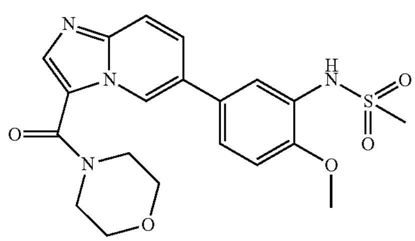 [SMILES: COc1ccc(-c2ccc3ncc(C(=O)N4CCOCC4)n3c2)cc1NS(C)(=O)=O] | | + | + | + | + | | | Calcd: 430.13 Found: 431.0 [M + H]$^+$ |
| 457 | 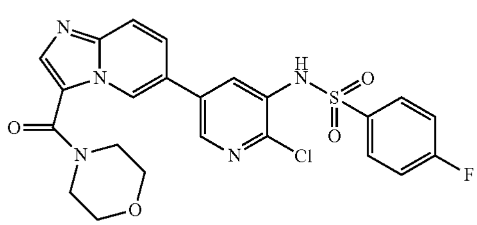 [SMILES: O=C(c1cnc2ccc(-c3cnc(Cl)c(NS(=O)(=O)c4ccc(F)cc4)c3)cn12)N1CCOCC1] | | ++++ | ++++ | ++++ | ++++ | +++ | | Calcd: 515.08 Found: 516.0 [M + H]$^+$ |
| 458 | 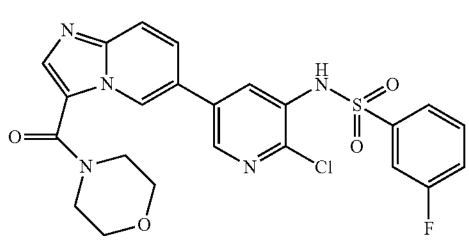 | | ++++ | ++++ | ++++ | ++++ | +++ | | Calcd: 515.08 Found: 516.0 [M + H]$^+$ |

//

TABLE 3-continued

In Vitro IC$_{50}$ data for selected compounds of the invention.

| Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | PC3 proliferation (nM)* | T47D proliferation (nM) | Mass Characterization |
|---|---|---|---|---|---|---|---|---|
| 459 | | +++ | + | + | +++ | | | Calcd: 496.10 Found: 497.0 [M + H]$^+$ |
| 460 | | ++ | + | + | + | | | Calcd: 434.08 Found: 435.0 [M + H]$^+$ |
| 461 | | +++ | ++ | ++ | +++ | | | Calcd: 532.08 Found: 533.0 [M + H]$^+$ |
| 462 | | ++++ | ++++ | ++++ | ++++ | +++ | | Calcd: 494.14 Found: 495.0 [M + H]$^+$ |
| 463 | | ++++ | ++ | ++ | +++ | | | Calcd: 377.15 Found: 378.2 [M + H]$^+$ |

TABLE 3-continued

In Vitro IC$_{50}$ data for selected compounds of the invention.

| | Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | PC3 proliferation (nM)* | T47D proliferation (nM) | Mass Characterization |
|---|---|---|---|---|---|---|---|---|---|
| 464 | 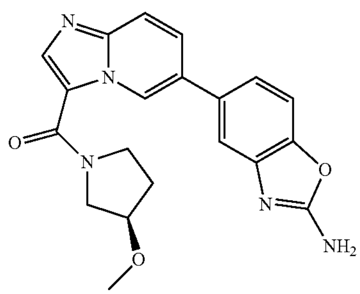 [SMILES: CO[C@@H]1CCN(C(=O)c2cnc3ccc(-c4ccc5oc(N)nc5c4)cn23)C1] | | ++++ | + | + | +++ | | ++ | Calcd: 377.15 Found: 378.2 [M + H]$^+$ |
| 465 | 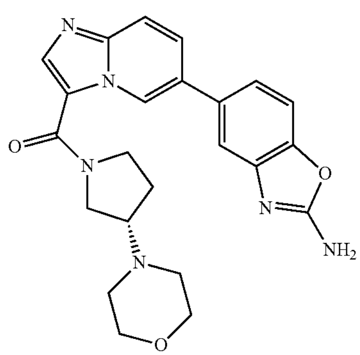 [SMILES: Nc1nc2cc(-c3ccc4ncc(C(=O)N5CC[C@H](N6CCOCC6)C5)n4c3)ccc2o1] | | ++++ | + | + | +++ | | | Calcd: 432.19 Found: 433.2 [M + H]$^+$ |
| 466 | 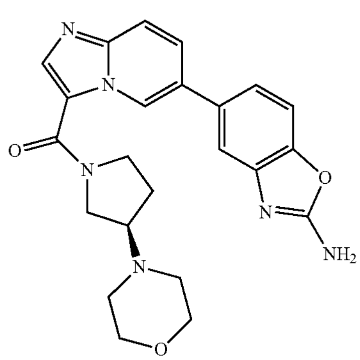 [SMILES: Nc1nc2cc(-c3ccc4ncc(C(=O)N5CC[C@@H](N6CCOCC6)C5)n4c3)ccc2o1] | | +++ | ++ | ++ | +++ | | | Calcd: 432.19 Found: 433.2 [M + H]$^+$ |
| 467 | 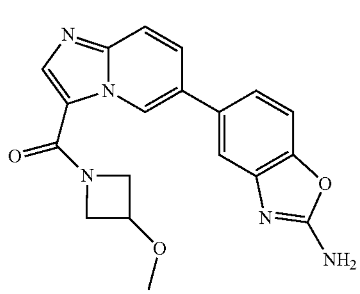 [SMILES: COC1CN(C(=O)c2cnc3ccc(-c4ccc5oc(N)nc5c4)cn23)C1] | | ++++ | ++ | ++ | ++++ | +++ | | Calcd: 363.13 Found: 364.0 [M + H]$^+$ |

TABLE 3-continued
In Vitro IC$_{50}$ data for selected compounds of the invention.
| Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | PC3 proliferation (nM)* | T47D proliferation (nM) | Mass Characterization |
|---|---|---|---|---|---|---|---|---|
| 468 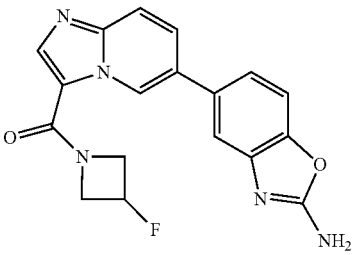 [SMILES: Nc1nc2cc(-c3ccc4ncc(C(=O)N5CC(F)C5)n4c3)ccc2o1] | | ++++ | ++ | + | ++++ | | | Calcd: 351.11 Found: 352.2 [M + H]$^+$ |
| 469 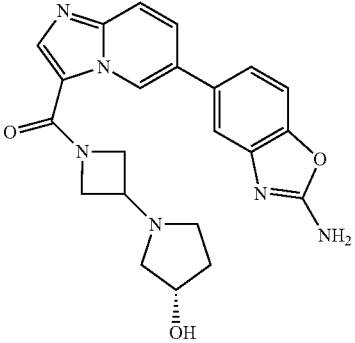 [SMILES: Nc1nc2cc(-c3ccc4ncc(C(=O)N5CC(N6CC[C@H](O)C6)C5)n4c3)ccc2o1] | | ++++ | ++ | ++ | +++ | ++ | | Calcd: 418.18 Found: 419.2 [M + H]$^+$ |
| 470 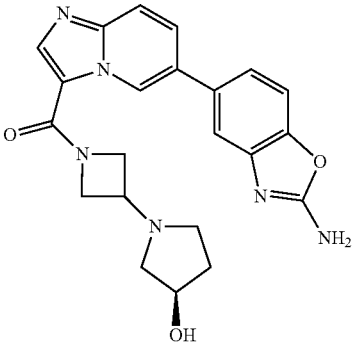 [SMILES: Nc1nc2cc(-c3ccc4ncc(C(=O)N5CC(N6CC[C@@H](O)C6)C5)n4c3)ccc2o1] | | ++++ | ++ | ++ | +++ | ++ | | Calcd: 418.18 Found: 419.2 [M + H]$^+$ |
| 471 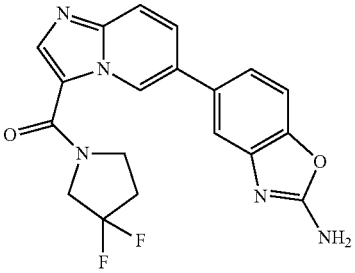 [SMILES: Nc1nc2cc(-c3ccc4ncc(C(=O)N5CCC(F)(F)C5)n4c3)ccc2o1] | | ++++ | + | + | ++++ | ++ | | Calcd: 383.12 Found: 384.2 [M + H]$^+$ |

TABLE 3-continued

In Vitro IC$_{50}$ data for selected compounds of the invention.

| Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | PC3 proliferation (nM)* | T47D proliferation (nM) | Mass Characterization |
|---|---|---|---|---|---|---|---|---|
| 472 | | ++++ | ++ | ++ | +++ | ++ | | Calcd: 391.16 Found: 392.2 [M + H]$^+$ |
| 473 | | ++++ | + | + | ++++ | +++ | | Calcd: 369.10 Found: 370.0 [M + H]$^+$ |
| 474 | | ++ | + | + | + | | | Calcd: 379.11 Found: 380.2 [M + H]$^+$ |
| 475 | | ++++ | + | ++ | ++++ | | | Calcd: 365.13 Found: 366.2 [M + H]$^+$ |
| 476 | | ++++ | + | + | ++++ | | | Calcd: 365.13 Found: 366.2 [M + H]$^+$ |

TABLE 3-continued

In Vitro IC$_{50}$ data for selected compounds of the invention.

| | Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | PC3 proliferation (nM)* | T47D proliferation (nM) | Mass Characterization |
|---|---|---|---|---|---|---|---|---|---|
| 477 | 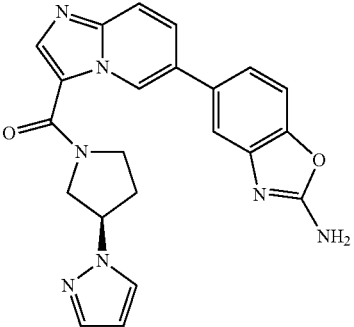 [SMILES: Nc1nc2cc(-c3ccc4ncc(C(=O)N5CC[C@@H](n6cccn6)C5)n4c3)ccc2o1] | | ++++ | + | ++ | +++ | | | Calcd: 413.16 Found: 414.2 [M + H]$^+$ |
| 478 | 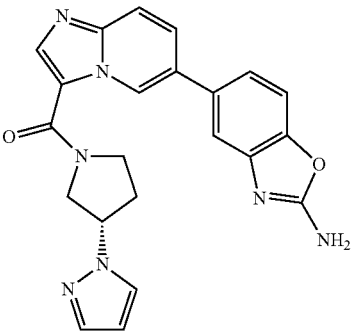 [SMILES: Nc1nc2cc(-c3ccc4ncc(C(=O)N5CC[C@H](n6cccn6)C5)n4c3)ccc2o1] | | ++++ | ++ | +++ | +++ | +++ | | Calcd: 413.16 Found: 414.2 [M + H]$^+$ |
| 479 | 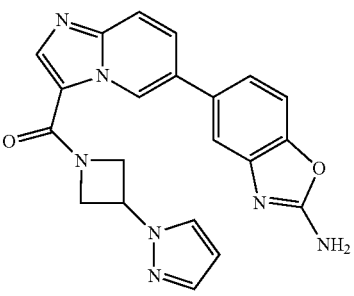 [SMILES: Nc1nc2cc(-c3ccc4ncc(C(=O)N5CC(n6cccn6)C5)n4c3)ccc2o1] | | ++++ | + | ++ | +++ | | | Calcd: 399.14 Found: 400.2 [M + H]$^+$ |
| 480 | 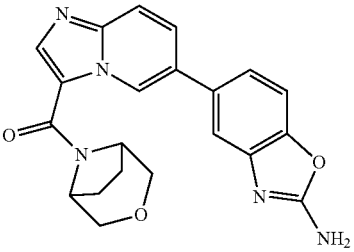 [SMILES: Nc1nc2cc(-c3ccc4ncc(C(=O)N5C6CCC5COC6)n4c3)ccc2o1] | | ++++ | + | ++ | +++ | +++ | | Calcd: 389.15 Found: 390.2 [M + H]$^+$ |
| 481 | 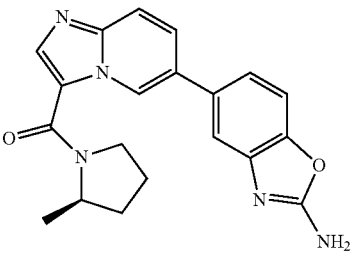 [SMILES: C[C@@H]1CCCN1C(=O)c1cnc2ccc(-c3ccc4oc(N)nc4c3)cn12] | | ++++ | ++ | ++ | +++ | | | Calcd: 361.15 Found: 362.0 [M + H]$^+$ |

TABLE 3-continued

In Vitro IC$_{50}$ data for selected compounds of the invention.

| Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | PC3 proliferation (nM)* | T47D proliferation (nM) | Mass Characterization |
|---|---|---|---|---|---|---|---|---|
| 482 | | ++++ | + | ++ | +++ | | | Calcd: 361.15 Found: 362.2 [M + H]$^+$ |
| 483 | | ++++ | ++ | + | ++ | ++ | | Calcd: 377.15 Found: 378.2 [M + H]$^+$ |
| 484 | | +++ | + | + | + | | | Calcd: 363.13 Found: 364.2 [M + H]$^+$ |
| 485 | | ++ | + | + | + | | | Calcd: 379.11 Found: 380.2 [M + H]$^+$ |
| 486 | | ++ | + | + | ++ | | | Calcd: 377.15 Found: 378.2 [M + H]$^+$ |

TABLE 3-continued

In Vitro IC$_{50}$ data for selected compounds of the invention.

| Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | PC3 proliferation (nM)* | T47D proliferation (nM) | Mass Characterization |
|---|---|---|---|---|---|---|---|---|
| 487 | | + | + | + | + | | | Calcd: 362.15 Found: 363.2 [M + H]$^+$ |
| 488 | | + | + | + | + | | | Calcd: 363.13 Found: 364.2 [M + H]$^+$ |
| 489 | | ++ | + | + | + | | | Calcd: 379.11 Found: 380.0 [M + H]$^+$ |
| 490 | | + | + | + | + | | | Calcd: 362.15 Found: 363.0 [M + H]$^+$ |
| 491 | | + | + | + | + | | | Calcd: 363.13 Found: 364.2 [M + H]$^+$ |
| 492 | | +++ | ++ | ++ | ++ | | | Calcd: 348.13 Found: 349.2 [M + H]$^+$ |

TABLE 3-continued

In Vitro IC$_{50}$ data for selected compounds of the invention.

| | Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | PC3 proliferation (nM)* | T47D proliferation (nM) | Mass Characterization |
|---|---|---|---|---|---|---|---|---|---|
| 493 | 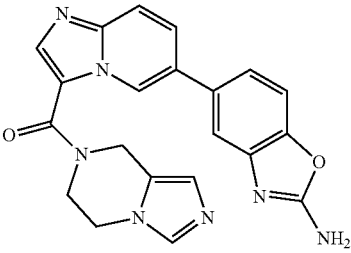 [SMILES: Nc1nc2cc(-c3ccc4ncc(C(=O)N5CCn6cncc6C5)n4c3)ccc2o1] | | ++++ | +++ | + | ++ | | | Calcd: 399.14 Found: 400.0 [M + H]$^+$ |
| 494 | 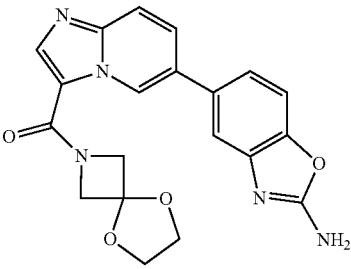 [SMILES: Nc1nc2cc(-c3ccc4ncc(C(=O)N5CC6(C5)OCCO6)n4c3)ccc2o1] | | ++++ | ++ | + | +++ | | | Calcd: 391.13 Found: 392.0 [M + H]$^+$ |
| 495 | 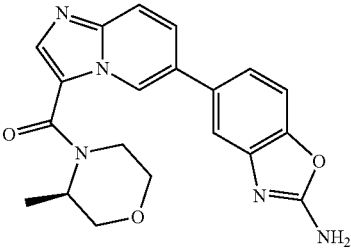 [SMILES: C[C@@H]1COCCN1C(=O)c1cnc2ccc(-c3ccc4oc(N)nc4c3)cn12] | | ++++ | ++ | + | +++ | | | Calcd: 377.15 Found: 378.2 [M + H]$^+$ |
| 496 | 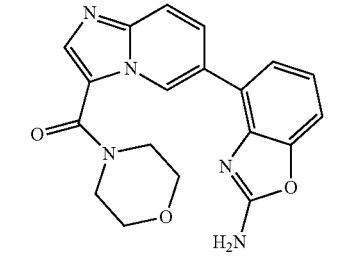 [SMILES: Nc1nc2c(-c3ccc4ncc(C(=O)N5CCOCC5)n4c3)cccc2o1] | | +++ | ++ | + | ++ | | | Calcd: 363.13 Found: 364.2 [M + H]$^+$ |
| 497 | 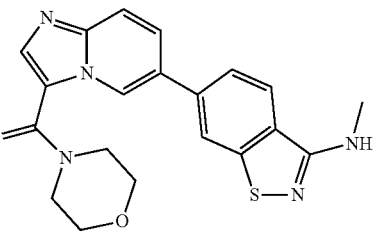 | | + | + | + | + | | | Calcd: 393.13 Found: 394.0 [M + H]$^+$ |

TABLE 3-continued
In Vitro IC$_{50}$ data for selected compounds of the invention.
| Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | PC3 proliferation (nM)* | T47D proliferation (nM) | Mass Characterization |
|---|---|---|---|---|---|---|---|---|
| 498 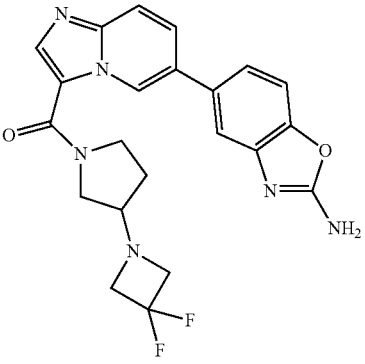 [SMILES: Nc1nc2cc(-c3ccc4ncc(C(=O)N5CCC(N6CC(F)(F)C6)C5)n4c3)ccc2o1] | | +++ | + | + | ++ | | | Calcd: 438.16 Found: 439.0 [M + H]$^+$ |
| 499 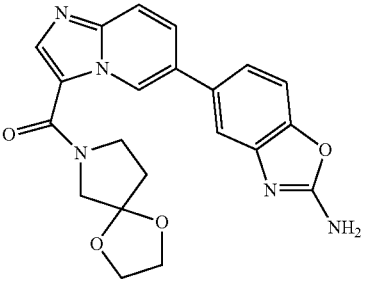 [SMILES: Nc1nc2cc(-c3ccc4ncc(C(=O)N5CCC6(C5)OCCO6)n4c3)ccc2o1] | | +++ | + | + | ++ | | | Calcd: 405.14 Found: 406.0 [M + H]$^+$ |
| 500 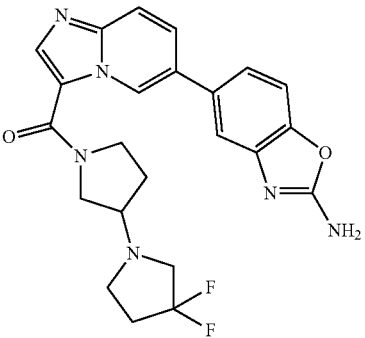 [SMILES: Nc1nc2cc(-c3ccc4ncc(C(=O)N5CCC(N6CCC(F)(F)C6)C5)n4c3)ccc2o1] | | +++ | + | ++ | ++ | | | Calcd: 452.18 Found: 452.2 [M + H]$^+$ |
| 501 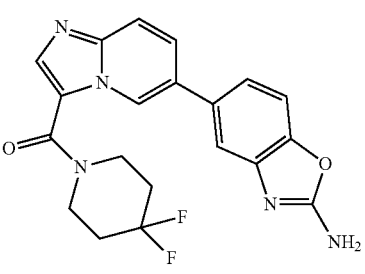 [SMILES: Nc1nc2cc(-c3ccc4ncc(C(=O)N5CCC(F)(F)CC5)n4c3)ccc2o1] | | +++ | + | + | ++ | | | Calcd: 397.14 Found: 398.0 [M + H]$^+$ |

TABLE 3-continued

In Vitro IC$_{50}$ data for selected compounds of the invention.

| Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | PC3 proliferation (nM)* | T47D proliferation (nM) | Mass Characterization |
|---|---|---|---|---|---|---|---|---|
| 502 | | ++++ | + | ++ | +++ | | | Calcd: 438.16 Found: 439.2 [M + H]$^+$ |
| 503 | | +++ | + | + | ++++ | | | Calcd: 379.14 Found: 380.2 [M + H]$^+$ |
| 504 | | +++ | ++ | + | ++++ | | | Calcd: 389.15 Found: 390.2 |
| 505 | | + | + | + | + | | | Calcd: 455.14 Found: 456.0 [M + H]$^+$ |
| 506 | | ++++ | + | + | + | | | Calcd: 348.13 Found: 349.2 [M + H]$^+$ |

TABLE 3-continued

In Vitro IC$_{50}$ data for selected compounds of the invention.

| Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | PC3 proliferation (nM)* | T47D proliferation (nM) | Mass Characterization |
|---|---|---|---|---|---|---|---|---|
| 507 | | + | + | + | + | | | Calcd: 377.15 Found: 378.2 [M + H]$^+$ |
| 508 | | ++++ | ++ | +++ | ++ | +++ | | Calcd: 445.22 Found: 446.2 [M + H]$^+$ |
| 509 | | + | + | + | + | | | Calcd: 439.16 Found: 440.0 [M + H]$^+$ |
| 510 | | ++++ | ++ | +++ | ++ | ++ | | Calcd: 431.21 Found: 432.2 [M + H]$^+$ |
| 511 | | ++++ | ++ | +++ | ++ | ++ | | Calcd: 431.21 Found: 432.2 [M + H]$^+$ |

TABLE 3-continued

In Vitro IC$_{50}$ data for selected compounds of the invention.

| Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | PC3 proliferation (nM)* | T47D proliferation (nM) | Mass Characterization |
|---|---|---|---|---|---|---|---|---|
| 512 | | ++++ | ++ | +++ | ++ | +++ | | Calcd: 445.22 Found: 446.2 [M + H]$^+$ |
| 513 | | +++ | + | + | ++ | | | Calcd: 391.16 Found: 392.2 [M + H]$^+$ |
| 514 | | +++ | + | + | + | | | Calcd: 391.16 Found: 392.2 [M + H]$^+$ |
| 515 | | ++++ | ++ | ++++ | +++ | +++ | | Calcd: 445.22 Found: 446.2 [M + H]$^+$ |
| 516 | | +++ | + | + | + | | | Calcd: 382.09 Found: 383.2 [M + H]$^+$ |

TABLE 3-continued

In Vitro IC$_{50}$ data for selected compounds of the invention.

| | Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | PC3 proliferation (nM)* | T47D proliferation (nM) | Mass Characterization |
|---|---|---|---|---|---|---|---|---|---|
| 517 | 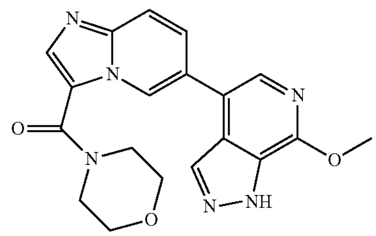 [SMILES: COc1ncc(-c2ccc3ncc(C(=O)N4CCOCC4)n3c2)c2cn[nH]c12] | | +++ | + | ++ | ++ | | | Calcd: 378.14 Found: 379.2 [M + H]$^+$ |
| 518 | 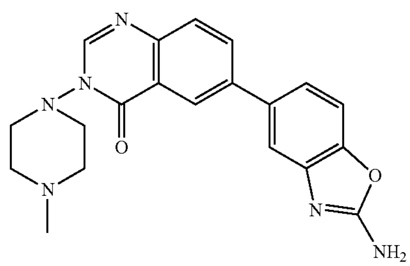 [SMILES: CN1CCN(n2cnc3ccc(-c4ccc5oc(N)nc5c4)cc3c2=O)CC1] | | +++ | + | + | + | | | Calcd: 376.16 Found: 377.2 [M + H]$^+$ |
| 519 | 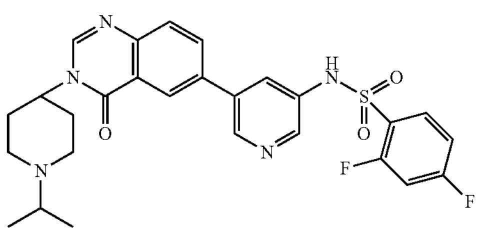 [SMILES: CC(C)N1CCC(n2cnc3ccc(-c4cncc(NS(=O)(=O)c5ccc(F)cc5F)c4)cc3c2=O)CC1] | | +++ | ++ | ++ | +++ | | | Calcd: 539.18 Found: 540.2 [M + H]$^+$ |
| 520 | 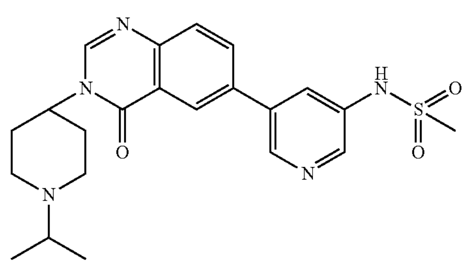 [SMILES: CC(C)N1CCC(n2cnc3ccc(-c4cncc(NS(C)(=O)=O)c4)cc3c2=O)CC1] | | + | + | + | + | | | Calcd: 441.18 Found: 442.2 [M + H]$^+$ |
| 521 | 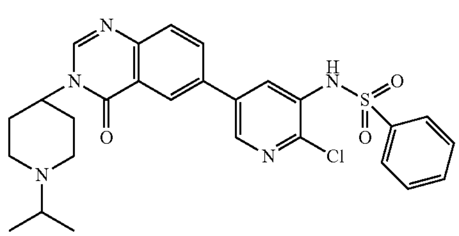 [SMILES: CC(C)N1CCC(n2cnc3ccc(-c4cnc(Cl)c(NS(=O)(=O)c5ccccc5)c4)cc3c2=O)CC1] | | ++++ | ++++ | ++++ | +++ | | | Calcd: 537.16 Found: 538.0 [M + H]$^+$ |
| 522 | 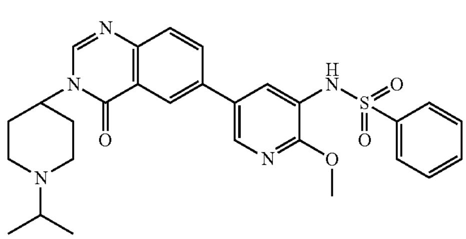 [SMILES: COc1ncc(-c2ccc3ncn(C4CCN(C(C)C)CC4)c(=O)c3c2)cc1NS(=O)(=O)c1ccccc1] | | ++++ | ++++ | ++++ | ++++ | +++ | | Calcd: 533.21 Found: 534.2 [M + H]$^+$ |

TABLE 3-continued

In Vitro IC$_{50}$ data for selected compounds of the invention.

| Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | PC3 proliferation (nM)* | T47D proliferation (nM) | Mass Characterization |
|---|---|---|---|---|---|---|---|---|
| 523 | | ++++ | +++ | ++++ | ++++ | ++ | | Calcd: 475.14 Found: 476.2 [M + H]$^+$ |
| 524 | | ++++ | ++++ | ++++ | +++ | +++ | | Calcd: 505.18 Found: 506.2 [M + H]$^+$ |
| 525 | | ++++ | +++ | ++++ | ++ | | | Calcd: 443.16 Found: 444.2 [M + H]$^+$ |
| 526 | | ++++ | ++ | +++ | + | ++ | | Calcd: 447.11 Found: 448.0 [M + H]$^+$ |
| 527 | | ++++ | ++++ | ++++ | +++ | | | Calcd: 509.13 Found: 510.2 [M + H]$^+$ |
| 528 | | +++ | ++ | + | + | | | Calcd: 347.14 Found: 348.2 [M + H]$^+$ |

TABLE 3-continued

In Vitro IC$_{50}$ data for selected compounds of the invention.

| | Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | PC3 proliferation (nM)* | T47D proliferation (nM) | Mass Characterization |
|---|---|---|---|---|---|---|---|---|---|
| 529 | 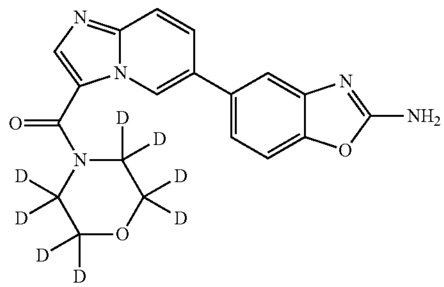 [SMILES: [2H]C1([2H])OC([2H])([2H])C([2H])([2H])N(C(=O)c2cnc3ccc(-c4ccc5oc(N)nc5c4)cn23)C1([2H])[2H]] | | +++ | + | + | ++ | | | Calcd: 371.18 Found: 372.2 [M + H]$^+$ |
| 530 | 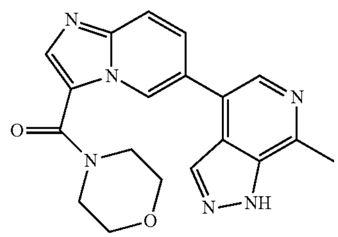 [SMILES: Cc1ncc(-c2ccc3ncc(C(=O)N4CCOCC4)n3c2)c2cn[nH]c12] | | ++++ | + | ++ | + | | | |
| 531 | 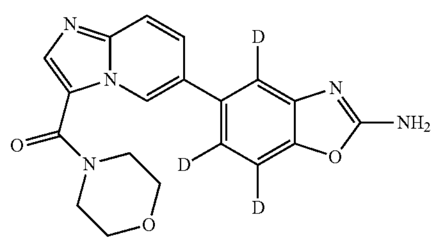 [SMILES: [2H]c1c(-c2ccc3ncc(C(=O)N4CCOCC4)n3c2)c([2H])c2nc(N)oc2c1[2H]] | | ++++ | ++ | + | ++++ | | | |
| 532 | 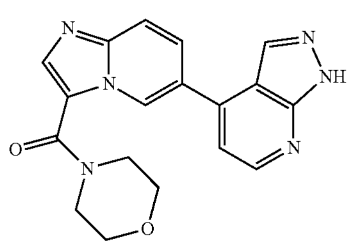 [SMILES: O=C(c1cnc2ccc(-c3ccnc4[nH]ncc34)cn12)N1CCOCC1] | + | ++ | + | + | + | | | |
| 533 | 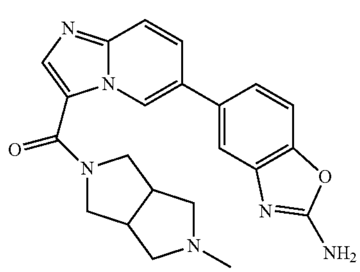 [SMILES: CN1CC2CN(C(=O)c3cnc4ccc(-c5ccc6oc(N)nc6c5)cn34)CC2C1] | + | ++++ | +++ | +++ | +++ | | | |

TABLE 3-continued

In Vitro IC$_{50}$ data for selected compounds of the invention.

| | Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | PC3 proliferation (nM)* | T47D proliferation (nM) | Mass Characterization |
|---|---|---|---|---|---|---|---|---|---|
| 534 | 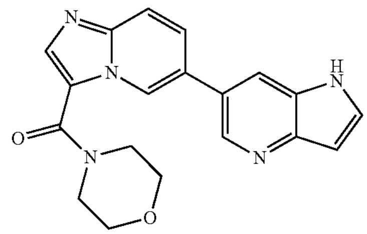 [SMILES: O=C(c1cnc2ccc(-c3cnc4cc[nH]c4c3)cn12)N1CCOCC1] | | ++ | + | + | + | | | |
| 535 | 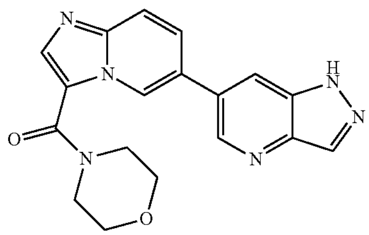 [SMILES: O=C(c1cnc2ccc(-c3cnc4cn[nH]c4c3)cn12)N1CCOCC1] | | ++ | + | + | + | | | |
| 536 | 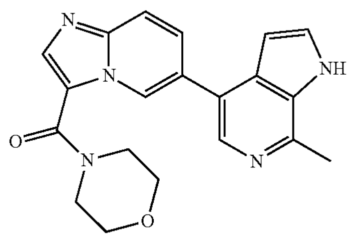 [SMILES: Cc1ncc(-c2ccc3ncc(C(=O)N4CCOCC4)n3c2)c2cc[nH]c12] | | ++ | + | + | + | | | |
| 537 | 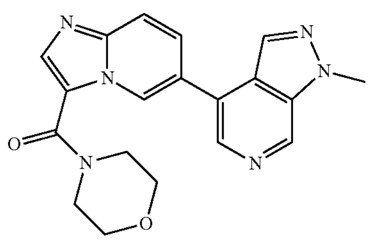 [SMILES: Cn1ncc2c(-c3ccc4ncc(C(=O)N5CCOCC5)n4c3)cncc21] | | ++ | + | + | ++ | | | |
| 538 | 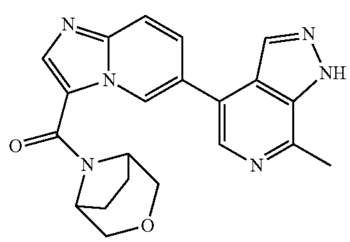 [SMILES: Cc1ncc(-c2ccc3ncc(C(=O)N4C5CCC4COC5)n3c2)c2cn[nH]c12] | + | ++++ | + | ++ | + | | | |
| 539 | 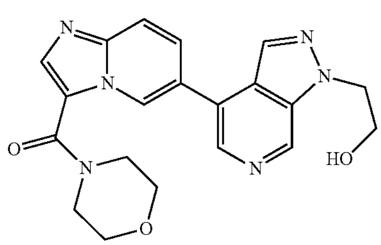 [SMILES: O=C(c1cnc2ccc(-c3cncc4c3cnn4CCO)cn12)N1CCOCC1] | | + | + | + | + | | | |

TABLE 3-continued

In Vitro IC$_{50}$ data for selected compounds of the invention.

| Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | PC3 proliferation (nM)* | T47D proliferation (nM) | Mass Characterization |
|---|---|---|---|---|---|---|---|---|
| 540 | | + | + | + | + | | | Calcd: 389.15 Found: 390.2 [M + H]$^+$ |
| 541 | | + | + | + | | | | Calcd: 363.13 Found: 364.2 [M + H]$^+$ |
| 542 | | + | + | + | + | | | Calcd: 349.17 Found: 350.20 [M + H]$^+$ |
| 543 | | + | ++ | + | + | | | Calcd: 342.12 Found: 343.2 [M + H]$^+$ |
| 544 | | +++ | + | + | + | | | Calcd: 362.15 Found: 363.20 [M + H]$^+$ |

TABLE 3-continued

In Vitro IC$_{50}$ data for selected compounds of the invention.

| Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | PC3 proliferation (nM)* | T47D proliferation (nM) | Mass Characterization |
|---|---|---|---|---|---|---|---|---|
| 545 | | | + | + | + | + | | | Calcd: 377.20 Found: 378.20 [M + H]$^+$ |
| 546 | | | + | + | + | + | | | Calcd: 363.18 Found: 364.2 [M + H]$^+$ |
| 547 | | | + | + | + | + | | | Calcd: 363.18 Found: 364.2 [M + H]$^+$ |
| 548 | | | + | + | + | + | | | Calcd: 391.2 Found: 392.2 [M + H]$^+$ |

TABLE 3-continued

In Vitro IC$_{50}$ data for selected compounds of the invention.

| Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | PC3 proliferation (nM)* | T47D proliferation (nM) | Mass Characterization |
|---|---|---|---|---|---|---|---|---|
| 549 | | + | + | + | + | | | Calcd: 377.2 Found: 378.2 [M + H]$^+$ |
| 550 | +++ | ++ | ++ | +++ | | | | Calcd: 381.1 Found: 382.2 [M + H]$^+$ |
| 551 | ++++ | +++ | ++ | ++++ | | | | Calcd: 395.1 Found: 396.0 [M + H]$^+$ |

The following symbols are used: + (greater than 10 microMolar), ++ (less than 10 microMolar), +++ (less than 1 microMolar), and ++++ (less than 100 nM).

Table 4 shows additional exemplary PI3K α inhibitors of the invention.

TABLE 4

In Vitro IC$_{50}$ data for selected compounds of the invention. The following symbols are used: + (greater than 10 microMolar), ++ (less than 10 microMolar), +++ (less than 1 microMolar), and ++++ (less than 100 nM).

| Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | MDA-MB-361 proliferation (nM)* | Mass Characterization |
|---|---|---|---|---|---|---|---|
| 552 | +++ | ++++ | ++ | ++ | ++ | | Calcd: 361.17 Found: 362.2 [M + H]$^+$ |

TABLE 4-continued

In Vitro IC$_{50}$ data for selected compounds of the invention. The following symbols are used: + (greater than 10 microMolar), ++ (less than 10 microMolar), +++ (less than 1 microMolar), and ++++ (less than 100 nM).

| | Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | MDA-MB-361 proliferation (nM)* | Mass Characterization |
|---|---|---|---|---|---|---|---|---|
| 553 | | | ++++ | +++ | + | ++++ | | +++ | Calcd: 348.13 Found: 349.2 [M + H]$^+$ |
| 554 | | | +++ | ++ | + | +++ | | | Calcd: 340.11 Found: 341.0 [M + H]$^+$ |
| 555 | | | +++ | +++ | ++ | ++ | | ++ | Calcd: 361.17 Found: 362.2 [M + H]$^+$ |
| 556 | 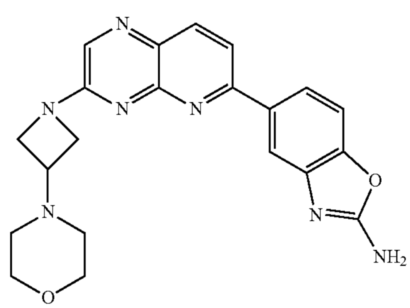 [SMILES: Nc1nc2cc(-c3ccc4ncc(N5CC(N6CCOCC6)C5)nc4n3)ccc2o1] | ++ | ++++ | + | ++ | ++ | ++ | Calcd: 403.18 Found: 404.2 [M + H]$^+$ |
| 557 | | | ++++ | +++ | +++ | +++ | | +++ | Calcd: 419.17 Found: 420.2 [M + H]$^+$ |

TABLE 4-continued

In Vitro IC$_{50}$ data for selected compounds of the invention. The following symbols are used: + (greater than 10 microMolar), ++ (less than 10 microMolar), +++ (less than 1 microMolar), and ++++ (less than 100 nM).

| Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | MDA-MB-361 proliferation (nM)* | Mass Characterization |
|---|---|---|---|---|---|---|---|
| 558 | | + | + | + | + | | Calcd: 348.13 Found: 349.2 [M + H]$^+$ |
| 559 | ++++ | + | ++ | +++ | ++ | | Calcd: 480.17 Found: 481.0 [M + H]$^+$ |
| 560 | ++++ | ++ | ++ | ++++ | +++ | | Calcd: 416.16 Found: 417.2 [M + H]$^+$ |
| 561 | ++ | ++++ | + | ++ | ++ | ++ | Calcd: 416.21 Found: 417.2 [M + H]$^+$ |

TABLE 4-continued

In Vitro IC$_{50}$ data for selected compounds of the invention. The following symbols are used: + (greater than 10 microMolar), ++ (less than 10 microMolar), +++ (less than 1 microMolar), and ++++ (less than 100 nM).

| | Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | MDA-MB-361 proliferation (nM)* | Mass Characterization |
|---|---|---|---|---|---|---|---|---|
| 562 | 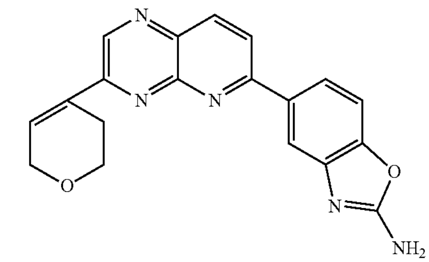 [SMILES: Nc1nc2cc(-c3ccc4ncc(C5=CCOCC5)nc4n3)ccc2o1] | | ++++ | ++ | + | ++++ | | Calcd: 345.12 Found: 346.0 [M + H]$^+$ |
| 563 | 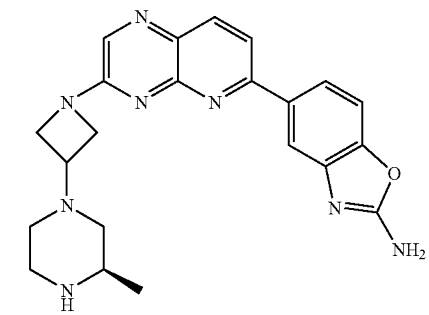 [SMILES: C[C@@H]1CN(C2CN(c3cnc4ccc(-c5ccc6oc(N)nc6c5)nc4n3)C2)CCN1] | + | ++++ | + | ++ | + | ++ | Calcd: 416.21 Found: 417.0 [M + H]$^+$ |
| 564 | 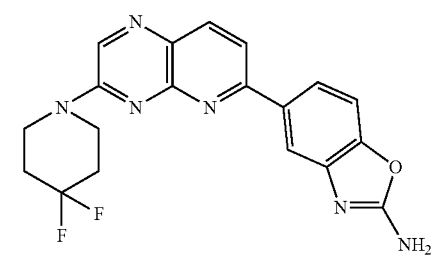 [SMILES: Nc1nc2cc(-c3ccc4ncc(N5CCC(F)(F)CC5)nc4n3)ccc2o1] | | ++++ | + | + | ++++ | ++ | Calcd: 382.14 Found: 383.2 [M + H]$^+$ |
| 565 | 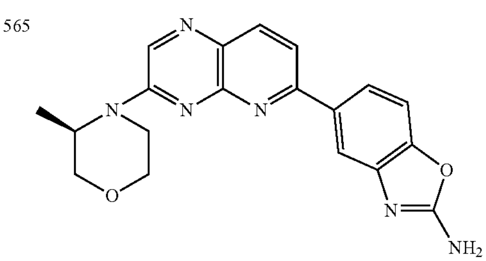 | | ++++ | ++ | ++ | ++++ | +++ | Calcd: 362.15 Found: 363.2 [M + H]$^+$ |
| 566 | 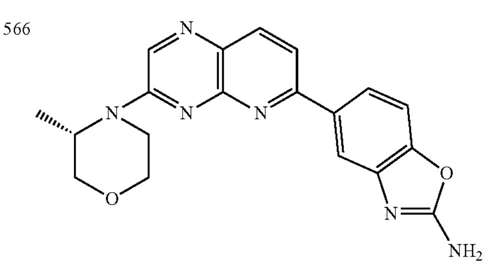 | | ++++ | ++ | + | ++++ | +++ | Calcd: 362.15 Found: 363.0 [M + H]$^+$ |

TABLE 4-continued

In Vitro IC$_{50}$ data for selected compounds of the invention. The following symbols are used: + (greater than 10 microMolar), ++ (less than 10 microMolar), +++ (less than 1 microMolar), and ++++ (less than 100 nM).

| | Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | MDA-MB-361 proliferation (nM)* | Mass Characterization |
|---|---|---|---|---|---|---|---|---|
| 567 | 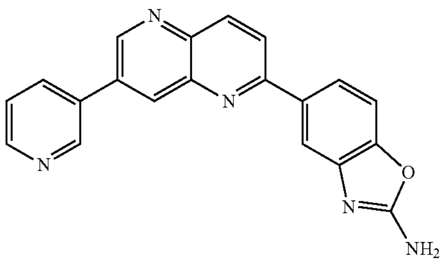 [SMILES: Nc1nc2cc(-c3ccc4ncc(-c5cccnc5)cc4n3)ccc2o1] | | ++++ | ++ | ++ | ++++ | + | Calcd: 339.11 Found: 340.0 [M + H]$^+$ |
| 568 | 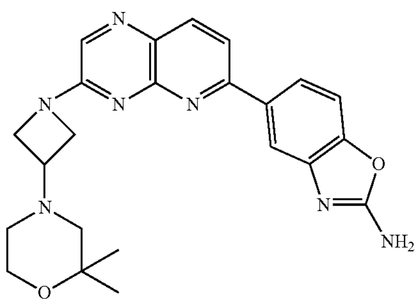 [SMILES: CC1(C)CN(C2CN(c3cnc4ccc(-c5ccc6oc(N)nc6c5)nc4n3)C2)CCO1] | | +++ | + | + | ++ | | Calcd: 431.21 Found: 432.2 [M + H]$^+$ |
| 569 | 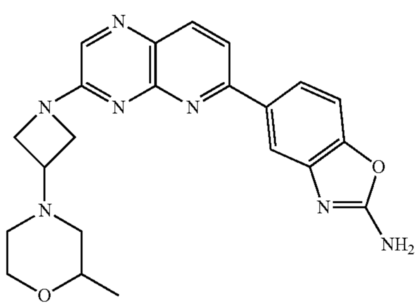 [SMILES: CC1CN(C2CN(c3cnc4ccc(-c5ccc6oc(N)nc6c5)nc4n3)C2)CCO1] | | +++ | + | + | ++ | | Calcd: 417.19 Found: 418.0 [M + H]$^+$ |
| 570 | 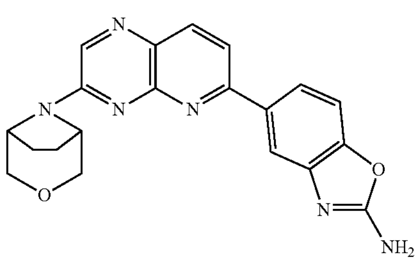 [SMILES: Nc1nc2cc(-c3ccc4ncc(N5C6CCC5COC6)nc4n3)ccc2o1] | + | ++++ | + | + | ++++ | +++ | Calcd: 374.15 Found: 375.0 [M + H]$^+$ |
| 571 | 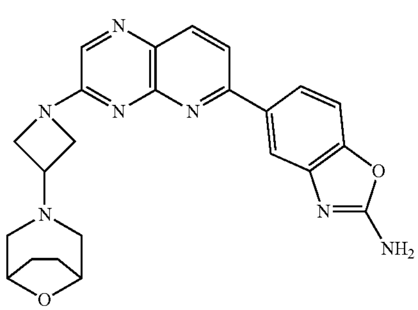 [SMILES: Nc1nc2cc(-c3ccc4ncc(N5CC(N6CC7CCC(C6)O7)C5)nc4n3)ccc2o1] | | +++ | + | + | ++ | | Calcd: 429.19 Found: 430.2 [M + H]$^+$ |

TABLE 4-continued

In Vitro IC$_{50}$ data for selected compounds of the invention. The following symbols are used: + (greater than 10 microMolar), ++ (less than 10 microMolar), +++ (less than 1 microMolar), and ++++ (less than 100 nM).

| | Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | MDA-MB-361 proliferation (nM)* | Mass Characterization |
|---|---|---|---|---|---|---|---|---|
| 572 | 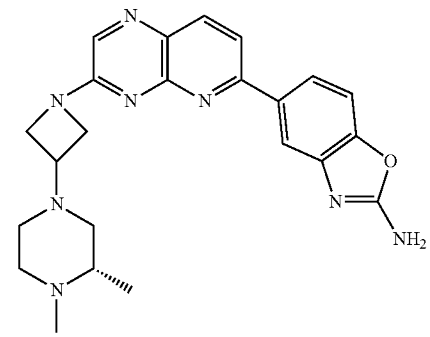 [SMILES: C[C@H]1CN(C2CN(c3cnc4ccc(-c5ccc6oc(N)nc6c5)nc4n3)C2)CCN1C] | ++++ | + | ++ | + | | ++ | Calcd: 430.22 Found: 431.0 [M + H]$^+$ |
| 573 | 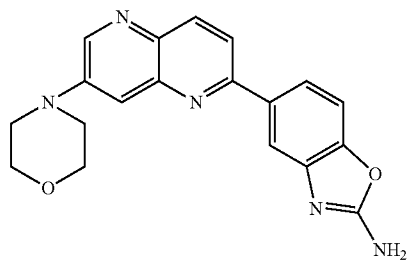 [SMILES: Nc1nc2cc(-c3ccc4ncc(N5CCOCC5)cc4n3)ccc2o1] | ++++ | +++ | + | ++++ | | ++ | Calcd: 347.14 Found: 348.0 [M + H]$^+$ |
| 574 | 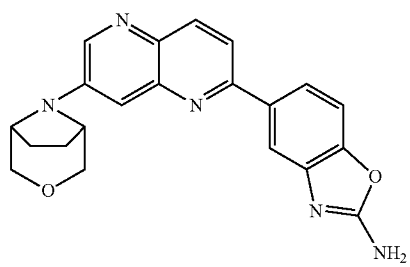 [SMILES: Nc1nc2cc(-c3ccc4ncc(N5C6CCC5COC6)cc4n3)ccc2o1] | ++++ | ++ | + | ++++ | | | Calcd: 373.15 Found: 374.2 [M + H]$^+$ |
| 575 | 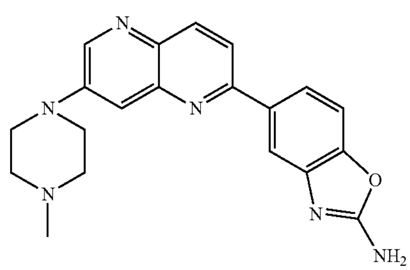 [SMILES: CN1CCN(c2cnc3ccc(-c4ccc5oc(N)nc5c4)nc3c2)CC1] | ++++ | ++++ | ++ | +++ | | ++ | Calcd: 360.17 Found: 361.2 [M + H]$^+$ |
| 576 | 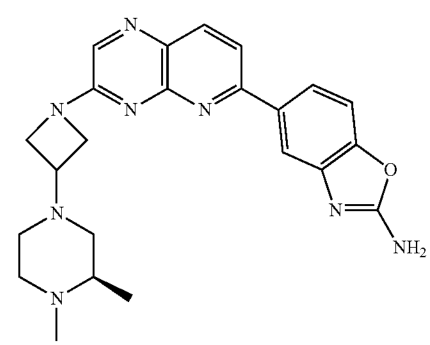 [SMILES: C[C@@H]1CN(C2CN(c3cnc4ccc(-c5ccc6oc(N)nc6c5)nc4n3)C2)CCN1C] | ++++ | + | ++ | ++ | | ++ | Calcd: 430.22 Found: 431.2 [M + H]$^+$ |

TABLE 4-continued

In Vitro IC$_{50}$ data for selected compounds of the invention. The following symbols are used: + (greater than 10 microMolar), ++ (less than 10 microMolar), +++ (less than 1 microMolar), and ++++ (less than 100 nM).

| | Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | MDA-MB-361 proliferation (nM)* | Mass Characterization |
|---|---|---|---|---|---|---|---|---|
| 577 | 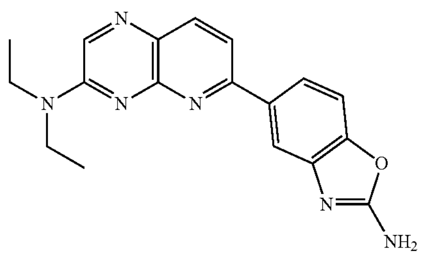 [SMILES: CCN(CC)c1cnc2ccc(-c3ccc4oc(N)nc4c3)nc2n1] | | +++ | + | ++ | +++ | | Calcd: 334.15 Found: 335.2 [M + H]$^+$ |
| 578 | 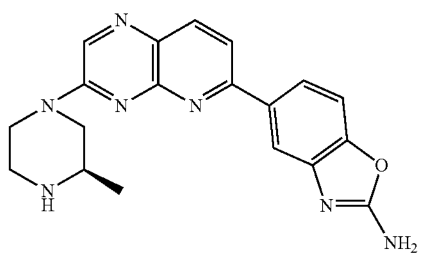 [SMILES: C[C@@H]1CN(c2cnc3ccc(-c4ccc5oc(N)nc5c4)nc3n2)CCN1] | | ++++ | ++++ | ++ | +++ | ++ | Calcd: 361.17 Found: 362.2 [M + H]$^+$ |
| 579 | 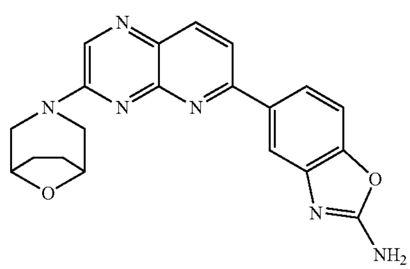 [SMILES: Nc1nc2cc(-c3ccc4ncc(N5CC6CCC(C5)O6)nc4n3)ccc2o1] | | ++++ | + | + | +++ | +++ | Calcd: 374.15 Found: 375.2 [M + H]$^+$ |
| 580 | 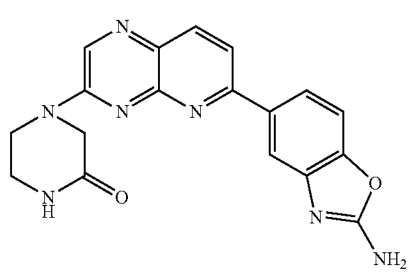 [SMILES: Nc1nc2cc(-c3ccc4ncc(N5CCNC(=O)C5)nc4n3)ccc2o1] | | ++++ | +++ | ++ | ++++ | +++ | Calcd: 361.13 Found: 362.0 [M + H]$^+$ |
| 581 | 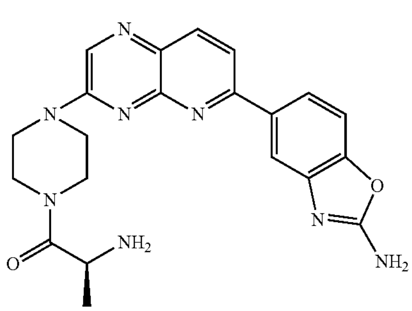 [SMILES: C[C@H](N)C(=O)N1CCN(c2cnc3ccc(-c4ccc5oc(N)nc5c4)nc3n2)CC1] | | ++++ | ++++ | ++++ | ++++ | | Calcd: 418.19 Found: 419.2 [M + H]$^+$ |

TABLE 4-continued

In Vitro IC$_{50}$ data for selected compounds of the invention. The following symbols are used: + (greater than 10 microMolar), ++ (less than 10 microMolar), +++ (less than 1 microMolar), and ++++ (less than 100 nM).

| | Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | MDA-MB-361 proliferation (nM)* | Mass Characterization |
|---|---|---|---|---|---|---|---|---|
| 582 | 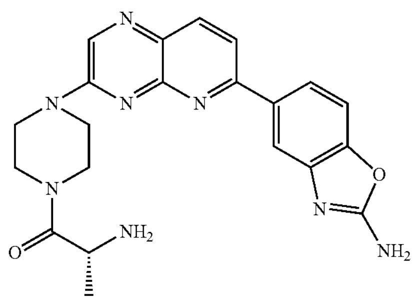 [SMILES: C[C@@H](N)C(=O)N1CCN(c2cnc3ccc(-c4ccc5oc(N)nc5c4)nc3n2)CC1] | ++++ | ++ | ++ | +++ | ++ | | Calcd: 418.91 Found: 419.2 [M + H]$^+$ |
| 583 | 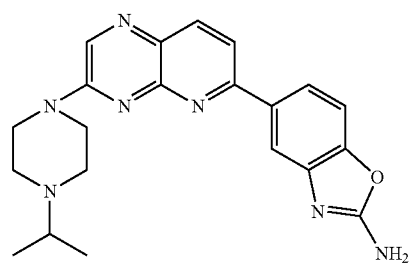 [SMILES: CC(C)N1CCN(c2cnc3ccc(-c4ccc5oc(N)nc5c4)nc3n2)CC1] | ++++ | +++ | ++ | +++ | ++ | | Calcd: 389.45 Found: 390.2 [M + H]$^+$ |
| 584 | 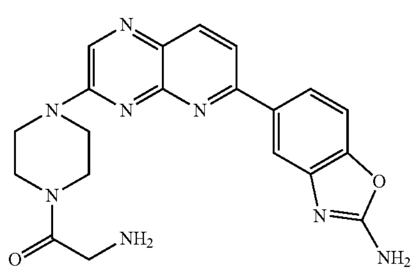 [SMILES: NCC(=O)N1CCN(c2cnc3ccc(-c4ccc5oc(N)nc5c4)nc3n2)CC1] | ++++ | ++ | ++ | ++ | + | | Calcd: 404.43 Found: 405.2 [M + H]$^+$ |
| 585 | 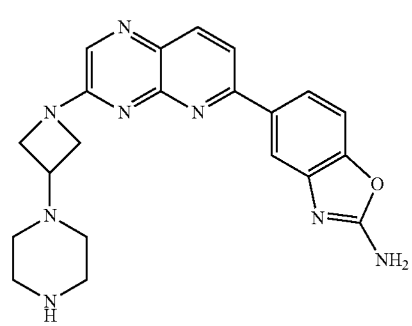 [SMILES: Nc1nc2cc(-c3ccc4ncc(N5CC(N6CCNCC6)C5)nc4n3)ccc2o1] | +++ | + | + | + | + | | Calcd: 402.19 Found: 403.0 [M + H]$^+$ |

TABLE 4-continued

In Vitro IC$_{50}$ data for selected compounds of the invention. The following symbols are used: + (greater than 10 microMolar), ++ (less than 10 microMolar), +++ (less than 1 microMolar), and ++++ (less than 100 nM).

| Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | MDA-MB-361 proliferation (nM)* | Mass Characterization |
|---|---|---|---|---|---|---|---|
| 586 | + | ++++ | ++ | ++ | ++ | ++ | Calcd: 456.24 Found: 457.2 [M + H]$^+$ |
| 587 | | ++++ | ++ | + | ++++ | +++ | Calcd: 418.18 Found: 419.0 [M + H]$^+$ |
| 588 | + | ++++ | +++ | +++ | +++ | ++ | Calcd: 403.18 Found: 404.2 [M + H]$^+$ |
| 589 | | ++++ | +++ | +++ | +++ | ++ | Calcd: 417.19 Found: 418.0 [M + H]$^+$ |

TABLE 4-continued

In Vitro IC$_{50}$ data for selected compounds of the invention. The following symbols are used: + (greater than 10 microMolar), ++ (less than 10 microMolar), +++ (less than 1 microMolar), and ++++ (less than 100 nM).

| | Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | MDA-MB-361 proliferation (nM)* | Mass Characterization |
|---|---|---|---|---|---|---|---|---|
| 590 | 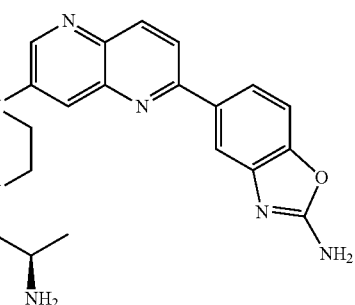 | | ++++ | ++++ | +++ | +++ | ++ | Calcd: 417.19<br>Found: 418.2<br>[M + H]$^+$ |
| 591 | 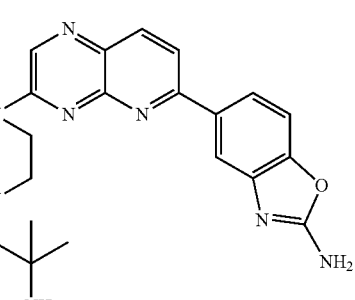 | + | ++++ | ++ | ++ | ++ | ++ | Calcd: 432.20<br>Found: 433.2<br>[M + H]$^+$ |
| 592 | 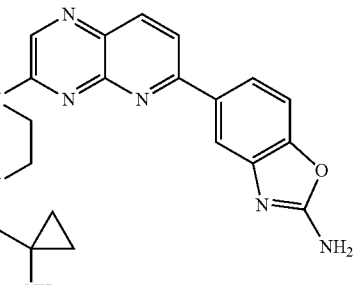 | ++ | ++++ | ++ | ++ | ++++ | ++ | Calcd: 430.19<br>Found: 431.0<br>[M + H]$^+$ |
| 593 | 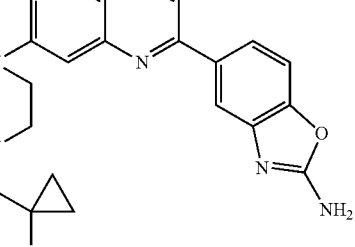 | ++++ | +++ | +++ | ++++ | +++ | | Calcd: 429.19<br>Found: 430.0<br>[M + H]$^+$ |

TABLE 4-continued

In Vitro IC$_{50}$ data for selected compounds of the invention. The following symbols are used: + (greater than 10 microMolar), ++ (less than 10 microMolar), +++ (less than 1 microMolar), and ++++ (less than 100 nM).

| | Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | MDA-MB-361 proliferation (nM)* | Mass Characterization |
|---|---|---|---|---|---|---|---|---|
| 594 | 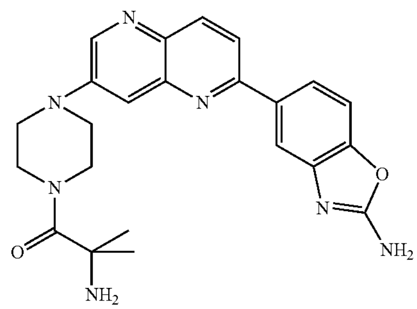 [SMILES: CC(C)(N)C(=O)N1CCN(c2cnc3ccc(-c4ccc5oc(N)nc5c4)nc3c2)CC1] | + | ++++ | ++ | +++ | +++ | +++ | Calcd: 431.21 Found: 432.2 [M + H]$^+$ |
| 595 | 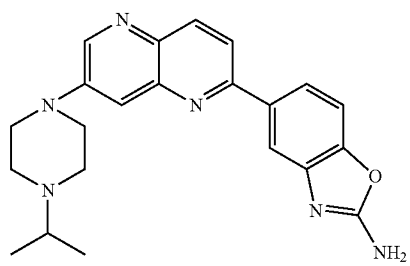 | + | ++++ | +++ | +++ | +++ | ++ | Calcd: 388.20 Found: 389.0 [M + H]$^+$ |
| 596 | 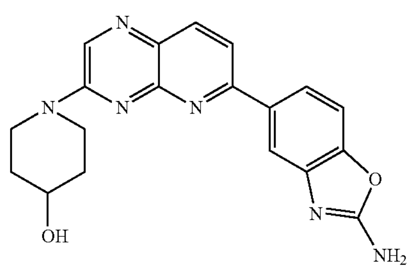 [SMILES: Nc1nc2cc(-c3ccc4ncc(N5CCC(O)CC5)nc4n3)ccc2o1] | | ++++ | ++ | + | ++++ | +++ | Calcd: 362.15 Found: 363.0 [M + H]$^+$ |
| 597 | 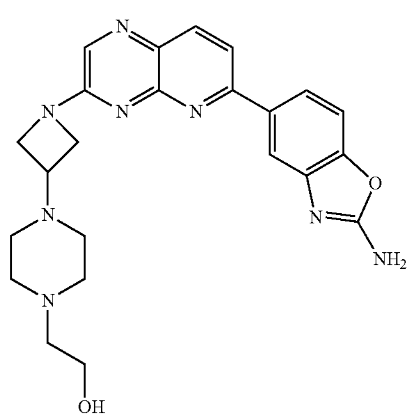 | + | ++++ | ++ | ++ | ++ | ++ | Calcd: 446.22 Found: 447.2 [M + H]$^+$ |

TABLE 4-continued

In Vitro IC$_{50}$ data for selected compounds of the invention. The following symbols are used: + (greater than 10 microMolar), ++ (less than 10 microMolar), +++ (less than 1 microMolar), and ++++ (less than 100 nM).

| | Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | MDA-MB-361 proliferation (nM)* | Mass Characterization |
|---|---|---|---|---|---|---|---|---|
| 598 | 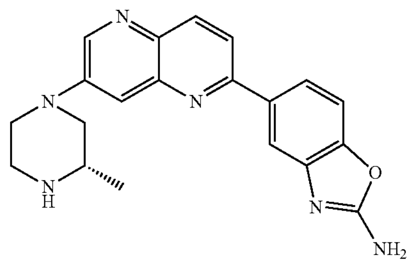 [SMILES: C[C@H]1CN(c2cnc3ccc(-c4ccc5oc(N)nc5c4)nc3c2)CCN1] | + | ++++ | ++++ | ++ | +++ | ++ | Calcd: 360.17 Found: 361.2 [M + H]$^+$ |
| 599 | 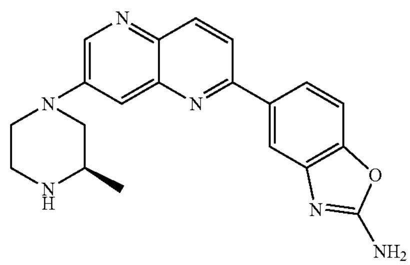 [SMILES: C[C@@H]1CN(c2cnc3ccc(-c4ccc5oc(N)nc5c4)nc3c2)CCN1] | + | ++++ | +++ | ++ | ++ | ++ | Calcd: 360.17 Found: 361.2 [M + H]$^+$ |
| 600 | 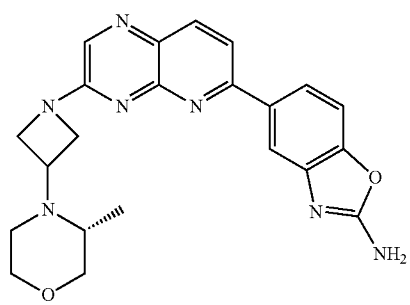 [SMILES: C[C@@H]1COCCN1C1CN(c2cnc3ccc(-c4ccc5oc(N)nc5c4)nc3n2)C1] | | ++ | + | + | ++ | | Calcd: 417.19 Found: 418.2 [M + H]$^+$ |
| 601 | 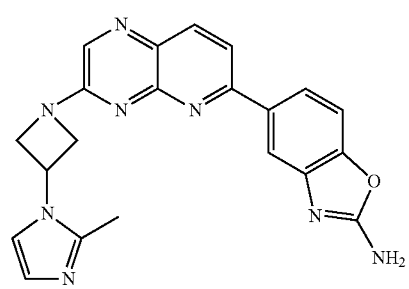 [SMILES: Cc1nccn1C1CN(c2cnc3ccc(-c4ccc5oc(N)nc5c4)nc3n2)C1] | + | ++++ | ++ | ++ | ++ | ++ | Calcd: 398.16 Found: 399.2 [M + H]$^+$ |
| 602 | 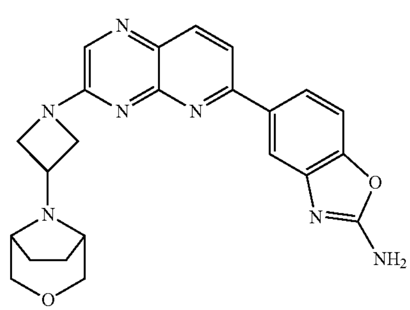 [SMILES: Nc1nc2cc(-c3ccc4ncc(N5CC(N6C7CCC6COC7)C5)nc4n3)ccc2o1] | | ++ | + | + | + | | Calcd: 429.19 Found: 430.2 [M + H]$^+$ |

TABLE 4-continued

In Vitro IC$_{50}$ data for selected compounds of the invention. The following symbols are used: + (greater than 10 microMolar), ++ (less than 10 microMolar), +++ (less than 1 microMolar), and ++++ (less than 100 nM).

| | Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | MDA-MB-361 proliferation (nM)* | Mass Characterization |
|---|---|---|---|---|---|---|---|---|
| 603 | 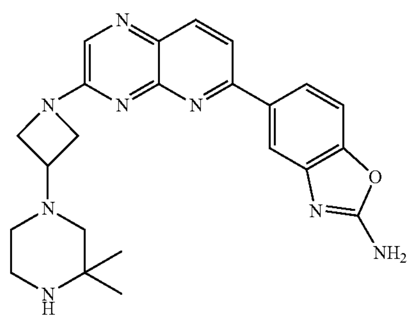 [SMILES: CC1(C)CN(C2CN(c3cnc4ccc(-c5ccc6oc(N)nc6c5)nc4n3)C2)CCN1] | + | ++++ | ++ | +++ | ++ | +++ | Calcd: 430.22 Found: 431.2 [M + H]$^+$ |
| 604 | 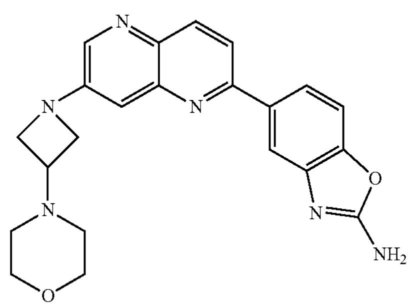 [SMILES: Nc1nc2cc(-c3ccc4ncc(N5CC(N6CCOCC6)C5)cc4n3)ccc2o1] | + | ++++ | ++ | ++ | +++ | ++ | Calcd: 402.18 Found: 403.2 [M + H]$^+$ |
| 605 | 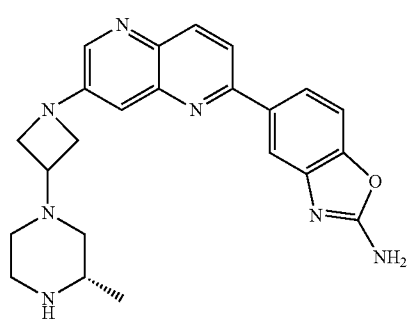 | + | ++++ | ++ | +++ | ++ | +++ | Calcd: 415.21 Found: 416.2 [M + H]$^+$ |
| 606 | 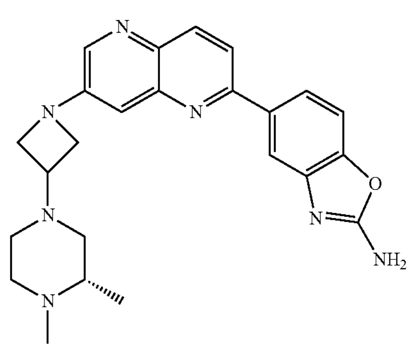 [SMILES: C[C@H]1CN(C2CN(c3cnc4ccc(-c5ccc6oc(N)nc6c5)nc4c3)C2)CCN1C] | + | ++++ | ++ | +++ | ++ | +++ | Calcd: 429.23 Found: 430.2 [M + H]$^+$ |

TABLE 4-continued

In Vitro IC$_{50}$ data for selected compounds of the invention. The following symbols are used: + (greater than 10 microMolar), ++ (less than 10 microMolar), +++ (less than 1 microMolar), and ++++ (less than 100 nM).

| | Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | MDA-MB-361 proliferation (nM)* | Mass Characterization |
|---|---|---|---|---|---|---|---|---|
| 607 | 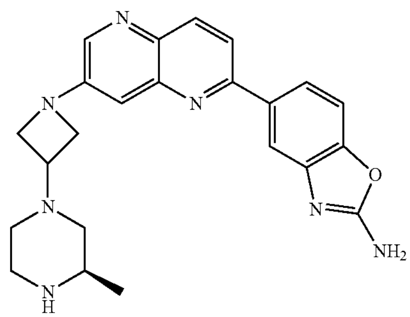 [SMILES: C[C@@H]1CN(C2CN(c3cnc4ccc(-c5ccc6oc(N)nc6c5)nc4c3)C2)CCN1] | + | ++++ | ++ | +++ | +++ | +++ | Calcd: 415.21 Found: 416.2 [M + H]$^+$ |
| 608 | 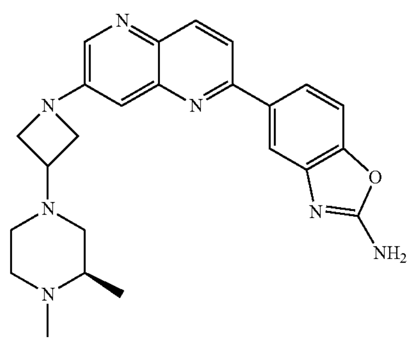 [SMILES: C[C@@H]1CN(C2CN(c3cnc4ccc(-c5ccc6oc(N)nc6c5)nc4c3)C2)CCN1C] | + | ++++ | ++ | +++ | ++ | +++ | Calcd: 429.23 Found: 430.2 [M + H]$^+$ |
| 609 | 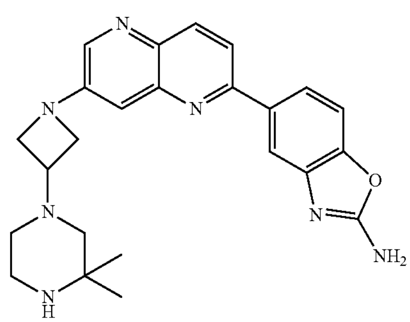 [SMILES: CC1(C)CN(C2CN(c3cnc4ccc(-c5ccc6oc(N)nc6c5)nc4c3)C2)CCN1] | + | ++++ | ++ | +++ | +++ | +++ | Calcd: 429.23 Found: 430.0 [M + H]$^+$ |
| 610 | 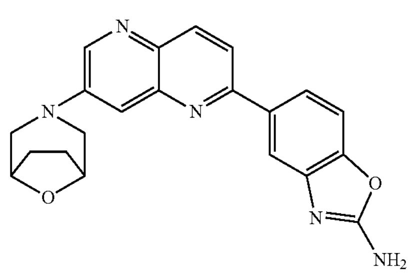 [SMILES: Nc1nc2cc(-c3ccc4ncc(N5CC6CCC(C5)O6)cc4n3)ccc2o1] | | ++++ | + | + | ++++ | +++ | Calcd: 373.15 Found: 374.0 [M + H]$^+$ |

TABLE 4-continued

In Vitro IC$_{50}$ data for selected compounds of the invention. The following symbols are used: + (greater than 10 microMolar), ++ (less than 10 microMolar), +++ (less than 1 microMolar), and ++++ (less than 100 nM).

| Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | MDA-MB-361 proliferation (nM)* | Mass Characterization |
|---|---|---|---|---|---|---|---|
| 611 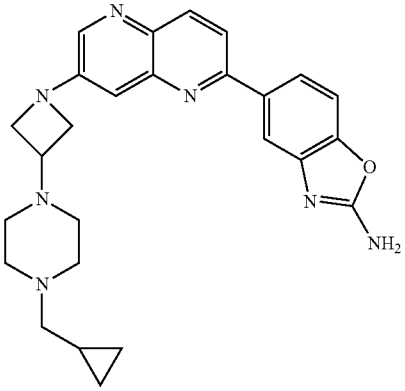 [SMILES: Nc1nc2cc(-c3ccc4ncc(N5CC(N6CCN(CC7CC7)CC6)C5)cc4n3)ccc2o1] | + | ++++ | ++ | +++ | ++ | +++ | Calcd: 455.24 Found: 456.2 [M + H]$^+$ |
| 612 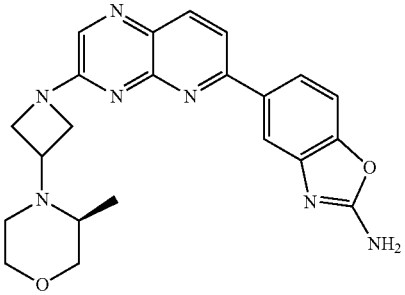 [SMILES: C[C@H]1COCCN1C1CN(c2cnc3ccc(-c4ccc5oc(N)nc5c4)nc3n2)C1] | + | ++++ | + | ++ | ++ | + | Calcd: 417.19 Found: 418.0 [M + H]$^+$ |
| 613 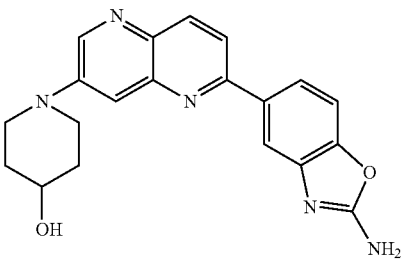 |  | ++++ | ++ | ++ | +++ | ++ | Calcd: 361.15 Found: 362.0 [M + H]$^+$ |
| 614 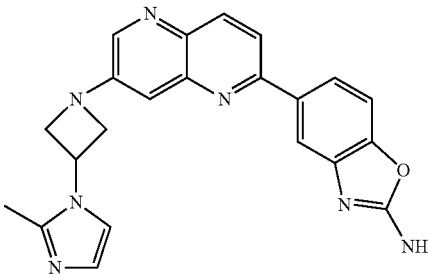 | + | ++++ | ++ | +++ | ++++ | ++ | Calcd: 397.17 Found: 398.2 [M + H]$^+$ |

TABLE 4-continued

In Vitro IC$_{50}$ data for selected compounds of the invention. The following symbols are used: + (greater than 10 microMolar), ++ (less than 10 microMolar), +++ (less than 1 microMolar), and ++++ (less than 100 nM).

| | Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | MDA-MB-361 proliferation (nM)* | Mass Characterization |
|---|---|---|---|---|---|---|---|---|
| 615 | 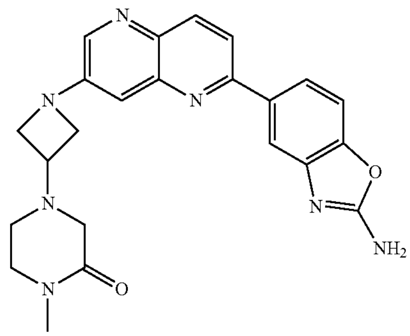 [SMILES: CN1CCN(C2CN(c3cnc4ccc(-c5ccc6oc(N)nc6c5)nc4c3)C2)CC1=O] | ++ | ++++ | ++ | +++ | ++++ | +++ | Calcd: 429.19; Found: 430.2 [M + H]$^+$ |
| 616 | 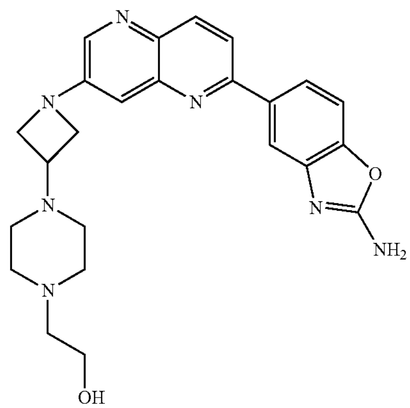 [SMILES: Nc1nc2cc(-c3ccc4ncc(N5CC(N6CCN(CCO)CC6)C5)cc4n3)ccc2o1] | + | ++++ | ++ | +++ | +++ | +++ | Calcd: 445.22 Found: 446.2 [M + H]$^+$ |
| 617 | 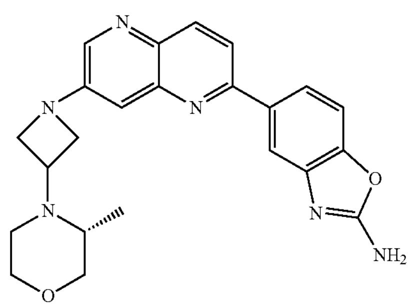 [SMILES: C[C@@H]1COCCN1C1CN(c2cnc3ccc(-c4ccc5oc(N)nc5c4)nc3c2)C1] | | ++++ | ++ | +++ | ++++ | ++ | Calcd: 416.20 Found: 417.2 [M + H]$^+$ |
| 618 | 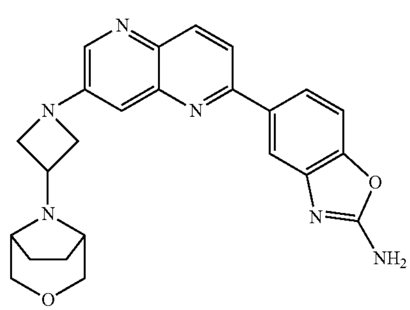 | | ++++ | + | ++ | +++ | ++ | Calcd: 428.49 Found: 429.2 [M + H]$^+$ |

TABLE 4-continued

In Vitro IC$_{50}$ data for selected compounds of the invention. The following symbols are used: + (greater than 10 microMolar), ++ (less than 10 microMolar), +++ (less than 1 microMolar), and ++++ (less than 100 nM).

| | Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | MDA-MB-361 proliferation (nM)* | Mass Characterization |
|---|---|---|---|---|---|---|---|---|
| 619 | | | ++++ | + | + | ++ | | ++ | Calcd: 416.20 Found: 417.2 [M + H]$^+$ |
| 620 | | | ++++ | ++ | ++ | ++ | | ++ | Calcd: 442.22 Found: 443.2 [M + H]$^+$ |
| 621 | | | ++++ | ++ | ++ | +++ | | ++ | Calcd: 441.23 Found: 442.2 [M + H]$^+$ |
| 622 | 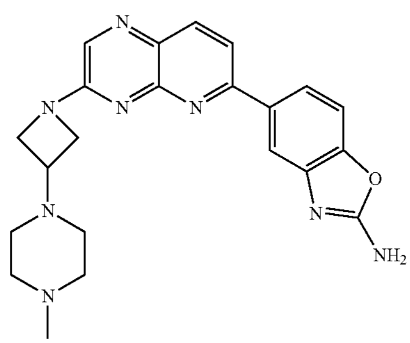 [SMILES: CN1CCN(C2CN(c3cnc4ccc(-c5ccc6oc(N)nc6c5)nc4n3)C2)CC1] | + | ++++ | ++ | +++ | + | ++ | Calcd: 416.21 Found: 417.2 [M + H]$^+$ |

TABLE 4-continued

In Vitro IC$_{50}$ data for selected compounds of the invention. The following symbols are used: + (greater than 10 microMolar), ++ (less than 10 microMolar), +++ (less than 1 microMolar), and ++++ (less than 100 nM).

| | Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | MDA-MB-361 proliferation (nM)* | Mass Characterization |
|---|---|---|---|---|---|---|---|---|
| 623 | 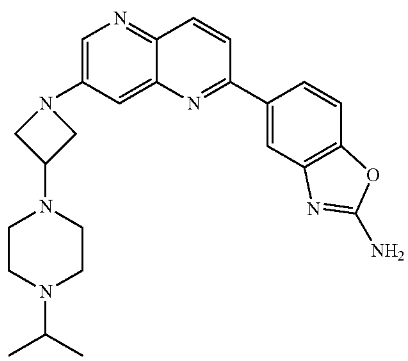 [SMILES: CC(C)N1CCN(C2CN(c3cnc4ccc(-c5ccc6oc(N)nc6c5)nc4c3)C2)CC1] | + | ++++ | +++ | +++ | ++ | +++ | Calcd: 443.24 Found: 444.2 [M + H]$^+$ |
| 624 | 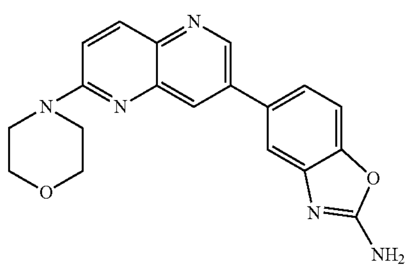 [SMILES: Nc1nc2cc(-c3cnc4ccc(N5CCOCC5)nc4c3)ccc2o1] | | ++ | + | + | ++ | | Calcd: 347.14 Found: 348.2 [M + H]$^+$ |
| 625 | 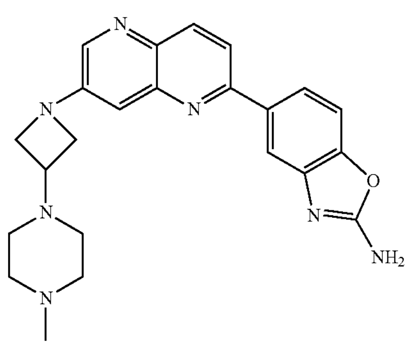 | + | ++++ | +++ | +++ | +++ | +++ | Calcd: 415.21 Found: 416.2 [M + H]$^+$ |
| 626 | 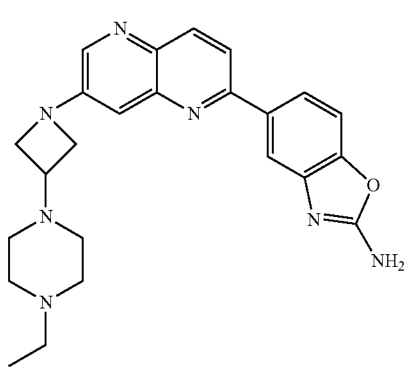 [SMILES: CCN1CCN(C2CN(c3cnc4ccc(-c5ccc6oc(N)nc6c5)nc4c3)C2)CC1] | + | ++++ | +++ | +++ | ++ | +++ | Calcd: 429.23 Found: 430.2 [M + H]$^+$ |

TABLE 4-continued

In Vitro IC$_{50}$ data for selected compounds of the invention. The following symbols are used: + (greater than 10 microMolar), ++ (less than 10 microMolar), +++ (less than 1 microMolar), and ++++ (less than 100 nM).

| | Structure | mTORC IC$_{50}$ (nM) | PI3K α IC$_{50}$ (nM) | PI3K β IC$_{50}$ (nM) | PI3K δ IC$_{50}$ (nM) | PI3K γ IC$_{50}$ (nM) | MDA-MB-361 proliferation (nM)* | Mass Characterization |
|---|---|---|---|---|---|---|---|---|
| 627 | 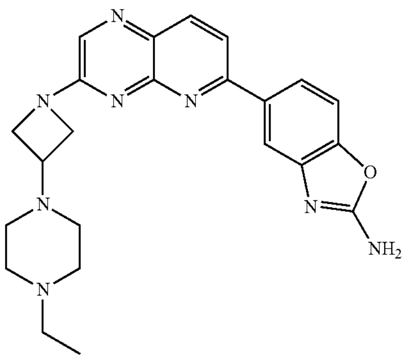 [SMILES: CCN1CCN(C2CN(c3cnc4ccc(-c5ccc6oc(N)nc6c5)nc4n3)C2)CC1] | ++ | ++++ | ++ | ++ | ++ | | Calcd: 430.22 Found: 431.2 [M + H]$^+$ |
| 628 | 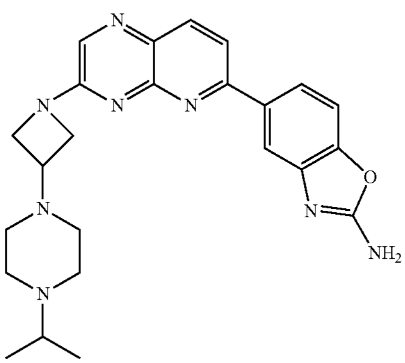 [SMILES: CC(C)N1CCN(C2CN(c3cnc4ccc(-c5ccc6oc(N)nc6c5)nc4n3)C2)CC1] | | ++ | + | + | + | | Calcd: 444.24 Found: 445.2 [M + H]$^+$ |
| 629 | 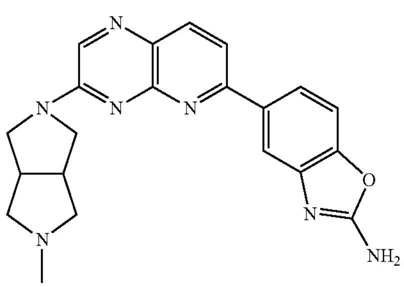 [SMILES: CN1CC2CN(c3cnc4ccc(-c5ccc6oc(N)nc6c5)nc4n3)CC2C1] | + | ++++ | +++ | +++ | ++ | ++ | Calcd: 387.18 Found: 388.2 [M + H]$^+$ |
| 630 | 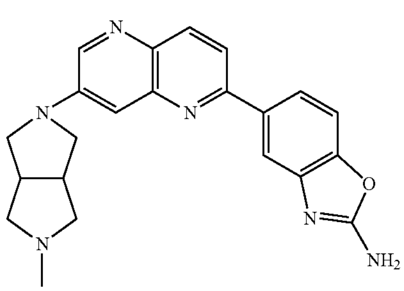 [SMILES: CN1CC2CN(c3cnc4ccc(-c5ccc6oc(N)nc6c5)nc4c3)CC2C1] | + | ++++ | +++ | +++ | +++ | ++ | Calcd: 386.19 Found: 387.2 [M + H]$^+$ |

TABLE 4-continued

In Vitro $IC_{50}$ data for selected compounds of the invention. The following symbols are used: + (greater than 10 microMolar), ++ (less than 10 microMolar), +++ (less than 1 microMolar), and ++++ (less than 100 nM).

| | Structure | mTORC $IC_{50}$ (nM) | PI3K α $IC_{50}$ (nM) | PI3K β $IC_{50}$ (nM) | PI3K δ $IC_{50}$ (nM) | PI3K γ $IC_{50}$ (nM) | MDA-MB-361 proliferation (nM)* | Mass Characterization |
|---|---|---|---|---|---|---|---|---|
| 631 | 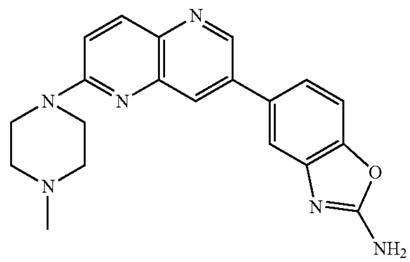 [SMILES: CN1CCN(c2ccc3ncc(-c4ccc5oc(N)nc5c4)cc3n2)CC1] | | ++ | ++ | + | + | | Calcd: 360.17 Found: 361.2 [M + H]+ |
| 632 | 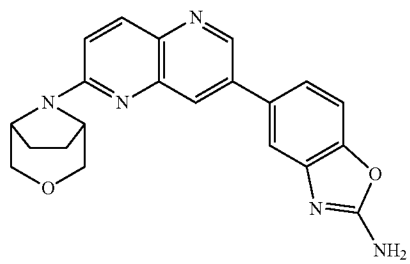 [SMILES: Nc1nc2cc(-c3cnc4ccc(N5C6CCC5COC6)nc4c3)ccc2o1] | | ++ | + | + | ++ | | Calcd: 373.15 Found: 374.2 [M + H]+ |
| 633 | 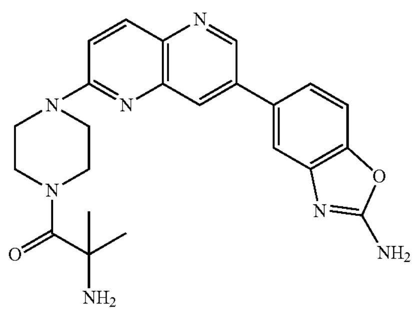 [SMILES: CC(C)(N)C(=O)N1CCN(c2ccc3ncc(-c4ccc5oc(N)nc5c4)cc3n2)CC1] | | ++ | + | + | ++ | | Calcd: 431.21 Found: 432.2 [M + H]+ |

In some embodiments, the invention provides a combination treatment comprising an mTor inhibitor, which can be a compound as provided herein and a PI3Kα inhibitor also as provided herein. In some embodiments, the mTor inhibitor is a compound of Formula I, Formula I-A, Formula I-B1, Formula I-C, Formula I-C1a, or a compound of Table 1 or Table 2, and the PI3Kα inhibitor is a compound of Formula II, Subformula IIa, Subformula IIb, Formula III, Subclass Inc, Subclass IIId, Formula VI-B, Formula VI-C, Formula VI-D, or Table 3. For example, the mTor inhibitor is a compound of Formula I where M1 is a bicyclic heteroaryl system, including, for instance, benzothiazolyl, quinolinyl, quinazolinyl, benzoxazolyl, and benzoimidazolyl, and the PI3Kα inhibitor is a compound of Formula II, Subformula IIa, Subformula II, Formula III, Subclass IIIc, Subclass IIId, Formula VI-B, Formula VI-C, Formula VI-D, or Table 3. In other embodiments, the mTor inhibitor is a compound of Formula I where M1 is of formula M1-A, M1-B, M1-C or M1-D, and the PI3Kα inhibitor is a compound of Formula II, Subformula IIa, Subformula IIb, Formula III, Subclass IIIc, Subclass IIId, Formula VI-B, Formula VI-C, Formula VI-D, or Table 3. In yet other embodiments, the mTor inhibitor is of Formula I-B1 and M1 is of formula M1-F1, and the PI3Kα inhibitor is a compound of Formula II, Subformula IIa, Subformula IIb, Formula III, Subclass IIIc, Subclass IIId, Formula VI-B, Formula VI-C, Formula VI-D, or Table 3. In still other embodiments, the mTor inhibitor is of Formula I-C, and the PI3Kα inhibitor is a compound of Formula II, Subformula IIa, Subformula IIb, Formula III, Subclass IIIc, Subclass IIId, Formula VI-B, Formula VI-C, Formula VI-D, or Table 3. In still other embodiments, the mTor inhibitor is of Formula I-C1a, and the PI3Kα inhibitor is a compound of Formula II, Subformula IIa, Subformula IIb, Formula III, Subclass IIIc, Subclass IIId, Formula VI-B, Formula VI-C, Formula VI-D, or Table 3.

In some embodiments, the mTor inhibitor is a compound of Formula I, Formula I-A, Formula I-B1, Formula I-C, Formula I-C1a, or a compound of Table 1 or Table 2, and the PI3Kα inhibitor is a compound of Formula II or Formula III. In other embodiments, the mTor inhibitor is a compound of Formula I, Formula I-A, Formula I-B1, Formula I-C, Formula I-C1a, or a compound of Table 1 or Table 2, and the PI3Kα inhibitor is a compound of Subformula IIa or Subformula IIb. In still other embodiments, the mTor inhibitor is a compound of Formula I, Formula I-A, Formula I-B1, Formula I-C, Formula I-C1a, or a compound of Table 1 or Table 2, and the PI3Kα inhibitor is a compound of Formula III, Subclass IIIc or Subclass IIId. In still other embodiments, the mTor inhibitor is a compound of Formula I, Formula I-A, Formula I-B1, Formula I-C, Formula I-C1a, or a compound of Table 1 or Table 2, and the PI3Kα inhibitor is a compound of Formula VI-B, VI-C, VI-D or of Table 3.

In some embodiments, the mTor inhibitor is a compound of Formula I where M1 is of formula M1-A, M1-B, M1-C or M1-D, and the PI3Kα inhibitor is a compound of Subclass IIIc or Subclass IIId. In other embodiments, the mTor inhibitor is a compound of Formula I-C and the PI3Kα inhibitor is a compound of Subclass IIIc or Subclass IIId.

In some embodiments, the mTor inhibitor is a compound of Table 1 or 2 and the PI3Kα inhibitor is a compound of Table 3.

Pharmaceutical Compositions and Administration

The invention provides, in one aspect, a combination treatment utilizing a PI3Kα inhibitor and an mTor inhibitor. The therapeutic agents (including compounds) that are provided for use in the combination therapies of the invention can be administered simultaneously or separately. This administration in combination includes, for example, simultaneous administration of two agents in the same dosage form, simultaneous administration in separate dosage forms, and separate administration. For example, multiple therapeutic agents can be formulated together in the same dosage form and administered simultaneously. Alternatively multiple therapeutic agents can be simultaneously administered, wherein both the agents are present in separate formulations. In another alternative, an inhibitor of the present invention can be administered just followed by and any of the agents described above, or vice versa. In the separate administration protocol, an inhibitor of the present invention and any of the agents described above may be administered a few minutes apart, or a few hours apart, or a few days apart. The term "combination treatments" also embraces the administration of the therapeutic agents as described herein in further combination with other biologically active compounds or ingredients and non-drug therapies (e.g., surgery or radiation treatment).

Administration of the compounds of the present invention can be effected by any method that enables delivery of the compounds to the site of action. An effective amount of an inhibitor of the invention may be administered in either single or multiple doses by any of the accepted modes of administration of agents having similar utilities, including rectal, buccal, intranasal and transdermal routes, by intra-arterial injection, intravenously, intraperitoneally, parenterally, intramuscularly, subcutaneously, orally, topically, as an inhalant, or via an impregnated or coated device such as a stent, for example, or an artery-inserted cylindrical polymer. Sequential or substantially simultaneous administration of each inhibitor or therapeutic agent can be effected by any appropriate route as noted above and including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. The sequence in which the therapeutic agents are administered is not narrowly critical.

In some embodiments, administration of the inhibitors of the invention can be effected in one dose, continuously or intermittently throughout the course of treatment. Methods of determining the most effective means and dosage of administration are well known to those of skill in the art and will vary with the composition used for therapy, the purpose of the therapy, the target cell or tissue being treated, and the subject being treated. Single or multiple administrations can be carried out with the dose level and pattern being selected by the treating physician.

The amount of each inhibitor or compound administered will be dependent on the mammal being treated, the severity of the disorder or condition, the rate of administration, the disposition of the compound and the discretion of the prescribing physician. However, an effective dosage is in the range of about 0.001 to about 100 mg per kg body weight per day, preferably about 1 to about 35 mg/kg/day, in single or divided doses. For a 70 kg human, this would amount to about 0.05 to 7 g/day, preferably about 0.05 to about 2.5 g/day. In some instances, dosage levels below the lower limit of the aforesaid range may be more than adequate, while in other cases still larger doses may be employed without causing any harmful side effect, e.g., by dividing such larger doses into several small doses for administration throughout the day.

In some embodiments, a combination treatment of the invention is administered in a single dose comprising at least a PI3Kα inhibitor and an mTor inhibitor. Typically, such administration will be by injection, e.g., intravenous injection, in order to introduce the agent quickly. However, other routes may be used as appropriate. A single dose of a combination treatment of the invention may also be used for treatment of an acute condition.

In some embodiments, a combination treatment of the invention is administered in multiple doses. Dosing may be about once, twice, three times, four times, five times, six times, or more than six times per day. Dosing may be about once a month, once every two weeks, once a week, or once every other day. In another embodiment a PI3Kα inhibitor and an mTor inhibitor are administered together about once per day to about 6 times per day. In another embodiment the administration of a a PI3Kα inhibitor and an mTor inhibitor continues for less than about 7 days. In yet another embodiment the administration continues for more than about 6, 10, 14, 28 days, two months, six months, or one year. In some cases, continuous dosing is achieved and maintained as long as necessary.

Administration of the combination treatments of the invention may continue as long as necessary. In some embodiments, an agent of the invention is administered for more than 1, 2, 3, 4, 5, 6, 7, 14, or 28 days. In some embodiments, an agent of the invention is administered for less than 28, 14, 7, 6, 5, 4, 3, 2, or 1 day. In some embodiments, an agent of the invention is administered chronically on an ongoing basis, e.g., for the treatment of chronic effects.

When a combination treatment of the invention is administered as a composition that comprises one or more compounds, and one compound has a shorter half-life than another compound, the unit dose forms may be adjusted accordingly.

In some embodiments, combination treatments of the invention are tested to estimate pharmacokinetic properties and expected side effect profile. Various assays are known in the art for this purpose. For example, oral availability can be estimated during early stages of drug development by performing a Caco-2 permeability assay. Further, oral pharmacokinetics in humans can be approximated by extrapolating from the results of assays in mice, rats or monkey. In some embodiments, compounds of the invention show good oral availability across multiple species of organisms.

Other assays examine the effect of an inhibitor on liver function and metabolism. Cytochrome P450 (CYP) proteins are the main enzyme involved in metabolizing drugs administered to mammalian organisms. As such, undesired interaction of a drug candidate can be a significant source of adverse drug interactions. Generally, it is desirable for a drug to not interact with CYP isozymes such as CYP1A2, CYP2C9, CYP2C19, CYP2D6, or CYP3A4. In some embodiments, an inhibitor of the invention exhibits an IC50 of greater than 10 μM for CYP1A2, CYP2C9, CYP2C19, CYP2D6, or CYP3A4. Additionally, liver microsome and hepatocyte metabolism assays using human preparations can be used to estimate the in-vitro half life of a drug candidate.

Cardiac toxicity is also an important consideration in evaluating compounds. For example, hERG is the gene coding for the Kv11.1 potassium ion channel, a protein is involved in mediating repolarizing current in the cardiac action potential in the heart Inhibition of the hERG gene product by a drug candidate can lead to an increase in the risk of sudden death and is therefore an undesirable property. In some embodiments, an inhibitor of the invention exhibits less than 10% hERG inhibition when administered at a suitable concentration.

Mutagenicity of compounds can be assayed via an Ames test or a modified Ames test using e.g., the liver S9 system. In some embodiments, compounds show negative activity in such a test.

Other undesired interactions of an inhibitor can also be ascertained via a receptor panel screen. In some embodiments, no significant interactions are detected for combination treatments of the invention. The subject pharmaceutical compositions can be formulated to provide a therapeutically effective amount of a combination of therapeutic agents of the present invention, or pharmaceutically acceptable salts, esters, prodrugs, solvates, hydrates or derivatives thereof. Where desired, the pharmaceutical compositions contain pharmaceutically acceptable salt and/or coordination complex thereof, and one or more pharmaceutically acceptable excipients, carriers, including inert solid diluents and fillers, diluents, including sterile aqueous solution and various organic solvents, permeation enhancers, solubilizers and adjuvants.

The subject pharmaceutical compositions can be administered as a combination of a PI3Kα inhibitor and an mTor inhibitor, or in further combination with one or more other agents, which are also typically administered in the form of pharmaceutical compositions. Where desired, the subject combinations and other agent(s) may be mixed into a preparation or both components may be formulated into separate preparations to use them in combination separately or at the same time.

In some embodiments, the concentration of one or more of the compounds provided in the pharmaceutical compositions of the present invention is less than 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v or v/v.

In some embodiments, the concentration of one or more of the compounds of the present invention is greater than 90%, 80%, 70%, 60%, 50%, 40%, 30%, 20%, 19.75%, 19.50%, 19.25% 19%, 18.75%, 18.50%, 18.25% 18%, 17.75%, 17.50%, 17.25% 17%, 16.75%, 16.50%, 16.25% 16%, 15.75%, 15.50%, 15.25% 15%, 14.75%, 14.50%, 14.25% 14%, 13.75%, 13.50%, 13.25% 13%, 12.75%, 12.50%, 12.25% 12%, 11.75%, 11.50%, 11.25% 11%, 10.75%, 10.50%, 10.25% 10%, 9.75%, 9.50%, 9.25% 9%, 8.75%, 8.50%, 8.25% 8%, 7.75%, 7.50%, 7.25% 7%, 6.75%, 6.50%, 6.25% 6%, 5.75%, 5.50%, 5.25% 5%, 4.75%, 4.50%, 4.25%, 4%, 3.75%, 3.50%, 3.25%, 3%, 2.75%, 2.50%, 2.25%, 2%, 1.75%, 1.50%, 125%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v, or v/v.

In some embodiments, the concentration of one or more of the compounds of the present invention is in the range from approximately 0.0001% to approximately 50%, approximately 0.001% to approximately 40%, approximately 0.01% to approximately 30%, approximately 0.02% to approximately 29%, approximately 0.03% to approximately 28%, approximately 0.04% to approximately 27%, approximately 0.05% to approximately 26%, approximately 0.06% to approximately 25%, approximately 0.07% to approximately 24%, approximately 0.08% to approximately 23%, approximately 0.09% to approximately 22%, approximately 0.1% to approximately 21%, approximately 0.2% to approximately 20%, approximately 0.3% to approximately 19%, approximately 0.4% to approximately 18%, approximately 0.5% to approximately 17%, approximately 0.6% to approximately 16%, approximately 0.7% to approximately 15%, approximately 0.8% to approximately 14%, approximately 0.9% to approximately 12%, approximately 1% to approximately 10% w/w, w/v or v/v. v/v.

In some embodiments, the concentration of one or more of the compounds of the present invention is in the range from approximately 0.001% to approximately 10%, approximately 0.01% to approximately 5%, approximately 0.02% to approximately 4.5%, approximately 0.03% to approximately 4%, approximately 0.04% to approximately 3.5%, approximately 0.05% to approximately 3%, approximately 0.06% to approximately 2.5%, approximately 0.07% to approximately 2%, approximately 0.08% to approximately 1.5%, approximately 0.09% to approximately 1%, approximately 0.1% to approximately 0.9% w/w, w/v or v/v.

In some embodiments, the amount of one or more of the compounds of the present invention is equal to or less than 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g.

In some embodiments, the amount of one or more of the compounds of the present invention is more than 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g, 0.15 g, 0.2 g, 0.25 g, 0.3 g, 0.35 g, 0.4 g, 0.45 g, 0.5 g, 0.55 g, 0.6 g, 0.65 g, 0.7 g, 0.75 g, 0.8 g, 0.85 g, 0.9 g, 0.95 g, 1 g, 1.5 g, 2 g, 2.5, 3 g, 3.5, 4 g, 4.5 g, 5 g, 5.5 g, 6 g, 6.5 g, 7 g, 7.5 g, 8 g, 8.5 g, 9 g, 9.5 g, or 10 g.

In some embodiments, the amount of one or more of the compounds of the present invention is in the range of 0.0001-10 g, 0.0005-9 g, 0.001-8 g, 0.005-7 g, 0.01-6 g, 0.05-5 g, 0.1-4 g, 0.5-4 g, or 1-3 g.

The combination treatments according to the invention are effective over a wide dosage range. For example, in the treatment of adult humans, dosages from 0.01 to 1000 mg, from 0.5 to 100 mg, from 1 to 50 mg per day, and from 5 to 40 mg per day are examples of dosages that may be used. An exemplary dosage is 10 to 30 mg per day. The exact dosage will depend upon the route of administration, the form in which the compound is administered, the subject to be treated, the body weight of the subject to be treated, and the preference and experience of the attending physician.

A pharmaceutical composition of the present invention typically contains an active ingredient (e.g., an inhibitor of the present invention or a pharmaceutically acceptable salt and/or coordination complex thereof, and one or more pharmaceutically acceptable excipients, carriers, including but not limited inert solid diluents and fillers, diluents, sterile aqueous solution and various organic solvents, permeation enhancers, solubilizers and adjuvants.

Described below are non-limiting exemplary pharmaceutical compositions and methods for preparing the same.

Pharmaceutical Compositions for Oral Administration

In some embodiments, the invention provides a pharmaceutical composition for oral administration containing at least one therapeutic agent, and a pharmaceutical excipient suitable for oral administration.

In some embodiments, the invention provides a solid pharmaceutical composition for oral administration containing: (i) a compound which is a PI3Kα inhibitor; (ii) a second compound which is an mTor inhibitor; and (iii) a pharmaceutical excipient suitable for oral administration. In some embodiments, the composition further contains: (iv) a third agent or even a fourth agent. In some embodiments, each compound or agent is present in a therapeutically effective amount. In other embodiments, one or more compounds or agents is present in a sub-therapeutic amount, and the compounds or agents act synergystically to provide a therapeutically effective pharmaceutical composition.

In some embodiments, the invention provides for a pharmaceutical composition comprising a combination of a PI3-kinase α inhibitor and an mTOR inhibitor. The PI3-kinase α inhibitor and the mTOR inhibitor can be packaged as a single oral dosage form. In other embodiments, the PI3-kinase α inhibitor and the mTOR inhibitor can be packaged as separate dosage forms, such as a tablet.

In one embodiment, the present invention provides an oral dosage form comprising 100 mg to 1.5 g of an inhibitor of the invention. The oral dosage form can be a tablet, formulated in form of liquid, in immediate or sustained release format.

In some embodiments, the pharmaceutical composition may be a liquid pharmaceutical composition suitable for oral consumption. Pharmaceutical compositions of the invention suitable for oral administration can be presented as discrete dosage forms, such as capsules, cachets, or tablets, or liquids or aerosol sprays each containing a predetermined amount of an active ingredient as a powder or in granules, a solution, or a suspension in an aqueous or non-aqueous liquid, an oil-in-water emulsion, or a water-in-oil liquid emulsion, including liquid dosage forms (e.g., a suspension or slurry), and oral solid dosage forms (e.g., a tablet or bulk powder). As used herein the term "tablet" refers generally to tablets, caplets, capsules, including soft gelatin capsules, and lozenges. Oral dosage forms may be formulated as tablets, pills, dragees, capsules, emulsions, lipophilic and hydrophilic suspensions, liquids, gels, syrups, slurries, suspensions and the like, for oral ingestion by an individual or a patient to be treated. Such dosage forms can be prepared by any of the methods of pharmacy, but all methods include the step of bringing the active ingredient into association with the carrier, which constitutes one or more necessary ingredients. In one embodiment, the inhibitor of the invention is contained in capsules. Capsules suitable for oral administration include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. Optionally, the inventive composition for oral use can be obtained by mixing the inhibitor with a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). In general, the compositions are prepared by uniformly and intimately admixing the active ingredient with liquid carriers or finely divided solid carriers or both, and then, if necessary, shaping the product into the desired presentation. For example, a tablet can be prepared by compression or molding, optionally with one or more accessory ingredients. Compressed tablets can be prepared by compressing in a suitable machine the active ingredient in a free-flowing form such as powder or granules, optionally mixed with an excipient such as, but not limited to, a binder, a lubricant, an inert diluent, and/or a surface active or dispersing agent. Molded tablets can be made by molding in a suitable machine a mixture of the powdered compound moistened with an inert liquid diluent.

This invention further encompasses anhydrous pharmaceutical compositions and dosage forms comprising an active ingredient, since water can facilitate the degradation of some compounds. For example, water may be added (e.g., 5%) in the pharmaceutical arts as a means of simulating long-term storage in order to determine characteristics such as shelf-life or the stability of formulations over time. Anhydrous pharmaceutical compositions and dosage forms of the invention can be prepared using anhydrous or low moisture containing ingredients and low moisture or low humidity conditions. Pharmaceutical compositions and dosage forms of the invention which contain lactose can be made anhydrous if substantial contact with moisture and/or humidity during manufacturing, packaging, and/or storage is expected. An anhydrous pharmaceutical composition may be prepared and stored such that its anhydrous nature is maintained. Accordingly, anhydrous compositions may be packaged using materials known to prevent exposure to water such that they can be included in suitable formulary kits. Examples of suitable packaging include, but are not limited to, hermetically sealed foils, plastic or the like, unit dose containers, blister packs, and strip packs.

An active ingredient can be combined in an intimate admixture with a pharmaceutical carrier according to conventional pharmaceutical compounding techniques. The carrier can take a wide variety of forms depending on the form of preparation desired for administration. In preparing the compositions for an oral dosage form, any of the usual pharmaceutical media can be employed as carriers, such as, for example, water, glycols, oils, alcohols, flavoring agents, preservatives, coloring agents, and the like in the case of oral liquid preparations (such as suspensions, solutions, and elixirs) or aerosols; or carriers such as starches, sugars, microcrystalline cellulose, diluents, granulating agents, lubricants, binders, and disintegrating agents can be used in the case of oral solid preparations, in some embodiments without employing the use of lactose. For example, suitable carriers include powders, capsules, and tablets, with the solid oral preparations. If desired, tablets can be coated by standard aqueous or nonaqueous techniques.

Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, microcrystalline cellulose, and mixtures thereof.

Examples of suitable fillers for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof.

Disintegrants may be used in the compositions of the invention to provide tablets that disintegrate when exposed to an aqueous environment. Too much of a disintegrant may produce tablets which may disintegrate in the bottle. Too little may be insufficient for disintegration to occur and may thus alter the rate and extent of release of the active ingredient(s) from the dosage form. Thus, a sufficient amount of disintegrant that is neither too little nor too much to detrimentally alter the release of the active ingredient(s) may be used to form the dosage forms of the compounds disclosed herein. The amount of disintegrant used may vary based upon the type of formulation and mode of administration, and may be readily discernible to those of ordinary skill in the art. About 0.5 to about 15 weight percent of disintegrant, or about 1 to about 5 weight percent of disintegrant, may be used in the pharmaceutical composition. Disintegrants that can be used to form pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums or mixtures thereof.

Lubricants which can be used to form pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethylaureate, agar, or mixtures thereof. Additional lubricants include, for example, a syloid silica gel, a coagulated aerosol of synthetic silica, or mixtures thereof. A lubricant can optionally be added, in an amount of less than about 1 weight percent of the pharmaceutical composition.

Lubricants can be also be used in conjunction with tissue barriers which include, but are not limited to, polysaccharides, polyglycans, seprafilm, interceed and hyaluronic acid.

When aqueous suspensions and/or elixirs are desired for oral administration, the essential active ingredient therein may be combined with various sweetening or flavoring agents, coloring matter or dyes and, if so desired, emulsifying and/or suspending agents, together with such diluents as water, ethanol, propylene glycol, glycerin and various combinations thereof.

The tablets can be uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Surfactant which can be used to form pharmaceutical compositions and dosage forms of the invention include, but are not limited to, hydrophilic surfactants, lipophilic surfactants, and mixtures thereof. That is, a mixture of hydrophilic surfactants may be employed, a mixture of lipophilic surfactants may be employed, or a mixture of at least one hydrophilic surfactant and at least one lipophilic surfactant may be employed.

A suitable hydrophilic surfactant may generally have an HLB value of at least 10, while suitable lipophilic surfactants may generally have an HLB value of or less than about 10. An empirical parameter used to characterize the relative hydrophilicity and hydrophobicity of non-ionic amphiphilic compounds is the hydrophilic-lipophilic balance ("HLB" value). Surfactants with lower HLB values are more lipophilic or hydrophobic, and have greater solubility in oils, while surfactants with higher HLB values are more hydrophilic, and have greater solubility in aqueous solutions. Hydrophilic surfactants are generally considered to be those compounds having an HLB value greater than about 10, as well as anionic, cationic, or zwitterionic compounds for which the HLB scale is not generally applicable. Similarly, lipophilic (i.e., hydrophobic) surfactants are compounds having an HLB value equal to or less than about 10. However, HLB value of a surfactant is merely a rough guide generally used to enable formulation of industrial, pharmaceutical and cosmetic emulsions.

Hydrophilic surfactants may be either ionic or non-ionic. Suitable ionic surfactants include, but are not limited to, alkylammonium salts; fusidic acid salts; fatty acid derivatives of amino acids, oligopeptides, and polypeptides; glyceride derivatives of amino acids, oligopeptides, and polypeptides; lecithins and hydrogenated lecithins; lysolecithins and hydrogenated lysolecithins; phospholipids and derivatives thereof; lysophospholipids and derivatives thereof; carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Within the aforementioned group, ionic surfactants include, by way of example: lecithins, lysolecithin, phospholipids, lysophospholipids and derivatives thereof; carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Ionic surfactants may be the ionized forms of lecithin, lysolecithin, phosphatidylcholine, phosphatidylethanolamine, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, cholylsarcosine, caproate, caprylate, caprate, laurate, myristate, palmitate, oleate, ricinoleate, linoleate, linolenate, stearate, lauryl sulfate, teracecyl sulfate, docusate, lauroyl carnitines, palmitoyl carnitines, myristoyl carnitines, and salts and mixtures thereof.

Hydrophilic non-ionic surfactants may include, but not limited to, alkylglucosides; alkylmaltosides; alkylthioglucosides; lauryl macrogolglycerides; polyoxyalkylene alkyl ethers such as polyethylene glycol alkyl ethers; polyoxyalkylene alkylphenols such as polyethylene glycol alkyl phenols; polyoxyalkylene alkyl phenol fatty acid esters such as polyethylene glycol fatty acids monoesters and polyethylene glycol fatty acids diesters; polyethylene glycol glycerol fatty acid esters; polyglycerol fatty acid esters; polyoxyalkylene sorbitan fatty acid esters such as polyethylene glycol sorbitan fatty acid esters; hydrophilic transesterification products of a polyol with at least one member of the group consisting of glycerides, vegetable oils, hydrogenated vegetable oils, fatty acids, and sterols; polyoxyethylene sterols, derivatives, and analogues thereof; polyoxyethylated vitamins and derivatives thereof; polyoxyethylene-polyoxypropylene block copolymers; and mixtures thereof; polyethylene glycol sorbitan fatty acid esters and hydrophilic transesterification products of a polyol with at least one member of the group consisting of triglycerides, vegetable oils, and hydrogenated vegetable oils. The polyol may be glycerol, ethylene glycol, polyethylene glycol, sorbitol, propylene glycol, pentaerythritol, or a saccharide.

Other hydrophilic-non-ionic surfactants include, without limitation, PEG-10 laurate, PEG-12 laurate, PEG-20 laurate, PEG-32 laurate, PEG-32 dilaurate, PEG-12 oleate, PEG-15 oleate, PEG-20 oleate, PEG-20 dioleate, PEG-32 oleate, PEG-200 oleate, PEG-400 oleate, PEG-15 stearate, PEG-32 distearate, PEG-40 stearate, PEG-100 stearate, PEG-20 dilaurate, PEG-25 glyceryl trioleate, PEG-32 dioleate, PEG-20 glyceryl laurate, PEG-30 glyceryl laurate, PEG-20 glyceryl stearate, PEG-20 glyceryl oleate, PEG-30 glyceryl oleate, PEG-30 glyceryl laurate, PEG-40 glyceryl laurate, PEG-40 palm kernel oil, PEG-50 hydrogenated castor oil, PEG-40 castor oil, PEG-35 castor oil, PEG-60 castor oil, PEG-40 hydrogenated castor oil, PEG-60 hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phyto sterol, PEG-30 soya sterol, PEG-20 trioleate, PEG-40 sorbitan oleate, PEG-80 sorbitan laurate, polysorbate 20, polysorbate 80, POE-9 lauryl ether, POE-23 lauryl ether, POE-10 oleyl ether, POE-20 oleyl ether, POE-20 stearyl ether, tocopheryl PEG-100 succinate, PEG-24 cholesterol, polyglyceryl-10oleate, Tween 40, Tween 60, sucrose monostearate, sucrose monolaurate, sucrose monopalmitate, PEG 10-100 nonyl phenol series, PEG 15-100 octyl phenol series, and poloxamers.

Suitable lipophilic surfactants include, by way of example only: fatty alcohols; glycerol fatty acid esters; acetylated glycerol fatty acid esters; lower alcohol fatty acids esters; propylene glycol fatty acid esters; sorbitan fatty acid esters; polyethylene glycol sorbitan fatty acid esters; sterols and sterol derivatives; polyoxyethylated sterols and sterol derivatives; polyethylene glycol alkyl ethers; sugar esters; sugar ethers; lactic acid derivatives of mono- and di-glycerides; hydrophobic transesterification products of a polyol with at least one member of the group consisting of glycerides, vegetable oils, hydrogenated vegetable oils, fatty acids and sterols; oil-soluble vitamins/vitamin derivatives; and mixtures thereof. Within this group, preferred lipophilic surfactants include glycerol fatty acid esters, propylene glycol fatty acid esters, and mixtures thereof, or are hydrophobic transesterification products of a polyol with at least one member of the group consisting of vegetable oils, hydrogenated vegetable oils, and triglycerides.

In one embodiment, the composition may include a solubilizer to ensure good solubilization and/or dissolution of the compound of the present invention and to minimize precipitation of the compound of the present invention. This can be especially important for compositions for non-oral use, e.g., compositions for injection. A solubilizer may also be added to increase the solubility of the hydrophilic drug and/or other components, such as surfactants, or to maintain the composition as a stable or homogeneous solution or dispersion.

Examples of suitable solubilizers include, but are not limited to, the following: alcohols and polyols, such as ethanol, isopropanol, butanol, benzyl alcohol, ethylene glycol, propylene glycol, butanediols and isomers thereof, glycerol, pentaerythritol, sorbitol, mannitol, transcutol, dimethyl isosorbide, polyethylene glycol, polypropylene glycol, polyvinylalcohol, hydroxypropyl methylcellulose and other cellulose derivatives, cyclodextrins and cyclodextrin derivatives; ethers of polyethylene glycols having an average molecular weight of about 200 to about 6000, such as tetrahydrofurfuryl alcohol PEG ether (glycofurol) or methoxy PEG; amides and other nitrogen-containing compounds such as 2-pyrrolidone, 2-piperidone, .epsilon.-caprolactam, N-alkylpyrrolidone, N-hydroxyalkylpyrrolidone, N-alkylpiperidone, N-alkylcaprolactam, dimethylacetamide and polyvinylpyrrolidone; esters such as ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, ε-caprolactone and isomers thereof, δ-valerolactone and isomers thereof, β-butyrolactone and isomers thereof; and other solubilizers known in the art, such as dimethyl acetamide, dimethyl isosorbide, N-methylpyrrolidones, monooctanoin, diethylene glycol monoethyl ether, and water.

Mixtures of solubilizers may also be used. Examples include, but not limited to, triacetin, triethylcitrate, ethyl oleate, ethyl caprylate, dimethylacetamide, N-methylpyrrolidone, N-hydroxyethylpyrrolidone, polyvinylpyrrolidone, hydroxypropyl methylcellulose, hydroxypropyl cyclodextrins, ethanol, polyethylene glycol 200-100, glycofurol, transcutol, propylene glycol, and dimethyl isosorbide. Particularly preferred solubilizers include sorbitol, glycerol, triacetin, ethyl alcohol, PEG-400, glycofurol and propylene glycol.

The amount of solubilizer that can be included is not particularly limited. The amount of a given solubilizer may be limited to a bioacceptable amount, which may be readily determined by one of skill in the art. In some circumstances, it may be advantageous to include amounts of solubilizers far in excess of bioacceptable amounts, for example to maximize the concentration of the drug, with excess solubilizer removed prior to providing the composition to a subject using conventional techniques, such as distillation or evaporation. Thus, if present, the solubilizer can be in a weight ratio of 10%, 25%, 50%, 100%, or up to about 200% by weight, based on the combined weight of the drug, and other excipients. If desired, very small amounts of solubilizer may also be used, such as 5%, 2%, 1% or even less. Typically, the solubilizer may be present in an amount of about 1% to about 100%, more typically about 5% to about 25% by weight.

The composition can further include one or more pharmaceutically acceptable additives and excipients. Such additives and excipients include, without limitation, detackifiers, antifoaming agents, buffering agents, polymers, antioxidants, preservatives, chelating agents, viscomodulators, tonicifiers, flavorants, colorants, odorants, opacifiers, suspending agents, binders, fillers, plasticizers, lubricants, and mixtures thereof.

In addition, an acid or a base may be incorporated into the composition to facilitate processing, to enhance stability, or for other reasons. Examples of pharmaceutically acceptable bases include amino acids, amino acid esters, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrocalcite, magnesium aluminum hydroxide, diisopropylethylamine, ethanolamine, ethylenediamine, triethanolamine, triethylamine, triisopropanolamine, trimethylamine, tris(hydroxymethyl) aminomethane (TRIS) and the like. Also suitable are bases that are salts of a pharmaceutically acceptable acid, such as acetic acid, acrylic acid, adipic acid, alginic acid, alkanesulfonic acid, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid, and the like. Salts of polyprotic acids, such as sodium phosphate, disodium hydrogen phosphate, and sodium dihydrogen phosphate can also be used. When the base is a salt, the cation can be any convenient and pharmaceutically acceptable cation, such as ammonium, alkali metals, alkaline earth metals, and the like. Example may include, but not limited to, sodium, potassium, lithium, magnesium, calcium and ammonium.

Suitable acids are pharmaceutically acceptable organic or inorganic acids. Examples of suitable inorganic acids include hydrochloric acid, hydrobromic acid, hydriodic acid, sulfuric acid, nitric acid, boric acid, phosphoric acid, and the like. Examples of suitable organic acids include acetic acid, acrylic acid, adipic acid, alginic acid, alkanesulfonic acids, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid and the like.

Pharmaceutical Compositions for Injection.

In some embodiments, the invention provides a pharmaceutical composition for injection containing at least one compound of the present invention and a pharmaceutical excipient suitable for injection. For example a pharmaceutical composition for injection is provided comprising at least one PI3Kα inhibitor and an mTor inhibitor. Also provided are pharmaceutical compositions comprising a PI3Kα inhibitor, and pharmaceutical compositions comprising an mTor inhibitor, where the PI3Kα inhibitor is administered separately or together with the mTor inhibitor. The PI3K α inhibitor and the mTor inhibitor may be formulated separately, and may further include a third therapeutic agent. Components and amounts of agents in the compositions are as described herein.

The forms in which the novel compositions of the present invention may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Aqueous solutions in saline are also conventionally used for injection. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, for the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating the compound of the present invention in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, certain desirable methods of preparation are vacuum-drying and freeze-drying techniques which yield a powder of the active ingredient plus any additional desired ingredient from a previously sterile-filtered solution thereof.

Pharmaceutical Compositions for Topical (e.g., Transdermal) Delivery.

In some embodiments, the invention provides a pharmaceutical composition for transdermal delivery containing at least one compound of the present invention and a pharmaceutical excipient suitable for transdermal delivery. For example a pharmaceutical composition for topical delivery is provided comprising at least one PI3Kα inhibitor and an mTor inhibitor. Also provided are pharmaceutical compositions for topical delivery comprising a PI3Kα inhibitor, and pharmaceutical compositions for topical delivery comprising an mTor inhibitor, where the PI3Kα inhibitor is administered separately or together with the mTor inhibitor. The PI3K α inhibitor and the mTor inhibitor may be formulated separately, and may further include a third therapeutic agent.

Compositions of the present invention can be formulated into preparations in solid, semi-solid, or liquid forms suitable for local or topical administration, such as gels, water soluble jellies, creams, lotions, suspensions, foams, powders, slurries, ointments, solutions, oils, pastes, suppositories, sprays, emulsions, saline solutions, dimethylsulfoxide (DMSO)-based solutions. In general, carriers with higher densities are capable of providing an area with a prolonged exposure to the active ingredients. In contrast, a solution formulation may provide more immediate exposure of the active ingredient to the chosen area.

The pharmaceutical compositions also may comprise suitable solid or gel phase carriers or excipients, which are compounds that allow increased penetration of, or assist in the delivery of, therapeutic molecules across the stratum corneum permeability barrier of the skin. There are many of these penetration-enhancing molecules known to those trained in the art of topical formulation. Examples of such carriers and excipients include, but are not limited to, humectants (e.g., urea), glycols (e.g., propylene glycol), alcohols (e.g., ethanol), fatty acids (e.g., oleic acid), surfactants (e.g., isopropyl myristate and sodium lauryl sulfate), pyrrolidones, glycerol monolaurate, sulfoxides, terpenes (e.g., menthol), amines, amides, alkanes, alkanols, water, calcium carbonate, calcium phosphate, various sugars, starches, cellulose derivatives, gelatin, and polymers such as polyethylene glycols.

Another exemplary formulation for use in the methods of the present invention employs transdermal delivery devices ("patches"). Such transdermal patches may be used to provide continuous or discontinuous infusion of an inhibitor of the present invention in controlled amounts, either with or without another agent.

The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

Pharmaceutical Compositions for Inhalation.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices that deliver the formulation in an appropriate manner. For example a pharmaceutical composition for topical delivery is provided comprising at least one PI3Kα inhibitor and an mTor inhibitor. Also provided are pharmaceutical compositions for topical delivery comprising a PI3Kα inhibitor, and pharmaceutical compositions for topical delivery comprising an mTor inhibitor, where the PI3Kα inhibitor is administered separately or together with the mTor inhibitor. Compositions comprising a PI3K α inhibitor and an mTor inhibitor may be formulated separately, and may further include a third therapeutic agent.

Other Pharmaceutical Compositions.

Pharmaceutical compositions may also be prepared from compositions described herein and one or more pharmaceutically acceptable excipients suitable for sublingual, buccal, rectal, intraosseous, intraocular, intranasal, epidural, or intraspinal administration. Preparations for such pharmaceutical compositions are well-known in the art. See, e.g., See, e.g., Anderson, Philip O.; Knoben, James E.; Troutman, William G, eds., Handbook of Clinical Drug Data, Tenth Edition, McGraw-Hill, 2002; Pratt and Taylor, eds., *Principles of Drug Action*, Third Edition, Churchill Livingston, New York, 1990; Katzung, ed., *Basic and Clinical Pharmacology*, Ninth Edition, McGraw Hill, 20037ybg; Goodman and Gilman, eds., *The Pharmacological Basis of Therapeutics*, Tenth Edition, McGraw Hill, 2001; *Remingtons Pharmaceutical Sciences,* 20th Ed., Lippincott Williams & Wilkins., 2000; Martindale, *The Extra Pharmacopoeia*, Thirty-Second Edition (The Pharmaceutical Press, London, 1999); all of which are incorporated by reference herein in their entirety.

Administration of each compounds or pharmaceutical composition of the present invention can be effected by any method that enables delivery of the compounds to the site of action. These methods include oral routes, intraduodenal routes, parenteral injection (including intravenous, intraarterial, subcutaneous, intramuscular, intravascular, intraperitoneal or infusion), topical (e.g., transdermal application), rectal administration, via local delivery by catheter or stent or through inhalation. Compounds can also be administered intraadiposally or intrathecally.

The amount of each compound administered will be dependent on the mammal being treated, the severity of the disorder or condition, the rate of administration, the disposition of the compound and the discretion of the prescribing physician. However, an effective dosage is in the range of about 0.001 to about 100 mg per kg body weight per day, preferably about 1 to about 35 mg/kg/day, in single or divided doses. For a 70 kg human, this would amount to about 0.05 to 7 g/day, preferably about 0.05 to about 2.5 g/day. In some instances, dosage levels below the lower limit of the aforesaid range may be more than adequate, while in other cases still larger doses may be employed without causing any harmful side effect, e.g., by dividing such larger doses into several small doses for administration throughout the day.

In some embodiments, an inhibitor of the invention is administered in a single dose. Typically, such administration will be by injection, e.g., intravenous injection, in order to introduce the agent quickly. However, other routes may be used as appropriate. A single dose of an inhibitor of the invention may also be used for treatment of an acute condition.

In some embodiments, an inhibitor of the invention is administered in multiple doses. Dosing may be about once, twice, three times, four times, five times, six times, or more than six times per day. Dosing may be about once a month, once every two weeks, once a week, or once every other day. In another embodiment an inhibitor of the invention and another agent are administered together about once per day to about 6 times per day. In another embodiment the administration of an inhibitor of the invention and an agent continues for less than about 7 days. In yet another embodiment the administration continues for more than about 6, 10, 14, 28 days, two months, six months, or one year. In some cases, continuous dosing is achieved and maintained as long as necessary.

Administration of the agents of the invention may continue as long as necessary. In some embodiments, an agent of the invention is administered for more than 1, 2, 3, 4, 5, 6, 7, 14, or 28 days. In some embodiments, an agent of the invention is administered for less than 28, 14, 7, 6, 5, 4, 3, 2, or 1 day. In some embodiments, an agent of the invention is administered chronically on an ongoing basis, e.g., for the treatment of chronic effects.

An effective amount of an inhibitor of the invention may be administered in either single or multiple doses by any of the accepted modes of administration of agents having similar utilities, including rectal, buccal, intranasal and transdermal routes, by intra-arterial injection, intravenously, intraperitoneally, parenterally, intramuscularly, subcutaneously, orally, topically, or as an inhalant.

The compositions of the invention may also be delivered via an impregnated or coated device such as a stent, for example, or an artery-inserted cylindrical polymer. Such a method of administration may, for example, aid in the prevention or amelioration of restenosis following procedures such as balloon angioplasty. Without being bound by theory, compounds of the invention may slow or inhibit the migration and proliferation of smooth muscle cells in the arterial wall which contribute to restenosis. An inhibitor of the invention may be administered, for example, by local delivery from the struts of a stent, from a stent graft, from grafts, or from the cover or sheath of a stent. In some embodiments, an inhibitor of the invention is admixed with a matrix. Such a matrix may be a polymeric matrix, and may serve to bond the compound to the stent. Polymeric matrices suitable for such use, include, for example, lactone-based polyesters or copolyesters such as polylactide, polycaprolactonglycolide, polyorthoesters, polyanhydrides, polyaminoacids, polysaccharides, polyphosphazenes, poly (ether-ester) copolymers (e.g., PEO-PLLA); polydimethylsiloxane, poly(ethylene-vinylacetate), acrylate-based polymers or copolymers (e.g., polyhydroxyethyl methylmethacrylate, polyvinyl pyrrolidinone), fluorinated polymers such as polytetrafluoroethylene and cellulose esters. Suitable matrices may be nondegrading or may degrade with time, releasing the compound or compounds. Compounds of the invention may be applied to the surface of the stent by various methods such as dip/spin coating, spray coating, dip-coating, and/or brush-coating. The compounds may be applied in a solvent and the solvent may be allowed to evaporate, thus forming a layer of compound onto the stent. Alternatively, the compound may be located in the body of the stent or graft, for example in microchannels or micropores. When implanted, the compound diffuses out of the body of the stent to contact the arterial wall. Such stents may be prepared by dipping a stent manufactured to contain such micropores or microchannels into a solution of the compound of the invention in a suitable solvent, followed by evaporation of the solvent. Excess drug on the surface of the stent may be removed via an additional brief solvent wash. In yet other embodiments, compounds of the invention may be covalently linked to a stent or graft. A covalent linker may be used which degrades in vivo, leading to the release of the compound of the invention. Any bio-labile linkage may be used for such a purpose, such as ester, amide or anhydride linkages. Compounds of the invention may additionally be administered intravascularly from a balloon used during angioplasty. Extravascular administration of the compounds via the pericard or via advential application of formulations of the invention may also be performed to decrease restenosis.

A variety of stent devices which may be used as described are disclosed, for example, in the following references, all of which are hereby incorporated by reference: U.S. Pat. No. 5,451,233; U.S. Pat. No. 5,040,548; U.S. Pat. No. 5,061,273; U.S. Pat. No. 5,496,346; U.S. Pat. No. 5,292,331; U.S. Pat. No. 5,674,278; U.S. Pat. No. 3,657,744; U.S. Pat. No. 4,739,762; U.S. Pat. No. 5,195,984; U.S. Pat. No. 5,292,331; U.S. Pat. No. 5,674,278; U.S. Pat. No. 5,879,382; U.S. Pat. No. 6,344,053.

The compounds of the invention may be administered in dosages. It is known in the art that due to intersubject variability in compound pharmacokinetics, individualization of dosing regimen is necessary for optimal therapy. Dosing for an inhibitor of the invention may be found by routine experimentation in light of the instant disclosure.

The subject pharmaceutical composition may, for example, be in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition will include a conventional pharmaceutical carrier or excipient and an inhibitor according to the invention as an active ingredient. In addition, it may include other medicinal or pharmaceutical agents, carriers, adjuvants, etc.

Exemplary parenteral administration forms include solutions or suspensions of active compound in sterile aqueous solutions, for example, aqueous propylene glycol or dextrose solutions. Such dosage forms can be suitably buffered, if desired.

The invention also provides kits. The kits include an inhibitor or compounds of the present invention as described herein, in suitable packaging, and written material that can include instructions for use, discussion of clinical studies, listing of side effects, and the like. Such kits may also include information, such as scientific literature references, package insert materials, clinical trial results, and/or summaries of these and the like, which indicate or establish the activities and/or advantages of the composition, and/or which describe dosing, administration, side effects, drug interactions, or other information useful to the health care provider. Such information may be based on the results of various studies, for example, studies using experimental animals involving in vivo models and studies based on human clinical trials. The kit may further contain another agent. In some embodiments, the compound of the present invention and the agent are provided as separate compositions in separate containers within the kit. In some embodiments, the compound of the present invention and the agent are provided as a single composition within a container in the kit. Suitable packaging and additional articles for use (e.g., measuring cup for liquid preparations, foil wrapping to minimize exposure to air, and the like) are known in the art and may be included in the kit. Kits described herein can be provided, marketed and/or promoted to health providers, including physicians, nurses, pharmacists, formulary officials, and the like. Kits may also, in some embodiments, be marketed directly to the consumer.

In some embodiments, the subject is a human in need of treatment for cancer, or a precancerous condition or lesion, wherein the cancer is preferably NSCL, breast, colon or pancreatic cancer. Subjects that can be treated with combination treatments of the present invention, or pharmaceutically acceptable salt, ester, prodrug, solvate, hydrate or derivatives of the therapeutic agents, according to the methods of this invention include, for example, subjects that have been diagnosed as having psoriasis; restenosis; atherosclerosis; BPH; breast cancer such as a ductal carcinoma in duct tissue in a mammary gland, medullary carcinomas, colloid carcinomas, tubular carcinomas, and inflammatory breast cancer; ovarian cancer, including epithelial ovarian tumors such as adenocarcinoma in the ovary and an adenocarcinoma that has migrated from the ovary into the abdominal cavity; uterine cancer; cervical cancer such as adenocarcinoma in the cervix epithelial including squamous cell carcinoma and adenocarcinomas; prostate cancer, such as a prostate cancer selected from the following: an adenocarcinoma or an adenocarinoma that has migrated to the bone; pancreatic cancer such as epitheliod carcinoma in the pancreatic duct tissue and an adenocarcinoma in a pancreatic duct; bladder cancer such as a transitional cell carcinoma in urinary bladder, urothelial carcinomas (transitional cell carcinomas), tumors in the urothelial cells that line the bladder, squamous cell carcinomas, adenocarcinomas, and small cell cancers; leukemia such as acute myeloid leukemia (AML), acute lymphocytic leukemia, chronic lymphocytic leukemia, chronic myeloid leukemia, hairy cell leukemia, myelodysplasia, myeloproliferative disorders, acute myelogenous leukemia (AML), chronic myelogenous leukemia (CML), mastocytosis, chronic lymphocytic leukemia (CLL), multiple myeloma (MM), and myelodysplastic syndrome (MDS); bone cancer; lung cancer such as non-small cell lung cancer (NSCLC), which is divided into squamous cell carcinomas, adenocarcinomas, and large cell undifferentiated carcinomas, and small cell lung cancer; skin cancer such as basal cell carcinoma, melanoma, squamous cell carcinoma and actinic keratosis, which is a skin condition that sometimes develops into squamous cell carcinoma; eye retinoblastoma; cutaneous or intraocular (eye) melanoma; primary liver cancer (cancer that begins in the liver); kidney cancer; thyroid cancer such as papillary, follicular, medullary and anaplastic; AIDS-related lymphoma such as diffuse large B-cell lymphoma, B-cell immunoblastic lymphoma and small non-cleaved cell lymphoma; Kaposi's Sarcoma; viral-induced cancers including hepatitis B virus (HBV), hepatitis C virus (HCV), and hepatocellular carcinoma; human lymphotropic virus-type 1 (HTLV-1) and adult T-cell leukemia/lymphoma; and human papilloma virus (HPV) and cervical cancer; central nervous system cancers (CNS) such as primary brain tumor, which includes gliomas (astrocytoma, anaplastic astrocytoma, or glioblastoma multiforme), Oligodendroglioma, Ependymoma, Meningioma, Lymphoma, Schwannoma, and Medulloblastoma; peripheral nervous system (PNS) cancers such as acoustic neuromas and malignant peripheral nerve sheath tumor (MPNST) including neurofibromas and schwannomas, malignant fibrous cytoma, malignant fibrous histiocytoma, malignant meningioma, malignant mesothelioma, and malignant mixed Müllerian tumor; oral cavity and oropharyngeal cancer such as, hypopharyngeal cancer, laryngeal cancer, nasopharyngeal cancer, and oropharyngeal cancer; stomach cancer such as lymphomas, gastric stromal tumors, and carcinoid tumors; testicular cancer such as germ cell tumors (GCTs), which include seminomas and nonseminomas, and gonadal stromal tumors, which include Leydig cell tumors and Sertoli cell tumors; thymus cancer such as to thymomas, thymic carcinomas, Hodgkin disease, non-Hodgkin lymphomas carcinoids or carcinoid tumors; rectal cancer; and colon cancer.

The invention also relates to a method of treating diabetes in a mammal that comprises administering to said mammal a therapeutically effective amount of a combination treatment of the present invention.

In addition, the combination treatments described herein may be used to treat acne.

In addition, the combination treatments described herein may be used for the treatment of arteriosclerosis, including atherosclerosis. Arteriosclerosis is a general term describing any hardening of medium or large arteries. Atherosclerosis is a hardening of an artery specifically due to an atheromatous plaque.

Further the combination treatments described herein may be used for the treatment of glomerulonephritis. Glomerulonephritis is a primary or secondary autoimmune renal disease characterized by inflammation of the glomeruli. It may be asymptomatic, or present with hematuria and/or proteinuria. There are many recognized types, divided in acute, subacute or chronic glomerulonephritis. Causes are infectious (bacterial, viral or parasitic pathogens), autoimmune or paraneoplastic.

Additionally, the combination treatments described herein may be used for the treatment of bursitis, lupus, acute disseminated encephalomyelitis (ADEM), addison's disease, antiphospholipid antibody syndrome (APS), aplastic anemia, autoimmune hepatitis, coeliac disease, crohn's disease, diabetes mellitus (type 1), goodpasture's syndrome, graves' disease, guillain-barre syndrome (GBS), hashimoto's disease, inflammatory bowel disease, lupus erythematosus, myasthenia gravis, opsoclonus myoclonus syndrome (OMS), optic neuritis, ord's thyroiditis, ostheoarthritis, uveoretinitis, pemphigus, polyarthritis, primary biliary cirrhosis, reiter's syndrome, takayasu's arteritis, temporal arteritis, warm autoimmune hemolytic anemia, wegener's granulomatosis, alopecia universalis, chagas' disease, chronic fatigue syndrome, dysautonomia, endometriosis, hidradenitis suppurativa, interstitial cystitis, neuromyotonia, sarcoidosis, scleroderma, ulcerative colitis, vitiligo, vulvodynia, appendicitis, arteritis, arthritis, blepharitis, bronchiolitis, bronchitis, cervicitis, cholangitis, cholecystitis, chorioamnionitis, colitis, conjunctivitis, cystitis, dacryoadenitis, dermatomyositis, endocarditis, endometritis, enteritis, enterocolitis, epicondylitis, epididymitis, fasciitis, fibrositis, gastritis, gastroenteritis, gingivitis, hepatitis, hidradenitis, ileitis, iritis, laryngitis, mastitis, meningitis, myelitis, myocarditis, myositis, nephritis, omphalitis, oophoritis, orchitis, osteitis, otitis, pancreatitis, parotitis, pericarditis, peritonitis, pharyngitis, pleuritis, phlebitis, pneumonitis, proctitis, prostatitis, pyelonephritis, rhinitis, salpingitis, sinusitis, stomatitis, synovitis, tendonitis, tonsillitis, uveitis, vaginitis, vasculitis, or vulvitis.

The invention also relates to a method of treating a cardiovascular disease in a mammal that comprises administering to said mammal a therapeutically effective amount of a combination treatment of the present invention. Examples of cardiovascular conditions include, but are not limited to, atherosclerosis, restenosis, vascular occlusion, carotid obstructive disease, or ischemic conditions.

In another aspect, the present invention provides methods of disrupting the function of a leukocyte or disrupting a function of an osteoclast. The method includes contacting the leukocyte or the osteoclast with a function disrupting amount of a combination treatment of the invention.

In another aspect of the present invention, methods are provided for treating ophthalmic disease by applying one or more of the subject combination treatments to the eye of a subject. Methods are further provided for administering the combination treatments of the present invention via eye drop, intraocular injection, intravitreal injection, topically, or through the use of a drug eluting device, microcapsule, implant, or microfluidic device. In some cases, combination treatments are administered with a carrier or excipient that increases the intraocular penetrance of the compound such as an oil and water emulsion with colloid particles having an oily core surrounded by an interfacial film.

In some cases, the colloid particles include at least one cationic agent and at least one non-ionic surfactant such as a poloxamer, tyloxapol, a polysorbate, a polyoxyethylene castor oil derivative, a sorbitan ester, or a polyoxyl stearate. In some cases, the cationic agent is an alkylamine, a tertiary alkyl amine, a quarternary ammonium compound, a cationic lipid, an amino alcohol, a biguanidine salt, a cationic compound or a mixture thereof. In some cases the cationic agent is a biguanidine salt such as chlorhexidine, polyaminopropyl biguanidine, phenformin, alkylbiguanidine, or a mixture thereof. In some cases, the quaternary ammonium compound is a benzalkonium halide, lauralkonium halide, cetrimide, hexadecyltrimethylammonium halide, tetradecyltrimethylammonium halide, dodecyltrimethylammonium halide, cetrimonium halide, benzethonium halide, behenalkonium halide, cetalkonium halide, cetethyldimonium halide, cetylpyridinium halide, benzododecinium halide, chlorallyl methenamine halide, rnyristylalkonium halide, stearalkonium halide or a mixture of two or more thereof. In some cases, cationic agent is a benzalkonium chloride, lauralkonium chloride, benzododecinium bromide, benzethenium chloride, hexadecyltrimethylammonium bromide, tetradecyltrimethylammonium bromide, dodecyltrimethylammonium bromide or a mixture of two or more thereof. In some cases, the oil phase is mineral oil and light mineral oil, medium chain triglycerides (MCT), coconut oil; hydrogenated oils comprising hydrogenated cottonseed oil, hydrogenated palm oil, hydrogenate castor oil or hydrogenated soybean oil; polyoxyethylene hydrogenated castor oil derivatives comprising poluoxyl-40 hydrogenated castor oil, polyoxyl-60 hydrogenated castor oil or polyoxyl-100 hydrogenated castor oil.

The invention further provides methods of modulating a PI3K and/or mTOR kinase activity by contacting the kinase with an effective amount of a composition comprising a PI3Kα inhibitor and an mTor inhibitor. Modulate can be inhibiting or activating kinase activity. In some embodiments, the invention provides methods of inhibiting kinase activity by contacting the kinase with an effective amount of a composition comprising a PI3Kα inhibitor and an mTor inhibitor in solution. In some embodiments, the invention provides methods of inhibiting the kinase activity by contacting a cell, tissue, or organ that expresses the kinase of interest. In some embodiments, the invention provides methods of inhibiting kinase activity in subject including but not limited to rodents and mammal (e.g., human) by administering into the subject an effective amount of a composition comprising a PI3Kα inhibitor and an mTor inhibitor. In some embodiments, the percentage of inhibiting exceeds 50%, 60%, 70%, 80%, or 90%.

Further Combination Therapies

The present invention also provides methods for further combination therapies in which, in addition to a PI3Kα inhibitor and an mTor inhibitor, an agent known to modulate other pathways, or other components of the same pathway, or even overlapping sets of target enzymes is used or a pharmaceutically acceptable salt, ester, prodrug, solvate, hydrate or derivative thereof. In one aspect, such therapy includes but is not limited to the combination of the composition comprising a PI3Kα inhibitor and an mTor inhibitor with chemotherapeutic agents, therapeutic antibodies, and radiation treatment, to provide, where desired, a synergistic or additive therapeutic effect.

For treatment of autoimmune diseases, the subject compounds or pharmaceutical compositions can be used in combination with commonly prescribed drugs including but not limited to Enbrel®, Remicade®, Humira®, Avonex®, and Rebif®. For treatment of respiratory diseaseses, the subject compounds or pharmaceutical compositions can be administered in combination with commonly prescribed drugs including but not limited to Xolair®, Advair®, Singulair®, and Spiriva®.

The compounds of the invention may be formulated or administered in conjunction with other agents that act to relieve the symptoms of inflammatory conditions such as encephalomyelitis, asthma, and the other diseases described herein. These agents include non-steroidal anti-inflammatory drugs (NSAIDs), e.g., acetylsalicylic acid; ibuprofen; naproxen; indomethacin; nabumetone; tolmetin; etc. Corticosteroids are used to reduce inflammation and suppress activity of the immune system. The most commonly prescribed drug of this type is Prednisone. Chloroquine (Aralen) or hydroxychloroquine (Plaquenil) may also be very useful in some individuals with lupus. They are most often prescribed for skin and joint symptoms of lupus. Azathioprine (Imuran) and cyclophosphamide (Cytoxan) suppress inflammation and tend to suppress the immune system. Other agents, e.g., methotrexate and cyclosporin are used to control the symptoms of lupus. Anticoagulants are employed to prevent blood from clotting rapidly. They range from aspirin at very low dose which prevents platelets from sticking, to heparin/coumadin.

In another one aspect, this invention also relates to methods and pharmaceutical compositions for inhibiting abnormal cell growth in a mammal which comprises an amount of an inhibitor of the present invention, or a pharmaceutically acceptable salt, ester, prodrug, solvate, hydrate or derivative thereof, in combination with an amount of an anti-cancer agent (e.g., a chemotherapeutic agent). Many chemotherapeutics are presently known in the art and can be used in combination with the compounds of the invention.

In some embodiments, the chemotherapeutic is selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, angiogenesis inhibitors, immunotherapeutic agents, proapoptotic agents, and anti-androgens. Non-limiting examples are chemotherapeutic agents, cytotoxic agents, and non-peptide small molecules such as Gleevec (Imatinib Mesylate), Velcade (bortezomib), Casodex (bicalutamide), Iressa (gefitinib), and Adriamycin as well as a host of chemotherapeutic agents. Non-limiting examples of chemotherapeutic agents include alkylating agents such as thiotepa and cyclosphosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, ranimustine; oxazaphosphorines; nitrosoureas; triazenes; antibiotics such as anthracyclins, actinomycins and bleomycins including aclacinomysins, actinomycin, anthramycin, azaserine, bleomycins, cactinomycin, calicheamicin, carabicin, caminomycin, carzinophilin, Casodex™, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfomithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofuran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g., paclitaxel (TAXOL™, Bristol-Myers Squibb Oncology, Princeton, N.J.) and docetaxel (TAXOTERE™, Rhone-Poulenc Rorer, Antony, France); retinoic acid; esperamicins; capecitabine; gemcitabine and pharmaceutically acceptable salts, acids or derivatives of any of the above. Also included as suitable chemotherapeutic cell conditioners are anti-hormonal agents that act to regulate or inhibit hormone action on tumors such as anti-estrogens including for example tamoxifen (Nolvadex™), raloxifene, aromatase inhibiting 4(5)-imidazoles, 4-hydroxytamoxifen, trioxifene, keoxifene, LY 117018, onapristone, and toremifene (Fareston); and anti-androgens such as flutamide, nilutamide, bicalutamide, leuprolide, and goserelin; chlorambucil; gemcitabine; 6-thioguanine; mercaptopurine; methotrexate; platinum or platinum analogs and complexes such as cisplatin and carboplatin; anti-microtubule such as diterpenoids, including paclitaxel and docetaxel, or Vinca alkaloids including vinblastine, vincristine, vinflunine, vindesine, and vinorelbine; etoposide (VP-16); ifosfamide; mitomycin C; mitoxantrone; vincristine; vinorelbine; navelbine; novantrone; teniposide; daunomycin; aminopterin; xeloda; ibandronate; topoisomerase I and II inhibitors including camptothecins (e.g., camptothecin-11), topotecan, irinotecan, and epipodophyllotoxins; topoisomerase inhibitor RFS 2000; epothilone A or B; difluoromethylornithine (DMFO); histone deacetylase inhibitors; compounds which induce cell differentiation processes; gonadorelin agonists; methionine aminopeptidase inhibitors; compounds targeting/decreasing a protein or lipid kinase activity; compounds which target, decrease or inhibit the activity of a protein or lipid phosphatase; anti-androgens; bisphosphonates; biological response modifiers; antiproliferative antibodies; heparanase inhibitors; inhibitors of Ras oncogenic isoforms; telomerase inhibitors; proteasome inhibitors; compounds used in the treatment of hematologic malignancies; compounds which target, decrease or inhibit the activity of Flt-3; Hsp90 inhibitors; temozolomide (TEMODAL®); Hsp90 inhibitors such as 17-AAG (17-allylaminogeldanamycin, NSC330507), 17-DMAG (17-dimethylaminoethylamino-17-demethoxy-geldanamycin, NSC707545), IPI-504, CNF1010, CNF2024, CNF1010 from Conforma Therapeutics; temozolomide (TEMODAL®); kinesin spindle protein inhibitors, such as SB715992 or SB743921 from GlaxoSmithKline, or pentamidine/chlorpromazine from CombinatoRx; MEK inhibitors such as ARRY142886 from Array PioPharma, AZD6244 from AstraZeneca, PD181461 or PD0325901 from Pfizer, leucovorin, EDG binders, antileukemia compounds, ribonucleotide reductase inhibitors, S-adenosylmethionine decarboxylase inhibitors, antiproliferative antibodies or other chemotherapeutic compounds. Where desired, the compounds or pharmaceutical composition of the present invention can be used in combination with commonly prescribed anti-cancer drugs such as Herceptin®, Avastin®, Erbitux®, Rituxan®, Taxol®, Arimidex®, Taxotere®, and Velcade®. Further information on compounds which may be used in conjunction with the compounds of the invention is provided below.

Proteasome inhibitors include compounds which target, decrease or inhibit the activity of the proteasome. Compounds which target, decrease or inhibit the activity of the proteasome include e.g., Bortezomid (Velcade™) and MLN 341. Matrix metalloproteinase inhibitors ("MMP" inhibitors) include, but are not limited to, collagen peptidomimetic and nonpeptidomimetic inhibitors, tetracycline derivatives, e.g., hydroxamate peptidomimetic inhibitor batimastat and its orally bioavailable analogue marimastat (BB-2516), prinomastat (AG3340), metastat (NSC 683551) BMS-279251, BAY 12-9566, TAA211, MMI270B or AAJ996. Compounds used in the treatment of hematologic malignancies include, but are not limited to, FMS-like tyrosine kinase inhibitors e.g., compounds targeting, decreasing or inhibiting the activity of FMS-like tyrosine kinase receptors (Flt-3R); interferon, 1-b-D-arabinofuransylcytosine (ara-c) and bisulfan; and ALK inhibitors e.g., compounds which target, decrease or inhibit anaplastic lymphoma kinase. Compounds which target, decrease or inhibit the activity of FMS-like tyrosine kinase receptors (Flt-3R) are especially compounds, proteins or antibodies which inhibit members of the Flt-3R receptor kinase family, e.g., PKC412, midostaurin, a staurosporine derivative, SU11248 and MLN518.

Hsp90 inhibitors include compounds such as 17-AAG (17-allylaminogeldanamycin, NSC330507), 17-DMAG (17-dimethylaminoethylamino-17-demethoxy-geldanamycin, NSC707545), IPI-504, CNF1010, CNF2024, CNF1010 from Conforma Therapeutics; temozo-lomide (TEMODAL®); kinesin spindle protein inhibitors, such as SB715992 or SB743921 from GlaxoSmithKline, or pentamidine/chlorpromazine from CombinatoRx; MEK inhibitors such as ARRY142886 from Array PioPharma, AZD6244 from AstraZeneca, PD181461 from Pfizer, leucovorin, EDG binders, antileukemia compounds, ribonucleotide reductase inhibitors, S-adenosylmethionine decarboxylase inhibitors, antiproliferative antibodies or other chemotherapeutic compounds.

Histone deacetylase inhibitors (or "HDAC inhibitors") include compounds which inhibit a histone deacetylase and which possess antiproliferative activity. This includes compounds disclosed in WO 02/22577, especially N-hydroxy-3-[4-[[(2-hydroxyethyl) [2-(1H-indol-3-yl)ethyl]-amino]methyl]phenyl]-2E-2-prop enamide, N-hydroxy-3-[4-[[[2-(2-methyl-1H-indol-3-yl)-ethyl]amino]methyl]phenyl]-2E-2-propenamide and pharmaceutically acceptable salts thereof. It further especially includes Suberoylanilide hydroxamic acid (SAHA).

Bisphosphonates for use in combination with the compounds of the invention include, but are not limited to, etridonic, clodronic, tiludronic, pamidronic, alendronic, ibandronic, risedronic and zoledronic acid.

Compounds of the invention may also be used in conjunction with compounds targeting or decreasing a protein or lipid kinase activity, a protein or lipid phosphatase activity, or further anti-angiogenic compounds. Such compounds include, but are not limited to, protein tyrosine kinase and/or serine and/or threonine kinase inhibitors or lipid kinase inhibitors, e.g.: compounds targeting, decreasing or inhibiting the activity of the platelet-derived growth factor-receptors (PDGFR), such as compounds which target, decrease or inhibit the activity of PDGFR, especially compounds which inhibit the PDGF receptor, e.g., a N-phenyl-2-pyrimidine-amine derivative, e.g., imatinib, SU101, SU6668 and GFB-111; compounds targeting, decreasing or inhibiting the activity of the fibroblast growth factor-receptors (FGFR); compounds targeting, decreasing or inhibiting the activity of the insulin-like growth factor receptor I (IGF-IR), such as compounds which target, decrease or inhibit the activity of IGF-IR, especially compounds which inhibit the kinase activity of IGF-I receptor, such as those compounds disclosed in WO 02/092599 or such as OSI906, or antibodies that target the extracellular domain of IGF-I receptor such as CP-751871, R1507, AVE1642, IMC-A12, AMG479, MK-0646, SCH717454 or its growth factors; compounds targeting, decreasing or inhibiting the activity of the Trk receptor tyrosine kinase family, or ephrin B4 inhibitors; compounds targeting, decreasing or inhibiting the activity of the Axl receptor tyrosine kinase family; compounds targeting, decreasing or inhibiting the activity of the Ret receptor tyrosine kinase; compounds targeting, decreasing or inhibiting the activity of the Kit/SCFR receptor tyrosine kinase, e.g., imatinib; compounds targeting, decreasing or inhibiting the activity of the C-kit receptor tyrosine kinases—(part of the PDGFR family), such as compounds which target, decrease or inhibit the activity of the c-Kit receptor tyrosine kinase family, especially compounds which inhibit the c-Kit receptor, e.g., imatinib; compounds targeting, decreasing or inhibiting the activity of members of the c-Abl family, their gene-fusion products (e.g., BCR-AbI kinase) and mutants, such as compounds which target decrease or inhibit the activity of c-Abl family members and their gene fusion products, e.g., a N-phenyl-2-pyrimidine-amine derivative, e g, imatinib or nilotinib (AMN107); PD180970; AG957; NSC 680410; PD173955 from ParkeDavis; or dasatinib (BMS-354825); compounds targeting, decreasing or inhibiting the activity of members of the protein kinase C (PKC) and Raf family of serine/threonine kinases, members of the MEK, SRC, JAK, FAK, PDK1, PKB/Akt, and Ras/MAPK family members, and/or members of the cyclin-dependent kinase family (CDK) and are especially those staurosporine derivatives disclosed in U.S. Pat. No. 5,093,330, e.g., midostaurin; examples of further compounds include e.g., UCN-01, safingol, BAY 43-9006, Bryostatin 1, Perifosine; Ilmofosine; RO 318220 and RO 320432; GO 6976; Isis 3521; LY333531/ LY379196; isochinoline compounds such as those disclosed in WO 00/09495; FTIs; PD184352 or QAN697 (a PI3K inhibitor) or AT7519 (CDK inhibitor); compounds targeting, decreasing or inhibiting the activity of protein-tyrosine kinase inhibitors, such as compounds which target, decrease or inhibit the activity of protein-tyrosine kinase inhibitors include imatinib mesylate (GLEEVEC) or tyrphostin. A tyrphostin is preferably a low molecular weight (Mr<1500) compound, or a pharmaceutically acceptable salt thereof, especially a compound selected from the benzylidenemalonitrile class or the S-arylbenzenemalonirile or bisubstrate quinoline class of compounds, more especially any compound selected from the group consisting of Tyrphostin A23/ RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl)methyl] amino}-benzoic acid adamantyl ester; NSC 680410, adaphostin).

Compounds of the invention may also be used in combination with compounds targeting, decreasing or inhibiting the activity of the epidermal growth factor family of receptor tyrosine kinases (EGFR, ErbB2, ErbB3, ErbB4 as homo- or heterodimers) and their mutants, such as compounds which target, decrease or inhibit the activity of the epidermal growth factor receptor family are especially compounds, proteins or antibodies which inhibit members of the EGF receptor tyrosine kinase family, e.g., EGF receptor, ErbB2, ErbB3 and ErbB4 or bind to EGF or EGF related ligands, and are in particular those compounds, proteins or monoclonal antibodies generically and specifically disclosed in WO 97/02266, e.g., the compound of ex. 39, or in EP 0 564 409, WO 99/03854, EP 0520722, EP 0 566 226, EP 0 787 722, EP 0 837 063, U.S. Pat. No. 5,747,498, WO 98/10767, WO 97/30034, WO 97/49688, WO 97/38983 and, especially, WO 96/30347 (e.g., compound known as CP 358774), WO 96/33980 (e.g., compound ZD 1839) and WO 95/03283 (e.g., compound ZM105180); e.g., trastuzumab (Herceptin™), cetuximab (Erbitux™), Iressa, Tarceva, OSI-774, CI-1033, EKB-569, GW-2016, E1.1, E2.4, E2.5, E6.2, E6.4, E2.1 1, E6.3 or E7.6.3, and 7H-pyrrolo-[2,3-d]pyrimidine derivatives which are disclosed in WO 03/013541; and compounds targeting, decreasing or inhibiting the activity of the c-Met receptor, such as compounds which target, decrease or inhibit the activity of c-Met, especially compounds which inhibit the kinase activity of c-Met receptor, or antibodies that target the extracellular domain of c-Met or bind to HGF. Further anti-angiogenic compounds include compounds having another mechanism for their activity, e.g., unrelated to protein or lipid kinase inhibition e.g., thalidomide (THALOMID) and TNP-470.

Non-receptor kinase angiogenesis inhibitors may also be useful in conjunction with the compounds of the present invention. Angiogenesis in general is linked to erbB21EGFR signaling since inhibitors of erbB2 and EGFR have been shown to inhibit angiogenesis, primarily VEGF expression. Accordingly, non-receptor tyrosine kinase inhibitors may be used in combination with the compounds of the present invention. For example, anti-VEGF antibodies, which do not recognize VEGFR (the receptor tyrosine kinase), but bind to the ligand; small molecule inhibitors of integrin (alphav beta3) that will inhibit angiogenesis; endostatin and angiostatin (non-RTK) may also prove useful in combination with the disclosed compounds. (See Bruns C J et al (2000), Cancer Res., 60: 2926-2935; Schreiber A B, Winkler M E, and Derynck R. (1986), Science, 232: 1250-1253; Yen L et al. (2000), Oncogene 19: 3460-3469).

Compounds which target, decrease or inhibit the activity of a protein or lipid phosphatase include e.g., inhibitors of phosphatase 1, phosphatase 2A, or CDC25, e.g., okadaic acid or a derivative thereof. Compounds which induce cell differentiation processes are e.g., retinoic acid, α- γ- or δ-tocopherol or α- γ- or δ-tocotrienol. Cyclooxygenase inhibitors include, but are not limited to, e.g., Cox-2 inhibitors, 5-alkyl substituted 2-arylaminophenylacetic acid and derivatives, such as celecoxib (CELEBREX), rofecoxib (VIOXX), etoricoxib, valdecoxib or a 5-alkyl-2-arylaminophenylacetic acid, e.g., 5-methyl-2-(2'-chloro-6'-fluoroanilino)phenyl acetic acid, and lumiracoxib.

Heparanase inhibitors includes compounds which target, decrease or inhibit heparin sulfate degradation, including, but not limited to, PI-88. Biological response modifiers include lymphokines and interferons, e.g., interferon γ. Inhibitors of Ras oncogenic isoforms include H-Ras, K-Ras, N-Ras, and other compounds which target, decrease or inhibit the oncogenic activity of Ras. Farnesyl transferase inhibitors include, but are not limited to, e.g., L-744832, DK8G557 and R115777 (Zarnestra).

Telomerase inhibitors include compounds which target, decrease or inhibit the activity of telomerase. Compounds which target, decrease or inhibit the activity of telomerase are especially compounds which inhibit the telomerase receptor, e.g., telomestatin. Methionine aminopeptidase inhibitors are, for example, compounds which target, decrease or inhibit the activity of methionine aminopeptidase. Compounds which target, decrease or inhibit the activity of methionine aminopeptidase are e.g., bengamide or a derivative thereof.

Antiproliferative antibodies include, but are not limited to, trastuzumab (Herceptin™), Trastuzumab-DM1, erbitux, bevacizumab (Avastin™), rituximab (Rituxan®), PRO64553 (anti-CD40) and 2C4 Antibody. By antibodies is meant e.g., intact monoclonal antibodies, polyclonal antibodies, multispecific antibodies formed from at least 2 intact antibodies, and antibodies fragments so long as they exhibit the desired biological activity.

For the treatment of acute myeloid leukemia (AML), compounds of the invention can be used in combination with standard leukemia therapies, especially in combination with therapies used for the treatment of AML. In particular, compounds of the invention can be administered in combination with, e.g., farnesyl transferase inhibitors and/or other drugs useful for the treatment of AML, such as Daunorubicin, Adriamycin, Ara-C, VP-16, Teniposide, Mitoxantrone, Idarubicin, Carboplatinum and PKC412.

Antileukemic compound for use in combination with compounds of the invention include, for example, Ara-C, a pyrimidine analog, which is the 2'-alpha-hydroxy ribose (arabinoside) derivative of deoxycytidine. Also included is the purine analog of hypoxanthine, 6-mercaptopurine (6-MP) and fludarabine phosphate. Compounds which target, decrease or inhibit activity of histone deacetylase (HDAC) inhibitors such as sodium butyrate and suberoylanilide hydroxamic acid (SAHA) inhibit the activity of the enzymes known as histone deacetylases. Specific HDAC inhibitors include MS275, SAHA, FK228 (formerly FR901228), Trichostatin A and compounds disclosed in U.S. Pat. No. 6,552,065, in particular, Λ/-hydroxy-3-[4-[[[2-(2-methyl-1H-indol-3-yl)-ethyl]-amino]methyl]phenyl]-2E-2-propenamide, or a pharmaceutically acceptable salt thereof and Λ/-hydroxy-3-[4-[(2-hydroxyethyl){2-(1/-/-indol-3-yl)ethyl]-amino]methyl]phenyl]-2E-2-propenamide, or a pharmaceutically acceptable salt thereof, e.g., the lactate salt.

Somatostatin receptor antagonists include compounds which target, treat or inhibit the somatostatin receptor such as octreotide, and SOM230 (pasireotide). Tumor cell damaging approaches include approaches such as ionizing radiation, e.g., ionizing radiation that occurs as either electromagnetic rays (such as X-rays and gamma rays) or particles (such as alpha and beta particles). Ionizing radiation is provided in, but not limited to, radiation therapy and is known in the art. See Hellman, Principles of Radiation Therapy, Cancer, in Principles and Practice of Oncology, Devita et al., Eds., 4th Edition, Vol. 1, pp. 248-275 (1993). EDG binders includes immunosuppressants that modulate lymphocyte recirculation, such as FTY720.

Ribonucleotide reductase inhibitors include pyrimidine or purine nucleoside analogs including, but not limited to, fludarabine and/or cytosine arabinoside (ara-C), 6-thioguanine, 5-fluorouracil, cladribine, 6-mercaptopurine (especially in combination with ara-C against ALL) and/or pentostatin. Ribonucleotide reductase inhibitors are e.g., hydroxyurea or 2-hydroxy-1/-/-isoindole-1,3-dione derivatives, such as PL-1, PL-2, PL-3, PL-4, PL-5, PL-6, PL-7 or PL-8 mentioned in Nandy et al., Acta Oncologica, Vol. 33, No. 8, pp. 953-961 (1994).

S-adenosylmethionine decarboxylase inhibitors include, but are not limited to the compounds disclosed in U.S. Pat. No. 5,461,076.

Also included are in particular those compounds, proteins or monoclonal antibodies of VEGF disclosed in WO 98/35958, e.g., 1-(4-chloroanilino)-4-(4-pyridylmethyl)phthalazine or a pharmaceutically acceptable salt thereof, e.g., the succinate, or in WO 00/09495, WO 00/27820, WO 00/59509, WO 98/11223, WO 00/27819 and EP 0 769 947; those as described by Prewett et al, Cancer Res, Vol. 59, pp. 5209-5218 (1999); Yuan et al., Proc Natl Acad Sci USA, Vol. 93, pp. 14765-14770 (1996); Zhu et al., Cancer Res, Vol. 58, pp. 3209-3214 (1998); and Mordenti et al., Toxicol Pathol, Vol. 27, No. 1, pp. 14-21 (1999); in WO 00/37502 and WO 94/10202; ANGIOSTATIN, described by O'Reilly et al., Cell, Vol. 79, pp. 315-328 (1994); ENDOSTATIN, described by O'Reilly et al., Cell, Vol. 88, pp. 277-285 (1997); anthranilic acid amides; ZD4190; ZD6474; SU5416; SU6668; bevacizumab; or anti-VEGF antibodies or anti-VEGF receptor antibodies, e.g., rhuMAb and RHUFab, VEGF aptamer e.g., Macugon; FLT-4 inhibitors, FLT-3 inhibitors, VEGFR-2 IgGI antibody, Angiozyme (RPI 4610) and Bevacizumab (Avastin™).

The compounds of the invention are also useful as co-therapeutic compounds for use in combination with other drug substances such as anti-inflammatory, bronchodilatory or antihistamine drug substances, particularly in the treatment of obstructive or inflammatory airways diseases such as those mentioned hereinbefore, for example as potentiators of therapeutic activity of such drugs or as a means of reducing required dosaging or potential side effects of such drugs. An inhibitor of the invention may be mixed with the other drug substance in a fixed pharmaceutical composition or it may be administered separately, before, simultaneously with or after the other drug substance. Accordingly the invention includes a combination of an inhibitor of the invention as described with an anti-inflammatory, bronchodilatory, antihistamine or anti-tussive drug substance, said compound of the invention and said drug substance being in the same or different pharmaceutical composition. Suitable anti-inflammatory drugs include steroids, in particular glucocorticosteroids such as budesonide, beclamethasone dipropionate, fluticasone propionate, ciclesonide or mometasone furoate, or steroids described in WO 02/88167, WO 02/12266, WO 02/100879, WO 02/00679 (especially those of Examples 3, 11, 14, 17, 19, 26, 34, 37, 39, 51, 60, 67, 72, 73, 90, 99 and 101), WO 03/035668, WO 03/048181, WO 03/062259, WO 03/064445, WO 03/072592, non-steroidal glucocorticoid receptor agonists such as those described in WO 00/00531, WO 02/10143, WO 03/082280, WO 03/082787, WO 03/104195, WO 04/005229; LTB4 antagonists such LY29311 1, CGS025019C, CP-195543, SC-53228, BIIL 284, ONO 4057, SB 209247 and those described in U.S. Pat. No. 5,451,700; LTD4 antagonists such as montelukast and zafirlukast; PDE4 inhibitors such cilomilast (Ariflo® GlaxoSmithKline), Roflumilast (Byk Gulden), V-1 1294A (Napp), BAY19-8004 (Bayer), SCH-351591 (Schering-Plough), Arofylline (Almirall Prodesfarma), PD189659/PD168787 (Parke-Davis), AWD-12-281 (Asta Medica), CDC-801 (Celgene), SelCID™ CC-10004 (Celgene), VM554/UM565 (Vernalis), T-440 (Tanabe), KW-4490 (Kyowa Hakko Kogyo), and those disclosed in WO 92/19594, WO 93/19749, WO 93/19750, WO 93/19751, WO 98/18796, WO 99/16766, WO 01/13953, WO 03/104204, WO 03/104205, WO 03/39544, WO 04/000814, WO 04/000839, WO 04/005258, WO 04/018450, WO 04/018451, WO 04/018457, WO 04/018465, WO 04/018431, WO 04/018449, WO 04/018450, WO 04/018451, WO 04/018457, WO 04/018465, WO 04/019944, WO 04/019945, WO 04/045607 and WO 04/037805; A2a agonists such as those disclosed in EP 409595A2, EP 1052264, EP 1241176, WO 94/17090, WO 96/02543, WO 96/02553, WO 98/28319, WO 99/24449, WO 99/24450, WO 99/24451, WO 99/38877, WO 99/41267, WO 99/67263, WO 99/67264, WO 99/67265, WO 99/67266, WO 00/23457, WO 00/77018, WO 00/78774, WO 01/23399, WO 01/27130, WO 01/27131, WO 01/60835, WO 01/94368, WO 02/00676, WO 02/22630, WO 02/96462, WO 03/086408, WO 04/039762, WO 04/039766, WO 04/045618 and WO 04/046083; A2b antagonists such as those described in WO 02/42298; and beta-2 adrenoceptor agonists such as albuterol (salbutamol), metaproterenol, terbutaline, salmeterol fenoterol, procaterol, and especially, formoterol and pharmaceutically acceptable salts thereof, and compounds (in free or salt or solvate form) of formula I of WO 0075114, which document is incorporated herein by reference, preferably compounds of the Examples thereof, as well as compounds (in free or salt or solvate form) of formula I of WO 04/16601, and also compounds of WO 04/033412. Suitable bronchodilatory drugs include anticholinergic or anti-muscarinic compounds, in particular ipratropium bromide, oxitropium bromide, tiotropium salts and CHF 4226 (Chiesi), and glycopyrrolate, but also those described in WO 01/041 18, WO 02/51841, WO 02/53564, WO 03/00840, WO 03/87094, WO 04/05285, WO 02/00652, WO 03/53966, EP 424021, U.S. Pat. No. 5,171,744, U.S. Pat. No. 3,714,357, WO 03/33495 and WO 04/018422.

Suitable antihistamine drug substances include cetirizine hydrochloride, acetaminophen, clemastine fumarate, promethazine, loratidine, desloratidine, diphenhydramine and fexofenadine hydrochloride, activastine, astemizole, azelastine, ebastine, epinastine, mizolastine and tefenadine as well as those disclosed in WO 03/099807, WO 04/026841 and JP 2004107299.

Other useful combinations of compounds of the invention with anti-inflammatory drugs are those with antagonists of chemokine receptors, e.g., CCR-1, CCR-2, CCR-3, CCR-4, CCR-5, CCR-6, CCR-7, CCR-8, CCR-9 and CCR10, CXCR1, CXCR2, CXCR3, CXCR4, CXCR5, particularly CCR-5 antagonists such as Schering-Plough antagonists SC-351 125, SCH-55700 and SCH-D, Takeda antagonists such as TAK-770, and CCR-5 antagonists described in U.S. Pat. No. 6,166,037 (particularly claims 18 and 19), WO 00/66558 (particularly claim 8), WO 00/66559 (particularly claim 9), WO 04/018425 and WO 04/026873.

Anti-microtubule or anti-mitotic agents include phase specific agents active against the microtubules of tumor cells during M or the mitosis phase of the cell cycle. Examples of anti-microtubule agents include, but are not limited to, diterpenoids and vinca alkaloids. Diterpenoids, which are derived from natural sources, are phase specific anti-cancer agents that operate at the $G_2$/M phases of the cell cycle. It is believed that the diterpenoids stabilize the β-tubulin subunit of the microtubules, by binding with this protein. Disassembly of the protein appears then to be inhibited with mitosis being arrested and cell death following. Examples of diterpenoids include, but are not limited to, paclitaxel and its analog docetaxel. Paclitaxel, 5β,20-epoxy-1,2α,4,7β,10β,13α-hexa-hydroxytax-11-en-9-one 4,10-diacetate 2-benzoate 13-ester with (2R,3S)—N-benzoyl-3-phenylisoserine; is a natural diterpene product isolated from the Pacific yew tree *Taxus brevifolia* and is commercially available as an injectable solution TAXOL®. It is a member of the taxane family of terpenes. One mechanism for its activity relates to paclitaxel's capacity to bind tubulin, thereby inhibiting cancer cell growth. Paclitaxel has been approved for clinical use in the treatment of refractory ovarian cancer in the United States and for the treatment of breast cancer. It is a potential candidate for treatment of neoplasms in the skin and head and neck carcinomas. The compound also shows potential for the treatment of polycystic kidney disease, lung cancer and malaria. Treatment of subjects with paclitaxel results in bone marrow suppression (multiple cell lineages, Ignoff, R. J. et. al, Cancer Chemotherapy Pocket Guide, 1998) related to the duration of dosing above a threshold concentration (50 nM) (Kearns, C. M. et. al., Seminars in Oncology, 3(6) p. 16-23, 1995). Docetaxel, (2R,3S)—N-carboxy-3-phenylisoserine, N-tert-butyl ester, 13-ester with 5β-20-epoxy-1,2α,4,7β,10β,13α-hexahydroxytax-1-1-en-9-one 4-acetate 2-benzoate, trihydrate; is commercially available as an injectable solution as TAXOTERE®. Docetaxel is indicated for the treatment of breast cancer. Docetaxel is a semisynthetic derivative of paclitaxel q.v., prepared using a natural precursor, 10-deacetyl-baccatin III, extracted from the needle of the European Yew tree. The dose limiting toxicity of docetaxel is neutropenia.

Other compounds that can regulate apoptosis (e.g., BCL-2 inhibitors) can be used in conjunction.

Vinca alkaloids include phase specific anti-neoplastic agents derived from the periwinkle plant. Vinca alkaloids act at the M phase (mitosis) of the cell cycle by binding specifically to tubulin. Consequently, the bound tubulin molecule is unable to polymerize into microtubules. Mitosis is believed to be arrested in metaphase with cell death following. Examples of vinca alkaloids include, but are not limited to, vinblastine, vincristine, and vinorelbine. Vinblastine, vincaleukoblastine sulfate, is commercially available as VELBAN® as an injectable solution. Although it has possible indication as a second line therapy of various solid tumors, it is primarily indicated in the treatment of testicular cancer and various lymphomas including Hodgkin's Disease, and lymphocytic and histiocytic lymphomas. Myelosuppression is the dose limiting side effect of vinblastine. Vincristine, vincaleukoblastine, 22-oxo-, sulfate, is commercially available as ONCOVINO as an injectable solution. Vincristine is indicated for the treatment of acute leukemias and has also found use in treatment regimens for Hodgkin's and non-Hodgkin's malignant lymphomas. Alopecia and neurologic effects are the most common side effect of vincristine and to a lesser extent myelosupression and gastrointestinal mucositis effects occur. Vinorelbine, 3',4'-didehydro-4'-deoxy-C'-norvincaleukoblastine [R—(R*,R*)-2,3-dihydroxybutanedioate (1:2) (salt)], commercially available as an injectable solution of vinorelbine tartrate (NAVELBINE®), is a semisynthetic vinca alkaloid. Vinorelbine is indicated as a single agent or in combination with other chemotherapeutic agents, such as cisplatin, in the treatment of various solid tumors, particularly non-small cell lung, advanced breast, and hormone refractory prostate cancers. Myelosuppression is the most common dose limiting side effect of vinorelbine.

Platinum coordination complexes include non-phase specific anti-cancer agents, which interact with DNA. The platinum complexes enter tumor cells, undergo, aquation and form intra- and interstrand crosslinks with DNA causing adverse biological effects to the tumor. Examples of platinum coordination complexes include, but are not limited to, cisplatin and carboplatin. Cisplatin, cis-diamminedichloroplatinum, is commercially available as PLATINOLO as an injectable solution. Cisplatin is primarily indicated in the treatment of metastatic testicular and ovarian cancer and advanced bladder cancer. The primary dose limiting side effects of cisplatin are nephrotoxicity, which may be controlled by hydration and diuresis, and ototoxicity. Carboplatin, platinum, diammine [1,1-cyclobutane-dicarboxylate(2-)-O,O'], is commercially available as PARAPLATIN® as an injectable solution. Carboplatin is primarily indicated in the first and second line treatment of advanced ovarian carcinoma. Bone marrow suppression is the dose limiting toxicity of carboplatin.

Alkylating agents include non-phase anti-cancer specific agents and strong electrophiles. Typically, alkylating agents form covalent linkages, by alkylation, to DNA through nucleophilic moieties of the DNA molecule such as phosphate, amino, sulfhydryl, hydroxyl, carboxyl, and imidazole groups. Such alkylation disrupts nucleic acid function leading to cell death. Examples of alkylating agents include, but are not limited to, nitrogen mustards such as cyclophosphamide, melphalan, and chlorambucil; alkyl sulfonates such as busulfan; nitrosoureas such as carmustine; and triazenes such as dacarbazine. Cyclophosphamide, 2-[bis(2-chloroethyl) amino]tetrahydro-2H-1,3,2-oxazaphosphorine 2-oxide monohydrate, is commercially available as an injectable solution or tablets as CYTOXAN®. Cyclophosphamide is indicated as a single agent or in combination with other chemotherapeutic agents, in the treatment of malignant lymphomas, multiple myeloma, and leukemias. Alopecia, nausea, vomiting and leukopenia are the most common dose limiting side effects of cyclophosphamide. Melphalan, 4-[bis(2-chloroethyl)amino]-L-phenylalanine, is commercially available as an injectable solution or tablets as ALKERAN®. Melphalan is indicated for the palliative treatment of multiple myeloma and non-resectable epithelial carcinoma of the ovary. Bone marrow suppression is the most common dose limiting side effect of melphalan. Chlorambucil, 4-[bis(2-chloroethyl) amino]benzenebutanoic acid, is commercially available as LEUKERAN® tablets. Chlorambucil is indicated for the palliative treatment of chronic lymphatic leukemia, and malignant lymphomas such as lymphosarcoma, giant follicular lymphoma, and Hodgkin's disease. Bone marrow suppression is the most common dose limiting side effect of chlorambucil. Busulfan, 1,4-butanediol dimethanesulfonate, is commercially available as MYLERAN® TABLETS. Busulfan is indicated for the palliative treatment of chronic myelogenous leukemia. Bone marrow suppression is the most common dose limiting side effects of busulfan. Carmustine, 1,3-[bis (2-chloroethyl)-1-nitrosourea, is commercially available as single vials of lyophilized material as BiCNUO. Carmustine is indicated for the palliative treatment as a single agent or in combination with other agents for brain tumors, multiple myeloma, Hodgkin's disease, and non-Hodgkin's lymphomas. Delayed myelosuppression is the most common dose limiting side effects of carmustine. Dacarbazine, 5-(3,3-dimethyl-1-triazeno)-imidazole-4-carboxamide, is commercially available as single vials of material as DTIC-Dome®. Dacarbazine is indicated for the treatment of metastatic malignant melanoma and in combination with other agents for the second line treatment of Hodgkin's Disease. Nausea, vomiting, and anorexia are the most common dose limiting side effects of dacarbazine.

Antibiotic anti-neoplastics include non-phase specific agents, which bind or intercalate with DNA. Typically, such action results in stable DNA complexes or strand breakage, which disrupts ordinary function of the nucleic acids leading to cell death. Examples of antibiotic anti-neoplastic agents include, but are not limited to, actinomycins such as dactinomycin, anthrocyclins such as daunorubicin and doxorubicin; and bleomycins. Dactinomycin, also know as Actinomycin D, is commercially available in injectable form as COSMEGEN®. Dactinomycin is indicated for the treatment of Wilm's tumor and rhabdomyosarcoma. Nausea, vomiting, and anorexia are the most common dose limiting side effects of dactinomycin. Daunorubicin, (8S-cis-)-8-acetyl-10-[(3-amino-2,3,6-trideoxy-α-L-lyxo-hexopyranosyl)oxy]-7,8,9, 10-tetrahydro-6,8,11-trihydroxy-1-methoxy-5,12 naphthacenedione hydrochloride, is commercially available as a liposomal injectable form as DAUNOXOME® or as an injectable as CERUBIDINE®. Daunorubicin is indicated for remission induction in the treatment of acute nonlymphocytic leukemia and advanced HIV associated Kaposi's sarcoma. Myelosuppression is the most common dose limiting side effect of daunorubicin. Doxorubicin, (8S,10S)-10-[(3-amino-2,3,6-trideoxy-α-L-lyxo-hexopyranosyl)oxy]-8-glycoloyl, 7,8,9,10-tetrahydro-6,8,11-trihydroxy-1-methoxy-5, 12 naphthacenedione hydrochloride, is commercially available as an injectable form as RUBEX® or ADRIAMYCIN RDF®. Doxorubicin is primarily indicated for the treatment of acute lymphoblastic leukemia and acute myeloblastic leukemia, but is also a useful component in the treatment of some solid tumors and lymphomas. Myelosuppression is the most common dose limiting side effect of doxorubicin. Bleomycin, a mixture of cytotoxic glycopeptide antibiotics isolated from a strain of *Streptomyces* verticillus, is commercially available as BLENOXANE®. Bleomycin is indicated as a palliative treatment, as a single agent or in combination with other agents, of squamous cell carcinoma, lymphomas, and testicular carcinomas Pulmonary and cutaneous toxicities are the most common dose limiting side effects of bleomycin.

Topoisomerase II inhibitors include, but are not limited to, epipodophyllotoxins. Epipodophyllotoxins are phase specific anti-neoplastic agents derived from the mandrake plant. Epipodophyllotoxins typically affect cells in the S and $G_2$ phases of the cell cycle by forming a ternary complex with topoisomerase II and DNA causing DNA strand breaks. The strand breaks accumulate and cell death follows. Examples of epipodophyllotoxins include, but are not limited to, etoposide and teniposide. Etoposide, 4'-demethyl-epipodophyllotoxin 9[4,6-0-(R)-ethylidene-β-D-glucopyranoside], is commercially available as an injectable solution or capsules as VePESID® and is commonly known as VP-16. Etoposide is indicated as a single agent or in combination with other chemotherapy agents in the treatment of testicular and non-small cell lung cancers. Myelosuppression is the most common side effect of etoposide. The incidence of leucopenia tends to be more severe than thrombocytopenia. Teniposide, 4'-demethyl-epipodophyllotoxin 9[4,6-0-(R)-thenylidene-β-D-glucopyranoside], is commercially available as an injectable solution as VUMON® and is commonly known as VM-26. Teniposide is indicated as a single agent or in combination with other chemotherapy agents in the treatment of acute leukemia in children. Myelosuppression is the most common dose limiting side effect of teniposide. Teniposide can induce both leucopenia and thrombocytopenia. Other topoisomerase II inhibitors include epirubicin, idarubicin, nemorubicin, mitoxantrone, and losoxantrone.

Antimetabolite neoplastic agents include phase specific anti-neoplastic agents that act at S phase (DNA synthesis) of the cell cycle by inhibiting DNA synthesis or by inhibiting purine or pyrimidine base synthesis and thereby limiting DNA synthesis. Consequently, S phase does not proceed and cell death follows. Examples of antimetabolite anti-neoplastic agents include, but are not limited to, fluorouracil, methotrexate, cytarabine, mercaptopurine, thioguanine, and gemcitabine. 5-fluorouracil, 5-fluoro-2,4-(1H,3H) pyrimidinedione, is commercially available as fluorouracil. Administration of 5-fluorouracil leads to inhibition of thymidylate synthesis and is also incorporated into both RNA and DNA. The result typically is cell death. 5-fluorouracil is indicated as a single agent or in combination with other chemotherapy agents in the treatment of carcinomas of the breast, colon, rectum, stomach and pancreas. Myelosuppression and mucositis are dose limiting side effects of 5-fluorouracil. Other fluoropyrimidine analogs include 5-fluoro deoxyuridine (floxuridine) and 5-fluorodeoxyuridine monophosphate. Cytarabine, 4-amino-1-β-D-arabinofuranosyl-2(1H)-pyrimidinone, is commercially available as CYTOSAR-U® and is commonly known as Ara-C. It is believed that cytarabine exhibits cell phase specificity at S-phase by inhibiting DNA chain elongation by terminal incorporation of cytarabine into the growing DNA chain. Cytarabine is indicated as a single agent or in combination with other chemotherapy agents in the treatment of acute leukemia. Other cytidine analogs include 5-azacytidine and 2',2'-difluorodeoxycytidine (gemcitabine). Cytarabine induces leucopenia, thrombocytopenia, and mucositis. Mercaptopurine, 1,7-dihydro-6H-purine-6-thione monohydrate, is commercially available as PURINETHOL®. Mercaptopurine exhibits cell phase specificity at S-phase by inhibiting DNA synthesis by an as of yet unspecified mechanism. Mercaptopurine is indicated as a single agent or in combination with other chemotherapy agents in the treatment of acute leukemia. Myelosuppression and gastrointestinal mucositis are expected side effects of mercaptopurine at high doses. A useful mercaptopurine analog is azathioprine. Thioguanine, 2-amino-1,7-dihydro-6H-purine-6-thione, is commercially available as TABLOID®. Thioguanine exhibits cell phase specificity at S-phase by inhibiting DNA synthesis by an as of yet unspecified mechanism. Thioguanine is indicated as a single agent or in combination with other chemotherapy agents in the treatment of acute leukemia. Myelosuppression, including leucopenia, thrombocytopenia, and anemia, is the most common dose limiting side effect of thioguanine administration. However, gastrointestinal side effects occur and can be dose limiting. Other purine analogs include pentostatin, erythrohydroxynonyladenine, fludarabine phosphate, and cladribine. Gemcitabine, 2'-deoxy-2',2'-difluorocytidine monohydrochloride (β-isomer), is commercially available as GEMZAR®. Gemcitabine exhibits cell phase specificity at S-phase and by blocking progression of cells through the G1/S boundary. Gemcitabine is indicated in combination with cisplatin in the treatment of locally advanced non-small cell lung cancer and alone in the treatment of locally advanced pancreatic cancer. Myelosuppression, including leucopenia, thrombocytopenia, and anemia, is the most common dose limiting side effect of gemcitabine administration. Methotrexate, N-[4-[[(2,4-diamino-6-pteridinyl)methyl]methylamino]benzoyl]-L-glutamic acid, is commercially available as methotrexate sodium. Methotrexate exhibits cell phase effects specifically at S-phase by inhibiting DNA synthesis, repair and/or replication through the inhibition of dyhydrofolic acid reductase which is required for synthesis of purine nucleotides and thymidylate. Methotrexate is indicated as a single agent or in combination with other chemotherapy agents in the treatment of choriocarcinoma, meningeal leukemia, non-Hodgkin's lymphoma, and carcinomas of the breast, head, neck, ovary and bladder. Myelosuppression (leucopenia, thrombocytopenia, and anemia) and mucositis are expected side effect of methotrexate administration.

Topoisomerase I inhibitors include camptothecins such as camptothecin and camptothecin derivatives. Camptothecin cytotoxic activity is believed to be related to its Topoisomerase I inhibitory activity. Examples of camptothecins include, but are not limited to irinotecan and topotecan. Irinotecan HCl, (4S)-4,11-diethyl-4-hydroxy-9-[(4-piperidinopiperidino) carbonyloxy]-1H-pyrano[3',4',6,7]indolizino[1,2-b]quinoline-3,14(4H,12H)-dione hydrochloride, is commercially available as the injectable solution CAMPTOSAR®. Irinotecan is a derivative of camptothecin which binds, along with its active metabolite SN-38, to the topoisomerase I-DNA complex. It is believed that cytotoxicity occurs as a result of irreparable double strand breaks caused by interaction of the topoisomerase I:DNA:irinotecan or SN-38 ternary complex with replication enzymes. Irinotecan is indicated for treatment of metastatic cancer of the colon or rectum. The dose limiting side effects of irinotecan HCl are myelosuppression, including neutropenia, and GI effects, including diarrhea. Topotecan HCl, (S)-10-[(dimethylamino) methyl]-4-ethyl-4,9-dihydroxy-1H-pyrano[3',4',6,7]-indolizino[1,2-b]quinoline-3,14-(4H,12H)-dione monohydrochloride, is commercially available as the injectable solution HYCAMTIN®. Topotecan is a derivative of camptothecin which binds to the topoisomerase I-DNA complex and prevents religation of singles strand breaks caused by Topoisomerase I in response to torsional strain of the DNA molecule. Topotecan is indicated for second line treatment of metastatic carcinoma of the ovary and small cell lung cancer. The dose limiting side effect of topotecan HCl is myelosuppression, primarily neutropenia.

Hormones and hormonal analogues are useful compounds for treating cancers in which there is a relationship between the hormone(s) and growth and/or lack of growth of the cancer. Examples of hormones and hormonal analogues useful in cancer treatment include, but are not limited to, adrenocorticosteroids such as prednisone and prednisolone which are useful in the treatment of malignant lymphoma and acute leukemia in children; aminoglutethimide and other aromatase inhibitors such as aminoglutethimide, roglethimide, pyridoglutethimide, trilostane, testolactone, ketokonazole, vorozole, fadrozole, anastrozole, letrazole, formestane, atamestane and exemestane useful in the treatment of adrenocortical carcinoma and hormone dependent breast carcinoma containing estrogen receptors; progestrins such as megestrol acetate useful in the treatment of hormone dependent breast cancer and endometrial carcinoma; estrogens, androgens, and antiandrogens such as flutamide, nilutamide, bicalutamide, cyproterone acetate and 5α-reductases such as finasteride and dutasteride, useful in the treatment of prostatic carcinoma and benign prostatic hypertrophy; anti-estrogens such as fulvestrant, tamoxifen, toremifene, raloxifene, droloxifene, iodoxyfene, as well as selective estrogen receptor modulators (SERMS) such those described in U.S. Pat. Nos. 5,681,835, 5,877,219, and 6,207,716, useful in the treatment of hormone dependent breast carcinoma and other susceptible cancers; and gonadotropin-releasing hormone (GnRH) and analogues thereof which stimulate the release of leutinizing hormone (LH) and/or follicle stimulating hormone (FSH) for the treatment prostatic carcinoma, for instance, LHRH agonists and antagonists such as abarelix, goserelin, goserelin acetate and luprolide. SH2/SH3 domain blockers are agents that disrupt SH2 or SH3 domain binding in a variety of enzymes or adaptor proteins including, PI3-K p85 subunit, Src family kinases, adaptor molecules (Shc, Crk, Nck, Grb2) and Ras-GAP. SH2/SH3 domains as targets for anti-cancer drugs are discussed in Smithgall, T. E. (1995), Journal of Pharmacological and Toxicological Methods. 34(3) 125-32 Inhibitors of Serine/Threonine Kinases including MAP kinase cascade blockers which include blockers of Raf kinases (rafk), Mitogen or Extracellular Regulated Kinase (MEKs), and Extracellular Regulated Kinases (ERKs); and Protein kinase C family member blockers including blockers of PKCs (alpha, beta, gamma, epsilon, mu, lambda, iota, zeta). IkB kinase family (IKKa, IKKb), PKB family kinases, akt kinase family members, and TGF beta receptor kinases. Such Serine/Threonine kinases and inhibitors thereof are described in Yamamoto, T., Taya, S., Kaibuchi, K., (1999), Journal of Biochemistry. 126 (5) 799-803; Brodt, P, Samani, A., and Navab, R. (2000), Biochemical Pharmacology, 60. 1101-1107; Massague, J., Weis-Garcia, F. (1996) Cancer Surveys. 27:41-64; Philip, P. A., and Harris, A. L. (1995), Cancer Treatment and Research. 78: 3-27, Lackey, K. et al Bioorganic and Medicinal Chemistry Letters, (10), 2000, 223-226; U.S. Pat. No. 6,268,391; and Martinez-Iacaci, L., et al, Int. J. Cancer (2000), 88(1), 44-52.

Also of interest for use with the compounds of the invention are Myo-inositol signaling inhibitors such as phospholipase C blockers and Myoinositol analogues. Such signal inhibitors are described in Powis, G., and Kozikowski A., (1994) New Molecular Targets for Cancer Chemotherapy ed., Paul Workman and David Kerr, CRC press 1994, London.

Another group of inhibitors are signal transduction pathway inhibitors such as inhibitors of Ras Oncogene. Such inhibitors include inhibitors of farnesyltransferase, geranyl-geranyl transferase, and CAAX proteases as well as antisense oligonucleotides, ribozymes and immunotherapy. Such inhibitors have been shown to block ras activation in cells containing wild type mutant ras, thereby acting as antiproliferation agents. Ras oncogene inhibition is discussed in Scharovsky, O. G., Rozados, V. R., Gervasoni, S. I. Matar, P. (2000), Journal of Biomedical Science. 7(4) 292-8; Ashby, M. N. (1998), Current Opinion in Lipidology. 9 (2) 99-102; and BioChim Biophys. Acta, (19899) 1423(3):19-30.

This invention further relates to a method for using the compounds or pharmaceutical composition in combination with other tumor treatment approaches, including surgery, ionizing radiation, photodynamic therapy, or implants, e.g., with corticosteroids, hormones, or used as radiosensitizers.

One such approach may be, for example, radiation therapy in inhibiting abnormal cell growth or treating the hyperproliferative disorder in the mammal. Techniques for administering radiation therapy are known in the art, and these techniques can be used in the combination therapy described herein. The administration of the compound of the invention in this combination therapy can be determined as described herein.

Radiation therapy can be administered through one of several methods, or a combination of methods, including without limitation external-beam therapy, internal radiation therapy, implant radiation, stereotactic radiosurgery, systemic radiation therapy, radiotherapy and permanent or temporary interstitial brachytherapy. The term "brachytherapy," as used herein, refers to radiation therapy delivered by a spatially confined radioactive material inserted into the body at or near a tumor or other proliferative tissue disease site. The term is intended without limitation to include exposure to radioactive isotopes (e.g., At-211, I-131, I-125, Y-90, Re-186, Re-188, Sm-153, Bi-212, P-32, and radioactive isotopes of Lu). Suitable radiation sources for use as a cell conditioner of the present invention include both solids and liquids. By way of non-limiting example, the radiation source can be a radionuclide, such as I-125, I-131, Yb-169, Ir-192 as a solid source, I-125 as a solid source, or other radionuclides that emit photons, beta particles, gamma radiation, or other therapeutic rays. The radioactive material can also be a fluid made from any solution of radionuclide(s), e.g., a solution of I-125 or I-131, or a radioactive fluid can be produced using a slurry of a suitable fluid containing small particles of solid radionuclides, such as Au-198, Y-90. Moreover, the radionuclide(s) can be embodied in a gel or radioactive micro spheres.

Without being limited by any theory, the compounds of the present invention can render abnormal cells more sensitive to treatment with radiation for purposes of killing and/or inhibiting the growth of such cells. Accordingly, this invention further relates to a method for sensitizing abnormal cells in a mammal to treatment with radiation which comprises administering to the mammal an amount of an inhibitor of the present invention or pharmaceutically acceptable salt, ester, prodrug, solvate, hydrate or derivative thereof, which amount is effective is sensitizing abnormal cells to treatment with radiation. The amount of the compound, salt, or solvate in this method can be determined according to the means for ascertaining effective amounts of such compounds described herein.

Photodynamic therapy includes therapy which uses certain chemicals known as photosensitizing compounds to treat or prevent cancers. Examples of photodynamic therapy include treatment with compounds, such as e.g., VISUDYNE and porfimer sodium. Angiostatic steroids include compounds which block or inhibit angiogenesis, such as, e.g., anecortave, triamcinolone, hydrocortisone, 11-α-epihydrocotisol, cortexolone, 17α-hydroxyprogesterone, corticosterone, desoxycorticosterone, testosterone, estrone and dexamethasone.

Implants containing corticosteroids include compounds, such as e.g., fluocinolone and dexamethasone. Other chemotherapeutic compounds include, but are not limited to, plant alkaloids, hormonal compounds and antagonists; biological response modifiers, preferably lymphokines or interferons; antisense oligonucleotides or oligonucleotide derivatives; shRNA or siRNA; or miscellaneous compounds or compounds with other or unknown mechanism of action.

The compounds or pharmaceutical compositions of the present invention can be used in combination with an amount of one or more substances selected from anti-angiogenesis agents, signal transduction inhibitors, and antiproliferative agents.

Anti-angiogenesis agents, such as MMP-2 (matrix-metalloproteinase 2) inhibitors, MMP-9 (matrix-metalloproteinase 9) inhibitors, and COX-11 (cyclooxygenase 11) inhibitors, can be used in conjunction with an inhibitor of the present invention and pharmaceutical compositions described herein. Examples of useful COX-II inhibitors include CELEBREX™ (alecoxib), valdecoxib, and rofecoxib. Examples of useful matrix metalloproteinase inhibitors are described in WO 96/33172 (published Oct. 24, 1996), WO 96/27583 (published Mar. 7, 1996), European Patent Application No. 97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published Jul. 13, 1994), European Patent Publication 931, 788 (published Jul. 28, 1999), WO 90/05719 (published May 31, 1990), WO 99/52910 (published Oct. 21, 1999), WO 99/52889 (published Oct. 21, 1999), WO 99/29667 (published Jun. 17, 1999), PCT International Application No. PCT/IB98/01113 (filed Jul. 21, 1998), European Patent Application No. 99302232.1 (filed Mar. 25, 1999), Great Britain Patent Application No. 9912961.1 (filed Jun. 3, 1999), U.S. Provisional Application No. 60/148,464 (filed Aug. 12, 1999), U.S. Pat. No. 5,863,949 (issued Jan. 26, 1999), U.S. Pat. No. 5,861,510 (issued Jan. 19, 1999), and European Patent Publication 780, 386 (published Jun. 25, 1997), all of which are incorporated herein in their entireties by reference. In some embodiments, MMP-2 and MMP-9 inhibitors have little or no activity inhibiting MMP-1, or selectively inhibit MMP-2 and/or AMP-9 relative to the other matrix-metalloproteinases (i.e., MAP-1, MMP-3, MMP-4, MMP-5, MMP-6, MMP-7, MMP-8, MMP-10, MMP-11, MMP-12, and MMP-13). Some specific examples of MMP inhibitors useful in the present invention are AG-3340, RO 32-3555, and RS13-0830.

The invention also relates to a method of and to a pharmaceutical composition of treating a cardiovascular disease in a mammal which comprises an amount of an inhibitor of the present invention, or a pharmaceutically acceptable salt, ester, prodrug, solvate, hydrate or derivative thereof, or an isotopically-labeled derivative thereof, and an amount of one or more therapeutic agents use for the treatment of cardiovascular diseases.

Exemplary agents for use in cardiovascular disease applications are anti-thrombotic agents, e.g., prostacyclin and salicylates, thrombolytic agents, e.g., streptokinase, urokinase, tissue plasminogen activator (TPA) and anisoylated plasminogen-streptokinase activator complex (APSAC), anti-platelets agents, e.g., acetyl-salicylic acid (ASA) and clopidrogel, vasodilating agents, e.g., nitrates, calcium channel blocking drugs, anti-proliferative agents, e.g., colchicine and alkylating agents, intercalating agents, growth modulating factors such as interleukins, transformation growth factor-beta and congeners of platelet derived growth factor, monoclonal antibodies directed against growth factors, anti-inflammatory agents, both steroidal and non-steroidal, and other agents that can modulate vessel tone, function, arteriosclerosis, and the healing response to vessel or organ injury post intervention. Antibiotics can also be included in combinations or coatings comprised by the invention. Moreover, a coating can be used to effect therapeutic delivery focally within the vessel wall. By incorporation of the active agent in a swellable polymer, the active agent will be released upon swelling of the polymer.

Medicaments which may be administered in conjunction with the compounds described herein include any suitable drugs usefully delivered by inhalation for example, analgesics, e.g., codeine, dihydromorphine, ergotamine, fentanyl or morphine; anginal preparations, e.g., diltiazem; antiallergics, e.g., cromoglycate, ketotifen or nedocromil; anti-infectives, e.g., cephalosporins, penicillins, streptomycin, sulphonamides, tetracyclines or pentamidine; antihistamines, e.g., methapyrilene; anti-inflammatories, e.g., beclomethasone, flunisolide, budesonide, tipredane, triamcinolone acetonide or fluticasone; antitussives, e.g., noscapine; bronchodilators, e.g., ephedrine, adrenaline, fenoterol, formoterol, isoprenaline, metaproterenol, phenylephrine, phenylpropanolamine, pirbuterol, reproterol, rimiterol, salbutamol, salmeterol, terbutalin, isoetharine, tulobuterol, orciprenaline or (−)-4-amino-3,5-dichloro-α-[[[6-[2-(2-pyridinyl)ethoxy]hexyl]-amino]methyl]benzenemethanol; diuretics, e.g., amiloride; anticholinergics e.g., ipratropium, atropine or oxitropium; hormones, e.g., cortisone, hydrocortisone or prednisolone; xanthines e.g., aminophylline, choline theophyllinate, lysine theophyllinate or theophylline; and therapeutic proteins and peptides, e.g., insulin or glucagon. It will be clear to a person skilled in the art that, where appropriate, the medicaments may be used in the form of salts (e.g., as alkali metal or amine salts or as acid addition salts) or as esters (e.g., lower alkyl esters) or as solvates (e.g., hydrates) to optimize the activity and/or stability of the medicament.

Other exemplary therapeutic agents useful for a combination therapy include but are not limited to agents as described above, radiation therapy, hormone antagonists, hormones and their releasing factors, thyroid and antithyroid drugs, estrogens and progestins, androgens, adrenocorticotropic hormone; adrenocortical steroids and their synthetic analogs; inhibitors of the synthesis and actions of adrenocortical hormones, insulin, oral hypoglycemic agents, and the pharmacology of the endocrine pancreas, agents affecting calcification and bone turnover: calcium, phosphate, parathyroid hormone, vitamin D, calcitonin, vitamins such as water-soluble vitamins, vitamin B complex, ascorbic acid, fat-soluble vitamins, vitamins A, K, and E, growth factors, cytokines, chemokines, muscarinic receptor agonists and antagonists; anticholinesterase agents; agents acting at the neuromuscular junction and/or autonomic ganglia; catecholamines, sympathomimetic drugs, and adrenergic receptor agonists or antagonists; and 5-hydroxytryptamine (5-HT, serotonin) receptor agonists and antagonists.

Therapeutic agents can also include agents for pain and inflammation such as histamine and histamine antagonists, bradykinin and bradykinin antagonists, 5-hydroxytryptamine (serotonin), lipid substances that are generated by biotransformation of the products of the selective hydrolysis of membrane phospholipids, eicosanoids, prostaglandins, thromboxanes, leukotrienes, aspirin, nonsteroidal anti-inflammatory agents, analgesic-antipyretic agents, agents that inhibit the synthesis of prostaglandins and thromboxanes, selective inhibitors of the inducible cyclooxygenase, selective inhibitors of the inducible cyclooxygenase-2, autacoids, paracrine hormones, somatostatin, gastrin, cytokines that mediate interactions involved in humoral and cellular immune responses, lipid-derived autacoids, eicosanoids, β-adrenergic agonists, ipratropium, glucocorticoids, methylxanthines, sodium channel blockers, opioid receptor agonists, calcium channel blockers, membrane stabilizers and leukotriene inhibitors.

Additional therapeutic agents contemplated herein include diuretics, vasopressin, agents affecting the renal conservation of water, rennin, angiotensin, agents useful in the treatment of myocardial ischemia, anti-hypertensive agents, angiotensin converting enzyme inhibitors, β-adrenergic receptor antagonists, agents for the treatment of hypercholesterolemia, and agents for the treatment of dyslipidemia.

Other therapeutic agents contemplated include drugs used for control of gastric acidity, agents for the treatment of peptic ulcers, agents for the treatment of gastroesophageal reflux disease, prokinetic agents, antiemetics, agents used in irritable bowel syndrome, agents used for diarrhea, agents used for constipation, agents used for inflammatory bowel disease, agents used for biliary disease, agents used for pancreatic disease. Therapeutic agents used to treat protozoan infections, drugs used to treat Malaria, Amebiasis, Giardiasis, Trichomoniasis, Trypanosomiasis, and/or Leishmaniasis, and/or drugs used in the chemotherapy of helminthiasis. Other therapeutic agents include antimicrobial agents, sulfonamides, trimethoprim-sulfamethoxazole quinolones, and agents for urinary tract infections, penicillins, cephalosporins, and other, β-Lactam antibiotics, an agent comprising an aminoglycoside, protein synthesis inhibitors, drugs used in the chemotherapy of tuberculosis, *mycobacterium avium* complex disease, and leprosy, antifungal agents, antiviral agents including nonretroviral agents and antiretroviral agents.

Examples of therapeutic antibodies that can be combined with a subject compound include but are not limited to anti-receptor tyrosine kinase antibodies (cetuximab, panitumumab, trastuzumab), anti CD20 antibodies (rituximab, tositumomab), and other antibodies such as alemtuzumab, bevacizumab, and gemtuzumab.

Moreover, therapeutic agents used for immunomodulation, such as immunomodulators, immunosuppressive agents, tolerogens, and immunostimulants are contemplated by the methods herein. In addition, therapeutic agents acting on the blood and the blood-forming organs, hematopoietic agents, growth factors, minerals, and vitamins, anticoagulant, thrombolytic, and antiplatelet drugs.

Further therapeutic agents that can be combined with a subject compound may be found in Goodman and Gilman's "The Pharmacological Basis of Therapeutics" Tenth Edition edited by Hardman, Limbird and Gilman or the Physician's Desk Reference, both of which are incorporated herein by reference in their entirety.

The examples and preparations provided below further illustrate and exemplify the compounds of the present invention and methods of preparing such compounds. It is to be understood that the scope of the present invention is not limited in any way by the scope of the following examples and preparations. In the following examples molecules with a single chiral center, unless otherwise noted, exist as a racemic mixture. Those molecules with two or more chiral centers, unless otherwise noted, exist as a racemic mixture of diastereomers. Single enantiomers/diastereomers may be obtained by methods known to those skilled in the art.

EXAMPLES

Example 1

Expression and Inhibition Assays of p110α/p85α, p110β/p85α, p110δ/p85α, and p110γ

Commercial kits or systems for assaying PI3-K activities are available. The commercially available kits or systems can be used to screen for inhibitors and/or agonists of PI3Ks including but not limited to PI3-Kinase α, β, δ, and γ. An exemplary system is PI 3-Kinase (human) HTRF™ Assay from Upstate. The assay can be carried out according to the procedures suggested by the manufacturer. Briefly, the assay is a time resolved FRET assay that indirectly measures PIP3 product formed by the activity of a PI3-K. The kinase reaction is performed in a microtitre plate (e.g., a 384 well microtitre plate). The total reaction volume is approximately 20 ul per well. In the first step, each well receives 2 ul of test compound in 20% dimethylsulphoxide resulting in a 2% DMSO final concentration. Next, approximately 14.5 ul of a kinase/PIP2 mixture (diluted in 1× reaction buffer) is added per well for a final concentration of 0.25-0.3 ug/ml kinase and 10 μM PIP2. The plate is sealed and incubated for 15 minutes at room temperature. To start the reaction, 3.5 ul of ATP (diluted in 1× reaction buffer) is added per well for a final concentration of 10 μM ATP. The plate is sealed and incubated for 1 hour at room temperature. The reaction is stopped by adding 5 ul of Stop Solution per well and then 5 ul of Detection Mix is added per well. The plate is sealed, incubated for 1 hour at room temperature, and then read on an appropriate plate reader. Data is analyzed and IC50s are generated using GraphPad Prism 5. For PI3K α, β, δ, and γ, the nM conentration of inhibitor to reach IC50 is provided. Inhibition of PI3K α at lower concentrations than those for β, δ, and γ provides evidence of specificity within this group of kinases. Similar assays, and others known in the art, can be used to measure the percent inhibition of other kinases, including but not limited to PI3K class II kinases, phosphoinositide 4 kinases (PI4K), and phosphoinositide 5 kinases (PI5K).

Example 2

Expression and Inhibition Assays of Abl

The cross-activity or lack thereof of one or more compounds of the present invention against Abl kinase can be measured according to any procedures known in the art or methods disclosed below. For example, the compounds described herein can be assayed in triplicate against recombinant full-length Abl or Abl (T315I) (Upstate) in an assay containing 25 mM HEPES, pH 7.4, 10 mM $MgCl_2$, 200 μM ATP (2.5 μCi of γ-32P-ATP), and 0.5 mg/mL BSA. The optimized Abl peptide substrate EAIYAAPFAKKK is used as phosphoacceptor (200 μM). Reactions are terminated by spotting onto phosphocellulose sheets, which are washed with 0.5% phosphoric acid (approximately 6 times, 5-10 minutes each). Sheets are dried and the transferred radioactivity quantitated by phosphorimaging.

Example 3

Expression and Inhibition Assays of Hck

The cross-activity or lack thereof of one or more compounds of the present invention against Hck kinase can be measured according to any procedures known in the art or methods disclosed below. The compounds described herein can be assayed in triplicate against recombinant full-length Hck in an assay containing 25 mM HEPES, pH 7.4, 10 mM $MgCl_2$, 200 μM ATP (2.5 μCi of γ-32P-ATP), and 0.5 mg/mL BSA. The optimized Src family kinase peptide substrate EIYGEFKKK is used as phosphoacceptor (200 μM). Reactions are terminated by spotting onto phosphocellulose sheets, which are washed with 0.5% phosphoric acid (approximately 6 times, 5-10 minutes each). Sheets are dried and the transferred radioactivity quantitated by phosphorimaging.

Example 4

Expression and Inhibition Assays of Insulin Receptor (IR)

The cross-activity or lack thereof of one or more compounds of the present invention against IR receptor kinase can be measured according to any procedures known in the art or methods disclosed below. The compounds described herein can be assayed in triplicate against recombinant insulin receptor kinase domain (Upstate) in an assay containing 25 mM HEPES, pH 7.4, 10 mM $MgCl_2$, 10 mM $MnCl_2$, 200 μM ATP (2.5 μCi of γ-32P-ATP), and 0.5 mg/mL BSA. Poly E-Y (Sigma; 2 mg/mL) is used as a substrate. Reactions are terminated by spotting onto nitrocellulose, which is washed with 1M NaCl/1% phosphoric acid (approximately 6 times, 5-10 minutes each). Sheets are dried and the transferred radioactivity quantitated by phosphorimaging.

Example 5

Expression and Inhibition Assays of Src

The cross-activity or lack thereof of one or more compounds of the present invention against Src kinase can be measured according to any procedures known in the art or methods disclosed below. The compounds described herein can be assayed in triplicate against recombinant full-length Src or Src (T338I) in an assay containing 25 mM HEPES, pH 7.4, 10 mM $MgCl_2$, 200 μM ATP (2.5 μCi of γ-32P-ATP), and 0.5 mg/mL BSA. The optimized Src family kinase peptide substrate EIYGEFKKK is used as phosphoacceptor (200 μM). Reactions are terminated by spotting onto phosphocellulose sheets, which are washed with 0.5% phosphoric acid (approximately 6 times, 5-10 minutes each). Sheets are dried and the transferred radioactivity quantitated by phosphorimaging.

Example 6

Expression and Inhibition Assays of DNA-PK (DNAK)

The cross-activity or lack thereof of one or more compounds of the present invention against DNAK kinase can be measured according to any procedures known in the art. DNA-PK can be purchased from Promega and assayed using the DNA-PK Assay System (Promega) according to the manufacturer's instructions.

Example 7

Expression and Inhibition Assays of mTOR

The cross-activity or lack thereof of one or more compounds of the present invention against mTor can be measured according to any procedures known in the art or methods disclosed below. The compounds described herein can be tested against recombinant mTOR (Invitrogen) in an assay containing 50 mM HEPES, pH 7.5, 1 mM EGTA, 10 mM MgCl$_2$, 2.5 mM, 0.01% Tween, 10 µM ATP (2.5 µCi of µ-32P-ATP), and 3 mg/mL BSA. Rat recombinant PHAS-1/4EBP1 (Calbiochem; 2 mg/mL) is used as a substrate. Reactions are terminated by spotting onto nitrocellulose, which is washed with 1M NaCl/1% phosphoric acid (approximately 6 times, 5-10 minutes each). Sheets are dried and the transferred radioactivity quantitated by phosphorimaging.

Other kits or systems for assaying mTOR activity are commercially avaiable. For instance, one can use Invitrogen's LanthaScreen™ Kinase assay to test the inhibitors of mTOR disclosed herein. This assay is a time resolved FRET platform that measures the phosphorylation of GFP labeled 4EBP1 by mTOR kinase. The kinase reaction is performed in a white 384 well microtitre plate. The total reaction volume is 20 ul per well and the reaction buffer composition is 50 mM HEPES pH7.5, 0.01% Polysorbate 20, 1 mM EGTA, 10 mM MnCl$_2$, and 2 mM DTT. In the first step, each well receives 2 ul of test compound in 20% dimethylsulphoxide resulting in a 2% DMSO final concentration. Next, 8 ul of mTOR diluted in reaction buffer is added per well for a 60 ng/ml final concentration. To start the reaction, 10 ul of an ATP/GFP-4EBP1 mixture (diluted in reaction buffer) is added per well for a final concentration of 10 µM ATP and 0.5 µM GFP-4EBP1. The plate is sealed and incubated for 1 hour at room temperature. The reaction is stopped by adding 10 ul per well of a Tb-anti-pT46 4EBP1 antibody/EDTA mixture (diluted in TR-FRET buffer) for a final concentration of 1.3 nM antibody and 6.7 mM EDTA. The plate is sealed, incubated for 1 hour at room temperature, and then read on a plate reader set up for LanthaScreen™ TR-FRET. Data is analyzed and IC50s are generated using GraphPad Prism 5.

Example 8

Expression and Inhibition Assays of Vascular Endothelial Growth Receptor

The cross-activity or lack thereof of one or more compounds of the present invention against VEGF receptor can be measured according to any procedures known in the art or methods disclosed below. The compounds described herein can be tested against recombinant KDR receptor kinase domain (Invitrogen) in an assay containing 25 mM HEPES, pH 7.4, 10 mM MgCl$_2$, 0.1% BME, 10 µM ATP (2.5 µCi of µ-32P-ATP), and 3 µg/mL BSA. Poly E-Y (Sigma; 2 mg/mL) is used as a substrate. Reactions are terminated by spotting onto nitrocellulose, which is washed with 1M NaCl/1% phosphoric acid (approximately 6 times, 5-10 minutes each). Sheets are dried and the transferred radioactivity quantitated by phosphorimaging.

Example 9

Expression and Inhibition Assays of Ephrin Receptor B4 (EphB4)

The cross-activity or lack thereof of one or more compounds of the present invention against EphB4 can be measured according to any procedures known in the art or methods disclosed below. The compounds described herein can be tested against recombinant Ephrin receptor B4 kinase domain (Invitrogen) in an assay containing 25 mM HEPES, pH 7.4, 10 mM MgCl$_2$, 0.1% BME, 10 µM ATP (2.5 µCi of µ-32P-ATP), and 3 µg/mL BSA. Poly E-Y (Sigma; 2 mg/mL) is used as a substrate. Reactions are terminated by spotting onto nitrocellulose, which is washed with 1M NaCl/1% phosphoric acid (approximately 6 times, 5-10 minutes each). Sheets are dried and the transferred radioactivity quantitated by phosphorimaging.

Example 10

Expression and Inhibition Assays of Epidermal Growth Factor Receptor (EGFR)

The cross-activity or lack thereof of one or more compounds of the present invention against EGFR kinase can be measured according to any procedures known in the art or methods disclosed below. The compounds described herein can be tested against recombinant EGF receptor kinase domain (Invitrogen) in an assay containing 25 mM HEPES, pH 7.4, 10 mM MgCl$_2$, 0.1% BME, 10 µM ATP (2.5 µCi of µ-32P-ATP), and 3 µg/mL BSA. Poly E-Y (Sigma; 2 mg/mL) is used as a substrate. Reactions are terminated by spotting onto nitrocellulose, which is washed with 1M NaCl/1% phosphoric acid (approximately 6 times, 5-10 minutes each). Sheets are dried and the transferred radioactivity quantitated by phosphorimaging.

Example 11

Expression and Inhibition Assays of KIT Assay

The cross-activity or lack thereof of one or more compounds of the present invention against KIT kinase can be measured according to any procedures known in the art or methods disclosed below. The compounds described herein can be tested against recombinant KIT kinase domain (Invitrogen) in an assay containing 25 mM HEPES, pH 7.4, 10 mM MgCl$_2$, 1 mM DTT, 10 mM MnCl$_2$, 10 ATP (2.5 µCi of µ-32P-ATP), and 3 mg/mL BSA. Poly E-Y (Sigma; 2 mg/mL) is used as a substrate. Reactions are terminated by spotting onto nitrocellulose, which is washed with 1M NaCl/1% phosphoric acid (approximately 6 times, 5-10 minutes each). Sheets are dried and the transferred radioactivity quantitated by phosphorimaging.

Example 12

Expression and Inhibition Assays of RET

The cross-activity or lack thereof of one or more compounds of the present invention against RET kinase can be measured according to any procedures known in the art or methods disclosed below. The compounds described herein can be tested against recombinant RET kinase domain (Invitrogen) in an assay containing 25 mM HEPES, pH 7.4, 10 mM MgCl$_2$, 2.5 mM DTT, 10 µM ATP (2.5 µCi of µ-32P-ATP), and 3 mg/mL BSA. The optimized Abl peptide substrate EAIYAAPFAKKK is used as phosphoacceptor (200 µM). Reactions are terminated by spotting onto phosphocellulose sheets, which are washed with 0.5% phosphoric acid (approximately 6 times, 5-10 minutes each). Sheets are dried and the transferred radioactivity quantitated by phosphorimaging.

Example 13

Expression and Inhibition Assays of Platelet Derived Growth Factor Receptor (PDGFR)

The cross-activity or lack thereof of one or more compounds of the present invention against PDGFR kinase can be measured according to any procedures known in the art or methods disclosed below. The compounds described herein can be tested against recombinant PDG receptor kinase domain (Invitrogen) in an assay containing 25 mM HEPES, pH 7.4, 10 mM $MgCl_2$, 2.5 mM DTT, 10 μM ATP (2.5 μCi of μ-32P-ATP), and 3 mg/mL BSA. The optimized Abl peptide substrate EAIYAAPFAKKK is used as phosphoacceptor (200 μM). Reactions are terminated by spotting onto phosphocellulose sheets, which are washed with 0.5% phosphoric acid (approximately 6 times, 5-10 minutes each). Sheets are dried and the transferred radioactivity quantitated by phosphorimaging.

Example 14

Expression and Inhibition Assays of FMS-Related Tyrosine Kinase 3 (FLT-3)

The cross-activity or lack thereof of one or more compounds of the present invention against FLT-3 kinase can be measured according to any procedures known in the art or methods disclosed below. The compounds described herein can be tested against recombinant FLT-3 kinase domain (Invitrogen) in an assay containing 25 mM HEPES, pH 7.4, 10 mM $MgCl_2$, 2.5 mM DTT, 10 μM ATP (2.5 μCi of μ-32P-ATP), and 3 mg/mL BSA. The optimized Abl peptide substrate EAIYAAPFAKKK is used as phosphoacceptor (200 μM). Reactions are terminated by spotting onto phosphocellulose sheets, which are washed with 0.5% phosphoric acid (approximately 6 times, 5-10 minutes each). Sheets are dried and the transferred radioactivity quantitated by phosphorimaging.

Example 15

Expression and Inhibition Assays of TEK Receptor Tyrosine Kinase (TIE2)

The cross-activity or lack thereof of one or more compounds of the present invention against TIE2 kinase can be measured according to any procedures known in the art or methods disclosed below. The compounds described herein can be tested against recombinant TIE2 kinase domain (Invitrogen) in an assay containing 25 mM HEPES, pH 7.4, 10 mM $MgCl_2$, 2 mM DTT, 10 mM $MnCl_2$, 10 ATP (2.5 μCi of μ-32P-ATP), and 3 μg/mL BSA. Poly E-Y (Sigma; 2 mg/mL) is used as a substrate. Reactions are terminated by spotting onto nitrocellulose, which is washed with 1M NaCl/1% phosphoric acid (approximately 6 times, 5-10 minutes each). Sheets are dried and the transferred radioactivity quantitated by phosphorimaging.

Example 16

B Cell Activation and Proliferation Assay

The ability of one or more subject compounds to inhibit B cell activitation and proliferation is determined according to standard procedures known in the art. For example, an in vitro cellular proliferation assay is established that measures the metabolic activity of live cells. The assay is performed in a 96 well microtiter plate using Alamar Blue reduction. Balb/c splenic B cells are purified over a Ficoll-Paque™ PLUS gradient followed by magnetic cell separation using a MACS B cell Isolation Kit (Miletenyi). Cells are plated in 90 ul at 50,000 cells/well in B Cell Media (RPMI+10% FBS+Penn/Strep+50 μM bME+5 mM HEPES). A compound disclosed herein is diluted in B Cell Media and added in a 10 ul volume. Plates are incubated for 30 min at 37 C and 5% $CO_2$ (0.2% DMSO final concentration). A 50 ul B cell stimulation cocktail is then added containing either 10 ug/ml LPS or 5 ug/ml F(ab')2 Donkey anti-mouse IgM plus 2 ng/ml recombinant mouse IL4 in B Cell Media. Plates are incubated for 72 hours at 37° C. and 5% $CO_2$. A volume of 15 mL of Alamar Blue reagent is added to each well and plates are incubated for 5 hours at 37 C and 5% $CO_2$. Alamar Blue fluoresce is read at 560Ex/590Em, and IC50 or EC50 values are calculated using GraphPad Prism 5.

Example 17

Tumor Cell Line Proliferation Assay

The ability of one or more subject compounds to inhibit tumor cell line proliferation is determined according to standard procedures known in the art. For instance, an in vitro cellular proliferation assay can be performed to measure the metabolic activity of live cells. The assay is performed in a 96 well microtiter plate using Alamar Blue reduction. Human tumor cell lines are obtained from ATCC (e.g., MCF7, U-87 MG, MDA-MB-468, PC-3), grown to confluency in T75 flasks, trypsinized with 0.25% trypsin, washed one time with Tumor Cell Media (DMEM+10% FBS), and plated in 90 ul at 5,000 cells/well in Tumor Cell Media. A compound disclosed herein is diluted in Tumor Cell Media and added in a 10 ul volume. Plates are incubated for 72 hours at 37 C and 5% $CO_2$. A volume of 10 uL of Alamar Blue reagent is added to each well and plates are incubated for 3 hours at 37 C and 5% $CO_2$. Alamar Blue fluoresce is read at 560Ex/590Em, and IC50 values are calculated using GraphPad Prism 5. The results are expected to show that some of the compounds of the present invention are potent inhibitors of tumor cell line proliferation under the conditions tested.

Example 18

Antitumor Activity In Vivo

The compounds described herein can be evaluated in a panel of human and murine tumor models.
Paclitaxel-refractory Tumor Models
1. Clinically-Derived Ovarian Carcinoma Model.
This tumor model is established from a tumor biopsy of an ovarian cancer patient. Tumor biopsy is taken from the patient.
The compounds described herein are administered to nude mice bearing staged tumors using an every 2 days×5 schedule.
2. A2780Tax Human Ovarian Carcinoma Xenograft (Mutated Tubulin).
A2780Tax is a paclitaxel-resistant human ovarian carcinoma model. It is derived from the sensitive parent A2780 line by co-incubation of cells with paclitaxel and verapamil, an MDR-reversal agent. Its resistance mechanism has been shown to be non-MDR related and is attributed to a mutation in the gene encoding the beta-tubulin protein.
The compounds described herein can be administered to mice bearing staged tumors on an every 2 days×5 schedule.
3. HCT116/VM46 Human Colon Carcinoma Xenograft (Multi-Drug Resistant).
HCT116/VM46 is an MDR-resistant colon carcinoma developed from the sensitive HCT116 parent line. In vivo, grown in nude mice, HCT116NM46 has consistently demonstrated high resistance to paclitaxel.

The compounds described herein can be administered to mice bearing staged tumors on an every 2 days×5 schedule.

5. M5076 Murine Sarcoma Model

M5076 is a mouse fibrosarcoma that is inherently refractory to paclitaxel in vivo.

The compounds described herein can be administered to mice bearing staged tumors on an every 2 days×5 schedule.

One or more compounds of the invention can be used in combination other therapeutic agents in vivo in the multidrug resistant human colon carcinoma xenografts HCT/VM46 or any other model known in the art including those described herein.

The results are expected to show that one or more compounds of the present invention are potent inhibitors of tumor growth in vivo under the conditions tested.

Example 19

Microsome Stability Assay

The stability of one or more subject compounds is determined according to standard procedures known in the art. For example, stability of one or more subject compounds is established by an in vitro assay. In particular, an in vitro microsome stability assay is established that measures stability of one or more subject compounds when reacting with mouse, rat or human microsomes from liver. The microsome reaction with compounds is performed in 1.5 mL Eppendorf tube. Each tube contains 0.1 μL, of 10.0 mg/ml NADPH; 75 μL of 20.0 mg/ml mouse, rat or human liver microsome; 0.4 μL, of 0.2 M phosphate buffer, and 425 μL, of ddH$_2$O, Negative control (without NADPH) tube contains 75 μL, of 20.0 mg/ml mouse, rat or human liver microsome; 0.4 μL, of 0.2 M phosphate buffer, and 525 μL, of ddH$_2$O. The reaction is started by adding 1.0 μL, of 10.0 mM tested compound. The reaction tubes are incubated at 37° C. 100 μL, sample is collected into new Eppendorf tube containing 300 μL cold Methanol at 0, 5, 10, 15, 30 and 60 minutes of reaction. Samples are centrifuged at 15,000 rpm to remove protein. Supernatant of centrifuged sample is transferred to new tube. Concentration of stable compound after reaction with microsome in the supernatant is measured by Liquid Chromatography/Mass Spectrometry (LC-MS).

Example 20

Plasma Stability Assay

The stability of one or more subject compounds in plasma is determined according to standard procedures known in the art. See, e.g., *Rapid Commun. Mass Spectrom.,* 10: 1019-1026. The following procedure is an HPLC-MS/MS assay using human plasma; other species including monkey, dog, rat, and mouse are also available. Frozen, heparinized human plasma is thawed in a cold water bath and spun for 10 minutes at 2000 rpm at 4° C. prior to use. A subject compound is added from a 400 μM stock solution to an aliquot of pre-warmed plasma to give a final assay volume of 400 μL (or 800 μL for half-life determination), containing 5 μM test compound and 0.5% DMSO. Reactions are incubated, with shaking, for 0 minutes and 60 minutes at 37° C., or for 0, 15, 30, 45 and 60 minutes at 37 C for half life determination. Reactions are stopped by transferring 50 μL of the incubation mixture to 200 μL, of ice-cold acetonitrile and mixed by shaking for 5 minutes. The samples are centrifuged at 6000×g for 15 minutes at 4° C. and 120 μL of supernatant removed into clean tubes. The samples are then evaporated to dryness and submitted for analysis by HPLC-MS/MS.

Where desired, one or more control or reference compounds (5 μM) are tested simultaneously with the test compounds: one compound, propoxycaine, with low plasma stability and another compound, propantheline, with intermediate plasma stability.

Samples are reconstituted in acetonitrile/methanol/water (1/1/2, v/v/v) and analyzed via (RP)HPLC-MS/MS using selected reaction monitoring (SRM). The HPLC conditions consist of a binary LC pump with autosampler, a mixed-mode, C12, 2×20 mm column, and a gradient program. Peak areas corresponding to the analytes are recorded by HPLC-MS/MS. The ratio of the parent compound remaining after 60 minutes relative to the amount remaining at time zero, expressed as percent, is reported as plasma stability. In case of half-life determination, the half-life is estimated from the slope of the initial linear range of the logarithmic curve of compound remaining (%) vs. time, assuming first order kinetics.

Example 21

Chemical Stability

The chemical stability of one or more subject compounds is determined according to standard procedures known in the art. The following details an exemplary procedure for ascertaining chemical stability of a subject compound. The default buffer used for the chemical stability assay is phosphate-buffered saline (PBS) at pH 7.4; other suitable buffers can be used. A subject compound is added from a 100 μM stock solution to an aliquot of PBS (in duplicate) to give a final assay volume of 400 μL, containing 5 μM test compound and 1% DMSO (for half-life determination a total sample volume of 700 μL, is prepared). Reactions are incubated, with shaking, for 0 minutes and 24 hours at 37° C.; for half-life determination samples are incubated for 0, 2, 4, 6, and 24 hours. Reactions are stopped by adding immediately 100 μL of the incubation mixture to 100 μL, of acetonitrile and vortexing for 5 minutes. The samples are then stored at −20° C. until analysis by HPLC-MS/MS. Where desired, a control compound or a reference compound such as chlorambucil (5 μM) is tested simultaneously with a subject compound of interest, as this compound is largely hydrolyzed over the course of 24 hours. Samples are analyzed via (RP)HPLC-MS/MS using selected reaction monitoring (SRM). The HPLC conditions consist of a binary LC pump with autosampler, a mixed-mode, C12, 2×20 mm column, and a gradient program. Peak areas corresponding to the analytes are recorded by HPLC-MS/MS. The ratio of the parent compound remaining after 24 hours relative to the amount remaining at time zero, expressed as percent, is reported as chemical stability. In case of half-life determination, the half-life is estimated from the slope of the initial linear range of the logarithmic curve of compound remaining (%) vs. time, assuming first order kinetics.

Example 22

Akt Kinase Assay

Cells comprising components of the Akt/mTOR pathway, including but not limited to L6 myoblasts, B-ALL cells, B-cells, T-cells, leukemia cells, bone marrow cells, p190 transduced cells, philladelphia chromosome positive cells (Ph+), and mouse embryonic fibroblasts, are typically grown in cell growth media such as DMEM supplemented with fetal bovine serum and/or antibiotics, and grown to confluency.

In order to compare the effect of one or more compounds disclosed herein on Akt activation, said cells are serum starved overnight and incubated with one or more compounds disclosed herein or about 0.1% DMSO for approximately 1 minute to about 1 hour prior to stimulation with insulin (e.g., 100 nM) for about 1 minutes to about 1 hour. Cells are lysed by scraping into ice cold lysis buffer containing detergents such as sodium dodecyl sulfate and protease inhibitors (e.g., PMSF). After contacting cells with lysis buffer, the solution is briefly sonicated, cleared by centrifugation, resolved by SDS-PAGE, transferred to nitrocellulose or PVDF and immunoblotted using antibodies to phospho-Akt S473, phospho-Akt T308, Akt, and β-actin (Cell Signaling Technologies).

Example 23

Kinase Signaling in Blood

PI3K/Akt/mTor signaling is measured in blood cells using the phosflow method (Methods Enzymol. 2007; 434:131-54). The advantage of this method is that it is by nature a single cell assay so that cellular heterogeneity can be detected rather than population averages. This allows concurrent dinstinction of signaling states in different populations defined by other markers. Phosflow is also highly quantitative. To test the effects of one or more compounds disclosed herein, unfractionated splenocytes, or peripheral blood mononuclear cells are stimulated with anti-CD3 to initiate T-cell receptor signaling. The cells are then fixed and stained for surface markers and intracellular phosphoproteins. It is expected that inhibitors disclosed herein inhibit anti-CD3 mediated phosphorylation of Akt-S473 and S6, whereas rapamycin inhibits S6 phosphorylation and enhances Akt phosphorylation under the conditions tested.

Similarly, aliquots of whole blood are incubated for 15 minutes with vehicle (e.g., 0.1% DMSO) or kinase inhibitors at various concentrations, before addition of stimuli to crosslink the T cell receptor (TCR) (anti-CD3 with secondary antibody) or the B cell receptor (BCR) using anti-kappa light chain antibody (Fab'2 fragments). After approximately 5 and 15 minutes, samples are fixed (e.g., with cold 4% paraformaldehyde) and used for phosflow. Surface staining is used to distinguish T and B cells using antibodies directed to cell surface markers that are known to the art. The level of phosphrylation of kinase substrates such as Akt and S6 are then measured by incubating the fixed cells with labeled antibodies specific to the phosphorylated isoforms of these proteins. The population of cells is then analyzed by flow cytometry.

The results are expected to show that one or more of the compounds of the present invention are potent and selective inhibitors of one or more members of one or more of PI3K, mTOR, and Akt signaling in blood cells under the conditions tested.

Example 24

Colony Formation Assay

Murine bone marrow cells freshly transformed with a p190 BCR-Abl retrovirus (herein referred to as p190 transduced cells) are plated in the presence of various drug combinations in M3630 methylcellulose media for about 7 days with recombinant human IL-7 in about 30% serum, and the number of colonies formed is counted by visual examination under a microscope.

Alternatively, human peripheral blood mononuclear cells are obtained from Philadelphia chromosome positive (Ph+) and negative (Ph−) patients upon initial diagnosis or relapse. Live cells are isolated and enriched for CD19+ CD34+ B cell progenitors. After overnight liquid culture, cells are plated in methocult GF+ H4435, Stem Cell Tehcnologies) suplemented with cytokines (IL-3, IL-6, IL-7, G-CSF, GM-CSF, CF, Flt3 ligand, and erythropoietin) and various concentrations of known chemotherapeutic agents in combination with either compounds of the present disclosure. Colonies are counted by microscopy 12-14 days later. This method can be used to test for evidence of additive or synergistic activity.

The results are expected to show that one or more the compounds of the present invention are potent and selective inhibitors of p190 transduced cell colony formation under the conditions tested.

Example 25

In Vivo Effect of Kinase Inhibitors on Leukemic Cells

Female recipient mice are lethally irradiated from a γ source in two doses about 4 hr apart, with approximately 5Gy each. About 1 hr after the second radiation dose, mice are injected i.v. with about $1 \times 10^6$ leukemic cells (e.g., Ph+ human or murine cells, or p190 transduced bone marrow cells). These cells are administered together with a radioprotective dose of about $5 \times 10^6$ normal bone marrow cells from 3-5 week old donor mice. Recipients are given antibiotics in the water and monitored daily. Mice who become sick after about 14 days are euthanized and lymphoid organs are harvested for analysis. Kinase inhibitor treatment begins about ten days after leukemic cell injection and continues daily until the mice become sick or a maximum of approximately 35 days post-transplant Inhibitors are given by oral lavage.

Peripheral blood cells are collected approximately on day 10 (pre-treatment) and upon euthanization (post treatment), contacted with labled anti-hCD4 antibodies and counted by flow cytometry. This method can be used to demonstrate that the synergistic effect of one or more compounds disclosed herein in combination with known chemotherapeutic agents significantly reduce leukemic blood cell counts as compared to treatment with known chemotherapeutic agents (e.g., Gleevec) alone under the conditions tested.

Example 26

Treatment of Lupus Disease Model Mice

Mice lacking the inhibitory receptor FcγRIIb that opposes PI3K signaling in B cells develop lupus with high penetrance. FcγRIIb knockout mice (R2KO, Jackson Labs) are considered a valid model of the human disease as some lupus patients show decreased expression or function of FcγRIIb (S. Bolland and J. V. Ravtech 2000. *Immunity* 12:277-285).

The R2KO mice develop lupus-like disease with antinuclear antibodies, glomerulonephritis and proteinurea within about 4-6 months of age. For these experiments, the rapamycin analogue RAD001 (available from LC Laboratories) is used as a benchmark compound, and administered orally. This compound has been shown to ameliorate lupus symptoms in the B6.Sle1z.Sle3z model (T. Wu et al. *J. Clin Invest.* 117:2186-2196).

Lupus disease model mice such as R2KO, BXSB or MLR/lpr are treated at about 2 months old, approximately for about two months. Mice are given doses of: vehicle, RAD001 at about 10 mg/kg, or compounds disclosed herein at approximately 1 mg/kg to about 500 mg/kg. Blood and urine samples are obtained at approximately throughout the testing period, and tested for antinuclear antibodies (in dilutions of serum) or protein concentration (in urine). Serum is also tested for anti-ssDNA and anti-dsDNA antibodies by ELISA. Animals are euthanized at day 60 and tissues harvested for measuring spleen weight and kidney disease. Glomerulonephritis is assessed in kidney sections stained with H&E. Other animals are studied for about two months after cessation of treatment, using the same endpoints.

This model established in the art can be employed to test that the kinase inhibitors disclosed herein can suppress or delay the onset of lupus symptoms in lupus disease model mice.

Example 27

Murine Bone Marrow Transplant Assay

Female recipient mice are lethally irradiated from a γ ray source. About 1 hr after the radiation dose, mice are injected with about $1 \times 10^6$ leukemic cells from early passage p190 transduced cultures (e.g., as described in *Cancer Genet Cytogenet*. 2005 August; 161(1):51-6). These cells are administered together with a radioprotective dose of approximately $5 \times 10^6$ normal bone marrow cells from 3-5 wk old donor mice. Recipients are given antibiotics in the water and monitored daily. Mice who become sick after about 14 days are euthanized and lymphoid organs harvested for flow cytometry and/or magnetic enrichment. Treatment begins on approximately day 10 and continues daily until mice become sick, or after a maximum of about 35 days post-transplant. Drugs are given by oral gavage (p.o.). In a pilot experiment a dose of chemotherapeutic that is not curative but delays leukemia onset by about one week or less is identified; controls are vehicle-treated or treated with chemotherapeutic agent, previously shown to delay but not cure leukemogenesis in this model (e.g., imatinib at about 70 mg/kg twice daily). For the first phase p190 cells that express eGFP are used, and post-mortem analysis is limited to enumeration of the percentage of leukemic cells in bone marrow, spleen and lymph node (LN) by flow cytometry. In the second phase, p190 cells that express a tailless form of human CD4 are used and the post-mortem analysis includes magnetic sorting of hCD4+ cells from spleen followed by immunoblot analysis of key signaling endpoints: p Akt-T308 and S473; pS6 and p4EBP-1. As controls for immunoblot detection, sorted cells are incubated in the presence or absence of kinase inhibitors of the present disclosure inhibitors before lysis. Optionally, "phosflow" is used to detect p Akt-S473 and pS6-S235/236 in hCD4-gated cells without prior sorting. These signaling studies are particularly useful if, for example, drug-treated mice have not developed clinical leukemia at the 35 day time point. Kaplan-Meier plots of survival are generated and statistical analysis done according to methods known in the art. Results from p190 cells are analyzed separated as well as cumulatively.

Samples of peripheral blood (100-200 µl) are obtained weekly from all mice, starting on day 10 immediately prior to commencing treatment. Plasma is used for measuring drug concentrations, and cells are analyzed for leukemia markers (eGFP or hCD4) and signaling biomarkers as described herein.

This general assay known in the art may be used to test that effective therapeutic doses of the compounds disclosed herein can be used for inhibiting the proliferation of leukemic cells.

Example 28

Rat Developing Type II Collagen Induced Arthritis Assay

In order to study the effects of the compounds of the present invention on the autoimmune disease arthritis, a collagen induced developing arthritis model is used. Female Lewis rats are given collagen injections at day 0. Bovine type II collagen is prepared as a 4 mg/ml solution in 0.01N acetic acid. Equal volumes of collagen and Freund's incomplete adjuvant are emulsified by hand mixing until a bead of the emulsified material holds its form in water. Each rodent receives a 300 µl injection of the mixture at each injection time spread over three subcutaneous sites on the back.

Oral compound administration begins on day 0 and continues through day 16 with vehicle (5% NMP, 85% PEG 400, 10% Solutol) or compounds of the present invention in vehicle or control (e.g., methotrexate) at 12 hour intervals daily. Rats are weighed on days 0, 3, 6, 9-17 and caliper measurements of ankles are taken on days 9-17. Final body weights are taken, and then the animals are euthanized on day 17. After euthanization, blood is drawn and hind paws and knees are removed. Blood is further processed for pharmacokinetics experiments as well as an anti-type II collagen antibody ELISA assay. Hind paws are weighed and then, with the knees, preserved in 10% formalin. The paws and knees are subsequently processed for microscopy. Livers, spleen and thymus are weighed. Sciatic nerves are prepared for histopathology.

Knee and ankle joints are fixed for 1-2 days and decalcified for 4-5 days. Ankle joints are cut in half longitudinally, and knees are cut in half along the frontal plane. Joints are processed, embedded, sectioned and stained with toluidine blue. Scoring of the joints is done according to the following criteria:

Knee and Ankle Inflammation
0=Normal
1=Minimal infiltration of inflammatory cells in synovium/periarticular tissue
2=Mild infiltration
3=Moderate infiltration with moderate edema
4=Marked infiltration with marked edema
5=Severe infiltration with severe edema Ankle Pannus
0=Normal
1=Minimal infiltration of pannus in cartilage and subchondral bone
2=Mild infiltration (<¼ of tibia or tarsals at marginal zones)
3=Moderate infiltration (¼ to ⅓ of tibia or small tarsals affected at marginal zones)
4=Marked infiltration (½-¾ of tibia or tarsals affected at marginal zones)
5=Severe infiltration (>¾ of tibia or tarsals affected at marginal zones, severe distortion of overall architecture)

Knee Pannus
0=Normal
1=Minimal infiltration of pannus in cartilage and subchondral bone
2=Mild infiltration (extends over up to ¼ of surface or subchondral area of tibia or femur)
3=Moderate infiltration (extends over >¼ but <½ of surface or subchondral area of tibia or femur)
4=Marked infiltration (extends over ½ to ¾ of tibial or femoral surface)
5=Severe infiltration (covers >¾ of surface)

Cartilage Damage (Ankle, Emphasis on Small Tarsals)
0=Normal
1=Minimal=minimal to mild loss of toluidine blue staining with no obvious chondrocyte loss or collagen disruption
2=Mild=mild loss of toluidine blue staining with focal mild (superficial) chondrocyte loss and/or collagen disruption
3=Moderate=moderate loss of toluidine blue staining with multifocal moderate (depth to middle zone) chondrocyte loss and/or collagen disruption, smaller tarsals affected to ½-¾ depth
4=Marked=marked loss of toluidine blue staining with multifocal marked (depth to deep zone) chondrocyte loss and/or collagen disruption, 1 or more small tarsals have full thickness loss of cartilage
5=Severe=severe diffuse loss of toluidine blue staining with multifocal severe (depth to tide mark) chondrocyte loss and/or collagen disruption Cartilage Damage (Knee, Emphasis on Femoral Condyles)
0=Normal
1=Minimal=minimal to mild loss of toluidine blue staining with no obvious chondrocyte loss or collagen disruption
2=Mild=mild loss of toluidine blue staining with focal mild (superficial) chondrocyte loss and/or collagen disruption
3=Moderate=moderate loss of toluidine blue staining with multifocal to diffuse moderate (depth to middle zone) chondrocyte loss and/or collagen disruption
4=Marked=marked loss of toluidine blue staining with multifocal to diffuse marked (depth to deep zone) chondrocyte loss and/or collagen disruption or single femoral surface with total or near total loss
5=Severe=severe diffuse loss of toluidine blue staining with multifocal severe (depth to tide mark) chondrocyte loss and/or collagen disruption on both femurs and/or tibias Bone Resorption (Ankle)
0=Normal
1=Minimal=small areas of resorption, not readily apparent on low magnification, rare osteoclasts
2=Mild=more numerous areas of resorption, not readily apparent on low magnification, osteoclasts more numerous, <¼ of tibia or tarsals at marginal zones resorbed
3=Moderate=obvious resorption of medullary trabecular and cortical bone without full thickness defects in cortex, loss of some medullary trabeculae, lesion apparent on low magnification, osteoclasts more numerous, ¼ to ⅓ of tibia or tarsals affected at marginal zones
4=Marked=Full thickness defects in cortical bone, often with distortion of profile of remaining cortical surface, marked loss of medullary bone, numerous osteoclasts, ½-¾ of tibia or tarsals affected at marginal zones
5=Severe=Full thickness defects in cortical bone, often with distortion of profile of remaining cortical surface, marked loss of medullary bone, numerous osteoclasts, >¾ of tibia or tarsals affected at marginal zones, severe distortion of overall architecture Bone Resorption (Knee)
0=Normal
1=Minimal=small areas of resorption, not readily apparent on low magnification, rare osteoclasts
2=Mild=more numerous areas of resorption, definite loss of subchondral bone involving ¼ of tibial or femoral surface (medial or lateral)
3=Moderate=obvious resorption of subchondral bone involving >¼ but <½ of tibial or femoral surface (medial or lateral)
4=Marked=obvious resorption of subchondral bone involving >½ but <¾ of tibial or femoral surface (medial or lateral)
5=Severe=distortion of entire joint due to destruction involving >¾ of tibial or femoral surface (medial or lateral)

Statistical analysis of body/paw weights, paw AUC parameters and histopathologic parameters were evaluated using a Student's t-test or other appropriate (ANOVA with post-test) with significance set at the 5% significance level. Percent inhibition of paw weight and AUC was calculated using the following formula:

$$\% \text{ Inhibition} = A - B/A \times 100$$

$A$=Mean Disease Control−Mean Normal $B$=Mean Treated−Mean Normal

The results are expected to show, relative to vehicle only control or to methotrexate control, that the compounds of the present invention exhibit a significant reduction in arthritis induced ankle diameter increase over time, and reduction of ankle histopathology in at least one or more of the categories of inflammation, pannus, cartilage damage, and bone resorption as described above. The results are expected to show that one or more compounds of the present invention may be useful for the treatment and reduction of arthritis disease symptoms.

The results further are expected to show a reduction at 10, 20, and 60 mg/kg dosage levels of serum anti-type II collagen levels for selected test compounds, suggesting that one or more compounds of the present invention may not only be useful for the treatment and reduction of arthritis disease symptoms, but may also be useful for the inhibition of the autoimmune reaction itself.

Example 29

Rat Established Type II Collagen Induced Arthritis Assay

In order to examine the dose responsive efficacy of the compounds of the present invention in inhibiting the inflammation, cartilage destruction and bone resorption of 10 day established type II collagen induced arthritis in rats, compounds are administered orally daily or twice daily for 6 days.

Female Lewis rats are anesthetized and given collagen injections prepared and administered as described previously on day 0. On day 6, animals are anesthetized and given a second collagen injection. Caliper measurements of normal (pre-disease) right and left ankle joints are performed on day 9. On days 10-11, arthritis typically occurs and rats are randomized into treatment groups. Randomization is performed after ankle joint swelling is obviously established and there is evidence of bilateral disease.

After an animal is selected for enrollment in the study, treatment is initiated by the oral route. Animals are given vehicle, control (Enbrel) or compound doses, twice daily or once daily (BID or QD respectively). Administration is performed on days 1-6 using a volume of 2.5 ml/kg (BID) or 5 ml/kg (QD) for oral solutions. Rats are weighed on days 1-7 following establishment of arthritis and caliper measurements of ankles taken every day. Final body weights are taken on day 7 and animals are euthanized.

The results are expected to show reduction in mean ankle diameter increase over time for selected test compounds under the conditions tested.

Example 30

Adjuvant Induced Arthritis Assay

Intrathecal Catheterization of Rats

Isoflurane-anesthetized Lewis rats (200-250 g) are implanted with an intrathecal (IT) catheter. After a 6 d recovery period, all animals except those that appeared to have sensory or motor abnormalities (generally fewer than 5% of the total number) are used for experiments. For IT administration, 10 µl of drug or saline followed by 10 µl of isotonic saline is injected through the catheter.

Adjuvant Arthritis and Drug Treatment

Lewis rats are immunized at the base of the tail with 0.1 ml of complete Freund's adjuvant (CFA) on day 0 several days after catheter implantation (n=6/group). Drug (e.g., one or more compounds of the present invention or vehicle) treatment is generally started on day 8 and is continued daily until day 20. Clinical signs of arthritis generally begin on day 10, and paw swelling is determined every second day by water displacement plethysmometry.

The results are expected to show that one or more compounds of the present invention may be useful for the treatment of one or more of the diseases or conditions described herein.

Example 31

Rodent Pharmacokinetic Assay

In order to study the pharmacokinetics of the compounds of the present invention a set of 4-10 week old mice are grouped according to the following table:

| Group# | Mice/group | Compound Administration | | |
|---|---|---|---|---|
| | | (mg/kg) | Route | Regimen |
| 1 | 3 | 1 | Po | One dose |
| 2 | 3 | 3 | | |
| 3 | 3 | 10 | | |
| 4 | 3 | 30 | | |
| 5 | 3 | 60 | | |

Compounds of the present invention are dissolved in an appropriate vehicle (e.g., 5% 1-methyl-2-pyrrolidinone, 85% polyethylene glycol 400, 10% Solutor) and administered orally at 12 hour intervals daily. All animals are euthanized in $CO_2$ 2 hours after the final compound is administered. Blood is collected immediately and kept on ice for plasma isolation. Plasma is isolated by centrifuging at 5000 rpm for 10 minutes. Harvested plasma is frozen for pharmacokinetic detection.

The results are expected to demonstrate the pharmacokinetic parameters such as absorption, distribution, metabolism, excretion, and toxicity for the compounds of the present invention.

Example 32

Basotest Assay

The barotest assay is performed using Orpegen Pharma Basotest reagent kit. Heparinized whole blood is pre-incubated with test compound or solvent at 37 C for 20 min. Blood is then incubated with assay kit stimulation buffer (to prime cells for response) followed by allergen (dust mite extract or grass extract) for 20 min. The degranulation process is stopped by incubating the blood samples on ice. The cells are then labeled with anti-IgE-PE to detect basophilic granulocytes, and anti-gp53-FITC to detect gp53 (a glycoprotein expressed on activated basophils). After staining red blood cells are lysed by addition of Lysing Solution. Cells are washed, and analyzed by flow cytometry. Test compounds, when evaluated in this assay inhibit allergen induced activation of basophilic granulocytes at sub micromolar range. The results are expected to demonstrate that under the conditions tested one or more compounds of the present invention are capable of inhibiting allergen induced activation of basophils.

Example 33

Use of the Compounds of the Present Invention for Inhibition of Tumor Growth Cell Lines Cell lines of interest (A549, U87, ZR-75-1 and 786-O) are obtained from American Type Culture Collection (ATCC, Manassas, Va.). Cells are proliferated and preserved cryogenically at early passage (e.g., passage 3). One aliquot is used for further proliferation to get enough cells for one TGI study (at about passage 9).

Animals

Female athymic nude mice are supplied by Harlan. Mice are received at 4 to 6 weeks of age. All mice are acclimated for about one day to two weeks prior to handling. The mice are housed in microisolator cages and maintained under specific pathogen-free conditions. The mice are fed with irradiated mouse chow and freely available autoclaved water is provided.

Tumor Xenograft Model

Mice are inoculated subcutaneously in the right flank with 0.01 to 0.5 ml of tumor cells (approximately $1.0 \times 10^5$ to $1.0 \times 10^8$ cells/mouse). Five to 10 days following inoculation, tumors are measured using calipers and tumor weight is calculated, for example using the animal study management software, such as Study Director V.1.6.70 (Study Log). Mice with tumor sizes of about 120 mg are pair-matched into desired groups using Study Director (Day 1). Body weights are recorded when the mice are pair-matched. Tumor volume and bodyweight measurements are taken one to four times weekly and gross observations are made at least once daily. On Day 1, compounds of the present invention and reference compounds as well as vehicle control are administered by oral gavage or iv as indicated. At the last day of the experiment, mice are sacrificed and their tumors are collected 1-4 hours after the final dose. The tumors are excised and cut into two sections. One third of the tumor is fixed in formalin and embedded in paraffin blocks and the remaining two thirds of tumor is snap frozen and stored at −80° C.

Data and Statistical Analysis

Mean tumor growth inhibition (TGI) is calculated utilizing the following formula:

$$TGI = \left[1 - \frac{\left(\bar{X}_{Treated(Final)} - \bar{X}_{Treated(Day1)}\right)}{\left(\bar{X}_{Control(Final)} - \bar{X}_{Control(Day1)}\right)}\right] \times 100\%$$

Tumors that regress from the Day 1 starting size are removed from the calculations. Individual tumor shrinkage (TS) is calculated using the formula below for tumors that show regression relative to Day 1 tumor weight. The mean tumor shrinkage of each group is calculated and reported.

$$TS = \left[1 - \frac{(\text{Tumor Weight}_{(Final)})}{(\text{Tumor Weight}_{(Day\,1)})}\right] \times 100\%$$

The model can be employed to show whether the compounds of the present invention can inhibit tumor cell growth such as renal carcinoma cell growth, breast cancer cell growth, lung cancer cell growth, or glioblastoma cell growth under the conditions tested.

Example 34

Inhibition of PI3K Pathway and Proliferation of Tumor Cells with PI3Kα Mutation

Figure 7:
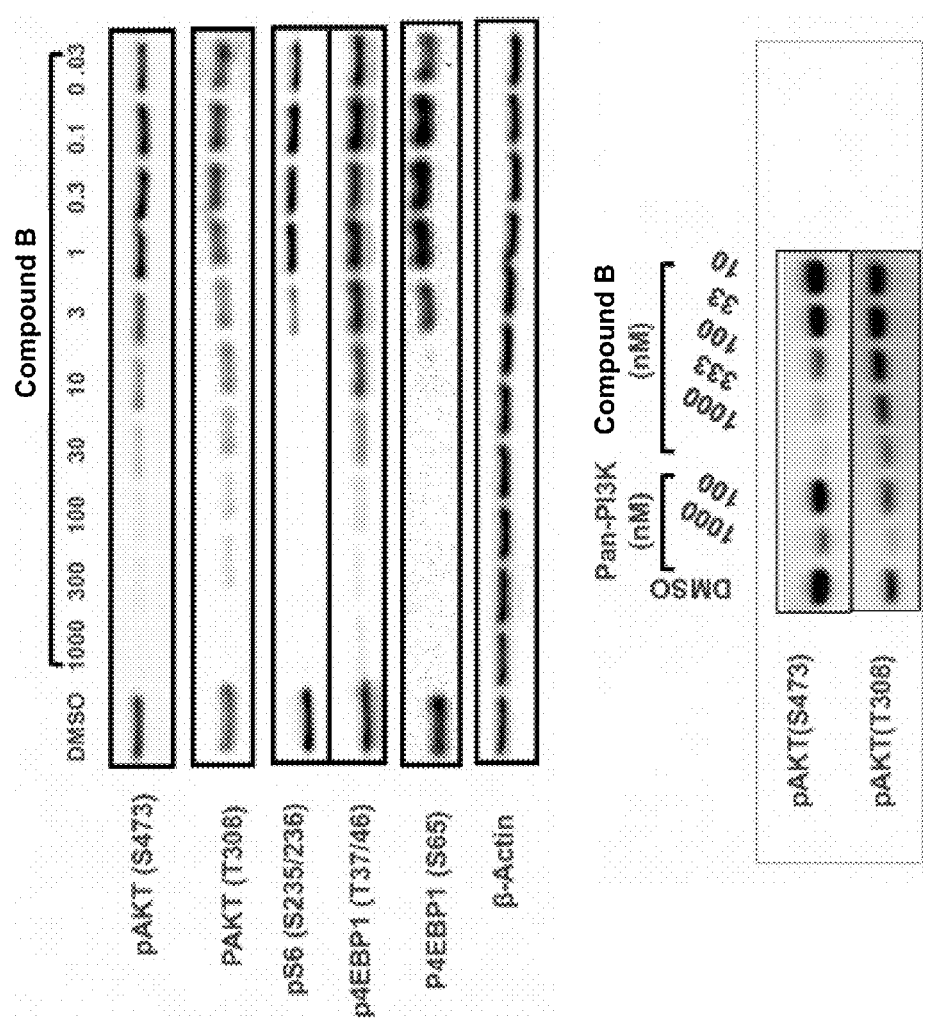
FIG. 7 is a western blot depicting differential inhibition of Akt phosphorylation at serine 473 over threonine 308 by Compound B (top panel). Also shown is the comparison of Akt phosphorylation inhibition for Pan-PI3K inhibitor versus Compound B.
Figure 12:
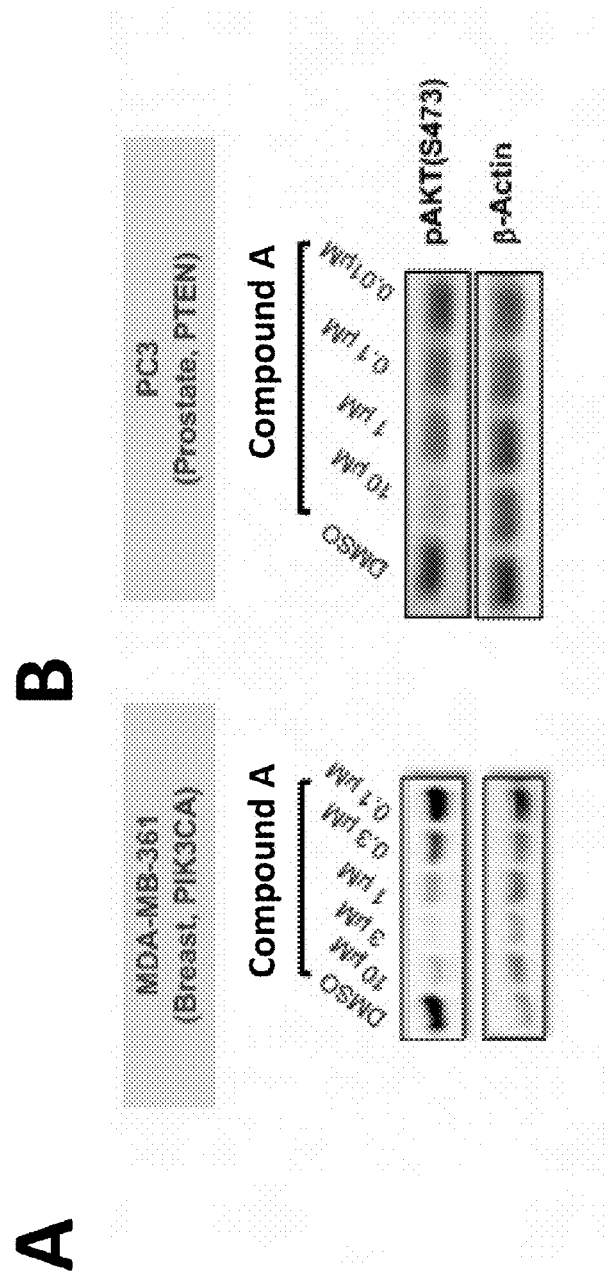
FIG. 12 shows A) a western blot showing inhibition of Akt phosphorylation at serine 473 by Compound A; and B) reduced inhibition of Akt phosphorylation at serine 473 by Compound A in a PTEN-mutant cell line.

Cells comprising one or more mutations in PI3Kα, including but not limited to breast cancer cells (e.g., MDA-MB-361, T47D, SKOV-3), and cells comprising one or more mutations in PTEN including but not limited to prostate cancer cells (e.g., PC3), are typically grown in cell growth media such as DMEM supplemented with fetal bovine serum and/or antibiotics, and grown to confluency. Cells are then treated with various concentrations of test compound for about 2 hours and subsequently lysed in cell lysis buffer. Lysates are subjected to SDS-PAGE followed by Western blot analysis to detect downstream signaling markers, including but not limited to pAKT(S473), pAKT(T308), pS6, and p4E-BP1. Degree of proliferation (and proliferation inhibition) can also be measured for cells at various doses of compound of the present invention such as Compound A (compound 54 of Table 3) or Compound B (compound 1 of Table 1). β-Actin can be used as a housekeeping protein to ascertain proper loading. FIG. 7 shows a Western blot depicting differential inhibition of Akt phosphorylation at serine 473 over threonine 308 by Compound B (top panel) in a PC3 model. Also shown is the comparison of Akt phosphorylation inhibition for Pan-PI3K inhibitor versus Compound B in a SKOV-3 model. FIG. 12 shows a Western blot depicting inhibition of Akt phosphorylation at serine 473 by Compound A in MDA-MB-361 cells relative to PC3 cells, indicating that compounds of the invention are preferentially capable of inhibiting tumor proliferation of cells with mutations in the PI3Kα pathway relative to cells with mutations in the PTEN pathway. Compound A inhibited pAKT with an IC50 of ~1000 nM for MDA-MB-361 cells vs. an IC50 of ~10,000 nM for PC3 cells. Similarly, Compound A inhibited cell proliferation with an IC50 of ~1900 for MDA-MB-361 cells vs. an IC50 of >10,000 nM for PC3 cells.

Figure 11:
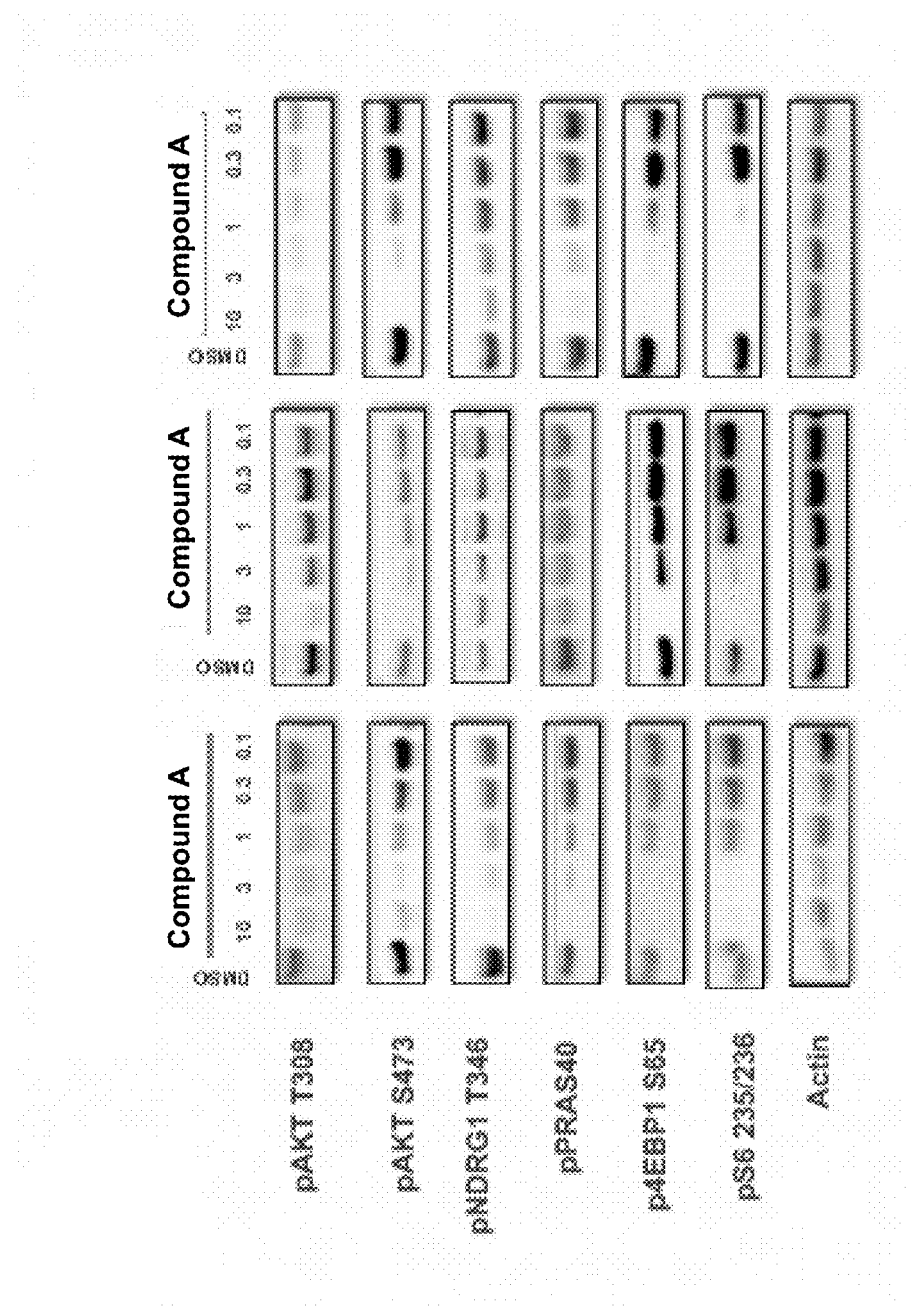
FIG. 11 is a western blot depicting inhibition of the PI3K pathway by Compound A in cell lines with elevated PI3K α activity. The left column shows data from MDA-MB-361 breast cancer cells harboring PIK3CA mutation. The middle column shows data from MDA-MB-453 breast cancer cells harboring PIK3CA mutation. The right column shows data from SKBr3 breast cancer cells harboring HER2 mutation.

A western blot depicting inhibition of the PI3K pathway by Compound A in cell lines with elevated PI3K α activity is shown in FIG. 11. MDA-MB-361(PIK3CA-E545K), MDA-MB-453 (PIK3CA-H1047R), and SK-Br3 (Her2) cells were treated with various concentrations of Compound A for 2 h and subsequently lysed. Lysates were subjected to SDS-PAGE followed by Western blot analysis as described above to detect downstream pathway markers. The left column shows data from MDA-MB-361 breast cancer cells harboring PIK3CA mutation. The middle column shows data from MDA-MB-453 breast cancer cells harboring PIK3CA mutation. The right column shows data from SKBr3 breast cancer cells harboring HER2 mutation.

The effect of Compound A on proliferation of tumor cells harboring PI3Kα mutations is shown in FIG. 13. Cells were seeded at 5000-10,000 per well in a 96 well flat bottom plate 90 ul growth media. Pre-diluted compound (at 10 times the final concentration) or DMSO (control) was added. The compounds were prepared such that the dose range extended from a final concentration of 30 μM to 14 nM via 3-fold serial dilutions (8 point curve). The final DMSO concentration was 0.3%. Cells were incubated for 72 hours at 37° C. in a $C_{O2}$ incubator. After 72 hours, proliferation was measured using CellTiter-Glo Luminescent reagent (Promega, PR-G7573). CellTiter-Glo reagent was added at 100 μL, per well which was equal to the volume of culture media present in each well. Contents were mixed for 30 minutes on an orbital shaker to lyse cells Luminescence was read on a PerkinElmer EnVision plate reader. Curves and IC50 values were generated in GraphPad Prism using a sigmoidal dose response non linear regression fit. Inhibition % was calculated as: 1–(cells+inhibitor)–background signal)/(cells+DMSO)–background signal)–100.

Example 35

In Vitro Inhibition of Angiogenesis

Inhibition of angiogenesis in the presence of test compound is evaluated using a tube formation assay, such as by using a tube formation assay kit (e.g., commerically available from Invitrogen). Angiogenic capacity can be measured in vitro using an endothelial cell line, such as human umbilical vein endothelial cells (HUVEC). The assay is conducted according to the kit instructions, in the presence or absence of compound. Briefly, a gel matrix is applied to a cell culture surface, cells are added to the matrix-covered surface along with growth factors, with some samples also receiving an inhibitor compound, cells are incubated at 37° C. and 5% $CO_2$ long enough for control samples (no compound added) to form tube structures (such as overnight), cells are stained using a cell-permeable dye (e.g., calcein), and cells are visualized to identify the degree of tube formation. Any decrease in tube formation relative to un-inhibited control cells is indicative of angiogenic inhibition. Based on doses tested and the corresponding degree of tube formation inhibition, IC50 values for tube formation are calculated. IC50 values for cell viability can be measured using any number of methods known in the art, such as staining methods that distinguish live from dead cells (e.g., Image-iT DEAD Green viability stain commercially available from Invitrogen.

Example 36

In Vivo Efficacy in Xenogenic Mouse Model of Breast Cancer

Nude mice harboring tumors (150-250 mm$^3$) derived from implantation of human breast adenocarcinoma cells MDA-MB-361 (PI3Kα/HER2 carcinoma) were separated into untreated control (vehicle only) and treatment groups. Mice in the treatment group were further divided into mice receiving 60 mg/kg (60 mpk) of a PI3Kα inhibitor (Compound A), 0.3 mg/kg of an mTor inhibitor (Compound B), or a combination of Compound A and Compound B. Groups receiving 5 mg/kg of paclitaxel (intravenously), alone or in combination with Compound B, were also included. Mice in the treatment group received the defined dose daily by oral lavage for 30 days, during which time tumor weight was calculated as described above (e.g. every 2-5 days). Blood glucose was monitored periodically following administration of treatment. 2 hours after the final treatment, tumors were harvested and proteins are analyzed by Western blot as described above.

Figure 2:
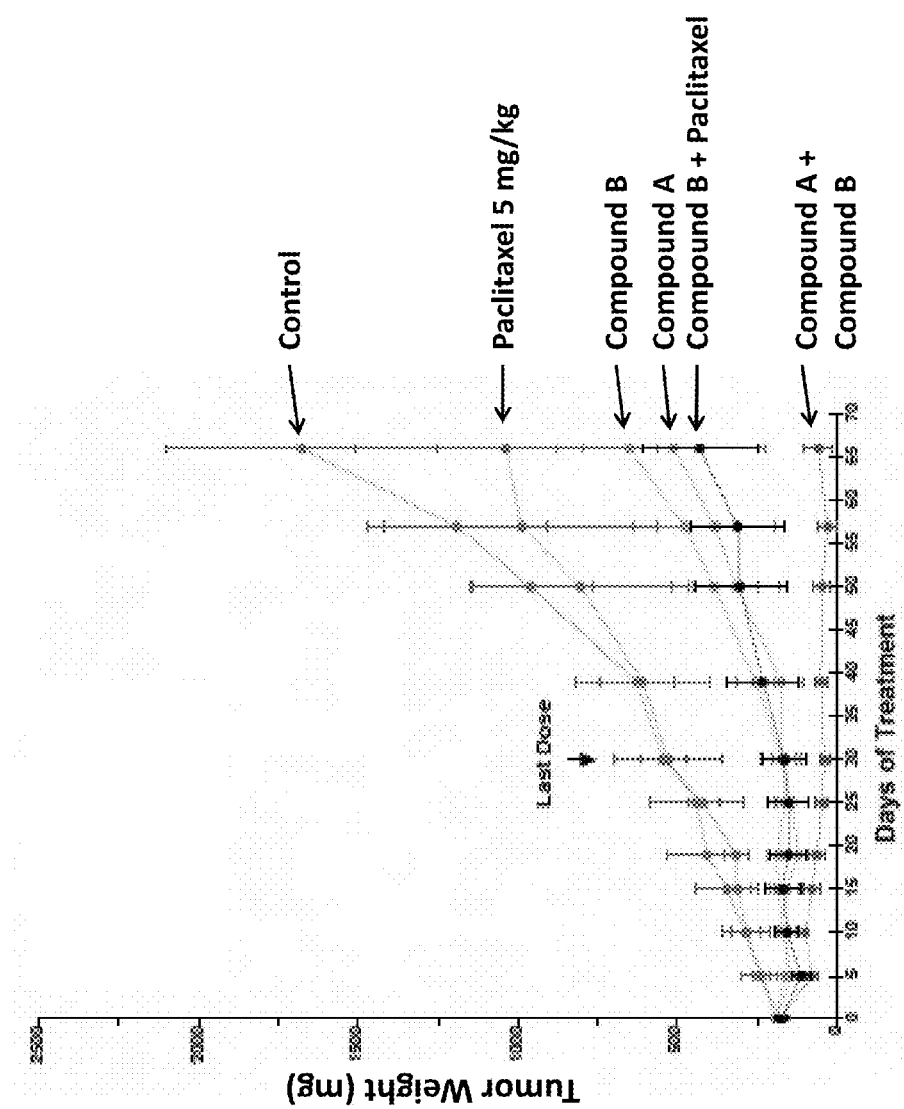
FIG. 2 is a graph showing the synergistic effect of combined treatment with a PI3-kinase α inhibitor (Compound A) and an mTor inhibitor (Compound B) on tumor weight in a preclinical breast cancer model.
Figure 3:
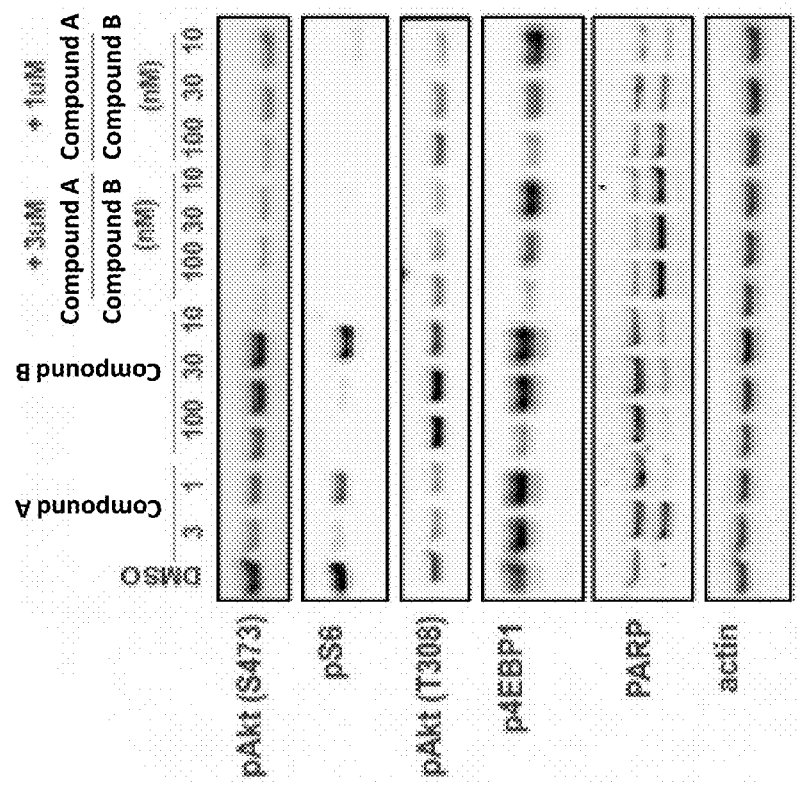
FIG. 3 is a western blot depicting the synergistic effect of combined treatment with Compound A and Compound B in terms of downregulating Akt and S6 phosphorylation.

The effect of the compounds on the localization/viability of marginal zone B cells in the spleen is also evaluated at the conclusion of treatment. The synergistic effect of combined treatment with Compound A and Compound B on tumor weight in a preclinical breast cancer model are shown in FIG. 2. These results are further supported by FIG. 3, which further shows Western Blot results for levels of various markers for kinase activity.

Figure 4:
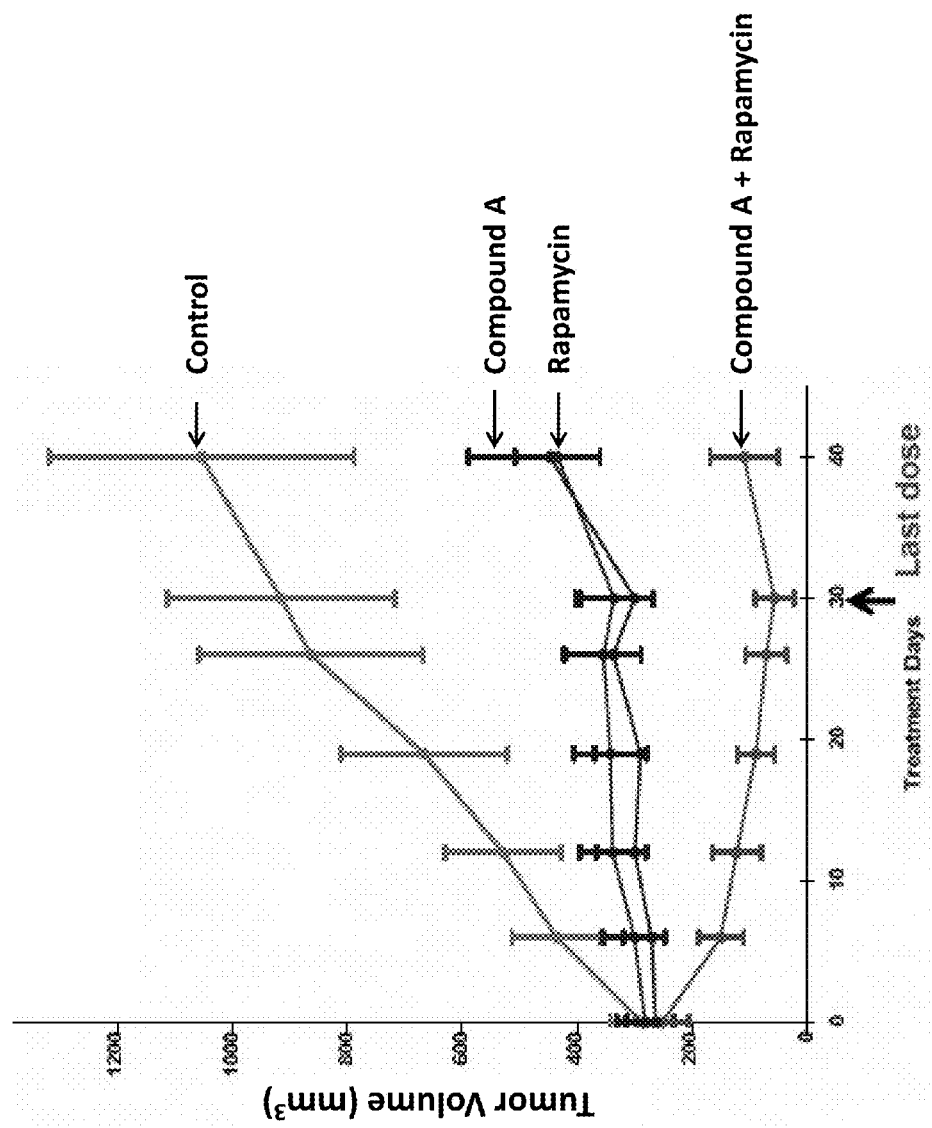
FIG. 4 is a graph showing the synergistic effect of combined treatment with Compound A and rapamycin in terms of reducing tumor volume of a preclinical breast cancer model.

A similar experiment was conducted in which nude mice harboring tumors derived from implantation of human breast adenocarcinoma cells MDA-MB-361 (PI3Kα/HER2 carcinoma) were separated into untreated control (vehicle only) and treatment groups. Mice in the treatment group were then further divided into mice receiving 60 mg/kg (60 mpk) of a PI3Kα inhibitor (Compound A), an mTor inhibitor which is rapamycin (0.5 mg/kg intraperitoneal), or a combination of Compound A and rapamycin. Treatment of tumors (MDA-MB-361) with compounds was discontinued on Day 30. Tumors were measured every 2-5 days. FIG. 4 shows a synergistic effect of combined treatment with Compound A and rapamycin in this preclinical breast cancer model.

A similar experiment using 786-O cells, a human kidney carcinoma cell line having a non-mutated PI3Kα, instead of MDA cells was used to further demonstrate the specificity of test compounds. Compound A was administered orally at 60 and 120 mg/kg and compound A was administered orally as a solution at 1 mg/kg (QD). For example, a PI3Kα inhibitor is compared to a kinase inhibitor with specificity for mTor. The inhibitor with affinity for mTor (Compound B) is effective at inhibiting kinase activity (measured by Western blot analysis of downstream markers) and tumor growth in this model, whereas a PI3Kα inhibitor (Compound A), while still showing some anti-tumor activity, has decreased activity by comparison to that seen in the MDA derived tumors (compare FIG. 2 and FIG. 6). FIG. 6C also provides biochemical potency data for the two compared inhibitors. PI3 Kinase α, β, γ and δ activity was assayed using the PI3 Kinase HTRF® assay kit (Millipore Corporation). Purified recombinant PI3Kα, PI3Kβ, PI3Kγ and PI3Kδ were obtained from Millipore Corporation. Purified recombinant PI3K was used to catalyze the phosphorylation of phosphatidylinositol 4,5-bisphosphate (PIP2) to phosphatidylinositol 3,4,5-trisphosphate (PIP3) in the presence of 10 µM ATP. Emission ratios were converted into percent inhibitions and imported into GraphPad Prism software. The concentration of Compound A or B necessary to achieve inhibition of enzyme activity by 50% (IC50) was calculated using concentrations ranging from 20 µM to 0.1 nM (12-point curve). IC50 values were determined using a nonlinear regression model available in GraphPad Prism 5.

Figure 9:
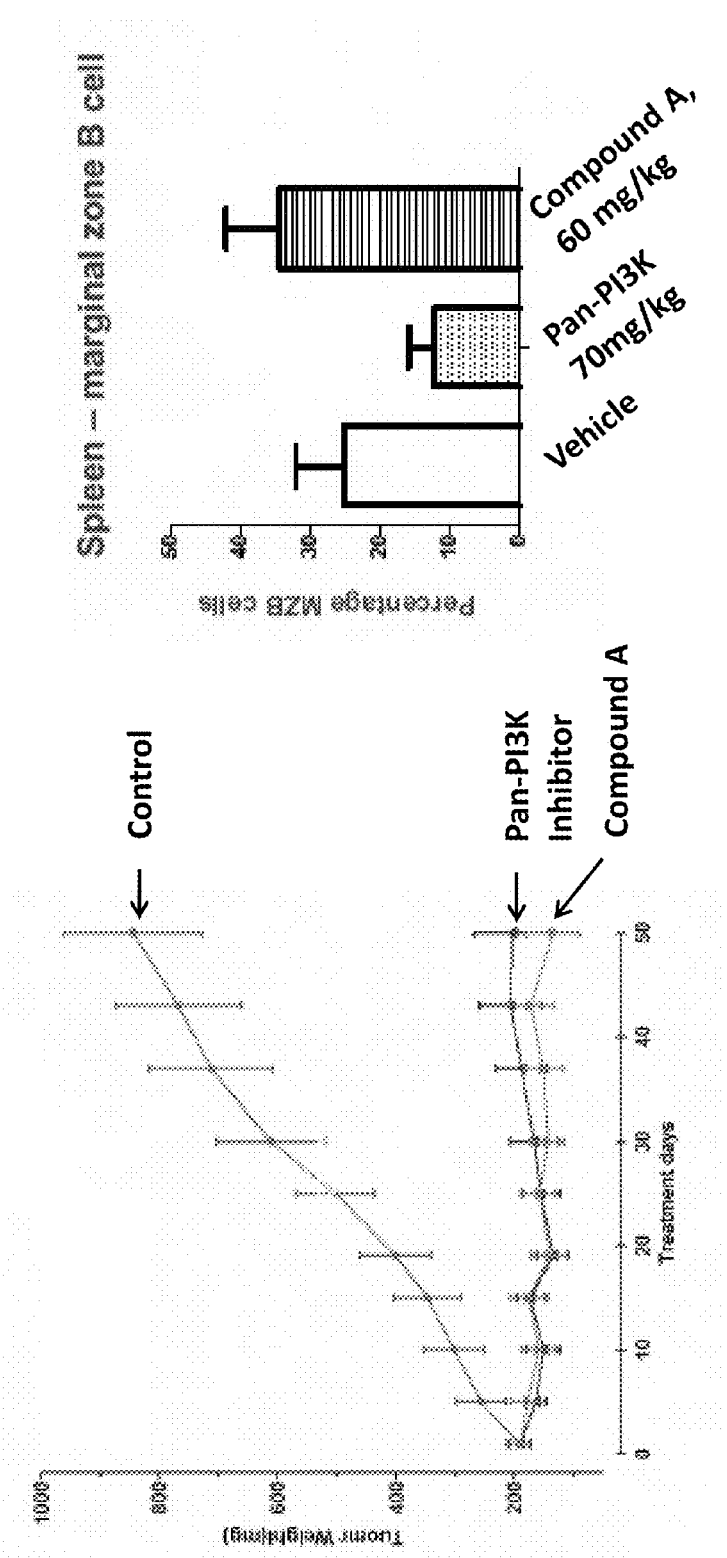
FIG. 9 shows, left panel, a graph showing reduction in tumor weight of a breast cancer model using 70 mg/kg Pan-PI3K inhibitor and 60 mg/kg compound A and, right panel, reduced presence of MZB cells in mouse spleen for 70 mg/kg Pan-PI3K inhibitor compared to 60 mg/kg Compound A.
Figure 10:
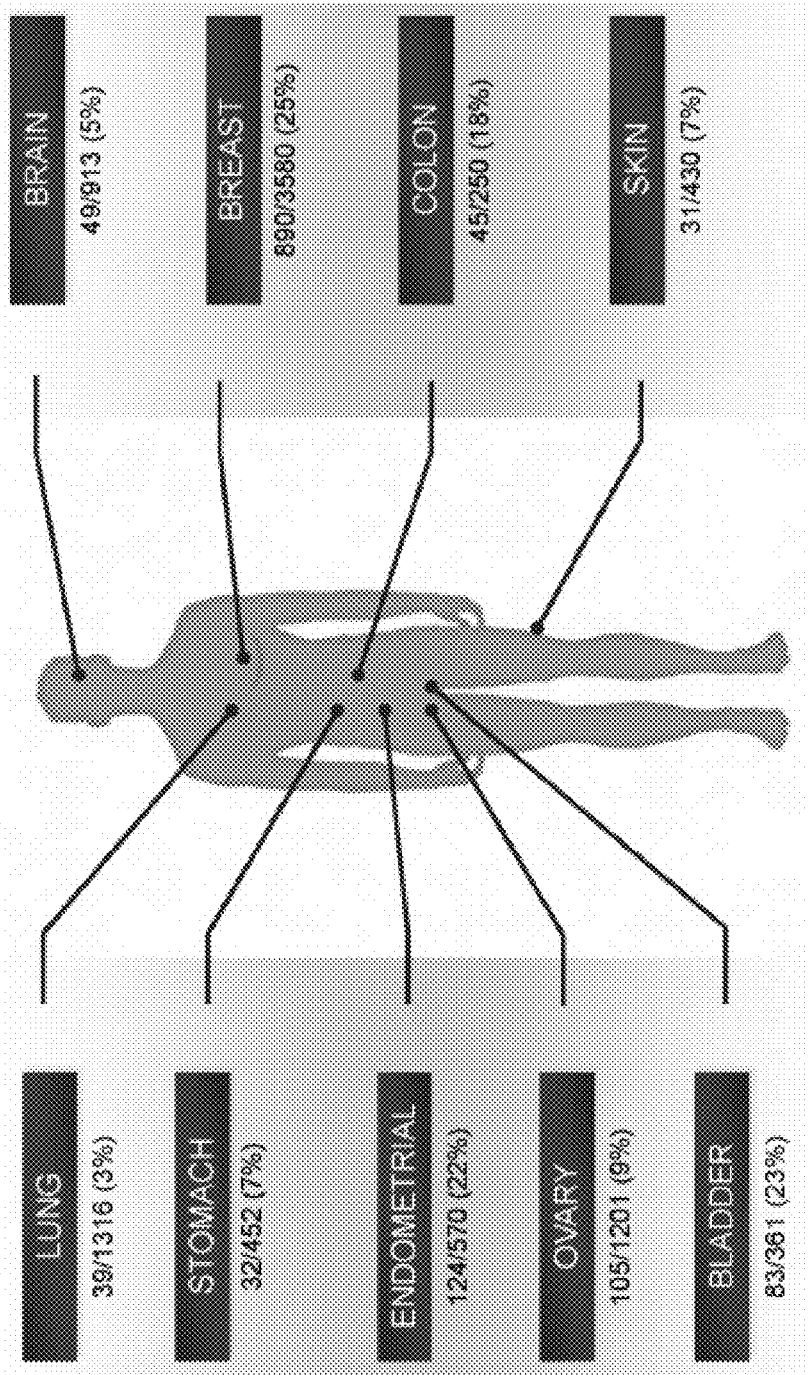
FIG. 10 illustrates the frequency of PI3K α mutation in various human cancers.

FIG. 9 shows a graph depicting reduction in tumor weight for breast cancer model using 70 mg/kg Pan-PI3K inhibitor and 60 mg/kg compound A (left panel) and a reduced presence of MZB cells in mouse spleen for 70 mg/kg Pan-PI3K inhibitor compared to 60 mg/kg Compound A (right panel). Spleens were harvested 2 hrs after the last dose, processed and stained with appropriate antibodies (marginal zone B cell: B220+; CD23−; CD21hi) and analyzed for staining on GUAVA EasyCyte FACS machine using Guava Cytosoft 5.2 software. This data shows that, in contrast to the Pan-PI3K inhibitor, a compound which is a selective PI3Kα inhibitor such as Compound A does not affect localization/viability of marginal zone B cells.

Example 37

TNP-Ficoll T-Cell Independent B-Cell Activation Assay

To test the effects of the compounds of the present invention in suppressing T cell independent antibody production, the TNP-Ficoll B-cell activation assay is used as described herein. Compounds of the present invention are dissolved in an appropriate vehicle (e.g. 5% 1-methyl-2-pyrrolidinone, 85% polyethylene glycol 400, 10% Solutor). Compounds are administered orally approximately 1 hr before TNP-Ficoll treatment to 4-10 week old mice. To study the effects of the compounds on B-cell activation, one set of mice are grouped according to the following table:

| Group# | Mice/group | Comp treated | Group | Antigen injection at day-1 TNP-F | Route | Compound Administration from day-1 to day-7 (mg/kg) | Route | Regimen |
|---|---|---|---|---|---|---|---|---|
| 1 | 4 | Vehicle | Antigen only | 200 uL | ip | 0 | Po | BID for 7 days |
| 2 | 8 | — | Antigen only | (0.5 mg/ml) | | 0 | | |
| 3 | 8 | Reference compound #1 | reference | | | 30 | | |
| 4 | 8 | Test | Antigen + | | | 1 | | |
| 5 | 8 | compound | cmp | | | 3 | | |
| 6 | 8 | | | | | 10 | | |
| 7 | 8 | | | | | 30 | | |
| 8 | 8 | | | | | 60 | | |

Four animals in group 1, and eight animals in groups 2 to 7 are euthanized in $CO_2$ 2 hours after the last compound administration on day 7. Blood is immediately collected by cadiopuncture and kept at 37° C. for 1 hr to clot followed by overnight incubation at 4° C. to allow the clot to contract. The following day, serum is collected by decanting and centrifugation at 3000 rpm for 10 min. The collected serum is then frozen at −80° C. for future analysis.

Serum samples are analyzed for anti-TNP antibody titers by ELISA as described herein. TNP-BSA is coated onto a Nunc Maxisorb microtiter plate with 100 µl/well at a concentration of 10 µg/ml in phosphate buffered saline (PBS). The Maxisorb plate is incubated for 1.5 hours at room temperature and the solution is removed. 200 µl/well of blocking buffer (e.g. 1% BSA in PBS) is added to each well and incubated 1 hr at room temperature. The plate is washed once with 200 µl/well of PBS 0.05% Tween-20 (wash buffer). A 1:2 dilution of serum from each mouse in blocking buffer is added to each well in the first column (1) of the microtiter plate. The serum in each well of column 1 is then diluted 3-fold in blocking buffer and added to column 2. The serum in each well of column 2 is diluted 3-fold in blocking buffer and added to column 3. The procedure is repeated across the twelve columns of the microtiter plate. The microtiter plate is incubated 1 hr at room temperature. Serum is removed from the plate and the plate is washed three times with wash buffer. 100 µl/well of goat anti-mouse IgG3-HRP diluted 1:250 in blocking buffer is added to each well and incubated 1 hr at room temperature. The anti-mouse IgG3-HRP is removed from the microtiter plate and the plate is washed six times with wash buffer. HRP substrate (200 µl ABTS solution+30% $H_2O_2$+10 ml citrate buffer) is added to each well at 100 µl/well, incubated 2-20 minutes in the dark and the amount of anti-TNP IgG3 is determined spectrophotometrically at 405 nm. Similarly, anti-TNP IgM and total anti-TNP Ab are determined using anti-mouse IgM-HRP and anti-mouse Ig-HRP respectively.

Figure 8:
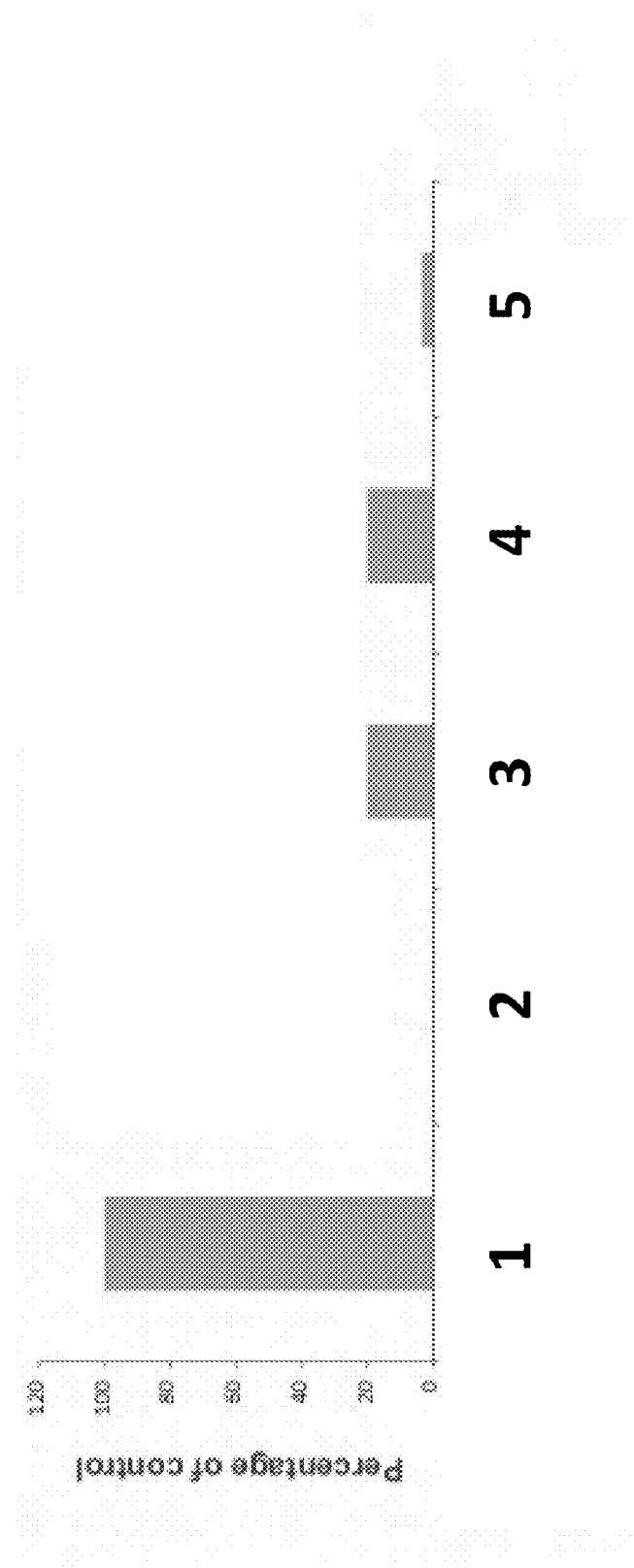
FIG. 8 is a graph showing that Pan-PI3K inhibitor, but not Compound A, blocks B cell function in vivo. Mice were immunized with TNP-Ficoll and treated with 1) vehicle; 2) 70 mg/kg GDC0941; 3) 30 mg/kg Compound A; 4) 60 mg/kg Compound A; or 5) 120 mg/kg Compound A for 7 days. Antibody production was measured as a percentage of control group that were treated with vehicle.

A graph showing that Pan-PI3K inhibitor, but not a PI3Kα inhibitor such as Compound A, blocks B cell function in vivo is shown in FIG. 8. Mice were immunized with TNP-Ficoll and treated with 1) vehicle 2) 70 mg/kg GDC0941 3) 30 mg/kg Compound A 4) 60 mg/kg Compound A or 5) 120 mg/kg Compound A for 7 days. Antibody production was measured using ELISA and plotted as as a percentage of control group that were treated with vehicle.

Example 38

In Vitro Effect on mTOR Pathways

Figure 5:
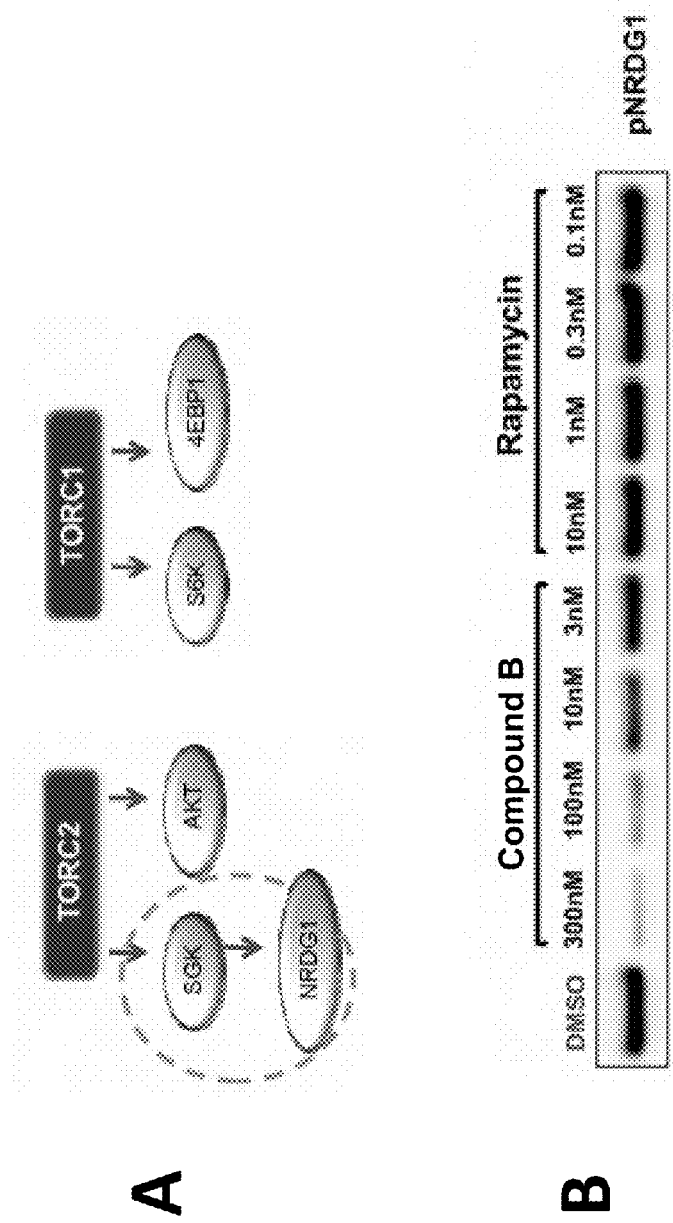
FIG. 5 shows A) an illustration of the distinct signaling pathways mediated by mTORC1 and mTORC2 and B) a western blot depicting sensitivity of mTORC1-dependent NRDG1 phosphorylation to Compound B, but not rapamycin.

An in vitro experiment using 786-O cells treated with various concentrations of Compound B or Rapamycin was performed as described in Example 34. Cells were subsequently lysed and lysates were subjected to SDS-PAGE followed by Western blot analysis to detect the downstream pathway marker, pNDRG1. Results, shown in FIG. 5, indicate the differential effects on mTORC1 and mTORC2 for rapamycin relative to Compound B.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for treating breast cancer comprising administering to a subject in need thereof a therapeutically effective amount of the mTOR inhibitor:

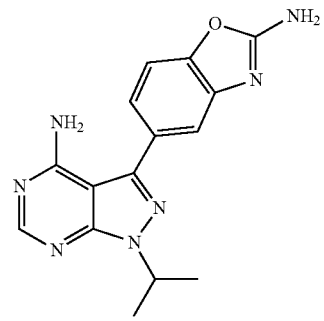 [SMILES: CC(C)n1nc(-c2ccc3oc(N)nc3c2)c2c(N)ncnc21]

or a pharmaceutically acceptable salt thereof; and
a therapeutically effective amount of the PI3-kinase α inhibitor:

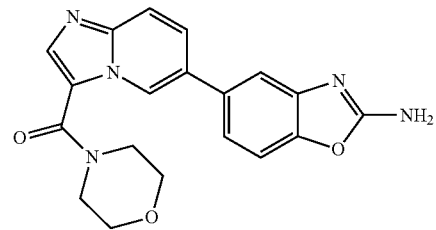 [SMILES: Nc1nc2cc(-c3ccc4ncc(C(=O)N5CCOCC5)n4c3)ccc2o1]

or a pharmaceutically acceptable salt thereof.

* * * * *